United States Patent
Bakthavatchalam et al.

(10) Patent No.: US 7,566,712 B2
(45) Date of Patent: *Jul. 28, 2009

(54) BIARYL PIPERAZINYL-PYRIDINE ANALOGUES

(75) Inventors: Rajagopal Bakthavatchalam, Madison, CT (US); Charles A. Blum, Westbrook, CT (US); Stéphane De Lombaert, Madison, CT (US); Taeyoung Yoon, Guilford, CT (US); Xiaozhang Zheng, Branford, CT (US)

(73) Assignee: Neurogen Corporation, Branford, CT (US)

( * ) Notice: Subject to any disclaimer, the term of this patent is extended or adjusted under 35 U.S.C. 154(b) by 743 days.

This patent is subject to a terminal disclaimer.

(21) Appl. No.: 10/893,799

(22) Filed: Jul. 16, 2004

(65) Prior Publication Data

US 2007/0027155 A1 Feb. 1, 2007

Related U.S. Application Data

(60) Provisional application No. 60/516,135, filed on Oct. 31, 2003, provisional application No. 60/488,564, filed on Jul. 16, 2003.

(51) Int. Cl.
C07D 401/14 (2006.01)
C07D 403/14 (2006.01)
A61K 31/53 (2006.01)
A61K 31/506 (2006.01)
A61P 19/02 (2006.01)

(52) U.S. Cl. .................. 514/245; 544/194; 544/206
(58) Field of Classification Search .......... 544/194, 544/206; 514/245
See application file for complete search history.

(56) References Cited

U.S. PATENT DOCUMENTS

| | | | |
|---|---|---|---|
| 4,260,621 A | 4/1981 | Roch et al. | |
| 4,824,846 A | 4/1989 | Kampe et al. | |
| 5,589,477 A | 12/1996 | Chokai et al. | |
| 5,962,453 A * | 10/1999 | Ueda et al. ................. | 514/245 |
| 6,414,149 B1 | 7/2002 | Chu-Moyer et al. | |
| 6,417,185 B1 | 7/2002 | Goff et al. | |
| 6,660,740 B1 | 12/2003 | Chu-Moyer et al. | |
| 6,710,058 B2 | 3/2004 | Jacobson et al. | |
| 6,894,047 B2 | 5/2005 | Mylari | |
| 2002/0132807 A1 | 9/2002 | Wang et al. | |
| 2003/0060466 A1 | 3/2003 | Binggeli et al. | |
| 2003/0236280 A1 | 12/2003 | Codd et al. | |
| 2006/0122394 A1 | 6/2006 | Blum et al. | |
| 2006/0229308 A1 | 10/2006 | Blum et al. | |
| 2008/0045525 A1 | 2/2008 | Bakthavatchalam et al. | |
| 2008/0124384 A1 | 5/2008 | Blum et al. | |

FOREIGN PATENT DOCUMENTS

| | | |
|---|---|---|
| EP | 0459830 A1 | 12/1991 |
| EP | 0 775 487 | 5/1997 |
| EP | 1 136 483 A1 | 9/2001 |
| FR | 2 262 512 | 9/1975 |
| WO | WO-98/24782 | 6/1998 |
| WO | WO 00/09496 | 2/2000 |
| WO | WO-01/70728 | 9/2001 |
| WO | WO-02/02539 | 1/2002 |
| WO | WO 03/055848 A2 | 7/2003 |
| WO | WO2004/000820 A2 | 12/2003 |
| WO | WO2004/028440 A2 | 4/2004 |
| WO | WO 2004/048365 | 6/2004 |

OTHER PUBLICATIONS

Valenzano et al. Curr. Med. Chem. 3185-3202, 2004.*
Szallasi et al, Journal of Medicinal Chemistry 47(20): 2716-2723, 2004.*
Cecil Textbook of Medicine, edited by Bennet, J.C., and Plum F., 20th edition, vol. 1, 1004-1010, 1996.*
Luo et al., "Microwave-assisted synthesis of aminopyrimidines," Tetrahedron Letters 43:5739-5742 (2002).
Ojea et al., "Synthesis of Pyrazino[1,2-a:4,5-a']D1[1,8]Naphthyridine and Pyrazino[1,2-a][1,8]Naphthyridines," Heterocycles 36:1337-1349 (1993).
Ram et al., "Synthesis of Pyrimidines and Fused Pyrimidines as Leishmanicides," Journal fuer Praktische Chemie 331:957-963 (1989).
Agarwal et al., "A diversity oriented synthesis of highly functionalized unsymmetrical biaryls through carbanion induced ring transformation of 2H-pyran-2-ones," Tetrahedron 58:8793-8798 (2002).
Ram et al., "One-pot synthesis of unsymmetrical biaryls from suitably functionalized 2H-pyran-2-ones through carbanion-induced ring-transformation reactions," J. Chem. Soc. Perkin Trans. 16:1953-1959 (2001).

(Continued)

Primary Examiner—Venkataraman Balasubramanian
(74) Attorney, Agent, or Firm—Edwards Angell Palmer & Dodge LLP; Peter F. Corless; Mark D. Russett

(57) ABSTRACT

Biaryl piperazinyl-pyridine analogues are provided, of the Formula:

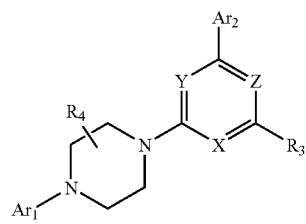

wherein variables are as described herein. Such compounds are ligands that may be used to modulate specific receptor activity in vivo or in vitro, and are particularly useful in the treatment of conditions associated with pathological receptor activation in humans, domesticated companion animals and livestock animals. Pharmaceutical compositions and methods for using such compounds to treat such disorders are provided, as are methods for using such ligands for receptor localization studies.

59 Claims, No Drawings

OTHER PUBLICATIONS

Chu-Moyer et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines," J. Med. Chem. 45:511-528 (2002).

Xia et al., "Substituted 1,3,5-Triazines as Cholesteryl Ester Transfer Protein Inhibitors," Biooraganic & Medical Chemistry Letters 6:919-922 (1996).

Farhanullah et al., "Synthesis of Aminonicotinonitriles and Diaminopyridines through Base-Catalyzed Ring Transformation of 2H-Pyran-2-ones," J. Org. Chem. 68:2983-2985 (2003).

Ram et al., "Synthesis of π-Deficient Pyrimidines as Leishmanicides," Arch. Pharm. 324:837-839 (1991).

Vishwakarma et al., "Reactions of Polarized Keten S,N-Acetals with Guanidine: A Facile General Route to Novel 5,6-Substituted 2-Amino-4-N-alkyl/aryl/N-azacycloalkylaminopyrimidines," Indian Journal of Chemistry 24B:466-471 (1985).

SciFinder Report for CAS Registry No. 477866-20-9.
SciFinder Report for CAS Registry No. 330981-81-2.
SciFinder Report for CAS Registry No. 380546-69-0.
SciFinder Report for CAS Registry No. 552286-80-3.
SciFinder Report for CAS Registry No. 339279-02-6.
SciFinder Report for CAS Registry No. 477863-89-1.
SciFinder Report for CAS Registry No. 477866-17-4.
SciFinder Report for CAS Registry No. 667895-91-2.

Johansen, M.E. et al., "TRPV1 Antagonists Elevate Cell Surface Populations of Receptor Protein and Exacerbate TRPV1-Mediated Toxicities in Human Lung Epithelial Cells", Toxicological Sciences 89(1), 278-286 (2006) (Advance Access publication Aug. 24, 2005).

Thomas, Karen C. et al., "Transient Receptor Potential Vanilloid 1 Agonists Cause Endoplasmic Reticulum Stress and Cell Death in Human Lung Cells," The Journal of Pharmacology and Experimental Therapeutics 321(3), 830-838 (2007).

Bolcskei, Kata et al., "Investigation of the role of TRPV1 receptors in acute and chronic nociceptive processes using gene-deficient mice," Pain 117, 368-376 (2005).

Helyes, Zsuzsanna et al., "Role of transient receptor potential vanilloid 1 receptors in endotoxin-induced airway inflammation in the mouse," Am J Physiol Lung Cell Mol Physiol. 292(5):L1173-81 (2007).

Banvolgyi, Agnes et al., "Evidence for a novel protective role of the vanilloid TRPV1 receptor in a cutaneous contact allergic dermatitis model," J Neuroimmunol. 169, 86-96 (2005).

Trevisani et al., "Antitussive activity of iodo-resiniferatoxin in guinea pigs," Thorax 59:769-772 (2004).

Garcia-Martinez et al., "Attenuation of thermal nociception and hyperalgesia by VR1 blockers," PNAS 99:2374-79 (2002).

Honore et al., "A-425619 [1-Isoquinolin-5-yl-3-(4-trifluoromethylbenzyl)-urea], a Novel Transient Receptor Potential Type V1 Receptor Antagonist, Relieves Pathophysiological Pain Associated with Inflammation and Tissue Injury in Rats," J. Pharmacol. Exp. Therap. 314:410-421 (2005).

Ghilardi et al., "Selective Blockade of the Capsaicin Receptor TRPV1 Attenuates Bone Cancer Pain," J. Neuroscience 25(12):3126-31 (2005).

Nagy et al., "The role of the vanilloid (capsaicin) receptor (TRPV1) in physiology and pathology," European J. Pharmacol. 500:351-369 (2004).

Xiang, et al., "Effects of airway inflammation on cough response in the guinea pig," J. Applied Physiol., 85:1847-54 (1998).

Sasaki et al., "Effect of NS-21, an Anticholinergic Drug with Calcium Antagonistic Activity, on Lower Urinary Tract Function in a Rat Model of Urinary Frequency," Int. J. Urol., 4:401-406 (1997).

* cited by examiner

BIARYL PIPERAZINYL-PYRIDINE ANALOGUES

CROSS-REFERENCE TO RELATED APPLICATION(S)

This application claims priority from U.S. Provisional Application Ser. No. 60/516,135, filed on Oct. 31, 2003 and U.S. Provisional Application Ser. No. 60/488,564, filed on Jul. 16, 2003.

FIELD OF THE INVENTION

This invention relates generally to biaryl piperazinyl-pyridine analogues, and to the use of such compounds for treating conditions related to capsaicin receptor activation. The invention further relates to the use such compounds as reagents for the identification of other agents that bind to capsaicin receptor, and as probes for the detection and localization of capsaicin receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain involves pain signal transmission in the absence of stimulus, and typically results from damage to the nervous system. In most instances, such pain is thought to occur because of sensitization in the peripheral and central nervous systems following initial damage to the peripheral system (e.g., via direct injury or systemic disease). Neuropathic pain is typically burning, shooting and unrelenting in its intensity and can sometimes be more debilitating that the initial injury or disease process that induced it.

Existing treatments for neuropathic pain are largely ineffective. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Topical treatment with capsaicin has been used to treat chronic and acute pain, including neuropathic pain. Capsaicin is a pungent substance derived from the plants of the Solanaceae family (which includes hot chili peppers) and appears to act selectively on the small diameter afferent nerve fibers (A-delta and C fibers) that are believed to mediate pain. The response to capsaicin is characterized by persistent activation of nociceptors in peripheral tissues, followed by eventual desensitization of peripheral nociceptors to one or more stimuli. From studies in animals, capsaicin appears to trigger C fiber membrane depolarization by opening cation selective channels for calcium and sodium.

Similar responses are also evoked by structural analogues of capsaicin that share a common vanilloid moiety. One such analogue is resiniferatoxin (RTX), a natural product of Euphorbia plants. The term vanilloid receptor (VR) was coined to describe the neuronal membrane recognition site for capsaicin and such related irritant compounds. The capsaicin response is competitively inhibited (and thereby antagonized) by another capsaicin analog, capsazepine, and is also inhibited by the non-selective cation channel blocker ruthenium red. These antagonists bind to VR with no more than moderate affinity (typically with $K_i$ values of no lower than 140 μM).

Rat and human vanilloid receptors have been cloned from dorsal root ganglion cells. The first type of vanilloid receptor to be identified is known as vanilloid receptor type I (VR1), and the terms "VR1" and "capsaicin receptor" are used interchangeably herein to refer to rat and/or human receptors of this type, as well as mammalian homologues. The role of VR1 in pain sensation has been confirmed using mice lacking this receptor, which exhibit no vanilloid-evoked pain behavior, and impaired responses to heat and inflammation. VR1 is a nonselective cation channel with a threshold for opening that is lowered in response to elevated temperatures, low pH, and capsaicin receptor agonists. For example, the channel usually opens at temperatures higher than about 45° C. Opening of the capsaicin receptor channel is generally followed by the release of inflammatory peptides from neurons expressing the receptor and other nearby neurons, increasing the pain response. After initial activation by capsaicin, the capsaicin receptor undergoes a rapid desensitization via phosphorylation by cAMP-dependent protein kinase.

Because of their ability to desensitize nociceptors in peripheral tissues, VR1 agonist vanilloid compounds have been used as topical anesthetics. However, agonist application may itself cause burning pain, which limits this therapeutic use. Recently, it has been reported that VR1 antagonists, including nonvanilloid compounds, are also useful for the treatment of pain (see PCT International Application Publication Number WO 02/08221, which published Jan. 31, 2002).

Thus, compounds that interact with VR1, but do not elicit the initial painful sensation of VR1 agonist vanilloid compounds, are desirable for the treatment of chronic and acute pain, including neuropathic pain. Antagonists of this receptor are particularly desirable for the treatment of pain, as well as conditions such as tear gas exposure, itch and urinary tract conditions such as urinary incontinence and overactive bladder. The present invention fulfills this need, and provides further related advantages.

SUMMARY OF THE INVENTION

The present invention provides biaryl piperazinyl-pyridine analogues of Formula I:

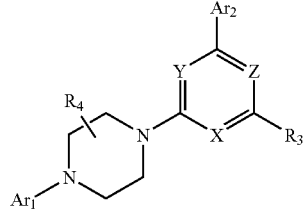

Formula I and pharmaceutically acceptable salts of such compounds. Within Formula I:

Ar$_1$ is phenyl or a 6-membered aromatic heterocycle, each of which is substituted with from 0 to 4 substituents (or more preferably 1 to 4 substituents) independently chosen from R$_1$;

Ar$_2$ is phenyl or a 6-membered aromatic heterocycle, each of which is substituted with from 0 to 4 substituents independently chosen from R$_2$;

X, Y and Z are independently CR$_x$ or N, such that at least one of X, Y and Z is N;

R$_x$ is independently chosen at each occurrence from hydrogen, C$_1$-C$_4$alkyl, amino, cyano and mono- and di-(C$_1$-C$_4$alkyl)amino;

Each R$_1$ is independently halogen, hydroxy, amino, cyano, C$_1$-C$_6$alkyl, C$_2$-C$_6$alkenyl, C$_2$-C$_6$alkynyl, C$_1$-C$_6$alkoxy, C$_2$-C$_6$alkyl ether, C$_2$-C$_6$alkanoyl, C$_3$-C$_6$alkanone, C$_1$-C$_6$haloalkyl, C$_1$-C$_6$haloalkoxy, mono- or di-(C$_1$-C$_6$alkyl)amino, C$_1$-C$_6$alkylsulfonyl, mono- or di-(C$_1$-C$_6$alkyl)sulfonamido or mono- or di-(C$_1$-C$_6$alkyl)aminocarbonyl;

Each R$_2$ is:
(a) independently chosen from (i) hydroxy, amino, cyano, halogen, —COOH, —SO$_2$NH$_2$, nitro and aminocarbonyl; and (ii) C$_1$-C$_6$alkyl, C$_2$-C$_6$alkenyl, C$_2$-C$_6$alkynyl, (C$_3$-C$_8$cycloalkyl)C$_0$-C$_4$alkyl, C$_1$-C$_6$haloalkyl, C$_1$-C$_6$alkoxy, C$_1$-C$_6$alkylthio, C$_2$-C$_6$alkyl ether, C$_2$-C$_6$alkanoyl, C$_1$-C$_6$alkoxycarbonyl, C$_2$-C$_6$alkanoyloxy, C$_3$-C$_6$alkanone, mono- and di-(C$_1$-C$_6$alkyl)aminoC$_0$-C$_6$alkyl, mono- and di-(C$_3$-C$_8$cycloalkyl)aminoC$_0$-C$_4$alkyl, (4- to 7-membered heterocycloalkyl)C$_0$-C$_4$alkyl, C$_1$-C$_6$alkylsulfonyl, mono- and di-(C$_1$-C$_6$alkyl)sulfonamido, and mono- and di-(C$_1$-C$_6$alkyl)aminocarbonyl, each of which is substituted with from 0 to 4 substituents independently chosen from halogen, hydroxy, cyano, amino, —COOH and oxo; or
(b) taken together with an adjacent R$_2$ to form a fused 5- to 13-membered carbocyclic or heterocyclic group that is substituted with from 0 to 3 substituents independently chosen from halogen, oxo and C$_1$-C$_6$alkyl;

R$_3$ is selected from:
(i) hydrogen and halogen;
(ii) C$_1$-C$_6$alkyl, (C$_3$-C$_8$cycloalkyl)C$_0$-C$_2$alkyl, C$_1$-C$_6$haloalkyl and phenylC$_0$-C$_2$alkyl; and
(iii) groups of the formula:

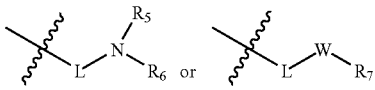

wherein:
L is C$_0$-C$_6$alkyl or C$_1$-C$_6$alkyl that is taken together with R$_5$, R$_6$ or R$_7$ to form a 4- to 7-membered carbocycle or heterocycle;

W is O, CO, S, SO or SO$_2$;

R$_5$ and R$_6$ are:
(a) independently chosen from hydrogen, C$_1$-C$_{12}$alkyl, C$_2$-C$_{12}$alkenyl, C$_2$-C$_{12}$alkynyl, (C$_3$-C$_8$cycloalkyl)C$_0$-C$_4$alkyl, C$_2$-C$_6$alkanoyl, C$_1$-C$_6$alkylsulfonyl, phenylC$_0$-C$_6$alkyl, (4- to 7-membered heterocycle)C$_0$-C$_6$alkyl and groups that are joined to L to form a 4- to 7-membered heterocycle; or
(b) joined to form a 4- to 12-membered heterocycle; and R$_7$ is hydrogen, C$_1$-C$_{12}$alkyl, C$_2$-C$_{12}$alkenyl, C$_2$-C$_{12}$alkynyl, (C$_3$-C$_8$cycloalkyl)C$_0$-C$_4$alkyl, C$_2$-C$_6$alkanoyl, phenylC$_0$-C$_6$alkyl, (4- to 7-membered heterocycle)C$_0$-C$_6$alkyl or a group that is joined to L to form a 4- to 7-membered carbocycle or heterocycle;

wherein each of (ii) and (iii) is substituted with from 0 to 4 substituents independently chosen from:
(1) halogen, hydroxy, amino, cyano, —COOH, —SO$_2$NH$_2$, oxo, nitro and aminocarbonyl; and
(2) C$_1$-C$_6$alkyl, C$_3$-C$_8$cycloalkyl, C$_1$-C$_6$alkoxy, C$_1$-C$_6$haloalkyl, C$_1$-C$_6$alkanoyl, C$_2$-C$_6$alkanoylamino, mono- and di-(C$_1$-C$_6$alkyl)aminoC$_0$-C$_4$alkyl, C$_1$-C$_6$alkylsulfonyl, mono- and di-(C$_1$-C$_6$alkyl)sulfonamido, mono- and di-(C$_1$-C$_6$alkyl)aminocarbonylC$_0$-C$_4$alkyl, phenylC$_0$-C$_4$alkyl and (4- to 7-membered heterocycle)C$_0$-C$_4$alkyl, each of which is substituted with from 0 to 4 secondary substituents independently chosen from halogen, hydroxy, cyano, oxo, imino, C$_0$-C$_4$alkyl, C$_1$-C$_4$alkoxy and C$_0$-C$_4$haloalkyl; and R$_4$ represents from 0 to 2 substituents independently chosen from C$_1$-C$_3$alkyl, C$_1$-C$_3$haloalkyl and oxo.

Within certain aspects, biaryl piperazinyl-pyridine analogues and pharmaceutically acceptable salts thereof provided herein are VR1 modulators and exhibit a K$_i$ of no greater than 1 micromolar, 100 nanomolar, 50 nanomolar, 10 nanomolar or 1 nanomolar in a capsaicin receptor binding assay and/or have an EC$_{50}$ or IC$_{50}$ value of no greater than 1 micromolar, 100 nanomolar, 50 nanomolar, 10 nanomolar or 1 nanomolar in an assay for determination of capsaicin receptor agonist or antagonist activity.

In certain embodiments, VR1 modulators as described herein are VR1 antagonists and exhibit no detectable agonist activity in an in vitro assay of capsaicin receptor activation at a concentration of compound equal to the IC$_{50}$.

Within certain aspects, compounds provided herein are labeled with a detectable marker (e.g., radiolabeled or fluorescein conjugated).

The present invention further provides, within other aspects, pharmaceutical compositions comprising at least one compound as provided herein or a pharmaceutically acceptable salt thereof in combination with a physiologically acceptable carrier or excipient.

Within further aspects, methods are provided for reducing calcium conductance of a cellular capsaicin receptor, comprising contacting a cell (e.g., neuronal) expressing a capsaicin receptor with a therapeutically effective amount of at least one VR1 modulator as described herein. Such contact may occur in vivo or in vitro.

Methods are further provided for inhibiting binding of vanilloid ligand to a capsaicin receptor. Within certain such aspects, the inhibition takes place in vitro. Such methods comprise contacting a capsaicin receptor with at least one VR1 modulator as described herein, under conditions and in an amount sufficient to detectably inhibit vanilloid ligand binding to the capsaicin receptor. Within other such aspects, the capsaicin receptor is in a patient. Such methods comprise contacting cells expressing a capsaicin receptor in a patient with at least one VR1 modulator as described herein in an amount sufficient to detectably inhibit vanilloid ligand binding to cells expressing a cloned capsaicin receptor in vitro, and thereby inhibiting binding of vanilloid ligand to the capsaicin receptor in the patient.

The present invention further provides methods for treating a condition responsive to capsaicin receptor modulation in a patient, comprising administering to the patient a therapeutically effective amount of at least one VR1 modulator as described herein.

Within other aspects, methods are provided for treating pain in a patient, comprising administering to a patient suffering from pain a therapeutically effective amount of at least one VR1 modulator as described herein.

Methods are further provided for treating itch, urinary incontinence, overactive bladder, cough and/or hiccup in a patient, comprising administering to a patient suffering from one or more of the foregoing conditions a therapeutically effective amount of at least one VR1 modulator as described herein.

The present invention further provides methods for promoting weight loss in an obese patient, comprising administering to an obese patient a therapeutically effective amount of at least one VR1 modulator as described herein.

Methods are further provided for identifying an agent that binds to capsaicin receptor, comprising: (a) contacting capsaicin receptor with a labeled VR1 modulator as described herein under conditions that permit binding of the VR1 modulator to capsaicin receptor, thereby generating bound, labeled VR1 modulator; (b) detecting a signal that corresponds to the amount of bound, labeled VR1 modulator in the absence of test agent; (c) contacting the bound, labeled VR1 modulator with a test agent; (d) detecting a signal that corresponds to the amount of bound labeled VR1 modulator in the presence of test agent; and (e) detecting a decrease in signal detected in step (d), as compared to the signal detected in step (b), and therefrom identifying an agent that binds to capsaicin receptor.

Within further aspects, the present invention provides methods for determining the presence or absence of capsaicin receptor in a sample, comprising: (a) contacting a sample with a VR1 modulator as described herein under conditions that permit binding of the VR1 modulator to capsaicin receptor; and (b) detecting a level of the VR1 modulator bound to capsaicin receptor.

The present invention also provides packaged pharmaceutical preparations, comprising: (a) a pharmaceutical composition as described herein in a container; and (b) instructions for using the composition to treat one or more conditions responsive to capsaicin receptor modulation, such as pain, itch, urinary incontinence, overactive bladder, cough, hiccup and/or obesity.

In yet another aspect, the invention provides methods of preparing the compounds disclosed herein, including the intermediates.

These and other aspects of the present invention will become apparent upon reference to the following detailed description.

DETAILED DESCRIPTION

As noted above, the present invention provides biaryl piperazinyl-pyridine analogues. Such compounds may be used in vitro or in vivo, to modulate capsaicin receptor activity in a variety of contexts.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E- forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$, X, $Ar_2$). Unless otherwise specified, each variable within such a formula is defined independently of any other variable, and any variable that occurs more than one time in a formula is defined independently at each occurrence.

The term "biaryl piperazinyl-pyridine analogue," as used herein, encompasses all compounds of Formula I, as well as compounds of other Formulas provided herein (including any enantiomers, racemates and stereoisomers) and pharmaceutically acceptable salts of such compounds. In other words, compounds in which the core ring

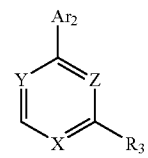

is pyridyl, pyrimidyl or triazinyl (e.g.,

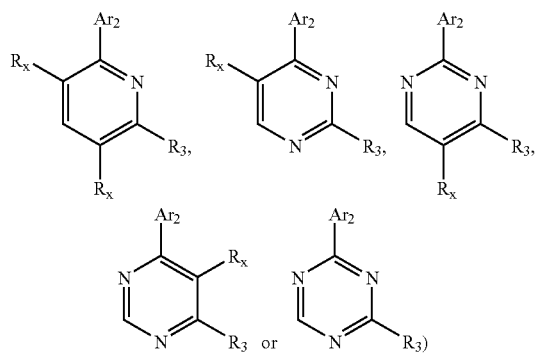

are specifically included within the definition of biaryl piperazinyl-pyridine analogues.

A "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

It will be apparent that each compound of Formula I may, but need not, be formulated as a hydrate, solvate or noncovalent complex. In addition, the various crystal forms and polymorphs are within the scope of the present invention. Also provided herein are prodrugs of the compounds of Formula I. A "prodrug" is a compound that may not fully satisfy the structural requirements of the compounds provided herein, but is modified in vivo, following administration to a patient, to produce a compound of Formula I, or other formula provided herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved in vivo to yield the parent compounds.

As used herein, the term "alkyl" refers to a straight or branched chain saturated aliphatic hydrocarbon. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. "$C_0$-$C_4$alkyl" refers to a single covalent bond or a $C_1$-$C_4$alkyl group; "$C_0$-$C_8$alkyl" refers to a single covalent bond or a $C_1$-$C_8$alkyl group. The term "hydroxyalkyl" refers to an alkyl group substituted with at least one hydroxy substituent.

Similarly, "alkenyl" refers to straight or branched chain alkene groups. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively.

A "cycloalkyl" is a saturated or partially saturated cyclic group in which all ring members are carbon, such as cyclopropyl, cyclobutyl, cyclopentyl and cyclohexyl. Certain cycloalkyl groups are $C_3$-$C_8$cycloalkyl, in which the ring contains from 3 to 8 ring members, all of which are carbon. A "($C_3$-$C_8$cycloalkyl)$C_0$-$C_4$alkyl" is a $C_3$-$C_8$cycloalkyl group linked via a single covalent bond or a $C_1$-$C_4$alkyl group.

By "alkoxy," as used herein, is meant an alkyl group as described above attached via an oxygen bridge. Alkoxy groups include $C_1$-$C_6$alkoxy and $C_1$-$C_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups.

Similarly, "alkylthio" refers to an alkyl group as described above attached via a sulfur bridge. Preferred alkoxy and alkylthio groups are those in which an alkyl group is attached via the heteroatom bridge.

The term "oxo," as used herein, refers to a keto (C=O) group. An oxo group that is a substituent of a nonaromatic carbon atom results in a conversion of —$CH_2$— to —C(=O)—.

Similarly, an "imino" refers to a group of the formula C=N. The term "iminoalkyl" refers to an alkyl group as described above substituted with an imine (e.g., a group of the formula

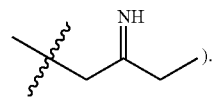

).

The term "alkanoyl" refers to an acyl group in a linear or branched arrangement (e.g., —(C=O)-alkyl), where attachment is through the carbon of the keto group. Alkanoyl groups include $C_2$-$C_8$alkanoyl, $C_2$-$C_6$alkanoyl and $C_2$-$C_4$alkanoyl groups, which have from 2 to 8, 2 to 6 or 2 to 4 carbon atoms, respectively. "$C_1$alkanoyl" refers to —(C=O)—H, which (along with $C_2$-$C_8$alkanoyl) is encompassed by the term "$C_1$-$C_8$alkanoyl." Ethanoyl is $C_2$alkanoyl.

An "alkanone" is a ketone group in which carbon atoms are in a linear or branched alkyl arrangement. "$C_3$-$C_8$alkanone," "$C_3$-$C_6$alkanone" and "$C_3$-$C_4$alkanone" refer to an alkanone having from 3 to 8, 6 or 4 carbon atoms, respectively. By way of example, a $C_3$ alkanone group has the structure —$CH_2$—(C=O)—$CH_3$.

Similarly, "alkyl ether" refers to a linear or branched ether substituent. Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. By way of example, a $C_2$ alkyl ether group has the structure —$CH_2$—O—$CH_3$.

The term "alkoxycarbonyl" refers to an alkoxy group linked via a carbonyl (i.e., a group having the general structure —C(=O)—alkyl). Alkoxycarbonyl groups include $C_2$-$C_8$, $C_2$-$C_6$ and $C_2$-$C_4$alkoxycarbonyl groups, which have from 2 to 8, 6 or 4 carbon atoms, respectively. "$C_1$alkoxycarbonyl" refers to —C(=O)—OH, which is encompassed by the term "$C_1$-$C_8$alkoxycarbonyl."

"Alkanoyloxy," as used herein, refers to an alkanoyl group linked via an oxygen bridge (i.e., a group having the general structure —O—C(=O)alkyl). Alkanoyloxy groups include $C_2$-$C_8$, $C_2$-$C_6$ and $C_2$-$C_4$alkanoyloxy groups, which have from 2 to 8, 6 or 4 carbon atoms, respectively.

Similarly, "alkanoylamino," as used herein, refers to an alkanoyl group linked via a nitrogen bridge (i.e., a group having the general structure —N—C(=O)alkyl). Alkanoyloxy groups include $C_2$-$C_8$, $C_2$-$C_6$ and $C_2$-$C_4$alkanoyloxy groups, which have from 2 to 8, 6 or 4 carbon atoms, respectively.

"Alkylsulfonyl" refers to groups of the formula —$SO_2$-alkyl, in which the sulfur atom is the point of attachment. Alkylsulfonyl groups include $C_1$-$C_6$alkylsulfonyl and $C_1$-$C_4$alkylsulfonyl groups, which have from 1 to 6 or 1 to 4 carbon atoms, respectively. Methylsulfonyl is one representative alkylsulfonyl group. "$C_1$-$C_4$haloalkylsulfonyl" is an alkylsulfonyl group of from 1 to 4 carbon atoms that is substituted with at least one halogen (e.g., trifluoromethylsulfonyl).

"Alkylsulfonylamino" refers to groups of the formula —NH—($SO_2$)-alkyl, in which the nitrogen atom is the point of attachment. Alkylsulfonylamino groups include $C_1$-$C_6$alkylsulfonylamino and $C_1$-$C_4$alkylsulfonylamino groups, which have from 1 to 6 or 1 to 4 carbon atoms, respectively. Methylsulfonylamino is a representative alkylsulfonylamino group.

"Alkylsulfonamido" refers to groups of the formula —($SO_2$)—N(R)$_2$, in which the sulfur atom is the point of attachment and each R is independently hydrogen or alkyl. The term "mono- or di-($C_1$-$C_6$alkyl)sulfonamido" refers to such groups in which one R is $C_1$-$C_6$alkyl and the other R is hydrogen or an independently chosen $C_1$-$C_6$alkyl.

"Alkylamino" refers to a secondary or tertiary amine having the general structure —NH-alkyl or —N(alkyl)(alkyl), wherein each alkyl may be the same or different. Such groups include, for example, mono- and di-($C_1$-$C_8$alkyl)amino groups, in which each alkyl may be the same or different and may contain from 1 to 8 carbon atoms, as well as mono- and di-($C_1$-$C_6$alkyl)amino groups and mono- and di-($C_1$-$C_4$alkyl) amino groups.

"Alkylaminoalkyl" refers to an alkylamino group linked via an alkyl group (i.e., a group having the general structure -alkyl-NH-alkyl or -alkyl-N(alkyl)(alkyl)) in which each alkyl is selected independently. Such groups include, for example, mono- and di-($C_1$-$C_8$alkyl)amino$C_1$-$C_8$alkyl, mono- and di-($C_1$-$C_6$alkyl)amino$C_1$-$C_6$alkyl and mono- and di-($C_1$-$C_6$alkyl)amino$C_1$-$C_4$alkyl, in which each alkyl may be the same or different. "Mono- or di-($C_1$-$C_6$alkyl)amino$C_0$-$C_6$alkyl" refers to a mono- or di-($C_1$-$C_6$alkyl)amino group linked via a direct bond or a $C_1$-$C_6$alkyl group. The following are representative alkylaminoalkyl groups:

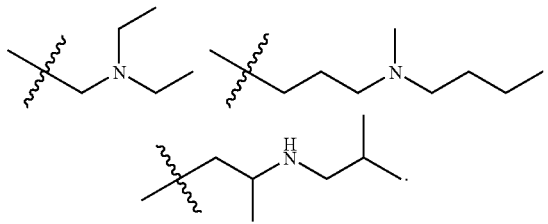

Similarly, "alkylaminoalkoxy" refers to an alkylamino group linked via an alkoxy group (i.e., a group having the general structure —O-alkyl-NH-alkyl or —O-alkyl-N(alkyl)(alkyl)) in which each alkyl is selected independently. Such groups include, for example, mono- and di-($C_1$-$C_6$alkyl)amino$C_1$-$C_4$alkoxy groups, such as

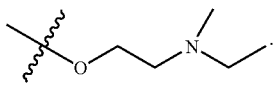

The term "aminocarbonyl" refers to an amide group (i.e., —(C=O)$NH_2$). "Mono- or di-($C_1$-$C_6$alkyl)aminocarbonyl$C_0$-$C_4$alkyl" is an aminocarbonyl group in which one or both of the hydrogen atoms is replaced with $C_1$-$C_6$alkyl, and which is linked via a single covalent bond (i.e., mono- or di-($C_1$-$C_6$alkyl)aminocarbonyl) or a $C_1$-$C_4$alkylene group (i.e., -($C_0$-$C_4$alkyl)-(C=O)N($C_1$-$C_8$alkyl)$_2$). If both hydrogen atoms are so replaced, the $C_1$-$C_6$alkyl groups may be the same or different.

The term "halogen" refers to fluorine, chlorine, bromine or iodine.

A "haloalkyl" is a branched, straight-chain or cyclic alkyl group, substituted with 1 or more halogen atoms (e.g., "$C_1$-$C_8$haloalkyl" groups have from 1 to 8 carbon atoms; "$C_1$-$C_6$haloalkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. The term "haloalkoxy" refers to a haloalkyl group as defined above attached via an oxygen bridge. "$C_1$-$C_8$haloalkoxy" groups have 1 to 8 carbon atoms.

A dash ("-") that is not between two letters or symbols is used to indicate a point of attachment for a substituent. For example, —$CONH_2$ is attached through the carbon atom.

A "heteroatom," as used herein, is oxygen, sulfur or nitrogen.

A "carbocycle" or "carbocyclic group" comprises at least one ring formed entirely by carbon-carbon bonds (referred to herein as a carbocyclic ring), and does not contain a heterocyclic ring. Unless otherwise specified, each carbocyclic ring within a carbocycle may be saturated, partially saturated or aromatic. A carbocycle generally has from 1 to 3 fused, pendant or spiro rings; carbocycles within certain embodiments have one ring or two fused rings. Typically, each ring contains from 3 to 8 ring members (i.e., $C_3$-$C_8$); $C_5$-$C_7$ rings are recited in certain embodiments. Carbocycles comprising fused, pendant or spiro rings typically contain from 9 to 14 ring members. Certain representative carbocycles are cycloalkyl (i.e., groups that comprise saturated and/or partially saturated rings, such as cyclopropyl, cyclobutyl, cyclopentyl, cyclohexyl, cycloheptyl, cyclooctyl, adamantyl, decahydro-naphthalenyl, octahydro-indenyl, and partially saturated variants of any of the foregoing, such as cyclohexenyl). Other carbocycles are aryl (i.e., contain at least one aromatic carbocyclic ring). Such carbocycles include, for example, phenyl, naphthyl, fluorenyl, indanyl and 1,2,3,4-tetrahydro-naphthyl.

Certain carbocycles recited herein are $C_6$-$C_{10}$aryl$C_0$-$C_8$alkyl groups (i.e., groups in which a carbocyclic group comprising at least one aromatic ring is linked via a direct bond or a $C_1$-$C_8$alkyl group). Such groups include, for example, phenyl and indanyl, as well as groups in which either of the foregoing is linked via $C_1$-$C_6$alkyl, preferably via $C_1$-$C_4$alkyl. Phenyl groups linked via a direct bond or $C_1$-$C_6$alkyl alkyl group are designated phenyl$C_0$-$C_6$alkyl (e.g., benzyl, 1-phenyl-ethyl, 1-phenyl-propyl and 2-phenyl-ethyl).

A "heterocycle" or "heterocyclic group" has from 1 to 3 fused, pendant or spiro rings, at least one of which is a heterocyclic ring (i.e., one or more ring atoms is a heteroatom, with the remaining ring atoms being carbon). Typically, a heterocyclic ring comprises 1, 2, 3 or 4 heteroatoms; within certain embodiments each heterocyclic ring has 1 or 2 heteroatoms per ring. Each heterocyclic ring generally contains from 3 to 8 ring members (rings having from 4 or 5 to 7 ring members are recited in certain embodiments) and heterocycles comprising fused, pendant or spiro rings typically contain from 9 to 14 ring members., Certain heterocycles comprise a sulfur atom as a ring member; in certain embodiments, the sulfur atom is oxidized to SO or $SO_2$. Heterocycles may be optionally substituted with a variety of substituents, as indicated. Unless otherwise specified, a heterocycle may be a heterocycloalkyl group (i.e., each ring is saturated or partially saturated) or a heteroaryl group (i.e., at least one ring within the group is aromatic).

A heterocyclic group may generally be linked via any ring or substituent atom, provided that a stable compound results. N-linked heterocyclic groups are linked via a ring nitrogen atom.

Heterocyclic groups include, for example, acridinyl, azepanyl, azocinyl, benzimidazolyl, benzimidazolinyl, benzisothiazolyl, benzisoxazolyl, benzofuranyl, benzothiofuranyl, benzothiophenyl, benzoxazolyl, benzothiazolyl, benzotriazolylcarbazolyl, benztetrazolyl, NH-carbazolyl, carbolinyl, chromanyl, chromenyl, cinnolinyl, decahydroquinolinyl, dihydrofuro[2,3-b]tetrahydrofuran, dihydroisoquinolinyl, dihydrotetrahydrofuranyl, 1,4-dioxa-8-aza-spiro[4.5]dec-8-yl, dithiazinyl, furanyl, furazanyl, imidazolinyl, imidazolidinyl, imidazolyl, indazolyl, indolenyl, indolinyl, indolizinyl, indolyl, isobenzofuranyl, isochromanyl, isoindazolyl, isoindolinyl, isoindolyl, isothiazolyl, isoxazolyl, isoquinolinyl, morpholinyl, naphthyridinyl, octahydroisoquinolinyl, oxadiazolyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, piperidinyl, piperidonyl, pteridinyl, purinyl, pyranyl, pyrazinyl, pyrazolidinyl, pyrazolinyl, pyrazolyl, pyridazinyl, pyridoimidazolyl, pyridooxazolyl, pyridothiazolyl, pyridyl, pyrimidyl, pyrrolidinyl, pyrrolidonyl, pyrrolinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienothiazolyl, thienooxazolyl, thienoimidazolyl, thienyl, thiophenyl, thiomorpholinyl and variants thereof in which the sulfur atom is oxidized, triazinyl, xanthenyl and any of the foregoing that are substituted with from 1 to 4 substituents as described above.

A "heterocycle$C_0$-$C_8$alkyl" is a heterocyclic group linked via a single covalent bond or $C_1$-$C_8$alkyl group. A (4- to 7-membered heterocycle)$C_0$-$C_8$alkyl is a heterocyclic group having from 4 to 7 ring members linked via a direct bond or an alkyl group having from 1 to 8 carbon atoms. A "(6-membered heteroaryl)$C_0$-$C_6$alkyl" refers to a heteroaryl group linked via a direct bond or $C_1$-$C_6$alkyl group.

Certain heterocycles are 4- to 12-membered, 5- to 10-membered, 3- to 7-membered, 4- to 7-membered or 5- to 7-membered groups that contain 1 heterocyclic ring or 2 fused, pendant or spiro rings, optionally substituted. 4- to 10-membered heterocycloalkyl groups include, for example, piperidinyl, piperazinyl, pyrrolidinyl, azepanyl, 1,4-dioxa-8-aza-spiro[4.5]dec-8-yl, morpholino, thiomorpholino and 1,1-dioxo-thiomorpholin-4-yl. Such groups may be substituted as indicated. Representative aromatic heterocycles are azocinyl, pyridyl, pyrimidyl, imidazolyl, tetrazolyl and 3,4-dihydro-1H-isoquinolin-2-yl.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, $C_1$-$C_8$haloalkyl, $C_1$-$C_8$haloalkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

The terms "VR1" and "capsaicin receptor" are used interchangeably herein to refer to a type 1 vanilloid receptor. Unless otherwise specified, these terms encompass both rat and human VR1 receptors (e.g., GenBank Accession Numbers AF327067, AJ277028 and NM_018727; sequences of certain human VR1 cDNAs are provided in SEQ ID NOs: 1-3, and the encoded amino acid sequences shown in SEQ ID NOs:4 and 5, of U.S. Pat. No. 6,482,611), as well as homologues thereof found in other species.

A "VR1 modulator," also referred to herein as a "modulator," is a compound that modulates VR1 activation and/or VR1-mediated signal transduction. VR1 modulators specifically provided herein are compounds of Formula I and pharmaceutically acceptable salts of compounds of Formula I. A VR1 modulator may be a VR1 agonist or antagonist. A modulator binds with "high affinity" if the $K_i$ at VR1 is less than 1 micromolar, preferably less than 100 nanomolar, 10 nanomolar or 1 nanomolar. A representative assay for determining $K_i$ at VR1 is provided in Example 5, herein.

A modulator is considered an "antagonist" if it detectably inhibits vanilloid ligand binding to VR1 and/or VR1-mediated signal transduction (using, for example, the representative assay provided in Example 6); in general, such an antagonist inhibits VR1 activation with a IC$_{50}$ value of less than 1 micromolar, preferably less than 100 nanomolar, and more preferably less than 10 nanomolar or 1 nanomolar within the assay provided in Example 6. VR1 antagonists include neutral antagonists and inverse agonists. In certain embodiments, capsaicin receptor antagonists provided herein are not vanilloids.

An "inverse agonist" of VR1 is a compound that reduces the activity of VR1 below its basal activity level in the absence of added vanilloid ligand. Inverse agonists of VR1 may also inhibit the activity of vanilloid ligand at VR1, and/or may also inhibit binding of vanilloid ligand to VR1. The ability of a compound to inhibit the binding of vanilloid ligand to VR1 may be measured by a binding assay, such as the binding assay given in Example 5. The basal activity of VR1, as well as the reduction in VR1 activity due to the presence of VR1 antagonist, may be determined from a calcium mobilization assay, such as the assay of Example 6.

A "neutral antagonist" of VR1 is a compound that inhibits the activity of vanilloid ligand at VR1, but does not significantly change the basal activity of the receptor (i.e., within a calcium mobilization assay as described in Example 6 performed in the absence of vanilloid ligand, VR1 activity is reduced by no more than 10%, more preferably by no more than 5%, and even more preferably by no more than 2%; most preferably, there is no detectable reduction in activity). Neutral antagonists of VR1 may inhibit the binding of vanilloid ligand to VR1.

As used herein a "capsaicin receptor agonist" or "VR1 agonist" is a compound that elevates the activity of the receptor above the basal activity level of the receptor (i.e., enhances VR1 activation and/or VR1-mediated signal transduction). Capsaicin receptor agonist activity may be identified using the representative assay provided in Example 6. In general, such an agonist has an $EC_{50}$ value of less than 1 micromolar, preferably less than 100 nanomolar, and more preferably less than 10 nanomolar within the assay provided in Example 6. In certain embodiments, capsaicin receptor agonists provided herein are not vanilloids.

A "vanilloid" is capsaicin or any capsaicin analogue that comprises a phenyl ring with two oxygen atoms bound to adjacent ring carbon atoms (one of which carbon atom is located para to the point of attachment of a third moiety that is bound to the phenyl ring). A vanilloid is a "vanilloid ligand" if it binds to VR1 with a $K_i$ (determined as described herein) that is no greater than 10 μM. Vanilloid ligand agonists include capsaicin, olvanil, N-arachidonoyl-dopamine and resiniferatoxin (RTX). Vanilloid ligand antagonists include capsazepine and iodo-resiniferatoxin.

A "therapeutically effective amount" (or dose) is an amount that, upon administration to a patient, results in a discernible patient benefit (e.g., provides detectable relief from a condition being treated). Such relief may be detected using any appropriate criteria, including alleviation of one or more symptoms such as pain. A therapeutically effective amount or dose generally results in a concentration of compound in a body fluid (such as blood, plasma, serum, CSF, synovial fluid, lymph, cellular interstitial fluid, tears or urine) that is sufficient to alter the binding of vanilloid ligand to VR1 in vitro (using the assay provided in Example 5) and/or VR1-mediated signal transduction (using an assay provided in Example 6).

A "patient" is any individual treated with a VR1 modulator as provided herein. Patients include humans, as well as other animals such as companion animals (e.g., dogs and cats) and livestock. Patients may be experiencing one or more symptoms of a condition responsive to capsaicin receptor modulation (e.g., pain, exposure to vanilloid ligand, itch, urinary incontinence, overactive bladder, respiratory disorders, cough and/or hiccup), or may be free of such symptom(s) (i.e., treatment may be prophylactic).

Biaryl Piperazinyl-Pyridine Analogues

As noted above, the present invention provides biaryl piperazinyl-pyridine analogues of Formula I and pharmaceutically acceptable salts of such compounds. Within certain aspects, such compounds are VR1 modulators that may be used in a variety of contexts, including in the treatment of pain (e.g., neuropathic or peripheral nerve-mediated pain); exposure to capsaicin; exposure to acid, heat, light, tear gas air pollutants, pepper spray or related agents; respiratory conditions such as asthma or chronic obstructive pulmonary disease; itch; urinary incontinence or overactive bladder; cough or hiccup; and/or obesity. VR1 modulators may also be used within in vitro assays (e.g., assays for receptor activity), as probes for detection and localization of VR1 and as standards in ligand binding and VR1-mediated signal transduction assays.

In general, VR1 modulators provided detectably modulate the binding of capsaicin to VR1 at nanomolar (i.e., submicromolar) concentrations, preferably at subnanomolar concentrations, more preferably at concentrations below 100 picomolar, 20 picomolar, 10 picomolar or 5 picomolar. Such modulators are preferably not vanilloids. Certain preferred modulators are VR1 antagonists and have no detectable agonist activity in the assay described in Example 6. Preferred VR1 modulators further bind with high affinity to VR1.

Within certain aspects, compounds provided herein are biaryl piperazinyl-pyridine analogues of Formula Ia:

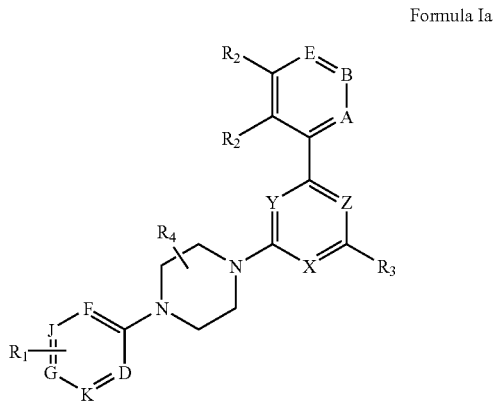

Formula Ia as well as pharmaceutically acceptable salts thereof. Within Formula Ia:

A, B and E are independently CH, $CR_{2a}$ or N, such that at least one of A, B and E is CH or $CR_{2a}$, preferably at least one of A, B and E is $CR_{2a}$; and more preferably at least one of B and E is $CR_{2a}$;

D, F, G, J and K are independently N, CH or carbon substituted with $R_1$;

$R_1$ represents from 0 to 3 substituents independently chosen from halogen, hydroxy, amino, cyano, $C_1$-$C_6$alkyl, $C_2$-$C_6$alkenyl, $C_2$-$C_6$alkynyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)sulfonamido or mono- or di-($C_1$-$C_6$alkyl)aminocarbonyl;

Each $R_2$ is independently CH or $CR_{2a}$;

Each $R_{2a}$ is:

(a) independently chosen from (i) hydroxy, amino, cyano, halogen, —COOH, —$SO_2NH_2$, nitro and aminocarbonyl; and (ii) $C_1$-$C_6$alkyl, $C_2$-$C_6$alkenyl, $C_2$-$C_6$alkynyl, ($C_3$-$C_8$cycloalkyl)$C_0$-$C_4$alkyl, $C_1$-$C_6$haloalkyl, $C_1$-$C_6$alkoxy, $C_1$-$C_6$alkylthio, $C_2$-$C_6$alkyl ether, $C_2$-$C_6$alkanoyl, $C_1$-$C_6$alkoxycarbonyl, $C_2$-$C_6$alkanoyloxy, $C_3$-$C_6$alkanone, mono- and di-($C_1$-$C_6$alkyl)amino$C_0$-$C_6$alkyl, mono- and di-($C_3$-$C_8$cycloalkyl)amino$C_0$-$C_4$alkyl, (4- to 7-membered heterocycloalkyl)$C_0$-$C_4$alkyl, $C_1$-$C_6$alkylsulfonyl, mono- and di-($C_1$-$C_6$alkyl)sulfonamido, and mono- and di-($C_1$-$C_6$alkyl)aminocarbonyl, each of which is substituted with from 0 to 4 substituents independently chosen from halogen, hydroxy, cyano, amino, —COOH and oxo; or (b) taken together with an adjacent $R_{2a}$ to form a fused 5- to 13-membered carbocyclic or heterocyclic group that is substituted with from 0 to 3 substituents independently chosen from halogen, oxo and $C_1$-$C_6$alkyl;

and the remaining variables are as described above for Formula I.

In certain embodiments, compounds provided herein satisfy one or more of Formulas II-IV, in which (unless otherwise specified) $R_4$, X, Y, and Z are as described for Formula I; $R_1$, A, B, E, D, F, J, K and G are as described for Formula Ia; and the remaining variables are as indicated below:

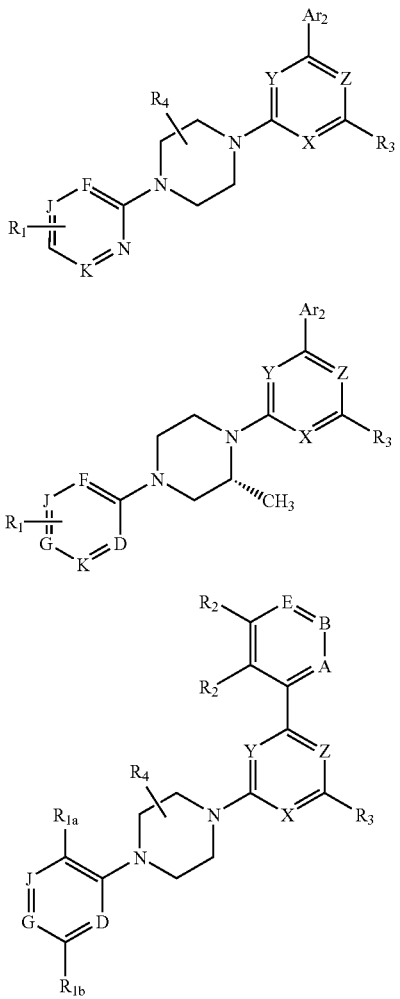

Formula II

Formula III

Formula IV

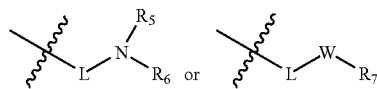

wherein:
L is $C_0$-$C_6$alkyl or $C_1$-$C_6$alkyl that is taken together with $R_5$, $R_6$ or $R_7$ to form a 4- to 7-membered carbocycle or heterocycle;

W is O, CO, S, SO or $SO_2$;

$R_5$ and $R_6$ are:
(a) independently chosen from hydrogen, $C_1$-$C_{12}$alkyl, $C_2$-$C_{12}$alkenyl, $C_2$-$C_{12}$alkynyl, ($C_3$-$C_8$cycloalkyl)$C_0$-$C_4$alkyl, $C_2$-$C_6$alkanoyl, $C_1$-$C_6$alkylsulfonyl, phenyl$C_0$-$C_6$alkyl, (4- to 7-membered heterocycle)$C_0$-$C_6$alkyl and groups that are joined to L to form a 4- to 7-membered heterocycle, such that if L is a single covalent bond then at least one of $R_5$ and $R_6$ is not hydrogen; or
(b) joined to form a 4- to 12-membered heterocycle; and $R_7$ is hydrogen, $C_1$-$C_{12}$alkyl, $C_2$-$C_{12}$alkenyl, $C_2$-$C_{12}$alkynyl, ($C_3$-$C_8$cycloalkyl)$C_0$-$C_4$alkyl, $C_2$-$C_6$alkanoyl, phenyl$C_0$-$C_6$alkyl, (4- to 7-membered heterocycle)$C_0$-$C_6$alkyl or a group that is joined to L to form a 4- to 7-membered carbocycle or heterocycle, such that if L is a single covalent bond, then $R_7$ is not hydrogen;

wherein each of (ii) and (iii) is substituted with from 0 to 4 substituents independently chosen from:
(I) halogen, hydroxy, amino, cyano, —COOH, —$SO_2NH_2$, oxo, nitro and aminocarbonyl; and
(2) $C_1$-$C_6$alkyl, $C_3$-$C_8$cycloalkyl, $C_1$-$C_6$alkoxy, $C_1$-$C_6$haloalkyl, $C_1$-$C_6$alkanoyl, mono- and di-($C_1$-$C_6$alkyl)amino$C_0$-$C_4$alkyl, $C_1$-$C_6$alkylsulfonyl, mono- and di-($C_1$-$C_6$alkyl)sulfonamido, $C_2$-$C_6$alkanoylamino, mono- and di-($C_1$-$C_6$alkyl)aminocarbonyl$C_0$-$C_4$alkyl, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, oxo, imino, $C_0$-$C_4$alkyl, $C_1$-$C_4$alkoxy and $C_1$-$C_4$haloalkyl; and Within Formula III, $Ar_2$ and $R_3$ are as described for Formula 1.

Within Formula IV:
A, B and E are independently CH, $CR_{2a}$ or N, such that at least one of B and E is $CR_{2a}$;

J, G and D are independently N or $CR_{1b}$;

$R_{1a}$ is halogen, hydroxy, amino, cyano, $C_1$-$C_6$alkyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)sulfonamido or mono- or di-($C_1$-$C_6$alkyl)aminocarbonyl;

Each $R_{1b}$ is independently hydrogen, halogen, hydroxy, amino, cyano, $C_1$-$C_6$alkyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)sulfonamido or mono- or di-($C_1$-$C_6$alkyl)aminocarbonyl;

Each $R_2$ is independently CH or $CR_{2a}$;

Each $R_{2a}$ is:
(a) independently chosen from (i) hydroxy, amino, cyano, halogen, —COOH, —$SO_2NH_2$ and nitro; and (ii)

Within Formula II:
$Ar_2$ is phenyl or a 6-membered aromatic heterocycle, each of which is substituted with from 0 to 4 substituents independently chosen from $R_2$;

Each $R_2$ is independently chosen from:
(a) hydroxy, amino, cyano, halogen, —COOH, —$SO_2NH_2$, nitro and aminocarbonyl; and
(b) $C_1$-$C_6$alkyl, $C_2$-$C_6$alkenyl, $C_2$-$C_6$alkynyl, ($C_3$-$C_8$cycloalkyl)$C_0$-$C_4$alkyl, $C_1$-$C_6$haloalkyl, $C_1$-$C_6$alkoxy, $C_1$-$C_6$alkylthio, $C_2$-$C_6$alkyl ether, $C_2$-$C_6$alkanoyl, $C_1$-$C_6$alkoxycarbonyl, $C_2$-$C_6$alkanoyloxy, $C_3$-$C_6$alkanone, mono- and di-($C_1$-$C_6$alkyl)amino$C_0$-$C_4$alkyl, (4- to 7-membered heterocycle)$C_0$-$C_4$alkyl, $C_1$-$C_6$alkylsulfonyl, mono- and di-($C_1$-$C_6$alkyl)sulfonamido, mono- and di-($C_3$-$C_8$cycloalkyl)amino$C_0$-$C_4$alkyl, and mono- and di-($C_1$-$C_6$alkyl)aminocarbonyl, each of which is substituted with from 0 to 4 substituents independently chosen from halogen, hydroxy, cyano, amino, —COOH and oxo; and $R_3$ is selected from:
(i) hydrogen and halogen;
(ii) phenyl$C_0$-$C_2$alkyl or ($C_4$-$C_7$cycloalkyl)$C_0$-$C_2$alkyl; and
(iii) groups of the formula:

C$_1$-C$_6$alkyl, (C$_3$-C$_8$cycloalkyl)C$_0$-C$_4$alkyl, C$_1$-C$_6$haloalkyl, C$_1$-C$_6$alkoxy, C$_1$-C$_6$alkylthio, C$_2$-C$_6$alkyl ether, C$_2$-C$_6$alkanoyl, C$_1$-C$_6$alkoxycarbonyl, C$_2$-C$_6$alkanoyloxy, C$_3$-C$_6$alkanone, mono- and di-(C$_1$-C$_6$alkyl)aminoC$_0$-C$_6$alkyl, mono- and di-(C$_3$-C$_8$cycloalkyl)aminoC$_0$-C$_4$alkyl, (4- to 7-membered heterocycle)C$_0$-C$_4$alkyl, C$_1$-C$_6$alkylsulfonyl, mono- and di-(C$_1$-C$_6$alkyl)sulfonamido, and mono- and di-(C$_1$-C$_6$alkyl)aminocarbonyl, each of which is substituted with from 0 to 4 substituents independently chosen from halogen, hydroxy, cyano, amino, —COOH and oxo; or (b) taken together with an adjacent R$_{2a}$ to form a fused 5- to 13-membered carbocyclic or heterocyclic group that is substituted with from 0 to 3 substituents independently chosen from halogen, oxo and C$_1$-C$_6$alkyl;

R$_3$ is selected from:
(i) hydrogen and halogen;
(ii) C$_1$-C$_6$alkyl, (C$_3$-C$_8$cycloalkyl)C$_0$-C$_2$alkyl, C$_1$-C$_6$haloalkyl and phenylC$_0$-C$_2$alkyl; and
(iii) groups of the formula:

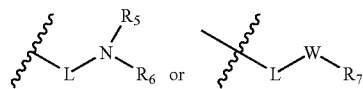

wherein:
L is C$_0$-C$_6$alkyl or C$_1$-C$_6$alkyl that is taken together with R$_5$, R$_6$ or R$_7$ to form a 4- to 7-membered heterocycle;
W is O, CO, S, SO or SO$_2$;
R$_5$ and R$_6$ are:
  (a) independently chosen from hydrogen, C$_1$-C$_{12}$alkyl, C$_2$-C$_{12}$alkenyl, (C$_3$-C$_8$cycloalkyl)C$_0$-C$_4$alkyl, C$_2$-C$_6$alkanoyl, C$_1$-C$_6$alkylsulfonyl, phenylC$_0$-C$_6$alkyl, (4- to 7-membered heterocycle)C$_0$-C$_6$alkyl and groups that are joined to L to form a 4- to 7-membered heterocycle; or
  (b) joined to form a 4- to 12-membered heterocycle; and
R$_7$ is hydrogen, C$_1$-C$_{12}$alkyl, C$_2$-C$_{12}$alkenyl, (C$_3$-C$_8$cycloalkyl)C$_0$-C$_4$alkyl, C$_2$-C$_6$alkanoyl, phenylC$_0$-C$_6$alkyl, (4- to 7-membered heterocycle)C$_0$-C$_6$alkyl or a group that is joined to L to form a 4- to 7-membered heterocycle, such that if L is a single covalent bond, then R$_7$ is not hydrogen;
wherein each of (ii) and (iii) is substituted with from 0 to 4 substituents independently chosen from:
(1) halogen, hydroxy, amino, cyano, —COOH, —SO$_2$NH$_2$, oxo, nitro and aminocarbonyl; and
(2) C$_1$-C$_6$alkyl, C$_3$-C$_8$cycloalkyl, C$_1$-C$_6$alkoxy, C$_1$-C$_6$haloalkyl, C$_1$-C$_6$alkanoyl, mono- and di-(C$_1$-C$_6$alkyl)aminoC$_0$-C$_4$alkyl, C$_1$-C$_6$alkylsulfonyl, mono- and di-(C$_1$-C$_6$alkyl)sulfonamido, C$_2$-C$_6$alkanoylamino, mono- and di-(C$_1$-C$_6$alkyl) aminocarbonylC$_0$-C$_4$alkyl, phenylC$_0$-C$_4$alkyl and (4- to 7-membered heterocycle)C$_0$-C$_4$alkyl, each of which is substituted with from 0 to 4 secondary substituents independently chosen from halogen, hydroxy, cyano, oxo, imino, C$_0$-C$_4$alkyl, C$_1$-C$_4$alkoxy and C$_0$-C$_4$haloalkyl; and Ar$_2$ is as described for Formula I.

Within certain embodiments of the above Formulas, variables are as follows:

Ar$_1$, R$_1$, R$_{1a}$, R$_{1b}$ and R$_{1c}$

Certain Ar$_1$ groups satisfy the formula:

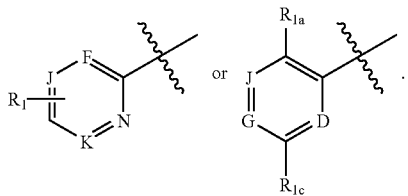

In certain embodiments, F is N, J is N and/or K is N. In other embodiments, G is N, J is N and/or D is N.

In certain compounds of Formulas II and III, R$_1$ represents from 0 to 3 substituents independently chosen from halogen, cyano, hydroxy, amino, C$_1$-C$_6$alkyl, C$_1$-C$_6$haloalkyl, C$_1$-C$_6$alkoxy, C$_2$-C$_6$alkyl ether, C$_2$-C$_6$alkanoyl, C$_3$-C$_6$alkanone, mono- and di-(C$_1$-C$_6$alkyl)amino, C$_1$-C$_6$alkylsulfonyl, mono- and di-(C$_1$-C$_6$alkyl)sulfonamido, and mono- and di-(C$_1$-C$_6$alkyl)aminocarbonyl. Within one category of such compounds, R$_1$ represents 1 or 2 substituents. In certain such compounds, at least one substituent represented by R$_1$ is C$_1$-C$_3$alkyl, C$_1$-C$_3$alkoxy, C$_1$-C$_3$alkylsulfonyl, mono- or di-(C$_1$-C$_4$alkyl)aminocarbonyl, mono- or di-(C$_1$-C$_6$alkyl)sulfonamido or mono- and di-(C$_1$-C$_3$alkyl)amino.

In certain compounds of Formula I, Ar$_1$ is substituted ortho to the point of attachment. Similarly, in certain compounds of Formula Ia, at least one of D and F is substituted carbon. In certain compounds of Formulas II and III, one substituent represented by R$_1$ is located ortho to the point of attachment (i.e., F is substituted carbon). For example, if the ring designated:

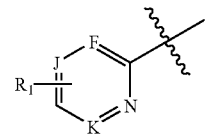

in Formula II is substituted 2-pyridyl, then one R$_1$ is located at the 3 position (i.e., the F position) of the pyridyl. Representative ortho substituents include, but are not limited to, halogen, amino, cyano, C$_1$-C$_6$alkyl, C$_1$-C$_6$alkoxy, C$_1$-C$_6$haloalkyl, C$_1$-C$_6$alkylsulfonyl and mono- and di-(C$_1$-C$_6$alkyl)sulfonamido; in certain embodiments, the ortho R$_1$ is halogen, cyano, methyl, trifluoromethyl or methylsulfonyl. In other such compounds, R$_1$ represents two substituents, one of which is located at the ortho position and the other of which is located para or meta to the point of attachment (e.g., R$_{1b}$ or R$_{1c}$ of Formula IIa, below). Representative para or meta substituents include, for example, halogen, hydroxy, amino, cyano, C$_1$-C$_6$alkyl, C$_1$-C$_6$haloalkyl, C$_1$-C$_6$alkoxy, C$_2$-C$_6$alkyl ether, C$_2$-C$_6$alkanoyl, mono- or di-(C$_1$-C$_6$alkyl) amino, C$_1$-C$_6$alkylsulfonyl, mono- or di-(C$_1$-C$_6$alkyl)sulfonamido, or mono- or di-(C$_1$-C$_6$alkyl)aminocarbonyl.

In certain compounds of Formula IV, G is N or D is N. Within certain compounds of Formula IV, G is CR$_{1b}$, and R$_{1b}$ at the G (para) position is not hydrogen. Within other compounds of Formula IV, R$_{1b}$ at the meta position is not hydrogen. Representative para and meta R$_{1b}$ groups include, for example, those described above for Formulas II and III.

Within certain compounds of Formula IV, $R_{1a}$ is halogen, amino, cyano, $C_1$-$C_6$alkyl, $C_1$-$C_6$alkoxy, $C_1$-$C_6$haloalkyl, $C_1$-$C_6$alkylsulfonyl or mono- or di-($C_1$-$C_6$alkyl)sulfonamido.

Representative such $R_{1a}$ groups include halogen, cyano, methyl, trifluoromethyl and methylsulfonyl.

Representative $Ar_1$ groups include those that satisfy the following subformulas:

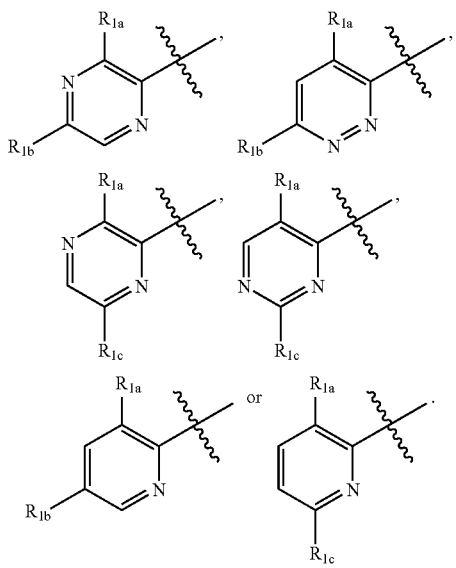

$Ar_2$, $R_2$ and $R_{2a}$

In certain compounds of Formulas I, II and III, $Ar_2$ is phenyl or pyridyl (i.e., 2-pyridyl, 3-pyridyl or 4-pyridyl). In certain compounds of Formulas I and III, $Ar_2$ is a 9- to 12-membered bicyclic aryl or heteroaryl group that is optionally substituted as described above. Preferably, $Ar_2$ is substituted with from 0 to 3 or from 1 to 3 substituents independently chosen from $R_2$ as described above. In certain compounds, $Ar_2$ has at least one substituent ($R_2$) and each $R_2$ is independently chosen from amino, cyano, halogen, —$SO_2NH_2$, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, $C_2$-$C_4$alkanoyl, $C_1$-$C_4$alkoxycarbonyl, $C_1$-$C_4$alkylsulfonyl $C_1$-$C_4$haloalkylsulfonyl and mono- and di-($C_1$-$C_4$alkyl)sulfonamido. More preferably, the substituents of $Ar_2$ are independently chosen from amino, cyano, halogen, $C_1$-$C_4$alkyl, $C_1$-$C_4$haloalkyl, $C_1$-$C_4$alkoxy, $C_1$-$C_4$haloalkoxy, $C_1$-$C_4$alkylthio and mono- and di-($C_1$-$C_4$alkyl)amino$C_0$-$C_4$alkyl. In certain such compounds, $Ar_2$ is substituted meta and/or para to the point of attachment. In other words, if $Ar_2$ is phenyl, the phenyl is mono-substituted at the 3-position, mono-substituted at the 4-position, or di-substituted and the 3- and 4-positions.

Within certain $Ar_2$ groups, one $R_2$ is taken together with an adjacent $R_2$ to form a fused carbocycle or heterocycle. Representative such groups include, for example, the following bicyclic groups, optionally substituted as described herein:

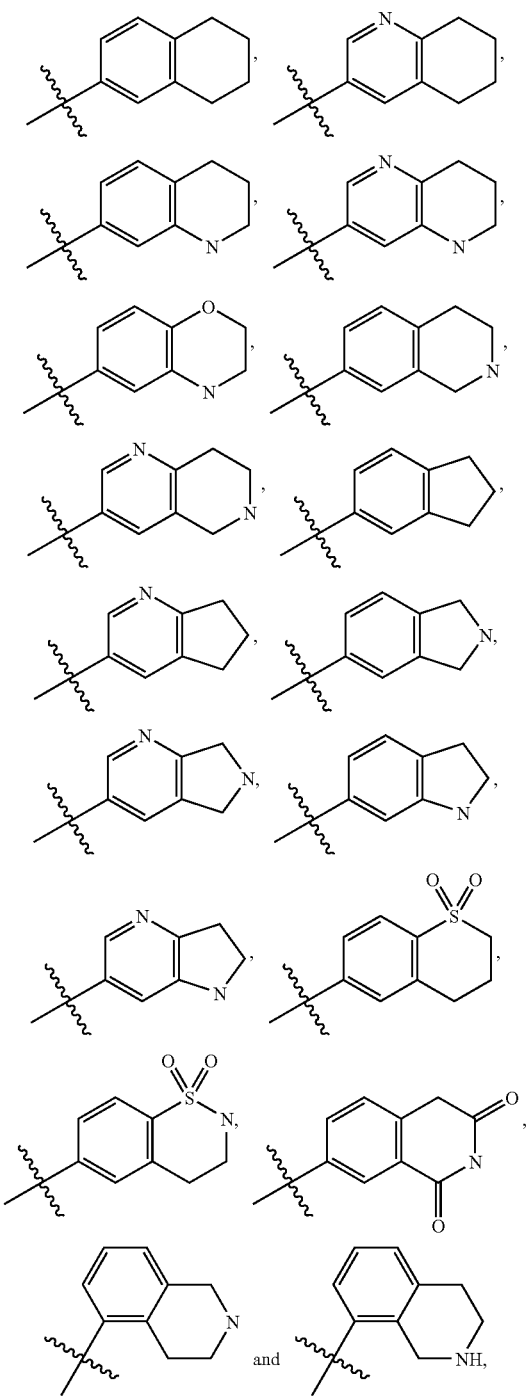

as well as variants of the foregoing in which the fused ring contains one or more additional double bonds, such as:

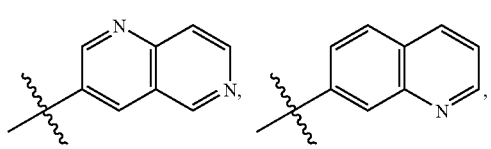

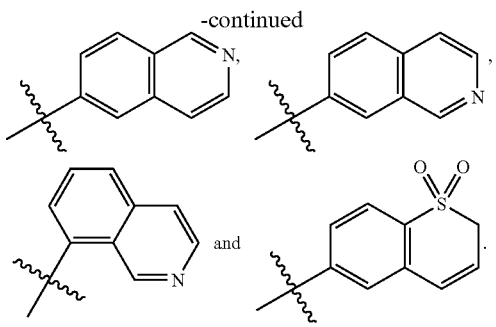

In certain compounds of Formulas Ia and IV, each $R_{2a}$ is independently chosen from amino, cyano, halogen, —$SO_2NH_2$, —COOH, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)sulfonamido. In further such compounds, A is CH or $CR_{2a}$, and each $R_{2a}$ is independently chosen from cyano, halogen, $C_1$-$C_4$alkyl, $C_1$-$C_4$haloalkyl, $C_1$-$C_4$alkoxy and mono- and di-($C_1$-$C_4$alkyl)amino$C_0$-$C_2$alkyl. In other such compounds, at least one of A, B and E is N.

$R_3$

In the definition of $R_3$, the variable "L" is defined as $C_0$-$C_6$alkyl or $C_1$-$C_6$alkyl that is taken together with $R_5$, $R_6$ or $R_7$ to form a 4- to 7-membered heterocycle. In any heterocycle so formed, at least one carbon atom present in L is also a ring atom, and is covalently bonded to a component atom of $R_5$, $R_6$ or $R_7$. The resulting heterocycle may be a heterocycloalkyl group (e.g., tetrahydrofuranyl, morpholinyl, piperidinyl or piperazinyl) or a heteroaryl group, such as pyridyl, pyrimidyl or tetrahydrofuranyl. $R_3$ groups comprising such a heterocycle include, for example:

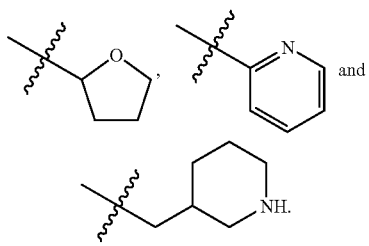

$R_3$, in certain embodiments of Formulas I, Ia and II-IV, is a group of the formula:

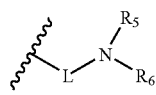

wherein:
L is $C_0$-$C_3$alkyl; and
$R_5$ and $R_6$ are:
(a) independently chosen from hydrogen, $C_1$-$C_6$alkyl, $C_2$-$C_6$alkenyl, ($C_5$-$C_7$cycloalkyl)$C_0$-$C_4$alkyl and $C_2$-$C_4$alkanoyl; or (b) joined to form a 4- to 12-membered heterocycloalkyl; each of which alkyl, alkenyl, (cycloalkyl)alkyl, alkanoyl and heterocycloalkyl is substituted with from 0 to 4 substituents independently chosen from (i) halogen, hydroxy, amino, aminocarbonyl, oxo, —COOH and —$SO_2NH_2$; and (ii) $C_1$-$C_4$alkyl, $C_5$-$C_7$cycloalkyl, $C_1$-$C_4$alkoxy, $C_2$-$C_4$alkanoyl, $C_1$-$C_4$haloalkyl, mono- and di-($C_1$-$C_4$alkyl)amino$C_0$-$C_2$alkyl, mono- and di-($C_1$-$C_4$alkyl)aminocarbonyl$C_0$-$C_2$alkyl, phenyl$C_0$-$C_4$alkyl and (4-to 7-membered heterocycle)$C_0$-$C_2$alkyl, each of which is substituted with from 0 to 4 secondary substituents independently chosen from halogen, hydroxy, cyano, $C_1$-$C_4$alkyl, $C_1$-$C_4$alkoxy and $C_1$-$C_4$haloalkyl.

Such $R_3$ groups include, for example, mono- and di-($C_1$-$C_4$alkyl)amino groups that are substituted with from 0 to 4 substituents independently chosen from halogen, hydroxy, amino, oxo, aminocarbonyl, —COOH, —$SO_2NH_2$, $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino.

Other $R_3$ groups include phenyl and 4- to 7-membered heterocycles, each of which is substituted with from 0 to 4 substituents independently chosen from (a) halogen, hydroxy, amino, oxo, aminocarbonyl, —$SO_2NH_2$ and —COOH; and (b) $C_1$-$C_4$alkyl, $C_1$-$C_4$haloalkyl, $C_2$-$C_4$alkenyl, ($C_5$-$C_7$cycloalkyl)$C_0$-$C_2$alkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino, mono- and di-($C_1$-$C_4$alkyl)amino, mono- and di-($C_1$-$C_4$alkyl)aminocarbonyl, mono- or di-($C_1$-$C_6$alkyl)sulfonamido, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, —COOH, $C_1$-$C_4$alkyl and $C_1$-$C_4$haloalkyl. Certain such $R_3$ groups include azetidinyl, pyrrolidinyl, morpholinyl, thiomorpholinyl, piperidinyl, piperazinyl, tetrahydropyridyl and azepanyl, each of which is substituted with from 0 to 4 substituents independently chosen from: (a) halogen, hydroxy, amino, oxo, aminocarbonyl, —$SO_2NH_2$ and —COOH; and (b) $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino, each of which is substituted with from 0 to 4 secondary substituents independently chosen from hydroxy and halogen. One example of such a $R_3$ group is:

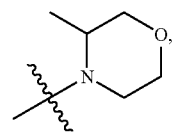

as well as enantiomers thereof (

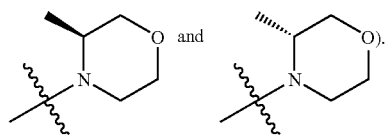

Other such R₃ groups are phenyl, pyridyl, pyrimidyl, pyrazinyl, pyridazinyl, imidazolyl, thienyl, oxazolyl or tetrahydrofuranyl, each of which is substituted with from 0 to 4 substituents independently chosen from halogen, hydroxy, amino, aminocarbonyl, —SO₂NH₂, —COOH, C₁-C₄alkyl, C₅-C₇cycloalkyl, C₂-C₄alkyl ether, C₁-C₄alkoxy, C₂-C₄alkanoyl, C₁-C₄haloalkyl and mono- and di-(C₁-C₄alkyl)amino. In certain embodiments, R₃ is not —NH₂. In other words, if L is a single covalent bond then at least one of R₅ and R₆ is not hydrogen.

In further embodiments of Formulas I, Ia and II-IV, R₃ is

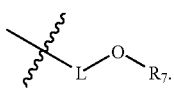

In certain such compounds, L is C₀-C₃alkyl; and R₇ is C₁-C₆alkyl, C₂-C₆alkenyl, (C₅-C₇cycloalkyl)C₀-C₄alkyl, C₂-C₄alkanoyl, phenylC₀-C₆alkyl or (6-membered heteroaryl)C₀-C₄alkyl, each of which is substituted with from 0 to 4 substituents independently chosen from halogen, hydroxy, amino, aminocarbonyl, —SO₂NH₂, —COOH, C₁-C₄alkyl, C₅-C₇cycloalkyl, C₂-C₄alkyl ether, C₁-C₄alkoxy, C₂-C₄alkanoyl, C₁-C₄haloalkyl and mono- and di-(C₁-C₄alkyl)amino. Such R₃ groups include, for example, benzyloxy and C₁-C₆alkoxy, each of which is optionally substituted with halogen, methyl, methoxy or trifluoromethyl.

Within still further embodiments of Formulas I, Ia and II-IV, R₃ is a halogen.

Within certain compounds of Formulas I, Ia, III and IV, R₃ is C₁-C₄alkyl, C₃-C₇cycloalkyl or C₁-C₄haloalkyl, each of which is substituted with from 0 to 4 substituents independently chosen from halogen, hydroxy, cyano, oxo, aminocarbonyl, —SO₂NH₂, —COOH, C₃-C₇cycloalkyl, phenyl and 4- to 7-membered heterocycle.

R₄

R₄, in certain compounds provided herein, represents zero substituents or one methyl, ethyl or oxo group, preferably located at the 2-position of the piperazine. The carbon to which a methyl or ethyl group is attached is chiral in certain embodiments. In other compounds, R₄ represents a single oxo substituent.

X, Y and Z

X, Y and Z, as noted above, are independently CR$_x$ or N, such that at least one of X, Y and Z is N. In certain embodiments, each R$_x$ is independently chosen from hydrogen and methyl, or each R$_x$ is hydrogen. In certain representative compounds, Z is N (e.g., X and Y are CH). In other compounds provided herein, X is N (e.g., Y and Z are CH). In further compounds Z and X are N, X and Y are N or Z and Y are N. In further compounds, X, Y and Z are each N. Representative subformulas illustrating some of these embodiments in the context of Formula II include:

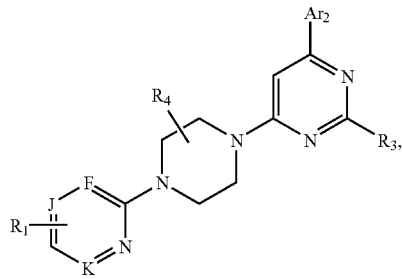

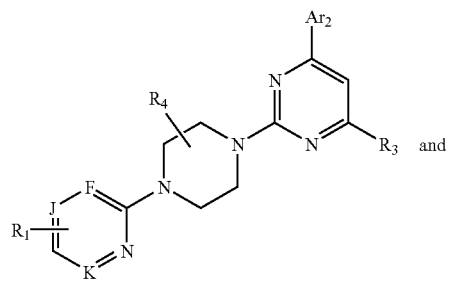

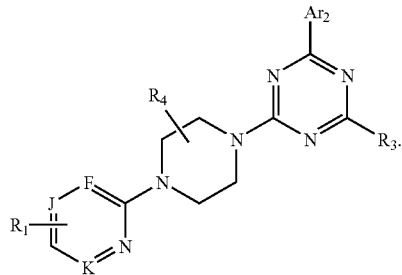

Certain compounds of Formula II satisfy at least one of Formulas IIa-IIh, or are a pharmaceutically acceptable salt thereof. Variables in each of these formulas are as described above for Formula II, and the certain specific embodiments thereof, except as described below:

Formula IIa

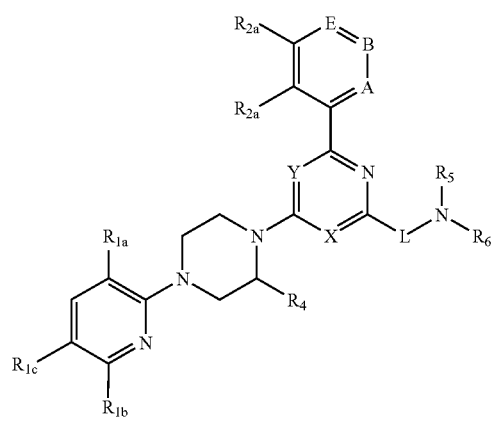

Formula IIb

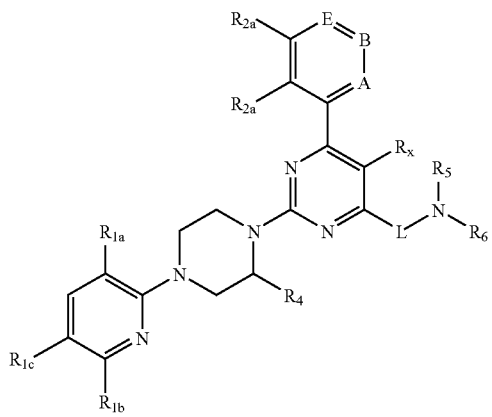

Within Formulas IIa and IIb:

A, B and E are independently nitrogen or $CR_{2a}$;

Each $R_{2a}$ is independently chosen from hydrogen, amino, cyano, halogen, —$SO_2NH_2$, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)sulfonamido, such that at least one $R_{2a}$ is not hydrogen; in certain embodiments, each $R_{2a}$ is independently chosen from hydrogen, halogen, cyano, amino, $C_1$-$C_4$alkyl, $C_1$-$C_4$alkoxy and $C_1$-$C_4$haloalkyl;

$R_{1a}$ is halogen, amino, cyano, $C_1$-$C_6$alkyl, $C_1$-$C_6$haloalkyl, $C_1$-$C_6$alkoxy, $C_1$-$C_6$alkylsulfonyl or mono- or di-($C_1$-$C_6$alkyl)sulfonamido; in certain embodiments, $R_{1a}$ is halogen, cyano, methyl or trifluoromethyl; and $R_{1b}$ and $R_{1c}$ are independently chosen from hydrogen, halogen, amino, cyano, $C_1$-$C_6$alkyl, $C_1$-$C_6$alkoxy, $C_1$-$C_6$haloalkyl, $C_1$-$C_6$alkylsulfonyl, mono- and di-($C_1$-$C_6$alkyl)aminocarbonyl, mono- and di-($C_1$-$C_6$alkyl)amino and mono- and di-($C_1$-$C_6$alkyl)sulfonamido;

$R_4$ is hydrogen, methyl, ethyl or oxo; and $R_x$ is independently selected at each occurrence from hydrogen, methyl, amino and cyano.

In certain embodiments of Formulas IIa and IIb:

$R_{1a}$ is halogen, cyano, methyl or trifluoromethyl;

$R_{1b}$ and $R_{1c}$ are independently hydrogen, halogen, amino, $C_1$-$C_3$alkyl, $C_1$-$C_3$alkoxy, mono- or di-($C_1$-$C_4$alkyl)amino, mono- or di-($C_1$-$C_4$alkyl)aminocarbonyl, $C_1$-$C_3$alkylsulfonyl, or mono- or di-($C_1$-$C_4$alkyl)sulfonamido;

Each $R_{2a}$ is independently chosen from hydrogen, halogen, cyano, amino, $C_1$-$C_4$alkyl, $C_1$-$C_4$alkoxy and $C_1$-$C_4$haloalkyl; and $R_5$ and $R_6$ are independently chosen from:
(i) hydrogen; and
(ii) $C_1$-$C_6$alkyl, $C_2$-$C_6$alkenyl, ($C_3$-$C_8$cycloalkyl)$C_0$-$C_2$alkyl, $C_2$-$C_6$alkanoyl, phenyl$C_0$-$C_2$alkyl and (4- to 7-membered heterocycloalkyl)$C_0$-$C_2$alkyl and groups that are joined to L to form a 4- to 7-membered heterocycle; each of which is substituted with from 0 to 2 substituents independently chosen from halogen, hydroxy, oxo, COOH, aminocarbonyl, —$SO_2NH_2$, $C_1$-$C_4$alkyl, $C_1$-$C_4$haloalkyl, $C_1$-$C_4$alkoxy, $C_1$-$C_4$alkoxycarbonyl, $C_1$-$C_4$alkylsulfonyl, and mono- and di-($C_1$-$C_6$alkyl)amino;

or $R_5$ and $R_6$, together with the N to which they are bound, form a 4- to 7-membered heterocycloalkyl that is substituted with from 0 to 2 substituents independently chosen from halogen, hydroxy, amino, oxo, aminocarbonyl, —$SO_2NH_2$, COOH, $C_1$-$C_4$alkyl, $C_1$-$C_4$alkoxy, $C_1$-$C_4$hydroxyalkyl, $C_2$-$C_4$alkyl ether, $C_1$-$C_4$alkoxycarbonyl, $C_2$-$C_4$alkanoyl, $C_2$-$C_4$alkanoylamino, ($C_3$-$C_7$cycloalkyl)$C_0$-$C_2$alkyl, (4- to 7-membered heterocycloalkyl)$C_0$-$C_2$alkyl, mono- and di-($C_1$-$C_6$alkyl)aminocarbonyl, $C_1$-$C_4$alkylsulfonyl, and mono- and di-($C_1$-$C_6$alkyl)amino$C_0$-$C_2$alkyl.

Formula IIc

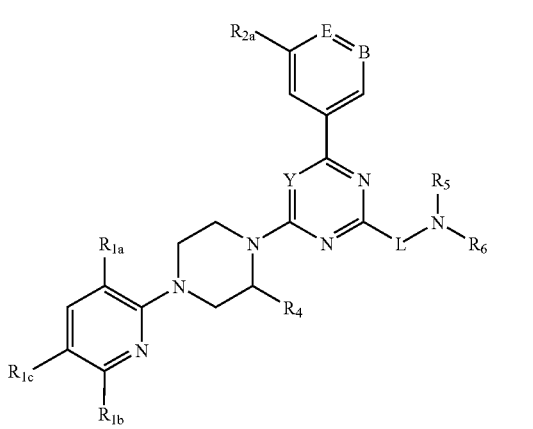

Formula IId

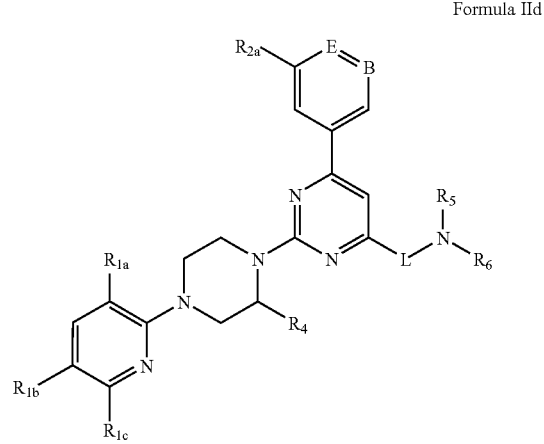

Within Formulas IIc and IId, variables are as described for Formula IIa. Preferably, L is a single covalent bond or methylene and at least one of B and E is $CR_{2a}$.

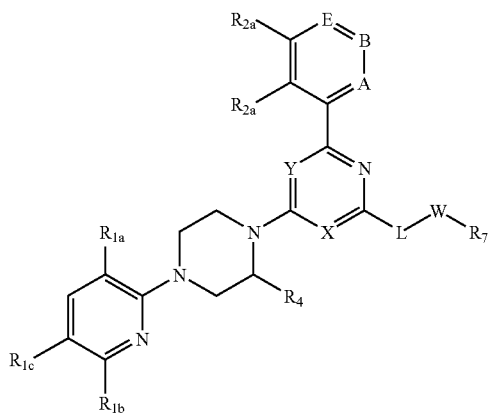

Formula IIe

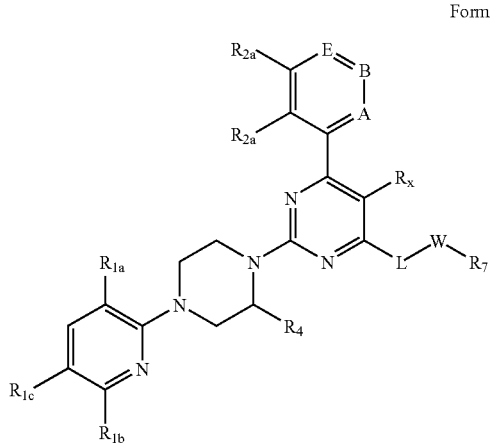

Formula IIf

Within Formulas IIe and IIf:

A, B and E are independently nitrogen or $CR_{2a}$;

Each $R_{2a}$ is independently hydrogen, amino, cyano, halogen, $—SO_2NH_2$, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- or di-($C_1$-$C_4$alkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl or mono- or di-($C_1$-$C_4$alkyl)sulfonamido, such that at least one $R_{2a}$ is not hydrogen; in certain embodiments, each $R_{2a}$ is independently chosen from hydrogen, halogen, cyano, amino, $C_1$-$C_4$alkyl, $C_1$-$C_4$alkoxy and $C_1$-$C_4$haloalkyl;

$R_{1a}$ is halogen, amino, cyano, $C_1$-$C_6$alkyl, $C_1$-$C_6$alkoxy, $C_1$-$C_6$haloalkyl, $C_1$-$C_6$alkylsulfonyl or mono- or di-($C_1$-$C_6$alkyl)sulfonamido; in certain embodiments, $R_{1a}$ is halogen, cyano, methyl or trifluoromethyl;

$R_{1b}$ and $R_1$, are independently chosen from hydrogen, halogen, amino, cyano, $C_1$-$C_6$alkyl, $C_1$-$C_6$alkoxy, $C_1$-$C_6$haloalkyl, $C_1$-$C_6$alkylsulfonyl, mono- and di-($C_1$-$C_6$alkyl)aminocarbonyl, mono- and di-($C_1$-$C_6$alkyl)amino and mono- and di-($C_1$-$C_6$alkyl)sulfonamido;

$R_4$ is hydrogen, methyl, ethyl or oxo; and $R_x$ is independently selected at each occurrence from hydrogen, methyl, amino and cyano.

In certain embodiments of Formulas IIe and IIf:

$R_{1a}$ is halogen, cyano, methyl or trifluoromethyl;

$R_{1b}$ and $R_1$, are independently hydrogen, halogen, amino, $C_1$-$C_3$alkyl, $C_1$-$C_3$alkoxy, mono- or di-($C_1$-$C_4$alkyl)amino, mono- or di-($C_1$-$C_4$alkyl)aminocarbonyl, $C_1$-$C_3$alkylsulfonyl, or mono- or di-($C_1$-$C_4$alkyl)sulfonamido;

each $R_{2a}$ is independently chosen from hydrogen, halogen, cyano, amino, $C_1$-$C_4$alkyl, $C_1$-$C_4$alkoxy, and $C_1$-$C_4$haloalkyl; and $R_7$ is $C_1$-$C_6$alkyl, $C_2$-$C_6$alkenyl, $C_1$-$C_6$alkyl ether, ($C_3$-$C_8$cycloalkyl)$C_0$-$C_2$alkyl, $C_2$-$C_6$alkanoyl, phenyl$C_0$-$C_2$alkyl or (4- to 7-membered heterocycloalkyl)$C_0$-$C_2$alkyl, each of which is substituted with from 0 to 2 substituents independently chosen from halogen, hydroxy, oxo, $C_1$-$C_4$alkyl, $C_1$-$C_4$haloalkyl and $C_2$-$C_4$alkanoyl.

Formula IIg

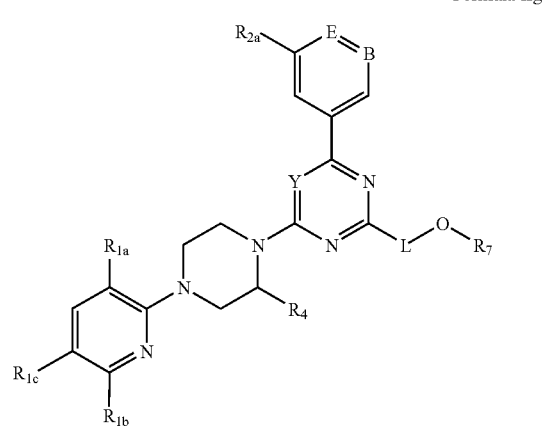

Formula IIh

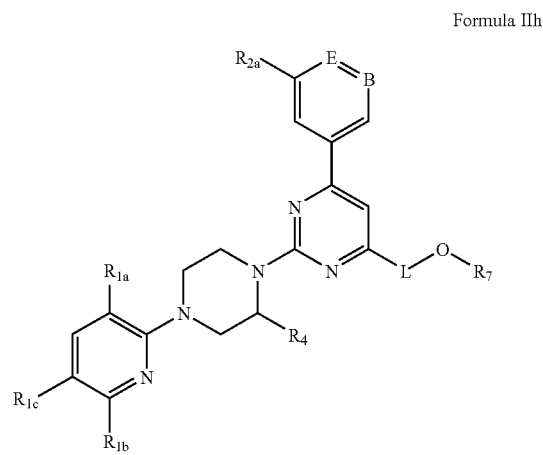

Within Formulas IIg and IIh, variables are as described for Formula IIa. Preferably, L is a single covalent bond or methylene, and at least one of B and E is $CR_{2a}$.

Certain compounds of Formula IV satisfy Formula IVa or Formula IVb, or are a pharmaceutically acceptable salt thereof:

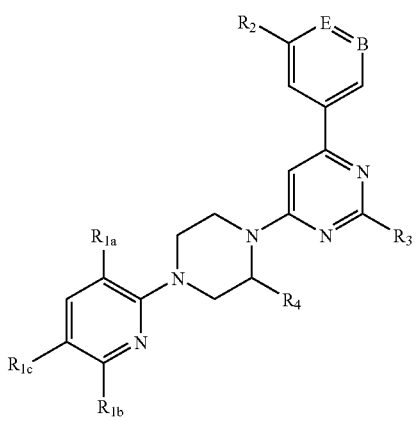

Formula IVa

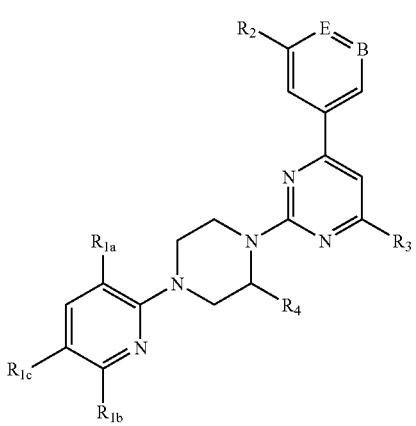

Formula IVb

Within Formulas IVa and IVb, variables are as described above for Formula IV, except that R₄ is hydrogen, methyl, ethyl or oxo. In certain compounds of Formulas IVa and IVb:

$R_{1a}$ is halogen, cyano, methyl or trifluoromethyl;

$R_{1b}$ and $R_{1c}$ are independently hydrogen, halogen, amino, $C_1$-$C_3$alkyl, $C_1$-$C_3$alkoxy, mono- or di-($C_1$-$C_3$alkyl)amino, mono- or di-($C_1$-$C_4$alkyl)aminocarbonyl, $C_1$-$C_3$alkylsulfonyl, or mono- or di-($C_1$-$C_4$alkyl)sulfonamido; and Each $R_{2a}$ is independently chosen from halogen, cyano, amino, $C_1$-$C_4$alkyl, $C_1$-$C_4$alkoxy, and $C_1$-$C_4$haloalkyl.

In certain compounds of Formulas IVa and IVb, R₃ is mono- or di-($C_1$-$C_4$alkyl)amino substituted with from 0 to 4 substituents independently chosen from halogen, hydroxy, amino, aminocarbonyl, —COOH, —SO₂NH₂, $C_1$-$C_4$alkyl, $C_2$-$C_4$alkenyl, $C_1$-$C_4$haloalkyl, $C_5$-$C_7$cycloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino. In other compounds of Formulas IVa and IVb, R₃ is phenyl or a 4- to 7-membered heterocycle, each of which is substituted with from 0 to 4 substituents independently chosen from (a) halogen, hydroxy, amino, oxo, aminocarbonyl, —SO₂NH₂ and —COOH; and (b) $C_1$-$C_4$alkyl, $C_1$-$C_4$haloalkyl, $C_2$-$C_4$alkenyl, ($C_5$-$C_7$cycloalkyl)$C_0$-$C_2$alkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino, mono- and di-($C_1$-$C_4$alkyl)amino, mono- and di-($C_1$-$C_4$alkyl)aminocarbonyl, mono- or di-($C_1$-$C_6$alkyl)sulfonamido, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, —COOH, $C_1$-$C_4$alkyl and $C_1$-$C_4$haloalkyl. Certain such R₃ groups include pyrrolidinyl, morpholinyl, thiomorpholinyl, piperidinyl, piperazinyl, tetrahydropyridyl and azepanyl, each of which is substituted with from 0 to 4 substituents independently chosen from: (a) halogen, hydroxy, amino, oxo, aminocarbonyl, —SO₂NH₂ and —COOH; and (b) $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino, each of which is substituted with from 0 to 4 secondary substituents independently chosen from hydroxy and halogen. Other such R₃ groups are phenyl, pyridyl, pyrimidyl, pyrazinyl, pyridazinyl, imidazolyl, oxazolyl or tetrahydrofuranyl, each of which is substituted with from 0 to 4 substituents independently chosen from halogen, hydroxy, amino, aminocarbonyl, —SO₂NH₂, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino.

In other compounds of Formulas IVa and IVb, R₃ is a group of the formula:

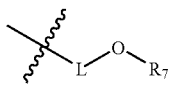

wherein L is $C_0$-$C_3$alkyl; and R₇ is $C_1$-$C_6$alkyl, $C_2$-$C_6$alkenyl, ($C_5$-$C_7$cycloalkyl)$C_0$-$C_4$alkyl, $C_2$-$C_4$alkanoyl, phenyl$C_0$-$C_6$alkyl or (6-membered heteroaryl)$C_0$-$C_4$alkyl, each of which is substituted with from 0 to 4 substituents independently chosen from halogen, hydroxy, amino, aminocarbonyl, —SO₂NH₂, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino. One such R₃ group is benzyloxy, optionally substituted with halogen, methyl, methoxy or trifluoromethyl.

Within further compounds of Formulas IVa and IVb, R₃ is $C_1$-$C_4$alkyl or $C_1$-$C_4$haloalkyl, each of which is substituted with from 0 to 4 substituents independently chosen from hydroxy, cyano, oxo, $C_3$-$C_7$cycloalkyl, phenyl and 4- to 7-membered heterocycle.

Representative compounds provided herein include, but are not limited to, those specifically described in Examples 1-3. It will be apparent that the specific compounds recited herein are representative only, and are not intended to limit the scope of the present invention. Further, as noted above, all compounds of the present invention may be present as a free acid or base or as a pharmaceutically acceptable salt.

Biaryl piperazinyl-pyridine analogues provided herein detectably alter (modulate) VR1 activity, as determined using an in vitro VR1 ligand binding assay and/or a functional assay such as a calcium mobilization assay, dorsal root ganglion assay or in vivo pain-relief assay. References herein to a "VR1 ligand binding assay" are intended to refer to a standard in vitro receptor binding assay such as that provided in Example 5, and a "calcium mobilization assay" (also referred to herein as a "signal transduction assay") may be performed as described in Example 6. Briefly, to assess binding to VR1, a competition assay may be performed in which a VR1 preparation is incubated with labeled (e.g., $^{125}I$ or $^{3}H$) compound that binds to VR1 (e.g., a capsaicin receptor agonist such as RTX) and unlabeled test compound. Within the assays provided herein, the VR1 used is preferably mammalian VR1, more preferably human or rat VR1. The receptor may be recombinantly expressed or naturally expressed. The VR1 preparation may be, for example, a membrane preparation from HEK293 or CHO cells that recombinantly express human VR1. Incubation with a compound that detectably modulates vanilloid ligand binding to VR1 results in a decrease or increase in the amount of label bound to the VR1 preparation, relative to the amount of label bound in the absence of the compound. This decrease or increase may be used to determine the $K_i$ at VR1 as described herein. In general, compounds that decrease the amount of label bound to the VR1 preparation within such an assay are preferred.

As noted above, compounds that are VR1 antagonists are preferred within certain embodiments. $IC_{50}$ values for such compounds may be determined using a standard in vitro VR1-mediated calcium mobilization assay, as provided in Example 6. Briefly, cells expressing capsaicin receptor are contacted with a compound of interest and with an indicator of intracellular calcium concentration (e.g., a membrane permeable calcium sensitivity dye such as Fluo-3 or Fura-2 (both of which are available, for example, from Molecular Probes, Eugene, Oreg.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1-2 hours). Cells are washed or filtered to remove excess dye and are then contacted with a vanilloid receptor agonist (e.g., capsaicin, RTX or olvanil), typically at a concentration equal to the $EC_{50}$ concentration, and a fluorescence response is measured. When agonist-contacted cells are contacted with a compound that is a VR1 antagonist the fluorescence response is generally reduced by at least 20%, preferably at least 50% and more preferably at least 80%, as compared to cells that are contacted with the agonist in the absence of test compound. The $IC_{50}$ for VR1 antagonists provided herein is preferably less than 1 micromolar, less than 100 nM, less than 10 nM or less than 1 nM. In certain embodiments, VR1 antagonists provided herein exhibit no detectable agonist activity an in vitro assay of capsaicin receptor agonism at a concentration of compound equal to the $IC_{50}$. Certain such antagonists exhibit no detectable agonist activity an in vitro assay of capsaicin receptor agonism at a concentration of compound that is 100-fold higher than the $IC_{50}$.

In other embodiments, compounds that are capsaicin receptor agonists are preferred. Capsaicin receptor agonist activity may generally be determined as described in Example 6. When cells are contacted with 1 micromolar of a compound that is a VR1 agonist, the fluorescence response is generally increased by an amount that is at least 30% of the increase observed when cells are contacted with 100 nM capsaicin. The $EC_{50}$ for VR1 agonists provided herein is preferably less than 1 micromolar, less than 100 nM or less than 10 nM.

VR1 modulating activity may also, or alternatively, be assessed using a cultured dorsal root ganglion assay as provided in Example 9 and/or an in vivo pain relief assay as provided in Example 10. Compounds provided herein preferably have a statistically significant specific effect on VR1 activity within one or more functional assays provided herein.

Within certain embodiments, VR1 modulators provided herein do not substantially modulate ligand binding to other cell surface receptors, such as EGF receptor tyrosine kinase or the nicotinic acetylcholine receptor. In other words, such modulators do not substantially inhibit activity of a cell surface receptor such as the human epidermal growth factor (EGF) receptor tyrosine kinase or the nicotinic acetylcholine receptor (e.g., the $IC_{50}$ or $IC_{40}$ at such a receptor is preferably greater than 1 micromolar, and most preferably greater than 10 micromolar). Preferably, a modulator does not detectably inhibit EGF receptor activity or nicotinic acetylcholine receptor activity at a concentration of 0.5 micromolar, 1 micromolar or more preferably 10 micromolar. Assays for determining cell surface receptor activity are commercially available, and include the tyrosine kinase assay kits available from Panvera (Madison, Wis.).

Preferred VR1 modulators provided herein are non-sedating. In other words, a dose of VR1 modulator that is twice the minimum dose sufficient to provide analgesia in an animal model for determining pain relief (such as a model provided in Example 10, herein) causes only transient (i.e., lasting for no more than ½ the time that pain relief lasts) or preferably no statistically significant sedation in an animal model assay of sedation (using the method described by Fitzgerald et al. (1988) *Toxicology* 49(2-3): 433-9). Preferably, a dose that is five times the minimum dose sufficient to provide analgesia does not produce statistically significant sedation. More preferably, a VR1 modulator provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, VR1 modulators provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred VR1 modulator is nontoxic when a therapeutically effective amount is administered to a subject), side effects (a preferred VR1 modulator produces side effects comparable to placebo when a therapeutically effective amount of the compound is administered to a subject), serum protein binding and in vitro and in vivo half-life (a preferred VR1 modulator exhibits an in vitro half-life that is equal to an in vivo half-life allowing for Q.I.D. dosing, preferably T.I.D. dosing, more preferably B.I.D. dosing, and most preferably once-a-day dosing). In addition, differential penetration of the blood brain barrier may be desirable for VR1 modulators used to treat pain by modulating CNS VR1 activity such that total daily oral doses as described above provide such modulation to a therapeutically effective extent, while low brain levels of VR1 modulators used to treat peripheral nerve mediated pain may be preferred (i.e., such doses do not provide brain (e.g., CSF) levels of the compound sufficient to significantly modulate VR1 activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the required frequency of dosage. In vitro half-lives of compounds may be predicted from assays of microsomal half-life as described within Example 7, herein.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, or (4) does not cause substantial release of liver enzymes.

As used herein, a compound that does not substantially inhibit cellular ATP production is a compound that satisfies the criteria set forth in Example 8, herein. In other words, cells treated as described in Example 8 with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that does not significantly prolong heart QT intervals is a compound that does not result in a statistically significant prolongation of heart QT intervals (as determined by electrocardiography) in guinea pigs, minipigs or dogs upon administration of a dose that yields a serum concentration equal to the $EC_{50}$ or $IC_{50}$ for the compound. In certain preferred embodiments, a dose of 0.01, 0.05. 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound does not cause substantial liver enlargement if daily treatment of laboratory rodents (e.g., mice or rats) for 5-10 days with a dose that yields a serum concentration equal to the $EC_{50}$ or $IC_{50}$ for the compound results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a compound does not promote substantial release of liver enzymes if administration of twice the minimum dose that yields a serum concentration equal to the $EC_{50}$ or $IC_{50}$ for the compound does not elevate serum levels of ALT, LDH or AST in laboratory rodents by more than 100% over matched mock-treated controls. In more highly preferred embodiments, such doses do not elevate such serum levels by more than 75% or 50% over matched controls. Alternatively, a VR1 modulator does not promote substantial release of liver enzymes if, in an in vitro hepatocyte assay, concentrations (in culture media or other such solutions that are contacted and incubated with hepatocytes in vitro) that are equal to the $EC_{50}$ or $IC_{50}$ for the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the $EC_{50}$ or $IC_{50}$ for the compound.

In other embodiments, certain preferred compounds do not inhibit or induce microsomal cytochrome P450 enzyme activities, such as CYP1A2 activity, CYP2A6 activity, CYP2C9 activity, CYP2C19 activity, CYP2D6 activity, CYP2E 1 activity or CYP3A4 activity at a concentration equal to the $EC_{50}$ or $IC_{50}$ for the compound.

Certain preferred compounds are not clastogenic (e.g., as determined using a mouse erythrocyte precursor cell micronucleus assay, an Ames micronucleus assay, a spiral micronucleus assay or the like) at a concentration equal the $EC_{50}$ or $IC_{50}$ for the compound. In other embodiments, certain preferred VR1 modulators do not induce sister chromatid exchange (e.g., in Chinese hamster ovary cells) at such concentrations.

For detection purposes, as discussed in more detail below, compounds provided herein may be isotopically-labeled or radiolabeled. For example, compounds recited in Formulas I-III may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation Of Biaryl Piperazinyl-Pyridrne Analogues

Biaryl piperazinyl-pyridine analogues may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

In the Schemes that follow the term "reduction" refers to the process of reducing a nitro functionality to an amino functionality, or the process of transforming an ester functionality to an alcohol. The reduction of a nitro group can be carried out in a number of ways well known to those skilled in the art of organic synthesis including, but not limited to, catalytic hydrogenation, reduction with $SnCl_2$ and reduction with titanium trichloride. The reduction of an ester group is typically performed using metal hydride reagents including, but not limited to, diisobutyl-aluminum hydride (DIBAL), lithium aluminum hydride (LAH), and sodium borohydride. For an overview of reduction methods see: Hudlicky, M. *Reductions in Organic Chemistry*, ACS Monograph 188, 1996.

In the Schemes that follow, the term "hydrolyze" refers to the reaction of a substrate or reactant with water. More specifically, "hydrolyze" refers to the conversion of an ester or nitrile functionality into a carboxylic acid. This process can be catalyzed by a variety of acids or bases well known to those skilled in the art of organic synthesis.

In the Schemes that follow, the term "catalyst" refers to a suitable transition metal catalyst such as, but not limited to, tetrakis(triphenylphosphine)palladium(0) or palladium(II) acetate. In addition, the catalytic systems may include ligands such as, but not limited to, 2-(Dicyclohexylphosphino)biphenyl and tri-tert-butylphosphine, and may also include a base such as $K_3PO_4$, $Na_2CO_3$ or sodium or potassium tert-butoxide. Transition metal-catalyzed reactions can be carried out at ambient or elevated temperatures using various inert solvents including, but not limited to, toluene, dioxane, DMF, N-methylpyrrolidinone, ethyleneglycol, dimethyl ether, diglyme and acetonitrile. When used in conjunction with suitable metallo-aryl reagents, transition metal-catalyzed (hetero)aryl/aryl coupling reactions can be used to prepare the compounds encompassed in general structures 1D and 1E (Scheme 1), and 2C (Scheme 2), 4E (Scheme 4), 5B (Scheme 5), 6-F (Scheme 6), 8B and 8D (Scheme 8), 9C (Scheme 9), and 10C (Scheme 10). Commonly employed reagent/catalyst pairs include aryl boronic acid/palladium(0) (Suzuki reaction; Miyaura and Suzuki (1995) *Chemical Reviews* 95:2457) and aryl trialkylstannane/palladium(0) (Stille reaction; T. N. Mitchell, (1992) *Synthesis* 9:803-815), arylzinc/palladium(0) and aryl Grignard/nickel(II). In addition, metal-catalyzed (hetero)aryl/amine coupling reactions (Buchwald-Hartwig cross-coupling reaction; J. F. Hartwig, *Angew. Chem. Int. Ed.* 37:2046-2067 (1998)) can be used to prepare the compounds encompassed in general structures 7F (Scheme 7), 9E (Scheme 9), and 10E (Scheme 10).

In Scheme 11, $R_8$ and $R_9$ are generally as described herein for $R_5$ and $R_6$ of Formula I.

Other definitions used in the following Schemes and elsewhere herein are:
BINAP (rac)-2,2'-Bis(diphenylphosphino)-1,1'-binaphthyl
$CDCl_3$ deuterated chloroform
d chemical shift
DCM dichloromethane or methylene chloride
DDQ 2,3-dichloro-5,6-dicyano-1,4-benzoquinone
DIEA N,N-diisopropylethylamine
DMA N,N-dimethylacetamide
DMF dimethylformamide
DMSO dimethylsulfoxide
DPPF 1,1'-bis(diphenylphosphino)ferrocene
$Et_3N$ triethylamine
EtOAc ethyl acetate
EtOH ethanol
$^1$H NMR proton nuclear magnetic resonance
HOAc acetic acid
HPLC high pressure liquid chromatography
Hz hertz
KOAc potassium acetate
LCMS liquid chromatography/mass spectrometry
MS mass spectrometry
(M+I) mass+1
m-CPBA m-chloroperbenzoic acid
MeOH methanol
MsCl methanesulfonyl chloride
n-BuLi n-butyl lithium
Tf —$SO_2CF_3$
$Pd_2(dba)_3$ tris(dibenzylideneacetone)dipalladium(0)
$Pd(PPh_3)_4$ tetrakis(triphenylphosphine)palladium(0)
$PhNEt_2$ diethyl-phenyl-amine, also referred to as N,N-diethylaniline
$PPh_3$ triphenylphosphine
t-BuOK Potassium tert-butoxide
THF tetrahydrofuran
TLC thin layer chromatography

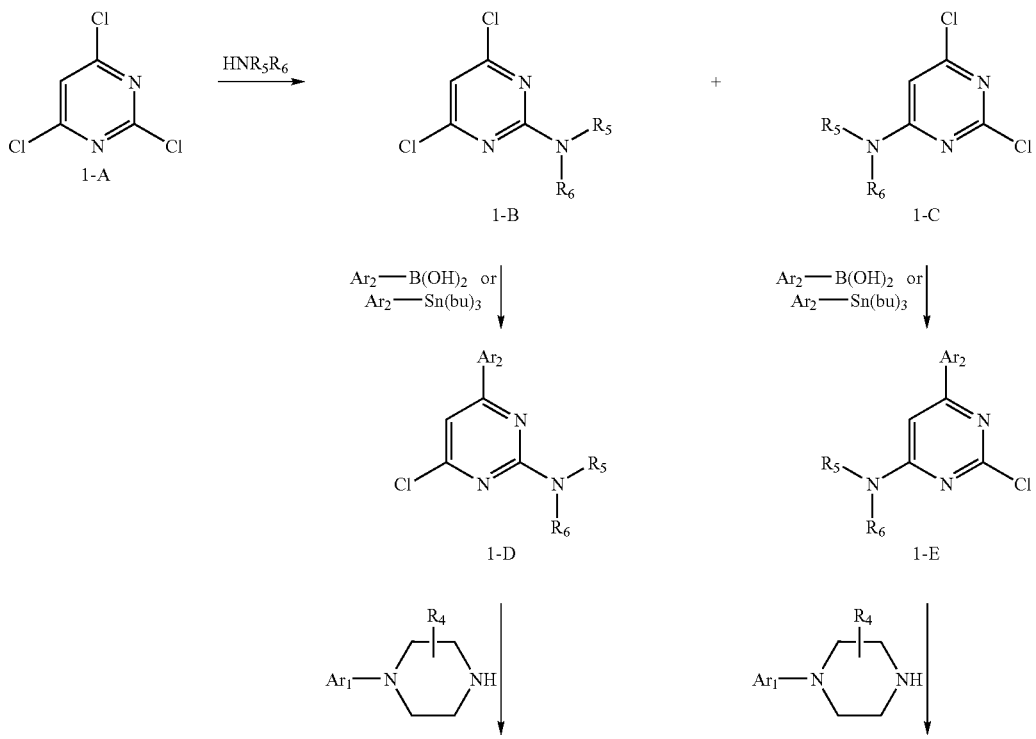

Scheme 1

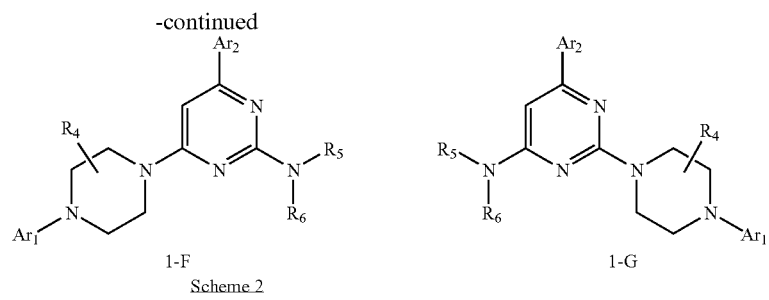
Scheme 2
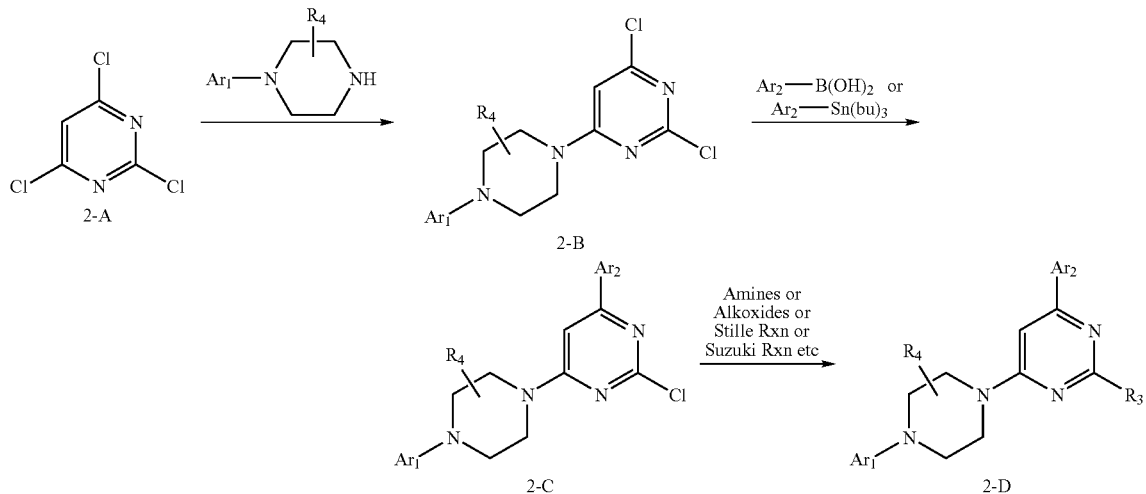
Scheme 3
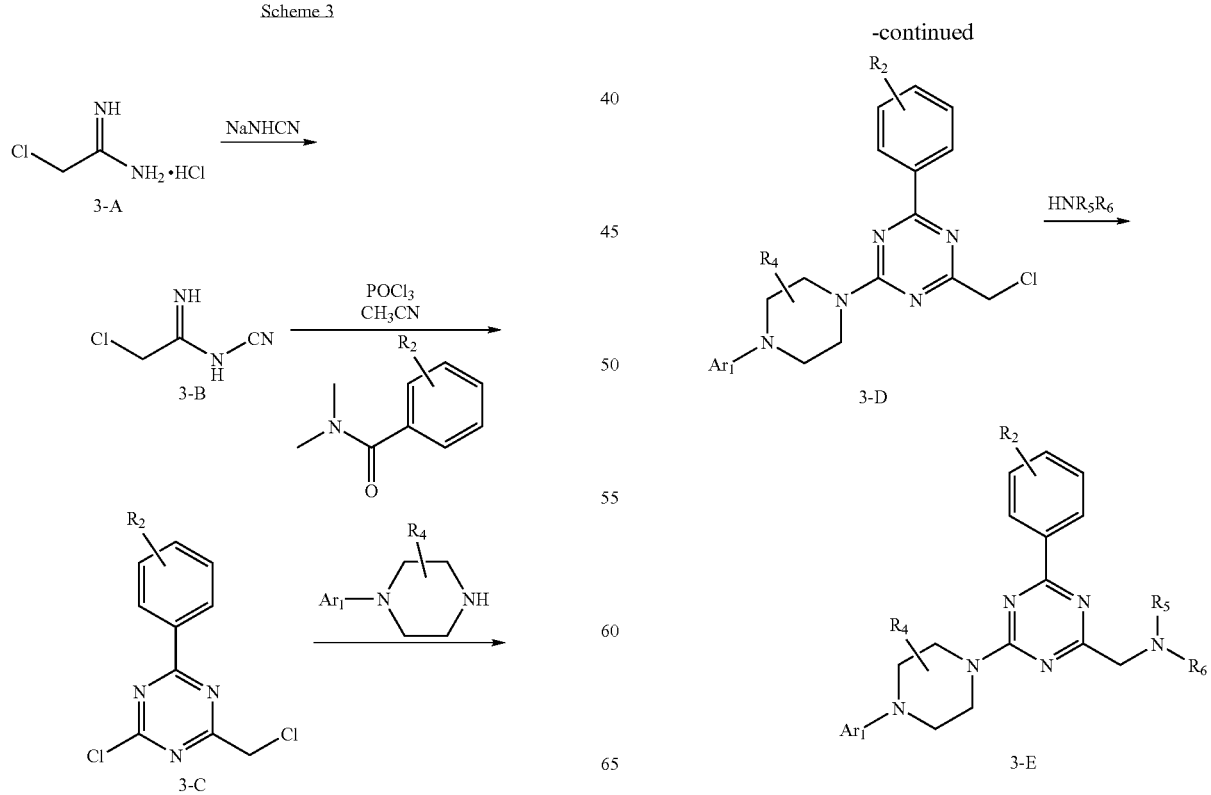

Scheme 4
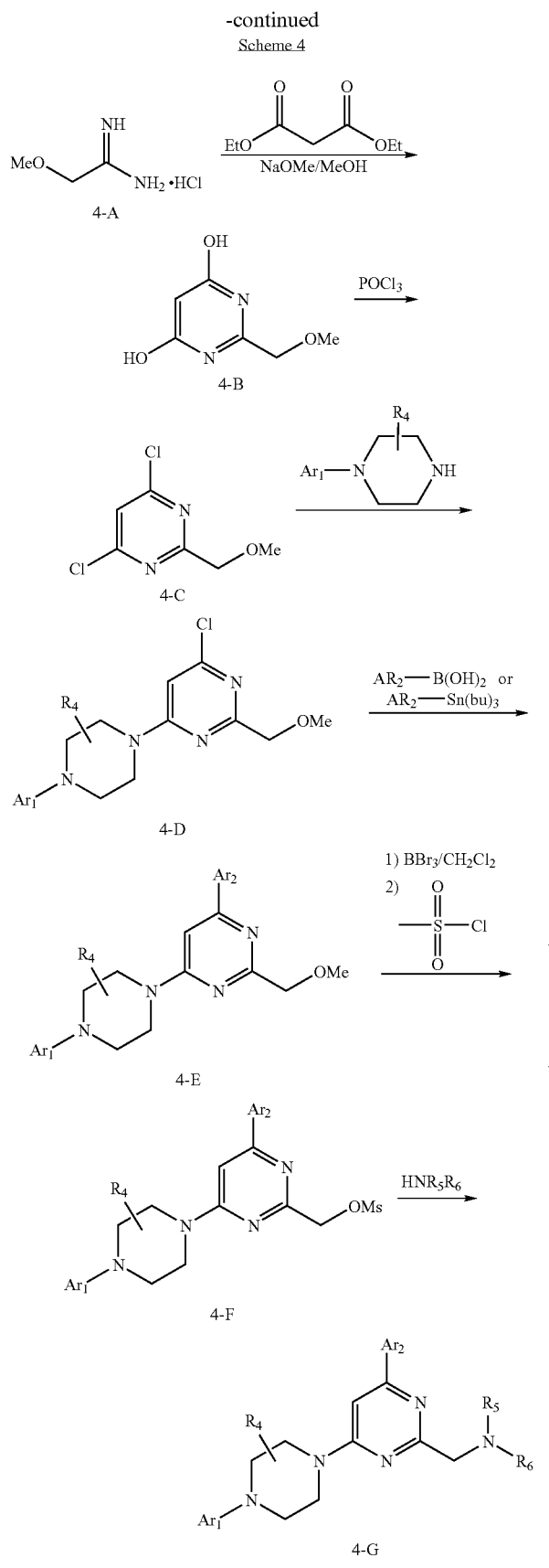
Scheme 5
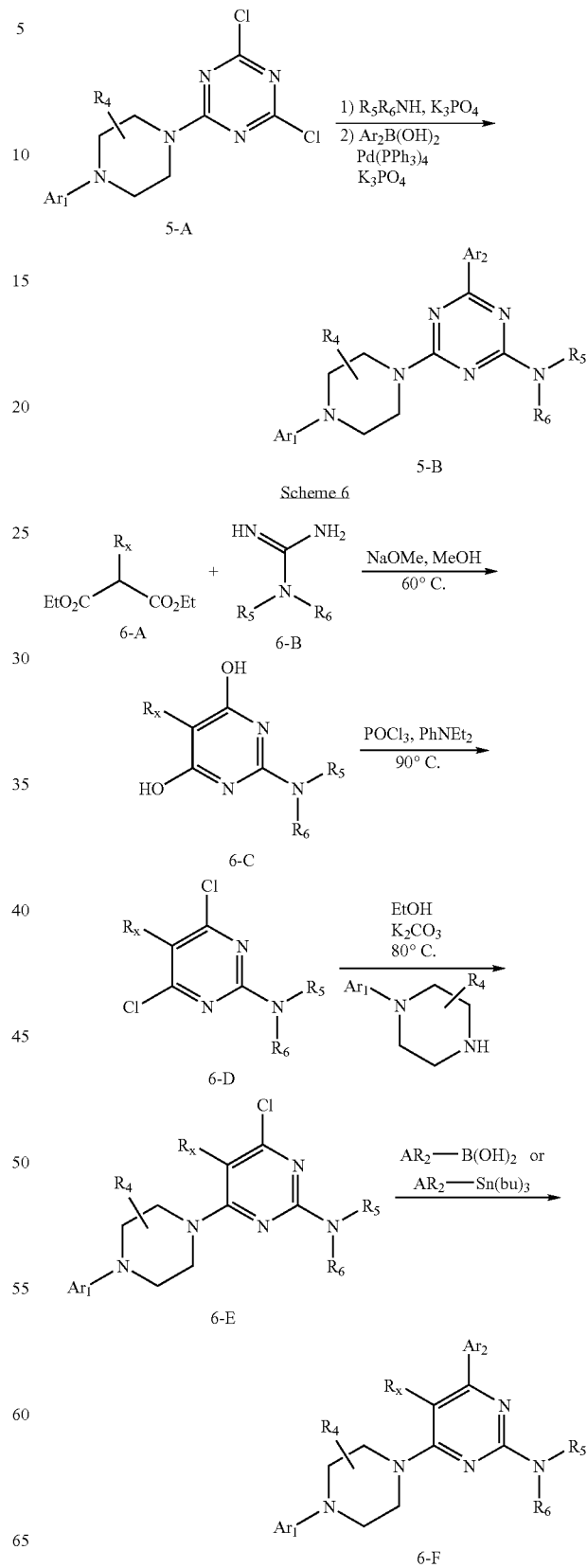

-continued
Scheme 7
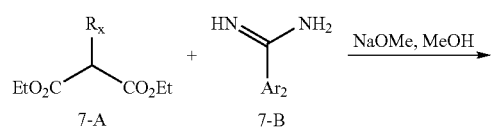
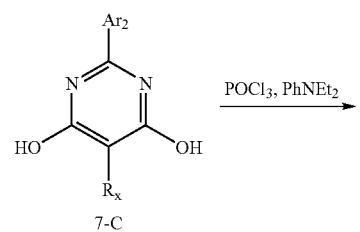
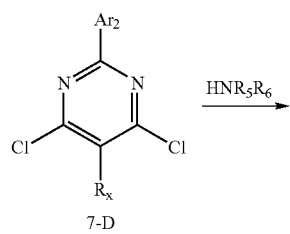
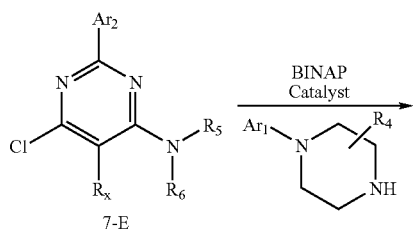
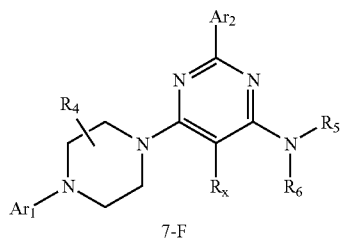
Scheme 8
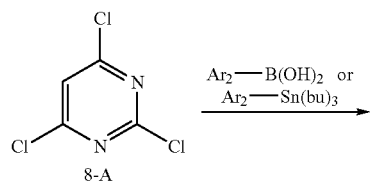
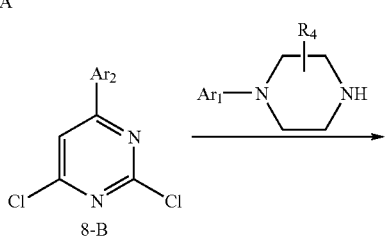
-continued
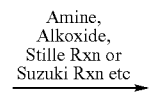
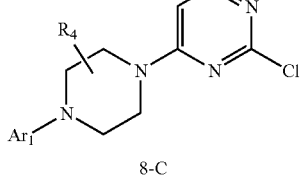
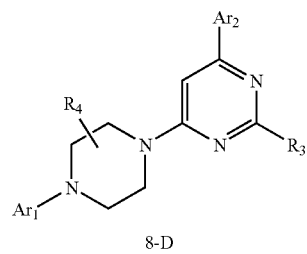
Scheme 9
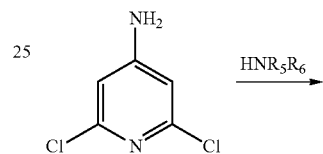
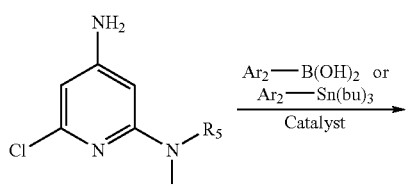
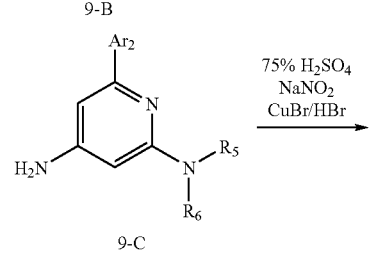
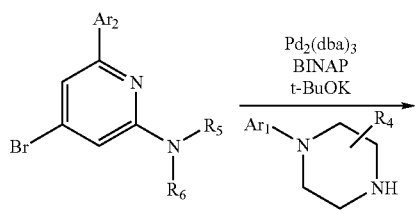
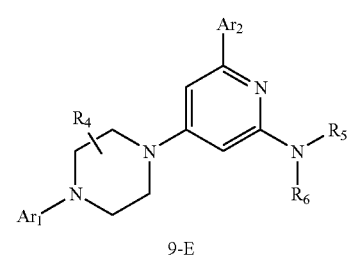

-continued
Scheme 10

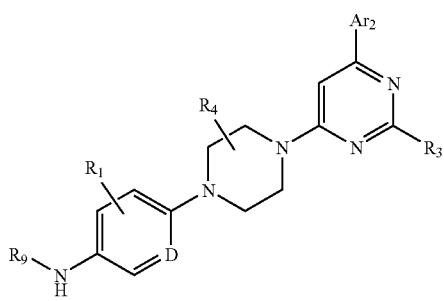

11-D $R_{20}$ = Br, Cl or OTf

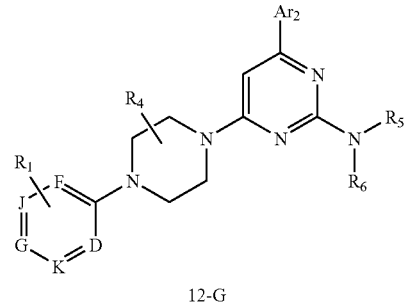

12-G

R = Me, CH$_2$Ph

Scheme 12

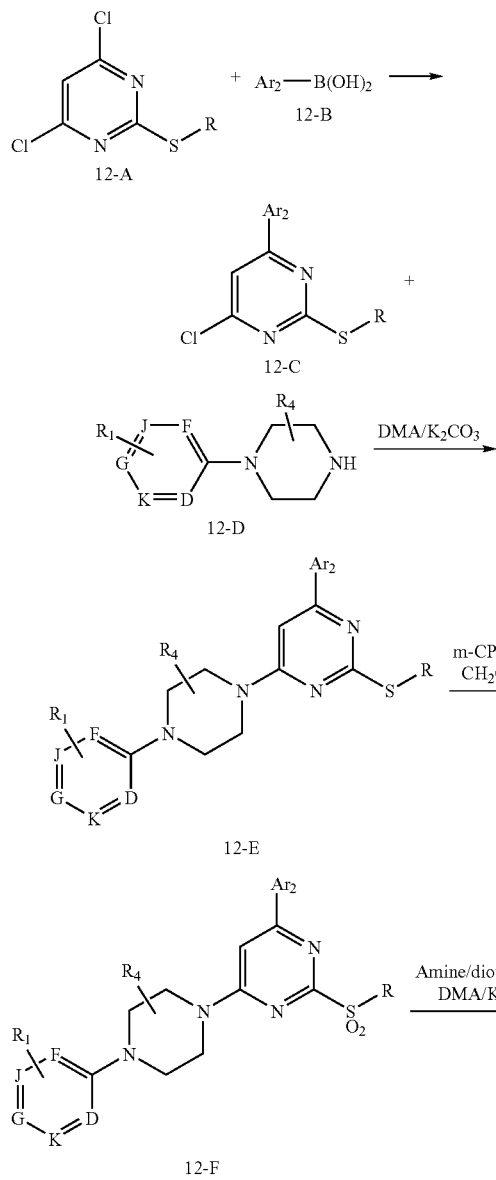

Scheme 13

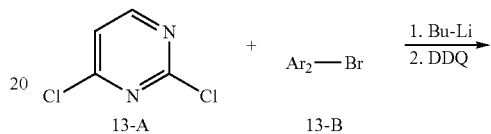

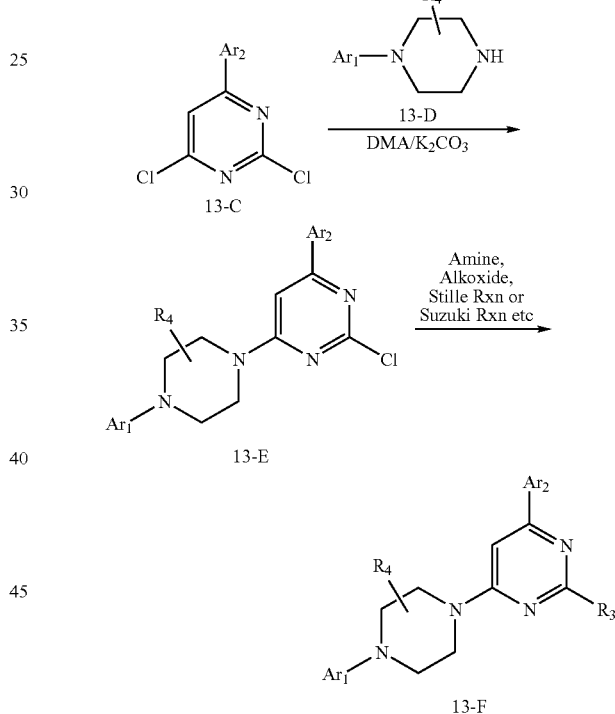

In certain embodiments, a compound provided herein may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}$C), hydrogen (e.g., $^3$H), sulfur (e.g., $^{35}$S), or iodine (e.g., $^{125}$I). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more compounds provided herein, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. In addition, other active ingredients may (but need not) be included in the pharmaceutical compositions provided herein. Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions suitable for oral use are preferred. Such compositions include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate. Formulation for topical administration may be preferred for certain conditions (e.g., in the treatment of skin conditions such as burns or itch). Formulation for direct administration into the bladder (intravesicular administration) may be preferred for treatment of urinary incontinence and overactive bladder.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and one or more sweetening agents, such as sucrose or saccharin.

Oily suspensions may be formulated by suspending the active ingredient(s) in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale-The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids and emulsions. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anticaking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

Modulators may also be formulated as suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a therapeutically effective amount. Preferred systemic doses are no higher than 50 mg per kilogram of body weight per day (e.g., ranging from about 0.001 mg to about 50 mg per kilogram of body weight per day), with oral doses generally being about 5-20 fold higher than intravenous doses (e.g., ranging from 0.01 to 40 mg per kilogram of body weight per day).

The amount of active ingredient that may be combined with the carrier materials to produce a single dosage unit will vary depending, for example, upon the patient being treated, the particular mode of administration and any other co-administered drugs. Dosage units will generally contain between from about 10 µg to about 500 mg of an active ingredient. Optimal dosages may be established using routine testing, and procedures that are well known in the art.

Pharmaceutical compositions may be packaged for treating conditions responsive to VR1 modulation (e.g., treatment of exposure to vanilloid ligand, pain, itch, obesity or urinary incontinence). Packaged pharmaceutical compositions may include a container holding a therapeutically effective amount of at least one VR1 modulator as described herein and instructions (e.g., labeling) indicating that the contained composition is to be used for treating a condition responsive to VR1 modulation in the patient.

Methods Of Use

VR1 modulators provided herein may be used to alter activity and/or activation of capsaicin receptors in a variety of contexts, both in vitro and in vivo. Within certain aspects, VR1 antagonists may be used to inhibit the binding of vanilloid ligand agonist (such as capsaicin and/or RTX) to capsaicin receptor in vitro or in vivo. In general, such methods comprise the step of contacting a capsaicin receptor with one or more VR1 modulators provided herein, in the presence of vanilloid ligand in aqueous solution and under conditions otherwise suitable for binding of the ligand to capsaicin receptor. The VR1 modulator(s) are generally present at a concentration that is sufficient to alter the binding of vanilloid ligand to VR1 in vitro (using the assay provided in Example 5) and/or VR1-mediated signal transduction (using an assay provided in Example 6). The capsaicin receptor may be present in solution or suspension (e.g., in an isolated membrane or cell preparation), or in a cultured or isolated cell. Within certain embodiments, the capsaicin receptor is expressed by a neuronal cell present in a patient, and the aqueous solution is a body fluid. Preferably, one or more VR1 modulators are administered to an animal in an amount such that the VR1 modulator is present in at least one body fluid of the animal at a therapeutically effective concentration that is 1 micromolar or less; preferably 500 nanomolar or less; more preferably 100 nanomolar or less, 50 nanomolar or less, 20 nanomolar or less, or 10 nanomolar or less. For example, such compounds may be administered at a dose that is less than 20 mg/kg body weight, preferably less than 5 mg/kg and, in some instances, less than 1 mg/kg.

Also provided herein are methods for modulating, preferably reducing, the signal-transducing activity (i.e., the calcium conductance) of a cellular capsaicin receptor. Such modulation may be achieved by contacting a capsaicin receptor (either in vitro or in vivo) with one or more VR1 modulators provided herein under conditions suitable for binding of the modulator(s) to the receptor. The VR1 modulator(s) are generally present at a concentration that is sufficient to alter the binding of vanilloid ligand to VR1 in vitro and/or VR1-mediated signal transduction as described herein. The receptor may be present in solution or suspension, in a cultured or isolated cell preparation or in a cell within a patient. For example, the cell may be a neuronal cell that is contacted in vivo in an animal. Alternatively, the cell may be an epithelial cell, such as a urinary bladder epithelial cell (urothelial cell) or an airway epithelial cell that is contacted in vivo in an animal. Modulation of signal transducing activity may be assessed by detecting an effect on calcium ion conductance (also referred to as calcium mobilization or flux). Modulation of signal transducing activity may alternatively be assessed by detecting an alteration of a symptom (e.g., pain, burning sensation, broncho-constriction, inflammation, cough, hiccup, itch, urinary incontinence or overactive bladder) of a patient being treated with one or more VR1 modulators provided herein.

VR1 modulator(s) provided herein are preferably administered to a patient (e.g., a human) orally or topically, and are present within at least one body fluid of the animal while modulating VR1 signal-transducing activity. Preferred VR1 modulators for use in such methods modulate VR1 signal-transducing activity in vitro at a concentration of 1 nanomolar or less, preferably 100 picomolar or less, more preferably 20 picomolar or less, and in vivo at a concentration of 1 micromolar or less, 500 nanomolar or less, or 100 nanomolar or less in a body fluid such as blood.

The present invention further provides methods for treating conditions responsive to VR1 modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to VR1 modulation" if it is characterized by inappropriate activity of a capsaicin receptor, regardless of the amount of vanilloid ligand present locally, and/or if modulation of capsaicin receptor activity results in alleviation of the condition or a symptom thereof. Such conditions include, for example, symptoms resulting from exposure to VR1-activating stimuli, pain, respiratory disorders such as asthma and chronic obstructive pulmonary disease, itch, urinary incontinence, overactive bladder, cough, hiccup, and obesity, as described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated. However, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Patients experiencing symptoms resulting from exposure to capsaicin receptor-activating stimuli include individuals with burns caused by heat, light, tear gas or acid and those whose mucous membranes are exposed (e.g., via ingestion, inhalation or eye contact) to capsaicin (e.g., from hot peppers or in pepper spray) or a related irritant such as acid, tear gas or air pollutants. The resulting symptoms (which may be treated using VR1 modulators, especially antagonists, provided herein) may include, for example, pain, broncho-constriction and inflammation.

Pain that may be treated using the VR1 modulators provided herein may be chronic or acute and includes, but is not limited to, peripheral nerve-mediated pain (especially neuropathic pain). Compounds provided herein may be used in the treatment of, for example, postmastectomy pain syndrome, stump pain, phantom limb pain, oral neuropathic pain, toothache (dental pain), denture pain, postherpetic neuralgia, diabetic neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome and/or bilateral peripheral neuropathy. Additional neuropathic pain conditions include causalgia (reflex sympathetic dystrophy —RSD, secondary to injury of a peripheral nerve), neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia), surgery-related pain, musculoskeletal pain, AIDS-related neuropathy, MS-related neuropathy, and spinal cord injury-related pain. Headache, including headaches involving peripheral nerve activity, such as sinus, cluster (i.e., migranous neuralgia) and some tension headaches and migraine, may also be treated as described herein. For example, migraine headaches may be prevented by administration of a compound provided herein as soon as a pre-migrainous aura is experienced by the patient. Further pain conditions that can be treated as described herein include "burning mouth syndrome," labor pains, Charcot's pains, intestinal gas pains, menstrual pain, acute and chronic back pain (e.g., lower back pain), hemorrhoidal pain, dyspeptic pains, angina, nerve root pain, homotopic pain and heterotopic pain—including cancer associated pain (e.g., in patients with bone cancer), pain (and inflammation) associated with venom exposure (e.g., due to snake bite, spider bite, or insect sting) and trauma associated pain (e.g., post-surgical pain, pain from cuts, bruises and broken bones, and burn pain). Additional pain conditions that may be treated as described herein include pain associated with inflammatory bowel disease, irritable bowel syndrome and/or inflammatory bowel disease.

Within certain aspects, VR1 modulators provided herein may be used for the treatment of mechanical pain. As used herein, the term "mechanical pain" refers to pain other than headache pain that is not neuropathic or a result of exposure to heat, cold or external chemical stimuli. Mechanical pain includes physical trauma (other than thermal or chemical burns or other irritating and/or painful exposures to noxious chemicals) such as post-surgical pain and pain from cuts, bruises and broken bones; toothache; denture pain; nerve root pain; osteoartiritis; rheumatoid arthritis; fibromyalgia; meralgia paresthetica; back pain; cancer-associated pain; angina; carpel tunnel syndrome; and pain resulting from bone fracture, labor, hemorrhoids, intestinal gas, dyspepsia, and menstruation.

Itching conditions that may be treated include psoriatic pruritis, itch due to hemodialysis, aguagenic pruritus, and itching associated with vulvar vestibulitis, contact dermatitis, insect bites and skin allergies. Urinary tract conditions that may be treated as described herein include urinary incontinence (including overflow incontinence, urge incontinence and stress incontinence), as well as overactive or unstable bladder conditions (including detrusor hyperflexia of spinal origin and bladder hypersensitivity). In certain such treatment methods, VR1 modulator is administered via a catheter or similar device, resulting in direct injection of VR1 modulator into the bladder. Compounds provided herein may also be used as anti-tussive agents (to prevent, relieve or suppress coughing) and for the treatment of hiccup, and to promote weight loss in an obese patient.

Within other aspects, VR1 modulators provided herein may be used within combination therapy for the treatment of conditions involving inflammatory components. Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebo-vascular disease and certain infectious diseases.

Within such combination therapy, a VR1 modulator is administered to a patient along with an anti-inflammatory agent. The VR1 modulator and anti-inflammatory agent may be present in the same pharmaceutical composition, or may be administered separately in either order. Anti-inflammatory agents include, for example, non-steroidal anti-inflammatory drugs (NSAIDs), non-specific and cyclooxygenase-2 (COX-2) specific cyclooxgenase enzyme inhibitors, gold compounds, corticosteroids, methotrexate, tumor necrosis factor (TNF) receptor antagonists, anti-TNF alpha antibodies, anti-C5 antibodies, and interleukin-1 (IL-1) receptor antagonists. Examples of NSAIDs include, but are not limited to ibuprofen (e.g., ADVIL™, MOTRIN™), flurbiprofen (ANSAID™), naproxen or naproxen sodium (e.g., NAPROSYN, ANAPROX, ALEVE™), diclofenac (e.g., CATAFLAM™, VOLTAREN™), combinations of diclofenac sodium and misoprostol (e.g., ARTHROTEC™), sulindac (CLINORIL™), oxaprozin (DAYPRO™), diflunisal (DOLOBID™), piroxicam (FELDENE™), indomethacin (INDOCIN™), etodolac (LODINE™), fenoprofen calcium (NALFON™), ketoprofen (e.g., ORUDIS™, ORUVAIL™), sodium nabumetone (RELAFEN™), sulfasalazine (AZULFIDINE™), tolmetin sodium (TOLECTIN™), and hydroxychloroquine (PLAQUENIL™). A particular class of NSAIDs consists of compounds that inhibit cyclooxygenase (COX) enzymes, such as celecoxib (CELEBREX™) and rofecoxib (VIOXX™). NSAIDs further include salicylates such as acetylsalicylic acid or aspirin, sodium salicylate, choline and magnesium salicylates (TRILISATE™), and salsalate (DISALCID™), as well as corticosteroids such as cortisone (CORTONE™ acetate), dexamethasone (e.g., DECADRON™), methylprednisolone (MEDROL™) prednisolone (PRELONE™), prednisolone sodium phosphate (PEDIAPRED™), and prednisone (e.g., PREDNICEN-M™, DELTASONE™, STERAPRED™).

Suitable dosages for VR1 modulator within such combination therapy are generally as described above. Dosages and methods of administration of anti-inflammatory agents can be found, for example, in the manufacturer's instructions in the *Physician's Desk Reference*. In certain embodiments, the combination administration of a VR1 modulator with an anti-inflammatory agent results in a reduction of the dosage of the anti-inflammatory agent required to produce a therapeutic effect (i.e., a decrease in the minimum therapeutically effective amount). Thus, preferably, the dosage of anti-inflammatory agent in a combination or combination treatment method of the invention is less than the maximum dose advised by the manufacturer for administration of the anti-inflammatory agent without combination administration of a VR1 antagonist. More preferably this dosage is less than %, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a VR1 antagonist. It will be apparent that the dosage amount of VR1 antagonist component of the combination needed to achieve the desired effect may similarly be affected by the dosage amount and potency of the anti-inflammatory agent component of the combination.

In certain preferred embodiments, the combination administration of a VR1 modulator with an anti-inflammatory agent is accomplished by packaging one or more VR1 modulators and one or more anti-inflammatory agents in the same package, either in separate containers within the package or in the same contained as a mixture of one or more VR1 antagonists and one or more anti-inflammatory agents. Preferred mixtures are formulated for oral administration (e.g., as pills, capsules, tablets or the like). In certain embodiments, the package comprises a label bearing indicia indicating that the one or more VR1 modulators and one or more anti-inflammatory agents are to be taken together for the treatment of an inflammatory pain condition. A highly preferred combination is one in which the anti-inflammatory agent(s) include at least one COX-2 specific cyclooxgenase enzyme inhibitor such as valdecoxib (BEXTRA®), lumiracoxib (PREXIGE™), etoricoxib (ARCOXIA®), celecoxib (CELEBREX®) and/or rofecoxib (VIOXX®).

Within further aspects, VR1 modulators provided herein may be used in combination with one or more additional pain relief medications. Certain such medications are also anti-inflammatory agents, and are listed above. Other such medications are narcotic analgesic agents, which typically act at one or more opioid receptor subtypes (e.g., μ, ? and/or d), preferably as agonists or partial agonists. Such agents include opiates, opiate derivatives and opioids, as well as pharmaceutically acceptable salts and hydrates thereof. Specific examples of narcotic analgesics include, within preferred embodiments, alfentanyl, alphaprodine, anileridine, bezitramide, buprenorphine, codeine, diacetyldihydromorphine, diacetylmorphine, dihydrocodeine, diphenoxylate, ethylmorphine, fentanyl, heroin, hydrocodone, hydromorphone, isomethadone, levomethorphan, levorphane, levorphanol, meperidine, metazocine, methadone, methorphan, metopon, morphine, opium extracts, opium fluid extracts, powdered opium, granulated opium, raw opium, tincture of opium, oxycodone, oxymorphone, paregoric, pentazocine, pethidine, phenazocine, piminodine, propoxyphene, racemethorphan, racemorphan, thebaine and pharmaceutically acceptable salts and hydrates of the foregoing agents.

Other examples of narcotic analgesic agents include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, butorphanol, clonitazene, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine methylpromide, morphine methylsulfonate, morphine-N-oxide, myrophin, naloxone, nalbuyphine, naltyhexone, nicocodeine, nicomorphine, noracymethadol, norlevorphanol, normethadone, normorphine, norpipanone, pentazocaine, phenadoxone, phenampromide, phenomorphan, phenoperidine, piritramide, pholcodine, proheptazoine, properidine, propiran, racemoramide, thebacon, trimeperidine and the pharmaceutically acceptable salts and hydrates thereof.

Further specific representative analgesic agents include, for example: TALWIN® Nx and DEMEROL® (both available from Sanofi Winthrop Pharmaceuticals; New York, N.Y.); LEVO-DROMORAN®; BUPRENEX® (Reckitt & Coleman Pharmaceuticals, Inc.; Richmond, Va.); MSIR® (Purdue Pharma L.P.; Norwalk, Conn.); DILAUDID® (Knoll Pharmaceutical Co.; Mount Olive, N.J.); SUBLIMAZE®; SUFENTA® (Janssen Pharmaceutica Inc.; Titusville, N.J.); PERCOCET®), NUBAIN®) and NUMORPHAN® (all available from Endo Pharmaceuticals Inc.; Chadds Ford, Pa.) HYDROSTAT® IR, MS/S and MS/L (all available from Richwood Pharmaceutical Co. Inc; Florence, Ky.), ORAMORPH® SR and ROXICODONE® (both available from Roxanne Laboratories; Columbus Ohio) and STADOL® (Bristol-Myers Squibb; New York, N.Y.). Still further analgesic agents include CB2-receptor agonists, such as AM1241, and compounds that bind to the a2d subunit, such as Neurontin (Gabapentin) and pregabalin.

Suitable dosages for VR1 modulator within such combination therapy are generally as described above. Dosages and methods of administration of other pain relief medications can be found, for example, in the manufacturer's instructions in the *Physician's Desk Reference*. In certain embodiments, the combination administration of a VR1 modulator with one or more additional pain medications results in a reduction of the dosage of each therapeutic agent required to produce a therapeutic effect (e.g., the dosage or one or both agent may less than ¾, less than ½, less than ¼ or less than 10% of the maximum dose listed above or advised by the manufacturer). In certain preferred embodiments, the combination administration of a VR1 modulator with one or more additional pain relief medications is accomplished by packaging one or more VR1 modulators and one or more additional pain relief medications in the same package, as described above.

Modulators that are VR1 agonists may further be used, for example, in crowd control (as a substitute for tear gas) or personal protection (e.g., in a spray formulation) or as pharmaceutical agents for the treatment of pain, itch, urinary incontinence or overactive bladder via capsaicin receptor desensitization. In general, compounds for use in crowd control or personal protection are formulated and used according to conventional tear gas or pepper spray technology.

Within separate aspects, the present invention provides a variety of non-pharmaceutical in vitro and in vivo uses for the compounds provided herein. For example, such compounds may be labeled and used as probes for the detection and localization of capsaicin receptor (in samples such as cell preparations or tissue sections, preparations or fractions thereof). In addition, compounds provided herein that comprise a suitable reactive group (such as an aryl carbonyl, nitro or azide group) may be used in photoaffinity labeling studies of receptor binding sites. In addition, compounds provided herein may be used as positive controls in assays for receptor activity, as standards for determining the ability of a candidate agent to bind to capsaicin receptor, or as radiotracers for positron emission tomography (PET) imaging or for single photon emission computerized tomography (SPECT). Such methods can be used to characterize capsaicin receptors in living subjects. For example, a VR1 modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of capsaicin receptor in the sample. Detection assays, including receptor autoradiography (receptor mapping) of capsaicin receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, capsaicin receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Modulators provided herein may further be used within assays for the identification of other agents that bind to capsaicin receptor. In general, such assays are standard competition binding assays, in which bound, labeled VR1 modulator is displaced by a test compound. Briefly, such assays are performed by: (a) contacting capsaicin receptor with a radiolabeled VR1 modulator as described herein, under conditions that permit binding of the VR1 modulator to capsaicin receptor, thereby generating bound, labeled VR1 modulator; (b) detecting a signal that corresponds to the amount of bound, labeled VR1 modulator in the absence of test agent; (c) contacting the bound, labeled VR1 modulator with a test agent; (d) detecting a signal that corresponds to the amount of bound labeled VR1 modulator in the presence of test agent; and (e) detecting a decrease in signal detected in step (d), as compared to the signal detected in step (b), and therefrom identifying an agent that binds to capsaicin receptor.

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

Example 1

Preparation of Representative Biaryl Piperazinyl-Pyridine Analogues

This Example illustrates the preparation of representative biaryl piperazinyl-pyridine analogues. Mass spectroscopy data in this and the following Examples is Electrospray MS, obtained in positive ion mode using a Micromass Time-of-Flight LCT (Micromass, Beverly Mass.), equipped with a Waters 600 pump (Waters Corp., Milford, Mass.), Waters 996 photodiode array detector, Gilson 215 autosampler (Gilson, Inc. Middleton, Wis.), and a Gilson 841 microinjector. MassLynx (Advanced Chemistry Development, Inc; Toronto, Canada) version 4.0 software with OpenLynx processing was used for data collection and analysis. MS conditions were as follows: capillary voltage=3.5 kV; cone voltage=30 V, desolvation and source temperature=350° C. and 120° C., respectively; mass range=181-750 with a scan time of 0.22 seconds and an interscan delay of 0.05 minutes.

Sample volume of 1 microliter was injected onto a 50×4.6 mm Chromolith SpeedROD RP-18e column (Merck KGaA, Darmstadt, Germany), and eluted using a 2-phase linear gradient at 6 ml/min flow rate. Sample was detected using total absorbance count over the 220-340 nm UV range. The elution conditions were: Mobile Phase A-95/5/0.05 Water/Methanol/TFA; Mobile Phase B-5/95/0.025 Water/Methanol/TFA.

If no method or "LCMS Method B" is indicated, the following gradient was used:

| Gradient: | |
| --- | --- |
| Time (min) | % B |
| 0 | 10 |
| 0.5 | 100 |
| 1.2 | 100 |
| 1.21 | 10 |

Inject to inject cycle 2.2 minutes.

If "Method A" is indicated, the following gradient was used:

| Gradient: | |
| --- | --- |
| Time (min) | % B |
| 0 | 10 |
| 0.3 | 100 |
| 1.7 | 100 |
| 1.71 | 10 |

Inject to inject cycle 2.7 minutes.

A. 4-{4-(3-chloro-4-fluoro-phenyl)-6-[4-(3-trifluoromethyl-pyridin-2-yl)-piperazin-1-yl]-pyrimidin-2-yl}-morpholine 1. 4,6-dichloro-2-morpholinopyrimidine

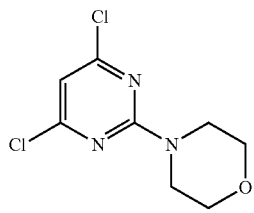

To an ice-cold solution containing 2,4,6-trichloropyrimidine (8 g, 44 mmol) in MeOH (80 mL) and NaHCO$_3$ (10 g) add slowly and dropwise a methanolic solution (20 mL) of morpholine (4 mL, 46 mmol). Allow the mixture to warm to 25° C. and stir overnight. Before diluting with water, vigorously stir for 1 hour, and filter to give white crystalline solid (10 g) as a mixture of regioisomers. Carefully recrystallize from toluene to give 6-morpholino-2,4-dichloropyrimidine. Concentrate the mother liquor and carefully recrystallize from EtOH to give 4,6-dichloro-2-morpholinopyrimidine.

2. 4-{4-(3-chloro-4-fluoro-phenyl)-6-[4-(3-trifluoromethyl-pyridin-2-yl)-piperazin-1-yl]-pyrimidin-2-yl}-morpholine

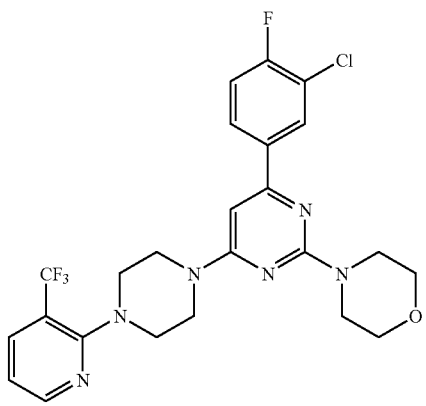

To a rubber-septum-capped vial containing 4,6-dichloro-2-morpholinopyrimidine (0.2 M in dioxane, 0.25 mL) and 1-(3-trifluoromethyl-pyridin-2-yl)-piperazine (0.2 M in dioxane, 0.28 mL) (Oakwood Products, Inc., West Columbia, S.C.) add aqueous K$_3$PO$_4$ (0.5 M, 0.125 mL). Heat the mixture at 90° C. for 24 hours. After cooling, add 3-chloro-4-fluorophenylboronic acid (0.2 M in dioxane, 0.35 mL) and K$_3$PO$_4$ (0.5 M in water, 0.10 mL) and flush the vial with argon. Add Pd(PPh$_3$)$_4$ (0.01 M in toluene, 0.125 mL). Heat the mixture at 80° C. overnight, add EtOAc(0.5 mL), separate the organic phase and load onto a 6-mL cartridge containing 1 g of SCX (a sulfonic acid-pregnated silica gel strong cation exchanger). Wash the SCX cartridge with 5 mL of MeOH and elute the product with 10% Et$_3$N in EtOAc (5 mL). Concentrate the eluent to give the pure product which can be converted to the HCl salt: LCMS (m/e); 523, $^1$H NMR (CDCl$_3$); d 3.4 (br s, 4 H), 3.8 (br s, 4 H), 4.0 (br s, 8 H), 6.4 (br s, 1H), 7.1 (br s, 1H), 7.2 (br s, 1H), 7.9 (m, 3 H), 8.5 (s, 1H).

B. Cyclopentyl-[4-[2-methyl-4-(3-trifluoromethyl-pyridin-2-yl)-piperazin-1-yl]-6-(3-trifluoromethyl-phenyl)-[1,3,5]triazin-2-ylmethyl]-amine 1. N,N-Dimethyl-3-trifluoromethyl-benzamide

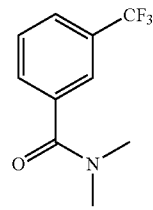

Vigorously stir a solution of 3-trifluoromethyl-benzoyl chloride (10.5 g, 0.05 mol) and dimethylamine HCl (8.3 g, 0.1 mol) in toluene (100 mL) and 1.0 M NaOH solution (300 mL) for 2 hours. Separate the organic layer, dry it (Na$_2$SO$_4$) and concentrate under reduced pressure to give the title compound as a crystalline solid.

2. 2-Chloro-4-chloromethyl-6-(3-trifluoromethyl-phenyl)-[1,3,5]triazine

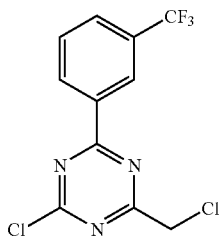

Add phosphorus oxychloride (POCl$_3$, 3.5 mL) to a solution of N,N-dimethyl-3-trifluoromethyl-benzamide (3.0 g, 0.0138 mol) in acetonitrile at room temperature. Add (N-cyano)-2-chloroacetamidine (1.62 g, 0.0138 mol) to the clear colorless solution all at once and stir at room temperature for 16 hours. Remove the solvent under reduced pressure and partition between EtOAc and aqueous NaHCO$_3$. Dry the organic layer (Na$_2$SO$_4$) and concentrate under reduced pressure. Chromatograph the crude product (hexanes to 15% EtOAc/hexanes eluent) and isolate the pure product as a clear colorless oil.

3. 3-Methyl-1-(3-trifluoromethyl-pyridin-2-yl)-piperazine

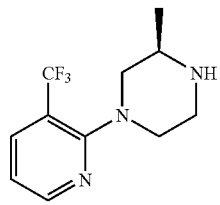

Dissolve 2-chloro-3-trifluoromethylpyridine (0.057 moles) and (R)-(−)-2-methylpiperazine (5.75 g, 0.057 moles) in DMA(125.0 mL) under nitrogen atmosphere. Add anhydrous powdered K$_2$CO$_3$ (23.75 g, 0.172 moles) to this mixture and stir at 135-140° C. for 48 hours. Cool the reaction mixture to room temperature, dilute with water (400 mL), extract with EtOAc (3×200 mL) and wash the combined organic extract 4. 2-Chloromethyl-4-[2-methyl-4-(3-trifluoromethyl-pyridin-2-yl)-piperazin-1-yl]-6-(3-trifluoromethyl-phenyl)-[1,3,5]triazine

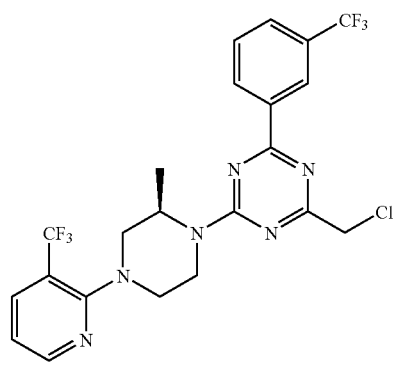

Dissolve 2-chloro-4-chloromethyl-6-(3-trifluoromethylphenyl)-[1,3,5]triazine (1.5 g, 0.0049 mol) in acetonitrile and add DIEA (1.28 mL, 0.0074 mol, 1.5 eq). Add 3-methyl-1-(3-trifluoromethyl-pyridin-2-yl)-piperazine (1.32 g, 0.0054 mol, 1.1 eq) and stir at room temperature for 2 hours. Concentrate under reduced pressure, partition between EtOAc and aqueous NaHCO$_3$ and dry the organic layer (Na$_2$SO$_4$). Filter the crude product through a silica gel plug (15% EtOAc/hexanes) to remove unreacted arylpiperazine. Removal of solvent under reduced pressure yields pure product.

5. Cyclopentyl-[4-[2-methyl-4-(3-trifluoromethyl-pyridin-2-yl)-piperazin-1-yl]-6-(3-trifluoromethyl-phenyl)-[1,3,5]triazin-2-ylmethyl]-amine

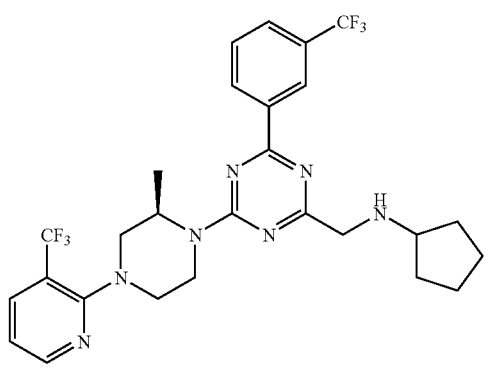

Dissolve 2-chloromethyl-4-[2-methyl-4-(3-trifluoromethyl-pyridin-2-yl)-piperazin-1-yl]-6-(3-trifluoromethyl-phenyl)-[1,3,5]triazine (50 mg, 0.097 mmol) in DMA (1 mL) and add cyclopentylamine (40 μL, 4 eq). Heat the solution at 80° C. for 1.5 hours, and then partition the reaction mixture between saturated aqueous NaHCO$_3$ and EtOAc. Wash the organic layer with water (3×), dry it (Na$_2$SO$_4$), and concentrate under reduced pressure. Chromatograph the crude product on preparative TLC plates (10% MeOH/DCM eluent) to afford pure product.

C. 4-(2-(3-Chlorophenyl)-6-{4-[3-(trifluoromethyl)(2-pyridyl)]piperazinyl}pyrimidin-4-yl)morpholine 1. 2-(3-Chlorophenyl)pyrimidine-4,6-diol

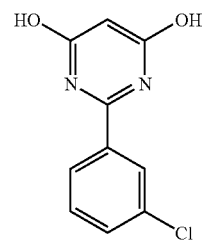

Heat a mixture of sodium methoxide in MeOH (19.2 ml, 96 mmol), 3-chloro-benzamidine hydrochloride (12.1 g, 64 mmol) and diethyl malonate (10.3 g, 64 mmol) at 50° C. for 8 hours. Cool the mixture and concentrate under reduced pressure. Dissolve the white gum in water and acidify the solution with concentrated sulfuric acid. Collect the resulting white solid by filtration, wash with water and air dry to give the title compound.

2. 4,6-Dichloro-2-(3-chlorophenyl)pyrimidine

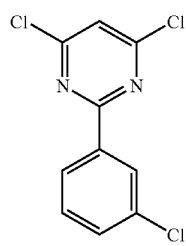

Heat a mixture of 2-(3-chlorophenyl)pyrimidine-4,6-diol (13.5 g, 61 mmol), PhNEt$_2$ (15 g, 122 mmol) and POCl$_3$ (75 mL) at 90° C. for 8 hours. Remove the excess POCl$_3$ by evaporation, add water (200 mL), collect the solid by filtration and air-dry to give the title compound.

3. 4-[6-Chloro-2-(3-chlorophenyl)pyrimidin-4-yl]morpholine

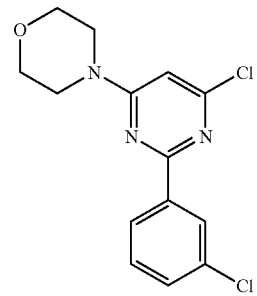

Heat a mixture of 4,6-dichloro-2-(3-chlorophenyl)pyrimidine (1.3 g, 5 mmol), morpholine (0.52 g, 6 mmol), potassium carbonate (0.828 g, 6 mmol) in toluene (15 mL) at 110° C. for 2 hours. Filter the reaction mixture and evaporate the filtrate. Add water to the residue and then extract with EtOAc (3×25 mL). Wash the combined extracts with brine (50 mL), dry 4. 4-(2-(3-Chlorophenyl)-6-{4-[3-(trifluoromethyl)(2-pyridyl)]piperazinyl}pyrimidin-4-yl)morpholine

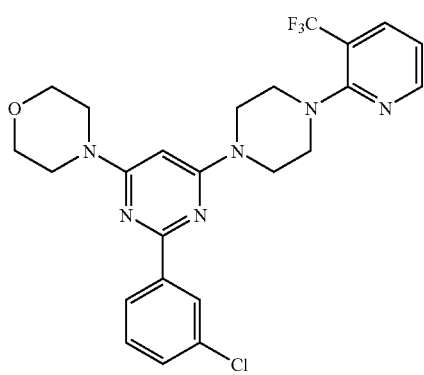

Add 4-(6-trifluoromethyl-2-pyridyl)piperazine (46 mg, 0.2 mmol) to a solution of 4-[6-chloro-2-(3-chlorophenyl)pyrimidin-4-yl]morpholine (62 mg, 0.2 mmol), Pd$_2$(dba)$_3$ (18 mg, 0.02 mmol), and BINAP (17 mg, 0.02 mmol) in toluene (2 mL) under nitrogen, followed by t-BuOK (45 mg, 0.4 mmol). Stir the mixture at 90° C. for 8 hours, dilute with aqueous ammonium chloride, and extract with EtOAc (3×10 mL). Dry (MgSO$_4$) the combined extracts and concentrate under reduced pressure. Purify the residue using flash chromatography on silica gel (50% hexane/50% ether) to give the title compound. MS 505 (M+1).

D. 4-(4-(3-Chloro-4-fluorophenyl)-5-methyl-6-{4-[3-(trifluoromethyl)(2-pyridyl)]piperazinyl}pyrimidin-2-yl)morpholine 1. 5-Methyl-2-morpholin-4-ylpyrimidine-4,6-diol

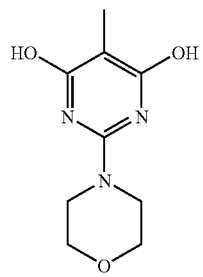

A mixture of sodium methoxide in MeOH (15 ml, 45 mmol), morpholinoformamidine hydrobromide (6.3 g, 30 mmol) and diethyl methylmalonate (5.22 g, 30 mmol) is heated at 50° C. for 2 hours. The mixture is cooled and concentrated under reduced pressure. The white gum is dissolved in water and the solution acidified with concentrated sulfuric acid. The resulting white solid is collected by filtration, washed with water and air dried to give the title compound.

2. 4-(4,6-Dichloro-5-methylpyrimidinyl-2-yl)morpholine

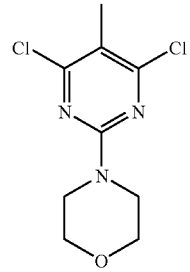

A mixture of 5-methyl-2-morpholin-4-ylpyrimidine-4,6-diol (3.57 g, 17 mmol), PhNEt$_2$ (4.37 g, 35 mmol) and POCl$_3$ (25 mL) is heated at 90° C. for 2 hours. The excess POCl$_3$ is removed by evaporation, water (100 mL) is added and the solution extracted with EtOAc (3×100 mL). The combined organics are washed with 1 M hydrochloric acid (100 mL), water (100 mL), brine (100 mL), dried (MgSO$_4$) and concentrated under reduced pressure to give the title compound, which is used without further purification.

3. 4-(4-Chloro-5-methyl-6-{4-[3-(trifluoromethyl)(2-pyridyl)]piperazinyl}pyrimidin-2-yl)morpholine

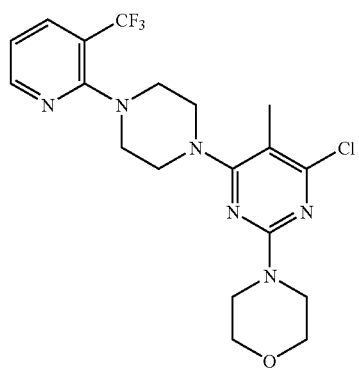

A mixture of 4-(4,6-dichloro-5-methylpyrimidinyl-2-yl)morpholine (496 mg, 2.0 mmol), 4-(6-trifluoromethyl-2-pyridyl)piperazine (462 mg, 2.0 mmol), potassium carbonate (345 mg, 2.5 mmol) and EtOH (10 mL) is heated at 78° C. for 8 hours. The mixture is cooled, diluted with water (20 mL) and extracted with EtOAc (3×25 mL). The combined organics are washed with brine (25 mL), dried (MgSO$_4$) and concentrated under reduced pressure. The residue is purified by flash chromatography on silica gel (80% hexane/20% ether) to give the title compound.

4. 4-(4-(3-Chloro-4-fluorophenyl)-5-methyl-6-{4-[3-(trifluoromethyl)(2-pyridyl)]piperazinyl}pyrimidin-2-yl)morpholine

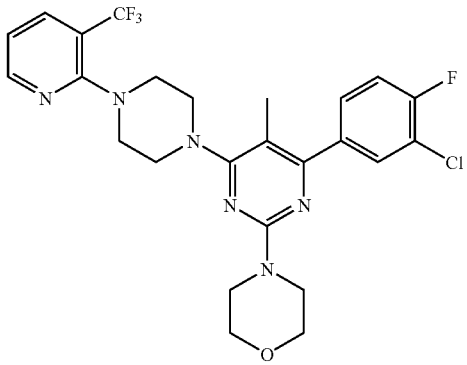

A mixture of 4-(4-chloro-5-methyl-6-{4-[3-(trifluoromethyl)(2-pyridyl)]piperazinyl}pyrimidin-2-yl)morpholine (66 mg, 0.15 mmol), 3-chloro-4-fluorophenylboronic acid (35 mg, 0.2 mmol), Pd(PPh$_3$)$_4$ (10 mg) and 2M potassium carbonate (0.2 mL) in toluene (3 mL) is heated, under a nitrogen atmosphere, at 80° C. for 4 hours. The reaction mixture is cooled and the layers separated. The aqueous layer is extracted with EtOAc (3×10 mL) and the combined organics washed with 4M NaOH (10 mL), water (10 mL), brine (10 mL), dried (MgSO$_4$) and concentrated under reduced pressure. The residue is purified by flash chromatography on silica gel (70% hexane/30% ether) to give the title compound. MS 537 (M+1).

E. {4-(3-Chloro-phenyl)-6-[4-(3-trifluoromethyl-pyridin-2-yl)-piperazin-1-yl]-pyrimidin-2-ylmethyl}-diethyl-amine 1. 2-methoxymethyl-pyrimidine-4,6-diol

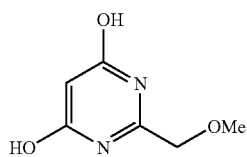

Reflux a mixture of malonic acid diethyl ester (7.96 g, 50 mmol), 2-methoxy-acetamidine hydrochloride (6.2 g, 50 mmol), and NaOMe MeOH solution (4.37 M, 22.7 mL, 100 mmol) in MeOH (30 mL) for 24 hours. Concentrate, dilute with H$_2$O (50 mL), wash with EtOAc, and concentrate the aqueous layer. Extract with MeOH and concentrate to yield 2-methoxymethyl-pyrimidine-4,6-diol.

2. 4,6-dichloro-2-methoxymethyl-pyrimidine

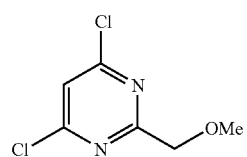

Reflux a mixture of 2-methoxymethyl-pyrimidine-4,6-diol (4.1 g) and POCl$_3$ (30 mL) for 2 hours. Cool to room temperature, concentrate, partition between sat. NaHCO$_3$ and EtOAc. Dry over Na$_2$SO$_4$, concentrate under vacuum, and purify by flash column (2:1 hexanes/EtOAc) to give 4,6-dichloro-2-methoxymethyl-pyrimidine.

3. 4-chloro-2-methoxymethyl-6-[4-(3-trifluoromethyl-pyridin-2-yl)-piperazin-1-yl]-pyrimidine

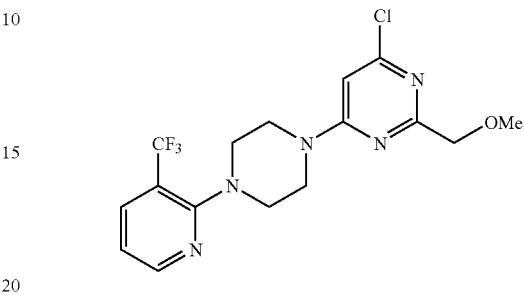

Combine 4,6-dichloro-2-methoxymethyl-pyrimidine (800 mg, 4.14 mmol), 1-(3-trifluoromethyl-pyridin-2-yl)-piperazine (960 mg, 4.14 mmol), sodium bicarbonate (500 mg), and EtOH (50 mL). Reflux for 4 hours, let cool to room temperature, vacuum filter, and evaporate the mother liquor. Purify the residue by column chromatography eluting with 20:1 DCM/MeOH to obtain 4-chloro-2-methoxymethyl-6-[4-(3-trifluoromethyl-pyridin-2-yl)-piperazin-1-yl]-pyrimidine as a white solid.

4. 4-(3-chloro-phenyl)-2-methoxymethyl-6-[4-(3-trifluoromethyl-pyridin-2-yl)-piperazin-1-yl]-pyrimidine

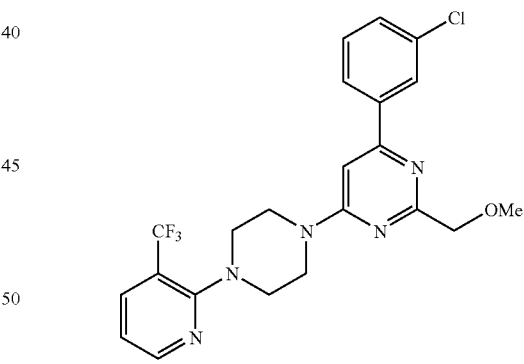

Combine 4-chloro-2-methoxymethyl-6-[4-(3-trifluoromethyl-pyridin-2-yl)-piperazin-1-yl]-pyrimidine (388 mg, 1 mmol), 3-chlorophenylboronic acid (157 mg, 1 mmol), Pd(P(Ph)$_3$)$_4$ (100 mg, 0.09 mmol), 2M aqueous sodium carbonate (1 mL), and 1,2-dimethoxyethane (5 mL) under nitrogen. Reflux for 16 hours. Evaporate and add water (5 mL), and extract with EtOAc. Dry the organic layer with sodium sulfate and purify by liquid chromatography, to obtain 4-(3-chloro-phenyl)-2-methoxymethyl-6-[4-(3-trifluoromethyl-pyridin-2-yl)-piperazin-1-yl]-pyrimidine as a white solid.

5. 2-bromomethyl-4-(3-chloro-phenyl)-6-[4-(3-trifluoromethyl-pyridin-2-yl)-piperazin-1-yl]-pyrimidine

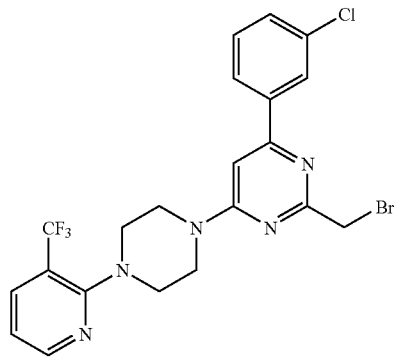

Stir a mixture of 4-(3-chloro-phenyl)-2-methoxymethyl-6-[4-(3-trifluoromethyl-pyridin-2-yl)-piperazin-1-yl]-pyrimidine in a solution of 30% HBr in HOAc (25 mL) at 60° C. for 3 hours. Evaporate the mixture, adjust the pH to basic with 1M NaOH, and collect a tan solid. Purify by liquid chromatography (3:1 hexanes/EtOAc) to obtain 2-bromomethyl-4-(3-chloro-phenyl)-6-[4-(3-trifluoromethyl-pyridin-2-yl)-piperazin-1-yl]-pyrimidine as a yellow solid.

6. {4-(3-Chloro-phenyl)-6-[4-(3-trifluoromethyl-pyridin-2-yl)-piperazin-1-yl]-pyrimidin-2-ylmethyl}-diethyl-amine

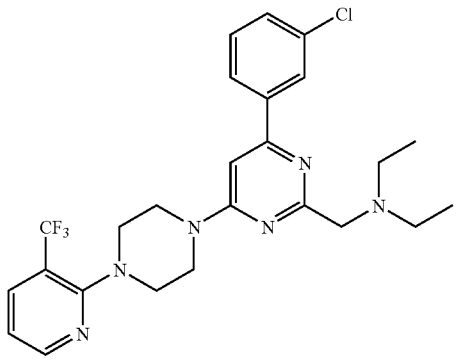

Combine 2-bromomethyl-4-(3-chloro-phenyl)-6-[4-(3-trifluoromethyl-pyridin-2-yl)-piperazin-1-yl]-pyrimidine (32 mg, 0.06 mmol), diethylamine (0.5 mL), DMA (2 mL) and heat at 80° C. for 3 hours. Let cool to room temperature and add water (5 mL). Extract with EtOAc (10 mL), wash with water (10 mL), dry ($Na_2SO_4$) and evaporate. Purify by column chromatography (1:1 hexanes/EtOAc) to obtain {4-(3-chloro-phenyl)-6-[4-(3-trifluoromethyl-pyridin-2-yl)-piperazin-1-yl]-pyrimidin-2-ylmethyl}-diethyl-amine as a yellow solid.

F. 4-(3-Chloro-4-fluoro-phenyl)-2-methoxy-6-[4-(3-trifluoromethyl-pyridin-2-yl)-piperazin-1-yl]-pyrimidine

1. 2,4-Dichloro-6-(3-chloro-4-fluoro-phenyl)-pyrimidine

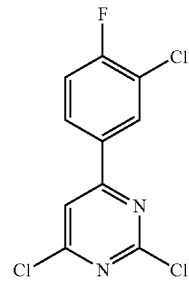

Combine 2,4,6-trichloropyrimidine (9.15 g, 0.05 mol), 3-chloro-4-fluorophenylboronic acid (8.7 g, 0.05 mol), 1,2-dimethoxyethane (300 mL), and 2M aqueous sodium carbonate (25 mL) and let stir under nitrogen for 10 minutes. Add palladium acetate (56 mg, 0.25 mmol) and $PPh_3$ (131 mg, 0.5 mmol) and reflux the mixture for 16 hours. Evaporate, add water (100 mL), and extract twice with DCM (25 mL each). Dry the organic layer with sodium sulfate and evaporate, giving a yellow gum. The mixture is chromatographed with 20:1 hexanes/EtOAc, affording 2,4-dichloro-6-(3-chloro-4-fluoro-phenyl)-pyrimidine as a white solid.

2. 2-Chloro-4-(3-chloro-4-fluoro-phenyl)-6-[4-(3-trifuoromethyl-pyridin-2-yl)-piperazin-1-yl]-pyrimidine

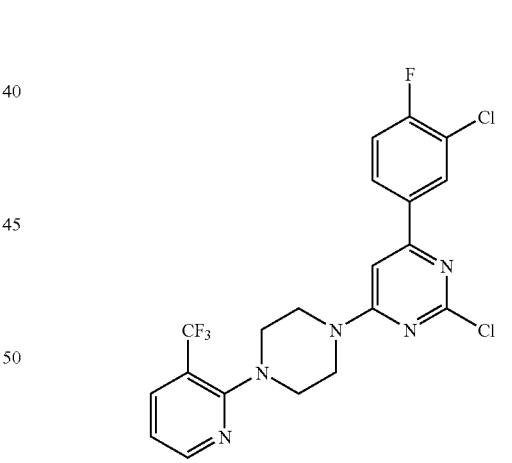

Combine 2,4-dichloro-6-(3-chloro-4-fluoro-phenyl)-pyrimidine (1.6 g, 5.75 mmol), sodium bicarbonate (1.28 g, 15 mmol), MeOH (100 mL) and cool over ice. Drip in a mixture of 1-(3-trifluoromethyl-pyridin-2-yl)-piperazine (1.33 g, 5.75 mmol) in MeOH (50 mL), and let the reaction stir for 16 hours at room temperature. Evaporate the mixture and purify directly using 10:1 hexanes/EtOAc, obtaining 2-chloro-4-(3-chloro-4-fluoro-phenyl)-6-[4-(3-trifluoromethyl-pyridin-2-yl)-piperazin-1-yl]-pyrimidine as a white solid.

3. 4-(3-chloro-4-fluoro-phenyl)-2-methoxy-6-[4-(3-trifluoromethyl-pyridin-2-yl)-piperazin-1-yl]-pyrimidine

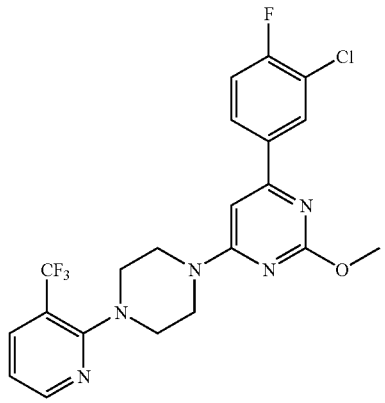

Combine a mixture of 2-chloro-4-(3-chloro-4-fluoro-phenyl)-6-[4-(3-trifluoromethyl-pyridin-2-yl)-piperazin-1-yl]-pyrimidine (47 mg, 1 mmol), tetrahydrofuran (1 mL), and a 21% solution of sodium methoxide in MeOH (0.5 mL). Let the reaction stir at 60° C. for 16 hours. Evaporate the mixture, add water (5 mL), and extract twice with EtOAc (5 mL each). Combine the organic layers, dry (Na$_2$SO$_4$), and purify by preparative TLC (8:1 hexanes/EtOAc) to obtain 4-(3-chloro-4-fluoro-phenyl)-2-methoxy-6-[4-(3-trifluoromethyl-pyridin-2-yl)-piperazin-1-yl]-pyrimidine.

G. {4-(3-Chloro-4-fluoro-phenyl)-6-[4-(3-trifluoromethyl-pyridin-2-yl)-piperazin-1-yl]pyrimidin-2-yl}-diethyl-amine

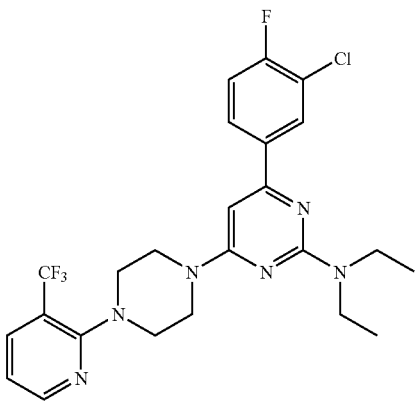

Combine a mixture of 2-chloro-4-(3-chloro-4-fluoro-phenyl)-6-[4-(3-trifluoromethyl-pyridin-2-yl)-piperazin-1-yl]-pyrimidine (47 mg, 1 mmol) and diethylamine (2 mL). Heat the mixture in a sealed tube at 60° C. for 16 hours. Cool to room temperature and evaporate. Add 1 M NaOH (1 mL) and extract 2× with EtOAc (2 mL each). Combine the organic layers, dry (Na$_2$SO$_4$), and purify using preparative TLC (9:1 hexanes/EtOAc) to obtain {4-(3-Chloro-4-fluoro-phenyl)-6-[4-(3-trifluoromethyl-pyridin-2-yl)-piperazin-1-yl]-pyrimidin-2-yl}-diethyl-amine as a white solid.

H. 4-{6-(3-chloro-4-fluoro-phenyl)-4-[4-(3-trifluoromethyl-pyridin-2-yl)-piperazin-1-yl]-pyridin-2-yl}-morpholine 1. 2-chloro-6-morpholino-4-yl-pyridin-4-ylamine

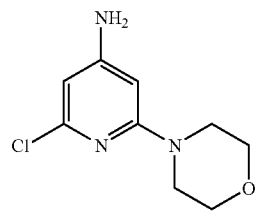

Stir the solution of 4-amino-2,6-dichloropyridine (3.3 g) in morpholine (15 mL) 4 hours at 150° C., concentrate, partition between H$_2$O and EtOAc, dry over Na$_2$SO$_4$, and concentrate under vacuum. Purify by flash chromatography (2:3 hexanes/EtOAc) to give 2-chloro-6-morpholino-4-yl-pyridin-4-ylamine.

2. 2-(3-chloro-4-fluoro-phenyl)-6-morpholino-4-yl-pyridin-4-ylamine

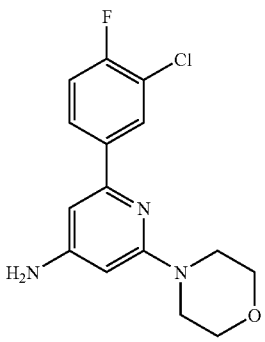

To a de-gassed mixture of 3-chloro-4-fluorophenylboronic acid (849 mg, 4.87 mmol)), 2-chloro-6-morpholino-4-yl-pyridin-4-ylamine (800 mg, 3.74 mmol), and 2M K$_3$PO$_4$ (7.5 mmol), in dioxane (15 mL) under nitrogen, add Pd(PPh$_3$)$_4$ (0.23 mmol). Stir the mixture at 80° C. overnight, concentrate, extract with EtOAc. Dry over Na$_2$SO$_4$, concentrate under vacuum, and purify by flash chromatography (1:1 hexanes/EtOAc) to give 2-(3-chloro-4-fluoro-phenyl)-6-morpholino-4-yl-pyridin-4-ylamine.

3. 4-{4-bromo-6-(3-chloro-4-fluoro-phenyl)-pyridin-2yl}-morpholine

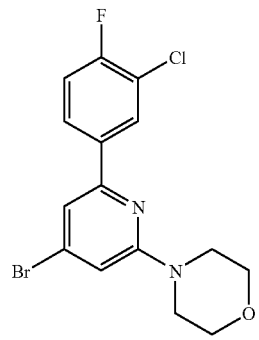

To an ice cooled solution of 2-(3-chloro-4-fluoro-phenyl)-6-morpholino-4-yl-pyridin-4-ylamine (250 mg, 0.81 mmol) in 75% H₂SO₄ (10 mL) add dropwise a solution of NaNO₂ (56 mg, 0.81 mmol) in 3 mL H₂O. Stir the mixture for 30 minutes at 0° C. Add CuBr (135 mg, 0.93 mmol) and 48% HBr (2 mL). Stir the mixture for 15 minutes at 0° C., and then for 30 minutes at 60° C. Cool to room temperature, neutralize to pH 8, extract with EtOAc, dry over Na₂SO₄, and concentrate under vacuum. Purify by flash chromatography (3:1 hexanes/EtOAc) to give 4-{4-bromo-6-(3-chloro-4-fluoro-phenyl)-pyridin-2yl}-morpholine.

4. 4-{6-(3-chloro-4-fluoro-phenyl)-4-[4-(3-trifluoromethyl-pyridin-2-yl)-piperazin-1-yl]-pyridin-2-yl}-morpholine

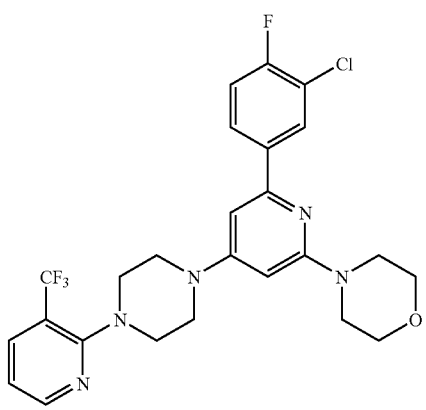

To a de-gassed mixture of 4-{4-bromo-6-(3-chloro-4-fluoro-phenyl)-pyridin-2yl}-morpholine (50 mg, 0.135 mmol)), 4-(6-trifluoromethyl-2-pyridyl)piperazine (37 mg, 0.162 mmol), and 1 M (THF) t-BuOK (0.162 mmol), in toluene (3 mL) under nitrogen add Pd₂(dba)₃ (0.0054 mmol) and BINAP (0.0067 mmol). Stir the mixture at 80° C. for overnight, concentrate, extract with EtOAc. Dry over Na₂SO₄, concentrate under vacuum, and purify by preparative TLC (3:1 hexanes/EtOAc) to give 4-{6-(3-chloro-4-fluoro-phenyl)-4-[4-(3-trifluoromethyl-pyridin-2-yl)-piperazin-1-yl]-pyridin-2-yl}-morpholine.

I. 4-{4-(3-chloro-4-fluoro-phenyl)-6-[4-(3-trifluoromethyl-pyridin-2-yl)-piperazin-1-yl]-pyridin-2-yl}-morpholine 1. 2,3-dichloro-4-(3-chloro-4-fluoro-phenyl)-pyridine

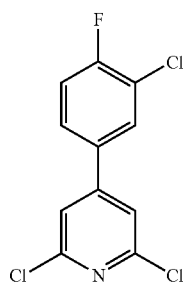

To a de-gassed mixture of 3-chloro-4-fluorophenylboronic acid (77 mg, 0.44 mmol)), 4-bromo-2,6-dichloro-pyridine (Talik and Plazek (1959) *Rocz. Chem.* 33:387-92; 100 mg, 0.44 mmol), and 2M Na₂CO₃ (0.55 mmol), in DME (4 mL) under nitrogen, add Pd(PPh₃)₄ (0.026 mmol). Stir the mixture at 80° C. overnight, concentrate, and extract with EtOAc. Dry over Na₂SO₄, concentrate under vacuum, and purify by preparative TLC (9:1 hexanes/EtOAc) to give 2,3-dichloro-4-(3-chloro-4-fluoro-phenyl)-pyridine.

2. 4-[6-chloro-4-(3-chloro-4-fluoro-phenyl)-pyridin-2-yl]-morpholine

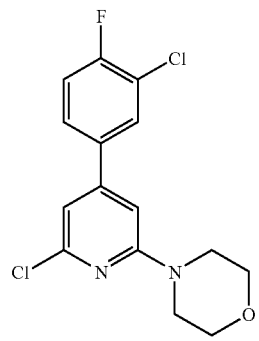

Stir the solution of 2,3-dichloro-4-(3-chloro-4-fluoro-phenyl)-pyridine (100 mg) in morpholine (2 mL) 3 hours at 80° C., concentrate, partition between H₂O and EtOAc, dry over Na₂SO₄, and concentrate under vacuum. Purify by preparative TLC (3:1 hexanes/EtOAc) to give 4-[6-chloro-4-(3-chloro-4-fluoro-phenyl)-pyridin-2-yl]-morpholine.

3. 4-{4-(3-chloro-4-fluoro-phenyl)-6-[4-(3-trifluoromethyl-pyridin-2-yl)-piperazin-1-yl]-pyridin-2-yl}-morpholine

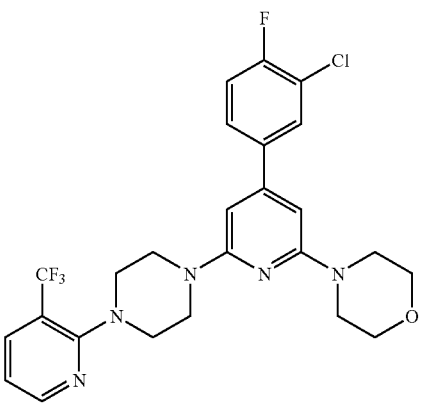

To a de-gassed mixture of 4-[6-chloro-4-(3-chloro-4-fluoro-phenyl)-pyridin-2-yl]-morpholine (50 mg, 0.153 mmol)), 4-(6-trifluoromethyl-2-pyridyl)piperazine (43 mg, 0.183 mmol), and 1 M (THF) t-BuOK (0.183 mmol), in toluene (3 mL) under nitrogen, add Pd₂(dba)₃ (0.006 mmol) and BINAP (0.008 mmol). Stir the mixture at 80° C. overnight, concentrate, extract with EtOAc. Dry over Na₂SO₄, concentrate under vacuum, and purify by preparative TLC (3:1 hexanes/EtOAc) to give 4-{4-(3-chloro-4-fluoro-phenyl)-6-[4-(3-trifluoromethyl-pyridin-2-yl)-piperazin-1-yl]-pyridin-2-yl}-morpholine.

J. 4-(3-Chloro-4-fluoro-phenyl)-2-(1-propyl-piperidin-4-yl)-6-[4-(3-trifluoromethyl-pyridin-2-yl)-piperazin-1-yl]-pyrimidine 1. 4-{4-(3-Chloro-4-fluoro-phenyl)-6-[4-(3-trifluoromethyl-pyridin-2-yl)-piperazin-1-yl]-pyrimidin-2-yl}-3,6-dihydro-2H-pyridine-1-carboxylic acid tert-butyl ester

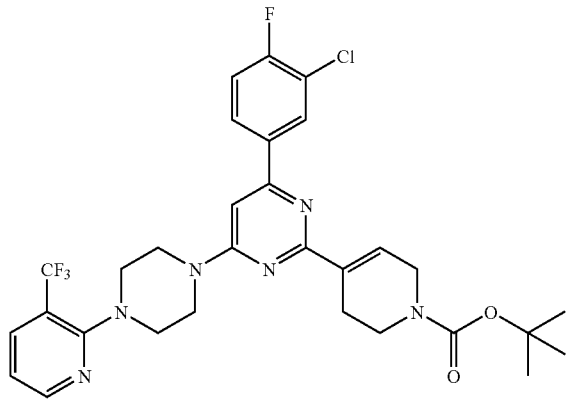

Heat a solution of 2-chloro-4-(3-chloro-4-fluoro-phenyl)-6-[4-(3-trifluoromethyl-pyridin-2-yl)-piperazin-1-yl]-pyrimidine (774 mg, 1.64 mmol), 4-(4,4,5,5-tetramethyl-[1,3,2]dioxaborolan-2-yl)-3,6-dihydro-2H-pyridine-1-carboxylic acid tert-butyl ester (608 mg, 1.97 mmol (prepared essentially as described by Eastwood (2000) Tetrahedron Letters 41 (19): 3705-3708), K$_3$PO$_4$ (2M, 1.64 mL) and Pd(PPh$_3$)$_4$ (76 mg, 0.07 mmol) in dioxane at 80° C. for 16 hours. Partition the reaction mixture between brine and EtOAc, dry the EtOAc layer (Na$_2$SO$_4$) and concentrate under reduced pressure. Flash chromatography (30% EtOAc in hexanes as eluent) yields 4-{4-(3-chloro-4-fluoro-phenyl)-6-[4-(3-trifluoromethyl-pyridin-2-yl)-piperazin-1-yl]-pyrimidin-2-yl}-3,6-dihydro-2H-pyridine-1-carboxylic acid tert-butyl ester as a foam.

2. 4-{4-(3-Chloro-4-fluoro-phenyl)-6-[4-3-trifluoromethyl-pyridin-2-yl)-piperazin-1-yl]-pyrimidin-2-yl}-piperidine-1-carboxylic acid tert-butyl ester

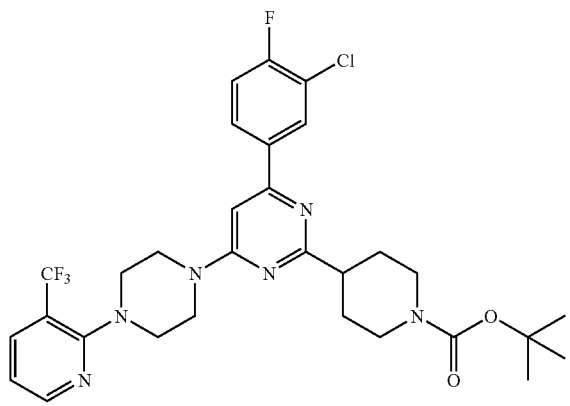

Dissolve 4-{4-(3-chloro-4-fluoro-phenyl)-6-[4-(3-trifluoromethyl-pyridin-2-yl)-piperazin-1-yl]-pyrimidin-2-yl}-3,6-dihydro-2H-pyridine-1-carboxylic acid tert-butyl ester (124 mg, 0.02 mmol) in MeOH and add 5% platinum (sulfided) on carbon (50 mg). Stir the reaction mixture for two days under 1 atmosphere of hydrogen gas. Filter the mixture through celite and concentrate under reduced pressure. Chromatograph the residue using 2 mm preparative TLC plates (20% EtOAc/hexanes eluent) to afford the title compound.

3. 4-(3-Chloro-4-fluoro-phenyl)-2-(1-propyl-piperidin-4-yl)-6-[4-(3-trifluoromethyl-pyridin-2-yl)-piperazin-1-yl]-pyrimidine

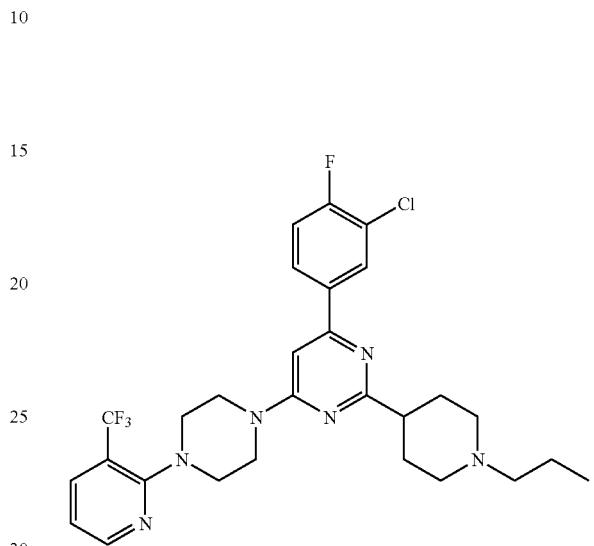

To a solution of 4-{4-(3-chloro-4-fluoro-phenyl)-6-[4-(3-trifluoromethyl-pyridin-2-yl)-piperazin-1-yl]-pyrimidin-2-yl}-piperidine-1-carboxylic acid tert-butyl ester (97 mg, 0.157 mmol) in dioxane, add 0.5 mL of HCl in dioxane (4M) and stir at room temperature for 2 hours. Concentrate the solution under reduced pressure and wash the residue with dry ether. Discard the ether wash, add additional ether and stir for one hour to give a pale yellow suspension. Collect the solid to afford 4-(3-chloro-4-fluoro-phenyl)-2-piperidin-4-yl-6-[4-(3-trifluoromethyl-pyridin-2-yl)-piperazin-1-yl]-pyrimidine as the HCl salt. Prepare the freebase by partitioning between EtOAc and 10% NaOH solution. Dry (Na$_2$SO$_4$) and evaporate the EtOAc layer. Dissolve the free base in dichloroethane and add propionaldehyde (0.09 mmol) and sodium triacetoxyborohydride (22 mg, 010 mmol) followed by one drop of HOAc. Stir the mixture for one hour, dilute with DCM and wash with 10% NaOH (1×). Dry the organic layer (Na$_2$SO$_4$) and concentrate under reduced pressure. Chromatograph the residue on a 2 mm preparative TLC plate (5% MeOH(1 N NH$_3$)/DCM eluent) to give 4-(3-chloro-4-fluoro-phenyl)-2-(1-propyl-piperidin-4-yl)-6-[4-(3-trifluoromethyl-pyridin-2-yl)-piperazin-1-yl]-pyrimidine. $^1$H NMR (CDCl$_3$): δ 0.93 (t, 3H), 1.59 (m, 2H), 2.05 (m, 6H), 2.37 (m, 2H), 2.75 (m, 1H), 3.08)m, 2H), 3.40 (m, 4H), 3.88 (m, 4H), 6.69 (s, 1H), 7.06 (m, 1H), 7.21 (t, 1H), 7.86-7.93 (m, 2H), 8.08 (d, 1H), 8.47 (m, 1H).

K. 1-{4-(3-Chloro-4-fluoro-phenyl)-6-[4-(3-trifluoromethyl-pyridin-2-yl)-piperazin-1-yl]-pyrimidin-2-yl}-4-propyl-piperazin-2-one 1. 4-{4-(3-Chloro-4-fluoro-phenyl)-6-[4-(3-trifluoromethyl-pyridin-2-yl)-piperazin-1-yl]-pyrimidin-2-yl}-3-oxo-piperazine-1-carboxylic acid tert-butyl ester

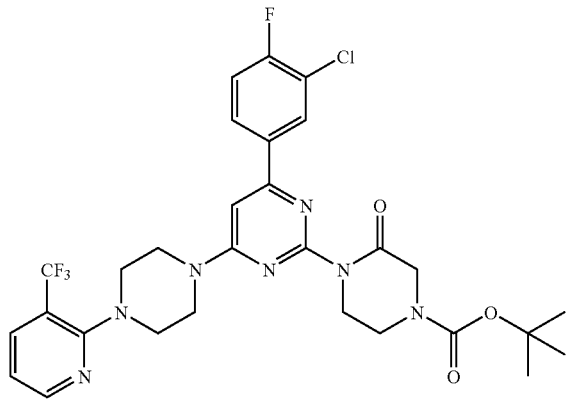

To a solution of 2-chloro-4-(3-chloro-4-fluoro-phenyl)-6-[4-(3-trifluoromethyl-pyridin-2-yl)-piperazin-1-yl]-pyrimidine (259 mg, 0.55 mmol), 3-oxo-piperazine-1-carboxylic acid tert-butyl ester (prepared essentially as described by Kane and Carr (1980) *Tet. Lett.* 21:3019-20; 132 mg, 0.66 mmol) and $Cs_2CO_3$ (250 mg, 0.77 mmol) in dioxane, add 4,5-bis(diphenylphosphino)-9,9-dimethylxanthene (19 mg, 0.03 mmol). Purge the reaction mixture for 10 minutes with nitrogen gas and then add $Pd_2(dba)_3$ (10 mg, 0.011 mmol). After purging with nitrogen gas for an additional 5 minutes, heat the mixture at 90° C. for 16 hours under nitrogen atmosphere. Filter the mixture through celite and concentrate under reduced pressure to give the title compound.

2. 1-{4-(3-Chloro-4-fluoro-phenyl)-6-[4-(3-trifluoromethyl-pyridin-2-yl)-piperazin-1-yl]-pyrimidin-2-yl}-piperazin-2-one

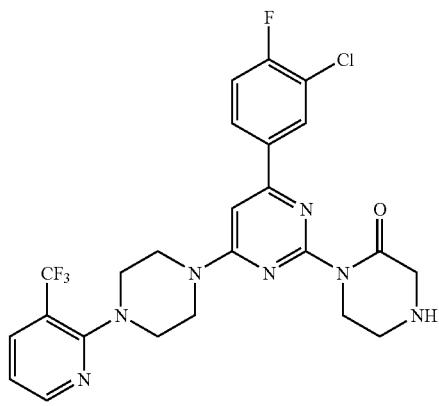

Treat 4-{4-(3-chloro-4-fluoro-phenyl)-6-[4-(3-trifluoromethyl-pyridin-2-yl)-piperazin-1-yl]-pyrimidin-2-yl}-3-oxo-piperazine-1-carboxylic acid tert-butyl ester with HCl/dioxane (4M) using the procedure described in Example 1-J step 3 to afford the title piperazine-one.

3. 1-{4-(3-Chloro-4-fluoro-phenyl)-6-[4-(3-trifluoromethyl-pyridin-2-yl)-piperazin-1-yl]-pyrimidin-2-yl}-4-propyl-piperazin-2-one

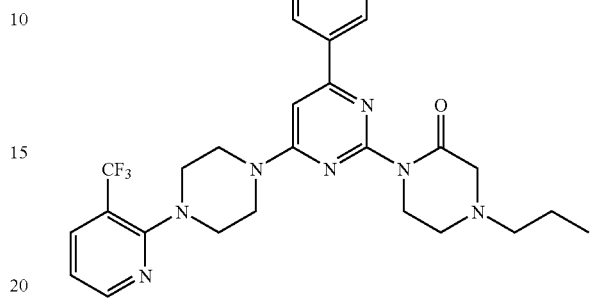

Convert 1-{4-(3-chloro-4-fluoro-phenyl)-6-[4-(3-trifluoromethyl-pyridin-2-yl)-piperazin-1-yl]-pyrimidin-2-yl}-piperazin-2-one to the title compound using the reductive amination procedure described in Example 1-J step 3. $^1$H NMR ($CDCl_3$): δ 0.96 (t, 3H), 1.55 (m, 2H), 2.43 (t, 2H), 2.83 (t, 2H), 3.35 (s, 2H), 3.41 (m, 4H), 3.87 (m, 4H), 3.40 (t, 2H), 6.69 (s, 1H), 7.06 (m, 1H), 7.21 (t, 1H), 7.91 (m, 2H), 8.06 (d, 1H, J=7.1 Hz), 8.46 (d, 1H, J=2.9 Hz).

L. Dimethyl-[3-(3-{2-morpholin-4-yl-6-[4-(3-trifluoromethyl-pyridin-2-yl)-piperazin-1-yl]-pyrimidin-4-yl}-phenyl)-propyl]-amine 1. 4-{4-Chloro-6-[4-(3-trifluoromethyl-pyridin-2-yl)-piperazin-1-yl]-pyrimidin-2-yl}-morpholine

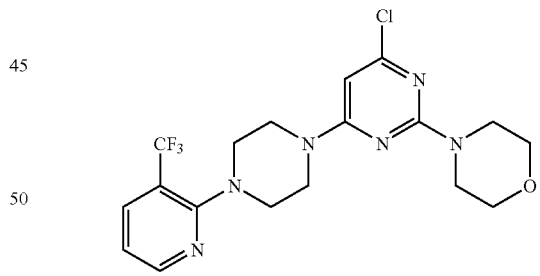

A mixture of 4,6-dichloro-2-morpholinopyrimidine (468 mg, 2.0 mmol), 4-(6-trifluoromethyl-2-pyridyl)piperazine (462 mg, 2.0 mmol), potassium carbonate (345 mg, 2.5 mmol) and EtOH (10 mL) is heated at 78° C. for 8 hours. The mixture is cooled, diluted with water (20 mL) and extracted with EtOAc (3×25 mL). The combined organics are washed with brine (25 mL), dried ($MgSO_4$) and concentrated under reduced pressure. The residue is purified by flash chromatography on silica gel (80% hexane/20% ether) to give the title compound.

2. 3-(3-{2-Morpholin-4-yl-6-[4-(3-trifluoromethyl-pyridin-2-yl)-piperazin-1-yl]-pyrimidin-4-yl}-phenyl)-propan-1-ol

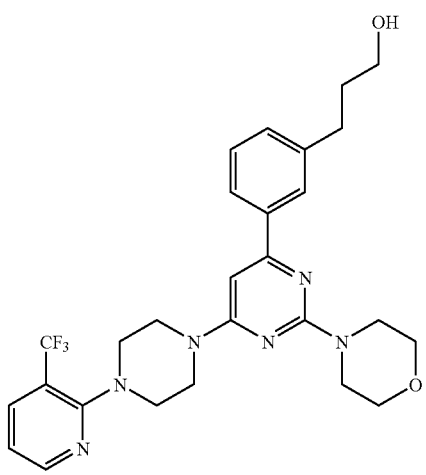

Purge a solution of 4-{4-chloro-6-[4-(3-trifluoromethyl-pyridin-2-yl)-piperazin-1-yl]-pyrimidin-2-yl}-morpholine (142 mg, 0.33 mmol), (3-(3-hydroxypropyl)phenyl)boronic acid (89 mg, 0.5 mmol) and K$_3$PO$_4$ (2M, 331 μL) in dioxane with nitrogen for 10 minutes. Add Pd(PPh$_3$)$_4$ (19 mg, 0.017 mmol) and purge for an additional 5 minutes. Seal the contents in a reaction vial and heat at 80° C. for 16 hours. Partition the mixture between EtOAc and water, dry (Na$_2$SO$_4$) the organic layer and concentrate under reduced pressure. Filter the residue through a small pad of silica gel eluting with 50% EtOAc/hexanes. Concentrate under reduced pressure to give the title compound.

3. Methanesulfonic acid 3-(3-{2-morpholin-4-yl-6-[4-(3-trifluoromethyl-pyridin-2-yl)-piperazin-1-yl]-pyrimidin-4-yl}-phenyl)-propyl ester

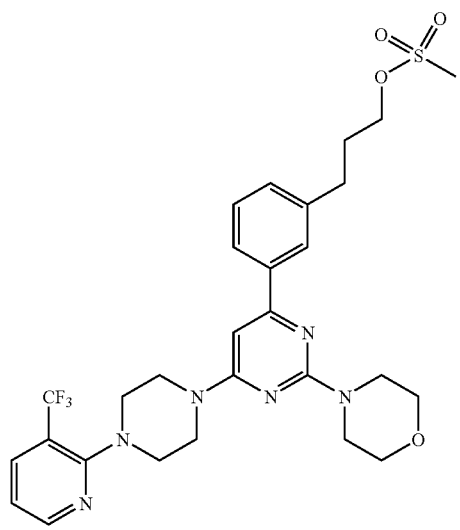

Dissolve 3-(3-{2-morpholin-4-yl-6-[4-(3-trifluoromethyl-pyridin-2-yl)-piperazin-1-yl]-pyrimidin-4-yl}-phenyl)-propan-1-ol (104 mg, 0.197 mmol) in methylene chloride and add triethylamine (55 μL, 0.394 mmol). Bring the solution to 0° C. with an ice bath and add methanesulfonyl chloride (23 μL, 0.394 mmol) dropwise. After 2 hours, dilute the reaction with additional methylene chloride and wash the mixture with brine (1×) in a separatory funnel. Dry the organic layer (Na$_2$SO$_4$) and concentrate under reduced pressure to give the title compound, which was used without further purification.

4. Dimethyl-[3-(3-{2-morpholin-4-yl-6-[4-(3-trifuorom-ethyl-pyridin-2-yl)-piperazin-1-yl]-pyrimidin-4-yl}-phenyl)-propyl]-amine

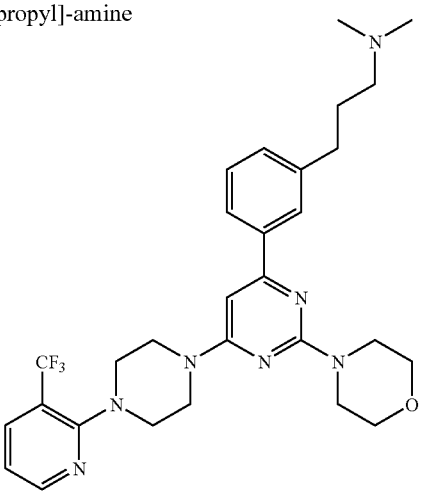

Dissolve the crude methanesulfonic acid 3-(3-{2-morpholin-4-yl-6-[4-(3-trifluoromethyl-pyridin-2-yl)-piperazin-1-yl]-pyrimidin-4-yl}-phenyl)-propyl ester obtained above in THF and heat with an excess of dimethylamine in a sealed tube at 55° C. Concentrate under reduced pressure and partition the residue between aqueous NaHCO$_3$ and EtOAc. Dry the organic layer (Na$_2$SO$_4$) and concentrate under reduced pressure. Purify the residue using preparative plate TLC (MeOH/DCM eluent) to afford the title compound. $^1$H NMR (CDCl$_3$): δ 1.17 (m, 2H), 2.27 (s, 6H), 2.37 (t, 2H), 2.72 (t, 2H), 3.40 (m, 4H), 3.80 (m, 8H), 3.87 (m, 4H), 6.37 (s, 1H), 7.03 (m, 1H), 7.25 (d, 1H, J=7.1 Hz), 7.35 (dd, 1H), 7.79 (m, 2H), 7.89 (d, 1H, J=7.87 Hz), 8.46 (d, 1H).

M. 3-(3-{2-Morpholin-4-yl-6-[4-(3-trifluoromethyl-pyridin-2-yl)-piperazin-1-yl]-pyrimidin-4-yl}-phenyl)-propionic acid 1. 3-(3-{2-Morpholin-4-yl-6-[4-(3-trifluoromethyl-pyridin-2-yl)-piperazin-1-yl]-pyrimidin-4-yl}-phenyl)-propionic acid methyl ester

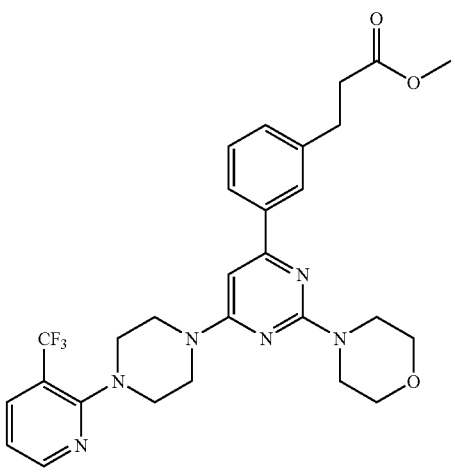

Purge a solution of 4-{4-chloro-6-[4-(3-trifluoromethyl-pyridin-2-yl)-piperazin-1-yl]-pyrimidin-2-yl}-morpholine (142 mg, 0.33 mmol), (3-(2-methoxycarbonylethyl)phenyl)boronic acid (Combi-Blocks, Inc., San Diego, Calif.; 104 mg, 0.5 mmol) and K$_3$PO$_4$ (2M, 331 μL) in dioxane with nitrogen for 10 minutes. Add Pd(PPh$_3$)$_4$ (19 mg, 0.017 mmol) and purge for an additional 5 minutes. Seal the contents in a reaction vial and heat at 80° C. for 16 hours. Partition the mixture between EtOAc and water, dry (Na$_2$SO$_4$) the organic layer and concentrate under reduced pressure. Filter the residue through a small pad of silica gel eluting with 50% EtOAc/hexanes. Concentrate under reduced pressure to give the title compound.

2. 3-(3-{2-Morpholin-4-yl-6-[4-(3-trifluoromethyl-pyridin-2-yl)-piperazin-1-yl]-pyrimidin-4-yl}-phenyl)-propionic acid

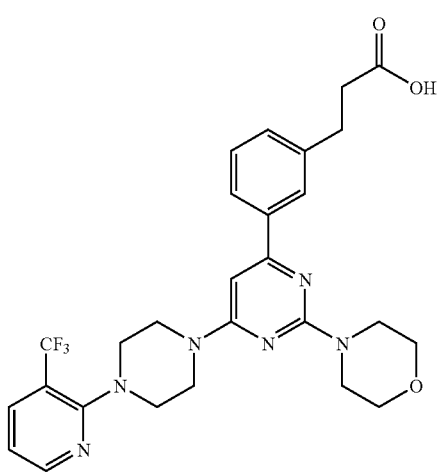

To a solution of 3-(3-{2-morpholin-4-yl-6-[4-(3-trifluoromethyl-pyridin-2-yl)-piperazin-1-yl]-pyrimidin-4-yl}-phenyl)-propionic acid methyl ester in THF, add water dropwise until the cloudiness almost persists. To this mixture add LiOH.H$_2$O (10 equivalents) followed by a small amount of ethanol to achieve heterogeneity. Heat the mixture at 55° C. for 2 hours then concentrate under reduced pressure. Add a small amount of water to the residue followed by 10 equivalents of HCl (3M solution). Adjust the final pH to 4 and collect the off-white solid via filtration. Wash the solid with water and dry to afford the title compound. $^1$H NMR (DMSO-D$_6$): δ 2.58 (t, 2H), 2.89 (t, 2H), 3.29 (br m, 4H), 3.66 (br m, 4H), 3.72 (br m, 4H), 3.79 (br m, 4H), 6.72 (s, 1H), 7.22 (m, 1H), 7.31-7.37 (m, 2H), 7.95 (m, 2H), 8.09 (d, 1H, J=7.87 Hz), 8.54 (d, 1H, J=3.3 Hz).

N. N-(6-{4-[6-(3-Chloro-4-fluoro-phenyl)-2-(2-methyl-pyrrolidin-1-yl)-pyrimidin-4-yl]-piperazin-1-yl}-5-methyl-pyridin-3-yl)-methanesulfonamide

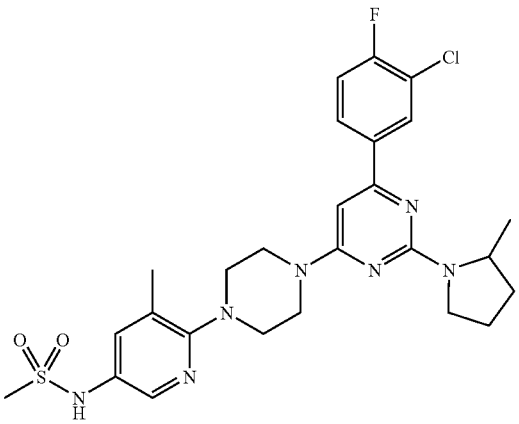

1. 4-[6-Chloro-2-(2-methyl-pyrrolidin-1-yl)-pyrimidin-4-yl]-piperazine-1-carboxylic acid tert-butyl ester

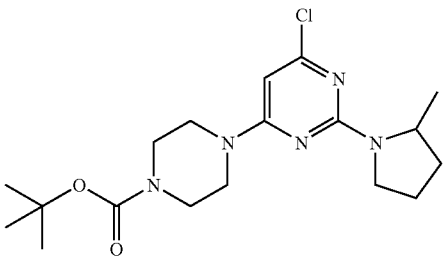

Heat a mixture of 4,6-dichloro-2-(2-methyl-pyrrolidin-1-yl)-pyrimidine (1 g, 4.3 mmol), and piperazine-1-carboxylic acid tert-butyl ester (886 mg, 4.76 mmol) and NaHCO$_3$ (730 mg, 8.66 mmol) in ethanol at 80° C. for 16 hours. Concentrate under reduced pressure and partition between ethyl acetate and water. Dry the organic layer (Na$_2$SO$_4$) and concentrate under reduced pressure. Chromatograph the residue on silica gel using ethyl acetate/hexanes eluent systems to afford the title compound.

2. 4-(3-Chloro-4-fluoro-phenyl)-2-(2-methyl-pyrrolidin-1-yl)-6-piperazin-1-yl-pyrimidine

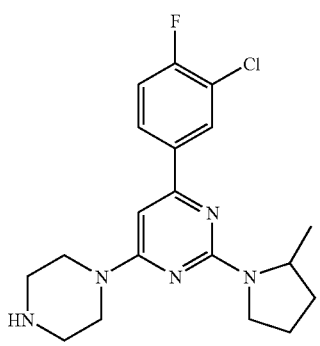

Heat a mixture of 4-[6-chloro-2-(2-methyl-pyrrolidin-1-yl)-pyrimidin-4-yl]-piperazine-1-carboxylic acid tert-butyl ester (1.6 g, 4.19 mmol), 3-chloro-4-fluoro-phenylboronic acid (877 mg, 5 mmol), K₃PO₄ (2M, 4.2 mL) and tetrakistriphenylphosphine palladium(0) in dioxane at 80° C. for 16 hours. Dilute the mixture with ethyl acetate and wash with brine solution. Dry the organic layer (Na₂SO₄) and concentrate under reduced pressure. Purify the residue using flash column chromatography eluting with hexanes followed by 10% ethyl acetate/hexanes. Dissolve the product in dry dioxane and add 4M HCl (excess) in dioxane at room temperature. After stirring for several hours concentrate the reaction under reduced pressure and wash the solid with ether to give the title compound as the HCl salt.

3. 4-(3-Chloro-4-fluoro-phenyl)-6-[4-(3-methyl-5-nitro-pyridin-2-yl)-piperazin-1-yl]-2-(2-methyl-pyrrolidin-1-yl)-pyrimidine

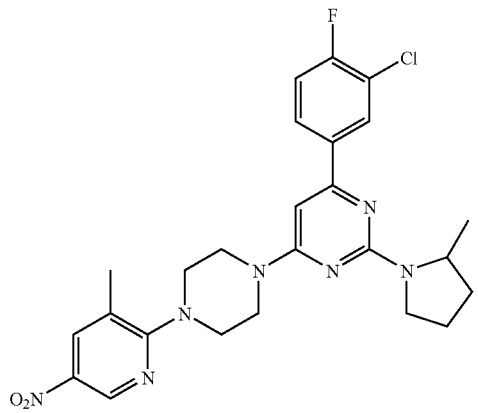

Heat a mixture of 4-(3-chloro-4-fluoro-phenyl)-2-(2-methyl-pyrrolidin-1-yl)-6-piperazin-1-yl-pyrimidine free base (270 mg, 0.72 mmol), 2-chloro-3-methyl-5-nitro-pyridine (149 mg, 0.86 mmol) and diisopropylethylamine (185 mg, 1.44 mmol) in dimethylacetamide at 120° C. for 16 hours. Dilute the mixture with ethyl acetate and water. Wash the organic layer several times with water then dry (Na₂SO₄) and concentrate under reduced pressure. Purify the residue using preparative thin layer chromatography eluting with ethyl acetate/hexanes solvent systems to give the title compound.

4. 6-{4-[6-(3-Chloro-4-fluoro-phenyl)-2-(2-methyl-pyrrolidin-1-yl)-pyrimidin-4-yl]-piperazin-1-yl}-5-methyl-pyridin-3-ylamine

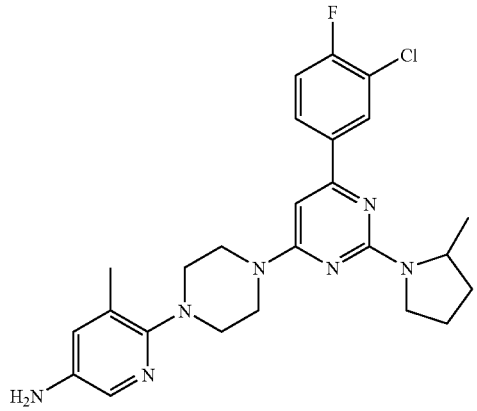

Reflux a mixture of 4-(3-chloro-4-fluoro-phenyl)-6-[4-(3-methyl-5-nitro-pyridin-2-yl)-piperazin-1-yl]-2-(2-methyl-pyrrolidin-1-yl)-pyrimidine (300 mg) with 4 equivalents of SnCl₂ in ethyl acetate (50 mL) for 16 hours. Partition the mixture between ethyl acetate and 1 N NaOH. Separate the organic layer, dry (Na₂SO₄) and concentrate under reduced pressure. Purify the residue by filtering through a plug of silica gel using ethyl acetate as eluent to afford the title compound.

5. N-(6-{4-[6-(3-Chloro-4-fluoro-phenyl)-2-(2-methyl-pyrrolidin-1-yl)-pyrimidin-4-yl]-piperazin-1-yl}-5-methyl-pyridin-3-yl)-methanesulfonamide

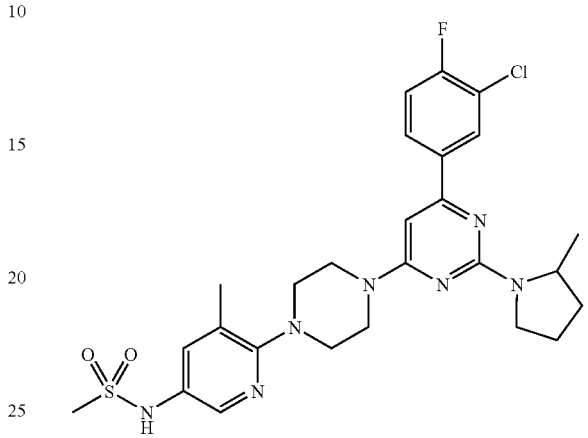

To a cooled solution of 6-{4-[6-(3-chloro-4-fluoro-phenyl)-2-(2-methyl-pyrrolidin-1-yl)-pyrimidin-4-yl]-piperazin-1-yl}-5-methyl-pyridin-3-yl-amine (50 mg, 0.103 mmol) in DCM add methanesulfonic anhydride (22 mg, 0.125 mmol). Stir the solution at room temperature for 5 hours. Wash with water, dry the solution (Na₂SO₄), and concentrate under reduced pressure. Purify the residue by flash column chromatography eluting with EtOAc:Hexanes (1:4) to afford N-(6-{4-[6-(3-chloro-4-fluoro-phenyl)-2-(2-methyl-pyrrolidin-1-yl)-pyrimidin-4-yl]-piperazin-1-yl}-5-methyl-pyridin-3-yl)-methanesulfonamide as a solid. $^1$H NMR (300 MHz, CDCl₃): δ 1.30 (m, CH₃); 1.72 (m, 1H, CH₂CH₂); 1.91 (m, 1H, CH₂CH₂); 2.06 (m, 2H, CH₂CH₂); 2.35 (s, 3H, Ar—CH₃); 3.01 (s, 3H, CH₃SO₂); 3.24 (m, 4H); 3.67 (m, 2H); 3.80 (m, 4H); 4.34 (m, 1H); 6.25 (s, 1H, Ar—H); 6.34 (s, 1H, Ar—H); 7.18 (m, 1H); 7.48 (d, J=2.4 Hz, 1H); 7.89 (m, 1H); 8.03 (m, 1H); 8.07 (m, 1H).

O. 6-{4-[6-(3-Chloro-4-fluoro-phenyl)-2-(2-methyl-pyrrolidin-1-yl)-pyrimidin-4-yl]-piperazin-1-yl}-5-methyl-pyridin-3-ol

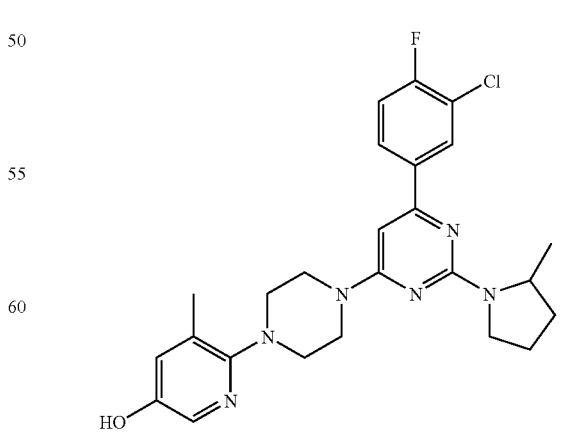

To a cooled solution of 6-{4-[6-(3-chloro-4-fluoro-phenyl)-2-(2-methyl-pyrrolidin-1-yl)-pyrimidin-4-yl]-piperazin-1-yl}-5-methyl-pyridin-3-ylamine (146 mg, 0.303 mmol) in 10% aqueous H₂SO₄ add NaNO₂ (22 mg, 0.318 mmol) in 1 ml of water, dropwise. Stir the solution at 0° C. for 30 minutes. Heat the mixture at 90° C. for 1 hour. Cool to room temperature, adjust the pH to 7, and extract with EtOAc. Wash with brine, dry the solution (Na₂SO₄), and concentrate under reduced pressure. Purify the residue by flash column chromatography eluting with EtOAc:Hexanes (1:1) to afford 6-{4-[6-(3-chloro-4-fluoro-phenyl)-2-(2-methyl-pyrrolidin-1-yl)-pyrimidin-4-yl]-piperazin-1-yl}-5-methyl-pyridin-3-ol as an off white solid. $^1$H NMR (300 MHz, CDCl₃): δ1.29 (t, 3H, J=6.3 Hz, CH₃); 1.69 (m, 1H, CH₂CH₂); 1.90 (m, 1H, CH₂CH₂); 2.05 (m, 2H, CH₂CH₂); 2.29 (s, 3H, Ar—CH₃); 3.11 (m, 4H); 3.67 (m, 4H); 3.78 (m, 4H); 4.35 (m, 1H); 6.23 (s, 1H, Ar—H); 7.03 (d, J=2.4 Hz, 1H); 7.16 (m, 1H); 7.72 (d, 1H, J=2.7 Hz); 7.86 (m, 1H); 8.04 (m, 1H).

P. 4-(3-Chloro-4-fluoro-phenyl)-6-[4-(5-methoxy-3-methyl-pyridin-2-yl)-piperazin-1-yl]-2-(2-methyl-pyrrolidin-1-yl)-pyrimidine

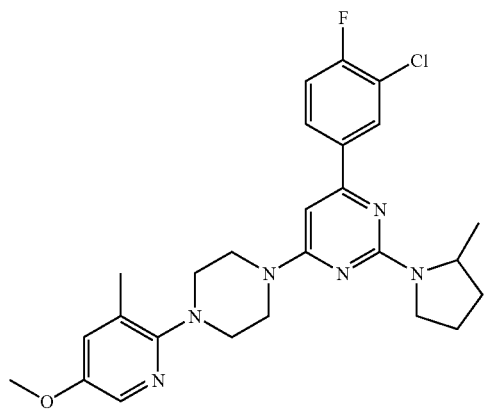

To a solution of 6-{4-[6-(3-chloro-4-fluoro-phenyl)-2-(2-methyl-pyrrolidin-1-yl)-pyrimidin-4-yl]-piperazin-1-yl}-5-methyl-pyridin-3-ol (50 mg, 0.10 mmol) in DMF add 60% NaH (12 mg, 0.30 mmol). Stir the solution at room temperature for 30 minutes. Add methyl iodide (0.3 mmol) and stir the solution at room temperature for 2 hours. Partition between EtOAc and water. Wash with brine, dry the solution (Na₂SO₄), and concentrate under reduced pressure. Purify the residue by flash column chromatography eluting with EtOAc: Hexanes (1:4) to afford 4-(3-chloro-4-fluoro-phenyl)-6-[4-(5-methoxy-3-methyl-pyridin-2-yl)-piperazin-1-yl]-2-(2-methyl-pyrrolidin-1-yl)-pyrimidine as a solid. $^1$H NMR (300 MHz, CDCl₃): δ1.30 (t, 3H, J=6.3 Hz, CH₃); 1.70 (m, 1H, CH₂CH₂); 1.91 (m, 1H, CH₂CH₂); 2.06 (m, 2H, CH₂CH₂); 2.33 (s, 3H, Ar—CH₃); 3.13 (m, 4H); 3.67 (m, 2H); 3.78 (m, 4H); 3.80 (s, OCH₃); 4.33 (m, 1H); 6.25 (s, 1H, Ar—H); 7.06 (d, J=2.4 Hz, 1H); 7.18 (m, 1H); 7.88 (m, 2 H); 7.86 (m, 1H); 8.07 (m, 1H).

Q. 4-[4-(3-Chloro-6-methoxy-pyridin-2-yl)-2-methyl-piperazin-1-yl]-6-(4-fluoro-phenyl)-2-(2-methyl-pyrrolidin-1-yl)-pyrimidine 1. 2-chloro-6-methoxy-pyridin-3-ylamine

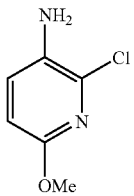

Reflux a mixture of 2-chloro-6-methoxy-3-nitro-pyridine (7 g, 0.37 mol) with 3 equivalents of SnCl₂ (22 g, 0.111 mol) in ethyl acetate (150 mL) for 16 hours. Partition the mixture between ethyl acetate and 1 N NaOH. Separate the organic layer, dry (Na₂SO₄) and concentrate under reduced pressure. Purify the residue by filtering through a plug of silica gel using ethyl acetate as eluent to afford the title compound.

2. 2,3-Dichloro-6-methoxy-pyridine

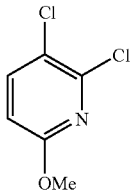

Bring a solution of 2-chloro-6-methoxy-3-nitro-pyridine (2.8 g, 0.018 mol) in 75% H₂SO₄ (15 mL) to 0° C. using an ice bath. Slowly add a solution of NaNO₂ in water (5 mL) to the reaction mixture and stir for 30 minutes. Add three molar equivalents of CuCl in concentrated HCl and stir for 15 minutes. Heat the mixture at 80° C. for 30 minutes. Pour onto ice, extract the aqueous with ethyl acetate, dry the organic layer (Na₂SO₄) and concentrate under reduced pressure. Purify using flash column chromatography (hexanes to 10% ethyl acetate/hexanes eluent) to afford the title compound.

3. 1-(3-Chloro-6-methoxy-pyridin-2-yl)-3-(R)-methyl-piperazine

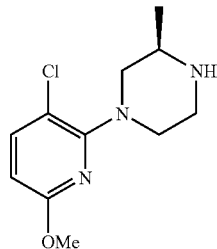

Heat a mixture of 2,3-dichloro-6-methoxy-pyridine (1.0 g, 5.62 mmol), 2-(R)-methylpiperazine (1.13 g, 11.23 mmol), and Na₂CO₃ (596 mg, 5.62 mmol) in DMA at 110° C. for 16 hours. Partition the mixture between EtOAc and water, dry (Na₂SO₄) the organic layer and concentrate under reduced pressure. Filter the residue through a small pad of silica gel eluting with 90:10:1 (DCM:MeOH:NH₄OH). Concentrate under reduced pressure to give the title compound.

4. 4,6-Dichloro-2-(2-methyl-pyrrolidin-1-yl)-pyrimidine

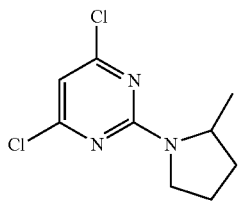

To an ice-cold solution containing 2,4,6-trichloropyrimidine (8 g, 44 mmol) in MeOH (80 mL) and NaHCO$_3$ (10 g) add slowly and dropwise a methanolic solution (20 mL) of 2-methylpyrrolidine (46 mmol). Allow the mixture to warm to 25° C. and stir overnight. Dilute with water, vigorously stir for 1 hour, and filter to give white crystalline solid as a mixture of regioisomers. Chromatograph the mixture using flash column chromatography (ethyl acetate/hexanes eluent systems) to give 4,6-dichloro-2-(2-methyl-pyrrolidin-1-yl)-pyrimidine.

5. 4-Chloro-6-(4-fluoro-phenyl)-2-(2-methyl-pyrrolidin-1-yl)-pyrimidine

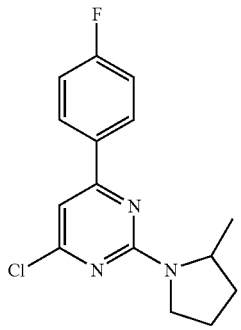

Heat a mixture of 4,6-dichloro-2-(2-methyl-pyrrolidin-1-yl)-pyrimidine (2.25 g, 9.74 mmol), 4-fluorophenyl-boronic acid (1.44 g, 10.2 mmol), K$_3$PO$_4$ (2M aqueous solution, 9.74 mL) and tetrakis-triphenylphosphine palladium(0) (562 mg) in dioxane (35 mL) at 80° C. for 16 hours. Dilute the mixture with ethyl acetate and wash with brine. Dry the organic layer (Na$_2$SO$_4$) concentrate under reduced pressure. Purify using flash column chromatography (ethyl acetate/hexanes eluent systems) to yield the title compound as an oil.

6. 4-[4-(3-Chloro-6-methoxy-pyridin-2-yl)-2-methyl-piperazin-1-yl]-6-(4-fluoro-phenyl)-2-(2-methyl-pyrrolidin-1-yl)-pyrimidine

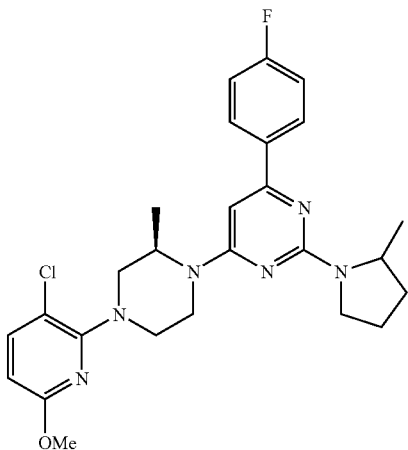

Heat a mixture of 4-chloro-6-(4-fluoro-phenyl)-2-(2-methyl-pyrrolidin-1-yl)-pyrimidine (440 mg, 1.51 mmol), 1-(3-chloro-6-methoxy-pyridin-2-yl)-3-(R)-methyl-piperazine (400 mg, 1.66 mmol), and K$_2$CO$_3$ (230 mg, 1.66 mmol) in DMA at 120° C. for 16 hours. Partition the mixture between EtOAc and water, dry (Na$_2$SO$_4$) the organic layer and concentrate under reduced pressure. Purify with flash silica gel column eluting with 10% EtOAc/hexanes. Concentrate under reduced pressure to give the title compound. $^1$H NMR (300 MHz, CDCl$_3$): δ1.36 (m, 6H, 2×CH$_3$); 1.70 (m, 1H, CH$_2$CH$_2$); 1.93 (m, 1H, CH$_2$CH$_2$); 2.06 (m, 2H, CH$_2$CH$_2$); 3.05 (m, 2H); 3.38 (m, 1H); 3.70 (m, 2H); 3.88 (s, 3H, OCH$_3$); 3.90 (m, 2H); 4.35 (m, 2H); 4.70 (m, 1H); 6.232 (s, 1H); 6.30 (d, 1H, J=8.4 Hz); 7.12 (m, 2H); 7.46 (d, J=9.0 Hz, 1H); 8.00 (m, 2H).

R. 5-Chloro-6-{4-[6-(4-fluoro-phenyl)-2-(2-methyl-pyrrolidin-1-yl)-pyrimidin-4-yl]-3-methyl-piperazin-1-yl}-pyridin-2-ol

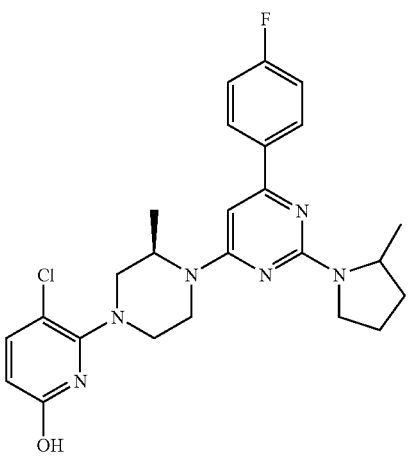

Heat a solution of 4-[4-(3-chloro-6-methoxy-pyridin-2-yl)-2-methyl-piperazin-1-yl]-6-(4-fluoro-phenyl)-2-(2-methyl-pyrrolidin-1-yl)-pyrimidine (120 mg, 0.241 mmol) in concentrated HCl at 90° C. for 24 hours. Cool to room temperature, adjust the pH to 7, and extract with EtOAc. Wash with brine, dry the solution (Na$_2$SO$_4$), and concentrate under reduced pressure. Purify the residue by flash column chromatography eluting with EtOAc:Hexanes (1:4) to afford 5-chloro-6-{4-[6-(4-fluoro-phenyl)-2-(2-methyl-pyrrolidin-1-yl)-pyrimidin-4-yl]-3-methyl-piperazin-1-yl}-pyridin-2-ol as an off-white solid. $^1$H NMR (300 MHz, CDCl$_3$): δ1.32 (m, 6H, 2×CH$_3$); 1.69 (m, 1H, CH$_2$CH$_2$); 1.91 (m, 1H, CH$_2$CH$_2$); 2.04 (m, 2H, CH$_2$CH$_2$); 3.06 (m, 1H); 3.24 (m, 1H); 3.36 (m, 1H); 3.67 (m, 4H); 4.33 (m, 2H); 4.71 (m, 1H); 6.22 (m, 2H); 7.10 (m, 2H); 7.45 (d, J=8.7 Hz, 1H); 8.01 (m, 2H); 9.27 (br, 1H, OH).

S. 2,4,4-Trimethyl-7-{2-(2-methyl-pyrrolidin-1-yl)-6-[4-(3-trifluoromethyl-pyridin-2-yl)-piperazin-1-yl]-pyrimidin-4-yl}-1,23,4-tetrahydro-isoquinoline 1. 7-Bromo-2,4,4-trimethyl-1,2,3,4-tetrahydro-isoquinoline

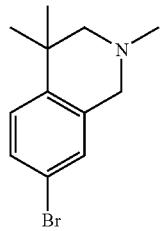

To a cooled solution of 2,4,4-trimethyl-1,2,3,4-tetrahydro-isoquinolin-7-ylamine (prepared essentially as described in PCT International Application Publication Numbers WO 00/009,486, WO 00/007,993 or WO 98/41507; 330 mg, 1.734 mmol) in 75% aqueous $H_2SO_4$, add $NaNO_2$ (132 mg, 1.91 mmol) in 1 ml of water, dropwise. Stir the solution at 0° C. for 30 minutes. Add CuBr (298 mg, 2.08 mmol) and 48% HBr (2 ml). Stir the mixture at 0° C. for 15 minutes. Heat the mixture at 60° C. for 30 minutes. Cool to room temperature, adjust the pH to 9-10, and extract with EtOAc. Wash with brine, dry the solution ($Na_2SO_4$), and concentrate under reduced pressure. Purify the residue by flash column chromatography eluting with EtOAc:Hexanes-(1:1) to afford 7-bromo-2,4,4-trimethyl-1,2,3,4-tetrahydro-isoquinoline.

2. 4-Chloro-2-(2-methyl-pyrrolidin-1-yl)-6-[4-(3-trifluoromethyl-pyridin-2-yl)-piperazin-1-yl]-pyrimidine

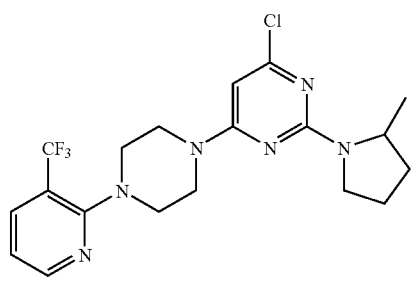

A mixture of 4,6-dichloro-2-(2-methyl-pyrrolidin-1-yl)-pyrimidine (2.0 mmol), 4-(6-trifluoromethyl-2-pyridyl)piperazine (462 mg, 2.0 mmol), potassium carbonate (345 mg, 2.5 mmol) and EtOH (10 mL) is heated at 78° C. for 8 hours. The mixture is cooled, diluted with water (20 mL) and extracted with EtOAc (3×25 mL). The combined organics are washed with brine (25 mL), dried ($MgSO_4$) and concentrated under reduced pressure. The residue is purified by flash chromatography on silica gel (80% hexane/20% ether) to give the title compound.

3. 2,4,4-Trimethyl-7-{2-(2-methyl-pyrrolidin-1-yl)-6-[4-(3-trifluoromethyl-pyridin-2-yl)-piperazin-1-yl]-pyrimidin-4-yl}-1,2,3,4-tetrahydro-isoquinoline

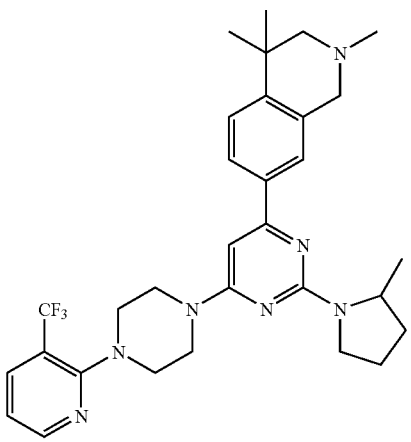

To a mixture of 7-bromo-2,4,4-trimethyl-1,2,3,4-tetrahydro-isoquinoline (140 mg, 0.55 mmol), 4,4,5,5,4',4',5',5'-octamethyl-[2,2']bi[[1,3,2]dioxaborolanyl] (140 mg, 0.55 mmol), DPPF (9 mg, 0.017 mmol), and KOAc (162 mg, 1.65 mmol) in DMSO, add $PdCl_2$(DPPF)-DCM complex (13 mg, 0.0165 mmol). Purge the reaction mixture for 10 minutes with dry $N_2$. Heat the stirring reaction mixture overnight at 80° C. Cool to room temperature. Add 4-chloro-2-(2-methyl-pyrrolidin-1-yl)-6-[4-(3-trifluoromethyl-pyridin-2-yl)-piperazin-1-yl]-pyrimidine (141 mg, 0.33 mmol), $Pd(PPh_3)_4$ (19 mg, 0.017 mmol), and $Cs_2CO_3$ (162 mg, 0.50 mmol). Heat the stirring reaction mixture overnight at 80° C., cool to room temperature, and partition between water and EtOAc. Dry the solution ($Na_2SO_4$), concentrate under reduced pressure. Purify the residue by flash column chromatography eluting with DCM:MeOH (9:1) to afford 2,4,4-trimethyl-7-{2-(2-methyl-pyrrolidin-1-yl)-6-[4-(3-trifluoromethyl-pyridin-2-yl)-piperazin-1-yl]-pyrimidin-4-yl}-1,2,3,4-tetrahydro-isoquinoline. $^1$H NMR (400 MHz, $CDCl_3$): δ 1.30 (m, 9H, 3×$CH_3$); 1.68 (m, 1H, $CH_2CH_2$); 1.91 (m, 1H, $CH_2CH_2$); 2.05 (m, 2H, $CH_2CH_2$); 2.40 (s, 2H); 2.43 (s, 3H, $NCH_3$); 3.39 (m, 4H); 3.61 (s, 2H); 3.67 (m, 2H); 3.79 (m, 4H); 4.34 (m, 1H); 6.27 (s, 1H, Ar—H); 7.01 (m, 1H); 7.35 (m, 1H); 7.63 (s, 1H); 7.88 (m, 1H); 7.88 (m, 1H); 8.44 (m, 1H).

T. 4-(3-Chloro-4-fluoro-phenyl)-2-(1-methyl-1H-imidazol-2-yl)-6-[4-(3-trifluoromethyl-pyridin-2-yl)-piperazin-1-yl]-pyrimidine

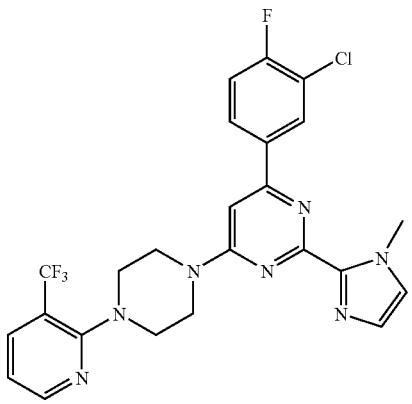

To a mixture of 2-chloro-4-(3-chloro-4-fluoro-phenyl)-6-[4-(3-trifluoromethyl-pyridin-2-yl)-piperazin-1-yl]-pyrimidine (200 mg, 0.43 mmol), 1-methyl-1H-imidazole (42 mg, 0.51 mmol), CuI (161 mg, 0.86 mmol), MgO (21 mg, 051 mmol), and PPh$_3$ (22 mg, 0.086 mmol) in dioxane add Pd(OAc)$_2$ (5 mg, mg, 0.021 mmol). Purge the reaction mixture for 10 minutes with dry N$_2$. Heat the mixture at 150° C. for 24 hours, cool to room temperature, and partition between water and EtOAc. Dry the solution (Na$_2$SO$_4$), concentrate under reduced pressure. Purify the residue by flash column chromatography eluting with DCM:MeOH:NH$_4$OH (95:5:1) to afford 4-(3-chloro-4-fluoro-phenyl)-2-(1-methyl-1H-imidazol-2-yl)-6-[4-(3-trifluoromethyl-pyridin-2-yl)-piperazin-1-yl]-pyrimidine. $^1$H NMR (2HCl salt, 300 MHz, DMSO-d$_6$): δ3.35 (m, 4H); 4.01 (m, 4H); 4.31 (s, 3H, NCH$_3$); 7.23 (m, 1H, Ar—H); 7.63 (m, 2H); 7.89 (s, 1H); 7.97 (s, 1H); 8.11 (m, 1H); 8.43 (m, 1H); 8.54 (m, 1H); 8.66 (m, 1H).

U. 4-(3-chloro-4-fluorophenyl)-6-((R)-4-(3-chloro-pyridin-2-yl)-2-methylpiperazin-1-yl)-2-(2-methylpyrrolidin-1-yl)pyrimidine 1. 2-(Benzylthio)-4-chloro-6-(3-chloro-4-fluorophenyl)pyrimidine

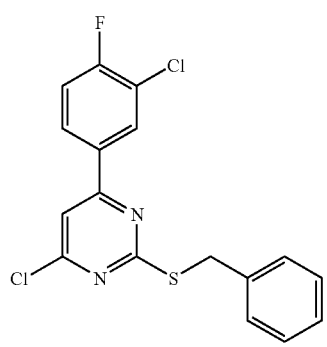

Dissolve 2-(benzylthio)-4,6-dichloropyrimidine (2.71 g, 0.01 moles) and 3-chloro-4-fluorophenylboronic acid (1.74 g, 0.01 moles) in dry dioxane (100 mL) under nitrogen atmosphere. Add aqueous K$_3$PO$_4$ (2.0 M, 7.5 mL) and Pd(PPh$_3$)$_4$ (578 mg). Reflux the mixture overnight, concentrate under vacuum, extract with CHCl$_3$ (150 mL), wash with water and dry with MgSO$_4$. Filter and evaporate under vacuum to afford a yellow oil. Purify the crude by flash column chromatography using 2% EtOAc/hexane to afford the title product as colorless oil.

2. (R)-1-(3-Chloro-pyridin-2-yl)-3-methyl-piperazine

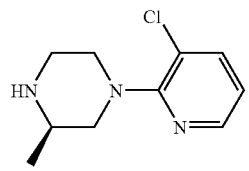

Dissolve 2,3-dichloropyridine (8.5 g, 0.057 moles) and (R)-(−)-2-methylpiperazine (5.75 g, 0.057 moles) in DMA (125.0 mL) under nitrogen atmosphere. Add anhydrous powdered K$_2$CO$_3$ (23.75 g, 0.172 moles) to this mixture and stir at 135-140° C. for 48 hours. Cool the reaction mixture to room temperature, dilute with water (400 mL), extract with EtOAc (3×200 mL) and wash the combined organic extract with brine (2×150 mL). Dry over MgSO$_4$, concentrate under vacuum to afford crude product as orange yellow liquid. Distil the crude under high vacuum to afford pyridylpiperazine derivative as yellow viscous oil.

3. 2-(Benzylthio)-4-(3-chloro-4-fluorophenyl)-6-((R)-4-(3-chloropyridin-2-yl)-2-methylpiperazin-1-yl)pyrimidine

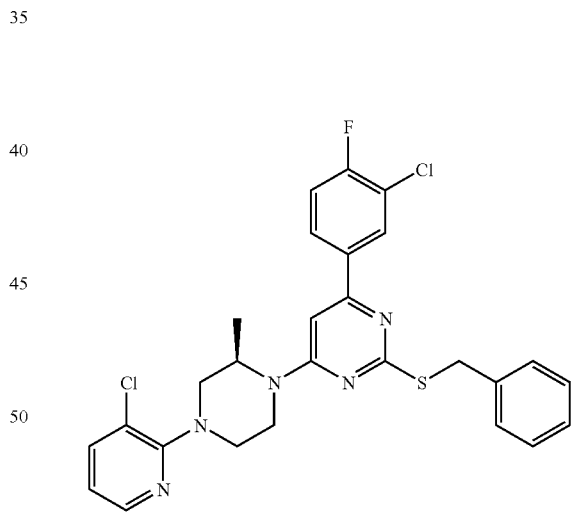

Dissolve 2-(benzylthio)-4-chloro-6-(3-chloro-4-fluorophenyl) pyrimidine (1.15 g, 0.00316 moles) and (R)-1-(3-chloro-pyridin-2-yl)-3-methyl-piperazine (0.65 g, 0.00316 moles) in CH$_3$CN (30.0 mL) under nitrogen atmosphere. Add anhydrous powdered K$_2$CO$_3$ (0.872 g, 0.00632 moles) to this mixture and reflux for 3 days. Concentrate the reaction mixture under vacuum, dilute with water (100 mL), extract with DCM (3×50 mL) and dry over MgSO$_4$. Filter, and concentrate under vacuum to afford crude product and purify by flash column chromatography using 15-20% EtOAc/hexane to afford the title product as white amorphous solid.

4. 2-(Benzylsulfonyl)-4-(3-chloro-4-fluorophenyl)-6-((R)-4-(3-chloropyridin-2-yl)-2-methylpiperazin-1-yl)pyrimidine

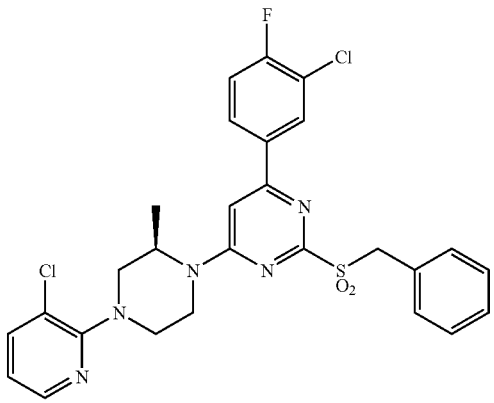

Dissolve 2-(benzylthio)-4-(3-chloro-4-fluorophenyl)-6-((R)-4-(3-chloropyridin-2-yl)-2-methylpiperazin-1-yl)pyrimidine (1.0 g) in DCM (25.0 mL) under nitrogen atmosphere and cool to −20° C. Add 77% m-CPBA (1.0 g) to this mixture in portions over a period of 15 minutes. Stir the reaction mixture at −20° C. for 4 hours. Wash the reaction mixture with saturated $Na_2CO_3$ and dry over $MgSO_4$. Filter, and concentrate under vacuum to afford the crude product and purify by flash column chromatography using 30-40% EtOAc/hexane to afford the title product as white amorphous solid.

5. 4-(3-chloro-4-fluorophenyl)-6-((R)-4-(3-chloropyridin-2-yl)-2-methylpiperazin-1-yl)-2-(2-methylpyrrolidin-1-yl)pyrimidine

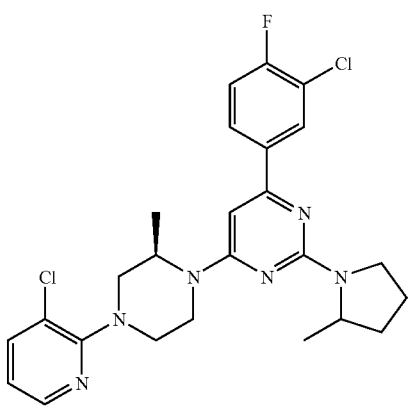

Dissolve 2-(benzylsulfonyl)-4-(3-chloro-4-fluorophenyl)-6-((R)-4-(3-chloropyridin-2-yl)-2-methylpiperazin-1-yl)pyrimidine (57 mg, 0.1 mmol) and 2-methylpyrrolidine (0.5 mmol) in dioxane (1.0 mL) under nitrogen atmosphere and beat at 110° C. for 72 hours. Concentrate under vacuum to afford crude product and purify by flash column chromatography using 5% EtOAc/hexane to afford the title product as white amorphous solid. NMR ($CDCl_3$) δ 1.31 (3H, d, J=1.5), 1.41 (3H, dd), 1.69 (1H, m), 1.9 (1H, m), 2.0 (2H, m), 2.98 (2H, m), 3.39 (1H, m), 3.65 (2H, m), 3.82 (2H, m), 4.35 (2H, m), 4.68 (1H, m), 6.22 (1H, s), 6.86 (1H, m), 7.16 (1H, t), 7.61 (1H, d, J=1.6), 7.88 (1H, m), 8.07 (1H, m), 8.20 (1H, m). Mass spec m/z=501.13.

V. 2-chloro-3-((R)-4-(6-(4-fluorophenyl)-2-((R)-2-methylpyrrolidin-1-yl)pyrimidin-4-yl)-3-methylpiperazin-1-yl)pyrazine 1. 2,4-dichloro-6-(4-fluorophenyl)pyrimidine

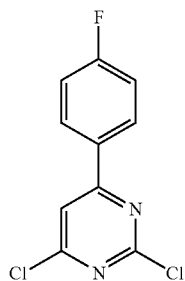

Dissolve 4-fluorobromobenzene (8.75 g, 0.05 moles) in anhydrous ether (80 mL) under nitrogen atmosphere and cool to −78° C. Add dropwise 1.6 M n-BuLi (34 mL, 0.055 moles) and stir at −78° C. for 45 minutes. Dissolve 2,4-dichloropyrimidine (7.45 g, 0.05 moles) in $Et_2O$ (100 mL) and add dropwise to the reaction mixture and warm the reaction mixture to −30° C. and stir at this temperature for 30 minutes followed by 0° C. for 30 minutes. Quench the reaction mixture with HOAc (3.15 mL, 0.055 moles) and water (0.5 mL, 0.027 moles) dissolved in THF (5.0 mL). Add dropwise THF (40 mL) solution of DDQ (11.9 g, 0.053 moles) to the reaction mixture. Bring the reaction mixture to room temperature and stir at room temperature for 30 minutes. Cool the reaction mixture to 0° C. and add 3.0 N aq. NaOH (35 mL) and stir for 30 minutes. Decant the organic layer from the reaction mixture and wash the brown solid with $Et_2O$ (3×100 mL). Combine the organic layers, wash several times with saturated NaCl solution and dry with $MgSO_4$. Filter and evaporate under vacuum to afford a brown colored solid. Purify the crude by flash column chromatography using 5% EtOAc/hexane to afford the title product as white solid.

2. 2-chloro-3-((R)-3-methylpiperazin-1-yl)pyrazine

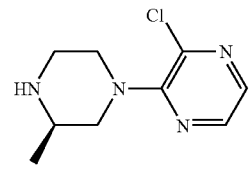

Dissolve 2,3-dichloropyrazine (3.0 g, 0.02 moles) and (R)-(−)-2-methylpiperazine (2.0 g, 0.02 moles) in DMA (30.0 mL) under nitrogen atmosphere. Add anhydrous powdered $K_2CO_3$ (8.3 g, 0.06 moles) to this mixture and stir at 110° C. for 4 hours. Cool the reaction mixture to room temperature, dilute with water (100 mL), extract with EtOAc (3×50 mL) and wash the combined organic extract with brine (2×50 mL). Dry over $MgSO_4$, concentrate under vacuum to afford crude product as orange yellow liquid. Purify the crude product by column chromatography using 2.5% MeOH in $CHCl_3$ to afford the title product as yellow viscous oil.

3. 2-Chloro-3-((R)-4-(2-chloro-6-(4-fluorophenyl)pyrimidin-4-yl)-3-methylpiperazin-1-yl)pyrazine

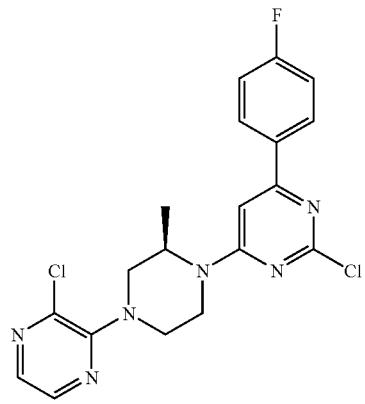

Dissolve 2,4-dichloro-6-(4-fluorophenyl)pyrimidine (486 mg, 2.0 mmoles) and 2-chloro-3-((R)-3-methylpiperazin-1-yl)pyrazine (424 mg, 2.0 mmoles) in CH$_3$CN (30.0 mL) under nitrogen atmosphere. Add anhydrous powdered K$_2$CO$_3$ (0.872 g, 0.00632 moles) to this mixture and stir at room temperature for 6 days. Concentrate the reaction mixture under vacuum, dilute with water (50 mL), extract with EtOAc (3×50 mL) and dry over MgSO$_4$. Filter, and concentrate under vacuum to afford crude product and purify by flash column chromatography using 5-20% EtOAc/hexane to afford the title product as viscous oil.

4. 2-chloro-3-((R)-4-(6-(4-fluorophenyl)-2-((R)-2-methylpyrrolidin-1-yl)pyrimidin-4-yl)-3-methylpiperazin-1-yl)pyrazine

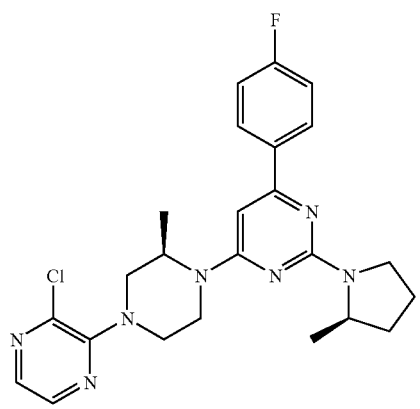

Dissolve 2-chloro-3-((R)-4-(2-chloro-6-(4-fluorophenyl)pyrimidin-4-yl)-3-methylpiperazin-1-yl)pyrazine (41.9 mg, 0.1 mmol) and (R)-2-methylpyrrolidine hydrobromide (0.3 mmol, prepared essentially as described by Nijhuis et. al. (1989) *J. Org. Chem.* 54:209-216) in CH$_3$CN (2.0 mL) under nitrogen atmosphere. Add K$_2$CO$_3$ (83 mg, 0.6 mmol) and heat at 80° C. for 48 hours. Concentrate under vacuum, dilute with water (5.0 mL), extract with EtOAc (3×3 mL) and dry with MgSO$_4$. Filter, and concentrate under vacuum to afford crude product and purify by flash column chromatography using 10-20% EtOAc/hexane to afford the title product as viscous oil. NMR (CDCl$_3$) δ 1.31 (3H, d, J=2.4), 1.38(3H, d, J=1.6), 1.69 (1H, m), 1.91 (1H, m), 2.06 (2H, m), 3.06 (1H, t), 3.17 (1H, dd), 3.375 (1H, t), 3.65 (2H, m), 3.97 (2H, m), 4.34 (2H, m), 4.70 (1H, bs), 6.24 (1H, s), 7.10 (2H, t), 7.91 (1H, s), 7.99 (2H, m), 8.13 (1H, m). Mass spec m/z=468.17.

W. 5-chloro-4-((R)-4-(6-(4-fluorophenyl)-2-((R)-2-methylpyrrolidin-1-yl)pyrimidin-4-yl)-3-methylpiperazin-1-yl)-2-methoxypyrimidine 1. 2,5-Dichloro-4-((R)-3-methylpiperazin-1-yl)pyrimidine

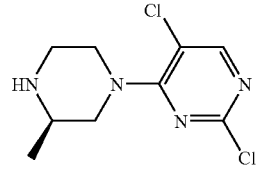

Dissolve 2,5,6-trichloropyrimidine (5.5 g, 0.03 moles) and (R)-(−)-2-methylpiperazine (3.0 g, 0.03 moles) in CH$_3$CN (100.0 mL) under nitrogen atmosphere. Add anhydrous powdered K$_2$CO$_3$ (8.3 g, 0.06 moles) to this mixture and stir at 25° C. for 4 hours. Concentrate the reaction mixture under vacuum, dilute with water (100 mL), extract with EtOAc (3×100 mL) and wash the combined organic extract with brine (2×50 mL). Dry over MgSO$_4$, and concentrate under vacuum to afford the title product as white solid.

2. 5-Chloro-2-methoxy-4-((R)-3-methylpiperazin-1-yl)pyrimidine

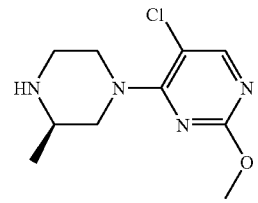

Dissolve 2,5-dichloro-4-((R)-3-methylpiperazin-1-yl)pyrimidine (2.5 g) in MeOH (25.0 mL) under nitrogen atmosphere. Add 25% NaOMe in MeOH (10 mL) to this mixture and reflux for 2 hours. Concentrate the reaction mixture under vacuum, dilute with water (100 mL), extract with CHCl$_3$ (3×50 mL) and wash the combined organic extract with brine (2×50 mL). Dry over MgSO$_4$, concentrate under vacuum and purify by flash column chromatography using 1% MeOH in CHCl$_3$ to afford the title product as colorless viscous oil.

3. 5-Chloro-4-((R)-4-(2-chloro-6-(4-fluorophenyl)pyrimidin-4-yl)-3-methylpiperazin-1-yl)-2-methoxypyrimidine

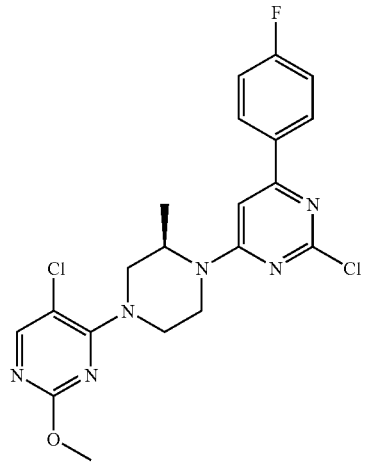

Dissolve 2,4-dichloro-6-(4-fluorophenyl)pyrimidine (486 mg, 2.0 mmoles) and 5-chloro-2-methoxy-4-((R)-3-methylpiperazin-1-yl)pyrimidine (484 mg, 2.0 mmoles) in CH₃CN (10.0 mL) under nitrogen atmosphere. Add anhydrous powdered K₂CO₃ (0.552 g, 0.004 moles) to this mixture and stir at room temperature for 3 days. Concentrate the reaction mixture under vacuum, dilute with water (50 mL), extract with EtOAc (3×50 mL) and dry over MgSO₄. Filter and concentrate under vacuum to afford crude product and purify by flash column chromatography using 10-40% EtOAc/hexane to afford the title product as white amorphous solid.

4. 5-chloro-4-((R)-4-(6-(4-fluorophenyl)-2-((R)-2-methylpyrrolidin-1-yl)pyrimidin-4-yl)-3-methylpiperazin-1-yl)-2-methoxypyrimidine

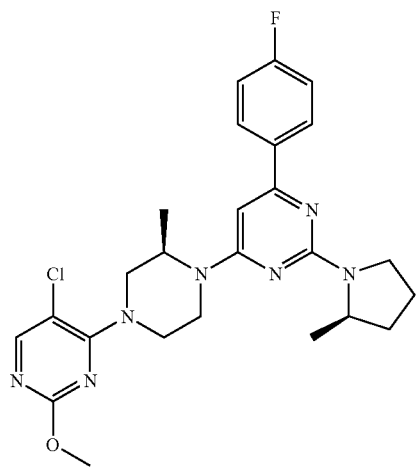

Dissolve 5-chloro-4-((R)-4-(2-chloro-6-(4-fluorophenyl)pyrimidin-4-yl)-3-methylpiperazin-1-yl)-2-methoxypyrimidine (45 mg, 0.1 mmol) and (R)-2-methylpyrrolidine hydrobromide (0.2 mmol, prepared essentially as described by Nijhuis et. al. (1989) *J. Org. Chem.* 54:209-216) in CH₃CN (2.0 mL) under nitrogen atmosphere. Add K₂CO₃ (55 mg, 0.4 mmol) and heat at 80° C. for 20 hours. Concentrate under vacuum, dilute with water (5.0 mL), extract with EtOAc (3×3 mL) and dry with MgSO₄. Filter, and concentrate under vacuum to afford crude product and purify by flash column chromatography using 20% EtOAc/hexane to afford the title product as viscous oil. NMR (CDCl₃) δ 1.3 (6H, m), 1.69 (1H, m), 1.91 (1H, m), 2.06 (2H, m), 3.21 (1H, m), 3.35 (2H, m), 3.63 (2H, m), 3.94 (3H, s), 4.28 (2H, m), 4.45 (2H, m), 4.64 (1H, bs), 6.19 (1H, s), 7.07 (2H, t), 7.97 (2H, m), 8.08 (1H, s). Mass spec m/z=498.17.

X. 4-((R)-4-(3-chloropyridin-2-yl)-2-methylpiperazin 1-yl)-6-(4-fluorophenyl)-2-(2,5-dimethyl-1H-pyrrol-1-yl)pyrimidine 1. 4,6-Dichloro-2-(2,5-dimethyl-1H-pyrrol-1-yl)pyrimidine

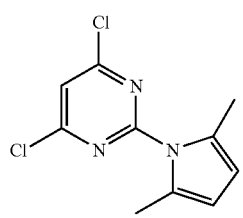

Dissolve 2-(amino-4,6-dichloropyrimidine (8.2 g, 0.05 moles) and hexane-2,5-dione (5.7 g, 0.05 moles) in toluene (150 mL) under nitrogen atmosphere. Add p-toluenesulfonic acid (300 mg) to the reaction mixture and reflux under Dean Stark conditions with removal of water over 6 hours. Cool and filter through silica gel and evaporate under vacuum to afford the title product as yellow solid.

2. 4-Chloro-6-(4-fluorophenyl)-2-(2,5-dimethyl-1H-pyrrol-1-yl)pyrimidine

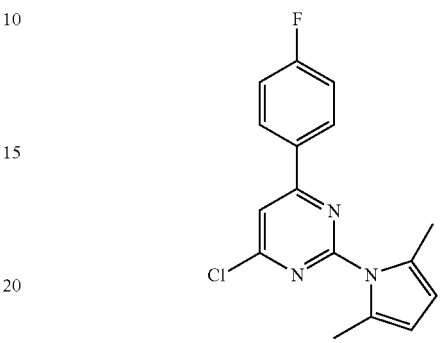

Dissolve 4,6-dichloro-2-(2,5-dimethyl-1H-pyrrol-1-yl)pyrimidine (1.2 g, 0.005 moles) and 4-fluorophenylboronic acid (0.7 g, 0.005 moles) in dry dioxane (25 mL) under nitrogen atmosphere. Add aqueous K₃PO₄ (2.0 M, 3.75 mL) and Pd(PPh₃)₄ (289 mg). Reflux the mixture overnight, concentrate under vacuum, extract with CHCl₃ (150 mL), wash with water and dry with MgSO₄. Filter and evaporate under vacuum to afford yellow oil. Purify the crude by flash column chromatography using 2% EtOAc/hexane to afford the title product as brown oil.

3. 4-((R)-4-(3-chloropyridin-2-yl)-2-methylpiperazin-1-yl)-6-(4-fluorophenyl)-2-(2,5-dimethyl-1H-pyrrol-1-yl)pyrimidine

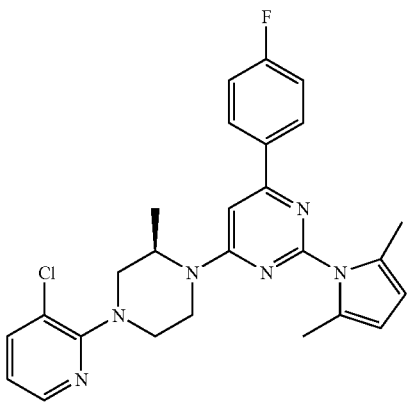

Dissolve 4-chloro-6-(4-fluorophenyl)-2-(2,5-dimethyl-1H-pyrrol-1-yl)pyrimidine (60.4 mg, 0.2 mmoles) and (R)-1-(3-chloro-pyridin-2-yl)-3-methyl-piperazine (42.4 mg, 0.2 mmoles) in DMA (2.0 mL) under nitrogen atmosphere. Add anhydrous powdered K₂CO₃ (0.4 mmoles) to this mixture and heat at 130° C. for 24 hours. Cool, dilute with water (5 mL), extract with EtOAc (3×2 mL) and dry over MgSO₄. Filter and concentrate under vacuum to afford crude product and purify by flash column chromatography using 10% EtOAc/hexane to afford the title product as white amorphous solid. NMR (CDCl₃) δ 1.47 (3H, d, J=1.7), 2.45 (6H, s), 3.04 (2H, m), 3.45 (1H, t), 3.84 (2H, t), 4.35 (1H, m), 4.85 (1H, bs), 5.9 (1H, s), 6.77 (1H, s), 6.89 (1H, m), 7.14 (2H, t), 7.63 (1H, d, J=2.3), 8.06 (2H, m), 8.21 (1H, m). Mass spec m/z=477.11.

Y. 4-(3-chloro-4-fluorophenyl)-6-(4-(3-(trifluoromethyl)pyridin-2-yl)piperazin-1-yl)-2-isopropylpyrimidine 1. Ethyl 3-(3-chloro-4-fluorophenyl)-3-oxopropanoate

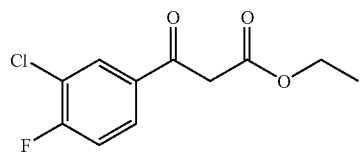

Dissolve mono ethylmalonate (11.88 g, 0.09 moles) and 2,2'-bipyridyl (10 mg) in anhydrous THF (200 mL) under nitrogen atmosphere and cool to −78° C. Add dropwise 2.5 M n-BuLi (80 mL, 0.2 moles) and allow the reaction mixture to war gradually to −5° C. Cool the reaction mixture back to −65° C. Add dropwise, 3-chloro-4-fluorobenzoyl chloride (9.65 g, 0.05 moles) and stir at −65° C. for 60 mins. Quench the reaction mixture with 1.0 N aq. HCl (200 mL), extract with Et$_2$O (3×200 mL). Combine the organic layers, wash with saturated NaCl solution and dry with MgSO$_4$. Filter and evaporate under vacuum to afford crude product. Purify the crude by flash column chromatography using 5% EtOAc/hexane to afford desired product as orange-yellow liquid.

2. 6-(3-Chloro-4-fluorophenyl)-2-isopropylpyrimidin-4-ol

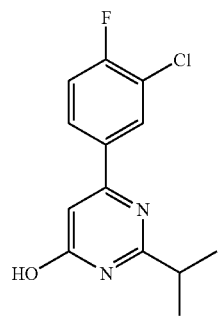

Dissolve ethyl 3-(3-chloro-4-fluorophenyl)-3-oxopropanoate (1.22 g, 0.005 moles) and isobutyramidine hydrochloride (0.73 g, 0.005 moles) in toluene (25.0 mL) under nitrogen atmosphere. Add K$_2$CO$_3$ (3.45 g, 0.05 moles) to the reaction mixture and stir at room temperature for 20 hours. Dilute the reaction mixture with water, acidify to pH 6.0 to 7.0, extract with DCM (3×100 mL), wash with water and dry with MgSO$_4$. Filter and evaporate under vacuum to afford the title product as white solid.

3. 4-Chloro-6-(3-chloro-4-fluorophenyl)-2-isopropyl-pyrimidine

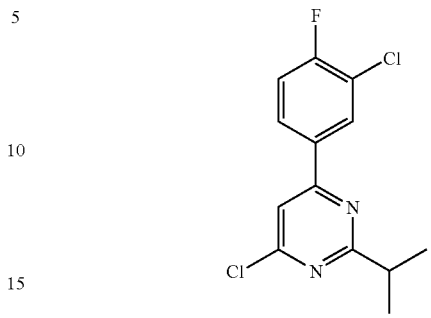

Dissolve 6-(3-chloro-4-fluorophenyl)-2-isopropylpyrimidin-4-ol (0.3 g, 1.13 mmoles) in POCl$_3$ (3.0 mL) under nitrogen atmosphere. Heat the mixture at 100° C. for 4 hours, concentrate under vacuum, quench with ice, neutralize with saturated NaHCO$_3$, extract with EtOAc (2×25 mL), wash with brine and dry with MgSO$_4$. Filter and evaporate under vacuum to afford yellow oil. Purify the crude by flash column chromatography using 15% EtOAc/hexane to afford the title product as colorless oil.

4. 4-(3-chloro-4-fluorophenyl)-6-(4-(3-(trifluoromethyl)pyridin-2-yl)piperazin-1-yl)-2-isopropylpyrimidine

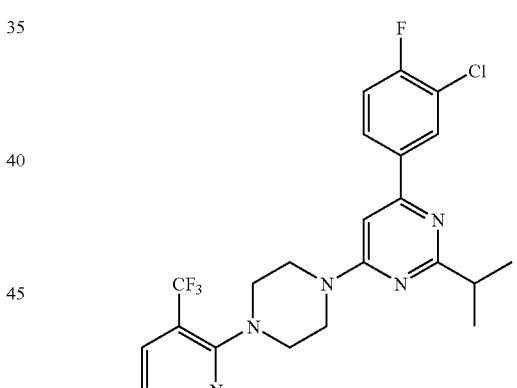

Dissolve 4-chloro-6-(3-chloro-4-fluorophenyl)-2-isopropyl-pyrimidine (56 mg, 0.2 mmoles) and 1-(3-(trifluoromethyl)-pyridin-2-yl)piperazine (46 mg, 0.2 mmoles) in DMA (1.5 mL) under nitrogen atmosphere. Add anhydrous powdered K$_2$CO$_3$ (55 mg, 0.4 mmoles) to this mixture and heat at 120° C. for 18 hours. Cool, dilute with water (5 mL), extract with EtOAc (3×2 mL) and dry over MgSO$_4$. Filter, and concentrate under vacuum to afford crude product and purify by flash column chromatography using 7% EtOAc/hexane to afford the title product as colorless viscous oil. NMR (CDCl$_3$) δ 1.33 (6H, d, J=1.8), 3.05 (1H, m), 3.40 (4H, m), 3.87 (4H, m), 6.68 (1H, s), 7.03 (1H, m), 7.19 (1H, t), 7.89 (2H, m), 8.07 (1H, d, J=2.3), 8.45 (1H, m). Mass spec m/z=480.22.

Z. 4-(3-Chloro-4-fluorophenyl)-6-(4-(3-(trifluoromethyl)pyridin-2-yl)piperazin-1-yl)-2-(pyridin-4-yl)pyrimidine

1. 6-(3-Chloro-4-fluorophenyl)-2-(pyridin-4-yl)pyrimidin-4-ol

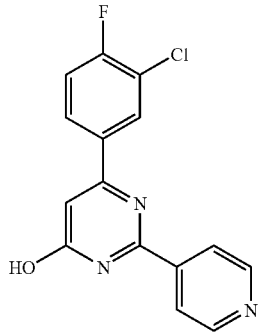

Dissolve ethyl 3-(3-chloro-4-fluorophenyl)-3-oxopropanoate (2.44 g, 0.01 moles) and isonicotinamidine hydrochloride (1.57 g, 0.01 moles) in EtOH (50.0 mL) under nitrogen atmosphere. Add 21% NaOEt (3.2 mL) to the reaction mixture and reflux for 3 days. Cool, filter the white solid separated from the reaction mixture, wash with water and dry under vacuum to afford the title product.

2. 4-Chloro-6-(3-chloro-4-fluorophenyl)-2-(pyridin-4-yl)pyrimidine

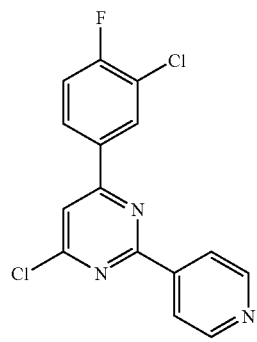

Dissolve 6-(3-chloro-4-fluorophenyl)-2-(pyridin-4-yl)pyrimidin-4-ol (0.26 g, 0.863 mmoles) in POCl$_3$ (3.0 mL) under nitrogen atmosphere. Heat the mixture at 100° C. for 20 hours, concentrate under vacuum, quench with ice, neutralize with saturated NaHCO$_3$, extract with CHCl$_3$ (2×50 mL), wash with brine and dry with MgSO$_4$. Filter and evaporate under vacuum to afford the title product as off-white solid

3. 4-(3-Chloro-4-fluorophenyl)-6-(4-(3-(trifluoromethyl)pyridin-2-yl)piperazin-1-yl)-2-(pyridin-4-yl)pyrimidine

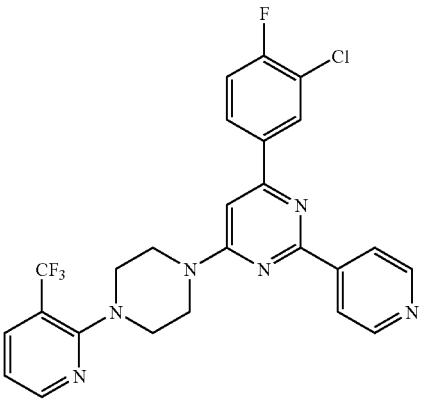

Dissolve 4-chloro-6-(3-chloro-4-fluorophenyl)-2-(pyridin-4-yl)pyrimidine (64 mg, 0.2 mmoles) and 1-(3-(trifluoromethyl)-pyridin-2-yl)piperazine (46 mg, 0.2 mmoles) in DMA (2.0 mL) under nitrogen atmosphere. Add anhydrous powdered K$_2$CO$_3$ (55 mg, 0.4 mmoles) to this mixture and heat at 140° C. for 20 hours. Cool, dilute with water (5 mL), extract with EtOAc (3×2 mL) and dry over MgSO$_4$. Filter, and concentrate under vacuum to afford crude product. Wash the crude product with Et$_2$O (2.0 mL) to afford the title product as cream colored solid. NMR (CDCl$_3$) δ 3.34 (4H, s), 3.99 (4H, s), 7.20 (1H, m), 7.47 (1H, s), 7.43 (1H, t), 8.09 (1H, d, J=2.0), 8.30 (2H, m), 8.35 (1H, m), 8.55 (2H, m), 8.70 (2H, m). Mass spec m/z=515.24.

AA. 4-(3-Chloro-4-fluorophenyl)-6-(4-(3-(trifluoromethyl)pyridin-2-yl)piperazin-1-yl)-2-(1,2,3,6-tetrahydro-1-isopropylpyridin-4-yl)pyrimidine

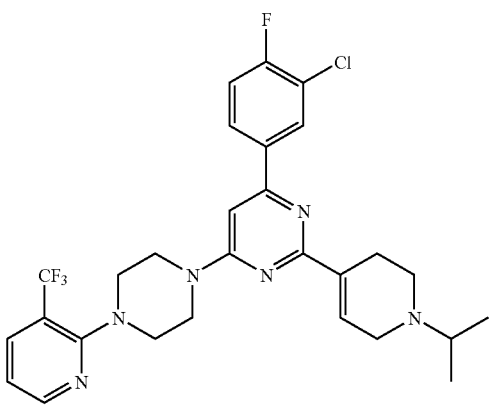

Dissolve 4-(3-chloro-4-fluorophenyl)-6-(4-(3-(trifluoromethyl)pyridin-2-yl)piperazin-1-yl)-2-(pyridin-4-yl)pyrimidine (40 mg) and 2-bromopropane (0.1 mL) in DMF (1.5 mL) under nitrogen atmosphere. Heat the mixture in a sealed tube at 120° C. for 48 hours. Cool the mixture to room temperature and then add NaBH$_4$ (50 mg). Stir the mixture at room temperature for 20 hours, dilute with water (5 mL), extract with EtOAc (3×3 mL) and dry over MgSO$_4$. Filter, and concentrate under vacuum to afford crude product and purify by flash column chromatography using 20% EtOAc/hexane to afford the title product as white solid. Mass spec m/z=561.27.

BB. 4-(3-chloro-4-fluorophenyl)-6-((S)-4-(3-chloro-pyridin-2-yl)-2-methylpiperazin-1-yl)-2-((S)-2-methylpyrrolidin-1-yl)pyrimidine 1. 2, 4-dichloro-6-(3-chloro-4-fluorophenyl)pyrimidine

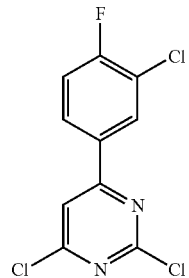

Dissolve 3-chloro-4-fluorobromobenzene (10.0 g, 0.04 moles) in anhydrous ether (80 mL) under nitrogen atmosphere and cool to −78° C. Add dropwise 1.6 M n-BuLi (36 mL, 0.048 moles) and stir at −78° C. for 45 minutes. Dissolve 2,4-dichloropyrimidine (7.1 g, 0.04 moles) in Et₂O (100 mL) and add dropwise to the reaction mixture and warm the reaction mixture to −30° C. and stir at this temperature for 30 minutes followed by 0° C. for 30 minutes. Quench the reaction mixture with HOAc (3.15 mL, 0.055 moles), and water (0.5 mL, 0.027 moles) dissolved in THF (5.0 mL). Add dropwise THF (40 mL) solution of DDQ (13 g) to the reaction mixture. Bring the reaction mixture to room temperature and stir at room temperature for 30 minutes. Cool the reaction mixture to 0° C., add 3.0 N aq. NaOH (35 mL) and stir for 30 minutes. Decant the organic layer from the reaction mixture and wash the brown solid with Et₂O (3×100 mL). Combine the organic layers, wash several times with saturated NaCl solution and dry with MgSO₄. Filter and evaporate under vacuum to afford brown colored solid. Purify the crude by flash column chromatography using 5% EtOAc/hexane to afford the title product as white solid.

2. (S)-1-(3-Chloro-pyridin-2-yl)-3-methyl-piperazine

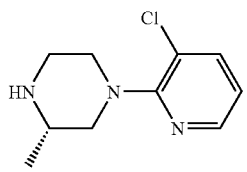

Dissolve 2,3-dichloropyridine (7.4 g, 0.05 moles) and (S)-(−)-2-methylpiperazine (5.0 g, 0.05 moles) in DMA (125.0 mL) under nitrogen atmosphere. Add anhydrous powdered K₂CO₃ (20.75 g, 0.15 moles) to this mixture and stir at 135-140° C. for 56 hours. Cool the reaction mixture to room temperature, dilute with water (400 mL), extract with EtOAc (3×200 mL) and wash the combined organic extract with brine (2×150 mL). Dry over MgSO₄, and concentrate under vacuum to afford crude product as yellow liquid. Purify by flash column chromatography using CHCl₃ to afford pyridylpiperazine derivative as yellow viscous oil.

3. 2-Chloro-4-(3-chloro-4-fluorophenyl)-6-((S)-4-(3-chloro-pyridin-2-yl)-2-methylpiperazin-1-yl)pyrimidine

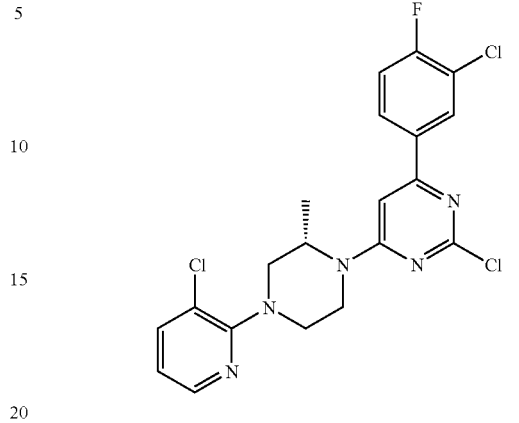

Dissolve 2,4-dichloro-6-(3-chloro-4-fluorophenyl)pyrimidine (554 mg, 2.0 mmoles) and 2-chloro-3-((S)-3-methylpiperazin-1-yl)pyrazine (424 mg, 2.0 mmoles) in CH₃CN (20.0 mL) under nitrogen atmosphere. Add anhydrous powdered K₂CO₃ (0.552 g, 4.0 mmoles) to this mixture and stir at room temperature for 40 hours. Concentrate the reaction mixture under vacuum, dilute with water (50 mL), extract with EtOAc (3×50 mL) and dry over MgSO₄. Filter and concentrate under vacuum to afford crude product and purify by flash column chromatography using 5-20% EtOAc/hexane to afford the title product as white solid.

4. 4-(3-chloro-4-fluorophenyl)-6-((S)-4-(3-chloropyridin-2-yl)-2-methylpiperazin-1-yl)-2-((S)-2-methylpyrrolidin-1-yl)pyrimidine

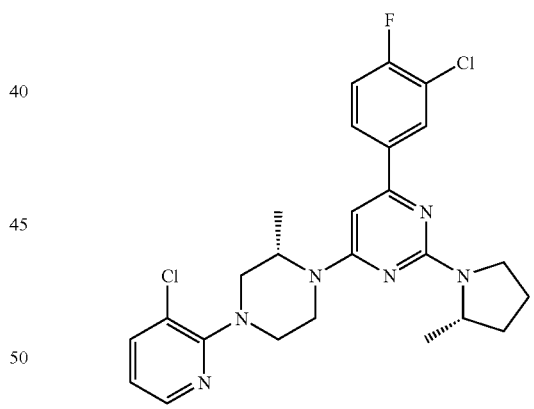

Dissolve 2-chloro-4-(3-chloro-4-fluorophenyl)-6-((S)-4-(3-chloropyridin-2-yl)-2-methylpiperazin-1-yl)pyrimidine (45 mg, 0.1 mmol) and (S)-2-methylpyrrolidine hydrobromide (0.2 mmol, prepared essentially as described by Nijhuis et. al. (1989) J. Org. Chem. 54:209-216) in CH₃CN; 2.0 mL) under nitrogen atmosphere. Add K₂CO₃ (55 mg, 0.4 mmol) and heat at 80° C. for 20 hours. Concentrate under vacuum, dilute with water (5.0 mL), extract with EtOAc (3×3 mL) and dry with MgSO₄. Filter, and concentrate under vacuum to afford crude product. Purify by flash column chromatography using 10-20% EtOAc/hexane to afford the title product as viscous oil. NMR (CDCl₃) δ1.31 (3H, d, J=2.1), 1.41(3H, d, J=2.3), 1.62 (2H, m), 1.93 (3H, m), 3.00 (2H, m), 3.35 (1H, t), 3.65 (2H, m), 3.81(2H, m), 4.35 (1H, m), 4.68 (1H, bs), 6.22

(1H, s), 6.87 (1H, m), 7.16 (1H, t), 7.61 (1H, m), 7.88 (1H, m), 8.06 (1H, m), 8.20 (1H, m). Mass spec m/z=501.22.

CC. 4-(3-chlorophenyl)-2-morpholino-6-(4-(3-(trifluoromethyl)pyridin-2-yl)piperazin-1-yl)pyrimidine-5-carbonitrile 1. 4-(3-chlorophenyl)-6-hydroxy-2-morpholinopyrimidine-5-carbonitrile

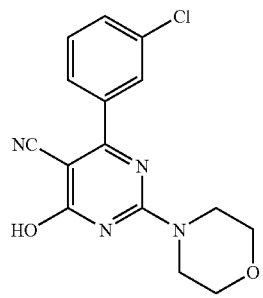

Dissolve sodium (230 mg, 0.01 moles) in dry EtOH (15 mL) under nitrogen atmosphere. Add morpholine-4-carboxamidine hydrobromide (2.1 g, 0.01 moles) to the reaction mixture and stir at room temperature for 30 minutes. Add ethyl cyanoacetate (1.13 g, 0.1 moles) and 3-chlorobenzaldehyde (1.4 g, 0.01 moles) to the reaction mixture and stir at room temperature for 2 hours. Dilute the reaction mixture with water (50 mL), acidify to pH 5.0 using AcOH, filter the white solid and concentrate under vacuum to afford the title product.

2. 4-Chloro-6-(3-chlorophenyl)-2-morpholinopyrimidine-5-carbotnitrile

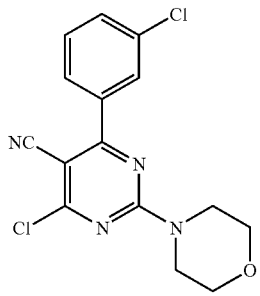

Dissolve 4-(3-chlorophenyl)-6-hydroxy-2-morpholinopyrimidine-5-carbonitrile (1.75 g, 0.0055 moles) in POCl$_3$ (3.0 mL) under nitrogen atmosphere. Add N,N-dimethylaniline (0.81 g, 0.0067 moles) and heat the mixture at 90° C. for 4 hours, concentrate under vacuum, quench with ice, extract with EtOAc(3×50 mL), wash with brine and dry with MgSO$_4$. Filter and evaporate under vacuum to afford yellow oil. Purify the crude by flash column chromatography to afford the title product as a white solid.

3. 4-(3-chlorophenyl)-2-morpholino-6-(4-(3-(trifluoromethyl)pyridin-2-yl)piperazin-1-yl)pyrimidine-5-carbonitrile

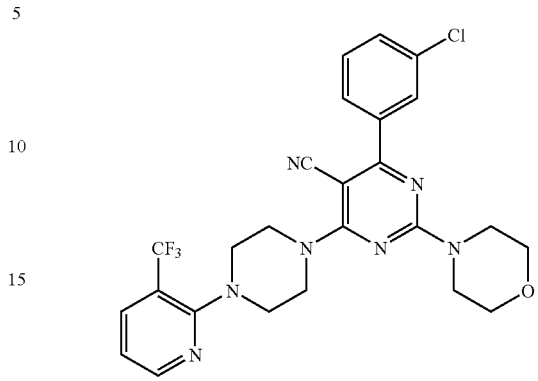

Dissolve 4-chloro-6-(3-chlorophenyl)-2-morpholinopyrimidine-5-carbonitrile (33.5 mg, 0.1 mmoles) and 1-(3-(trifluoromethyl)-pyridin-2-yl)piperazine (23 mg, 0.1 mmoles) in CH$_3$CN (1.0 mL) under nitrogen atmosphere. Add anhydrous powdered K$_2$CO$_3$ (28 mg, 0.2 mmoles) to this mixture and heat at 80° C. for 24 hours. Cool, dilute with water (5 mL), extract with EtOAc (3×2 mL) and dry over MgSO$_4$. Filter, and concentrate under vacuum to afford crude product Purify by flash column chromatography using 30% EtOAc/hexane to afford the title product as white solid. NMR (DMSO-D$_6$) δ 3.30 (4H, s), 3.62 (4H, m), 3.80 (4H, s), 3.93 (4H, s), 7.19 (1H, m), 7.51 (1H, m), 7.59 (1H, m), 7.76 (1H, m), 7.83 (1H, s), 8.07 (1H, d, J=2.0), 8.52 (1H, d, J=1.2). Mass spec m/z=530.12.

DD. 4-(3-Chloro-4-fluorophenyl)-2-pyridin-3-yl-6-[4-(3-trifluoromethylpyridin-2-yl)-piperazin-1-yl]-pyrimidine

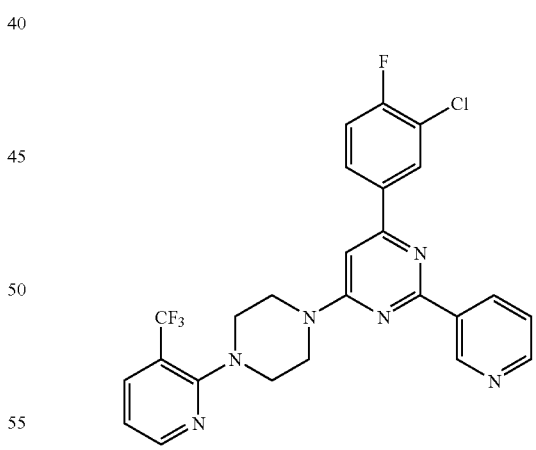

Heat a mixture of 2-chloro-4-(3-chloro-4-fluoro-phenyl)-6-[4-(3-trifluoromethylpyridin-2-yl)-piperazin-1-yl]-pyrimidine, (47 mg, 0.1 mmol), 3-tri-n-butylstannylpyridine (92 mg, 0.25 mmol), Pd(PPh$_3$)$_4$ (6 mg, 0.005 mmol), in toluene (5 mL) at 110° C. for 16 hours. Let cool to room temperature, filter off the catalyst, and add water (5 mL). Extract with EtOAc, dry (Na$_2$SO$_4$), and evaporate. Purify using flash chromatography (9:1 hexanes/EtOAc) to give pure 4-(3-chloro-4-fluorophenyl)-3-pyridin-3-yl-6-[4-(3-trifluoromethylpyridin-2-yl)-piperazin-1-yl]-pyrimidine as a tan solid. $^1$H NMR (DMSO D$_6$): 9.75 (s, 1H). 9.21 (d, 1H), 8.97 (d, 1H), 8.62 (d, 1H), 8.58 (d, 1H), 8.40 (dd, 1H), 8.19 (d, 1H), 8.00 (d, 1H), 7.61 (d, 1H), 7.58 (s, 1H), 7.21 (dd, 1H), 4.01 (br m, 8H).

EE. 3-{4-[6-(3-Chloro-4-fluorophenyl)-2-(2-methylpyrrolidin-1-yl)-pyrimidin-4-yl]-piperazin-1-yl}-4-methylpyridazine

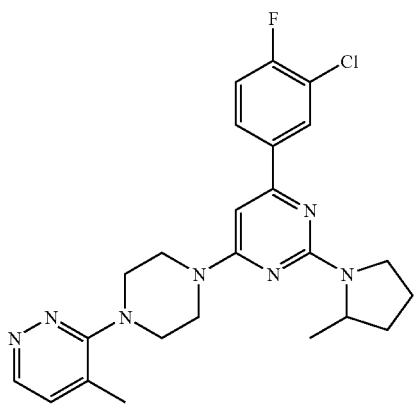

Heat a mixture of 4-(3-chloro-4-fluorophenyl-2-(2-methylpyrrolidin-1-yl)-6-piperazin-1-yl-pyrimidine (125 mg, 0.33 mmol), 3-chloro-4-methylpyridazine (43 mg, 0.33 mmol; see Takahayashi (1957) *Chem. Pharm. Bull* 5(3):229), DIEA (85 mg, 0.66 mmol), in DMA (5 mL) for 16 hours at 120° C. Cool to room temperature, add water (5 mL), extract with EtOAc (2×10 mL), wash with water (3×5 mL), dry (Na$_2$SO$_4$) and evaporate. Purify by column chromatography (1:1 hexanes/EtOAc) to provide 3-{4-[6-(3-chloro-4-fluorophenyl)-2-(2-methylpyrrolinin-1-yl)-pyrimidin-4-yl]-piperazin-1-yl}-4-methylpyridazine.

Example 2

Parallel Array Synthesis of Additional Representative Biaryl piperazinyl-Pyridine Analogues This Example illustrates the preparation of 2,4-bis(dialkylamino)-6-arylpyrimidines.

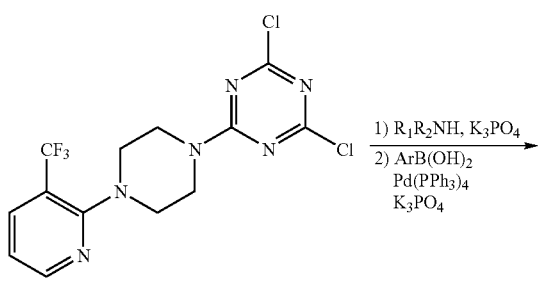

-continued

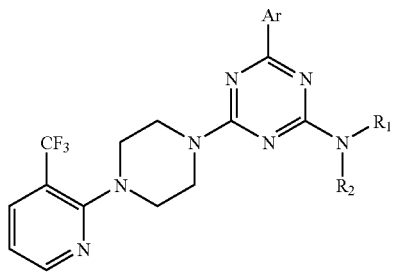

2,4-dichloro-6-[4-(3-trifluoromethyl-pyridin-2-yl)-piperazin-1-yl]-[1,3,5]triazine is prepared in a manner analogous to that described by Kreutzberger (1987) *Arzneimittel-Forschung* 37(9):999-1002. To vials containing 2,4-dichloro-6-[4-(3-trifluoromethyl-pyridin-2-yl)-piperazin-1-yl]-[1,3,5]triazine (0.2 M in dioxane, 0.1 mL) and the secondary amines (0.2 M in toluene, 0.1 mL) add K$_3$PO$_4$ (0.5 M aqueous, 0.05 mL). Heat the vials in a block heater-shaker at 60° C. for 30 minutes. Cool to room temperature, add arylboronic acids (0.2 M in dioxane, 0.15 mL) and another portion of K$_3$PO$_4$ (0.5 M aqueous, 0.05 mL). Charge the vials with argon and add Pd(PPh$_3$)$_4$ (0.01 M in toluene, 0.05 mL). Heat the mixtures at 80° C. for 16 hours, cool, dilute with EtOAc (0.5 mL), and directly load onto SCX cartridges. Wash with EtOAc (4 mL) followed by elution with 10% Et$_3$N in EtOAc. The eluents are concentrated to give essentially pure products (by LC/MS) in quantitative yields.

Example 3

Additional Representative Biaryl piperazinyl-Pyridine Analogues

Using routine modifications, the starting materials may be varied and additional steps employed to produce other compounds provided herein. Compounds listed in Tables I and II were prepared using such methods. All compounds listed in Table I have an IC$_{50}$ (determined as described in Example 6, herein) of 1 micromolar or less. For compounds in Table II, a "*" in the column labeled "IC$_{50}$" indicates that the IC$_{50}$ determined as described in Example 6 is 1 micromolar or less. The mass spectroscopy data (column labeled "MS") in Table I was obtained using Method B above and is presented as M+1. MS data in Table II was obtained using Method A or Method B, above, as indicated. Retention times shown in Table II are presented in minutes.

TABLE 1
Representative Biaryl Piperazinyl-Pyridine Analogues
| Compound | | Name | MS (M + 1) |
|---|---|---|---|
| 1 | 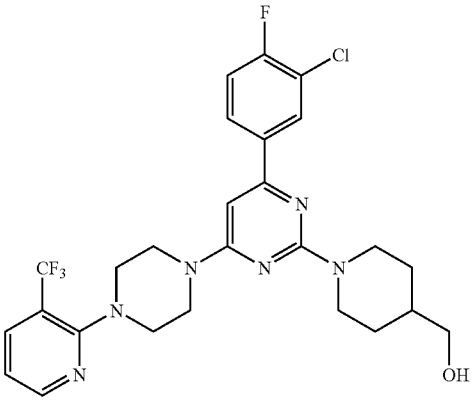 | (1-{4-(3-Chloro-4-fluoro-phenyl)-6-[4-(3-trifluoromethyl-pyridin-2-yl)-piperazin-1-yl]-pyrimidin-2-yl}-piperidin-4-yl)-methanol | 551.2 |
| 2 | 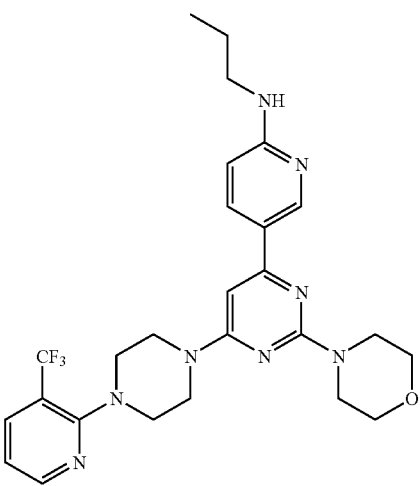 | (5-{2-Morpholin-4-yl-6-[4-(3-trifluoromethyl-pyridin-2-yl)-piperazin-1-yl]-pyrimidin-4-yl}-pyridin-2-yl)-propyl-amine | 529.3 |
| 3 | 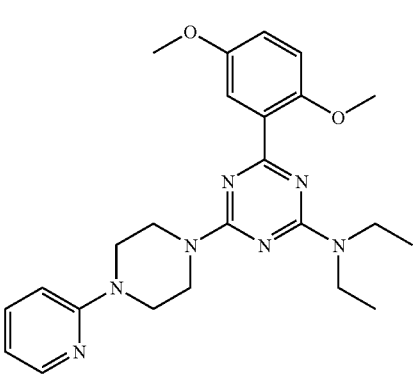 | [4-(2,5-Dimethoxy-phenyl)-6-(4-pyridin-2-yl-piperazin-1-yl)-[1,3,5]triazin-2-yl]-diethyl-amine | 450.3 |

TABLE 1-continued
Representative Biaryl Piperazinyl-Pyridine Analogues
| Compound | | Name | MS (M + 1) |
|---|---|---|---|
| 4 | 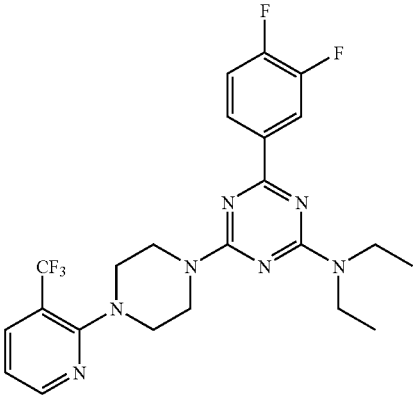 | {4-(3,4-Difluoro-phenyl)-6-[4-(3-trifluoromethyl-pyridin-2-yl)-piperazin-1-yl]-[1,3,5]triazin-2-yl}-diethyl-amine | 494.3 |
| 5 | 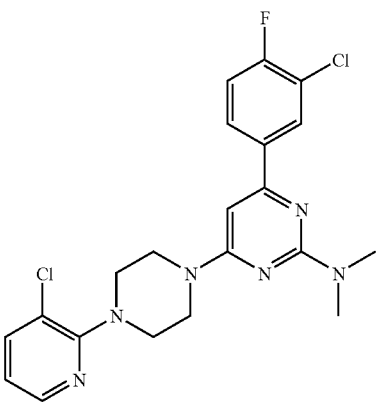 | {4-(3-Chloro-4-fluoro-phenyl)-6-[4-(3-chloro-pyridin-2-yl)-piperazin-1-yl]-pyrimidin-2-yl}-dimethyl-amine | 447.1 |
| 6 | 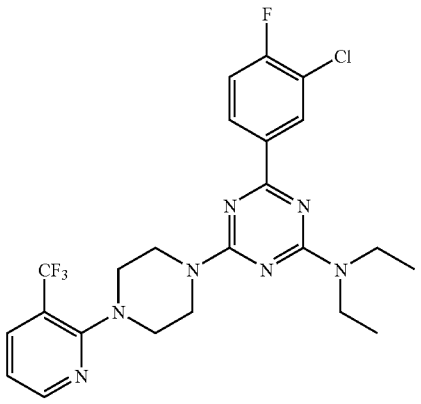 | {4-(3-Chloro-4-fluoro-phenyl)-6-[4-(3-trifluoromethyl-pyridin-2-yl)-piperazin-1-yl]-[1,3,5]triazin-2-yl}-diethyl-amine | |

TABLE 1-continued

Representative Biaryl Piperazinyl-Pyridine Analogues

| Compound | | Name | MS (M + 1) |
|---|---|---|---|
| 7 | 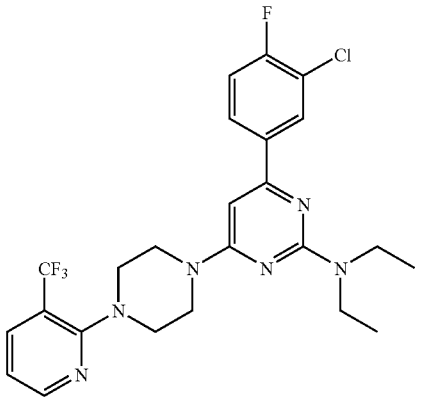 | {4-(3-Chloro-4-fluoro-phenyl)-6-[4-(3-trifluoromethyl-pyridin-2-yl)-piperazin-1-yl]-pyrimidin-2-yl}-diethyl-amine | 509.2 |
| 8 | 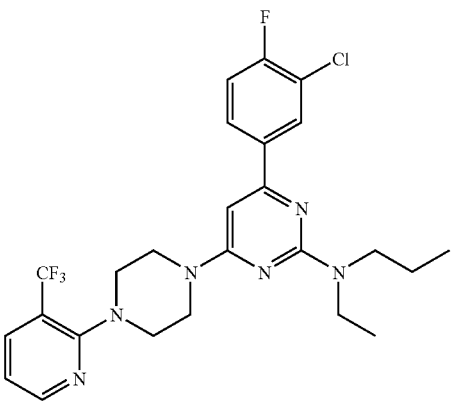 | {4-(3-Chloro-4-fluoro-phenyl)-6-[4-(3-trifluoromethyl-pyridin-2-yl)-piperazin-1-yl]-pyrimidin-2-yl}-ethyl-propyl-amine | 523.2 |
| 9 | 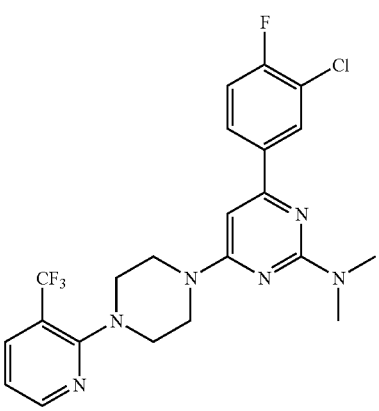 | {4-(3-Chloro-4-fluoro-phenyl)-6-[4-(3-trifluoromethyl-pyridin-2-yl)-piperazin-1-yl]-pyrimidin-2-yl}-dimethyl-amine | 481.2 |

TABLE 1-continued

Representative Biaryl Piperazinyl-Pyridine Analogues

| Compound | | Name | MS (M + 1) |
|---|---|---|---|
| 10 | 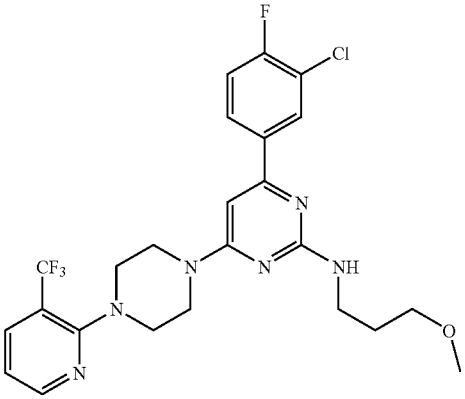 | {4-(3-Chloro-4-fluoro-phenyl)-6-[4-(3-trifluoromethyl-pyridin-2-yl)-piperazin-1-yl]-pyrimidin-2-yl}-(3-methoxy-propyl)-amine | 525.2 |
| 11 | 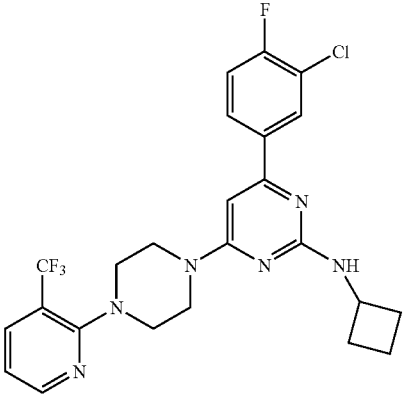 | {4-(3-Chloro-4-fluoro-phenyl)-6-[4-(3-trifluoromethyl-pyridin-2-yl)-piperazin-1-yl]-pyrimidin-2-yl}-cyclobutyl-amine | 507.2 |
| 12 | 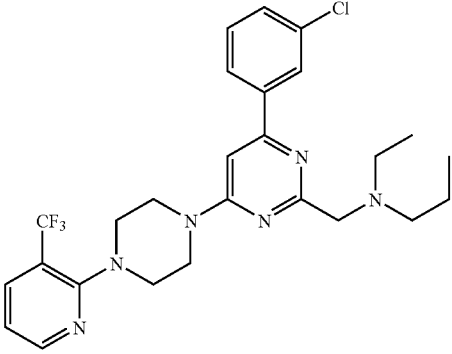 | {4-(3-Chloro-phenyl)-6-[4-(3-trifluoromethyl-pyridin-2-yl)-piperazin-1-yl]-pyrimidin-2-ylmethyl}-ethyl-propyl-amine | 519.2 |
| 13 | 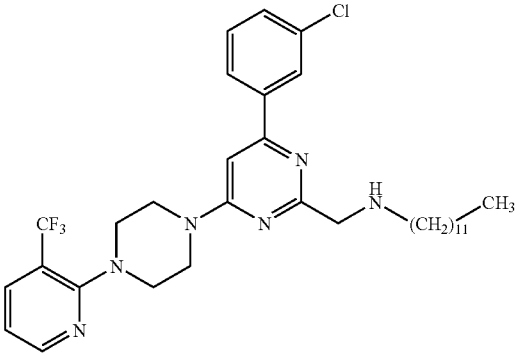 | {4-(3-Chloro-phenyl)-6-[4-(3-trifluoromethyl-pyridin-2-yl)-piperazin-1-yl]-pyrimidin-2-ylmethyl}-dodecyl-amine | 617.3 |

TABLE 1-continued

Representative Biaryl Piperazinyl-Pyridine Analogues

| Compound | | Name | MS (M + 1) |
|---|---|---|---|
| 14 | 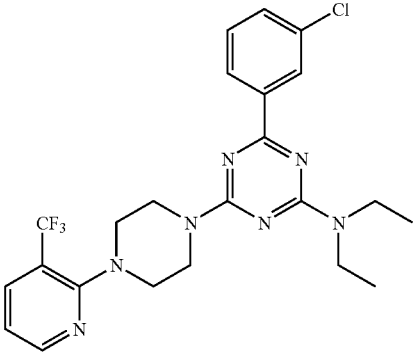 | {4-(3-Chloro-phenyl)-6-[4-(3-trifluoromethyl-pyridin-2-yl)-piperazin-1-yl]-[1,3,5]triazin-2-yl}-diethyl-amine | |
| 15 | 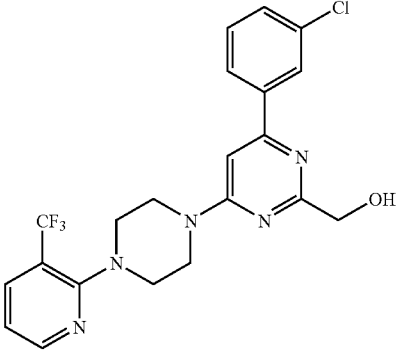 | {4-(3-Chloro-phenyl)-6-[4-(3-trifluoromethyl-pyridin-2-yl)-piperazin-1-yl]-pyrimidin-2-yl}-methanol | 450.1 |
| 16 | 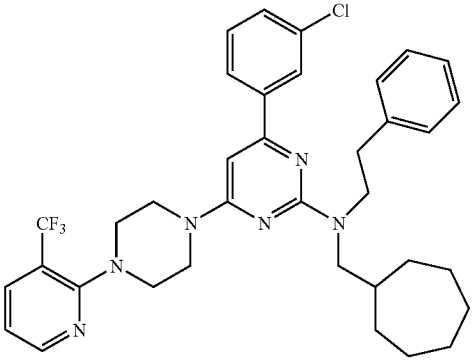 | {4-(3-Chloro-phenyl)-6-[4-(3-trifluoromethyl-pyridin-2-yl)-piperazin-1-yl]-pyrimidin-2-yl}-cycloheptylmethyl-phenethyl-amine | 664.4 |
| 17 | 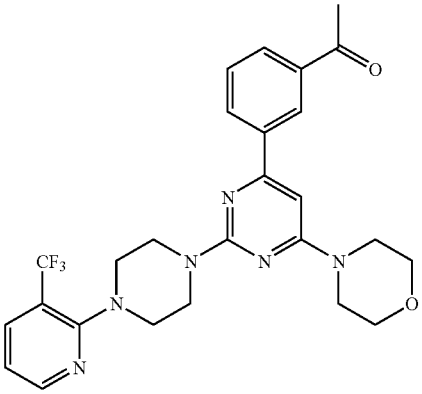 | 1-(3-{6-Morpholin-4-yl-2-[4-(3-trifluoromethyl-pyridin-2-yl)-piperazin-1-yl]-pyrimidin-4-yl}-phenyl)-ethanone | 513.3 |

TABLE 1-continued

Representative Biaryl Piperazinyl-Pyridine Analogues

| Compound | | Name | MS (M + 1) |
|---|---|---|---|
| 18 | 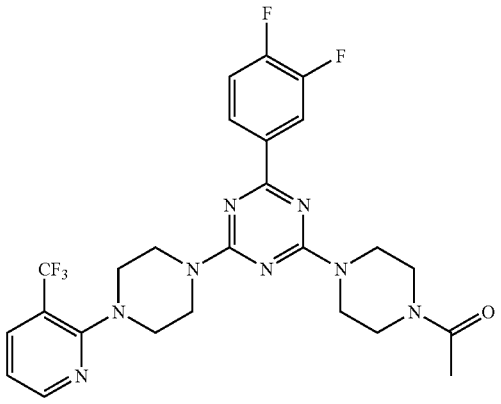 | 1-(4-{4-(3,4-Difluoro-phenyl)-6-[4-(3-trifluoromethyl-pyridin-2-yl)-piperazin-1-yl]-[1,3,5]triazin-2-yl}-piperazin-1-yl)-ethanone | 549.4 |
| 19 | 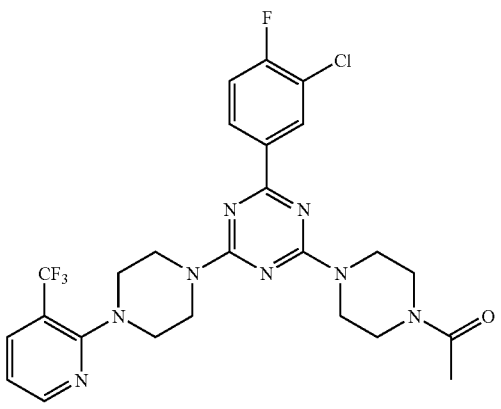 | 1-(4-{4-(3-Chloro-4-fluoro-phenyl)-6-[4-(3-trifluoromethyl-pyridin-2-yl)-piperazin-l-yl]-[1,3,5]triazin-2-yl}-piperazin-1-yl)-ethanone | 565.3 |
| 20 | 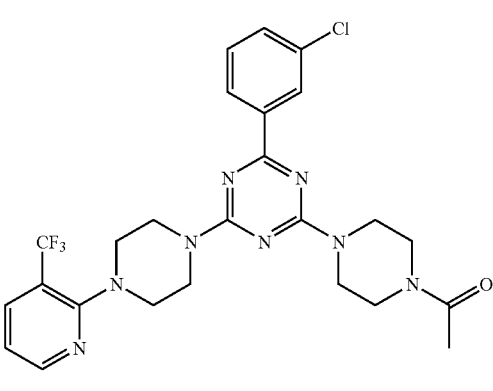 | 1-(4-{4-(3-Chloro-phenyl)-6-[4-(3-trifluoromethyl-pyridin-2-yl)-piperazin-1-yl]-[1,3,5]triazin-2-yl}-piperazin-1-yl)-ethanone | 547.3 |
| 21 | 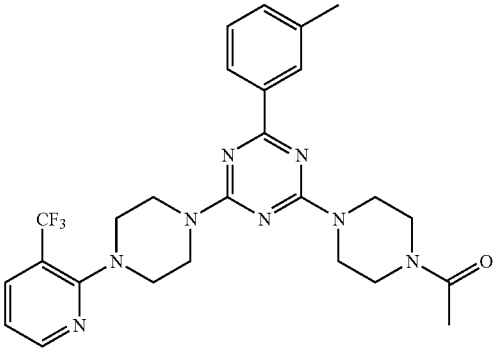 | 1-(4-{4-m-Tolyl-6-[4-(3-trifluoromethyl-pyridin-2-yl)-piperazin-1-yl]-[1,3,5]triazin-2-yl}-piperazin-1-yl)-ethanone | 527.4 |

TABLE 1-continued

Representative Biaryl Piperazinyl-Pyridine Analogues

| Compound | | Name | MS (M + 1) |
|---|---|---|---|
| 22 | 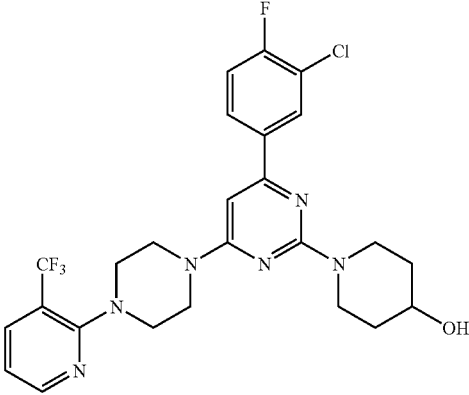 | 1-{4-(3-Chloro-4-fluoro-phenyl)-6-[4-(3-trifluoromethyl-pyridin-2-yl)-piperazin-1-yl]-pyrimidin-2-yl}-piperidin-4-ol | 537.2 |
| 23 | 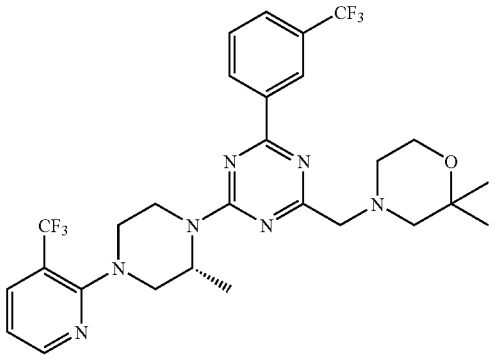 | 2-(2,2-Dimethyl-morpholin-4-ylmethyl)-4-[2-methyl-4-(3-trifluoromethyl-pyridin-2-yl)-piperazin-1-yl]-6-(3-trifluoromethyl-phenyl)-[1,3,5]triazine (R) | 596.4 |
| 24 | 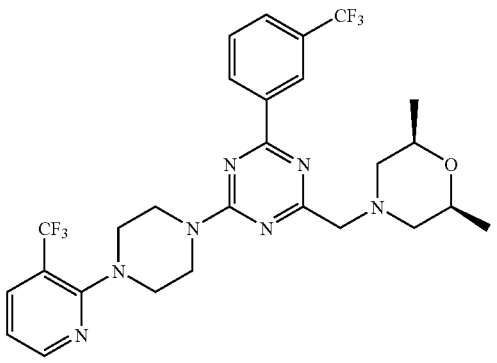 | 2-(2,6-Dimethyl-morpholin-4-ylmethyl)-4-(3-trifluoromethyl-phenyl)-6-[4-(3-trifluoromethyl-pyridin-2-yl)-piperazin-1-yl)]-[1,3,5]triazine (cis) | 582.4 |
| 25 | 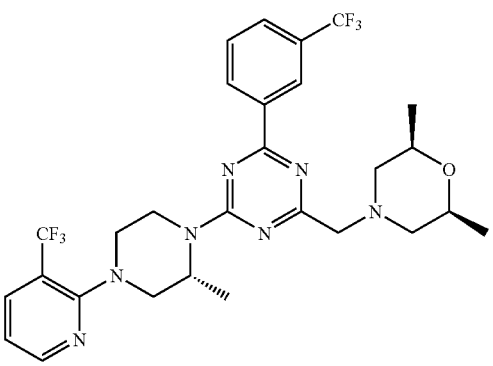 | 2-(2,6-Dimethyl-morpholin-4-ylmethyl)-4-{2-methyl-4-(3-trifluoromethyl-pyridin-2-yl)-piperazin-1-yl]-6-(3-trifluoromethyl-phenyl)-[1,3,5]triazine (R; cis) | 596.4 |

TABLE 1-continued

Representative Biaryl Piperazinyl-Pyridine Analogues

| Compound | | Name | MS (M + 1) |
|---|---|---|---|
| 26 | 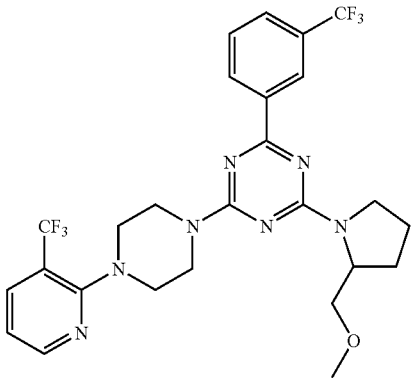 | 2-(2-Methoxymethyl-pyrrolidin-1-yl)-4-(3-trifluoromethyl-phenyl)-6-[4-(3-trifluoromethyl-pyridin-2-yl)-piperazin-1-yl]-[1,3,5]triazine | 568.3 |
| 27 | 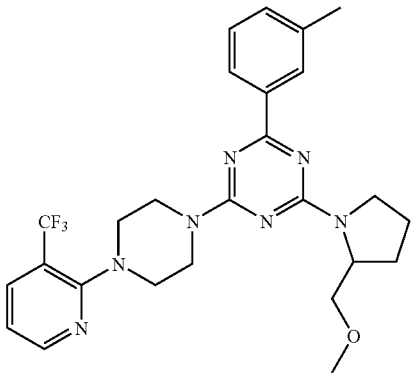 | 2-(2-Methoxymethyl-pyrrolidin-1-yl)-4-m-tolyl-6-[4-(3-trifluoromethyl-pyridin-2-yl)-piperazin-1-yl]-[1,3,5]triazine | 514.3 |
| 28 | 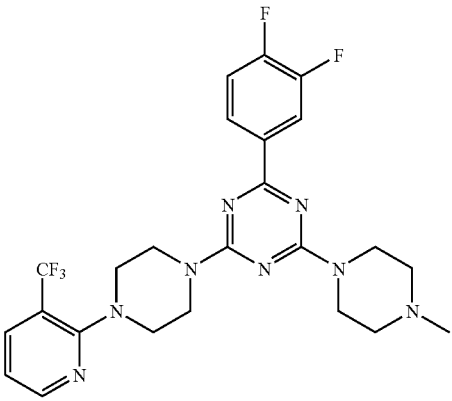 | 2-(3,4-Difluoro-phenyl)-4-(4-methyl-piperazin-1-yl)-6-[4-(3-trifluoromethyl-pyridin-2-yl)-piperazin-1-yl]-[1,3,5]triazine | 521.3 |

TABLE 1-continued

Representative Biaryl Piperazinyl-Pyridine Analogues

| Compound | | Name | MS (M + 1) |
|---|---|---|---|
| 29 | 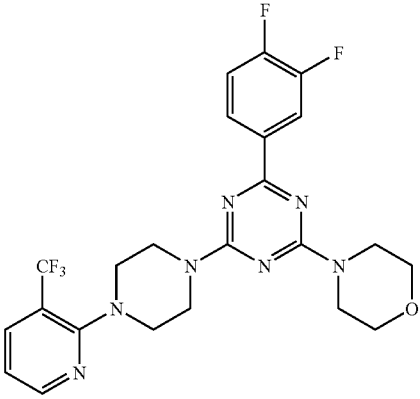 | 2-(3,4-Difluoro-phenyl)-4-morpholin-4-yl-6-[4-(3-trifluoromethyl-pyridin-2-yl)-piperazin-1-yl]-[1,3,5]triazine | 508.3 |
| 30 | 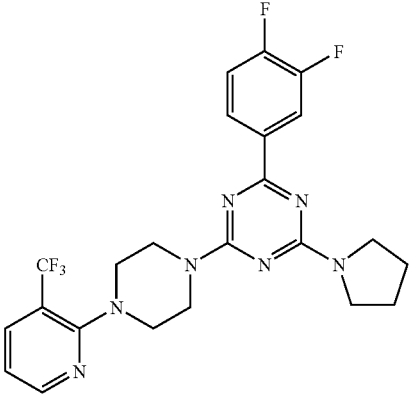 | 2-(3,4-Difluoro-phenyl)-4-pyrrolidin-1-yl-6-[4-(3-trifluoromethyl-pyridin-2-yl)-piperazin-1-yl]-[1,3,5]triazine | 492.3 |
| 31 | 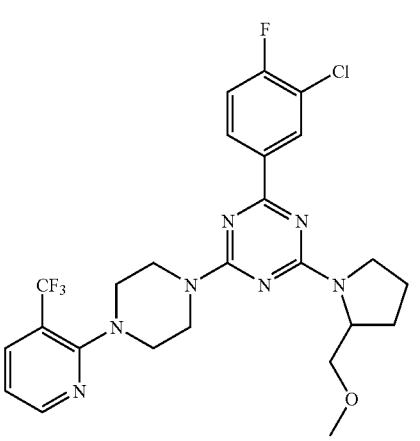 | 2-(3-Chloro-4-fluoro-phenyl)-4-(2-methoxymethyl-pyrrolidin-1-yl)-6-[4-(3-trifluoromethyl-pyridin-2-yl)-piperazin-1-yl]-[1,3,5]triazine | 552.3 |

TABLE 1-continued

Representative Biaryl Piperazinyl-Pyridine Analogues

| Compound | | Name | MS (M + 1) |
|---|---|---|---|
| 32 | 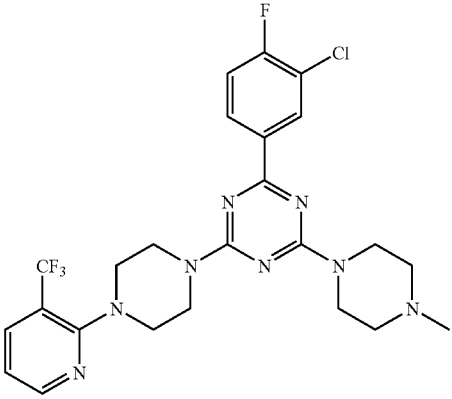 | 2-(3-Chloro-4-fluoro-phenyl)-4-(4-methyl-piperazin-1-yl)-6-[4-(3-trifluoromethyl-pyridin-2-yl)-piperazin-1-yl]-[1,3,5]triazine | 537.3 |
| 33 | 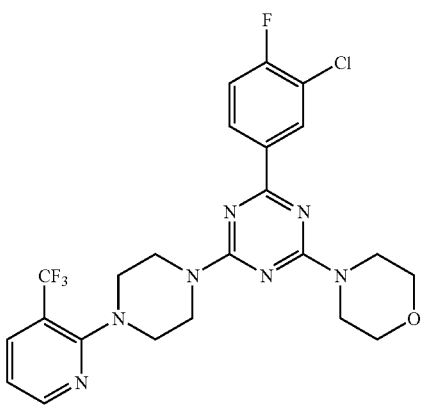 | 2-(3-Chloro-4-fluoro-phenyl)-4-morpholin-4-yl-6-[4-(3-trifluoromethyl-pyridin-2-yl)-piperazin-1-yl]-[1,3,5]triazine | 524.3 |
| 34 | 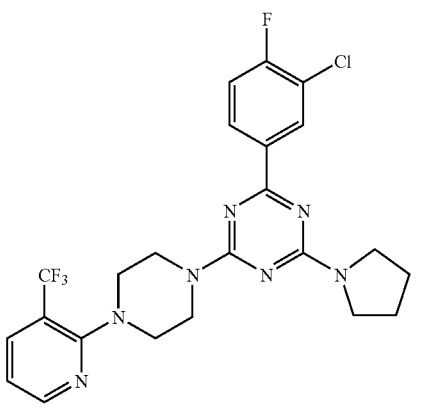 | 2-(3-Chloro-4-fluoro-phenyl)-4-pyrrolidin-1-yl-6-[4-(3-trifluoromethyl-pyridin-2-yl)-piperazin-1-yl]-[1,3,5]triazine | |

TABLE 1-continued

Representative Biaryl Piperazinyl-Pyridine Analogues

| Compound | | Name | MS (M + 1) |
|---|---|---|---|
| 35 | 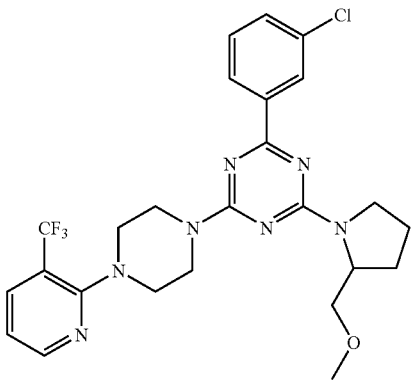 | 2-(3-Chloro-phenyl)-4-(2-methoxymethyl-pyrrolidin-1-yl)-6-[4-(3-trifluoromethyl-pyridin-2-yl)-piperazin-1-yl]-[1,3,5]triazine | 534.3 |
| 36 | 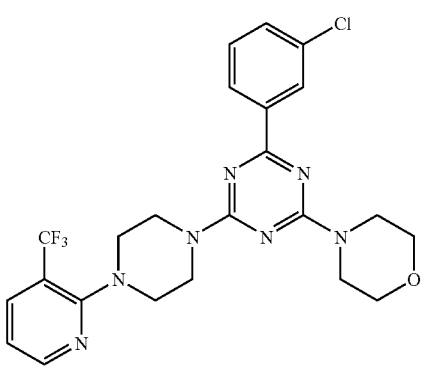 | 2-(3-Chloro-phenyl)-4-morpholin-4-yl-6-[4-(3-trifluoromethyl-pyridin-2-yl)-piperazin-1-yl]-[1,3,5]triazine | 506.3 |
| 37 | 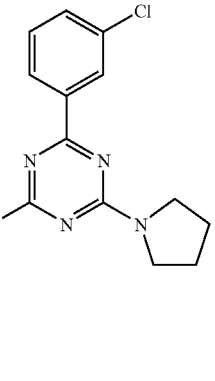 | 2-(3-Chloro-phenyl)-4-pyrrolidin-1-yl-6-[4-(3 trifluoromethyl-pyridin-2-yl)-piperazin-1-yl]-[1,3,5]triazine | 490.3 |
| 38 | 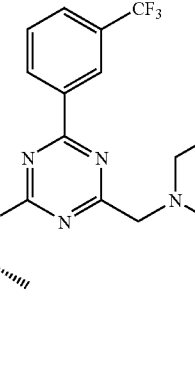 | 2-[2-Methyl-4-(3-trifluoromethyl-pyridin-2-yl)-piperazin-1-yl]-4-morpholin-4-ylmethyl-6-(3-trifluoromethyl-phenyl)-[1,3,5]triazine (R) | 568.4 |

TABLE 1-continued

Representative Biaryl Piperazinyl-Pyridine Analogues

| Compound | | Name | MS (M + 1) |
|---|---|---|---|
| 39 | 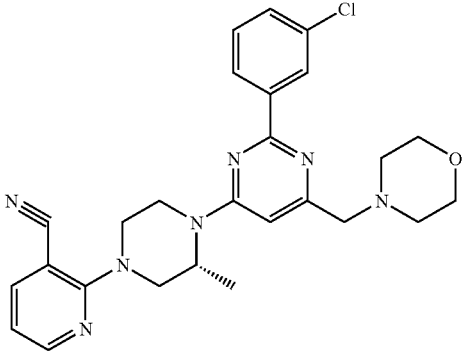 | 2-{4-[2-(3-Chloro-phenyl)-6-morpholin-4-ylmethyl-pyrimidin-4-yl]-3-methyl-piperazin-1-yl}nicotinonitrile (R) | 476.3 |
| 40 | 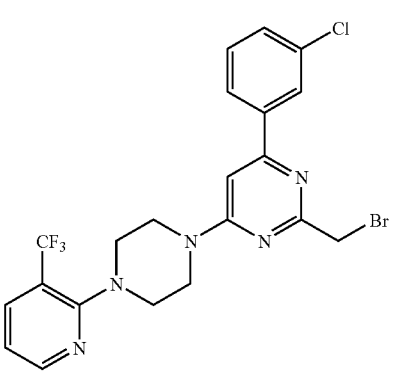 | 2-Bromomethyl-4-(3-chloro-phenyl)-6-[4-(3-trifluoromethyl-pyridin-2-yl)-piperazin-1-yl]-pyrimidine | |
| 41 | 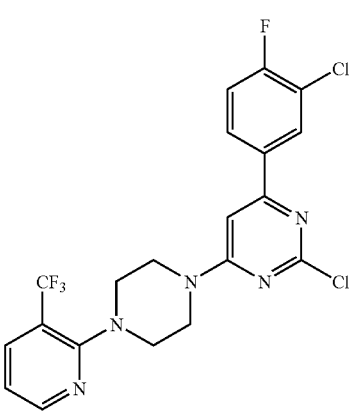 | 2-Chloro-4-(3-chloro-4-fluoro-phenyl)-6-[4-(3-chloro-pyridin-2-yl)-piperazin-1-yl]-pyrimidine | 438.0 |
| 42 | 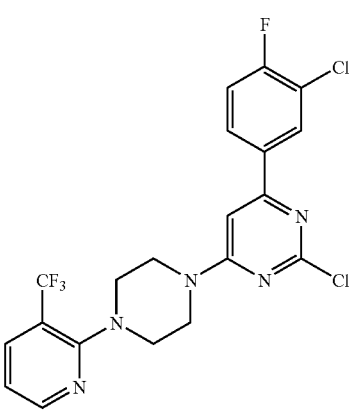 | 2-Chloro-4-(3-chloro-4-fluoro-phenyl)-6-[4-(3-trifluoromethyl-pyridin-2-yl)-piperazin-1-yl]-pyrimidine | 472.1 |

TABLE 1-continued
Representative Biaryl Piperazinyl-Pyridine Analogues
| Compound | | Name | MS (M + 1) |
|---|---|---|---|
| 43 | 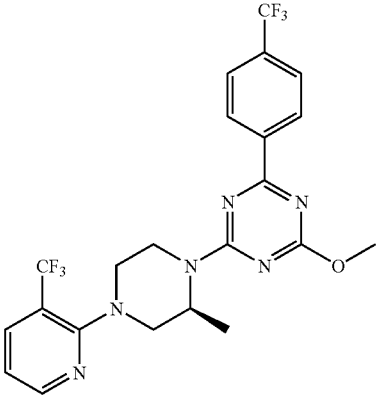 | 2-Methoxy-4-[2-methyl-4-(3-trifluoromethyl-pyridin-2-yl)-piperazin-1-yl]-6-(4-trifluoromethyl-phenyl)-[1,3,5]triazine (S) | 499.2 |
| 44 | 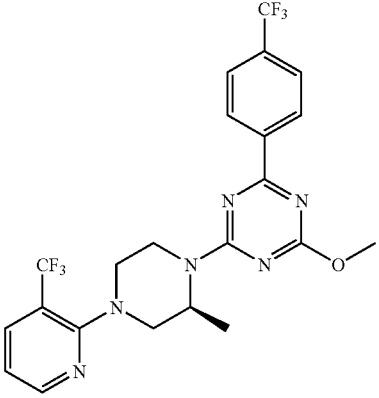 | 2-Methoxy-4-[2-methyl-4-(3-trifluoromethyl-pyridin-2-yl)-piperazin-1-yl]-6-pyridin-4-yl-[1,3,5]triazine (S) | 432.2 |
| 45 | 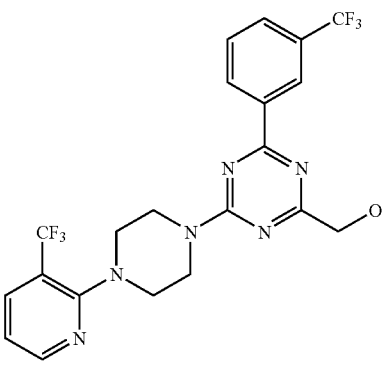 | 2-Methoxymethyl-4-(3-trifluoromethyl-phenyl)-6-[4-(3-trifluoromethyl-pyridin-2-yl)-piperazin-1-yl]-[1,3,5]triazine | 499.2 |

TABLE 1-continued

Representative Biaryl Piperazinyl-Pyridine Analogues

| Compound | | Name | MS (M + 1) |
|---|---|---|---|
| 46 | 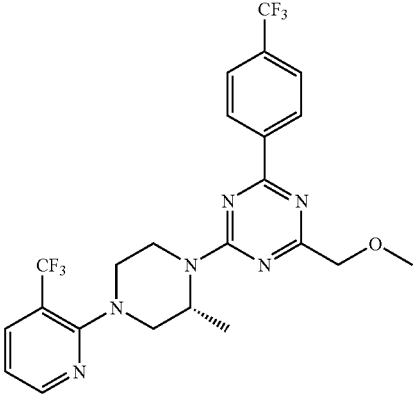 | 2-Methoxymethyl-4-[2-methyl-4-(3-trifluoromethyl-pyridin-2-yl)-piperazin-1-yl]-6-(4-trifluoromethyl-phenyl)-[1,3,5]triazine (R) | 513.3 |
| 47 | 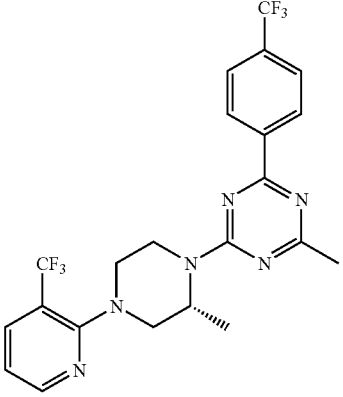 | 2-Methyl-4-[2-methyl-4-(3-trifluoromethyl-pyridin-2-yl)-piperazin-1-yl]-6-(4-trifluoromethyl-phenyl)-[1,3,5]triazine (R) | 483.3 |
| 48 | 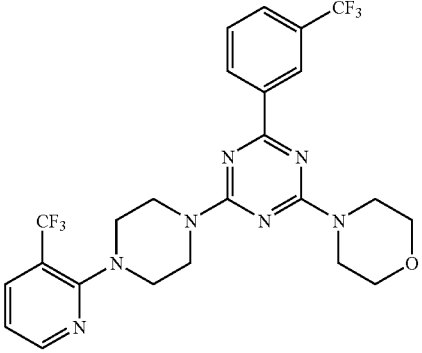 | 2-Morpholin-4-yl-4-(3-trifluoromethyl-phenyl)-6-[4-(3-trifluoromethyl-pyridin-2-yl)-piperazin-1-yl]-[1,3,5]triazine | 540.3 |
| 49 | 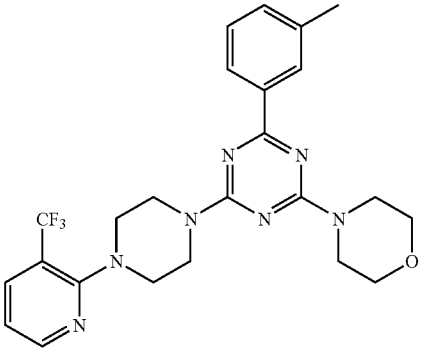 | 2-Morpholin-4-yl-4-m-tolyl-6-[4-(3-trifluoromethyl-pyridin-2-yl)-piperazin-1-yl]-[1,3,5]triazine | 486.3 |

TABLE 1-continued

Representative Biaryl Piperazinyl-Pyridine Analogues

| Compound | | Name | MS (M + 1) |
|---|---|---|---|
| 50 | 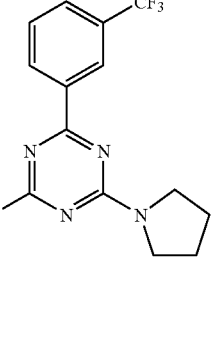 | 2-Pyrrolidin-1-yl-4-(3-trifluoromethyl-phenyl)-6-[4-(3-trifluoromethyl-pyridin-2-yl)-piperazin-1-yl]-[1,3,5]triazine | 524.3 |
| 51 | 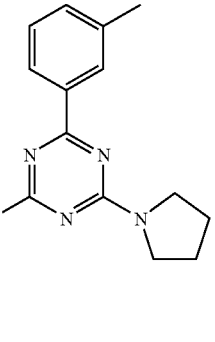 | 2-Pyrrolidin-1-yl-4-m-tolyl-6-[4-(3-trifluoromethyl-pyridin-2-yl)-piperazin-1-yl]-[1,3,5]triazine | 470.3 |
| 52 | 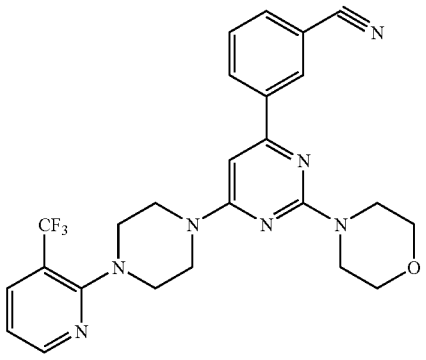 | 3-{2-Morpholin-4-yl-6-[4-(3-trifluoromethyl-pyridin-2-yl)-piperazin-1-yl]-pyrimidin-4-yl}-benzonitrile | 496.3 |
| 53 | 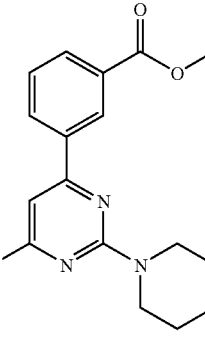 | 3-{2-Morpholin-4-yl-6-[4-(3-trifluoromethyl-pyridin-2-yl)-piperazin-1-yl]-pyrimidin-4-yl}-benzoic acid ethyl ester | 544.3 |

TABLE 1-continued

Representative Biaryl Piperazinyl-Pyridine Analogues

| Compound | | Name | MS (M + 1) |
|---|---|---|---|
| 54 | 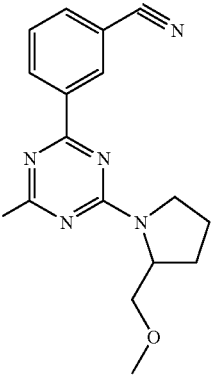 | 3-{4-(2-Methoxymethyl-pyrrolidin-1-yl)-6-[4-(3-trifluoromethyl-pyridin-2-yl)-piperazin-1-yl]-[1,3,5]triazin-2-yl}-benzonitrile | 525.3 |
| 55 | 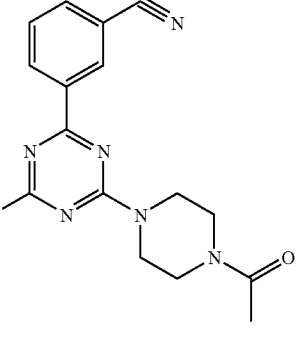 | 3-{4-(4-Acetyl-piperazin-1-yl)-6-[4-(3-trifluoromethyl-pyridin-2-yl)-piperazin-1-yl]-[1,3,5]triazin-2-yl}-benzonitrile | 538.4 |
| 56 | 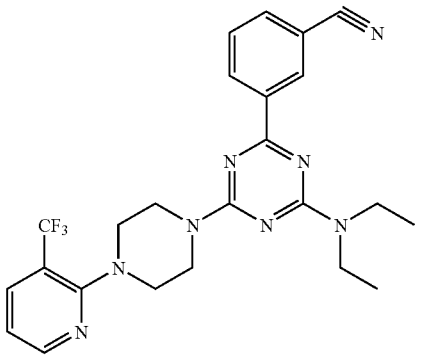 | 3-{4-Diethylamino-6-[4-(3-trifluoromethyl-pyridin-2-yl)-piperazin-1-yl]-[1,3,5]triazin-2-yl}-benzonitrile | 483.3 |
| 57 | 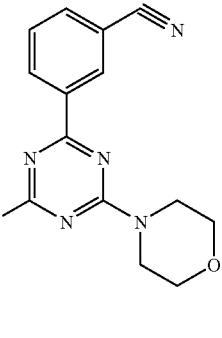 | 3-{4-Morpholin-4-yl-6-[4-(3-trifluoromethyl-pyridin-2-yl)-piperazin-1-yl]-[1,3,5]triazin-2-yl}-benzonitrile | 497.3 |

TABLE 1-continued

Representative Biaryl Piperazinyl-Pyridine Analogues

| Compound | | Name | MS (M + 1) |
|---|---|---|---|
| 58 | 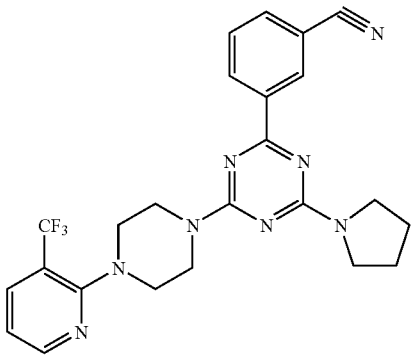 | 3-{4-Pyrrolidin-1-yl-6-[4-(3-trifluoromethyl-pyridin-2-yl)-piperazin-1-yl]-[1,3,5]triazin-2-yl}-benzonitrile | 481.3 |
| 59 | 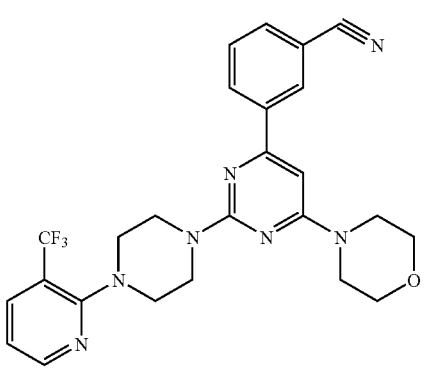 | 3-{6-Morpholin-4-yl-2-[4-(3-trifluoromethyl-pyridin-2-yl)-piperazin-1-yl]-pyrimidin-4-yl}-benzonitrile | 496.3 |
| 60 | 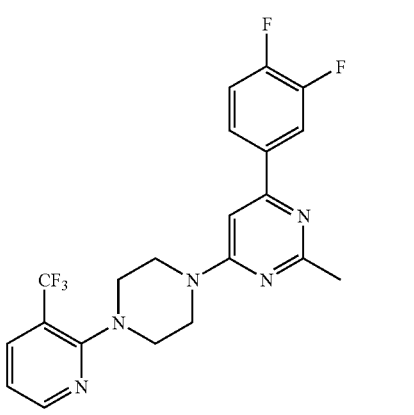 | 4-(3,4-Difluoro-phenyl)-2-methyl-6-[4-(3-trifluoromethyl-pyridin-2-yl)-piperazin-1-yl]-pyrimidine | 436.2 |
| 61 | 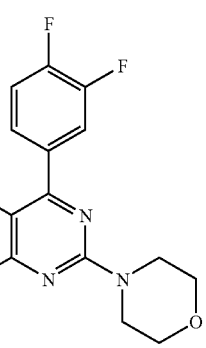 | 4-(3,4-Difluoro-phenyl)-2-morpholin-4-yl-6-[4-(3-trifluoromethyl-pyridin-2-yl)-piperazin-1-yl]-pyrimidine-5-carbonitrile | 532.3 |

TABLE 1-continued
Representative Biaryl Piperazinyl-Pyridine Analogues
| Compound | | Name | MS (M + 1) |
|---|---|---|---|
| 62 | 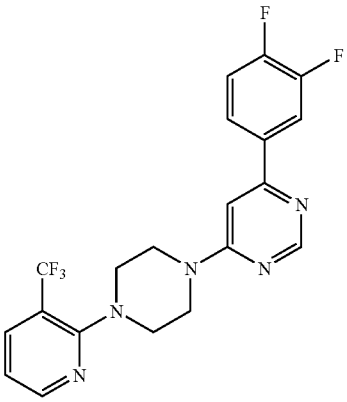 | 4-(3,4-Difluoro-phenyl)-6-[4-(3-trifluoromethyl-pyridin-2-yl)-piperazin-1-yl]-pyrimidine | 422.2 |
| 63 | 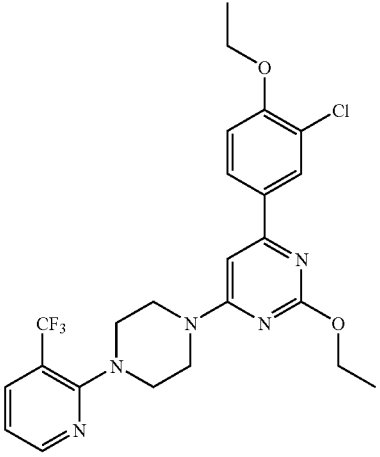 | 4-(3-Chloro-4-ethoxy-phenyl)-2-ethoxy-6-[4-(3-trifluoromethyl-pyridin-2-yl)-piperazin-1-yl]-pyrimidine | 508.2 |
| 64 | 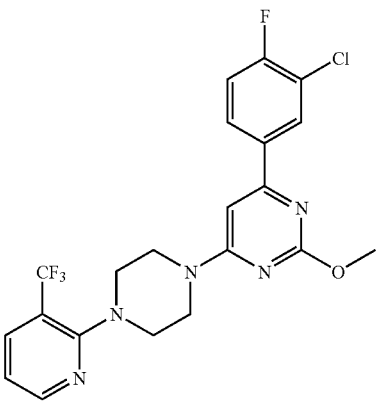 | 4-(3-Chloro-4-fluoro-phenyl)-2-methoxy-6-[4-(3-trifluoromethyl-pyridin-2-yl)-piperazin-1-yl]-pyrimidine | 468.2 |

TABLE 1-continued
Representative Biaryl Piperazinyl-Pyridine Analogues
| Compound | | Name | MS (M + 1) |
|---|---|---|---|
| 65 | 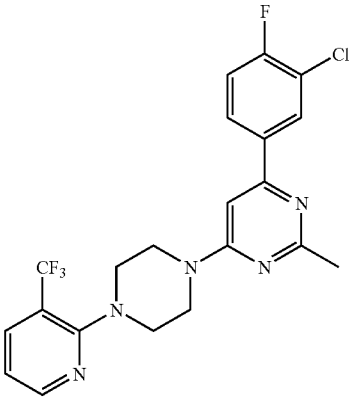 | 4-(3-Chloro-4-fluoro-phenyl)-2-methyl-6-[4-(3-trifluoromethyl-pyridin-2-yl)-piperazin-1-yl]-pyrimidine | 452.2 |
| 66 | 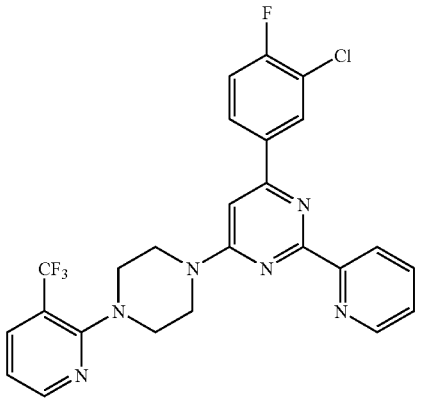 | 4-(3-Chloro-4-fluoro-phenyl)-2-pyridin-2-yl-6-[4-(3-trifluoromethyl-pyridin-2-yl)-piperazin-1-yl]-pyrimidine | 515.1 |
| 67 | 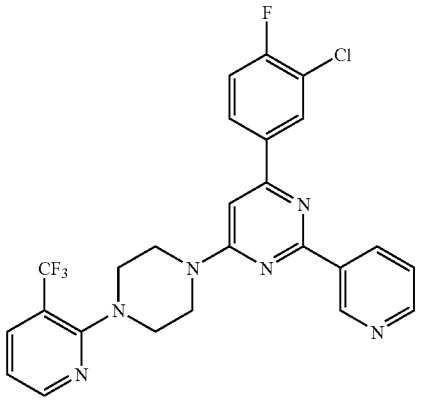 | 4-(3-Chloro-4-fluoro-phenyl)-2-pyridin-3-yl-6-[4-(3-trifluoromethyl-pyridin-2-yl)-piperazin-1-yl]-pyrimidine | 515.1 |

TABLE 1-continued

Representative Biaryl Piperazinyl-Pyridine Analogues

| Compound | | Name | MS (M + 1) |
|---|---|---|---|
| 68 | 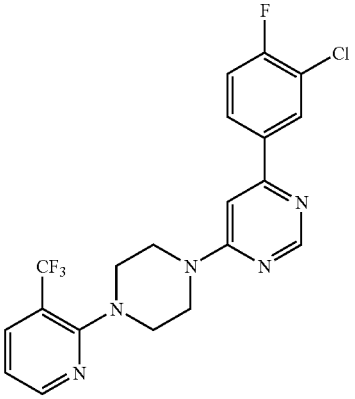 | 4-(3-Chloro-4-fluoro-phenyl)-6-[4-(3-trifluoromethyl-pyridin-2-yl)-piperazin-1-yl]-pyrimidine | 438.2 |
| 69 | 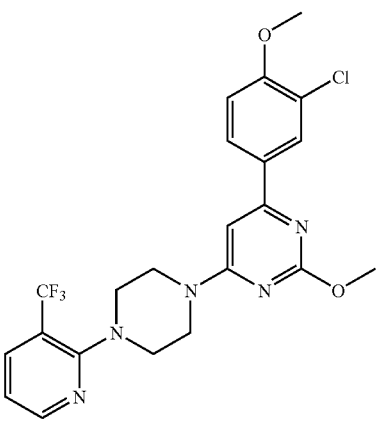 | 4-(3-Chloro-4-methoxy-phenyl)-2-methoxy-6-[4-(3-trifluoromethyl-pyridin-2-yl)-piperazin-1-yl]-pyrimidine | 480.2 |
| 70 | 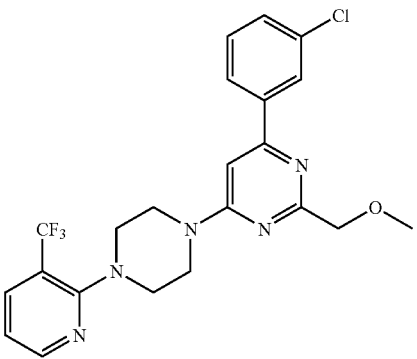 | 4-(3-Chloro-phenyl)-2-methoxymethyl-6-[4-(3-trifluoromethyl-pyridin-2-yl)-piperazin-1-yl]-pyrimidine | 464.2 |
| 71 | 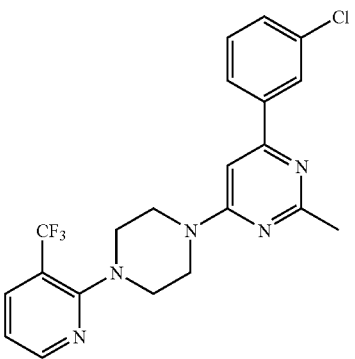 | 4-(3-Chloro-phenyl)-2-methyl-6-[4-(3-trifluoromethyl-pyridin-2-yl)-piperazin-1-yl]-pyrimidine | 434.2 |

TABLE 1-continued

Representative Biaryl Piperazinyl-Pyridine Analogues

| Compound | | Name | MS (M + 1) |
|---|---|---|---|
| 72 | 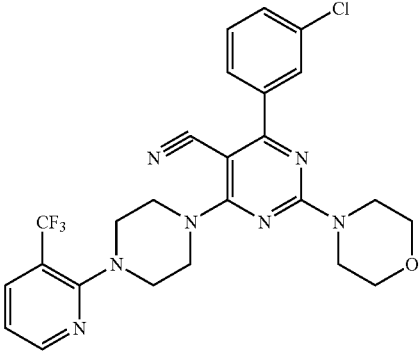 | 4-(3-Chloro-phenyl)-2-morpholin-4-yl-6-[4-(3-trifluoromethyl-pyridin-2-yl)-piperazin-1-yl]-pyrimidine-5-carbonitrile | 530.1 |
| 73 | 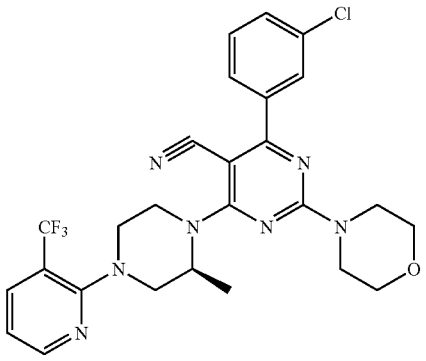 | 4-(3-Chloro-phenyl)-6-[2-methyl-4-(3-trifluoromethyl-pyridin-2-yl)-piperazin-1-yl]-2-morpholin-4-yl-pyrimidine-5-carbonitrile (S) | 544.1 |
| 74 | 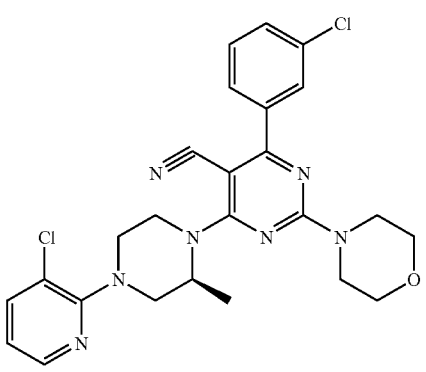 | 4-(3-Chloro-phenyl)-6-[4-(3-chloro-pyridin-2-yl)-2-methyl-piperazin-1-yl]-2-morpholin-4-yl-pyrimidine-5-carbonitrile (S) | 510.1 |
| 75 | 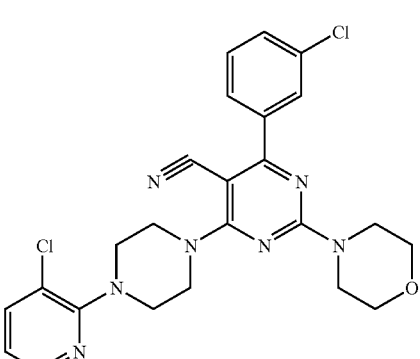 | 4-(3-Chloro-phenyl)-6-[4-(3-chloro-pyridin-2-yl)-piperazin-1-yl]-2-morpholin-4-yl-pyrimidine-5-carbonitrile | 496.1 |

TABLE 1-continued

Representative Biaryl Piperazinyl-Pyridine Analogues

| Compound | | Name | MS (M + 1) |
|---|---|---|---|
| 76 | 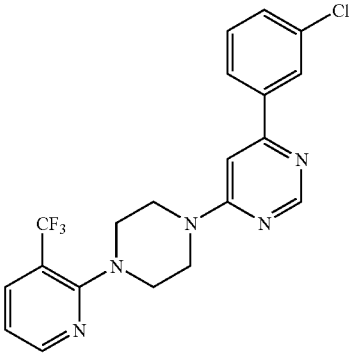 | 4-(3-Chloro-phenyl)-6-[4-(3-trifluoromethyl-pyridin-2-yl)-piperazln-1-yl]-pyrimidine | 420.2 |
| 77 | 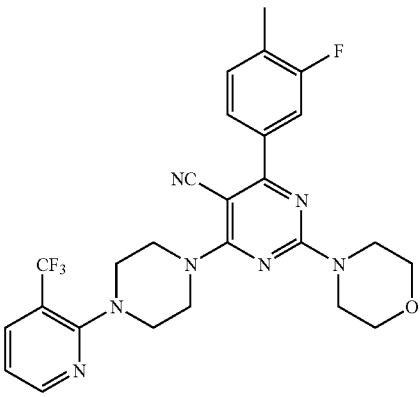 | 4-(3-Fluoro-4-methyl-phenyl)-2-morpholin-4-yl-6-[4-(3-trifluoromethyl-pyridin-2-yl)-piperazin-1-yl]-pyrimidine-5-carbonitrile | 528.3 |
| 78 | 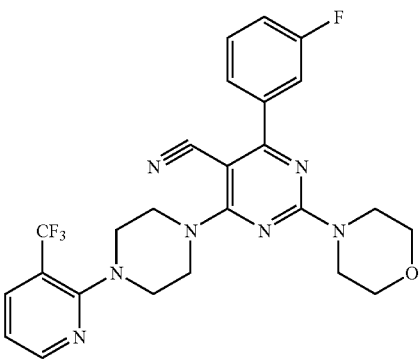 | 4-(3-Fluoro-phenyl)-2-morpholin-4-yl-6-[4-(3-trifluoromethyl-pyridin-2-yl)-piperazin-1-yl]-pyrimidine-5-carbonitrile | 514.2 |
| 79 | 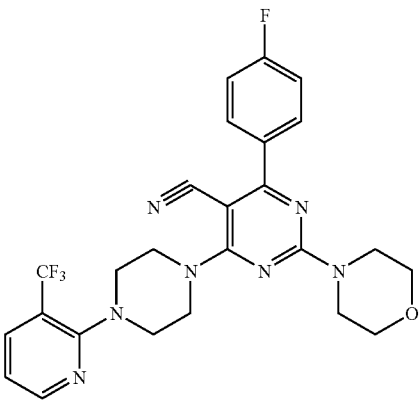 | 4-(4-Fluoro-phenyl)-2-morpholin-4-yl-6-[4-(3-trifluoromethyl-pyridin-2-yl)-piperazin-1-yl]-pyrimidine-5-carbonitrile | 514.2 |

TABLE 1-continued
Representative Biaryl Piperazinyl-Pyridine Analogues
| Compound | | Name | MS (M + 1) |
|---|---|---|---|
| 80 | 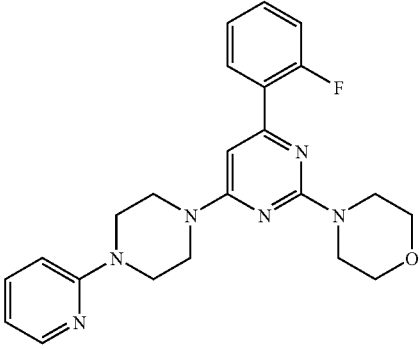 | 4-[4-(2-Fluoro-phenyl)-6-(4-pyridin-2-yl-piperazin-1-yl)-pyrimidin-2-yl]-morpholine | 421.3 |
| 81 | 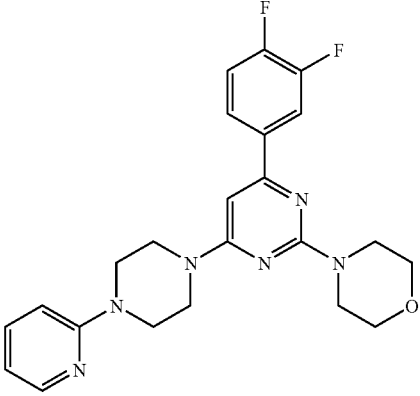 | 4-[4-(3,4-Difluoro-phenyl)-6-(4-pyridin-2-yl-piperazin-1-yl)-pyrimidin-2-yl]-morpholine | 439.3 |
| 82 | 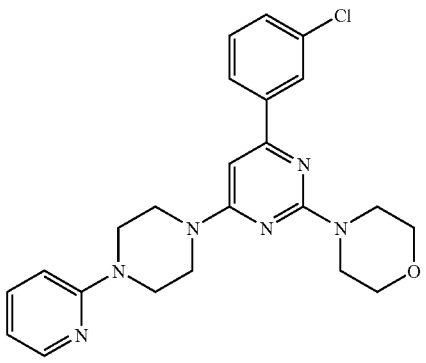 | 4-[4-(3-Chloro-phenyl)-6-(4-pyridin-2-yl-piperazin-1-yl)-pyrimidin-2-yl]-morpholine | 437.2 |
| 83 | 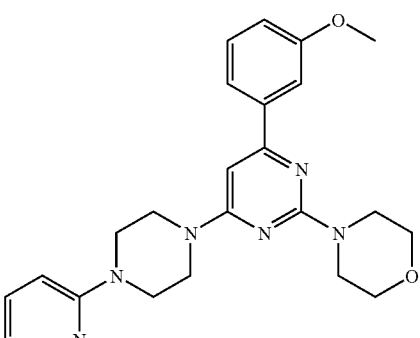 | 4-[4-(3-Methoxy-phenyl)-6-(4-pyridin-2-yl-piperazin-1-yl)-pyrimidin-2-yl]-morpholine | 433.3 |

TABLE 1-continued
Representative Biaryl Piperazinyl-Pyridine Analogues
| Compound | | Name | MS (M + 1) |
|---|---|---|---|
| 84 | 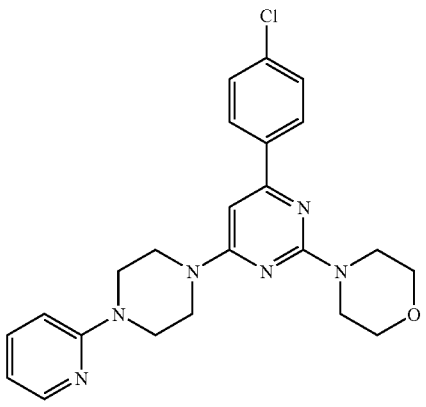 | 4-[4-(4-Chloro-phenyl)-6-(4-pyridin-2-yl-piperazin-1-yl)-pyrimidin-2-yl]-morpholine | 437.2 |
| 85 | 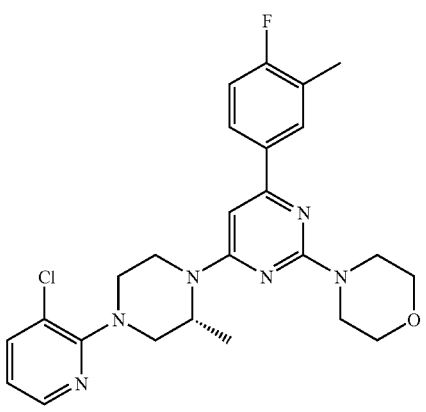 | 4-[4-[4-(3-Chloro-pyridin-2-yl)-2-methyl-piperazin-1-yl]-6-(4-fluoro-3-methyl-phenyl)-pyrimidin-2-yl]-morpholine (R) | |
| 86 | 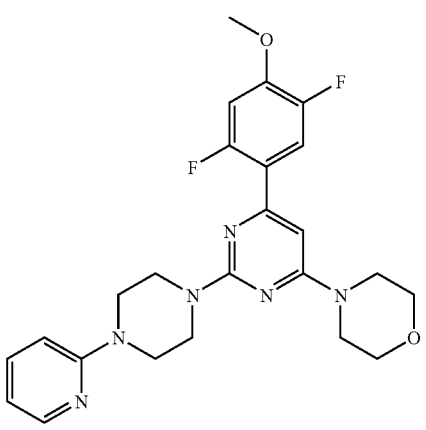 | 4-[6-(2,5-Difluoro-4-methoxy-phenyl)-2-(4-pyridin-2-yl-piperazin-1-yl)-pyrimidin-4-yl]-morpholine | 469.3 |

TABLE 1-continued
Representative Biaryl Piperazinyl-Pyridine Analogues
| Compound | | Name | MS (M + 1) |
|---|---|---|---|
| 87 | 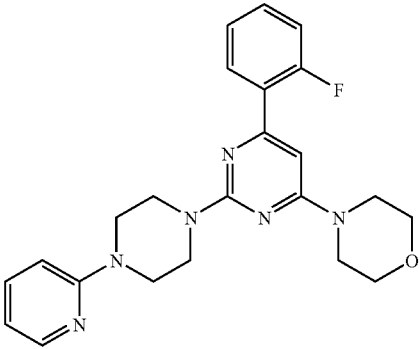 | 4-[6-(2-Fluoro-phenyl)-2-(4-pyridin-2-yl-piperazin-1-yl)-pyrimidin-4-yl]-morpholine | 421.3 |
| 88 | 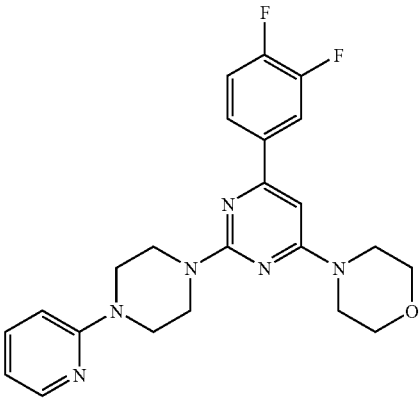 | 4-[6-(3,4-Difluoro-phenyl)-2-(4-pyridin-2-yl-piperazin-1-yl)-pyrimidin-4-yl]-morpholine | 439.3 |
| 89 | 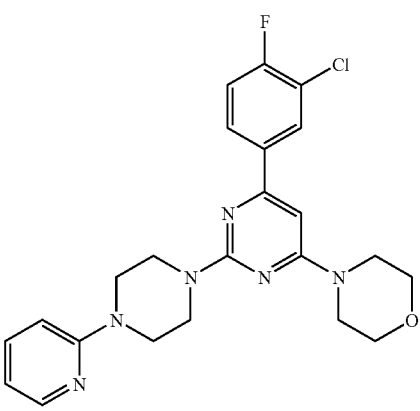 | 4-[6-(3-Chloro-4-fluoro-phenyl)-2-(4-pyridin-2-yl-piperazin-1-yl)-pyrimidin-4-yl]-morpholine | 455.3 |

TABLE 1-continued

Representative Biaryl Piperazinyl-Pyridine Analogues

| Compound | | Name | MS (M + 1) |
|---|---|---|---|
| 90 | | 4-[6-(4-Chloro-3-trifluoromethyl-phenyl)-2-(4-pyridin-2-yl-piperazin-1-yl)-pyrimidin-4-yl]-morpholine | 505.3 |
| 91 | | 4-[6-(4-Chloro-phenyl)-2-(4-pyridin-2-yl-piperazin-1-yl)-pyrimidin-4-yl]-morpholine | 437.2 |
| 92 | | 4-[6-[4-(3-Chloro-pyridin-2-yl)-2-methyl-piperazin-1-yl]-2-(3,4-difluoro-phenyl)-pyrimidin-4-yl]-morpholine (S) | 487.3 |

TABLE 1-continued

Representative Biaryl Piperazinyl-Pyridine Analogues

| Compound | | Name | MS (M + 1) |
|---|---|---|---|
| 93 | 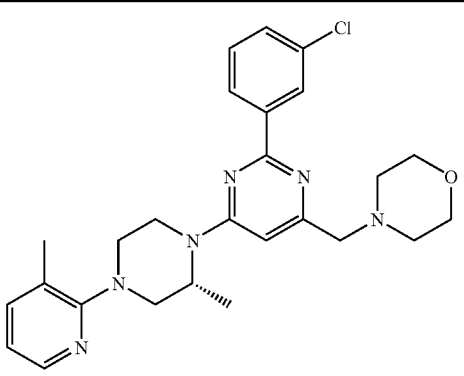 | 4-{2-(3-Chloro-phenyl)-6-[2-methyl-4-(3-methyl-pyridin-2-yl)-piperazin-1-yl]-pyrimidin-4-ylmethyl}-morpholine (R) | 465.3 |
| 94 | 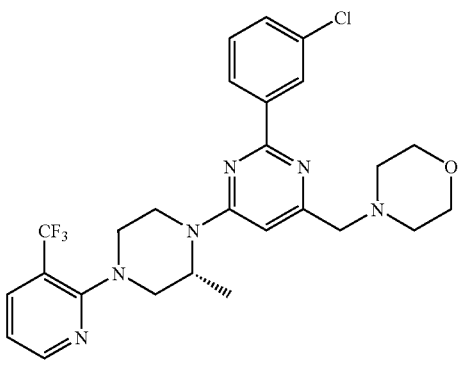 | 4-{2-(3-Chloro-phenyl)-6-[2-methyl-4-(3-trifluoromethyl-pyridin-2-yl)-piperazin-1-yl]-pyrimidin-4-ylmethyl}-morpholine (R) | 519.3 |
| 95 | 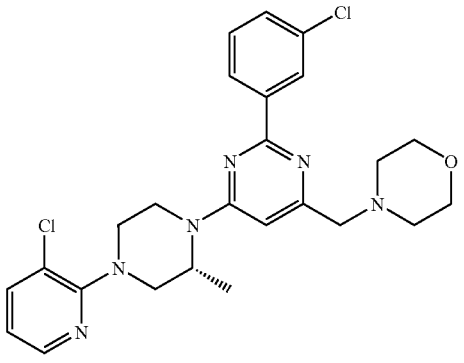 | 4-{2-(3-Ghloro-phenyl)-6-[4-(3-Chloro-pyridin-2-yl)-2-methyl-piperazin-1-yl]-pyrimidin-4-ylmethyl}-morpholine (R) | 485.3 |
| 96 | 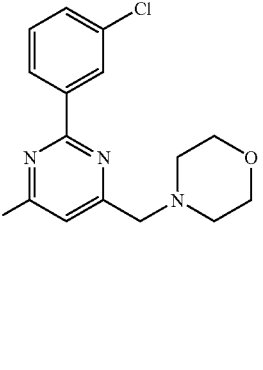 | 4-{2-(3-Chloro-phenyl)-6-[4-(3-trifluoromethyl-pyridin-2-yl)-piperazin-1-yl]-pyrimidin-4-ylmethyl}-morpholine | 505.3 |

TABLE 1-continued

Representative Biaryl Piperazinyl-Pyridine Analogues

| Compound | | Name | MS (M + 1) |
|---|---|---|---|
| 97 | 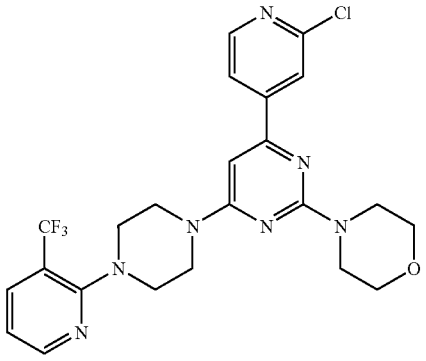 | 4-{4-(2-Chloro-pyridin-4-yl)-6-[4-(3-trifluoromethyl-pyridin-2-yl)-piperazin-1-yl]-pyrimidin-2-yl}-morpholine | 506.1 |
| 98 | 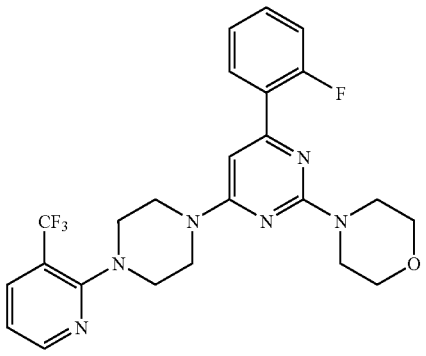 | 4-{4-(2-Fluoro-phenyl)-6-[4-(3-trifluoromethyl-pyridin-2-yl)-piperazin-1-yl]-pyrimidin-2-yl}-morpholine | 489.3 |
| 99 | 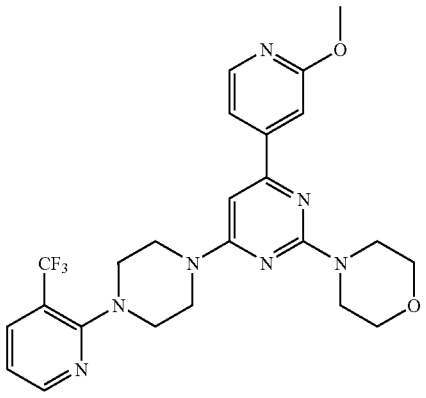 | 4-{4-(2-Methoxy-pyridin-4-yl)-6-[4-(3-trifluoromethyl-pyridin-2-yl)-piperazin-1-yl]-pyrimidin-2-yl}-morpholine | 502.2 |
| 100 | 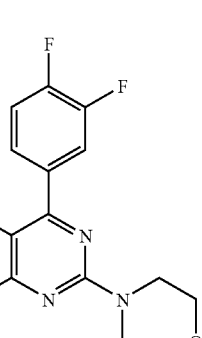 | 4-{4-(3,4-Difluoro-phenyl)-5-methyl-6-[4-(3-trifluoromethyl-pyridin-2-yl)-piperazin-1-yl]-pyrimidin-2-yl}-morpholine | 521.2 |

TABLE 1-continued

Representative Biaryl Piperazinyl-Pyridine Analogues

| Compound | | Name | MS (M + 1) |
|---|---|---|---|
| 101 | 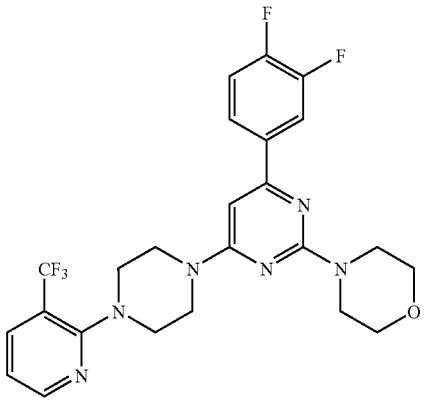 | 4-{4-(3,4-Difluoro-phenyl)-6-[4-(3-trifluoromethyl-pyridin-2-yl)-piperazin-1-yl]-pyrimidin-2-yl}-morpholine | 507.3 |
| 102 | 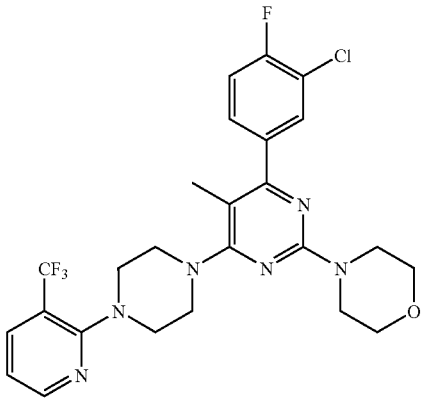 | 4-{4-(3-Chloro-4-fluoro-phenyl)-5-methyl-6-[4-(3-trifluoromethyl-pyridin-2-yl)-piperazin-1-yl]-pyrimidin-2-yl}-morpholine | 537.1 |
| 103 | 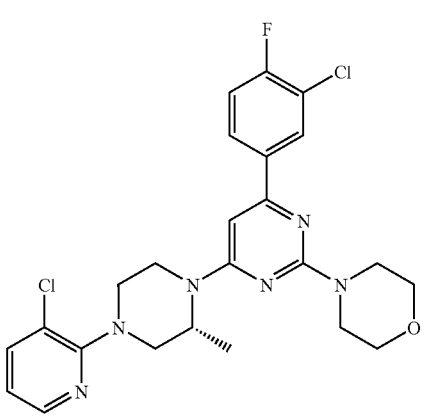 | 4-{4-(3-Chloro-4-fluoro-phenyl)-6-[4-(3-chloro-pyridin-2-yl)-2-methyl-piperazin-1-yl]-pyrimidin-2-yl}-morpholine (R) | 503.1 |

TABLE 1-continued
Representative Biaryl Piperazinyl-Pyridine Analogues
| Compound | | Name | MS (M + 1) |
|---|---|---|---|
| 104 | 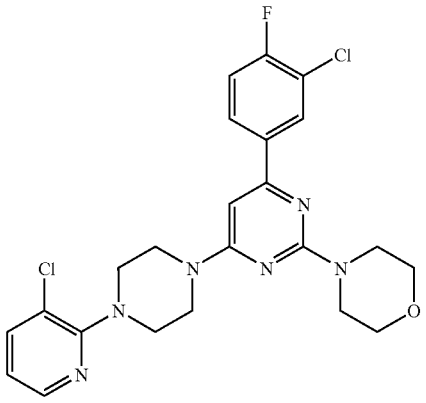 | 4-{4-(3-Chloro-4-fluoro-phenyl)-6-[4-(3-chloro-pyridin-2-yl)-piperazin-1-yl]-pyrimidin-2-yl}-morpholine | 491.2 |
| 105 | 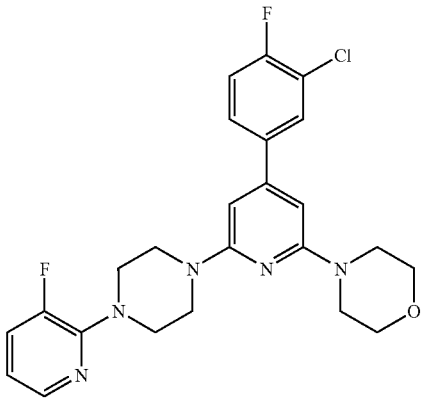 | 4-{4-(3-Chloro-4-fluoro-phenyl)-6-[4-(3-fluoro-pyridin-2-yl)-piperazin-1-yl]-pyridin-2-yl}-morpholine | 472.2 |
| 106 | 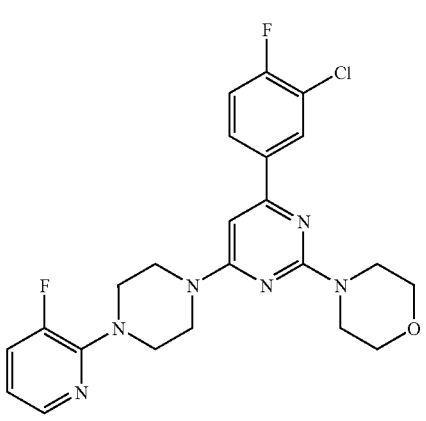 | 4-{4-(3-Chloro-4-fluoro-phenyl)-6-[4-(3-fluoro-pyridin-2-yl)-piperazin-1-yl]-pyrimidin-2-yl}-morpholine | 473.2 |

TABLE 1-continued

Representative Biaryl Piperazinyl-Pyridine Analogues

| Compound | | Name | MS (M + 1) |
|---|---|---|---|
| 107 | 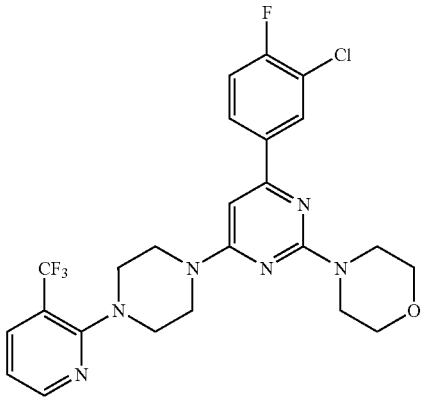 | 4-{4-(3-Chloro-4-fluoro-phenyl)-6-[4-(3-trifluoromethyl-pyridin-2-yl)-piperazin-1-yl]-pyrimidin-2-yl}-morpholine | 523.3 |
| 108 | 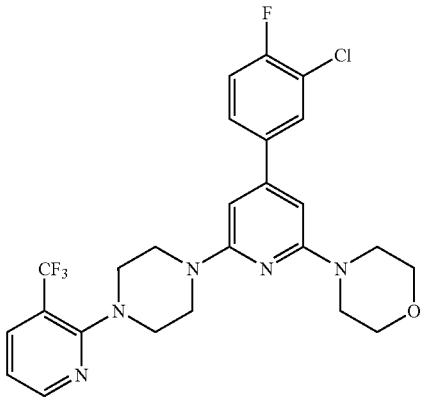 | 4-{4-(3-Chloro-4-fluoro-phenyl)-6-[4-(3-trifluoromethyl-pyridin-2-yl)-piperazin-1-yl]-pyridin-2-yl}-morpholine | 522.2 |
| 109 | 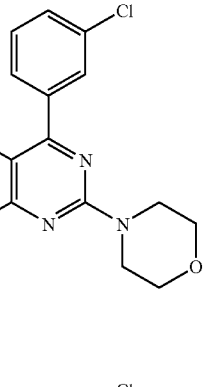 | 4-{4-(3-Chloro-phenyl)-5-methyl-6-[4-(3-trifluoromethyl-pyridin-2-yl)-piperazin-1-yl]-pyrimidin-2-yl}-morpholine | 519.2 |
| 110 | 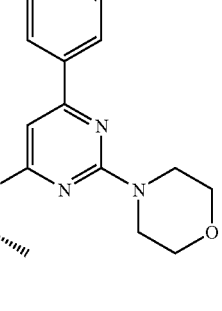 | 4-{4-(3-Chloro-phenyl)-6-[2-methyl-4-(3-trifluoromethyl-pyridin-2-yl)-piperazin-1-yl]-pyrimidin-2-yl}-morpholine (R) | 519.2 |

TABLE 1-continued

Representative Biaryl Piperazinyl-Pyridine Analogues

| Compound | | Name | MS (M + 1) |
|---|---|---|---|
| 111 | 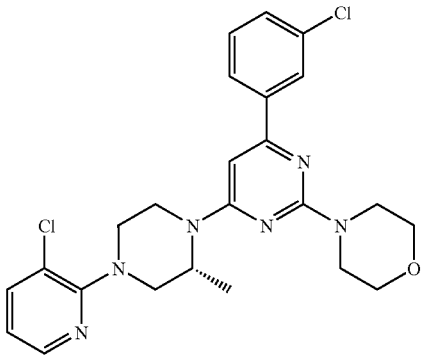 | 4-{4-(3-Chloro-phenyl)-6-[4-(3-chloro-pyridin-2-yl)-2-methyl-piperazin-1-yl]-pyrimidin-2-yl}-morpholine (R) | 485.3 |
| 112 | 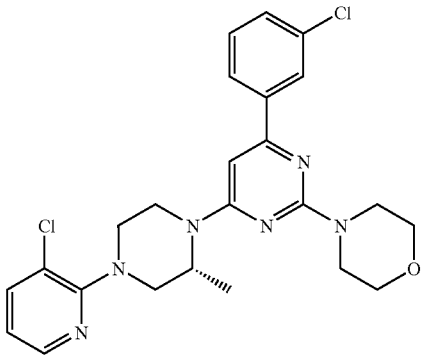 | 4-{4-(3-Chloro-phenyl)-6-[4-(3-chloro-pyridin-2-yl)-2-methyl-piperazin-1-yl]-pyrimidin-2-yl}-morpholine (R) | |
| 113 | 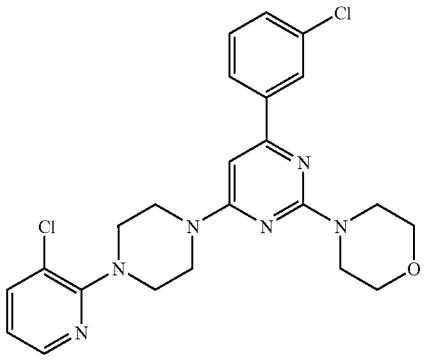 | 4-{4-(3-Chloro-phenyl)-6-[4-(3-chloro-pyridin-2-yl)-piperazin-1-yl]-pyrimidin-2-yl}-morpholine | 470.2 |
| 114 | 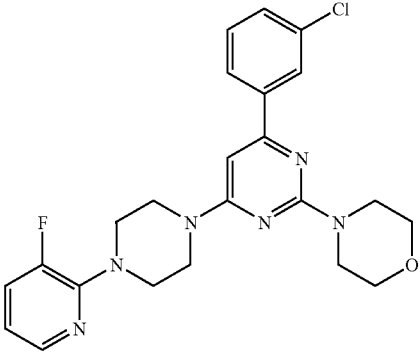 | 4-{4-(3-Chloro-phenyl)-6-[4-(3-fluoro-pyridin-2-yl)-piperazin-1-yl]-pyrimidin-2-yl}-morpholine | 455.2 |

TABLE 1-continued

Representative Biaryl Piperazinyl-Pyridine Analogues

| Compound | Name | MS (M + 1) |
|---|---|---|
| 115 | 4-{4-(3-Chloro-phenyl)-6-[4-(3-trifluoromethyl-pyridin-2-yl)-piperazin-1-yl]-pyrimidin-2-ylmethyl}-morpholine | 519.2 |
| 116 | 4-{4-(3-Chloro-phenyl)-6-[4-(3-trifluoromethyl-pyridin-2-yl)-piperazin-1-yl]-pyrimidin-2-ylmethyl}-2,6-dimethyl-morpholine (cis) | 547.2 |
| 117 | 4-{4-(3-Chloro-phenyl)-6-[4-(3-trifluoromethyl-pyridin-2-yl)-piperazin-1-yl]-pyrimidin-2-yl}-morpholine | 505.3 |
| 118 | 4-{4-(3-Chloro-phenyl)-6-[4-(3-trifluoromethyl-pyridin-2-yl)-piperazin-1-yl]-pyridin-2-yl}-morpholine | 504.2 |

TABLE 1-continued

Representative Biaryl Piperazinyl-Pyridine Analogues

| Compound | | Name | MS (M + 1) |
|---|---|---|---|
| 119 | 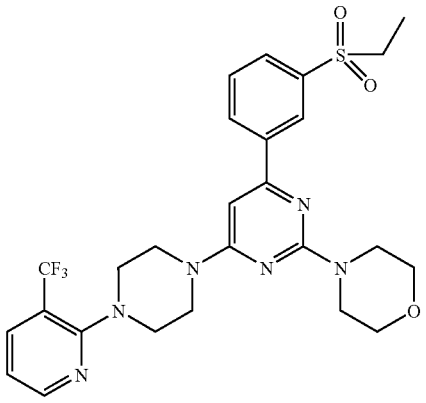 | 4-{4-(3-Ethanesulfonyl-phenyl)-6-[4-(3-trifluoromethyl-pyridin-2-yl)-piperazin-1-yl]-pyrimidin-2-yl}-morpholine | 563.2 |
| 120 | 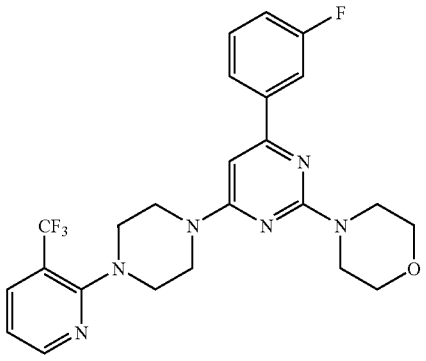 | 4-{4-(3-Fluoro-phenyl)-6-[4-(3-trifluoromethyl-pyridin-2-yl)-piperazin-1-yl]-pyrimidin-2-yl}-morpholine | 489.3 |
| 121 | 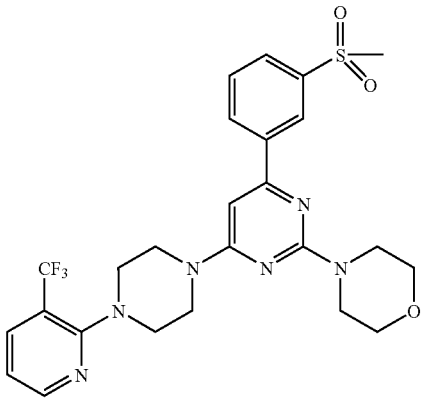 | 4-{4-(3-Methanesulfonyl-phenyl)-6-[4-(3-trifluoromethyl-pyridin-2-yl)-piperazin-1-yl]-pyrimidin-2-yl}-morpholine | 549.2 |
| 122 | 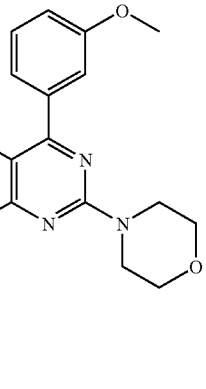 | 4-{4-(3-Methoxy-phenyl)-5-methyl-6-[4-(3-trifluoromethyl-pyridin-2-yl)-piperazin-1-yl]-pyrimidin-2-yl}-morpholine | 515.2 |

TABLE 1-continued

Representative Biaryl Piperazinyl-Pyridine Analogues

| Compound | | Name | MS (M + 1) |
|---|---|---|---|
| 123 | 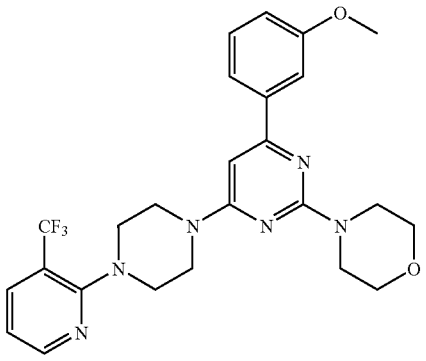 | 4-{4-(3-Methoxy-phenyl)-6-[4-(3-trifluoromethyl-pyridin-2-yl)-piperazin-1-yl]-pyrimidin-2-yl}-morpholine | 501.3 |
| 124 | 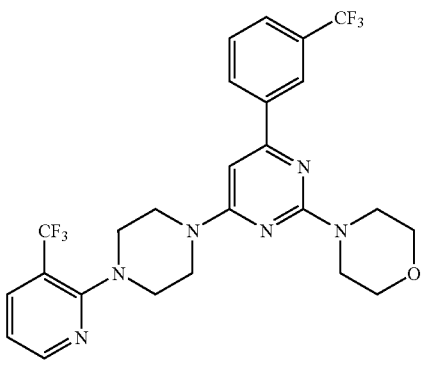 | 4-{4-(3-Trifluoromethyl-phenyl)-6-[4-(3-trifluoromethyl-pyridin-2-yl)-piperazin-1-yl]-pyrimidin-2-yl}-morpholine | 539.3 |
| 125 | 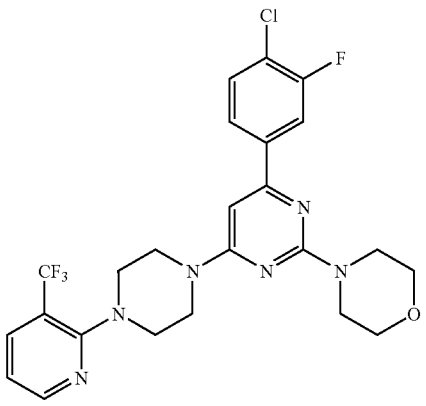 | 4-{4-(4-Chloro-3-fluoro-phenyl)-6-[4-(3-trifluoromethyl-pyridin-2-yl)-piperazin-1-yl]-pyrimidin-2-yl}-morpholine | 523.3 |
| 126 | 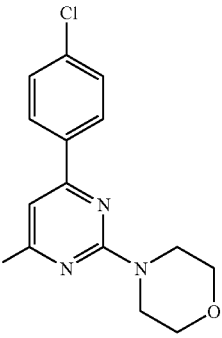 | 4-{4-(4-Chloro-phenyl)-6-[4-(3-trifluoromethyl-pyridin-2-yl)-piperazin-1-yl]-pyrimidin-2-yl}-morpholine | 505.3 |

TABLE 1-continued
Representative Biaryl Piperazinyl-Pyridine Analogues
| Compound | | Name | MS (M + 1) |
|---|---|---|---|
| 127 | 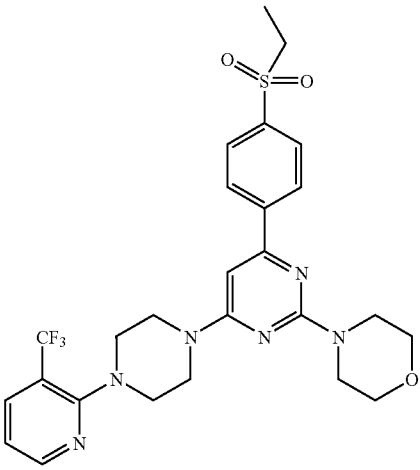 | 4-{4-(4-Ethanesulfonyl-phenyl)-6-[4-(3-trifluoromethyl-pyridin-2-yl)-piperazin-1-yl]-pyrimidin-2-yl}-morpholine | 563.2 |
| 128 | 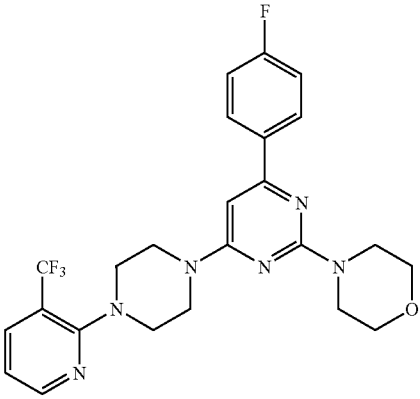 | 4-{4-(4-Fluoro-phenyl)-6-[4-(3-trifluoromethyl-pyridin-2-yl)-piperazin-1-yl]-pyrimidin-2-yl}-morpholine | 489.3 |
| 129 | 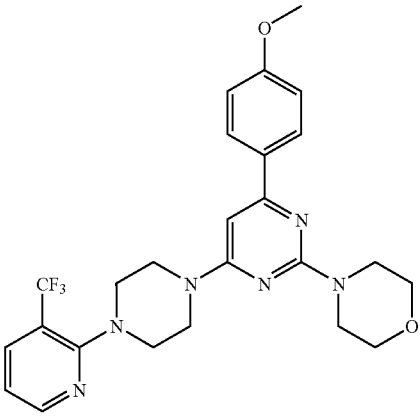 | 4-{4-(4-Methoxy-phenyl)-6-[4-(3-trifluoromethyl-pyridin-2-yl)-piperazin-1-yl]-pyrimidin-2-yl}-morpholine | 501.3 |

TABLE 1-continued
Representative Biaryl Piperazinyl-Pyridine Analogues
| Compound | | Name | MS (M + 1) |
|---|---|---|---|
| 130 | 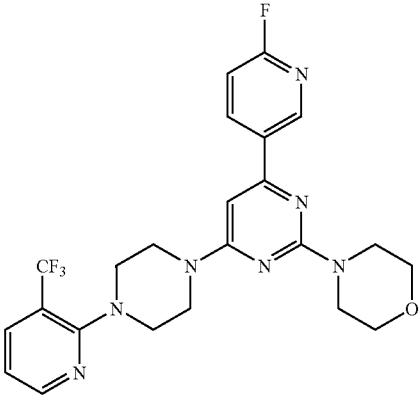 | 4-{4-(6-Fluoro-pyridin-3-yl)-6-[4-(3-trifluoromethyl-pyridin-2-yl)-piperazin-1-yl]-pyrimidin-2-yl}-morpholine | 490.2 |
| 131 | 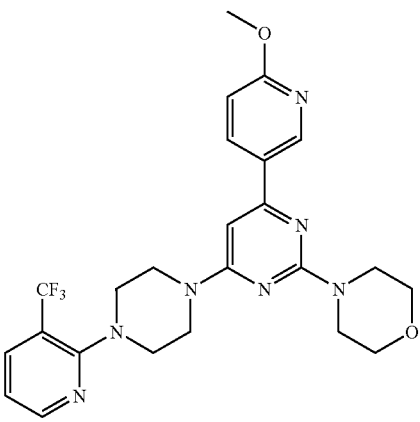 | 4-{4-(6-Methoxy-pyridin-3-yl)-6-[4-(3-trifluoromethyl-pyridin-2-yl)-piperazin-1-yl]-pyrimidin-2-yl}-morpholine | 502.2 |
| 132 | 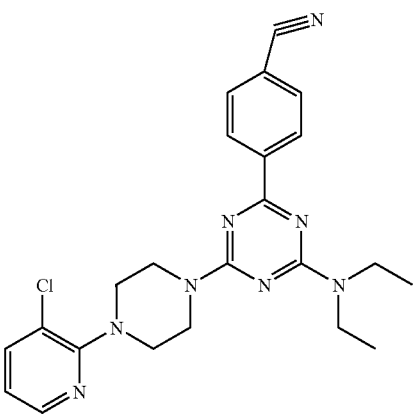 | 4-{4-[4-(3-Chloro-pyridin-2-yl)-piperazin-1-yl]-6-diethylamino-[1,3,5]triazin-2-yl}-benzonitrile | 449.3 |

TABLE 1-continued

Representative Biaryl Piperazinyl-Pyridine Analogues

| Compound | | Name | MS (M + 1) |
|---|---|---|---|
| 133 | 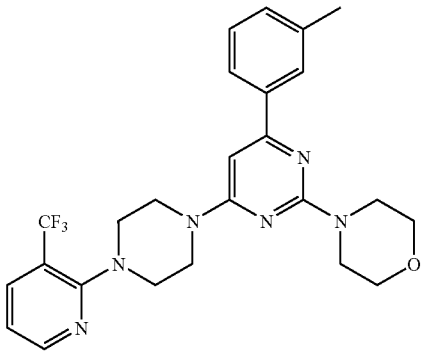 | 4-{4-m-Tolyl-6-[4-(3-trifluoromethyl-pyridin-2-yl)-piperazin-1-yl]-pyrimidin-2-yl}-morpholine | 485.3 |
| 134 | 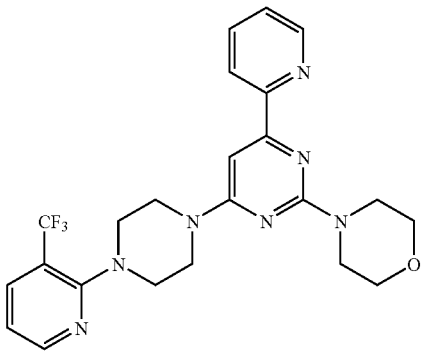 | 4-{4-Pyridin-2-yl-6-[4-(3-trifluoromethyl-pyridin-2-yl)-piperazin-1-yl]-pyrimidin-2-yl}-morpholine | 472.2 |
| 135 | 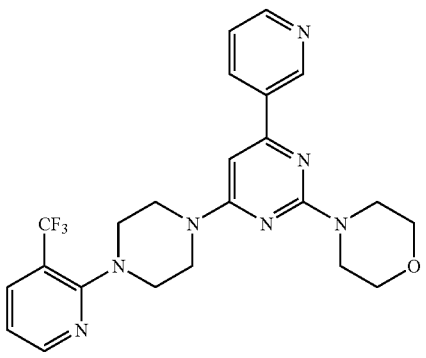 | 4-{4-Pyridin-3-yl-6-[4-(3-trifluoromethyl-pyridin-2-yl)-piperazin-1-yl]-pyrimidin-2-yl}-morpholine | 472.2 |
| 136 | 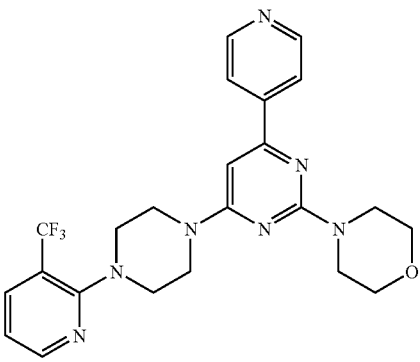 | 4-{4-Pyridin-4-yl-6-[4-(3-trifluoromethyl-pyridin-2-yl)-piperazin-1-yl]-pyrimidin-2-yl}-morpholine | 472.2 |

TABLE 1-continued
Representative Biaryl Piperazinyl-Pyridine Analogues
| Compound | | Name | MS (M + 1) |
|---|---|---|---|
| 137 | 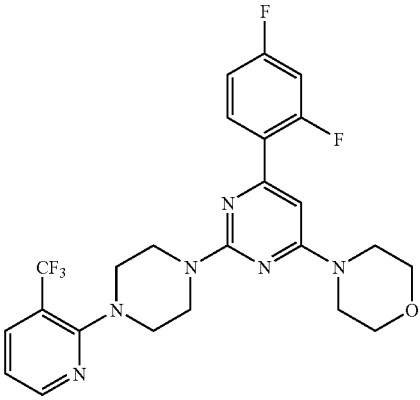 | 4-{6-(2,4-Difluoro-phenyl)-2-[4-(3-trifluoromethyl-pyridin-2-yl)-piperazin-1-yl]-pyrimidin-4-yl}-morpholine | 507.3 |
| 138 | 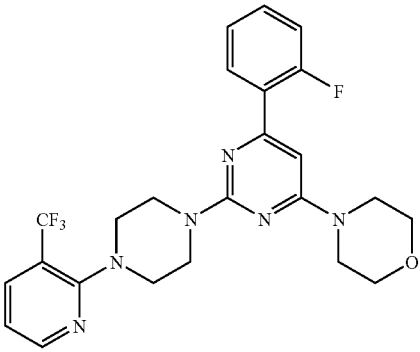 | 4-{6-(2-Fluoro-phenyl)-2-[4-(3-trifluoromethyl-pyridin-2-yl)-piperazin-1-yl]-pyrimidin-4-yl}-morpholine | 489.3 |
| 139 | 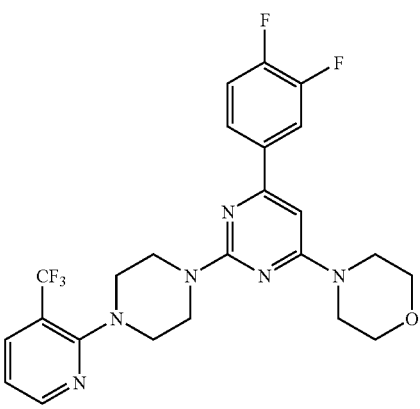 | 4-{6-(3,4-Difluoro-phenyl)-2-[4-(3-trifluoromethyl-pyridin-2-yl)-piperazin-1-yl]-pyrimidin-4-yl}-morpholine | 507.3 |

TABLE 1-continued
Representative Biaryl Piperazinyl-Pyridine Analogues
| Compound | | Name | MS (M + 1) |
|---|---|---|---|
| 140 | 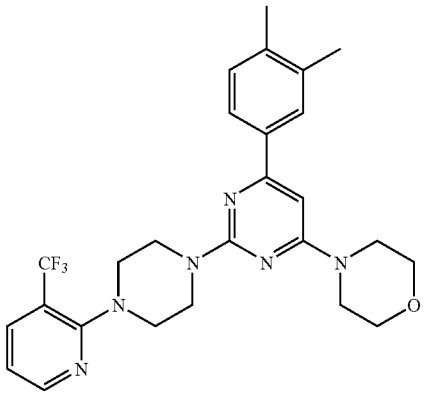 | 4-{6-(3,4-Dimethyl-phenyl)-2-[4-(3-trifluoromethyl-pyridin-2-yl)-piperazin-1-yl]-pyrimidin-4-yl}-morpholine | 499.3 |
| 141 | 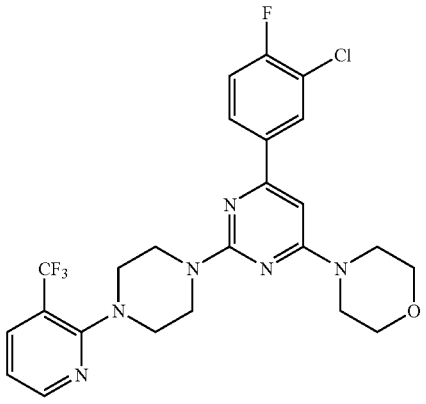 | 4-{6-(3-Chloro-4-fluoro-phenyl)-2-[4-(3-trifluoromethyl-pyridin-2-yl)-piperazin-1-yl]-pyrimidin-4-yl}-morpholine | 523.3 |
| 142 | 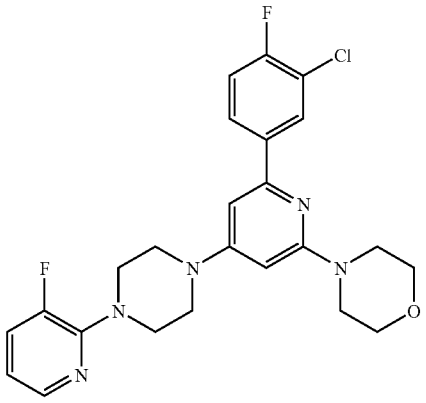 | 4-{6-(3-Chloro-4-fluoro-phenyl)-4-[4-(3-fluoro-pyridin-2-yl)-piperazin-1-yl]-pyridin-2-yl}-morpholine | 472.2 |

TABLE 1-continued

Representative Biaryl Piperazinyl-Pyridine Analogues

| Compound | | Name | MS (M + 1) |
|---|---|---|---|
| 143 | 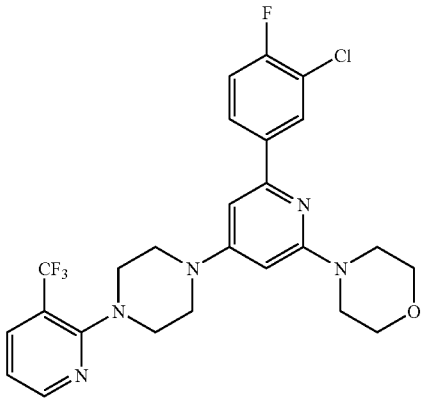 | 4-{6-(3-Chloro-4-fluoro-phenyl)-4-[4-(3-trifluoromethyl-pyridin-2-yl)-piperazin-1-yl]-pyridin-2-yl}-morpholine | 522.2 |
| 144 | 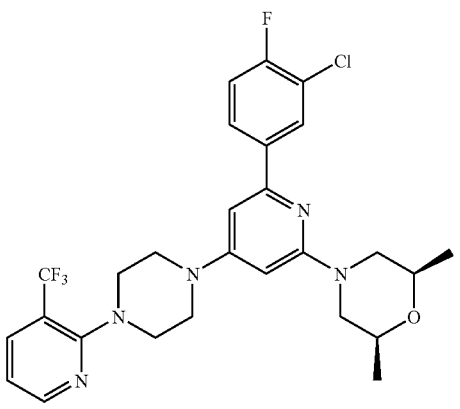 | 4-{6-(3-Chloro-4-fluoro-phenyl)-4-[4-(3-trifluoromethyl-pyridin-2-yl)-piperazin-1-yl]-pyridin-2-yl}-2,6-dimethyl-morpholine (cis) | 550.2 |
| 145 | 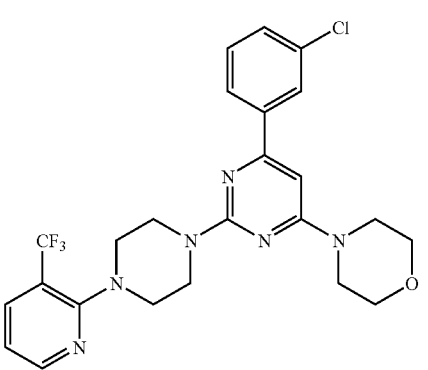 | 4-{6-(3-Chloro-phenyl)-2-[4-(3-trifluoromethyl-pyridin-2-yl)-piperazin-1-yl]-pyrimidin-4-yl}-morpholine | 505.3 |
| 146 | 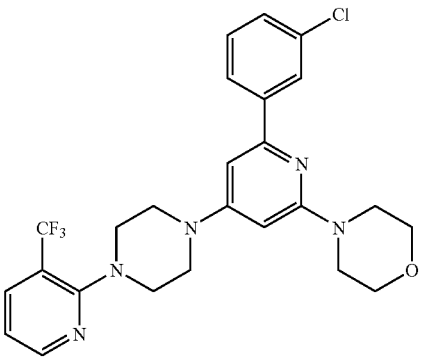 | 4-{6-(3-Chloro-phenyl)-4-[4-(3-trifluoromethyl-pyridin-2-yl)-piperazin-1-yl]-pyridin-2-yl}-morpholine | 504.2 |

TABLE 1-continued

Representative Biaryl Piperazinyl-Pyridine Analogues

| Compound | | Name | MS (M + 1) |
|---|---|---|---|
| 147 | 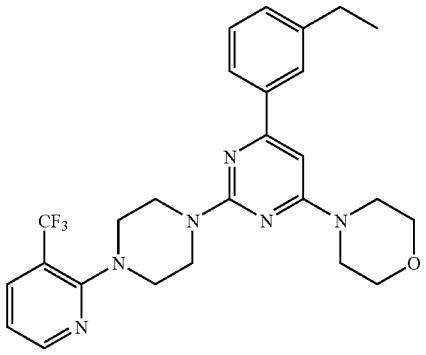 | 4-{6-(3-Ethyl-phenyl)-2-[4-(3-trifluoromethyl-pyridin-2-yl)-piperazin-1-yl]-pyrimidin-4-yl}-morpholine | 499.3 |
| 148 | 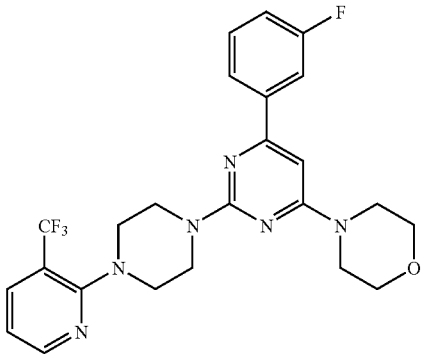 | 4-{6-(3-Fluoro-phenyl)-2-[4-(3-trifluoromethyl-pyridin-2-yl)-piperazin-1-yl]-pyrimidin-4-yl}-morpholine | 489.3 |
| 149 | 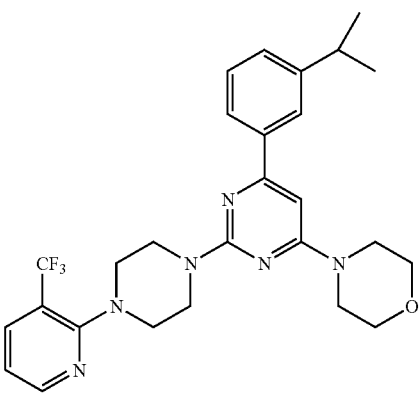 | 4-{6-(3-Isopropyl-phenyl)-2-[4-(3-trifluoromethyl-pyridin-2-yl)-piperazin-1-yl]-pyrimidin-4-yl}-morpholine | 513.3 |
| 150 | 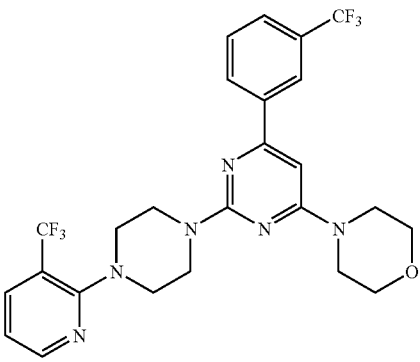 | 4-{6-(3-Trifluoromethyl-phenyl)-2-[4-(3-trifluoromethyl-pyridin-2-yl)-piperazin-1-yl]-pyrimidin-4-yl}-morpholine | 539.3 |

TABLE 1-continued
Representative Biaryl Piperazinyl-Pyridine Analogues
| Compound | | Name | MS (M + 1) |
|---|---|---|---|
| 151 | 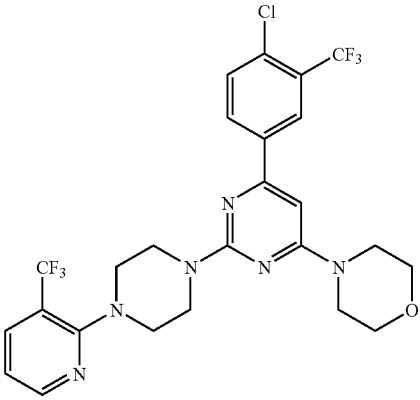 | 4-{6-(4-Chloro-3-trifluoromethyl-phenyl)-2-[4-(3-trifluoromethyl-pyridin-2-yl)-piperazin-1-yl}-pyrimidin-4-yl}-morpholine | 573.3 |
| 152 | 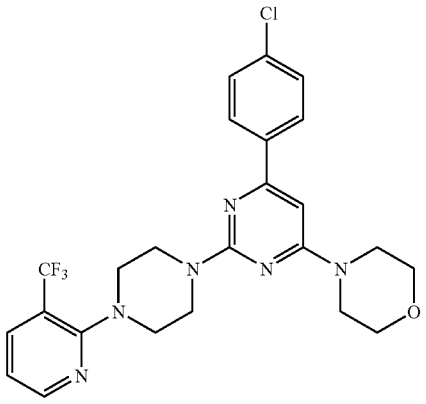 | 4-{6-(4-Chloro-phenyl)-2-[4-(3-trifluoromethyl-pyridin-2-yl)-piperazin-1-yl]-pyrimidin-4-yl}-morpholine | 505.3 |
| 153 | 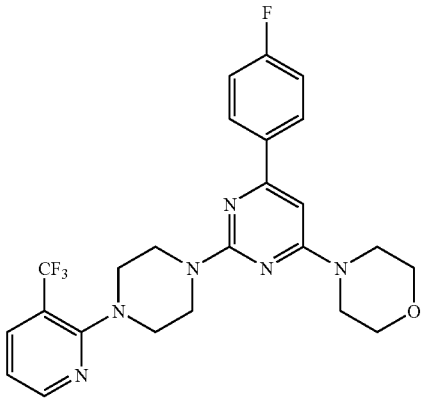 | 4-{6-(4-Fluoro-phenyl)-2-[4-(3-trifluoromethyl-pyridin-2-yl)-piperazin-1-yl]-pyrimidin-4-yl}-morpholine | 489.3 |

TABLE 1-continued
Representative Biaryl Piperazinyl-Pyridine Analogues
| Compound | | Name | MS (M + 1) |
|---|---|---|---|
| 154 | 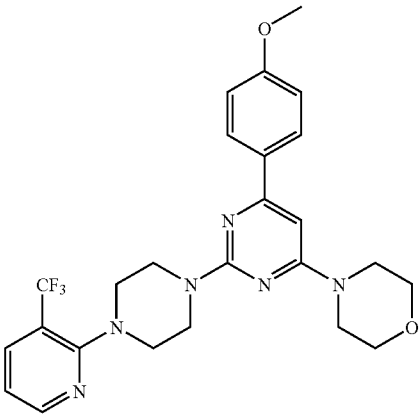 | 4-{6-(4-Methoxy-phenyl)-2-[4-(3-trifluoromethyl-pyridin-2-yl)-piperazin-1-yl]-pyrimidin-4-yl}-morpholine | 501.3 |
| 155 | 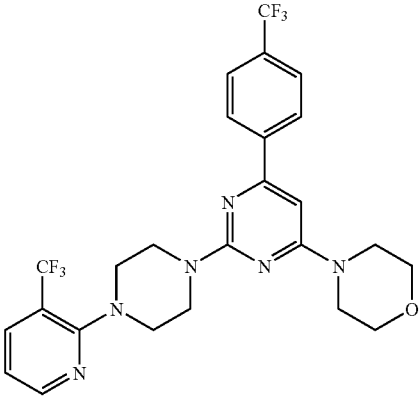 | 4-{6-(4-Trifluoromethyl-phenyl)-2-[4-(3-tnfluoromethyl-pyridin-2-yl)-piperazin-1-yl]-pyrimidin-4-yl}-morpholine | 539.3 |
| 156 | 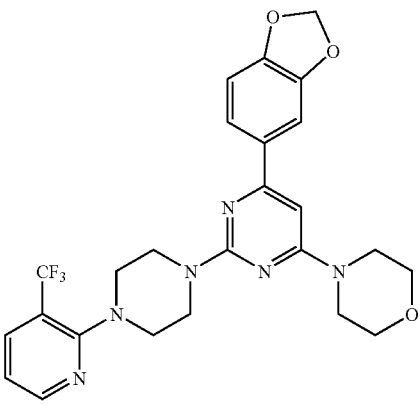 | 4-{6-Benzo[1,3]dioxol-5-yl-2-[4-(3-trifluoromethyl-pyridin-2-yl)-piperazin-1-yl]-pyrimidin-4-yl}-morpholine | 515.3 |

TABLE 1-continued

Representative Biaryl Piperazinyl-Pyridine Analogues

| Compound | Name | MS (M + 1) |
|---|---|---|
| 157 | 4-{6-m-Tolyl-2-[4-(3-trifluoromethyl-pyridin-2-yl)-piperazin-1-yl]-pyrimidin-4-yl}-morpholine | 485.3 |
| 158 | 4-{6-Naphthalen-2-yl-2-[4-(3-trifluoromethyl-pyridin-2-yl)-piperazin-1-yl]-pyrimidin-4-yl}-morpholine | 521.3 |
| 159 | 4-{6-Phenyl-2-[4-(3-trifluoromethyl-pyridin-2-yl)-piperazin-1-yl]-pyrimidin-4-yl}-morpholine | 471.3 |
| 160 | 4-{6-p-Tolyl-2-[4-(3-trifluoromethyl-pyridin-2-yl)-piperazin-1-yl]-pyrimidin-4-yl}-morpholine | 485.3 |

TABLE 1-continued

Representative Biaryl Piperazinyl-Pyridine Analogues

| Compound | | Name | MS (M + 1) |
|---|---|---|---|
| 161 | 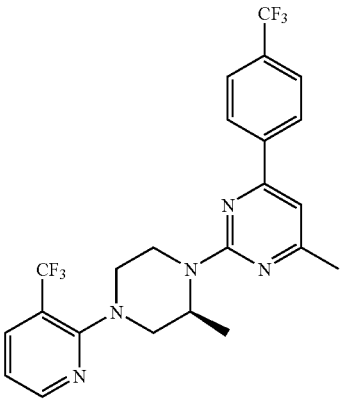 | 4-Methyl-2-[2-methyl-4-(3-trifluoromethyl-pyridin-2-yl)-piperazin-1-yl]-6-(4-trifluoromethyl-phenyl)-pyrimidine (S) | 482.3 |
| 162 | 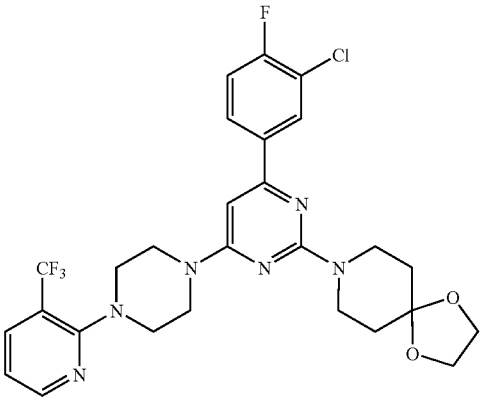 | 8-{4-(3-Chloro-4-fluoro-phenyl)-6-[4-(3-trifluoromethyl-pyridin-2-yl)-piperazin-l-yl]-pyrimidin-2-yl}-1,4-dioxa-8-aza-spiro[4.5]decane | 579.2 |
| 163 | 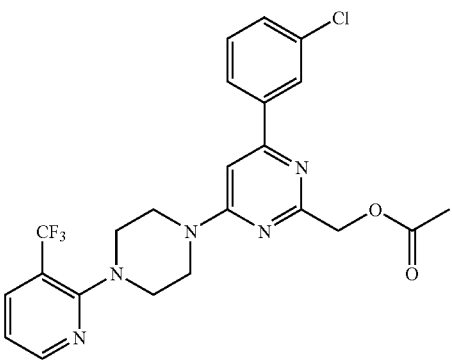 | Acetic acid 4-(3-chloro-phenyl)-6-[4-(3-trifluoromethyl-pyridin-2-yl)-piperazin-1-yl]-pyrimidin-2-yl methyl ester | 492.1 |

TABLE 1-continued

Representative Biaryl Piperazinyl-Pyridine Analogues

| Compound | Name | MS (M + 1) |
|---|---|---|
| 164 | Butyl-{4-(3-chloro-4-fluoro-phenyl)-6-[4-(3-trifluoromethyl-pyridin-2-yl)-piperazin-1-yl]-pynmidin-2-yl}-amine | 509.2 |
| 165 | Diethyl-(3-{2-morpholin-4-yl-6-[4-(3-trifluoromethyl-pyridin-2-yl)-piperazin-1-yl]-pyrimidin-4-yl}-benzyl)-amine | 556.3 |
| 166 | Diethyl-(4-{2-morpholin-4-yl-6-[4-(3-trifluoromethyl-pyridin-2-yl)-piperazin-1-yl]-pyrimidin-4-yl}-pyridin-2-yl)-amine | 543.3 |
| 167 | Diethyl-[4-(2-fluoro-phenyl)-6-(4-pyridin-2-yl-piperazin-1-yl)-[1,3,5]triazin-2-yl]-amine | 408.3 |

TABLE 1-continued

Representative Biaryl Piperazinyl-Pyridine Analogues

| Compound | | Name | MS (M + 1) |
|---|---|---|---|
| 168 | 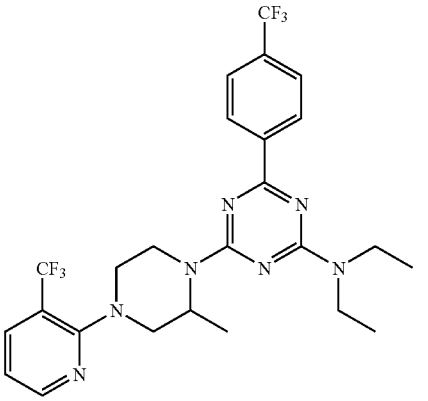 | Diethyl-[4-[2-methyl-4-(3-trifluoromethyl-pyridin-2-yl)-piperazin-1-yl]-6-(4-trifluoromethyl-phenyl)-[1,3,5]triazin-2-yl]-amine | 540.4 |
| 169 | 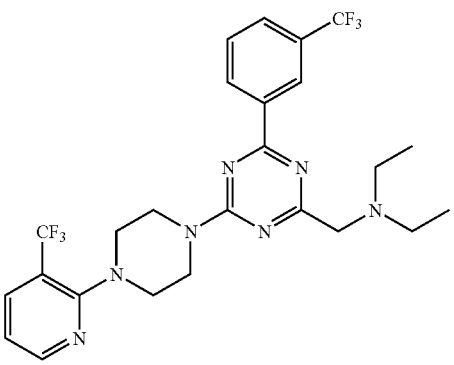 | Diethyl-{4-(3-trifluoromethyl-phenyl)-6-[4-(3-trifluoromethyl-pyridin-2-yl)-piperazin-1-yl]-[1,3,5]triazin-2-ylmethyl}-amine | 540.3 |
| 170 | 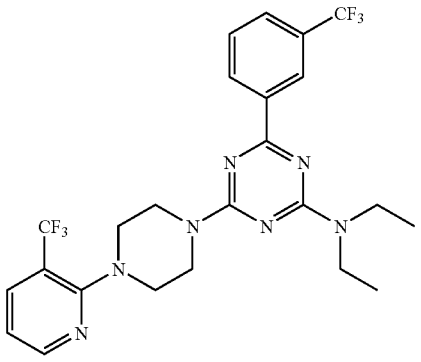 | Diethyl-{4-(3-trifluoromethyl-phenyl)-6-[4-(3-trifluoromethyl-pyridin-2-yl)-piperazin-1-yl]-[1,3,5]triazin-2-yl}-amine | 527.3 |
| 171 | 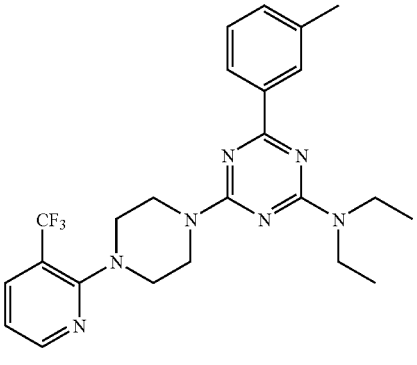 | Diethyl-{4-m-tolyl-6-[4-(3-trifluoromethyl-pyridin-2-yl)-piperazin-1-yl]-[1,3,5]triazin-2-yl}-amine | 472.3 |

TABLE 1-continued
Representative Biaryl Piperazinyl-Pyridine Analogues
| Compound | | Name | MS (M + 1) |
|---|---|---|---|
| 172 | 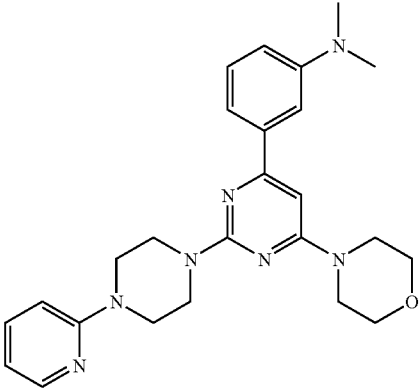 | Dimethyl-{3-[6-morpholin-4-yl-2-(4-pyridin-2-yl-piperazin-1-yl)-pyrimidin-4-yl]-phenyl}-amine | 446.3 |
| 173 | 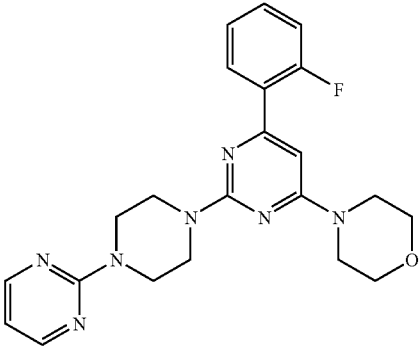 | 4-[6-(2-Fluoro-phenyl)-2-(4-pyrimidin-2-yl-piperazin-1-yl)-pyrimidin-4-yl]-morpholine | 422.3 |
TABLE II
| Compound | | Name | IC$_{50}$ | Ret. Time | MS (M + 1) | LCMS Method |
|---|---|---|---|---|---|---|
| 174 | 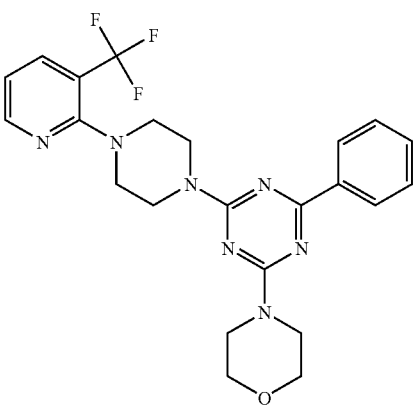 | 2-morpholin-4-yl-4-phenyl-6-{4-[3-(trifluoromethyl)pyridin-2-yl]piperazin-1-yl}-1,3,5-triazine | | 1.34 | 474.19 | A |

TABLE II-continued

| Compound | | Name | IC$_{50}$ | Ret. Time | MS (M + 1) | LCMS Method |
|---|---|---|---|---|---|---|
| 175 | 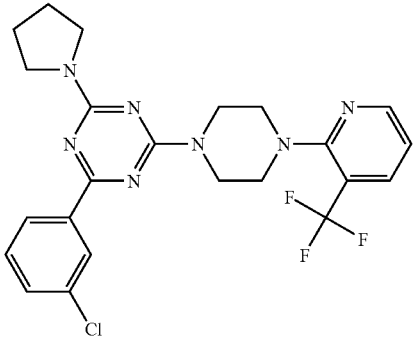 | 2-(3-chlorophenyl)-4-pyrrolidin-1-yl-6-{4-[3-(trifluoromethyl)pyridin-2-yl]piperazin-1-yl}-1,3,5-triazine | | 1.51 | 490.16 | A |
| 176 | 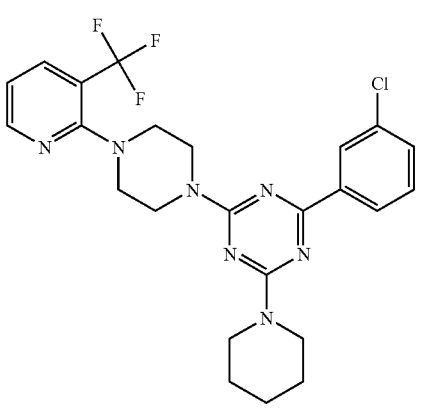 | 2-(3-chlorophenyl)-4-piperidin-1-yl-6-{4-[3-(trifluoromethyl)pyridin-2-yl]piperazin-1-yl}-1,3,5-triazine | | 1.62 | 504.18 | A |
| 177 | 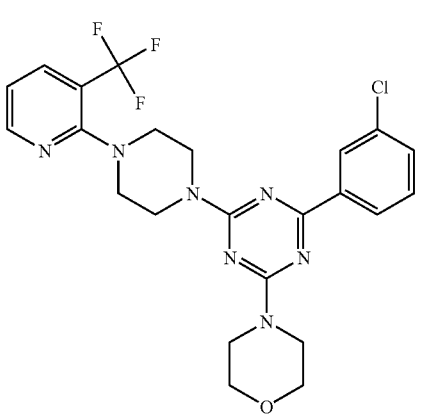 | 2-(3-chlorophenyl)-4-morpholin-4-yl-6-{4-[3-(trifluoromethyl)pyridin-2-yl]piperazin-1-yl}-1,3,5-triazine | | 1.45 | 506.16 | A |
| 178 | 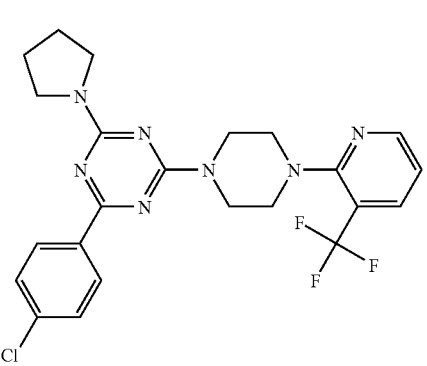 | 2-(4-chlorophenyl)-4-pyrrolidin-1-yl-6-{4-[3-(trifluoromethyl)pyridin-2-yl]piperazin-1-yl}-1,3,5-triazine | | 1.49 | 490.16 | A |

TABLE II-continued

| Compound | Name | IC$_{50}$ | Ret. Time | MS (M + 1) | LCMS Method |
|---|---|---|---|---|---|
| 179 | 2-(4-chlorophenyl)-4-piperidin-1-yl-6-{4-[3-(trifluoromethyl)pyridin-2-yl]piperazin-1-yl}-1,3,5-triazine | | 1.61 | 504.17 | A |
| 180 | 2-(4-chlorophenyl)-4-morpholin-4-yl-6-{4-[3-(trifluoromethyl)pyridin-2-yl]piperazin-1-yl}-1,3,5-triazine | | 1.46 | 506.15 | A |
| 181 | 2-(4-fluorophenyl)-4-pyrrolidin-1-yl-6-{4-[3-(trifluoromethyl)pyridin-2-yl]piperazin-1-yl}-1,3,5-triazine | | 1.38 | 474.18 | A |

TABLE II-continued
| Compound | | Name | IC$_{50}$ | Ret. Time | MS (M + 1) | LCMS Method |
|---|---|---|---|---|---|---|
| 182 | 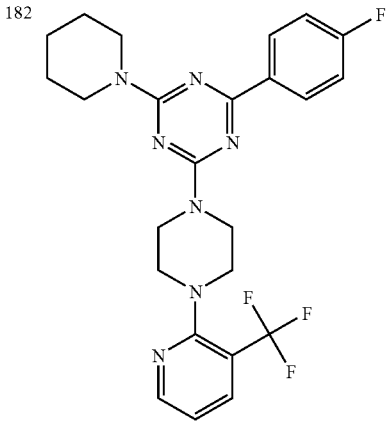 | 2-(4-fluorophenyl)-4-piperidin-1-yl-6-{4-[3-(trifluoromethyl)pyridin-2-yl]piperazin-1-yl}-1,3,5-triazine | | 1.47 | 488.19 | A |
| 183 | 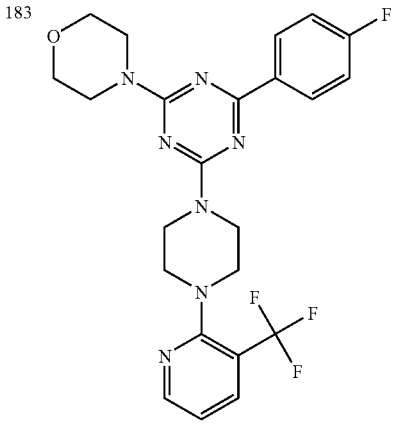 | 2-(4-fluorophenyl)-4-morpholin-4-yl-6-{4-[3-(trifluoromethyl)pyridin-2-yl]piperazin-1-yl}-1,3,5-triazine | | 1.37 | 490.17 | A |
| 184 | 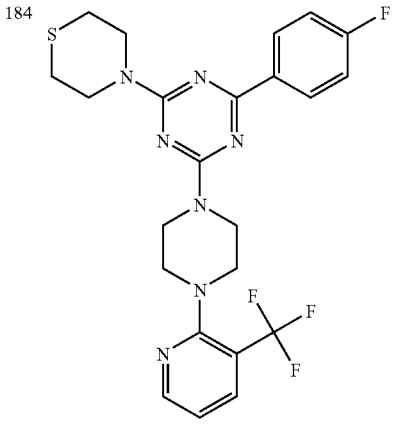 | 2-(4-fluorophenyl)-4-thiomorpholin-4-yl-6-{4-[3-(trifluoromethyl)pyridin-2-yl]piperazin-1-yl}-1,3,5-triazine | | 1.46 | 506.16 | A |

TABLE II-continued

| Compound | Name | IC$_{50}$ | Ret. Time | MS (M + 1) | LCMS Method |
|---|---|---|---|---|---|
| 185 | 2-(3-fluorophenyl)-4-pyrrolidin-1-yl-6-{4-[3-(trifluoromethyl)pyridin-2-yl]piperazin-1-yl}-1,3,5-triazine | | 1.43 | 474.18 | A |
| 186 | 2-(3-fluorophenyl)-4-piperidin-1-yl-6-{4-[3-(trifluoromethyl)pyridin-2-yl]piperazin-1-yl}-1,3,5-triazine | | 1.51 | 488.19 | A |
| 187 | 2-(3-fluorophenyl)-4-morpholin-4-yl-6-{4-[3-(trifluoromethyl)pyridin-2-yl]piperazin-1-yl}-1,3,5-triazine | | 1.38 | 490.18 | A |
| 188 | 2-(2-fluorophenyl)-4-morphohn-4-yl-.6-{4-[3-(trifluoromethyl)pyridin-2-yl]piperazin-1-yl}-1,3,5-triazine | | 1.28 | 490.17 | A |

TABLE II-continued
| Compound | | Name | IC$_{50}$ | Ret. Time | MS (M + 1) | LCMS Method |
|---|---|---|---|---|---|---|
| 189 | 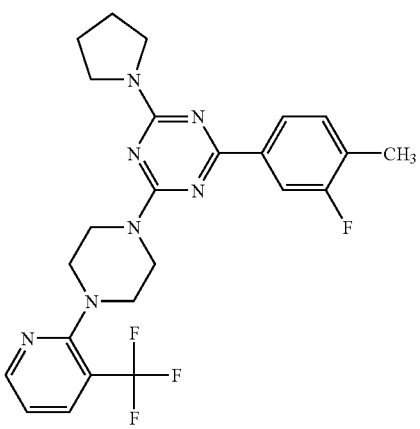 | 2-(3-fluoro-4-methylphenyl)-4-pyrrolidin-1-yl-6-{4-[3-(trifluoromethyl)pyridin-2-yl]piperazin-1-yl}-1,3,5-triazine | | 1.46 | 488.19 | A |
| 190 | 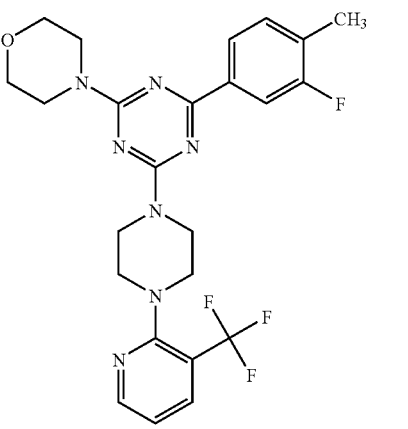 | 2-(3-fluoro-4-methylphenyl)-4-morpholin-4-yl-6-{4-[3-(trifluoromethyl)pyridin-2-yl]piperazin-1-yl}-1,3,5-triazine | | 1.45 | 504.19 | A |
| 191 | 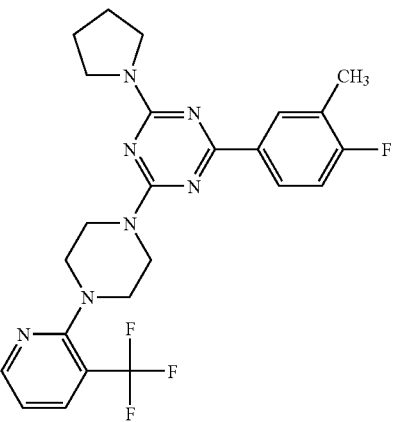 | 2-(4-fluoro-3-methylphenyl)-4-pyrrolidin-1-yl-6-{4-[3-(trifluoromethyl)pyridin-2-yl]piperazin-1-yl}-1,3,5-triazine | | 1.39 | 488.19 | A |

TABLE II-continued

| Compound | Name | IC$_{50}$ | Ret. Time | MS (M + 1) | LCMS Method |
|---|---|---|---|---|---|
| 192 | 2-(4-fluoro-3-methylphenyl)-4-piperidin-1-yl-6-{4-[3-(trifluoromethyl)pyridin-2-yl]piperazin-1-yl}-1,3,5-triazine | | 1.53 | 502.20 | A |
| 193 | 2-(4-fluoro-3-methylphenyl)-4-morpholin-4-yl-6-{4-[3-(trifluoromethyl)pyridin-2-yl]piperazin-1-yl}-1,3,5-triazine | | 1.41 | 504.18 | A |
| 194 | 2-(4-fluoro-3-methylphenyl)-4-thiomorpholin-4-yl-6-{4-[3-(trifluoromethyl)pyridin-2-yl]piperazin-1-yl}-1,3,5-triazine | | 1.52 | 520.17 | A |

TABLE II-continued

| Compound | | Name | IC$_{50}$ | Ret. Time | MS (M + 1) | LCMS Method |
|---|---|---|---|---|---|---|
| 195 | | 2-(3-methylphenyl)-4-pyrrolidin-1-yl-6-{4-[3-(trifluoromethyl)pyridin-2-yl]piperazin-1-yl}-1,3,5-triazine | | 1.31 | 470.19 | A |
| 196 | | 2-(3-methylphenyl)-4-piperidin-1-yl-6-{4-[3-(trifluoromethyl)pyridin-2-yl]piperazin-1-yl}-1,3,5-triazine | | 1.44 | 484.21 | A |
| 197 | | 2-(3-methylphenyl)-4-morpholin-4-yl-6-{4-[3-(trifluoromethyl)pyridin-2-yl]piperazin-1-yl}-1,3,5-triazine | | 1.38 | 486.20 | A |
| 198 | | 2-(3-methylphenyl)-4-thiomorpholin-4-yl-6-{4-[3-(trifluoromethyl)pyridin-2-yl]piperazin-1-yl}-1,3,5-triazine | | 1.48 | 502.17 | A |

TABLE II-continued

| Compound | | Name | IC$_{50}$ | Ret. Time | MS (M + 1) | LCMS Method |
|---|---|---|---|---|---|---|
| 199 | | 2-(4-methylphenyl)-4-pyrrolidin-1-yl-6-{4-[3-(trifluoromethyl)pyridin-2-2-yl]piperazin-1-yl}-1,3,5-triazine | | 1.3 | 470.20 | A |
| 200 | | 2-(4-methylphenyl)-4-piperidin-1-yl-6-{4-[3-(trifluoromethyl)pyridin-2-yl]piperazin-1-yl}-1,3,5-triazine | | 1.43 | 484.21 | A |
| 201 | | 2-(4-methylphenyl)-4-morpholin-4-yl-6-{4-[3-(trifluoromethyl)pyridin-2-yl]piperazin-1-yl}-1,3,5-triazine | | 1.39 | 486.19 | A |

TABLE II-continued

| Compound | Name | IC$_{50}$ | Ret. Time | MS (M + 1) | LCMS Method |
|---|---|---|---|---|---|
| 202 | 2-(3,4-dimethylphenyl)-4-pyrrolidin-1-yl-6-{4-[3-(trifluoromethyl)pyridin-2-yl]piperazin-1-yl}-1,3,5-triazine | | 1.31 | 484.21 | A |
| 203 | 2-(3,4-dimethylphenyl)-4-morpholin-4-yl-6-{4-[3-(trifluoromethyl)pyridin-2-yl]piperazin-1-yl}-1,3,5-triazine | | 1.4 | 500.20 | A |
| 204 | 2-(3-methoxyphenyl)-4-pyrrolidin-1-yl-6-{4-[3-(trifluoromethyl)pyridin-2-yl]piperazin-1-yl}-1,3,5-triazine | | 1.31 | 486.21 | A |

TABLE II-continued

| Compound | | Name | IC$_{50}$ | Ret. Time | MS (M + 1) | LCMS Method |
|---|---|---|---|---|---|---|
| 205 | | 2-(3-methoxyphenyl)-4-piperidin-1-yl-6-{4-[3-(trifluoromethyl)pyridin-2-yl]piperazin-1-yl}-1,3,5-triazine | | 1.41 | 500.23 | A |
| 206 | | 2-(3-methoxyphenyl)-4-morpholin-4-yl-6-{4-[3-(trifluoromethyl)pyridin-2-yl]piperazin-1-yl}-1,3,5-triazine | | 1.33 | 502.21 | A |
| 207 | | 2-morpholin-4-yl-4-[4-(trifluoromethoxy)phenyl]-6-{4-[3-(trifluoromethyl)pyridin-2-yl]piperazin-1-yl}-1,3,5-triazine | | 1.42 | 556.19 | A |

TABLE II-continued
| Compound | | Name | IC$_{50}$ | Ret. Time | MS (M + 1) | LCMS Method |
|---|---|---|---|---|---|---|
| 208 | 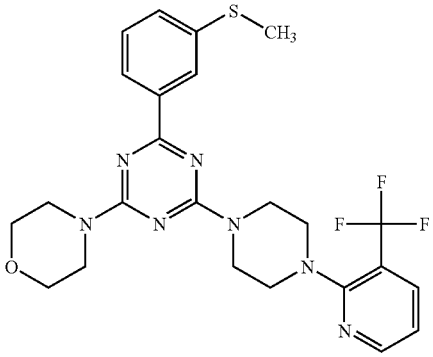 | 2-[3-(methylthio)phenyl]-4-morpholin-4-yl-6-{4-[3-(trifluoromethyl)pyridin-2-yl]piperazin-1-yl}-1,3,5-triazine | | 1.39 | 518.20 | A |
| 209 | 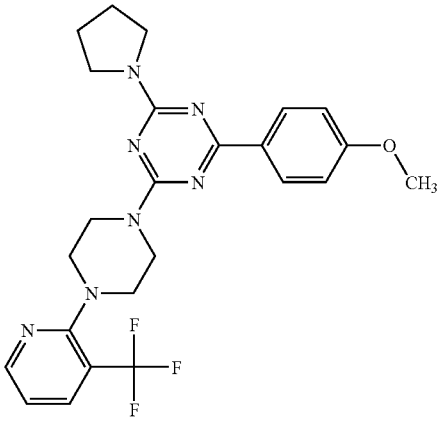 | 2-(4-methoxyphenyl)-4-pyrrolidin-1-yl-6-{4-[3-(trifluoromethyl)pyridin-2-yl]piperazin-1-yl}-1,3,5-triazine | | 1.24 | 486.20 | A |
| 210 | 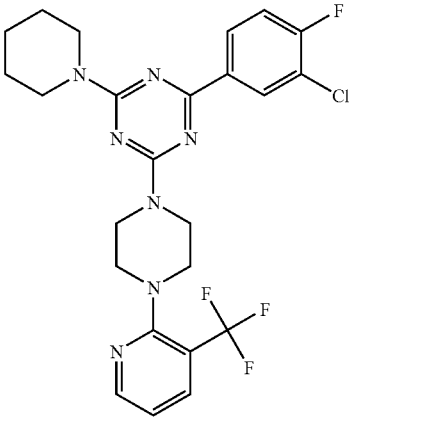 | 2-(3-chloro-4-fluorophenyl)-4-piperidin-1-yl-6-{4-[3-(trifluoromethyl)pyridin-2-yl]piperazin-1-yl}-1,3,5-triazine | | 1.67 | 522.17 | A |

TABLE II-continued
| Compound | | Name | IC$_{50}$ | Ret. Time | MS (M + 1) | LCMS Method |
|---|---|---|---|---|---|---|
| 211 | 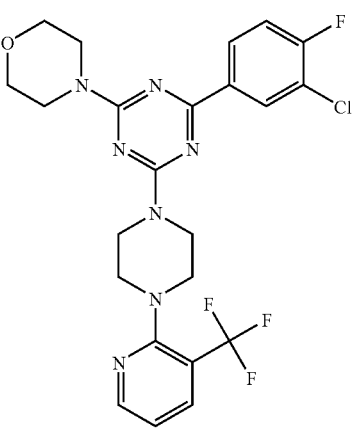 | 2-(3-chloro-4-fluorophenyl)-4-morpholin-4-yl-6-{4-[3-(trifluoromethyl)pyridin-2-yl]piperazin-1-yl}-1,3,5-triazine | | 1.48 | 524.15 | A |
| 212 | 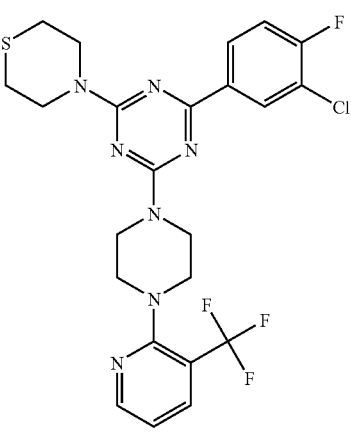 | 2-(3-chloro-4-fluorophenyl)-4-thiomorpholin-4-yl-6-{4-{3-(trifluoromethyl)pyridin-2-yl]piperazin-1-yl}-1,3,5-triazine | | 1.6 | 540.13 | A |
| 213 | 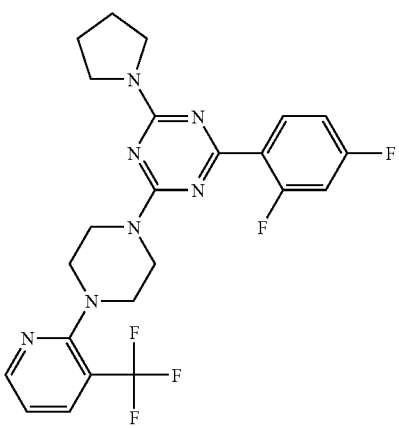 | 2-(2,4-difluorophenyl)-4-pyrrolidin-1-yl-6-{4-[3-(trifluoromethyl)pyridin-2-yl]piperazin-1-yl}-1,3,5-triazine | | 1.28 | 492.17 | A |

TABLE II-continued
| Compound | | Name | IC$_{50}$ | Ret. Time | MS (M + 1) | LCMS Method |
|---|---|---|---|---|---|---|
| 214 | 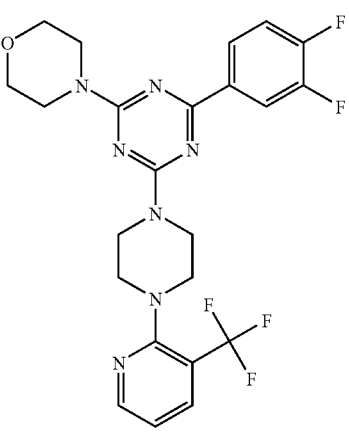 | 2-(3,4-difluorophenyl)-4-morpholin-4-yl-6-{4-[3-(trifluoromethyl)pyridin-2-yl]piperazin-1-yl}-1,3,5-triazine | | 1.42 | 508.18 | A |
| 215 | 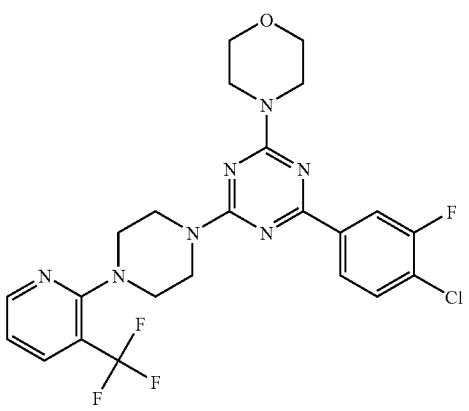 | 2-(4-chloro-3-fluorophenyl)-4-morpholin-4-yl-6-{4-[3-(trifluoromethyl)pyridin-2-yl]piperazin-1-yl}-1,3,5-triazine | | 1.5 | 524.15 | A |
| 216 | 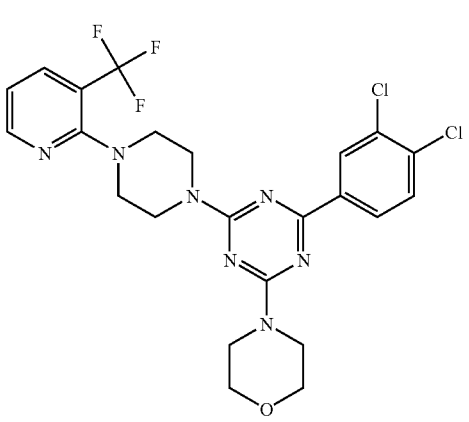 | 2-(3,4-dichlorophenyl)-4-morpholin-4-yl-6-{4-[3-(trifluoromethyl)pyridin-2-yl]piperazin-1-yl}-1,3,5-triazine | | 1.59 | 540.12 | A |

TABLE II-continued

| Compound | | Name | IC$_{50}$ | Ret. Time | MS (M + 1) | LCMS Method |
|---|---|---|---|---|---|---|
| 217 | | 2-(2,4-dichlorophenyl)-4-pyrrolidin-1-yl-6-{4-[3-(trifluoromethyl)pyridin-2-pyrrolidin-1-yl-6-{4-[3-yl]piperazin-1-yl}-1,3,5-triazine | | 1.36 | 524.12 | A |
| 218 | | 2-(2,4-dichlorophenyl)-4-morpholin-4-yl-6-{4-[3-(trifluoromethyl)pyridin-2-yl]piperazin-1-yl}-1,3,5-triazine | | 1.41 | 540.11 | A |
| 219 | | 2-morpholin-4-yl-4-phenyl-6-(4-pyridin-2-yl]piperazin-1-yl)-1,3,5-triazine | | 1.06 | 404.22 | A |
| 220 | | 2-(3-chlorophenyl)-4-morpholin-4-yl-6-(4-pyridin-2-ylpiperazin-1-yl)-1,3,5-triazine | | 1.11 | 438.17 | A |

TABLE II-continued

| Compound | Name | IC$_{50}$ | Ret. Time | MS (M + 1) | LCMS Method |
|---|---|---|---|---|---|
| 221 | 2-(4-fluorophenyl)-4-morpholin-4-yl-6-(4-pyridin-2-ylpiperazin-1-yl)-1,3,5-triazine | | 1.09 | 422.21 | A |
| 222 | 2-(3-fluorophenyl)-4-morpholin-4-yl-6-(4-pyridin-2-ylpiperazin-1-yl)-1,3,5-triazine | | 1.08 | 422.21 | A |
| 223 | 2-(2-fluorophenyl)-4-morpholin-4-yl-6-(4-pyridin-2-ylpiperazin-1-yl)-1,3,5-triazine | | 1.04 | 422.21 | A |

TABLE II-continued

| Compound | Name | IC$_{50}$ | Ret. Time | MS (M + 1) | LCMS Method |
|---|---|---|---|---|---|
| 224 | 2-morpholin-4-yl-4-(2-naphthyl)-6-(4-pyridin-2-ylpiperazin-1-yl)-1,3,5-triazine | | 1.13 | 454.23 | A |
| 225 | 2-(2-fluoro-5-methylphenyl)-4-morpholin-4-yl-6-(4-pyridin-2-ylpiperazin-1-yl)-1,3,5-triazine | | 1.06 | 436.22 | A |
| 226 | 2-morpholin-4-yl-4-phenyl-6-{4-[3-(trifluoromethyl)pyridin-2-yl]piperazin-1-yl}-1,3,5-triazine | | 1.34 | 472.19 | A |

TABLE II-continued
| Compound | | Name | IC$_{50}$ | Ret. Time | MS (M + 1) | LCMS Method |
|---|---|---|---|---|---|---|
| 227 | 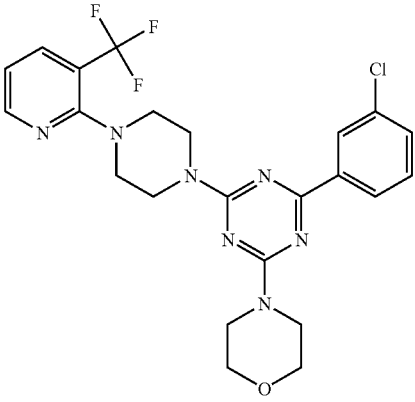 | 2-(3-chlorophenyl)-4-morpholin-4-yl-6-{4-[3-(trifluoromethyl)pyridin-2-yl]piperazin-1-yl}-1,3,5-triazine | | 1.46 | 506.16 | A |
| 228 | 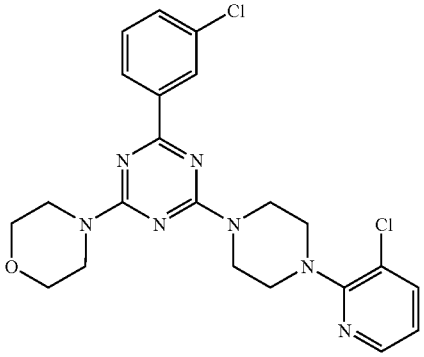 | 2-(3-chlorophenyl)-4-[4-(3-chloropyridin-2-yl)piperazin-1-yl]-6-morpholin-4-yl-1,3,5-triazine | | 1.46 | 472.13 | A |
| 229 | 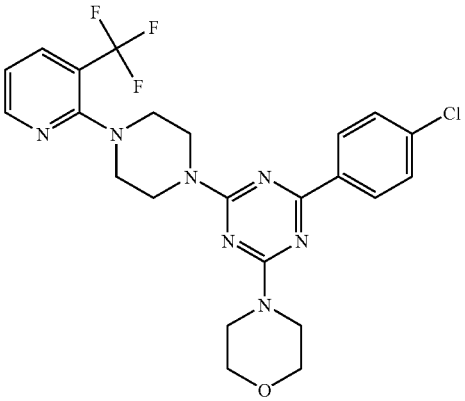 | 2-(4-chlorophenyl)-4-morpholin-4-yl-6-{4-[3-(trifluoromethyl)pyridin-2-yl]piperazin-1-yl}-1,3,5-triazine | | 1.46 | 506.16 | A |

TABLE II-continued
| Compound | | Name | IC$_{50}$ | Ret. Time | MS (M + 1) | LCMS Method |
|---|---|---|---|---|---|---|
| 230 | 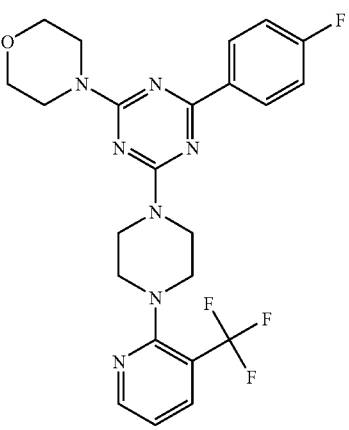 | 2-(4-fluorophenyl)-4-morpholin-4-yl-6-{4-[3-(trifluoromethyl)pyridin-2-yl]piperazin-1-yl}-1,3,5-triazine | | 1.37 | 490.18 | A |
| 231 | 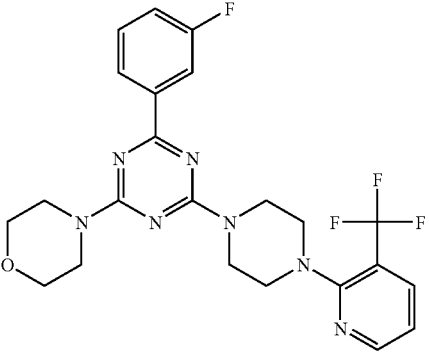 | 2-(3-fluorophenyl)-4-morpholin-4-yl-6-{4-[3-(trifluoromethyl)pyridin-2-yl]piperazin-1-yl}-1,3,5-triazine | | 1.38 | 490.18 | A |
| 232 | 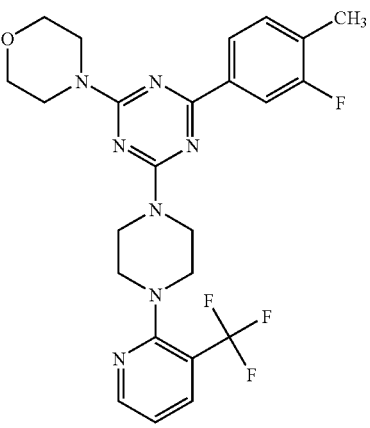 | 2-(3-fluoro-4-methylphenyl)-4-morpholin-4-yl-6-{4-[3-(trifluoromethyl)pyridin-2-yl]piperazin-1-yl}-1,3,5-triazine | | 1.44 | 504.20 | A |

TABLE II-continued

| Compound | | Name | IC$_{50}$ | Ret. Time | MS (M + 1) | LCMS Method |
|---|---|---|---|---|---|---|
| 233 | | 2-(4-fluoro-3-methylphenyl)-4-morpholin-4-yl-6-{4-[3-(trifluoromethyl)pyridin-2-yl]piperazin-1 -yl}-1,3,5-triazine | | 1.42 | 504.19 | A |
| 234 | | 2-(3-methylphenyl)-4-morpholin-4-yl-6-(4-pyridin-2-yl)piperazin-1-yl)-1,3,5-triazine | * | 1.11 | 418.23 | A |
| 235 | | 2-(3-isopropylphenyl)-4-morpholin-4-yl-6-(4-pyridin-2-ylpiperazin-1-yl)-1,3,5-triazine | * | 1.13 | 446.32 | A |
| 236 | | 2-(3,5-dimethylphenyl)-4-morpholin-4-yl-6-(4-pyridin-2-ylpiperazin-1-yl)-1,3,5-triazine | * | 1.11 | 432.30 | A |

TABLE II-continued

| Compound | | Name | IC$_{50}$ | Ret. Time | MS (M + 1) | LCMS Method |
|---|---|---|---|---|---|---|
| 237 | | 2-(3-ethylphenyl)-4-morpholin-4-yl-6-(4-pyridin-2-ylpiperazin-1-yl)-1,3,5-triazine | * | 1.11 | 432.25 | A |
| 238 | | 2-(3-methylphenyl)-4-morpholin-4-yl-6-{4-[3-(trifluoromethyl)pyridin-2-yl]piperazin-1-yl}-1,3,5-triazine | * | 1.36 | 486.30 | A |
| 239 | | 2-[4-(3-chloropyridin-2-yl)piperazin-1-yl]-4-(3-methylphenyl)-6-morpholin-4-yl-1,3,5-triazine | | 1.35 | 452.26 | A |
| 240 | | 2-(4-methylphenyl)-4-morpholin-4-yl-6-{4-[3-(trifluoromethyl)pyridin-2-yl]piperazin-1-yl}-1,3,5-triazine | | 1.36 | 486.30 | A |

TABLE II-continued
| Compound | | Name | IC$_{50}$ | Ret. Time | MS (M + 1) | LCMS Method |
|---|---|---|---|---|---|---|
| 241 | 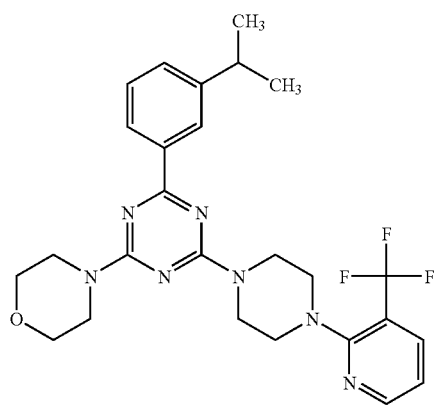 | 2-(3-isopropylphenyl)-4-morpholin-4-yl-6-{4-[3-(trifluoromethyl)pyridin-2-yl]piperazin-1-yl}-1,3,5-triazine | | 1.39 | 514.35 | A |
| 242 | 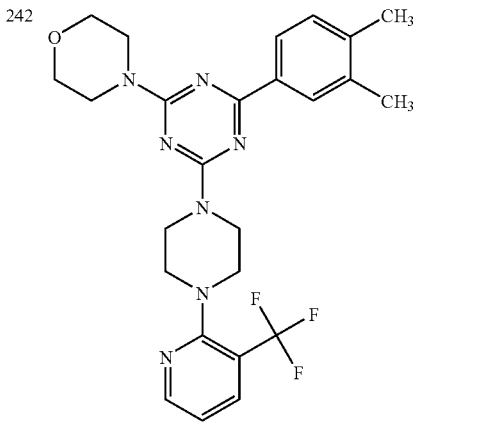 | 2-(3,4-dimethylphenyl)-4-morpholin-4-yl-6-{4-[3-(trifluoromethyl)pyridin-2-yl]piperazin-1 -yl}-1,3,5-triazine | | 1.38 | 500.34 | A |
| 243 | 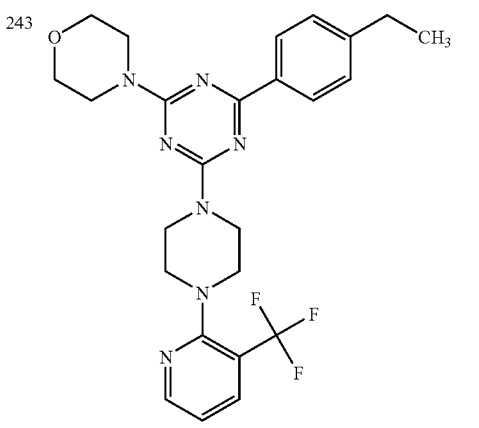 | 2-(4-ethylphenyl)-4-morpholin-4-yl-6-{4-[3-(trifluoromethyl)pyridin-2-yl]piperazin-1-yl}-1,3,5-triazine | | 1.38 | 500.32 | A |

TABLE II-continued

| Compound | Name | IC$_{50}$ | Ret. Time | MS (M + 1) | LCMS Method |
|---|---|---|---|---|---|
| 244 | 2-morpholin-4-yl-4-(4-propylphenyl)-6-{4-[3-(trifluoromethyl)pyridin-2-yl]piperazin-1-yl}-1,3,5-triazine | | 1.44 | 514.35 | A |
| 245 | 4-(3-chlorophenyl)-N-ethyl-N-methyl-6-{4-[3-(trifluoromethyl)pyridin-2-yl]piperazin-1-yl}-1,3,5-triazin-2-amine | | 1.52 | 478.18 | A |
| 246 | 4-(4-chlorophenyl)-N-methyl-N-propyl-6-{4-[3-(trifluoromethyl)pyridin-2-yl]piperazin-1-yl}-1,3,5-triazin-2-amine | | 1.58 | 492.19 | A |

TABLE II-continued
| Compound | | Name | IC$_{50}$ | Ret. Time | MS (M + 1) | LCMS Method |
|---|---|---|---|---|---|---|
| 247 | 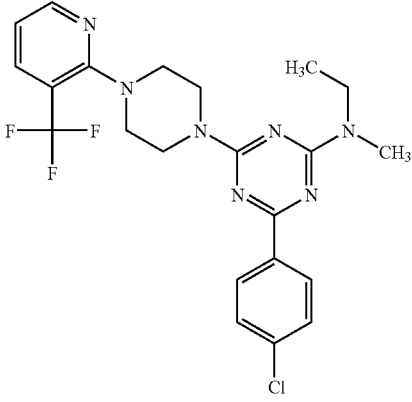 | 4-(4-chlorophenyl)-N-ethyl-N-methyl-6-{4-[3-(trifluoromethyl)pyridin-2-yl]piperazin-1-yl}-1,3,5-triazin-2-amine | | 1.52 | 478.18 | A |
| 248 | 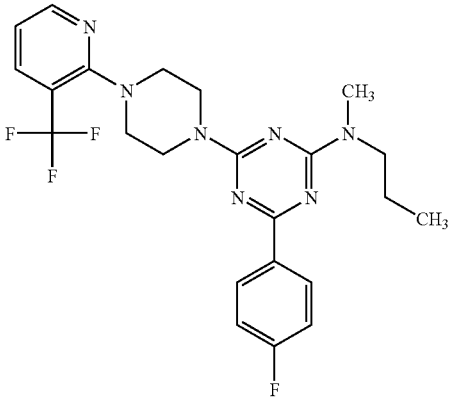 | 4-(4-fluorophenyl)-N-methyl-N-propyl-6-{4-[3-(trifluoromethyl)pyridin-2-yl]piperazin-1-yl}-1,3,5-triazin-2-amine | | 1.46 | 476.22 | A |
| 249 | 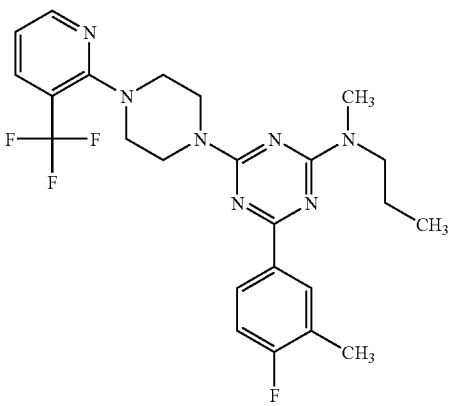 | 4-(4-fluoro-3-methylphenyl)-N-methyl-N-propyl-6-{4-[3-(trifluoromethyl)pyridin-2-yl]piperazin-1-yl}-1,3,5-triazin-2-amine | | 1.49 | 490.23 | A |

TABLE II-continued
| Compound | | Name | IC$_{50}$ | Ret. Time | MS (M + 1) | LCMS Method |
|---|---|---|---|---|---|---|
| 250 | 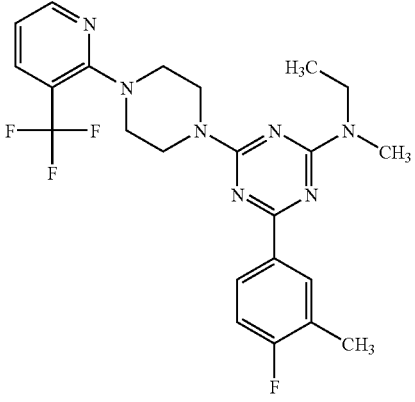 | N-ethyl-4-(4-fluoro-3-methylphenyl)-N-methyl-6-{4-[3-(trifluoromethyl)pyridin-2-yl]piperazin-1-yl}-1,3,5-triazin-2-amine | | 1.44 | 476.21 | A |
| 251 | 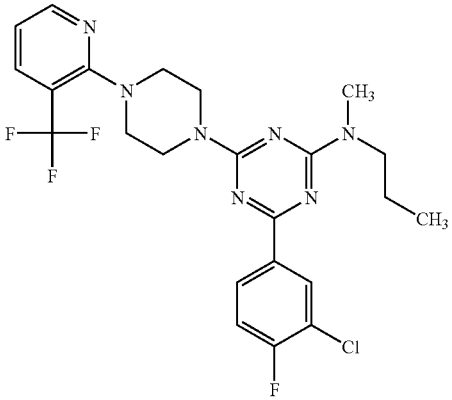 | 4-(3-chloro-4-fluorophenyl)-N-methyl-N-propyl-6-{4-[3-(trifluoromethyl)pyridin-2-yl]piperazin-1-yl}-1,3,5-triazin-2-amine | | 1.62 | 510.19 | A |
| 252 | 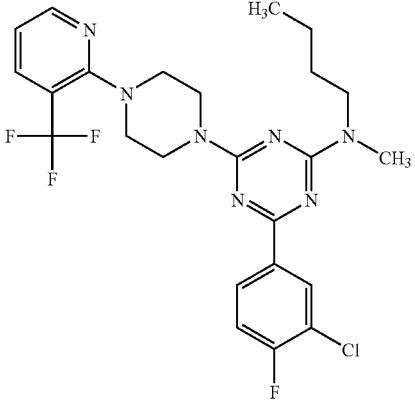 | N-butyl-4-(3-chloro-4-fluorophenyl)-N-methyl-6-{4-[3-(trifluoromethyl)pyridin-2-yl]piperazin-1-yl}-1,3,5-triazin-2-amine | | 1.71 | 524.21 | A |

TABLE II-continued

| Compound | | Name | IC$_{50}$ | Ret. Time | MS (M + 1) | LCMS Method |
|---|---|---|---|---|---|---|
| 253 | | 4-(3-chloro-4-fluorophenyl)-N-ethyl-N-methyl-6-{4-[3-(trifluoromethyl)pyridin-2-yl]piperazin-1-yl}-1,3,5-triazin-2-amine | | 1.55 | 496.18 | A |
| 254 | | 4-(3,4-difluorophenyl)-N-ethyl-N-methyl-6-{4-[3-(trifluoromethyl)pyridin-2-yl]piperazin-1-yl}-1,3,5-triazin-2-amine | | 1.49 | 480.20 | A |
| 255 | | 4-(3,4-dichlorophenyl)-N-ethyl-N-methyl-6-{4-[3-(trifluoromethyl)pyridin-2-yl]piperazin-1-yl}-1,3,5-triazin-2-amine | | 1.7 | 512.15 | A |

TABLE II-continued
| Compound | | Name | IC$_{50}$ | Ret. Time | MS (M + 1) | LCMS Method |
|---|---|---|---|---|---|---|
| 256 | 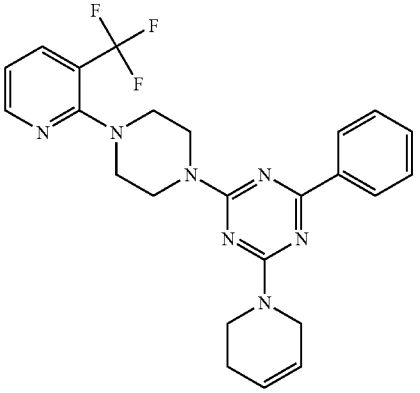 | 2-(3,6-dihydropyridin-1(2H)-yl)-4-phenyl-6-{4-[3-(trifluoromethyl)pyridin-2-yl]piperazin-1-yl}-1,3,5-triazine | | 1.42 | 468.18 | A |
| 257 | 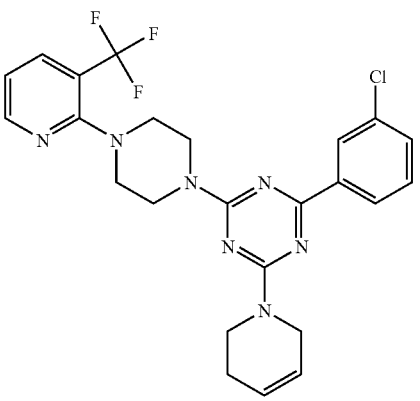 | 2-(3-chlorophenyl)-4-(3,6-dihydropyridin-1(2H)-yl)-6-{4-[3-(trifluoromethyl)pyridin-2-yl]piperazin-1-yl}-1,3,5-triazine | 456.4 | 1.59 | 502.14 | A |
| 258 | 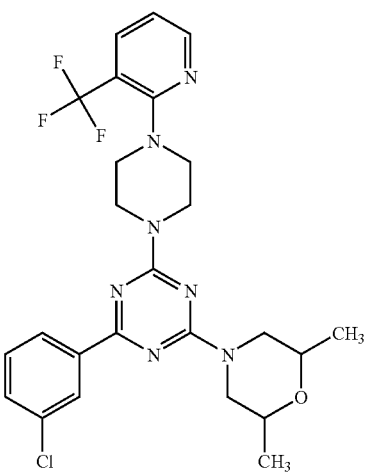 | 2-(3-chlorophenyl)-4-(2,6-dimethylmorpholin-4-yl)-6-{4-[3-(trifluoromethyl)pyridin-2-yl]piperazin-1-yl}-1,3,5-triazine | 161.8 | 1.52 | 534.16 | A |

TABLE II-continued
| Compound | | Name | IC$_{50}$ | Ret. Time | MS (M + 1) | LCMS Method |
|---|---|---|---|---|---|---|
| 259 | 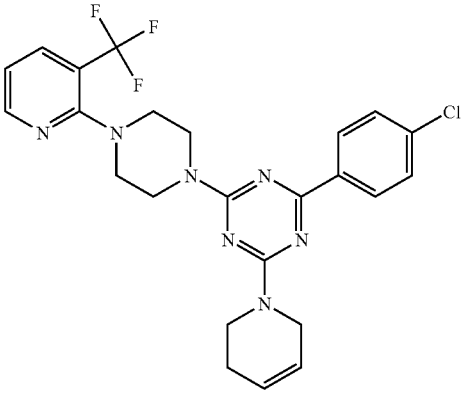 | 2-(4-chlorophenyl)-4-(3,6-dihydropyridin-1(2H)-yl)-6-{4-[3-(trifluoromethyl)pyridin-2-yl]piperazin-1-yl}-1,3,5-triazine | | 1.59 | 502.14 | A |
| 260 | 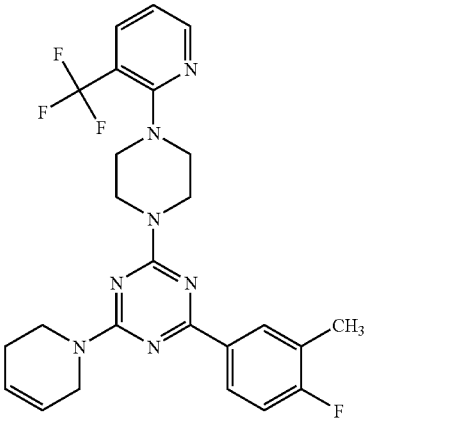 | 2-(3,6-dihydropyridin-1(2H)-yl)-4-(4-fluoro-3-methylphenyl)-6-{4-[3-(trifluoromethyl)pyridin-2-yl]piperazin-1-yl}-1,3,5-triazine | | 1.52 | 500.19 | A |
| 261 | 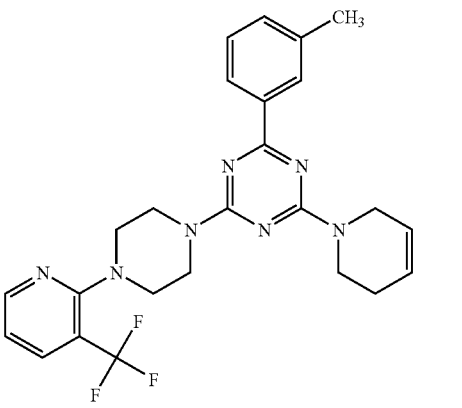 | 2-(3,6-dihydropyridin-1(2H)-yl)-4-(3-methylphenyl)-6-{4-[3-(trifluoromethyl)pyridin-2-yl]piperazin-1-yl}-1,3,5-triazine | | 1.44 | 482.20 | A |

TABLE II-continued
| Compound | | Name | IC$_{50}$ | Ret. Time | MS (M + 1) | LCMS Method |
|---|---|---|---|---|---|---|
| 262 | 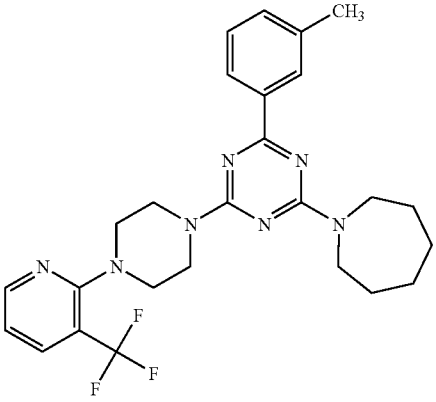 | 1-(4-(3-methylphenyl)-6-{4-[3-(trifluoromethyl)pyridin-2-yl]piperazin-1-yl}-1,3,5-triazin-2-yl)azepane | * | 1.46 | 498.22 | A |
| 263 | 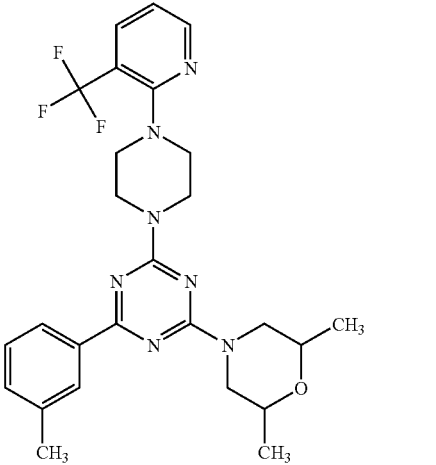 | 2-(2,6-dimethylmorpholin-4-yl)-4-(3-methylphenyl)-6-{4-[3-(trifluoromethyl)pyridin-2-yl]piperazin-1-yl}-1,3,5-triazine | * | 1.43 | 514.22 | A |
| 264 | 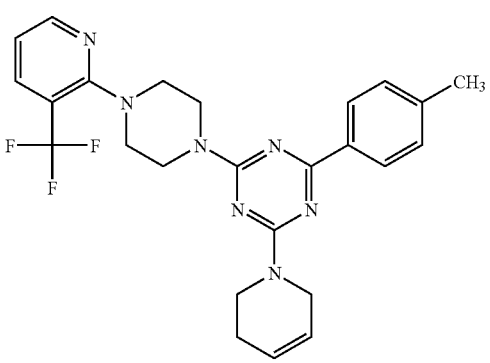 | 2-(3,6-dihydropyridin-1(2H)-yl)-4-(4-methylphenyl)-6-{4-[3-(trifluoromethyl)pyridin-2-yl]piperazin-1-yl}-1,3,5-triazine | | 1.44 | 482.20 | A |

TABLE II-continued

| Compound | | Name | IC$_{50}$ | Ret. Time | MS (M + 1) | LCMS Method |
|---|---|---|---|---|---|---|
| 265 | 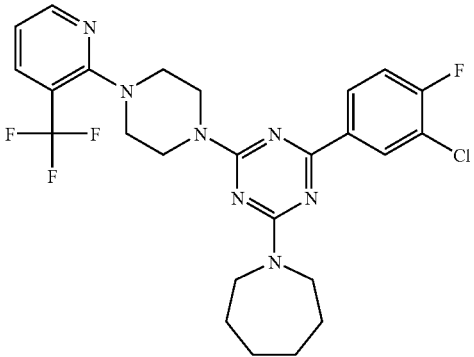 | 1-(4-(3-chloro-4-fluorophenyl)-6-{4-[3-(trifluoromethyl)pyridin-2-yl]piperazin-1-yl}-1,3,5-triazin-2-yl)azepane | * | 1.7 | 536.33 | A |
| 266 | 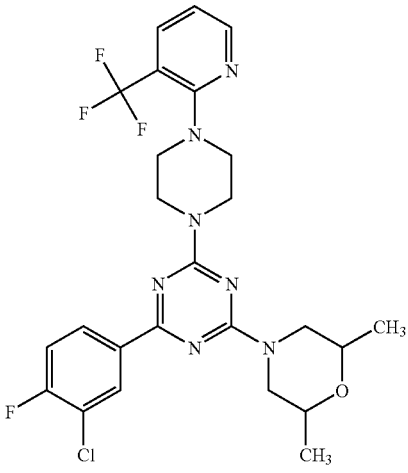 | 2-(3-chloro-4-fluorophenyl)-4-(2,6-dimethylmorpholin-4-yl)-6-{4-[3-(trifluoromethyl)pyridin-2-yl]piperazin-1-yl}-1,3,5-triazine | * | 1.53 | 552.33 | A |
| 267 | 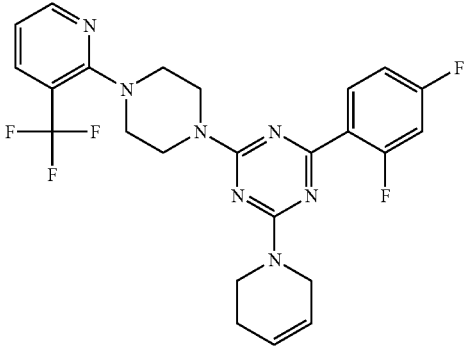 | 2-(2,4-difluorophenyl)-4-(3,6-dihydropyridin-1(2H)-(trifluoromethyl)pyridin-2-yl]piperazin-1-yl}-1,3,5-triazine | | 1.38 | 504.24 | A |
| 268 | 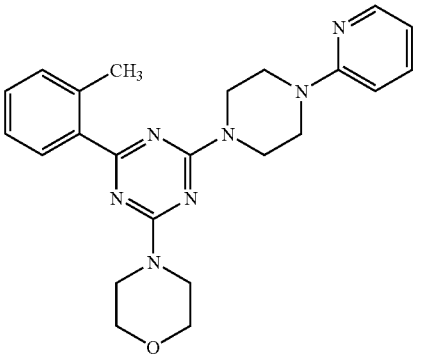 | 2-(2-methylphenyl)-4-morpholin-4-yl-6-(4-pyridin-2-ylpiperazin-1-yl)-1,3,5-triazine | * | 1.05 | 418.25 | A |

TABLE II-continued

| Compound | Name | IC$_{50}$ | Ret. Time | MS (M + 1) | LCMS Method |
|---|---|---|---|---|---|
| 269 | 2-(2,5-dimethylphenyl)-4-morpholin-4-yl-6-(4-pyridin-2-ylpiperazin-1-yl)-1,3,5-triazine | * | 1.07 | 432.29 | A |
| 270 | 2-morpholin-4-yl-4-(1-naphthyl)-6-(4-pyridin-2-ylpiperazin-1-yl)-1,3,5-triazine | * | 1.07 | 454.26 | A |
| 271 | 2-(2,3-dimethylphenyl)-4-morpholin-4-yl-6-(4-pyridin-2-ylpiperazin-1-yl)-1,3,5-triazine | * | 1.06 | 432.30 | A |

TABLE II-continued

| Compound | Name | IC$_{50}$ | Ret. Time | MS (M + 1) | LCMS Method |
|---|---|---|---|---|---|
| 272 | 2-(5-fluoro-2-methylphenyl)-4-morpholin-4-yl-6-(4-pyridin-2-ylpiperazin-1-yl)-1,3,5-triazine | * | 1.07 | 436.27 | A |
| 273 | 2-(4-fluoro-2-methylphenyl)-4-morpholin-4-yl-6-(4-pyridin-2-ylpiperazin-1-yl)-1,3,5-triazine | * | 1.07 | 436.28 | A |
| 274 | 2-(2-ethylphenyl)-4-morpholin-4-yl-6-(4-pyridin-2-ylpiperazin-1-yl)-1,3,5-triazine | * | 1.07 | 432.30 | A |
| 275 | 2-morpholin-4-yl-4-(4-pyridin-2-ylpiperazin-1-yl)-6-(2,4,5-trimethylphenyl)-1,3,5-triazine | | 1.09 | 446.32 | A |

TABLE II-continued
| Compound | | Name | IC$_{50}$ | Ret. Time | MS (M + 1) | LCMS Method |
|---|---|---|---|---|---|---|
| 276 | 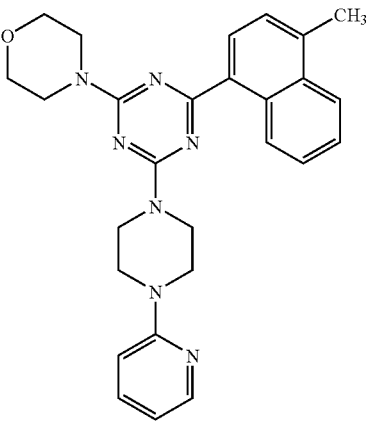 | 2-(4-methyl-1-naphthyl)-4-morpholin-4-yl-6-(4-pyridin-2-ylpiperazin-1-yl)-1,3,5-triazine | * | 1.09 | 468.32 | A |
| 277 | 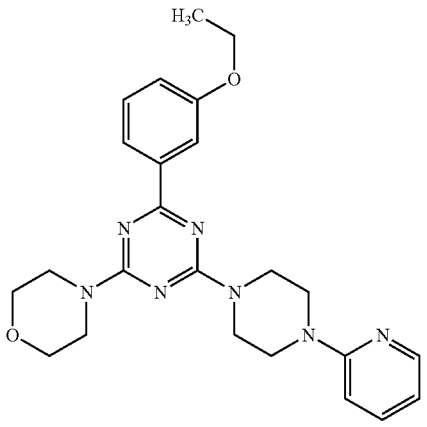 | 2-(3-ethoxyphenyl)-4-morpholin-4-yl-6-(4-pyridin-2-ylpiperazin-1-yl)-1,3,5-triazine | | 1.08 | 448.30 | A |
| 278 | 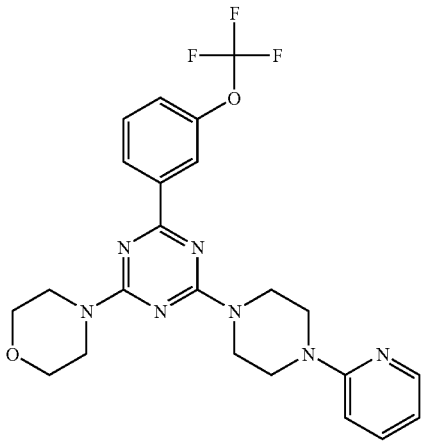 | 2-morpholin-4-yl-4-(4-pyridin-2-ylpiperazin-1-yl)-6-[3-(trifluoromethoxy)phenyl]-1,3,5-triazine | | 1.11 | 488.28 | A |

TABLE II-continued

| Compound | Name | IC$_{50}$ | Ret. Time | MS (M + 1) | LCMS Method |
|---|---|---|---|---|---|
| 279 | 2-[3-(methylthio)phenyl]-4-morpholin-4-yl-6-(4-pyridin-2-ylpiperazin-1-yl)-1,3,5-triazine | | 1.09 | 450.26 | A |
| 280 | 2-(3-isopropoxyphenyl)-4-morpholin-4-yl-6-(4-pyridin-2-ylpiperazin-1-yl)-1,3,5-triazine | | 1.1 | 462.32 | A |
| 281 | 2-[3-(methylthio)phenyl]-4-morpholin-4-yl-6-{4-[3-(trifluoromethyl)pyridin-2-yl]piperazin-1-yl}-1,3,5-triazine | | 1.36 | 518.30 | A |
| 282 | N,N-diethyl-4-phenyl-6-{4-[3-(trifluoromethyl)pyridin-2-yl]piperazin-1-yl}-1,3,5-triazin-2-amine | | 1.37 | 458.26 | A |

TABLE II-continued

| Compound | Name | IC$_{50}$ | Ret. Time | MS (M + 1) | LCMS Method |
|---|---|---|---|---|---|
| 283 | 4-(3-chlorophenyl)-N,N-diethyl-6-{4-[3-(trifluoromethyl)pyridin-2-yl]piperazin-1-yl}-1,3,5-triazin-2-amine | | 1.52 | 492.25 | A |
| 284 | 4-(3-chlorophenyl)-N,N-dipropyl-6-{4-[3-(trifluoromethyl)pyridin-2-yl]piperazin-1-yl}-1,3,5-triazin-2-amine | | 1.67 | 520.30 | A |
| 285 | 4-(4-chlorophenyl)-N,N-diethyl-6-{4-[3-(trifluoromethyl)pyridin-2-yl]piperazin-1-yl}-1,3,5-triazin-2-amine | | 1.54 | 492.25 | A |
| 286 | N,N-diethyl-4-(4-fluorophenyl)-6-{4-[3-(trifluoromethyl)pyridin-2-yl]piperazin-1-yl}-1,3,5-triazin-2-amine | | 1.42 | 476.26 | A |

TABLE II-continued
| Compound | | Name | IC$_{50}$ | Ret. Time | MS (M + 1) | LCMS Method |
|---|---|---|---|---|---|---|
| 287 | 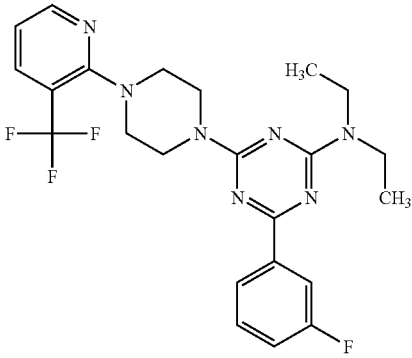 | N,N-diethyl-4-(3-fluorophenyl)-6-{4-[3-(trifluoromethyl)pyridin-2-yl]piperazin-1-yl}-1,3,5-triazin-2-amine | | 1.44 | 476.27 | A |
| 288 | 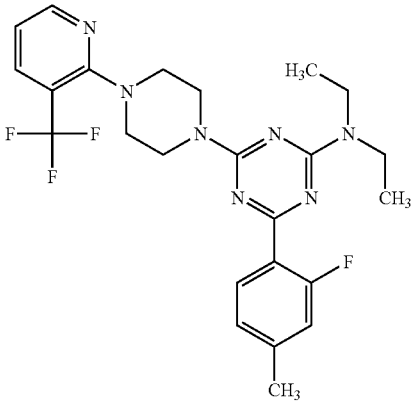 | N,N-diethyl-4-(2-fluoro-4-methylphenyl)-6-{4-[3-(trifluoromethyl)pyridin-2-yl]piperazin-1-yl}-1,3,5-triazin-2-amine | | 1.28 | 490.27 | A |
| 289 | 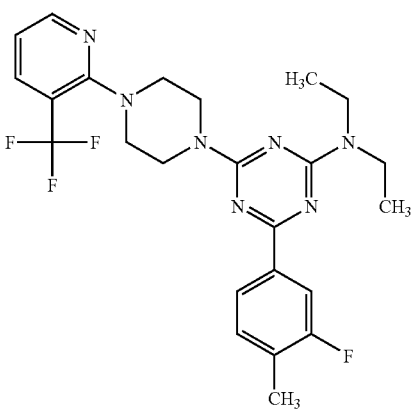 | N,N-diethyl-4-(3-fluoro-4-methylphenyl)-6-{4-[3-(trifluoromethyl)pyridin-2-yl]piperazin-1-yl}-1,3,5-triazin-2-amine | | 1.5 | 490.29 | A |

TABLE II-continued

| Compound | Name | IC$_{50}$ | Ret. Time | MS (M + 1) | LCMS Method |
|---|---|---|---|---|---|
| 290 | N,N-diethyl-4-(4-fluoro-3-methylphenyl)-6-{4-[3-(trifluoromethyl)pyridin-2-yl]piperazin-1-yl}-1,3,5-triazin-2-amine | | 1.46 | 490.28 | A |
| 291 | 4-(4-fluoro-3-methylphenyl)-N,N-dipropyl-6-{4-[3-(trifluoromethyl)pyridin-2-yl]piperazin-1-yl}-1,3,5-triazin-2-amine | | 1.58 | 519.37 | A |
| 292 | N-butyl-N-ethyl-4-(4-fluoro-3-methylphenyl)-6-{4-[3-(trifluoromethyl)pyridin-2-yl]piperazin-1-yl}-1,3,5-triazin-2-amine | | 1.58 | 519.37 | A |

TABLE II-continued

| Compound | | Name | IC$_{50}$ | Ret. Time | MS (M + 1) | LCMS Method |
|---|---|---|---|---|---|---|
| 293 | | N,N-diethyl-4-(3-methylphenyl)-6-{4-[3-(trifluoromethyl)pyridin-2-yl]piperazin-1-yl}-1,3,5-triazin-2-amine | | 1.41 | 472.15 | A |
| 294 | | N,N-diethyl-4-(4-methylphenyl)-6-{4-[3-(trifluoromethyl)pyridin-2-yl]piperazin-1-yl}-1,3,5-triazin-2-amine | | 1.4 | 472.15 | A |
| 295 | | N,N-diethyl-4-(3-isopropylphenyl)-6-{4-[3-(trifluoromethyl)pyridin-2-yl]piperazin-1-yl}-1,3,5-triazin-2-amine | | 1.46 | 500.18 | A |

TABLE II-continued
| Compound | | Name | IC$_{50}$ | Ret. Time | MS (M + 1) | LCMS Method |
|---|---|---|---|---|---|---|
| 296 | 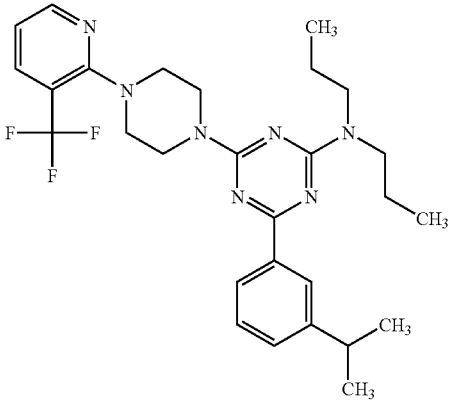 | 4-(3-isopropylphenyl)-N,N-dipropyl-6-{4-[3-(trifluoromethyl)pyridin-2-yl]piperazin-1-yl}-1,3,5-triazin-2-amine | | 1.59 | 528.21 | A |
| 297 | 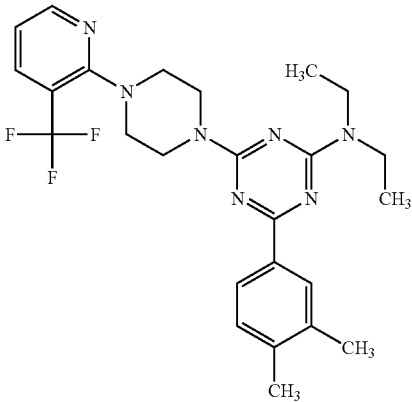 | 4-(3,4-dimethylphenyl)-N,N-diethyl-6-{4-[3-(trifluoromethyl)pyridin-2-yl]piperazin-1-yl}-1,3,5-triazin-2-amine | | 1.41 | 486.18 | A |
| 298 | 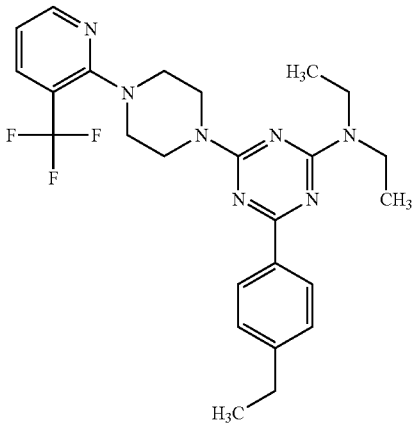 | N,N-diethyl-4-(4-ethylphenyl)-6-{4-[3-(trifluoromethyl)pyridin-2-yl]piperazin-1-yl}-1,3,5-triazin-2-amine | | 1.43 | 486.19 | A |

TABLE II-continued
| Compound | | Name | IC$_{50}$ | Ret. Time | MS (M + 1) | LCMS Method |
|---|---|---|---|---|---|---|
| 299 | 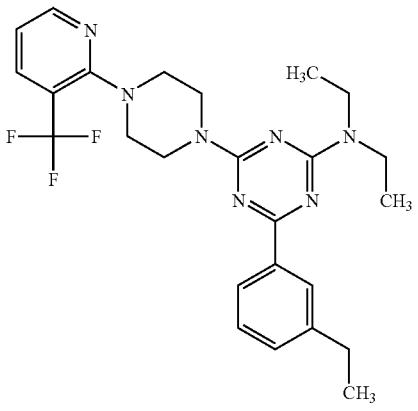 | N,N-diethyl-4-(3-ethylphenyl)-6-{4-[3-(trifluoromethyl)pyridin-2-yl]piperazin-1-yl}-1,3,5-triazin-2-amine | | 1.44 | 486.19 | A |
| 300 | 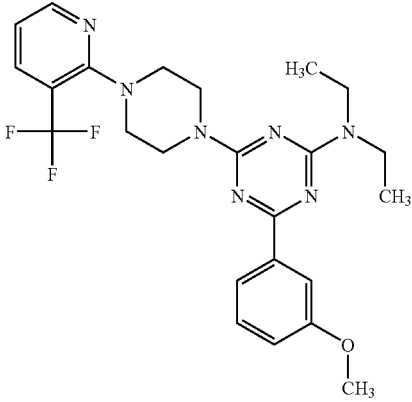 | N,N-diethyl-4-(3-methoxyphenyl)-6-{4-[3-(trifluoromethyl)pyridin-2-yl]piperazin-1-yl}-1,3,5-triazin-2-amine | | 1.39 | 488.17 | A |
| 301 | 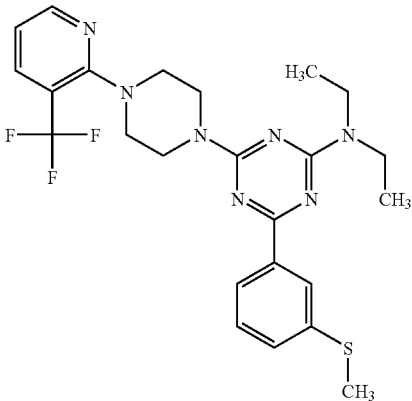 | N,N-diethyl-4-[3-(methylthio)phenyl]-6-{4-[3-(trifluoromethyl)pyridin-2-yl]piperazin-1-yl}-1,3,5-triazin-2-amine | | 1.46 | 504.15 | A |

TABLE II-continued
| Compound | | Name | IC$_{50}$ | Ret. Time | MS (M + 1) | LCMS Method |
|---|---|---|---|---|---|---|
| 302 | 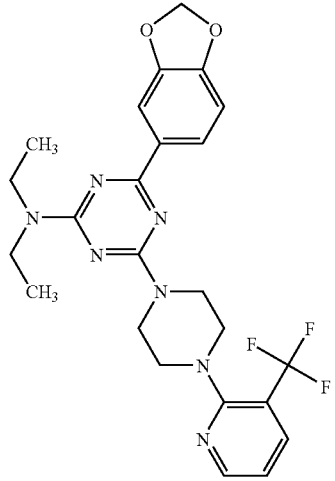 | 4-(1,3-benzodioxol-5-yl)-N,N-diethyl-6-{4-[3-(trifluoromethyl)pyridin-2-yl]piperazin-1-yl}1,3,5-triazin-2-amine | | 1.38 | 502.17 | A |
| 303 | 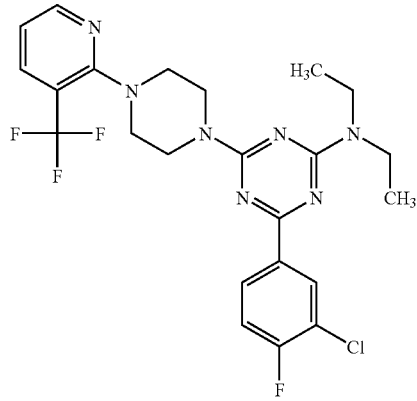 | 4-(3-chloro-4-fluorophenyl)-N,N-diethyl-6-{4-[3-(trifluoromethyl)pyridin-2-yl]piperazin-1-yl}-1,3,5-triazin-2-amine | | 1.56 | 510.24 | A |
| 304 | 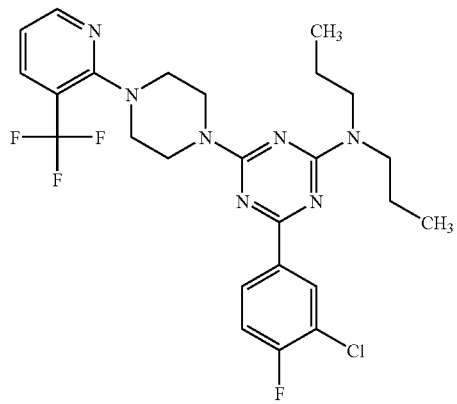 | 4-(3-chloro-4-fluorophenyl)-N,N-dipropyl-6-{4-[3-(trifluoromethyl)pyridin-2-yl]piperazin-1-yl}-1,3,5-triazin-2-amine | | 1.72 | 538.29 | A |

TABLE II-continued

| Compound | Name | IC$_{50}$ | Ret. Time | MS (M + 1) | LCMS Method |
|---|---|---|---|---|---|
| 305 | N-butyl-4-(3-chloro-4-fluorophenyl)-N-ethyl-6-{4-[3-(trifluoromethyl)pyridin-2-yl]piperazin-1-yl}-1,3,5-triazin-2-amine | | 1.71 | 538.28 | A |
| 306 | 4-(3-chloro-4-fluorophenyl)-N-(cyclopropylmethyl)-N-propyl-6-{4-[3-(trifluoromethyl)pyridin-2-yl]piperazin-1-yl}-1,3,5-triazin-2-amine | | 1.7 | 550.30 | A |
| 307 | 4-(2,4-difluorophenyl)-N,N-diethyl-6-{4-[3-(trifluoromethyl)pyridin-2-yl]piperazin-1-yl}-1,3,5-triazin-2-amine | | 1.33 | 494.25 | A |

TABLE II-continued

| Compound | | Name | IC$_{50}$ | Ret. Time | MS (M + 1) | LCMS Method |
|---|---|---|---|---|---|---|
| 308 | 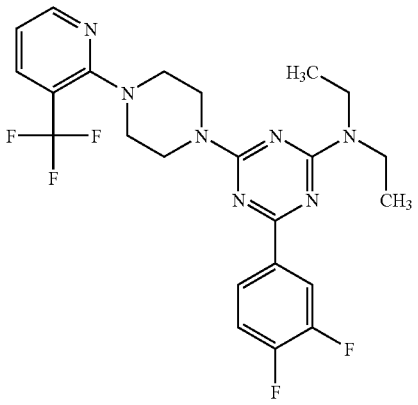 | 4-(3,4-difluorophenyl)-N,N-diethyl-6-{4-[3-(trifluoromethyl)pyridin-2-yl]piperazin-1-yl}-1,3,5-triazin-2-amine | | 1.48 | 494.26 | A |
| 309 | 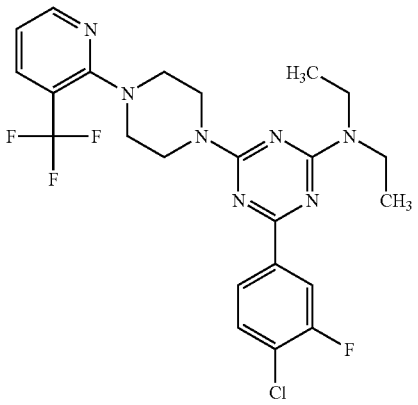 | 4-(4-chloro-3-fluorophenyl)-N,N-diethyl-6-{4-[3-(trifluoromethyl)pyridin-2-yl]piperazin-1-yl}-1,3,5-triazin-2-amine | | 1.59 | 510.26 | A |
| 310 | 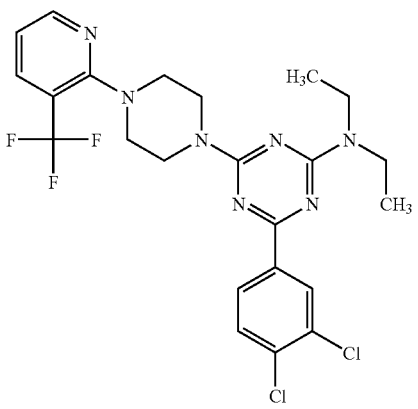 | 4-(3,4-dichtorophenyl)-N,N-diethyl-6-{4-[3-(trifluoromethyl)pyridin-2-yl]piperazin-1-yl}-1,3,5-triazin-2-amine | | 1.7 | 526.25 | A |
| 311 | 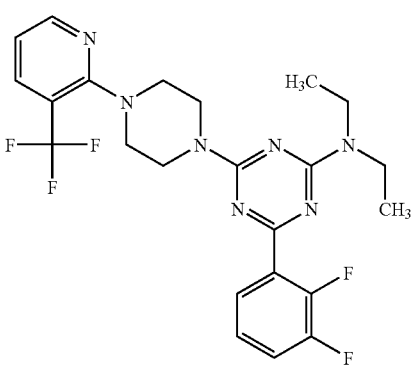 | 4-(2,3-difluorophenyl)-N,N-diethyl-6-{4-[3-(trifluoromethyl)pyridin-2-yl]piperazin-1-yl}-1,3,5-triazin-2-amine | | 1.35 | 494.27 | A |

TABLE II-continued

| Compound | Name | IC$_{50}$ | Ret. Time | MS (M + 1) | LCMS Method |
|---|---|---|---|---|---|
| 312 | 4-(2,3-dichlorophenyl)-N,N-diethyl-6-{4-[3-(trifluoromethyl)pyridin-2-yl]piperazin-1-yl}-1,3,5-triazin-2-amine | | 1.38 | 526.09 | A |
| 313 | 2-morpholin-4-yl-4-(4-pyridin-2-ylpiperazin-1-yl)-6-(3,4,5-trimethoxyphenyl)-1,3,5-triazine | | 1.03 | 494.33 | A |
| 314 | 2-(4-methoxyphenyl)-4-morpholin-4-yl-6-(4-pyridin-2-ylpiperazin-1-yl)-1,3,5-triazine | | 1.05 | 434.26 | A |

TABLE II-continued

| Compound | Name | IC$_{50}$ | Ret. Time | MS (M + 1) | LCMS Method |
|---|---|---|---|---|---|
| 315 | 2-(4-ethoxyphenyl)-4-morpholin-4-yl-6-(4-pyridin-2-ylpiperazin-1-yl)-1,3,5-triazine | | 1.08 | 448.29 | A |
| 316 | N,N-dimethyl-3-[4-morpholin-4-yl-6-(4-pyridin-2-ylpiperazin-1-yl)-1,3,5-triazin-2-yl]aniline | | 0.99 | 447.31 | A |
| 317 | 2-(1,3-benzodioxol-5-yl)-4-morpholin-4-yl-6-{4-[3-(trifluoromethyl)pyridin-2-yl]piperazin-1-yl}-1,3,5-triazine | | 1.3 | 516.28 | A |

TABLE II-continued

| Compound | | Name | IC$_{50}$ | Ret. Time | MS (M + 1) | LCMS Method |
|---|---|---|---|---|---|---|
| 318 | | 2-(2-methylpiperidin-1-yl)-4-phenyl-6-{4-[3-(trifluoromethyl)pyridin-2-yl]piperazin-1-yl}-1,3,5-triazine | | 1.42 | 484.27 | A |
| 319 | | 2-(2-methylpyrrolidin-1-yl)-4-phenyl-6-{4-[3-(trifluoromethyl)pyridin-2-yl]piperazin-1-yl}-1,3,5-triazine | | 1.36 | 470.26 | A |
| 320 | | 4-(3-chlorophenyl)-N-isopropyl-N-methyl-6-{4-[3-(trifluoromethyl)pyridin-2-yl]piperazin-1-yl}-1,3,5-triazin-2-amine | | 1.51 | 492.25 | A |
| 321 | | 2-(3-chlorophenyl)-4-(2-methylpiperidin-1-yl)-6-{4-[3-(trifluoromethyl)pyridin-2-yl]piperazin-1-yl}-1,3,5-triazine | | 1.6 | 518.28 | A |

TABLE II-continued

| Compound | Name | IC$_{50}$ | Ret. Time | MS (M + 1) | LCMS Method |
|---|---|---|---|---|---|
| 322 | 2-(3-chlorophenyl)-4-(2-ethylpiperidin-1-yl)-6-{4-[3-(trifluoromethyl)pyridin-2-yl]piperazin-1-yl}-1,3,5-triazine | | 1.64 | 532.30 | A |
| 323 | 2-(3-chlorophenyl)-4-(2-methylpyrrolidin-1-yl)-6-{4-[3-(trifluoromethyl)pyridin-2-yl]piperazin-1-yl}-1,3,5-triazine | | 1.54 | 504.25 | A |
| 324 | 4-(4-chlorophenyl)-N-isopropyl-N-methyl-6-{4-[3-(trifluoromethyl)pyridin-2-yl]piperazin-1-yl}-1,3,5-triazin-2-amine | | 1.53 | 492.25 | A |

TABLE II-continued
| Compound | | Name | IC$_{50}$ | Ret. Time | MS (M + 1) | LCMS Method |
|---|---|---|---|---|---|---|
| 325 | 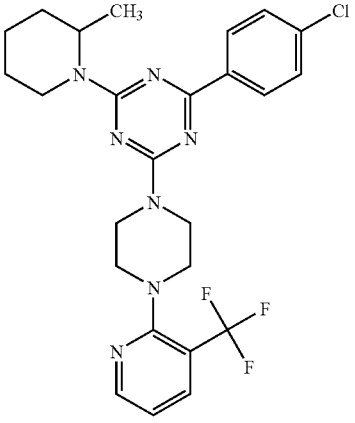 | 2-(4-chlorophenyl)-4-(2-methylpiperidin-1-yl)-6-{4-[3-(trifluoromethyl)pyridin-2-yl]piperazin-1-yl}-1,3,5-triazine | | 1.6 | 518.28 | A |
| 326 | 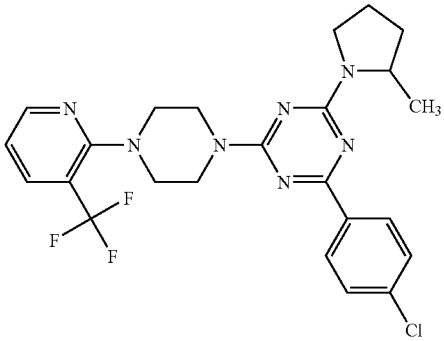 | 2-(4-chlorophenyl)-4-(2-methylpyrrolidin-1-yl)-6-{4[3-(trifluoromethyl)pyridin-2-yl]piperazin-1-yl}-1,3,5-triazine | | 1.53 | 504.26 | A |
| 327 | 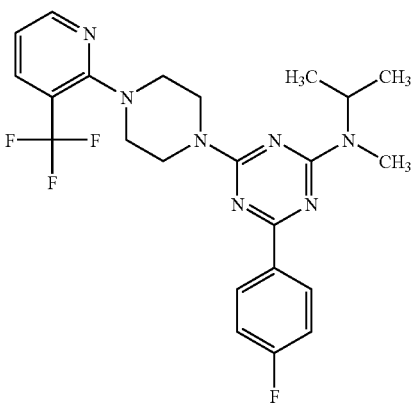 | 4-(4-fluorophenyl)-N-isopropyl-N-methyl-6-{4-[3-(trifluoromethyl)pyridin-2-yl]piperazin-1-yl}-1,3,5-triazin-2-amine | | 1.43 | 476.26 | A |

TABLE II-continued
| Compound | | Name | IC$_{50}$ | Ret. Time | MS (M + 1) | LCMS Method |
|---|---|---|---|---|---|---|
| 328 | 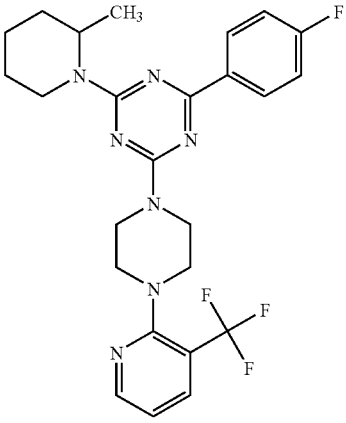 | 2-(4-fluorophenyl)-4-(2-methylpiperidin-1-yl)-6-{4-[3-(trifluoromethyl)pyridin-2-yl]piperazin-1-yl}-1,3,5-triazine | | 1.48 | 502.29 | A |
| 329 | 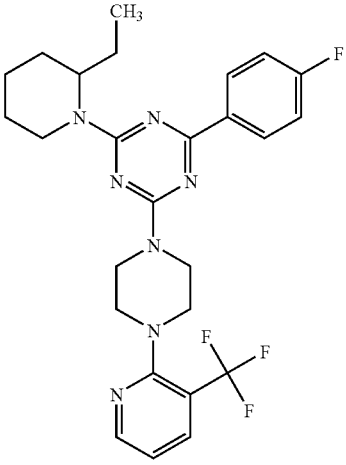 | 2-(2-ethylpiperidin-1-yl)-4-(4-fluorophenyl)-6-{4-[3-(trifluoromethyl)pyridin-2-yl]piperazin-1-yl}-1,3,5-triazine | | 1.5 | 516.32 | A |
| 330 | 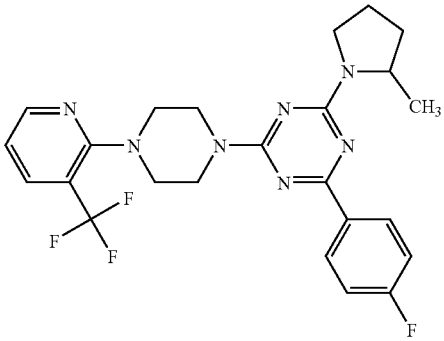 | 2-(4-fluorophenyl)-4-(2-methylpyrrolidin-1-yl)-6-{4-[3-(trifluoromethyl)pyridin-2-yl]piperazin-1-yl}-1,3,5-triazine | | 1.43 | 488.27 | A |

TABLE II-continued

| Compound | | Name | IC$_{50}$ | Ret. Time | MS (M + 1) | LCMS Method |
|---|---|---|---|---|---|---|
| 331 | 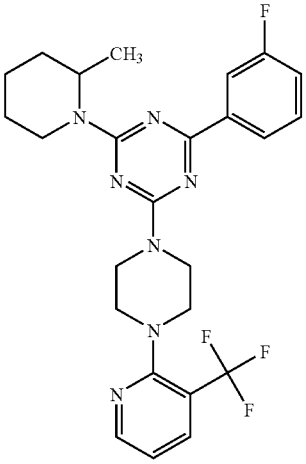 | 2-(3-fluorophenyl)-4-(2-methylpiperidin-1-yl)-6-{4-[3-(trifluoromethyl)pyridin-2-yl]piperazin-1-yl}-1,3,5-triazine | | 1.5 | 502.29 | A |
| 332 | 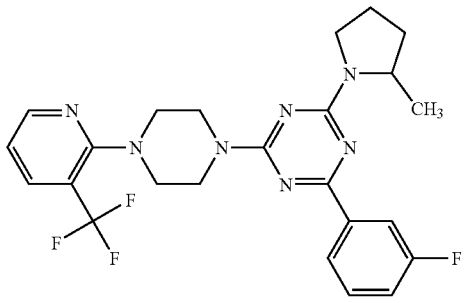 | 2-(3-fluorophenyl)-4-(2-methylpyrrolidin-1-yl)-6-{4-[3-(trifluoromethyl)pyridin-2-yl]piperazin-1-yl}-1,3,5-triazine | | 1.47 | 488.27 | A |
| 333 | 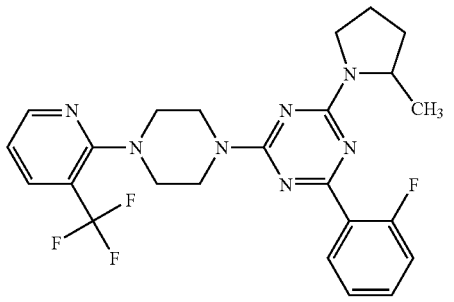 | 2-(2-fluorophenyl)-4-(2-methylpyrrolidin-1-yl)-6-{4-[3-(trifluoromethyl)pyridin-2-yl]piperazin-1-yl}-1,3,5-triazine | | 1.22 | 488.27 | A |
| 334 | 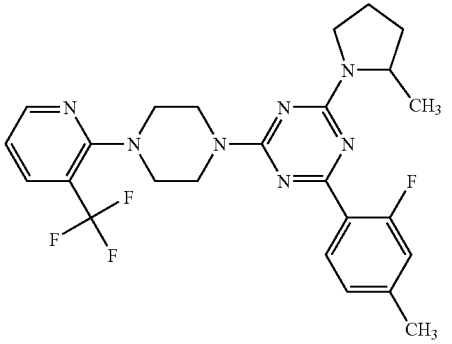 | 2-(2-fluoro-4-methylphenyl)-4-(2-methylpyrrolidin-1-yl)-6-{4-[3-(trifluoromethyl)pyridin-2-yl]piperazin-1-yl}-1,3,5-triazine | | 1.23 | 502.29 | A |

TABLE II-continued

| Compound | Name | IC$_{50}$ | Ret. Time | MS (M + 1) | LCMS Method |
|---|---|---|---|---|---|
| 335 | 4-(3-fluoro-4-methylphenyl)-N-isopropyl-N-methyl-6-{4-[3-(trifluoromethyl)pyridin-2-yl]piperazin-1-yl}-1,3,5-triazin-2-amine | | 1.48 | 490.30 | A |
| 336 | 2-(3-fluoro-4-methylphenyl)-4-(2-methylpiperidin-1-yl)-6-{4-[3-(trifluoromethyl)pyridin-2-yl]piperazin-1-yl}-1,3,5-triazine | | 1.57 | 516.33 | A |
| 337 | 2-(3-fluoro-4-methylphenyl)-4-(2-methylpyrrolidin-1-yl)-6-{4-[3-(trifluoromethyl)pyridin-2-yl]piperazin-1-yl}-1,3,5-triazine | | 1.47 | 502.30 | A |

TABLE II-continued

| Compound | | Name | IC$_{50}$ | Ret. Time | MS (M + 1) | LCMS Method |
|---|---|---|---|---|---|---|
| 338 | | 4-(4-fluoro-3-methylphenyl)-N-isopropyl-N-methyl-6-{4-[3-(trifluoromethyl)pyridin-2-yl]piperazin-1-yl}-1,3,5-triazin-2-amine | | 1.42 | 490.31 | A |
| 339 | | 2-(4-fluoro-3-methytphenyl)-4-(2-methylpiperidin-1-yl)-6-{4-[3-(trifluoromethyl)pyridin-2-yl]piperazin-1-yl}-1,3,5-triazine | | 1.52 | 516.33 | A |
| 340 | | 2-(2-ethylpiperidin-1-yl)-4-(4-fluoro-3-methylphenyl)-6-{4-[3-(trifluoromethyl)pyridin-2-yl]piperazin-1-yl}-1,3,5-triazine | | 1.56 | 530.35 | A |

TABLE II-continued

| Compound | | Name | IC$_{50}$ | Ret. Time | MS (M + 1) | LCMS Method |
|---|---|---|---|---|---|---|
| 341 | (structure) | 2-(4-fluoro-3-methylphenyl)-4-(2-methylpyrrolidin-1-yl)-6-{4-[3-(trifluoromethyl)pyridin-2-yl]piperazin-1-yl}-1,3,5-triazine | | 1.41 | 502.31 | A |
| 342 | (structure) | N-isopropyl-N-methyl-4-(3-methylphenyl)-6-{4-[3-(trifluoromethyl)pyridin-2-yl]piperazin-1-yl}-1,3,5-triazin-2-amine | | 1.39 | 472.30 | A |
| 343 | (structure) | 2-(3-methylphenyl)-4-(2-methylpiperidin-1-yl)-6-{4-[3-(trifluoromethyl)pyridin-2-yl]piperazin-1-yl}-1,3,5-triazine | | 1.43 | 498.32 | A |
| 344 | (structure) | 2-(3-methylphenyl)-4-(2-methylpyrrolidin-1-yl)-6-{4-[3-(trifluoromethyl)pyridin-2-yl]piperazin-1-yl}-1,3,5-triazine | | 1.34 | 484.29 | A |

TABLE II-continued

| Compound | Name | IC$_{50}$ | Ret. Time | MS (M + 1) | LCMS Method |
|---|---|---|---|---|---|
| 345 | N-isopropyl-N-methyl-4-(4-methylphenyl)-6-{4-[3-(trifluoromethyl)pyridin-2-yl]piperazin-1-yl}-1,3,5-triazin-2-amine | | 1.36 | 472.29 | A |
| 346 | 2-(4-methylphenyl)-4-(2-methylpiperidin-1-yl)-6-{4-[3-(trifluoromethyl)pyridin-2-yl]piperazin-1-yl}-1,3,5-triazine | | 1.42 | 498.32 | A |
| 347 | 2-(4-methylphenyl)-4-(2-methylpyrrolidin-1-yl)-6-{4-[3-(trifluoromethyl)pyridin-2-yl]piperazin-1-yl}-1,3,5-triazine | | 1.32 | 484.30 | A |

TABLE II-continued
| Compound | | Name | IC$_{50}$ | Ret. Time | MS (M + 1) | LCMS Method |
|---|---|---|---|---|---|---|
| 348 | 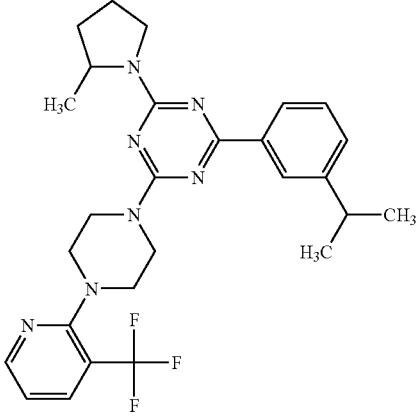 | 2-(3-isopropylphenyl)-4-(2-methylpyrrolidin-1-yl)-6-{4-[3-(trifluoromethyl)pyridin-2-yl]piperazin-1-yl}-1,3,5-triazine | | 1.38 | 512.34 | A |
| 349 | 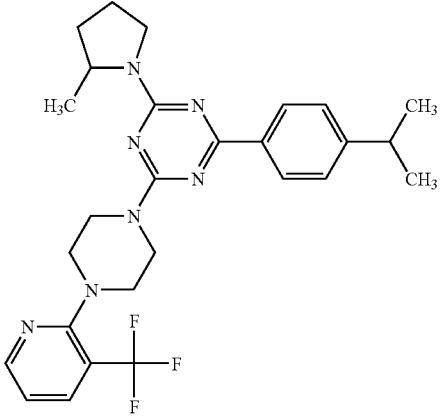 | 2-(4-isopropylphenyl)-4-(2-methylpyrrolidin-1-yl)-6-{4-[3-(trifluoromethyl)pyridin-2-yl]piperazin-1-yl}-1,3,5-triazine | | 1.37 | 512.35 | A |
| 350 | 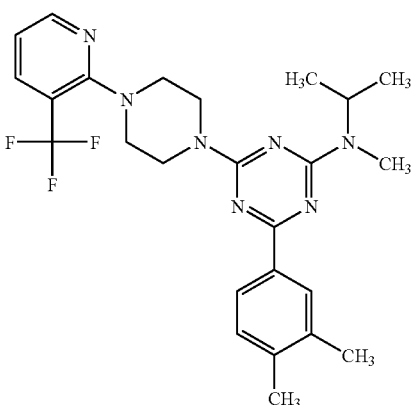 | 4-(3,4-dimethylphenyl)-N-isopropyl-N-methyl-6-{4-[3-(trifluoromethyl)pyridin-2-yl]piperazin-1-yl}-1,3,5-triazin-2-amine | | 1.36 | 486.32 | A |

TABLE II-continued

| Compound | Name | IC$_{50}$ | Ret. Time | MS (M + 1) | LCMS Method |
|---|---|---|---|---|---|
| 351 | 2-(3,4-dimethylphenyl)-4-(2-methylpiperidin-1-yl)-6-{4-[3-(trifluoromethyl)pyridin-2-yl]piperazin-1-yl}-1,3,5-triazine | | 1.43 | 512.35 | A |
| 352 | 2-(3,4-dimethylphenyl)-4-(2-methylpyrrolidin-1-yl)-6-{4-[3-(trifluoromethyl)pyridin-2-yl]piperazin-1-yl}-1,3,5-triazine | | 1.32 | 498.32 | A |
| 353 | 2-(4-ethylphenyl)-4-(2-methylpyrrolidin-1-yl)-6-{4-[3-(trifluoromethyl)pyridin-2-yl]piperazin-1-yl}-1,3,5-triazine | | 1.36 | 498.33 | A |

TABLE II-continued
| Compound | | Name | IC$_{50}$ | Ret. Time | MS (M + 1) | LCMS Method |
|---|---|---|---|---|---|---|
| 354 | 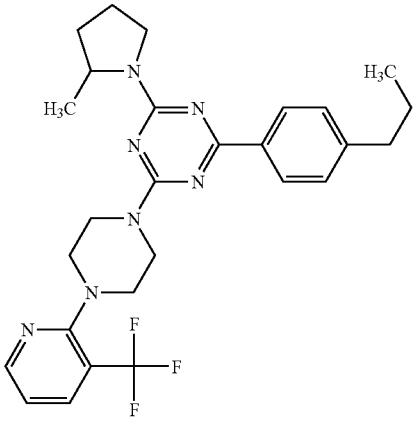 | 2-(2-methylpyrrolidin-1-yl)-4-(4-propylphenyl)-6-{4-[3-(trifluoromethyl)pyridin-2-yl]piperazin-1-yl}-1,3,5-triazine | | 1.39 | 512.36 | A |
| 355 | 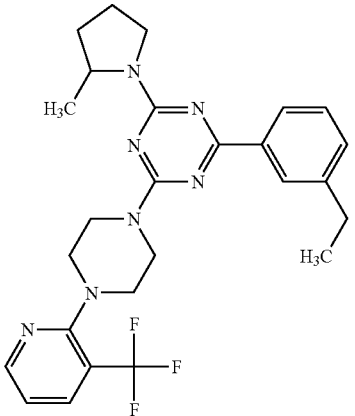 | 2-(3-ethylphenyl)-4-(2-methylpyrrolidin-1-yl)-6-{4-[3-(trifluoromethyl)pyridin-2-yl]piperazin-1-yl}-1,3,5-triazine | | 1.36 | 498.34 | A |
| 356 | 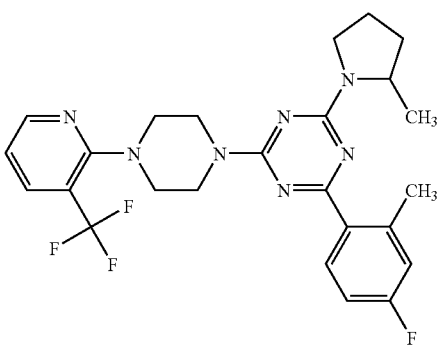 | 2(4-fluoro-2-methylphenyl)-4-(2-methylpyrrolidin-1-yl)-6-{4-[3-(trifluoromethyl)pyridin-2-yl]piperazin-1-yl}-1,3,5-triazine | | 1.26 | 502.31 | A |

TABLE II-continued

| Compound | Name | IC$_{50}$ | Ret. Time | MS (M + 1) | LCMS Method |
|---|---|---|---|---|---|
| 357 | 2-(3-methoxyphenyl)-4-(2-methylpyrrolidin-1-yl)-6-{4-[3-(trifluoromethyl)pyridin-2-yl]piperazin-1-yl}-1,3,5-triazine | | 1.33 | 500.31 | A |
| 358 | 2-(2-methylpyrrolidin-1-yl)-4-[3-(trifluoromethoxy)phenyl]-6-{4-[3-(trifluoromethyl)pyridin-2-yl]piperazin-1-yl}-1,3,5-triazine | | 1.51 | 554.31 | A |
| 359 | 2-(2-methylpiperidin-1-yl)-4-[3-(methylthio)phenyl]-6-{4-[3-(trifluoromethyl)pyridin-2-yl]piperazin-1-yl}-1,3,5-triazine | | 1.5 | 530.32 | A |
| 360 | 2-(2-methylpyrrolidin-1-yl)-4-[3-(methylthio)phenyl]-6-{4-[3-(trifluoromethyl)pyridin-2-yl]piperazin-1-yl}-1,3,5-triazine | | 1.41 | 516.30 | A |

TABLE II-continued

| Compound | Name | IC₅₀ | Ret. Time | MS (M + 1) | LCMS Method |
|---|---|---|---|---|---|
| 361 | 2-(3-fluoro-4-methoxyphenyl)-4-(2-methylpyrrolidin-1-yl)-6-{4-[3-(trifluoromethyl)pyridin-2-yl]piperazin-1-yl}-1,3,5-triazine | | 1.36 | 518.31 | A |
| 362 | 2-(4-methoxyphenyl)-4-(2-methylpyrrolidin-1-yl)-6-{4-[3-(trifluoromethyl)pyridin-2-yl]piperazin-1-yl}-1,3,5-triazine | | 1.26 | 500.30 | A |
| 363 | 4-(1,3-benzodioxol-5-yl)-N-isopropyl-N-methyl-6-{4-[3-(trifluoromethyl)pyridin-2-yl]piperazin-1-yl}-1,3,5-triazin-2-amine | | 1.34 | 502.29 | A |

TABLE II-continued

| Compound | | Name | IC$_{50}$ | Ret. Time | MS (M + 1) | LCMS Method |
|---|---|---|---|---|---|---|
| 364 | | 2-(1,3-benzodioxol-5-yl)-4-(2-methylpiperidin-1-yl)-6-{4-[3-(trifluoromethyl)pyridin-2-yl]piperazin-1-yl}-1,3,5-triazine | | 1.4 | 528.32 | A |
| 365 | | 2-(1,3-benzodioxol-5-yl)-4-(2-methylpyrrolidin-1-yl)-6-{4-[3-(trifluoromethyl)pyridin-2-yl]piperazin-1-yl}-1,3,5-triazine | | 1.32 | 514.29 | A |
| 366 | | 4-[4-(dimethylamino)phenyl]-N-isopropyl-N-methyl-6-{4-[3-(trifluoromethyl)pyridin-2-yl]piperazin-1-yl}-1,3,5-triazin-2-amine | | 1.19 | 501.35 | A |

TABLE II-continued

| Compound | Name | IC$_{50}$ | Ret. Time | MS (M + 1) | LCMS Method |
|---|---|---|---|---|---|
| 367 | N,N-dimethyl-4-(4-(2-methylpyrrolidin-1-yl)-6-{4-[3-(trifluoromethyl)pyridin-2-yl]piperazin-1-yl}-1,3,5-triazin-2-yl)aniline | | 1.17 | 513.36 | A |
| 368 | 2-(2,3-dihydro-1,4-benzodioxin-6-yl)-4-(2-methylpyrrolidin-1-yl)-6-{4-[3-(trifluoromethyl)pyridin-2-yl]piperazin-1-yl}-1,3,5-triazine | | 1.27 | 528.32 | A |
| 369 | N,N-dimethyl-3-(4-(2-methylpyrrolidin-1-yl)-6-{4-[3-(trifluoromethyl)pyridin-2-yl]piperazin-1-yl}-1,3,5-triazin-2-yl)aniline | | 1.23 | 513.36 | A |
| 370 | 4-(3-chloro-4-fluorophenyl)-N-isopropyl-N-methyl-6-{4-[3-(trifluoromethyl)pyridin-2-yl]piperazin-1-yl}-1,3,5-triazin-2-amine | | 1.56 | 510.27 | A |

TABLE II-continued

| Compound | Name | IC$_{50}$ | Ret. Time | MS (M + 1) | LCMS Method |
|---|---|---|---|---|---|
| 371 | 2-(3-chloro-4-fluorophenyl)-4-(2-methylpiperidin-1-yl)-6-{4-[3-(trifluoromethyl)pyridin-2-yl]piperazin-1-yl}-1,3,5-triazine | | 1.66 | 536.31 | A |
| 372 | 2-(3-chloro-4-fluorophenyl)-4-(2-ethylpiperidin-1-yl)-6-{4-[3-(trifluoromethyl)pyridin-2-yl]piperazin-1-yl}-1,3,5-triazine | | 1.72 | 550.33 | A |
| 373 | 2-(3-chloro-4-fluorophenyl)-4-(2-methylpyrrolidin-1-yl)-6-{4-[3-(trifluoromethyl)pyridin-2-yl]piperazin-1-yl}-1,3,5-triazine | | 1.59 | 522.28 | A |

TABLE II-continued
| Compound | | Name | IC$_{50}$ | Ret. Time | MS (M + 1) | LCMS Method |
|---|---|---|---|---|---|---|
| 374 | 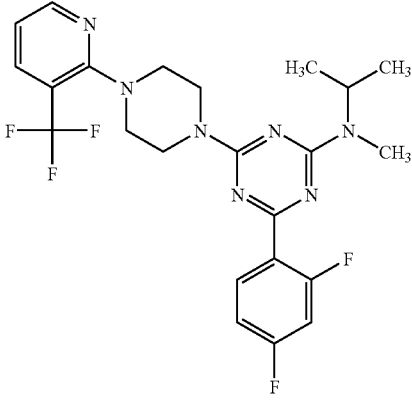 | 4-(2,4-difluorophenyl)-N-isopropyl-N-methyl-6-{4-[3-(trifluoromethyl)pyridin-2-yl]piperazin-1-yl}-1,3,5-triazin-2-amine | | 1.33 | 494.28 | A |
| 375 | 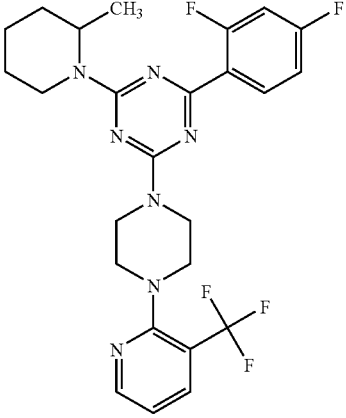 | 2-(2,4-difluorophenyl)-4-(2-methylpiperidin-1-yl)-6-{4-[3-(trifluoromethyl)pyridin-2-yl]piperazin-1-yl}-1,3,5-triazine | | 1.39 | 520.30 | A |
| 376 | 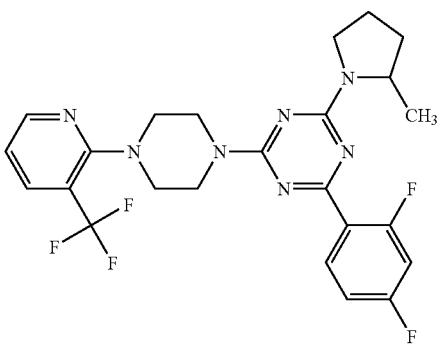 | 2-(2,4-difluorophenyl)-4-(2-methylpyrrolidin-1-yl)-6-{4-[3-(trifluoromethyl)pyridin-2-yl]piperazin-1-yl}-1,3,5-triazine | | 1.3 | 506.28 | A |

TABLE II-continued
| Compound | | Name | IC₅₀ | Ret. Time | MS (M + 1) | LCMS Method |
|---|---|---|---|---|---|---|
| 377 | 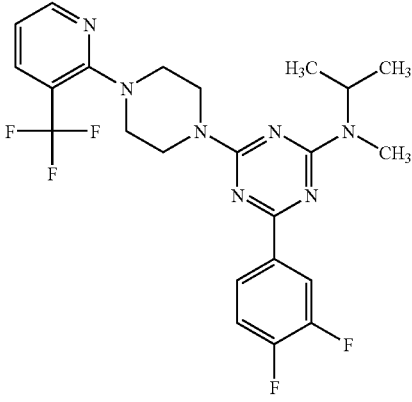 | 4-(3,4-difluorophenyl)-N-isopropyl-N-methyl-6-{4-[3-(trifluoromethyl)pyridin-2-yl]piperazin-1-yl}-1,3,5-triazin-2-amine | | 1.48 | 494.29 | A |
| 378 | 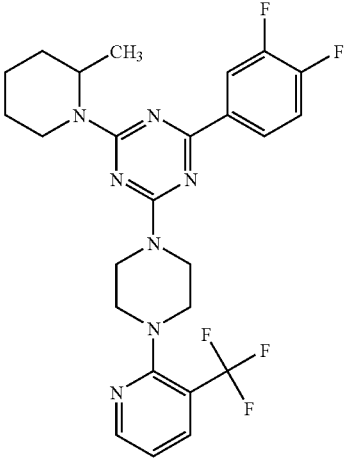 | 2-(3,4-difluorophenyl)-4-(2-methylpiperidin-1-yl)-6-{4-[3-(trifluoromethyl)pyridin-2-yl]piperazin-1-yl}-1,3,5-triazine | | 1.57 | 520.32 | A |
| 379 | 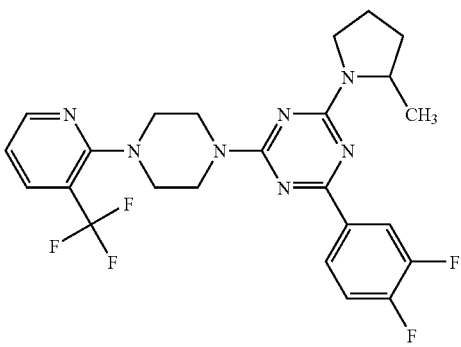 | 2-(3,4-difluorophenyl)-4-(2-methylpyrrolidin-1-yl)-6-{4-[3-(trifluoromethyl)pyridin-2-yl]piperazin-1-yl}-1,3,5-triazine | | 1.51 | 506.29 | A |

TABLE II-continued

| Compound | Name | IC$_{50}$ | Ret. Time | MS (M + 1) | LCMS Method |
|---|---|---|---|---|---|
| 380 | 4-(4-chloro-2-fluorophenyl)-N-isopropyl-N-methyl-6-{4-[3-(trifluoromethyl)pyridin-2-yl]piperazin-1-yl}-1,3,5-triazin-2-amine | | 1.42 | 510.27 | A |
| 381 | 2-(4-chloro-2-fluorophenyl)-4-(2-methylpyrrolidin-1-yl)-6-{4-[3-(trifluoromethyl)pyridin-2-yl]piperazin-1-yl}-1,3,5-triazine | | 1.39 | 522.27 | A |
| 382 | 4-(4-chloro-3-fluorophenyl)-N-isopropyl-N-methyl-6-{4-[3-(trifluoromethyl)pyridin-2-yl]piperazin-1-yl}-1,3,5-triazin-2-amine | | 1.58 | 510.28 | A |

TABLE II-continued

| Compound | Name | IC$_{50}$ | Ret. Time | MS (M + 1) | LCMS Method |
|---|---|---|---|---|---|
| 383 | 2-(4-chloro-3-fluorophenyl)-4-(2-methylpiperidin-1-yl)-6-{4-[3-(trifluoromethyl)pyridin-2-yl]piperazin-1-yl}-1,3,5-triazine | | 1.7 | 536.31 | A |
| 384 | 2-(4-chloro-3-fluorophenyl)-4-(2-methylpyrrolidin-1-yl)-6-{4-[3-(trifluoromethyl)pyridin-2-yl]piperazin-1-yl}-1,3,5-triazine | | 1.63 | 522.28 | A |
| 385 | 4-(3,4-dichlorophenyl)-N-isopropyl-N-methyl-6-{4-[3-(trifluoromethyl)pyridin-2-yl]piperazin-1-yl}-1,3,5-triazin-2-amine | | 1.68 | 526.27 | A |

TABLE II-continued

| Compound | Name | IC$_{50}$ | Ret. Time | MS (M + 1) | LCMS Method |
|---|---|---|---|---|---|
| 386 | 2-(3,4-dichlorophenyl)-4-(2-methylpiperidin-1-yl)-6-{4-[3-(trifluoromethyl)pyridin-2-yl]piperazin-1-yl}-1,3,5-triazine | | 1.83 | 552.31 | A |
| 387 | 2-(3,4-dichlorophenyl)-4-(2-methylpyrrolidin-1-yl)-6-{4-[3-(trifluoromethyl)pyridin-2-yl]piperazin-1-yl}-1,3,5-triazine | | 1.75 | 538.28 | A |
| 388 | 2-(3,5-difluorophenyl)-4-(2-methylpyrrolidin-1-yl)-6-{4-[3-(trifluoromethyl)pyridin-2-yl]piperazin-1-yl}-1,3,5-triazine | | 1.56 | 506.29 | A |
| 389 | 2-(2,3-difluorophenyl)-4-(2-methylpyrrolidin-1-yl)-6-{4-[3-(trifluoromethyl)pyridin-2-yl]piperazin-1-yl}-1,3,5-triazine | | 1.34 | 506.29 | A |

TABLE II-continued

| Compound | Name | IC$_{50}$ | Ret. Time | MS (M + 1) | LCMS Method |
|---|---|---|---|---|---|
| 390 | 4-(2,3-dichlorophenyl)-N-isopropyl-N-methyl-6-{4-[3-(trifluoromethyl)pyridin-2-yl]piperazin-1-yl}-1,3,5-triazin-2-amine | | 1.36 | 526.27 | A |
| 391 | 2-(2,3-dichlorophenyl)-4-(2-methylpyrrolidin-1-yl)-6-{4-[3-(trifluoromethyl)pyridin-2-yl]piperazin-1-yl}-1,3,5-triazine | | 1.32 | 538.28 | A |
| 392 | 2-(2,4-dichlorophenyl)-4-(2-methylpyrrolidin-1-yl)-6-{4-[3-(trifluoromethyl)pyridin-2-yl]piperazin-1-yl}-1,3,5-triazine | | 1.38 | 538.29 | A |
| 393 | 2-(2,5-dichlorophenyl)-4-(2-methylpyrrolidin-1-yl)-6-{4-[3-(trifluoromethyl)pyridin-2-yl]piperazin-1-yl}-1,3,5-triazine | | 1.39 | 538.27 | A |

TABLE II-continued

| Compound | Name | IC$_{50}$ | Ret. Time | MS (M + 1) | LCMS Method |
|---|---|---|---|---|---|
| 394 | 4-(3-chlorophenyl)-N-ethyl-N-isopropyl-6-{4-[3-(trifluoromethyl)pyridin-2-yl]piperazin-1-yl}-1,3,5-triazin-2-amine | | 1.6 | 506.19 | A |
| 395 | 4-(3-chlorophenyl)-N-cyclohexyl-N-methyl-6-{4-[3-(trifluoromethyl)pyridin-2-yl]piperazin-1-yl}-1,3,5-triazin-2-amine | | 1.75 | 532.21 | A |
| 396 | 4-(3-chlorophenyl)-N-cyclohexyl-N-ethyl-6-{4-[3-(trifluoromethyl)pyridin-2-yl]piperazin-1-yl}-1,3,5-triazin-2-amine | | 1.87 | 546.22 | A |

TABLE II-continued

| Compound | Name | IC$_{50}$ | Ret. Time | MS (M + 1) | LCMS Method |
|---|---|---|---|---|---|
| 397 | 1-(4-(3-chlorophenyl)-6-{4-[3-(trifluoromethyl)pyridin-2-yl]piperazin-1-yl}-1,3,5-trazin-2-yl)decahydroquinoline | | 1.93 | 558.23 | A |
| 398 | 4-(4-chlorophenyl)-N-cyclohexyl-N-methyl-6-{4-[3-(trifluoromethyl)pyridin-2-yl]piperazin-1-yl}-1,3,5-triazin-2-amine | | 1.74 | 532.21 | A |
| 399 | 4-(4-chlorophenyl)-N-cyclohexyl-N-ethyl-6-{4-[3-(trifluoromethyl)pyridin-2-yl]piperazin-1-yl}-1,3,5-triazin-2-amine | | 1.87 | 546.23 | A |

TABLE II-continued
| Compound | | Name | IC$_{50}$ | Ret. Time | MS (M + 1) | LCMS Method |
|---|---|---|---|---|---|---|
| 400 | 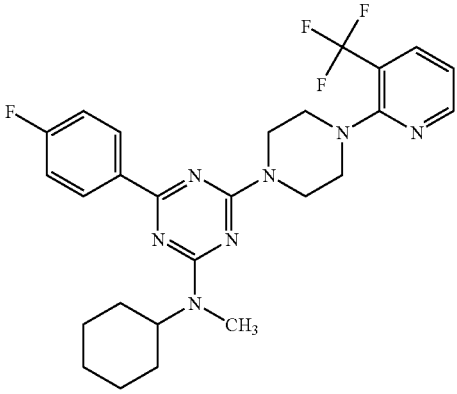 | N-cyclohexyl-4-(4-fluorophenyl)-N-methyl-6-{4-[3-(trifluoromethyl)pyridin-2-yl]piperazin-1-yl}-1,3,5-triazin-2-amine | | 1.57 | 516.24 | A |
| 401 | 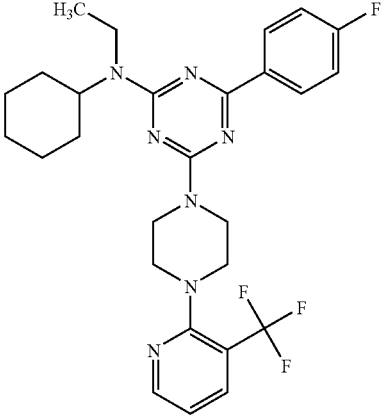 | N-cyclohexyl-N-ethyl-4-(4-fluorophenyl)-6-{4-(3-(trifluoromethyl)pyridin-2-yl]piperazin-1-yl}-1,3,5-triazin-2-amine | | 1.65 | 530.25 | A |
| 402 | 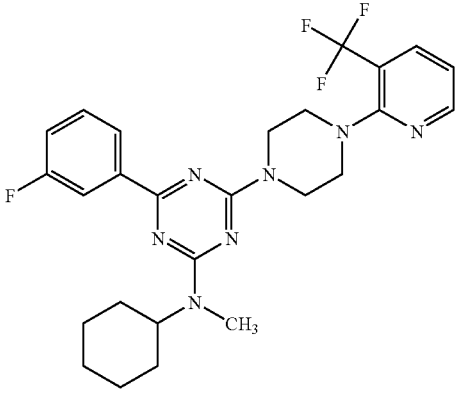 | N-cyclohexyl-4-(3-fluorophenyl)-N-methyl-6-{4-[3-(trifluoromethyl)pyridin-2-yl]piperazin-1-yl}-1,3,5-triazin-2-amine | | 1.61 | 516.24 | A |

TABLE II-continued

| Compound | | Name | IC$_{50}$ | Ret. Time | MS (M + 1) | LCMS Method |
|---|---|---|---|---|---|---|
| 403 | | N-ethyl-4-(4-fluoro-3-methylphenyl)-N-isopropyl-6-{4-[3-(trifluoromethyl)pyridin-2-yl]piperazin-1-yl}-1,3,5-triazin-2-amine | | 1.51 | 504.27 | A |
| 404 | | N-cyclohexyl-4-(4-fluoro-3-methylphenyl)-N-methyl-6-{4-[3-(trifluoromethyl)pyridin-2-yl]piperazin-1-yl}-1,3,5-triazin-2-amine | | 1.61 | 530.27 | A |
| 405 | | N-cyclohexyl-N-ethyl-4-(4-fluoro-3-methylphenyl)-6-{4-[3-(trifluoromethyl)pyridin-2-yl]piperazin-1-yl}-1,3,5-triazin-2-amine | | 1.71 | 544.28 | A |

TABLE II-continued

| Compound | | Name | IC$_{50}$ | Ret. Time | MS (M + 1) | LCMS Method |
|---|---|---|---|---|---|---|
| 406 | | 1-(4-(4-fluoro-3-methylphenyl)-6-{4-[3-(trifluoromethyl)pyridin-2-yl]piperazin-1-yl}-1,3,5-triazin-2-yl)decahydroquinoline | | 1.74 | 556.29 | A |
| 407 | | N-ethyl-N-isopropyl-4-(3-methylphenyl)-6-{4-[3-(trifluoromethyl)pyridin-2-yl]piperazin-1-yl}-1,3,5-triazin-2-amine | | 1.44 | 486.28 | A |
| 408 | | N-cyclohexyl-N-methyl-4-(3-methylphenyl)-6-{4-[3-(trifluoromethyl)pyridin-2-yl]piperazin-1-yl}-1,3,5-triazin-2-amine | | 1.51 | 512.28 | A |

TABLE II-continued

| Compound | | Name | IC$_{50}$ | Ret. Time | MS (M + 1) | LCMS Method |
|---|---|---|---|---|---|---|
| 409 | | N-cyclohexyl-N-methyl-4-(4-methylphenyl)-6-{4-(3-(trifluoromethyl)pyridin-2-yl]piperazin-1-yl}-1,3,5-triazin-2-amine | | 1.49 | 512.28 | A |
| 410 | | N-cyclohexyl-4-(3,4-dimethylphenyl)-N-methyt-6-{4-[3-(trifluoromethyl)pyridin-2-yl]piperazin-1-yl}-1,3,5-triazin-2-amine | | 1.49 | 526.30 | A |
| 411 | | 4-(1,3-benzodioxol-5-yl)-N-cyclohexyl-N-methyl-6-{4-[3-(trifluoromethyl)pyridin-2-yl]piperazin-1-yl}-1,3,5-triazin-2-amine | | 1.48 | 542.22 | A |

TABLE II-continued

| Compound | Name | IC$_{50}$ | Ret. Time | MS (M + 1) | LCMS Method |
|---|---|---|---|---|---|
| 412 | 4-(3-chloro-4-fluorophenyl)-N-ethyl-N-isopropyl-6-{4-[3-(trifluoromethyl)pyridin-2-yl]piperazin-1-yl}-1,3,5-triazin-2-amine | | 1.65 | 524.18 | A |
| 413 | 4-(3-chloro-4-fluorophenyl)-N-cyclohexy-N-methyl-6-{4-[3-(trifluoromethyl)pyridin-2-yl]piperazin-1-yl}-1,3,5-triazin-2-amine | | 1.82 | 550.19 | A |
| 414 | 4-(3-chloro-4-fluorophenyl)-N-cyclohexyl-N-ethyl-6-{4-[3-(trifluoromethyl)pyridin-2-yl]piperazin-1-yl}-1,3,5-triazin-2-amine | | 1.95 | 564.21 | A |

TABLE II-continued

| Compound | | Name | IC$_{50}$ | Ret. Time | MS (M + 1) | LCMS Method |
|---|---|---|---|---|---|---|
| 415 | | 1-(4-(3-chloro-4-fluorophenyl)-6-{4-[3-(trifluoromethyl)pyridin-2-yl]piperazin-1-yl}-1,3,5-triazin-2-yl)decahydroquinoline | | 2.05 | 576.21 | A |
| 416 | | N-cyclohexyl-4-(2,4-difluorophenyl)-N-methyl-6-{4-[3-(trifluoromethyl)pyridin-2-yl]piperazin-1-yl}-1,3,5-triazin-2-amine | | 1.45 | 534.20 | A |
| 417 | | 4-(3,4-difluorophenyl)-N-ethyl-N-isopropyl-6-{4-[3-(trifluoromethyl)pyridin-2-yl]piperazin-1-yl}-1,3,5-triazin-2-amine | | 1.56 | 508.21 | A |

TABLE II-continued

| Compound | | Name | IC$_{50}$ | Ret. Time | MS (M + 1) | LCMS Method |
|---|---|---|---|---|---|---|
| 418 | 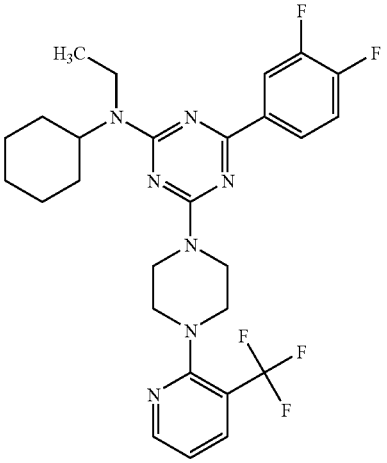 | N-cyclohexyl-4-(3,4-difluorophenyl)-N-ethyl-6-{4-[3-(trifluoromethyl)pyridin-2-yl]piperazin-1-yl}-1,3,5-triazin-2-amine | | 1.79 | 548.23 | A |
| 419 | 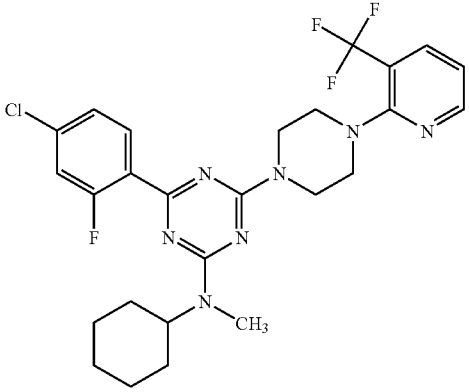 | 4-(4-chloro-2-fluorophenyl)-N-cyclohexyl-N-methyl-6-{4-[3-(trifluoromethyl)pyridin-2-yl]piperazin-1-yl}-1,3,5-triazin-2-amine | | 1.59 | 550.18 | A |
| 420 | 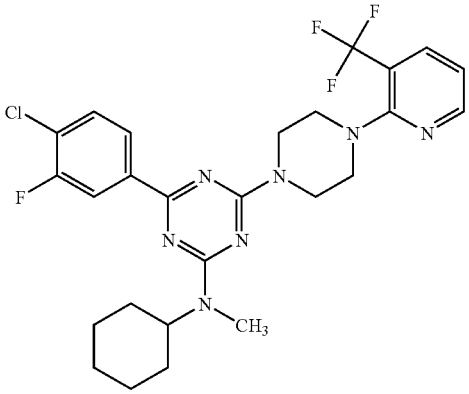 | 4-(4-chloro-3-fluorophenyl)-N-cyclohexyl-N-methyl-6-{4-[3-(trifluoromethyl)pyridin-2-yl]piperazin-1-yl}-1,3,5-triazin-2-amine | | 1.87 | 550.19 | A |

TABLE II-continued

| Compound | | Name | IC$_{50}$ | Ret. Time | MS (M + 1) | LCMS Method |
|---|---|---|---|---|---|---|
| 421 | | 4-(3,4-dichlorophenyl)-N-ethyl-N-isopropyl-6-{4-[3-(trifluoromethyl)pyridin-2-yl]piperazin-1-yl}-1,3,5-triazin-2-amine | | 1.82 | 540.16 | A |
| 422 | | 2-(2,5-difluorophenyl)-4-morpholin-4-yl-6-(4-pyridin-2-ylpiperazin-1-yl)-1,3,5-triazine | * | 1.05 | 440.22 | A |
| 423 | | 2-(2,4-difluorophenyl)-4-morpholin-4-yl-6-(4-pyridin-2-ylpiperazin-1-yl)-1,3,5-triazine | * | 1.06 | 440.21 | A |

TABLE II-continued

| Compound | | Name | IC$_{50}$ | Ret. Time | MS (M + 1) | LCMS Method |
|---|---|---|---|---|---|---|
| 424 | | 2-(3,4-difluorophenyl)-4-morpholin-4-yl-6-(4-pyridin-2-ylpiperazin-1-yl)-1,3,5-triazine | * | 1.09 | 440.22 | A |
| 425 | | 2-(3,5-difluorophenyl)-4-morpholin-4-yl-6-(4-pyridin-2-ylpiperazin-1-yl)-1,3,5-triazine | | 1.1 | 440.21 | A |
| 426 | | 2-(3-chioro-4-fluorophenyl)-4-morpholin-4-yl-6-{4-[3-(trifluoromethyl)pyridin-2-yl]piperazin-1-yl}-1,3,5-triazine | * | 1.43 | 524.23 | A |

TABLE II-continued
| Compound | | Name | IC$_{50}$ | Ret. Time | MS (M + 1) | LCMS Method |
|---|---|---|---|---|---|---|
| 427 | 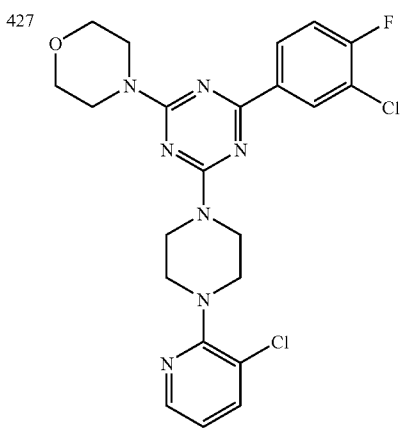 | 2-(3-chloro-4-fluorophenyl)-4-[4-(3-chloropyridin-2-yl)piperazin-1-yl]-6-morpholin-4-yl-1,3,5-triazine | * | 1.44 | 490.18 | A |
| 428 | 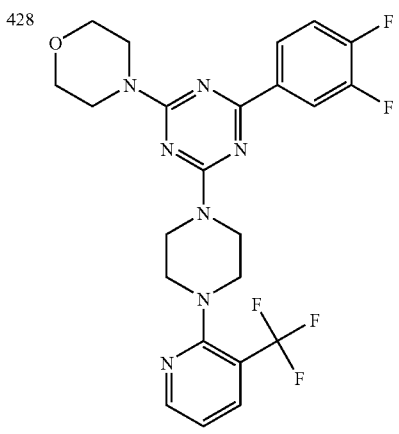 | 2-(3,4-difluorophenyl)-4-morpholin-4-yl-6-{4-[3-(trifluoromethyl)pyridin-2-yl]piperazin-1-yl}-1,3,5-triazine | * | 1.37 | 508.24 | A |
| 429 | 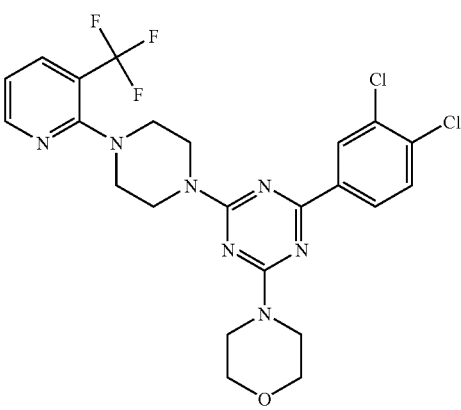 | 2-(3,4-dichlorophenyl)-4-morpholin-4-yl-6-{4-[3-(trifluoromethyl)pyridin-2-yl]piperazin-1-yl}-1,3,5-triazine | | 1.53 | 540.21 | A |

TABLE II-continued

| Compound | | Name | IC$_{50}$ | Ret. Time | MS (M + 1) | LCMS Method |
|---|---|---|---|---|---|---|
| 430 | | 2-(5-isopropyl-2-methoxyphenyl)-4-morpholin-4-yl-6-(4-pyridin-2-ylpiperazin-1-yl)-1,3,5-triazine | * | 1.02 | 476.31 | A |
| 431 | | 2-(5-chloro-2-methoxyphenyl)-4-morpholin-4-yl-6-(4-pyridin-2-ylpiperazin-1-yl)-1,3,5-triazine | * | 1.03 | 468.23 | A |
| 432 | | 2-dibenzo[b,d]furan-4-yl-4-morpholin-4-yl-6-(4-pyridin-2-ylpiperazin-1-yl)-1,3,5-triazine | * | 1.12 | 494.27 | A |
| 433 | | 2-[3,5-bis(trifluoromethyl)phenyl]-4-morpholin-4-yl-6-(4-pyridin-2-ylpiperazin-1-yl)-1,3,5-triazine | | 1.16 | 540.19 | A |

TABLE II-continued

| Compound | Name | IC$_{50}$ | Ret. Time | MS (M + 1) | LCMS Method |
|---|---|---|---|---|---|
| 434 | ethyl 3-[4-morpholin-4-yl-6-(4-pyridin-2-ylpiperazin-1-yl)-1,3,5-triazin-2-yl]benzoate | * | 1.09 | 476.24 | A |
| 435 | 3-(4-morpholin-4-yl-6-{4-[3-(trifluoromethyl)pyridin-2-yl]piperazin-1-yl}-1,3,5-triazin-2-yl)benzonitrile | * | 1.3 | 497.20 | A |
| 436 | 4-(4-morpholin-4-yl-6-{4-[3-(trifluoromethyl)pyridin-2-yl]piperazin-1-yl}-1,3,5-triazin-2-yl)benzonitrile | * | 1.3 | 497.20 | A |

TABLE II-continued

| Compound | Name | IC$_{50}$ | Ret. Time | MS (M + 1) | LCMS Method |
|---|---|---|---|---|---|
| 437 | 2-morpholin-4-yl-4-[4-(trifluoromethyl)phenyl]-6-{4-[3-(trifluoromethyl)pyridin-2-yl]piperazin-1-yl}-1,3,5-triazine | * | 1.4 | 540.18 | A |
| 438 | 2-morpholin-4-yl-4-[3-(trifluoromethyl)phenyl]-6-{4-[3-(trifluoromethyl)pyridin-2-yl]piperazin-1-yl}-1,3,5-triazine | * | 1.39 | 540.18 | A |
| 449 | 2-[4-chloro-3-(trifluoromethyl)phenyl]-4-morpholin-4-yl-6-{4-[3-(trifluoromethyl)pyridin-2-yl]piperazin-1-yl}-1,3,5-triazine | | 1.47 | 574.15 | A |

TABLE II-continued
| Compound | | Name | IC$_{50}$ | Ret. Time | MS (M + 1) | LCMS Method |
|---|---|---|---|---|---|---|
| 440 | 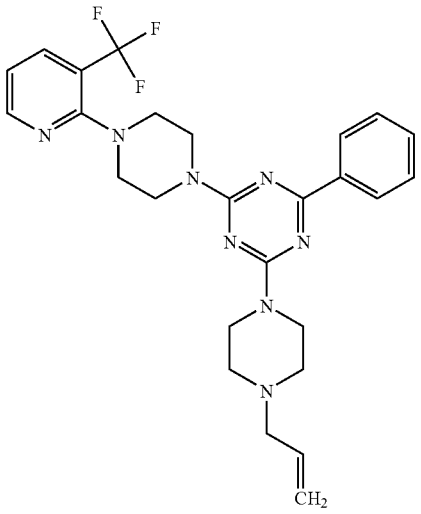 | 2-(4-allylpiperazin-1-yl)-4-phenyl-6-{4-[3-(trifluoromethyl)pyridin-2-yl]piperazin-1-yl}-1,3,5-triazine | * | 1.14 | 511.20 | A |
| 441 | 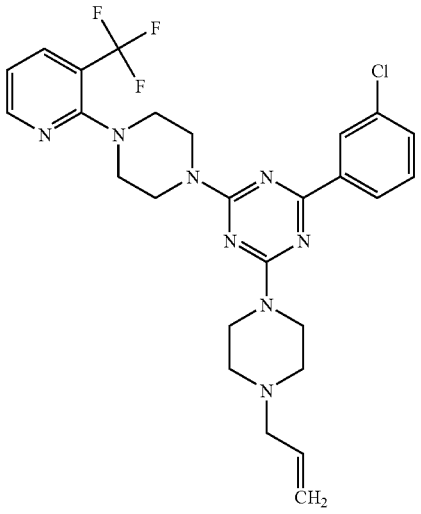 | 2-(4-allylpiperazin-1-yl)-4-(3-chlorophenyl)-6-{4-[3-(trifluoromethyl)pyridin-2-yl]piperazin-1-yl}-1,3,5-triazine | * | 1.17 | 545.16 | A |
| 442 | 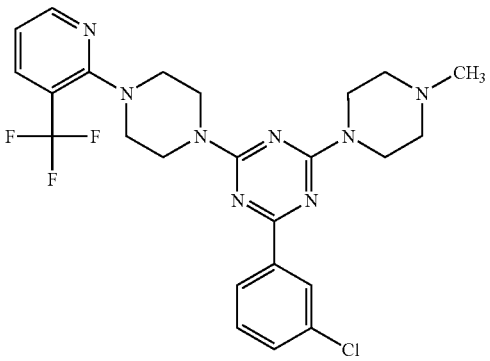 | 2-(3-chlorophenyl)-4-(4-methylpiperazin-1-yl)-6-{4-[3-(trifluoromethyl)pyridin-2-yl]piperazin-1-yl}-1,3,5-triazine | | 1.17 | 519.15 | A |

TABLE II-continued

| Compound | Name | IC$_{50}$ | Ret. Time | MS (M + 1) | LCMS Method |
|---|---|---|---|---|---|
| 443 | 2-(3-chlorophenyl)-4-(4-ethylpiperazin-1-yl)-6-{4-[3-(trifluoromethyl)pyridin-2-yl]piperazin-1-yl}-1,3,5-triazine | | 1.16 | 533.16 | A |
| 444 | 2-(4-butylpiperazin-1-yl)-4-(3-chlorophenyl)-6-{4-[3-(trifluoromethyl)pyridin-2-yl]piperazin-1-yl}-1,3,5-triazine | * | 1.17 | 561.19 | A |
| 445 | 2-(4-allylpiperazin-1-yl)-4-(4-chlorophenyl)-6-{4-[3-(trifluoromethyl)pyridin-2-yl]piperazin-1-yl}-1,3,5-triazine | * | 1.17 | 545.16 | A |

TABLE II-continued

| Compound | | Name | IC$_{50}$ | Ret. Time | MS (M + 1) | LCMS Method |
|---|---|---|---|---|---|---|
| 446 | | 2-(4-allylpiperazin-1-yl)-4-(4-fluorophenyl)-6-{4-[3-(trifluoromethyl)pyridin-2-yl]piperazin-1-yl}-1,3,5-triazine | * | 1.15 | 529.19 | A |
| 447 | | 2-(4-butylpiperazin-1-yl)-4-(4-fluorophenyl)-6-{4-[3-(trifluoromethyl)pyridin-2-yl]piperazin-1-yl}-1,3,5-triazine | | 1.15 | 545.22 | A |
| 448 | | 2-(4-allylpiperazin-1-yl)-4-(3-fluorophenyl)-6-{4-[3-(trifluoromethyl)pyridin-2-yl]piperazin-1-yl}-1,3,5-triazine | * | 1.15 | 529.19 | A |

TABLE II-continued

| Compound | Name | IC$_{50}$ | Ret. Time | MS (M + 1) | LCMS Method |
|---|---|---|---|---|---|
| 449 | 2-(4-allylpiperazin-1-yl)-4-(3-fluoro-4-methylphenyl)-6-{4-[3-(trifluoromethyl)pyridin-2-yl]piperazin-1-yl}-1,3,5-triazine | | 1.17 | 543.21 | A |
| 450 | 2-(4-allylpiperazin-1-yl)-4-(4-fluoro-3-methylphenyl)-6-{4-[3-(trifluoromethyl)pyridin-2-yl]piperazin-1-yl}-1,3,5-triazine | * | 1.17 | 543.21 | A |
| 451 | 2-(4-ethylpiperazin-1-yl)-4-(4-fluoro-3-methylphenyl)-6-{4-[3-(trifluoromethyl)pyridin-2-yl]piperazin-1-yl}-1,3,5-triazine | | 1.17 | 531.21 | A |

TABLE II-continued
| Compound | | Name | IC$_{50}$ | Ret. Time | MS (M + 1) | LCMS Method |
|---|---|---|---|---|---|---|
| 452 | 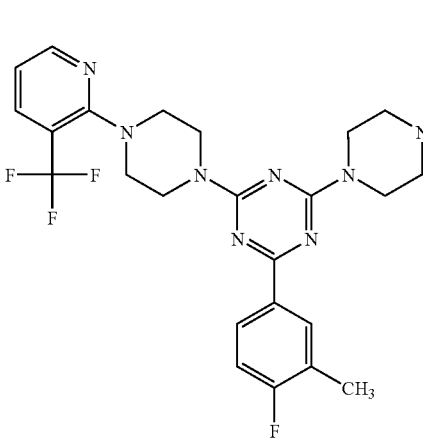 | 2-(4-butylpiperazin-1-yl)-4-(4-fluoro-3-methylphenyl)-6-{4-[3-(trifluoromethyl)pyridin-2-yl]piperazin-1-yl}-1,3,5-triazine | * | 1.17 | 559.24 | A |
| 453 | 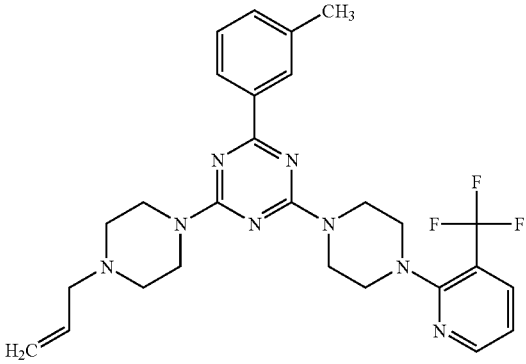 | 2-(4-allylpiperazin-1-yl)-4-(3-methylphenyl)-6-{4-[3-(trifluoromethyl)pyridin-2-yl]piperazin-1-yl}-1,3,5-triazine | * | 1.16 | 525.22 | A |
| 454 | 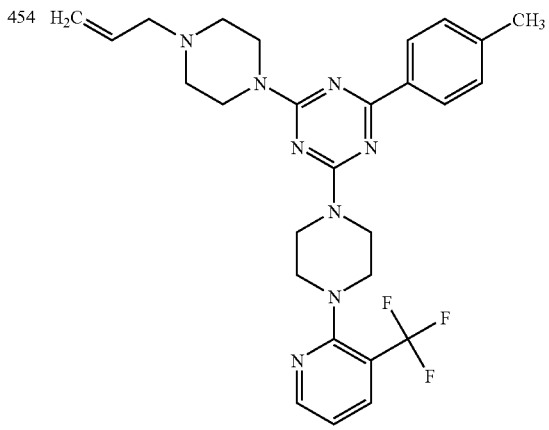 | 2-(4-allylpiperazin-1-yl)-4-(4-methylphenyl)-6-{4-[3-(trifluoromethyl)pyridin-2-yl]piperazin-1-yl}-1,3,5-triazine | | 1.16 | 525.22 | A |

TABLE II-continued

| Compound | | Name | IC$_{50}$ | Ret. Time | MS (M + 1) | LCMS Method |
|---|---|---|---|---|---|---|
| 455 | | 2-(4-allylpiperazin-1-yl)-4-(3,4-dimethylphenyl)-6-{4-[3-(trifluoromethyl)pyridin-2-yl]piperazin-1-yl}-1,3,5-triazine | | 1.17 | 539.24 | A |
| 456 | | 2-(4-allylpiperazin-1-yl)-4-[3-(methylthio)phenyl]-6-{4-[3-(trifluoromethyl)pyridin-2-yl]piperazin-1-yl}-1,3,5-triazine | | 1.15 | 557.19 | A |
| 457 | | N,N-diethyl-4-(3-fluorophenyl)-6-[4-(4-methoxyphenyl)piperazin-1-yl]-1,3,5-triazin-2-amine | | 1.26 | 437.22 | A |
| 458 | | N,N-diethyl-4-phenyl-6-(4-phenylpiperazin-1-yl)-1,3,5-triazin-2-amine | | 1.34 | 389.18 | A |

TABLE II-continued

| Compound | Name | IC$_{50}$ | Ret. Time | MS (M + 1) | LCMS Method |
|---|---|---|---|---|---|
| 459 | N,N-diethyl-4-[4-(2-fluorophenyl)piperazin-1-yl]-6-phenyl-1,3,5-triazin-2-amine | | 1.41 | 407.17 | A |
| 460 | N,N-diethyl-4-[4-(4-fluorophenyl)piperazin-1-yl]-6-(4-methylphenyl)-1,3,5-triazin-2-amine | | 1.37 | 421.19 | A |
| 461 | N,N-diethyl-4-(3-isopropylphenyl)-6-(4-phenylpiperazin-1-yl)-1,3,5-triazin-2-amine | | 1.41 | 431.23 | A |

TABLE II-continued
| Compound | | Name | IC$_{50}$ | Ret. Time | MS (M + 1) | LCMS Method |
|---|---|---|---|---|---|---|
| 462 | 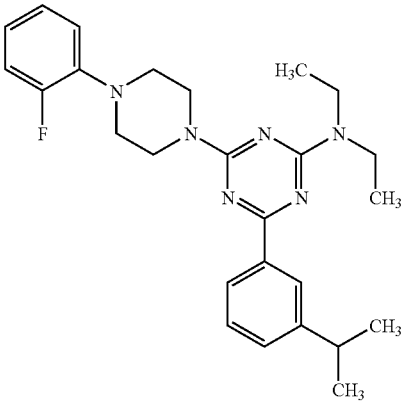 | N,N-diethyl-4-[4-(2-fluorophenyl)piperazin-1-yl]-6-(3-isopropylphenyl)-1,3,5-triazin-2-amine | | 1.48 | 449.22 | A |
| 463 | 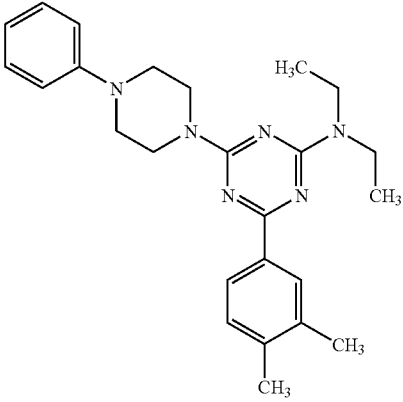 | 4-(3,4-dimethylphenyl)-N,N-diethyl-6-(4-phenylpiperazin-1-yl)-1,3,5-triazin-2-amine | | 1.37 | 417.24 | A |
| 464 | 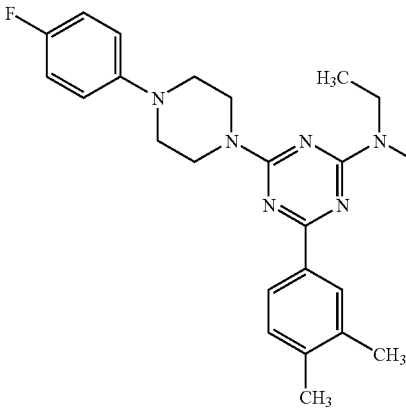 | 4-(3,4-dimethylphenyl)-N,N-diethyl-6-[4-(4-fluorophenyl)piperazin-1-yl]-1,3,5-triazin-2-amine | | 1.38 | 435.24 | A |

TABLE II-continued
| Compound | | Name | IC$_{50}$ | Ret. Time | MS (M + 1) | LCMS Method |
|---|---|---|---|---|---|---|
| 465 | 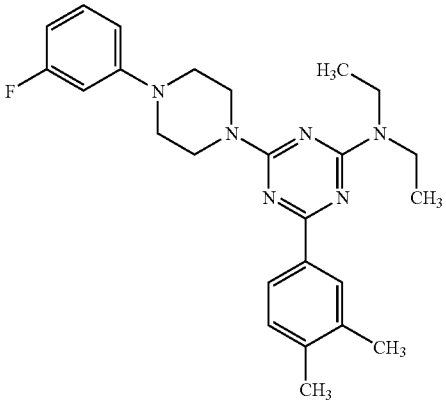 | 4-(3,4-dimethylphenyl)-N,N-diethyl-6-[4-(3-fluorophenyl)piperazin-1-yl]-1,3,5-triazin-2-amine | | 1.42 | 435.24 | A |
| 466 | 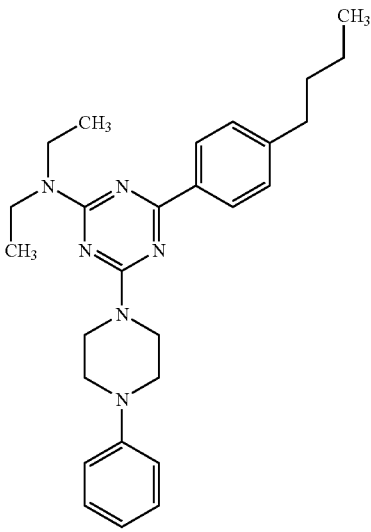 | 4-(4-butylphenyl)-N,N-diethyl-6-(4-phenylpiperazin-1-yl)-1,3,5-triazin-2-amine | | 1.49 | 445.28 | A |
| 467 | 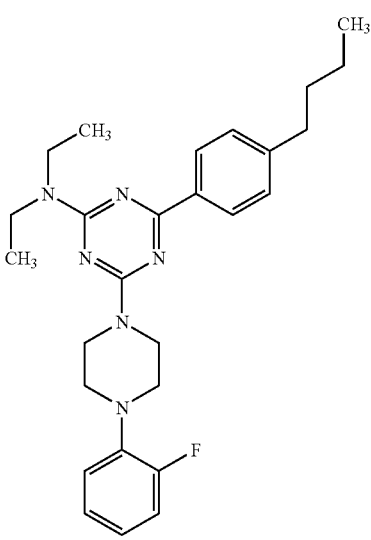 | 4-(4-butylphenyl)-N,N-diethyl-6-[4-(2-fluorophenyl)piperazin-1-yl]-1,3,5-triazin-2-amine | | 1.56 | 463.27 | A |

TABLE II-continued

| Compound | Name | IC₅₀ | Ret. Time | MS (M + 1) | LCMS Method |
|---|---|---|---|---|---|
| 468 | 4-(4-butylphenyl)-N,N-diethyl-6-[4-(3-fluorophenyl)piperazin-1-yl]-1,3,5-triazin-2-amine | | 1.54 | 463.27 | A |
| 469 | 4-(3,5-dimethylphenyl)-N,N-diethyl-6-(4-phenylpiperazin-1-yl)-1,3,5-triazin-2-amine | | 1.38 | 417.25 | A |
| 470 | 4-[4-(4-chlorophenyl)piperazin-1-yl]-N,N-diethyl-6-(3-methylphenyl)-1,3,5-triazin-2-amine | | 1.45 | 437.21 | A |

TABLE II-continued

| Compound | | Name | IC$_{50}$ | Ret. Time | MS (M + 1) | LCMS Method |
|---|---|---|---|---|---|---|
| 471 | | 4[4-(3,4-dichlorophenyl)piperazin-1-yl]-N,N-diethyl-6-(3-methylphenyl)-1,3,5-triazin-2-amine | | 1.53 | 471.17 | A |
| 472 | | 4-[4-(3,5-dichlorophenyl)piperazin-1-yl]-N,N-diethyt-6-(3-methylphenyl)-1,3,5-triazin-2-amine | | 1.61 | 471.17 | A |
| 473 | | 4-[4-(3-chlorophenyl)piperazin-1-yl]-6-(3,5-dimethylphenyl)-N,N-diethyl-1,3,5-triazin-2-amine | | 1.49 | 451.24 | A |

TABLE II-continued
| Compound | | Name | IC$_{50}$ | Ret. Time | MS (M + 1) | LCMS Method |
|---|---|---|---|---|---|---|
| 474 | 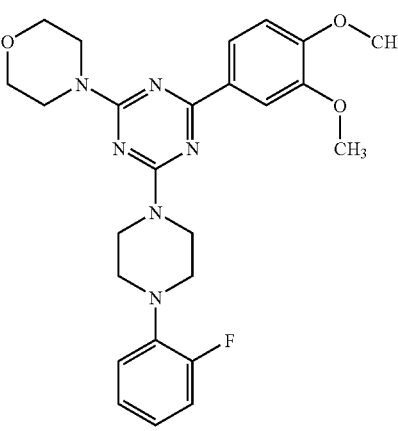 | 2-(3,4-dimethoxyphenyl)-4-[4-(2-fluorophenyl)piperazin-1-yl]-6-morpholin-4-yl-1,3,5-triazine | | 1.22 | 481.29 | A |
| 475 | 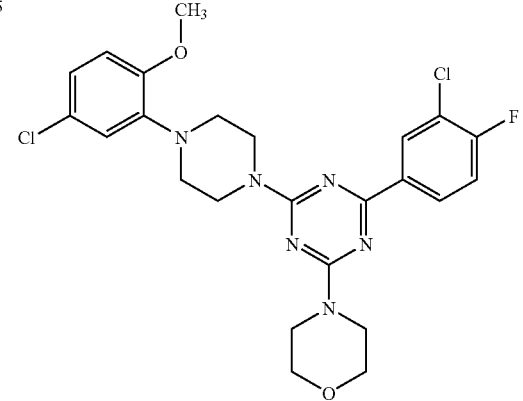 | 2-(3-chloro-4-fluorophenyl)-4-[4-(5-chloro-2-methoxyphenyl)piperazin-1-yl]-6-morpholin-4-yl-1,3,5-triazine | | 1.43 | 519.23 | A |
| 476 | 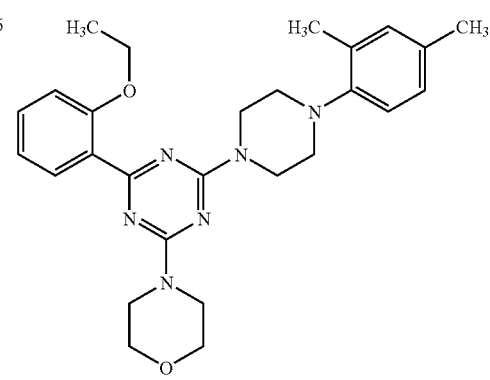 | 2-[4-(2,4-dimethylphenyl)piperazin-1-yl]-4-(2-ethoxyphenyl)-6-morpholin-4-yl-1,3,5-triazine | | 1.15 | 475.31 | A |

TABLE II-continued

| Compound | Name | IC$_{50}$ | Ret. Time | MS (M + 1) | LCMS Method |
|---|---|---|---|---|---|
| 477 | 2-methyl-4-[4-(3-methylphenyl)piperazin-1-yl]-6-morpholin-4-yl-1,3,5-triazine | | 1.25 | 459.25 | A |
| 478 Chiral | 4-(4-{(2R)-2-methyl-4-[3-(trifluoromethyl)pyridin-2-yl]piperazin-1-yl}-6-phenylpyrimidin-2-yl)morpholine | * | 1.2 | 485.31 | B |
| 479 Chiral | 4-{4-[(2R)-4-(3-chloropyridin-2-yl)-2-methylpiperazin-1-yl]-6-phenylpyrimidin-2-yl}morpholine | * | 1.18 | 451.27 | B |

TABLE II-continued

| Compound | | Name | IC$_{50}$ | Ret. Time | MS (M + 1) | LCMS Method |
|---|---|---|---|---|---|---|
| 480 | Chiral | 4-{4-(3-chlorophenyl)-6-[(2R)-2-methyl-4-(3-methylpyridin-2-yl)piperazin-1-yl]pyrimidin-2-yl}morpholine | * | 1.15 | 465.30 | B |
| 481 | Chiral | 4-{4-(3-chlorophenyl)-6-[(2R)-4-(3-chloropyridin-2-yl)-2-methylpiperazin-1-yl]pyrimidin-2-yl}morpholine | * | 1.26 | 485.25 | B |
| 482 | Chiral | 2-{(3R)-4-[6-(4-chlorophenyl)-2-morpholin-4-ylpyrimidin-4-yl]-3-methylpiperazin-1-yl}nicotinonitrile | * | 1.2 | 476.28 | B |

TABLE II-continued

| Compound | | Name | IC$_{50}$ | Ret. Time | MS (M + 1) | LCMS Method |
|---|---|---|---|---|---|---|
| 483 | Chiral | 4-{4-(4-chlorophenyl)-6-[(2R)-2-methyl-4-(3-methylpyridin-2-yl)piperazin-1-yl]pyrimidin-2-yl}morpholine | * | 1.13 | 465.30 | B |
| 484 | Chiral | 4-(4-(4-chlorophenyl)-6-{(2R)-2-methyl-4-[3-(trifluoromethyl)pyridin-2-yl]piperazin-1-yl}pyrimidin-2-yl)morpholine | * | 1.25 | 519.30 | B |
| 485 | Chiral | 4-{4-(4-chlorophenyl)-6-[(2R)-4-(3-chloropyridin-2-yl)-2-methylpiperazin-1-yl]pyrimidin-2-yl}morpholine | * | 1.24 | 485.26 | B |

TABLE II-continued

| Compound | | Name | IC$_{50}$ | Ret. Time | MS (M + 1) | LCMS Method |
|---|---|---|---|---|---|---|
| 486 | Chiral | 2-{(3R)-4-[6-(4-fluorophenyl)-2-morpholin-4-ylpyrimidin-4-yl]-3-methylpiperazin-1-yl}nicotinonitrile | * | 1.16 | 460.30 | B |
| 487 | Chiral | 4-[4-[(2R)-4-(3-chloropyridin-2-yl)-2-methylpiperazin-1-yl]-6-(4-fluorophenyl)pyrimidin-2-yl]morpholine | * | 1.2 | 469.27 | B |
| 488 | Chiral | 4-[4-[(2R)-4-(3-chloropyridin-2-yl)-2-methylpiperazin-1-yl]-6-(3-fluorophenyl)pyrimidin-2-yl]morpholine | * | 1.23 | 469.27 | B |

TABLE II-continued
| Compound | | Name | IC$_{50}$ | Ret. Time | MS (M + 1) | LCMS Method |
|---|---|---|---|---|---|---|
| 489 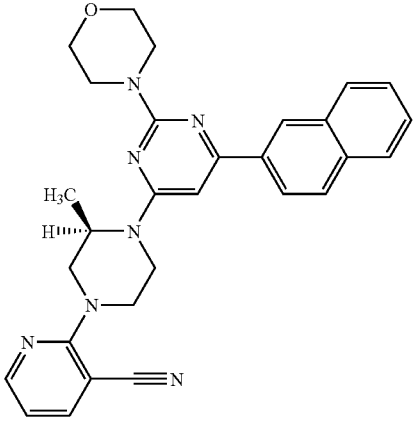 | Chiral | 2-{(3R)-3-methyl-4-[2-morpholin-4-yl-6-(2-naphthyl)pyrimidin-4-yl]piperazin-1-yl}nicotinonitrile | * | 1.2 | 492.35 | B |
| 490 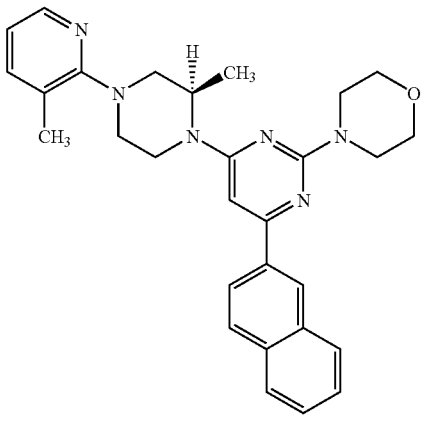 | Chiral | 4-[4-[(2R)-2-methyl-4-(3-methylpyridin-2-yl)piperazin-1-yl]-6-(2-naphthyl)pyrimidin-2-yl]morpholine | * | 1.14 | 481.35 | B |
| 491 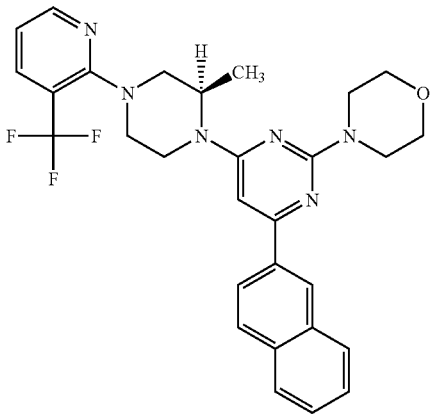 | Chiral | 4-[4-{(2R)-2-methyl-4-[3-(trifluoromethyl)pyridin-2-yl]piperazin-1-yl}-6-(2-naphthyl)pyrimidin-2-yl]morpholine | * | 1.25 | 535.36 | B |

TABLE II-continued
| Compound | | Name | IC$_{50}$ | Ret. Time | MS (M + 1) | LCMS Method |
|---|---|---|---|---|---|---|
| 492 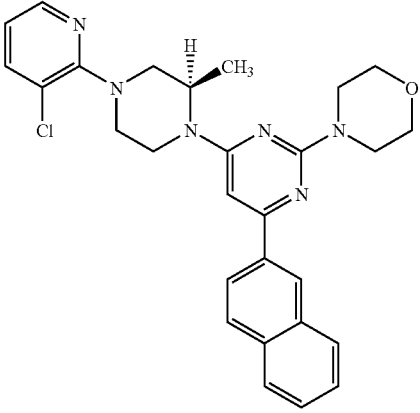 | Chiral | 4-[4-[(2R)-4-(3-chloropyridin-2-yl)-2-methylpiperazin-1-yl]-6-(2-naphthyl)pyrimidin-2-yl]morpholine | * | 1.24 | 501.32 | B |
| 493 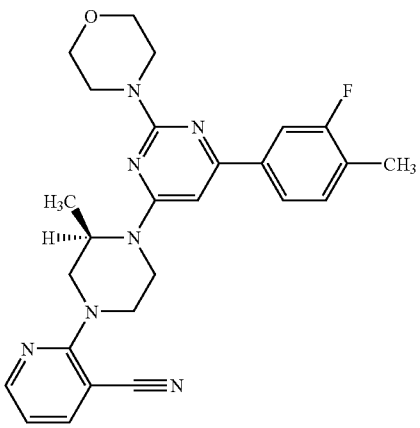 | Chiral | 2-{(3R)-4-[6-(3-fluoro-4-methylphenyl)-2-morpholin-4-ylpyrimidin-4-yl]-3-methylpiperazin-1-yl}nicotinonitrile | * | 1.2 | 474.33 | B |
| 494 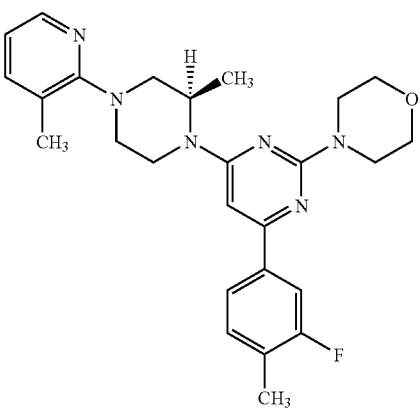 | Chiral | 4-{4-(3-fluoro-4-methylphenyl)-6-[(2R)-2-methyl-4-(3-methylpyridin-2-yl)piperazin-1-yl]pyrimidin-2-yl}morpholine | * | 1.14 | 463.33 | B |

TABLE II-continued

| Compound | | | Name | IC$_{50}$ | Ret. Time | MS (M + 1) | LCMS Method |
|---|---|---|---|---|---|---|---|
| 495 | | Chiral | 4-(4-(3-fluoro-4-methylphenyl)-6-{(2R)-2-methyl-4-[3-(trifluoromethyl)pyridin-2-yl]piperazin-1-yl}pyrimidin-2-yl)morpholine | * | 1.26 | 517.34 | B |
| 496 | | Chiral | 4-[4-[(2R)-4-(3-chloropyridin-2-yl)-2-methylpiperazin-1-yl]-6-(3-fluoro-4-methylphenyl)pyrimidin-2-yl]morpholine | * | 1.24 | 483.29 | B |
| 497 | | Chiral | 4-(4-(4-fluoro-3-methylphenyl)-6-{(2R)-2-methyl-4-[3-(trifluoromethyl)pyridin-2-yl]piperazin-1-yl}pyrimidin-2-yl)morpholine | * | 1.23 | 517.34 | B |

TABLE II-continued
| Compound | | | Name | IC$_{50}$ | Ret. Time | MS (M + 1) | LCMS Method |
|---|---|---|---|---|---|---|---|
| 498 | 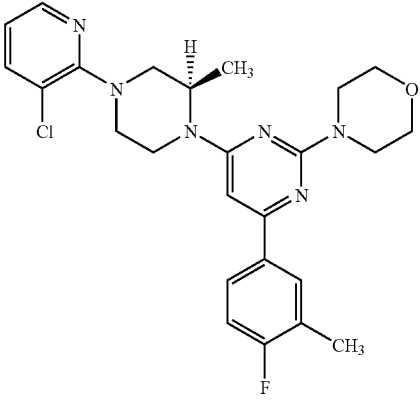 | Chiral | 4-[4-[(2R)-4-(3-chloropyridin-2-yl)-2-methylpiperazin-1-yl]-6-(4-fluoro-3-methytphenyl)pyrimidin-2-yl]morpholine | * | 1.22 | 483.29 | B |
| 499 | 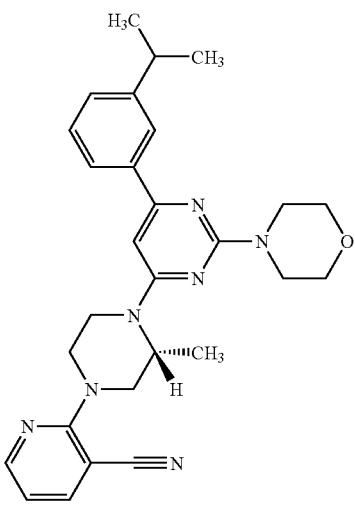 | Chiral | 2-{(3R)-4-[6-(3-isopropylphenyl)-2-morpholin-4-ylpyrimidin-4-yl]-3-methylpiperazin-1-yl}nicotinonitrile | * | 1.2 | 484.36 | B |
| 500 | 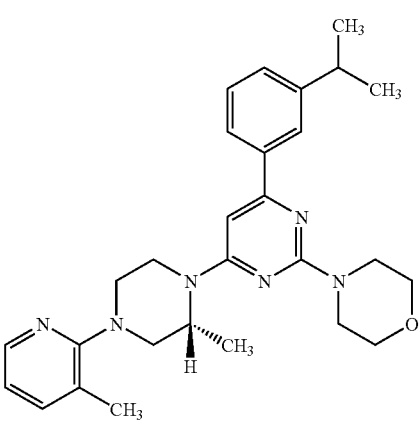 | Chiral | 4-{4-(3-isopropylphenyl)-6-[(2R)-2-methyl-4-(3-methylpyridin-2-yl)piperazin-1-yl]pyrimidin-2-yl}morpholine | * | 1.16 | 473.38 | B |

TABLE II-continued
| Compound | | Name | IC$_{50}$ | Ret. Time | MS (M + 1) | LCMS Method |
|---|---|---|---|---|---|---|
| 501 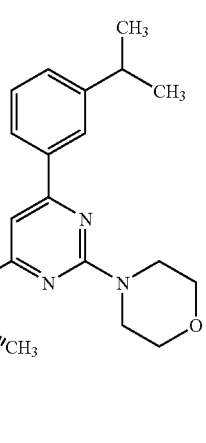 | Chiral | 4-(4-(3-isopropylphenyl)-6-{(2R)-2-methyl-4-[3-(trifluoromethyl)pyridin-2-yl]piperazin-1-yl}pyrimidin-2-yl)morpholine | * | 1.26 | 527.38 | B |
| 502 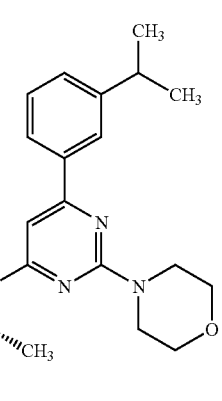 | Chiral | 4-[4-[(2R)-4-(3-chloropyridin-2-yl)-2-methylpiperazin-1-yl]-6-(3-isopropylphenyl)pyrimidin-2-yl]morpholine | * | 1.25 | 493.34 | B |
| 503 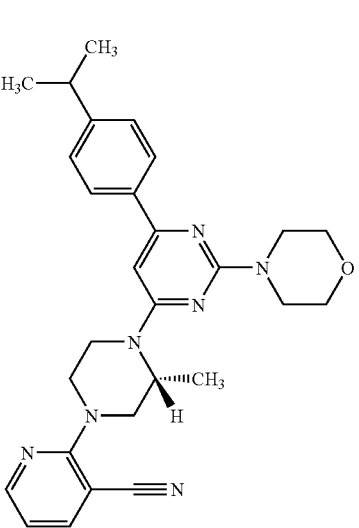 | Chiral | 2-{(3R)-4-[6-(4-isopropylphenyl)-2-morpholin-4-ylpyrimidin-4-yl]-3-methylpiperazin-1-yl}nicotinonitrile | * | 1.21 | 484.36 | B |

TABLE II-continued

| Compound | | Name | IC$_{50}$ | Ret. Time | MS (M + 1) | LCMS Method |
|---|---|---|---|---|---|---|
| 504 | Chiral | 4-{4-(4-isopropylphenyl)-6-[(2R)-2-methyl-4-(3-methylpyridin-2-yl)piperazin-1-yl]pyrimidin-2-yl}morpholine | * | 1.15 | 473.37 | B |
| 505 | Chiral | 4-[4-[(2R)-4-(3-chloropyridin-2-yl)-2-methylpiperazin-1-yl]-6-(4-isopropylphenyl)pyrimidin-2-yl]morpholine | * | 1.25 | 493.34 | B |
| 506 | Chiral | 2-{(3R)-4-[6-(3,4-dimethylphenyl)-2-morpholin-4-ylpyrimidin-4-yl]-3-methylpiperazin-1-yl}nicotinonitrile | * | 1.18 | 470.34 | B |

TABLE II-continued

| Compound | | Name | IC$_{50}$ | Ret. Time | MS (M + 1) | LCMS Method |
|---|---|---|---|---|---|---|
| 507 | Chiral | 4-[4-(3,4-dimethylphenyl)-6-[(2R)-2-methyl-4-(3-methylpyridin-2-yl)piperazin-1-yl]pyrimidin-2-yl}morpholine | * | 1.13 | 459.35 | B |
| 508 | Chiral | 4-{4-[(2R)-4-(3-chloropyridin-2-yl)-2-methylpiperazin-1-yl]-6-(3,4-dimethylphenyl)pyrimidin-2-yl}morpholine | * | 1.22 | 479.31 | B |
| 509 | Chiral | 2-{(3R)-4-[6-(4-ethylphenyl)-2-morpholin-4-ylpyrimidin-4-yl]-3-methylpiperazin-1-yl}nicotinonitrile | * | 1.18 | 470.34 | B |

TABLE II-continued

| Compound | | Name | IC$_{50}$ | Ret. Time | MS (M + 1) | LCMS Method |
|---|---|---|---|---|---|---|
| 510 | Chiral | 4-{4-(4-ethylphenyl)-6-[(2R)-2-methyl-4-(3-methylpyridin-2-yl)piperazin-1-yl]pyrimidin-2-yl}morpholine | * | 1.12 | 459.35 | B |
| 511 | Chiral | 4-[4-[(2R)-4-(3-chloropyridin-2-yl)-2-methylpiperazin-1-yl]-6-(4-ethylphenyl)pyrimidin-2-yl]morpholine | * | 1.23 | 479.31 | B |
| 512 | Chiral | 2-{(3R)-3-methyl-4-[2-morpholin-4-yl-6-(4-propylphenyl)pyrimidin-4-yl]piperazin-1-yl}nicotinonitrile | * | 1.21 | 484.36 | B |

TABLE II-continued

| Compound | | Name | IC$_{50}$ | Ret. Time | MS (M + 1) | LCMS Method |
|---|---|---|---|---|---|---|
| 513 | Chiral | 4-[4-[(2R)-4-(3-chloropyridin-2-yl)-2-methylpiperazin-1-yl]-6-(4-propylphenyl)pyrimidin-2-yl]morpholine | * | 1.25 | 493.34 | B |
| 514 | Chiral | 2-{(3R)-4-[6-(3-ethylphenyl)-2-morpholin-4-ylpyrimidin-4-yl]-3-methylpiperazin-1-yl}nicotinonitrile | * | 1.19 | 470.34 | B |
| 515 | Chiral | 4-{4-(3-ethylphenyl)-6-[(2R)-2-methyl-4-(3-methylpyridin-2-yl)piperazin-1-yl]pyrimidin-2-yl}morpholine | * | 1.13 | 459.35 | B |

TABLE II-continued
| Compound | | Name | IC$_{50}$ | Ret. Time | MS (M + 1) | LCMS Method |
|---|---|---|---|---|---|---|
| 516 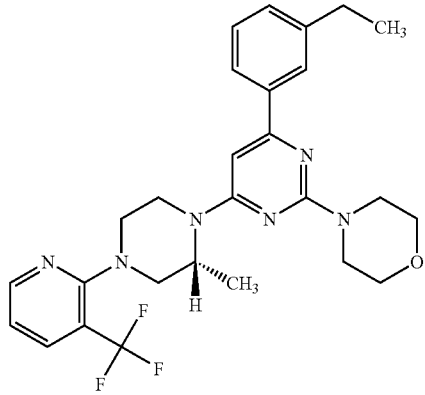 | Chiral | 4-(4-(3-ethylphenyl)-6-{(2R)-2-methyl-4-[3-(trifluoromethyl)pyridin-2-yl]piperazin-1-yl}pyrimidin-2-yl)morpholine | * | 1.24 | 513.35 | B |
| 517 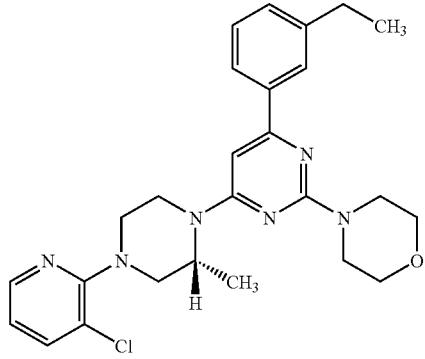 | Chiral | 4-[4-[(2R)-4-(3-chloropyridin-2-yl)-2-methylpiperazin-1-yl]-6-(3-ethylphenyl)pyrimidin-2-yl]morpholine | * | 1.24 | 479.31 | B |
| 518 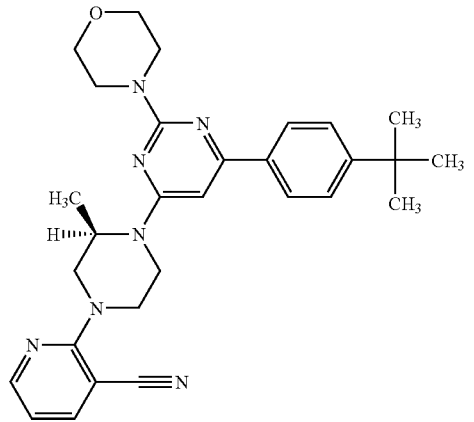 | Chiral | 2-{(3R)-4-[6-(4-tert-butylphenyl)-2-morpholin-4-ylpyrimidin-4-yl]-3-methylpiperazin-1-yl}nicotinonitrile | * | 1.22 | 498.38 | B |

TABLE II-continued

| Compound | | Name | IC$_{50}$ | Ret. Time | MS (M + 1) | LCMS Method |
|---|---|---|---|---|---|---|
| 519 | Chiral | 4-(4-(4-tert-butylphenyl)-6-{(2R)-2-methyl-4-[3-(trifluoromethyl)pyridin-2-yl]piperazin-1-yl}pyrimidin-2-yl)morpholine | * | 1.27 | 541.39 | B |
| 520 | Chiral | 4-{4-(4-tert-butylphenyl)-6-[(2R)-4-(3-chloropyridin-2-yl)-2-methylpiperazin-1-yl]pyrimidin-2-yl}morpholine | * | 1.26 | 507.36 | B |
| 521 | Chiral | 4-[4-[(2R)-2-methyl-4-(3-methylpyridin-2-yl)piperazin-1-yl]-6-(1-naphthyl)pyrimidin-2-yl]morpholine | * | 1.11 | 481.35 | B |

TABLE II-continued
| Compound | | Name | IC$_{50}$ | Ret. Time | MS (M + 1) | LCMS Method |
|---|---|---|---|---|---|---|
| 522 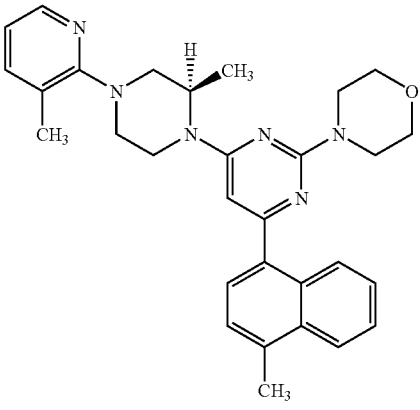 | Chiral | 4-[4-[(2R)-2-methyl-4-(3-methylpyridin-2-yl)piperazin-1-yl]-6-(4-methyl-1-naphthyl)pyrimidin-2-yl]morpholine | * | 1.13 | 495.37 | B |
| 523 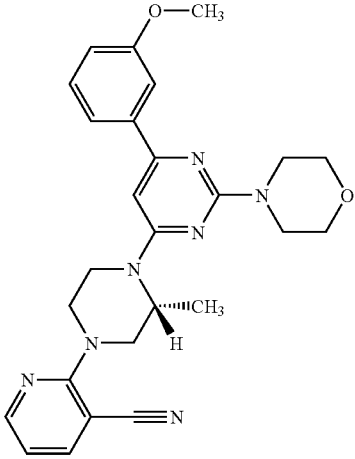 | Chiral | 2-{(3R)-4-[6-(3-methoxyphenyl)-2-morpholin-4-ylpyrimidin-4-yl]-3-methylpiperazin-1-yl}nicotinonitrile | * | 1.16 | 472.33 | B |
| 524 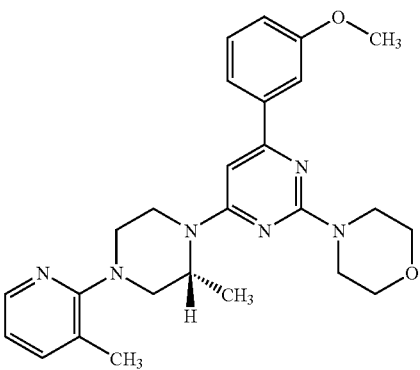 | Chiral | 4-{4-(3-methoxyphenyl)-6-[(2R)-2-methyl-4-(3-methylpyridin-2-yl)piperazin-1-yl]pyrimidin-2-yl}morpholine | * | 1.09 | 461.34 | B |

TABLE II-continued

| Compound | | Name | IC$_{50}$ | Ret. Time | MS (M + 1) | LCMS Method |
|---|---|---|---|---|---|---|
| 525 | Chiral | 4-(4-(3-methoxyphenyl)-6-{(2R)-2-methyl-4-[3-(trifluoromethyl)pyridin-2-yl]piperazin-1-yl}pyrimidin-2-yl)morpholine | * | 1.21 | 515.34 | B |
| 526 | Chiral | 4-[4-[(2R)-4-(3-chloropyridin-2-yl)-2-methylpiperazin-1-yl]-6-(3-methoxyphenyl)pyrimidin-2-yl]morpholine | * | 1.21 | 481.30 | B |
| 527 | Chiral | 4{4[(2R)-2-methyl-4-(3-methylpyridin-2-yl)piperazin-1-yl]-6-[4-(trifluoromethoxy)phenyl]pyrimidin-2-yl}morpholine | * | 1.17 | 515.34 | B |

TABLE II-continued

| Compound | | Name | IC$_{50}$ | Ret. Time | MS (M + 1) | LCMS Method |
|---|---|---|---|---|---|---|
| 528 | Chiral | 4-{4-{(2R)-2-methyl-4-(3-(trifluoromethyl)pyridin-2-yl]piperazin-1-yl}-6-[4-(trifluoromethoxy)phenyl]pyrimidin-2-yl}morpholine | * | 1.28 | 569.34 | B |
| 529 | Chiral | 4-{4-(3-ethoxyphenyl)-6-[(2R)-2-methyl-4-(3-methylpyridin-2-yl)piperazin-1-yl]pyrimidin-2-yl}morpholine | * | 1.12 | 475.36 | B |
| 530 | Chiral | 4-(4-(3-ethoxyphenyl)-6-{(2R)-2-methyl-4-[3-(trifluoromethyl)pyridin-2-yl]piperazin-1-yl}pyrimidin-2-yl)morpholine | * | 1.23 | 529.36 | B |

TABLE II-continued

| Compound | | Name | IC$_{50}$ | Ret. Time | MS (M + 1) | LCMS Method |
|---|---|---|---|---|---|---|
| 531 | Chiral | 4-[4-[(2R)-4-(3-chloropyridin-2-yl)-2-methylpiperazin-1-yl]-6-(3-ethoxyphenyl)pyrimidin-2-yl]morpholine | * | 1.22 | 495.32 | B |
| 532 | Chiral | 2-((3R)-3-methyl-4-{2-morpholin-4-yl-6-[3-(trifluoromethoxy)phenyl]pyrimidin-4-yl}piperazin-1-yl)nicotinonitrile | * | 1.26 | 526.33 | B |
| 533 | Chiral | 4-{4-[(2R)-2-methyl-4-(3-methylpyridin-2-yl)piperazin-1-yl]-6-[3-(trifluoromethoxy)phenyl]pyrimidin-2-yl}morpholine | * | 1.2 | 515.34 | B |

TABLE II-continued

| Compound | | | Name | IC$_{50}$ | Ret. Time | MS (M + 1) | LCMS Method |
|---|---|---|---|---|---|---|---|
| 534 | 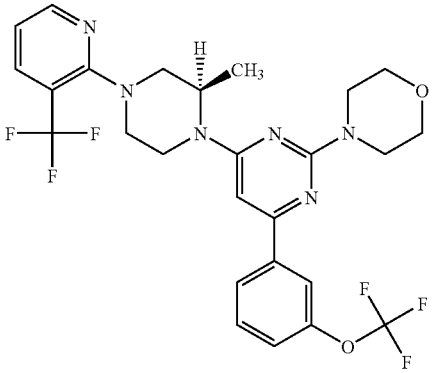 | Chiral | 4-{4-{(2R)-2-methyl-4-[3-(trifluoromethyl)pyridin-2-yl]piperazin-1-yl}-6-[3-(trifluoromethoxy)phenyl]pyrimidin-2-yl}morpholine | * | 1.31 | 569.34 | B |
| 535 | 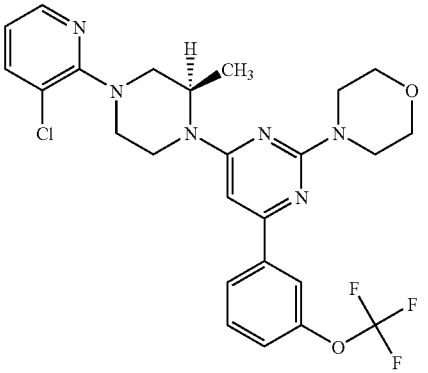 | Chiral | 4-{4-[(2R)-4-(3-chloropyridin-2-yl)-2-methylpiperazin-1-yl]-6-[3-(trifluoromethoxy)phenyl]pyrimidin-2-yl}morpholine | * | 1.3 | 535.31 | B |
| 536 | 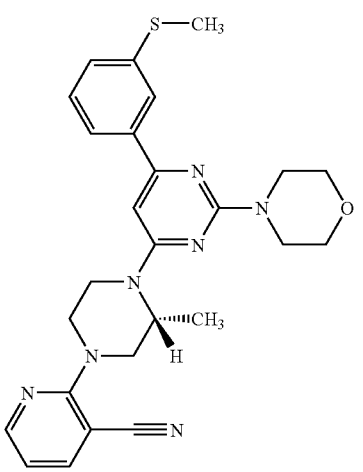 | Chiral | 2-((3R)-3-methyl-4-{6-[3-(methylthio)phenyl]-2-morpholin-4-ylpyrimidin-4-yl}piperazin-1-yl)nicotinonitrile | * | 1.19 | 488.32 | B |

TABLE II-continued

| Compound | Name | IC₅₀ | Ret. Time | MS (M + 1) | LCMS Method |
|---|---|---|---|---|---|
| 537 Chiral | 4-{4-[(2R)-2-methyl-4-(3-methylpyridin-2-yl)piperazin-1-yl]-6-[3-(methylthio)phenyl]pyrimidin-2-yl}morpholine | * | 1.12 | 477.33 | B |
| 538 Chiral | 4-(4-[3-(methylthio)phenyl]-6-{(2R)-2-methyl-4-[3-(trifluoromethyl)pyridin-2-yl]piperazin-1-yl}pyrimidin-2-yl)morpholine | * | 1.24 | 531.33 | B |
| 539 Chiral | 4-{4-[(2R)-4-(3-chloropyridin-2-yl)-2-methylpiperazin-1-yl]-6-[3-(methylthio)phenyl]pyrimidin-2-yl}morpholine | * | 1.23 | 497.29 | B |

TABLE II-continued

| Compound | | Name | IC$_{50}$ | Ret. Time | MS (M + 1) | LCMS Method |
|---|---|---|---|---|---|---|
| 540 | Chiral | 4-{4-(3-fluoro-4-methoxyphenyl)-6-[(2R)-2-methyl-4-(3-methylpyridin-2-yl)piperazin-1-yl]pyrimidin-2-yl}morpholine | * | 1.1 | 479.35 | B |
| 541 | Chiral | 4-(4-(3-fluoro-4-methoxyphenyi)-6-{(2R)-2-methyl-4-[3-(trifluoromethyl)pyridin-2-yl]piperazin-1-yl}pyrimidin-2-yl)morpholine | * | 1.22 | 533.35 | B |
| 542 | Chiral | 4-[4-[(2R)-4-(3-chloropyridin-2-yl)-2-methylpiperazin-1-yl]-6-(3-fluoro-4-methoxyphenyl)pyrimidin-2-yl]morpholine | * | 1.2 | 499.31 | B |

TABLE II-continued

| Compound | | Name | IC$_{50}$ | Ret. Time | MS (M + 1) | LCMS Method |
|---|---|---|---|---|---|---|
| 543 | Chiral | 4{4-(3-isopropoxyphenyl)-6-[(2R)-2-methyl-4-(3-methylpyridin-2-yl)piperazin-1-yl]pyrimidin-2-yl}morpholine | * | 1.14 | 489.39 | B |
| 544 | Chiral | 4-[4-[(2R)-4-(3-chloropyridin-2-yl)-2-methylpiperazin-1-yl]-6-(3-isopropoxyphenyl)pyrimidin-2-yl]morpholine | * | 1.23 | 509.36 | B |
| 545 | | 4-(3-chloro-4-fluorophenyl)-2-[(3S)-tetrahydrofuran-3-yloxy]-6-{4-[3-(trifluoromethyl)pyridin-2-yl]piperazin-1-yl}pyrimidine | * | 1.31 | 524.21 | B |

TABLE II-continued
| Compound | | Name | IC$_{50}$ | Ret. Time | MS (M + 1) | LCMS Method |
|---|---|---|---|---|---|---|
| 546 | 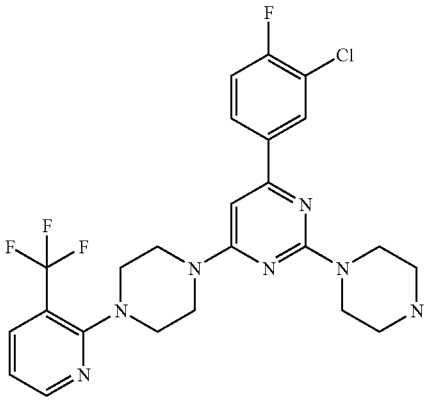 | 4-(3-chloro-4-fluorophenyl)-2-piperazin-1-yl-6-{4-[3-(trifluoromethyl)pyridin-2-yl]piperazin-1-yl}pyrimidine | * | 1.26 | 522.24 | B |
| 547 | 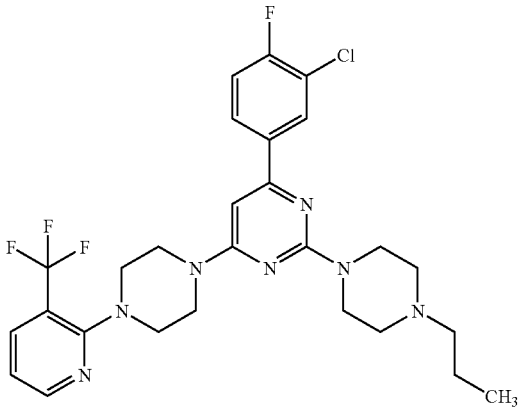 | 4-(3-chloro-4-fluorophenyl)-2-(4-propylpiperazin-1-yl)-6-{4-[3-(trifluoromethyl)pyridin-2-yl]piperazin-1-yl}pyrimidine | * | 1.26 | 564.29 | B |
| 548 | 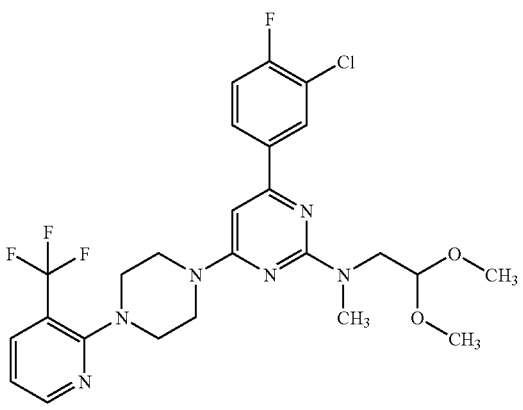 | 4-(3-chloro-4-fluorophenyl)-N-(2,2-dimethoxyethyl)-N-methyl-6-{4-[3-(trifluoromethyl)pyridin-2-yl]piperazin-1-yl}pyrimidin-2-amine | * | 1.28 | 555.27 | B |

TABLE II-continued
| Compound | | Name | IC$_{50}$ | Ret. Time | MS (M + 1) | LCMS Method |
|---|---|---|---|---|---|---|
| 549 |  | 2-[(4-(3-chloro-4-fluorophenyl)-6-{4-[3-(trifluoromethyl)pyridin-2-yl]piperazin-1-yl}pyrimidin-2-yl)(methyl)amino]ethanol | * | 1.21 | 511.22 | B |
| 550 | | 4-(3-chloro-4-fluorophenyl)-2-[(2S)-2-(methoxymethyl)pyrrolidin-1-yl]-6-{4-[3-(trifluoromethyl)pyridin-2-yl]piperazin-1-yl}pyrimidine | * | 1.25 | 551.25 | B |
| 551 | Chiral 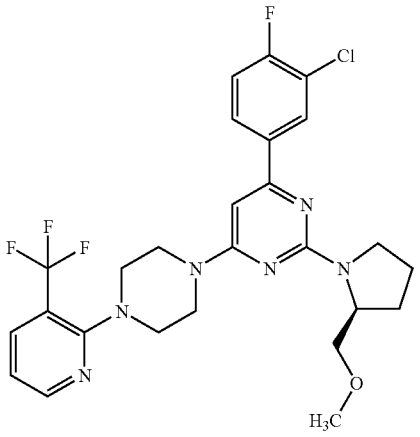 | | * | 1.24 | 551.25 | B |

TABLE II-continued
| Compound | | Name | IC$_{50}$ | Ret. Time | MS (M + 1) | LCMS Method |
|---|---|---|---|---|---|---|
| 552 | 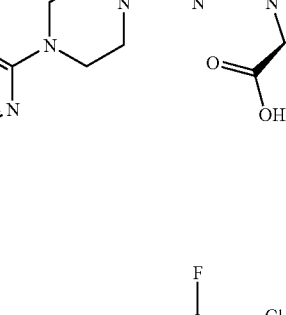 | 1-(4-(3-chloro-4-fluorophenyl)-6-{4-[3-(trifluoromethyl)pyridin-2-yl]piperazin-1-yl}pyrimidin-2-yl)-L-proline | * | 1.22 | 551.24 | B |
| 553 | 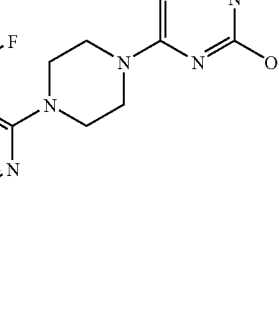 | 4-(3-chloro-4-fluorophenyl)-2-(cyclopropylmethoxy)-6-{4-[3-(trifluoromethyl)pyridin-2-yl]piperazin-1-yl}pyrimidine | * | 1.32 | 508.23 | B |
| 554 | 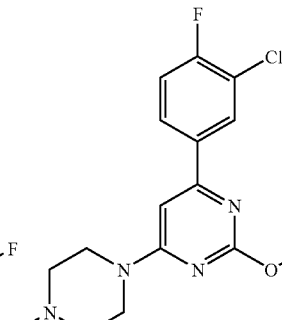 | 4-(3-chloro-4-fluorophenyl)-2-(2-methoxyethoxy)-6-{4-[3-(trifluoromethyl)pyridin-2-yl]piperazin-1-yl}pyrimidine | * | 1.28 | 512.23 | B |

TABLE II-continued

| Compound | | Name | IC$_{50}$ | Ret. Time | MS (M + 1) | LCMS Method |
|---|---|---|---|---|---|---|
| 555 | 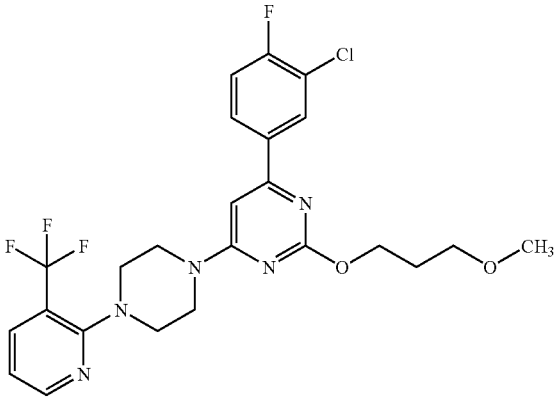 | 4-(3-chloro-4-fluorophenyl)-2-(3-methoxypropoxy)-6-{4-[3-(trifluoromethyl)pyridin-2-yl]piperazin-1-yl}pyrimidine | * | 1.29 | 526.24 | B |
| 556 | 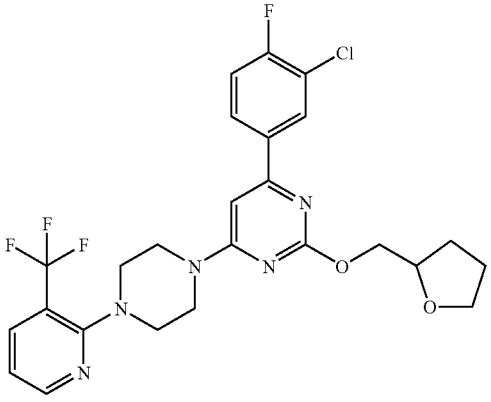 | 4-(3-chloro-4-fluorophenyl)-2-(tetrahydrofuran-2-ylmethoxy)-6-{4-[3-(trifluoromethyl)pyridin-2-yl]piperazin-1-yl}pyrimidine | * | 1.3 | 538.25 | B |
| 557 | 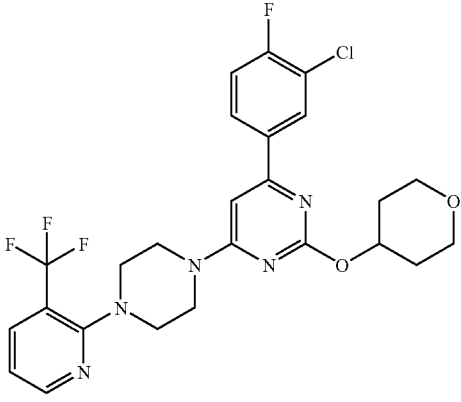 | 4-(3-chloro-4-fluorophenyl)-2-(tetrahydro-2H-pyran-4-yloxy)-6-{4-[3-(trifluoromethyl)pyridin-2-yl]piperazin-1-yl}pyrimidane | * | 1.3 | 538.25 | B |

TABLE II-continued

| Compound | Name | IC$_{50}$ | Ret. Time | MS (M + 1) | LCMS Method |
|---|---|---|---|---|---|
| 558 | 4-(3-chloro-4-fluorophenyl)-2-(2-pyrrolidin-1-ylethoxy)-6-{4-[3-(trifluoromethyl)pyridin-2-yl]piperazin-1-yl}pyrimidine | * | 1.23 | 551.29 | B |
| 559 | 4-(3-chloro-4-fluorophenyl)-2-[(1-methylpiperidin-3-yl)oxy]-6-{4-[3-(trifluoromethyl)pyridin-2-yl]piperazin-1-yl}pyrimidine | * | 1.25 | 551.30 | B |
| 560 | 4-(3-chloro-4-fluorophenyl)-2-(pyrrolidin-3-ylmethoxy)-6-{4-(3-(trifluoromethyl)pyridin-2-yl]piperazin-1-yl}pyrimidine | * | 1.24 | 537.25 | B |

TABLE II-continued

| Compound | Name | IC$_{50}$ | Ret. Time | MS (M + 1) | LCMS Method |
|---|---|---|---|---|---|
| 561 | 4-(3-chloro-4-fluorophenyl)-2-(piperidin-4-yloxy)-6-{4-[3-(trifluoromethyl)pyridin-2-yl]piperazin-1-yl}pyrimidine | * | 1.24 | 537.29 | B |
| 562 | 1-(4-(3-chloro-4-fluorophenyl)-6-{4-[3-(trifluoromethyl)pyridin-2-yl]piperazin-1-yl}pyrimidin-2-yl)-N,N-dimethylpyrrolidin-3-amine | * | 1.19 | 550.37 | B |
| 563 | 1-(4-(3-chloro-4-fluorophenyl)-6-{4-[3-(trifluoromethyl)pyridin-2-yl]piperazin-1-yl}pyrimidin-2-yl)-N,N-diethylpiperidin-4-amine | * | 1.22 | 592.42 | B |

TABLE II-continued

| Compound | | Name | IC$_{50}$ | Ret. Time | MS (M + 1) | LCMS Method |
|---|---|---|---|---|---|---|
| 564 | 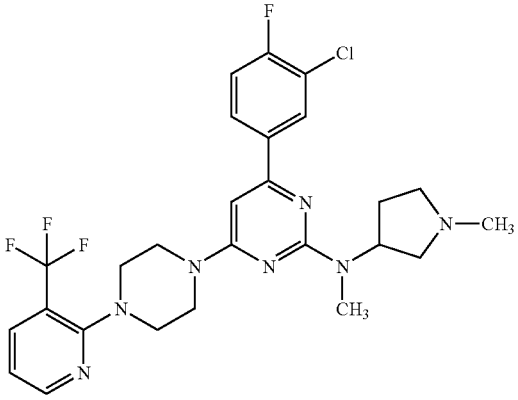 | 4-(3-chloro-4-fluorophenyl)-N-methyl-N-(1-methylpyrrolidin-3-yl)-6-{4-[3-(trifluoromethyl)pyridin-2-yl]piperazin-1-yl}pyrimidin-2-amine | * | 1.24 | 550.38 | B |
| 565 | 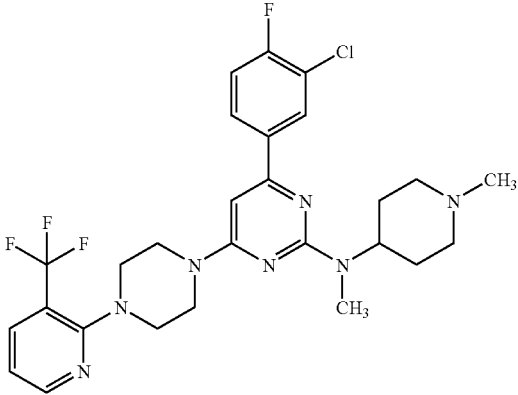 | 4-(3-chloro-4-fluorophenyl)-N-methyl-N-(1-methylpiperidin-4-yl)-6-{4-[3-(trifluoromethyl)pyridin-2-yl]piperazin-1-yl}pyrimidin-2-amine | * | 1.19 | 564.39 | B |
| 566 | 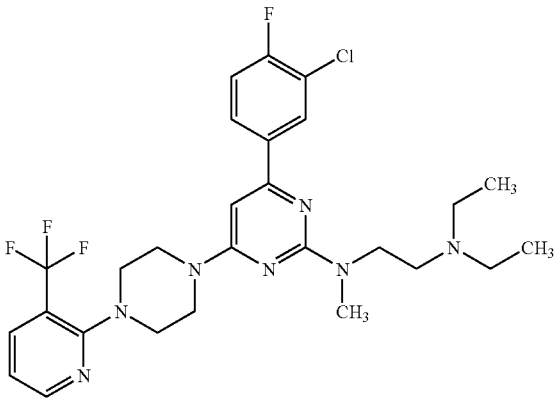 | N-1-(4-(3-chloro-4-fluorophenyl)-6-{4-[3-(trifluoromethyl)pyridin-2-yl]piperazin-1-yl}pyrimidin-2-yl)-N-2-,N-2-diethyl-N-1-methylethane-1,2-diamine | * | 1.25 | 566.39 | B |

TABLE II-continued

| Compound | Name | IC$_{50}$ | Ret. Time | MS (M + 1) | LCMS Method |
|---|---|---|---|---|---|
| 567 | 1-(4-(3-chloro-4-fluorophenyl)-6-{4-[3-(trifluoromethyl)pyridin-2-yl]piperazin-1-yl}pyrimidin-2-yl)-L-prolinamide | * | 1.19 | 550.34 | B |
| 568 | 1-(4-(3-chloro-4-fluorophenyl)-6-{4-[3-(trifluoromethyl)pyridin-2-yl]piperazin-1-yl}pyrimidin-2-yl)pyrrolidin-3-amine | * | 1.16 | 522.33 | B |
| 569 | 1-(4-(3-chloro-4-fluorophenyl)-6-{4-[3-(trifluoromethyl)pyridin-2-yl]piperazin-1-yl}pyrimidin-2-yl)piperidin-4-amine | * | 1.21 | 536.35 | B |

TABLE II-continued

| Compound | | Name | IC$_{50}$ | Ret. Time | MS (M + 1) | LCMS Method |
|---|---|---|---|---|---|---|
| 570 | 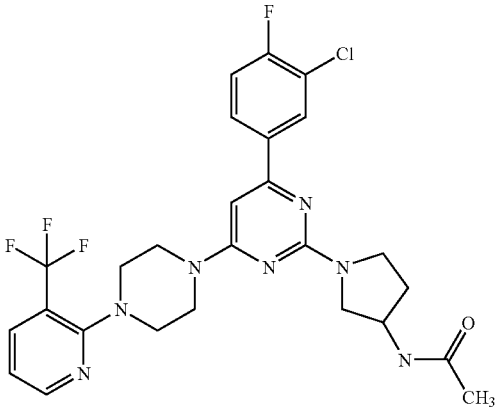 | N-[1-(4-(3-chloro-4-fluorophenyl)-6-{4-[3-(trifluoromethyl)pyridin-2-yl]piperazin-1-yl}pyrimidin-2-yl)pyrrolidin-3-yl]acetamide | * | 1.2 | 564.36 | B |
| 571 | 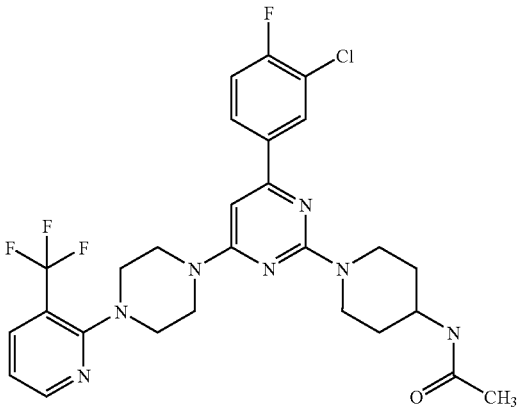 | N-[1-(4-(3-chloro-4-fluorophenyl)-6-{4-[3-(trifluoromethyl)pyridin-2-yl]piperazin-1-yl}pyrimidin-2-yl)piperidin-4-yl]acetamide | * | 1.5 | 295.00 | B |
| 572 | 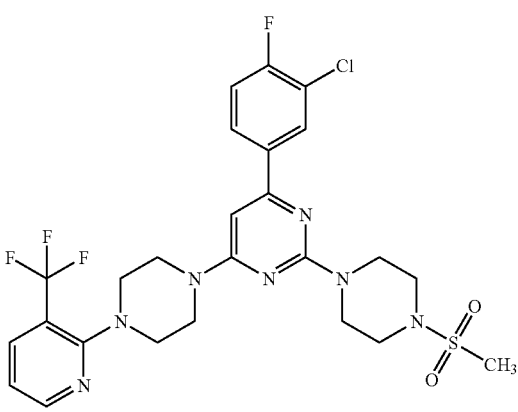 | 4-(3-chloro-4-fluorophenyl)-2-[4-(methylsulfonyl)piperazin-1-yl]-6-{4-[3-(trifluoromethyl)pyridin-2-yl]piperazin-1-yl}pyrimidine | * | 1.3 | 600.33 | B |

TABLE II-continued

| Compound | | Name | IC$_{50}$ | Ret. Time | MS (M + 1) | LCMS Method |
|---|---|---|---|---|---|---|
| 573 | | 4-(3-chloro-4-fluorophenyl)-N,N-diethyl-6-{4-[3-(trifluoromethyl)pyridin-2-yl]piperazin-1-yl}pyrimidin-2-amine | * | 1.27 | 509.20 | B |
| 574 | | 4-(4-phenyl-6-{4-[3-(trifluoromethyl)pyridin-2-yl]piperazin-1-yl}pyrimidin-2-yl)morpholine | * | 1.19 | 471.22 | B |
| 575 | | 4-(4-(2-methylpyridin-4-yl)-6-{4-[3-(trifluoromethyl)pyridin-2-yl]piperazin-1-yl}pyrimidin-2-yl)morpholine | * | 1.2 | 486.24 | B |
| 576 | | 4-(4-(4-fluoro-3-methylphenyl)-6-{4-[3-(trifluoromethyl)pyridin-2-yl]piperazin-1-yl}pyrimidin-2-yl)morpholifle | * | 1.24 | 503.29 | B |

TABLE II-continued
| Compound | | Name | IC₅₀ | Ret. Time | MS (M + 1) | LCMS Method |
|---|---|---|---|---|---|---|
| 577 | 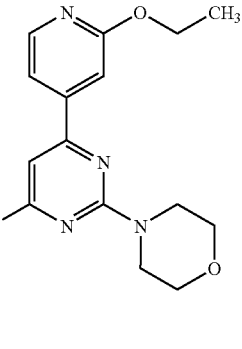 | 4-(4-(2-ethoxypyridin-4-yl)-6-{4-[3-(trifluoromethyl)pyridin-2-yl]piperazin-1-yl}pyrimidin-2-yl)morpholine | * | 1.31 | 516.30 | B |
| 578 | 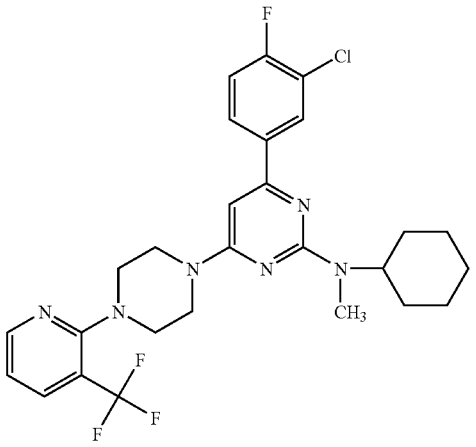 | 4-(3-chloro-4-fluorophenyl)-N-cyclohexyl-N-methyt-6-{4-[3-(trifluoromethyl)pyridin-2-yl]piperazin-1-yl}pyrimidin-2-amine | * | 1.32 | 549.28 | B |
| 579 | 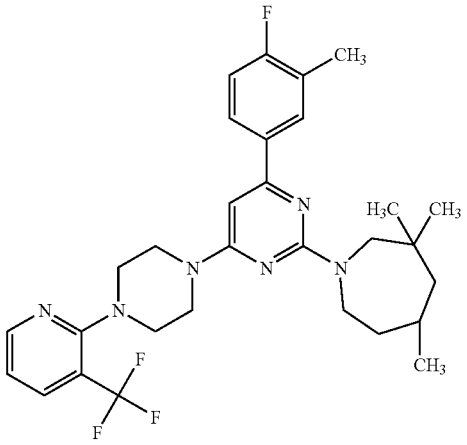 | 1-(4-(3-chloro-4-fluorophenyl)-6-{4-[3-(trifluoromethyl)pyridin-2-yl]piperazin-1-yl}pyrimidin-2-yl)-3,3,5-trimethylazepane | * | 1.36 | 577.32 | B |

TABLE II-continued

| Compound | | Name | IC$_{50}$ | Ret. Time | MS (M + 1) | LCMS Method |
|---|---|---|---|---|---|---|
| 580 | 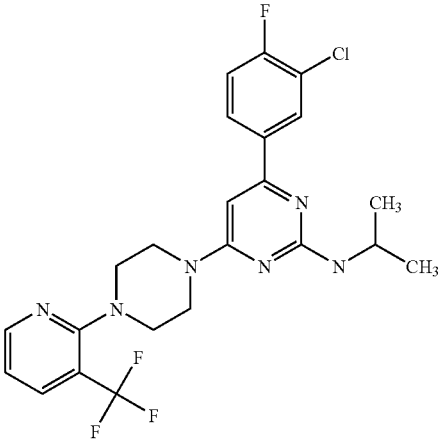 | 4-(3-chloro-4-fluorophenyl)-N-isopropyl-6-{4-[3-(trifluoromethyl)pyridin-2-yl]piperazin-1-yl}pyrimidin-2-amine | * | 1.25 | 495.24 | B |
| 581 | 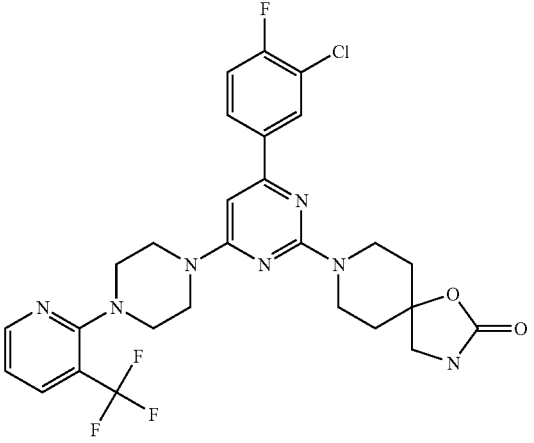 | 8-(4-(3-chloro-4-fluorophenyl)-6-{4-[3-(trifluoromethyl)pyridin-2-yl]piperazin-1-yl}pyrimidin-2-yl)-1-oxa-3,8-diazaspiro[4.5]decan-2-one | * | 1.25 | 592.31 | B |
| 582 | 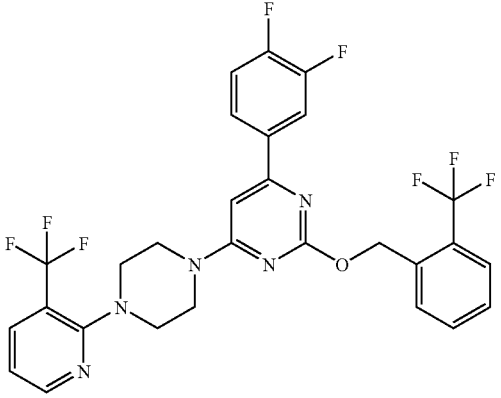 | 4-(3,4-difluorophenyl)-2-{[2-(trifluoromethyl)benzyl]oxy}-6-{4-[3-(trifluoromethyl)pyridin-2-yl]piperazin-1-yl}pyrimidine | * | 1.42 | 596.24 | B |

TABLE II-continued
| Compound | | Name | IC$_{50}$ | Ret. Time | MS (M + 1) | LCMS Method |
|---|---|---|---|---|---|---|
| 583 | 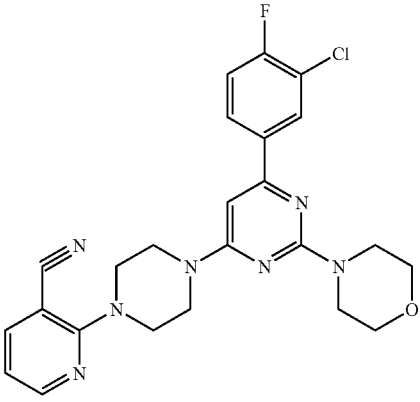 | 2-{4-[6-(3-chloro-4-fluorophenyl)-2-morpholin-4-ylpyrimidin-4-yl]piperazin-1-yl}nicotinonitrile | * | 1.26 | 480.28 | B |
| 584 | 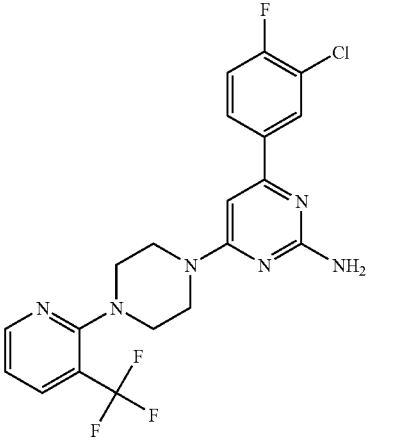 | 4-(3-chloro-4-fluorophenyl)-6-{4-[3-(trifluoromethyl)pyridin-2-yl]piperazin-1-yl}pyrimidin-2-amine | * | 1.2 | 453.19 | B |
| 585 | 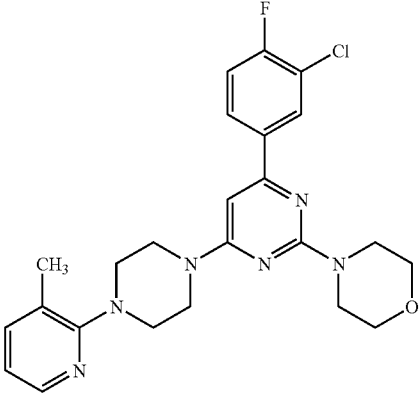 | 4-{4-(3-chloro-4-fluorophenyl)-6-[4-(3-methylpyridin-2-yl)piperazin-1-yl]pyrimidin-2-yl}morpholine | * | 1.17 | 469.28 | B |

TABLE II-continued

| Compound | | Name | IC$_{50}$ | Ret. Time | MS (M + 1) | LCMS Method |
|---|---|---|---|---|---|---|
| 586 | | 4-{4-(3-chloro-4-fluorophenyl)-6-[4-(3-methoxypyridin-2-yl)piperazan-1-yl]pyrimidin-2-yl}morpholine | * | 1.18 | 485.28 | B |
| 587 | | 2-{4-[6-(3-chloro-4-fluorophenyl)-2-morpholin-4-ylpyrimidin-4-yl]piperazin-1-yl}pyridin-3-amine | * | 1.12 | 470.28 | B |
| 588 | | N-(2-{4-[6-(3-chloro-4-fluorophenyl)-2-morpholin-4-ylpyrimidin-4-yl]piperazin-1-yl}pyridin-3-yl)methanesulfonamide | * | 1.17 | 548.28 | B |
| 589 | | 3-(2-morpholin-4-yl-6-{4-[3-(trifluoromethyl)pyridin-2-yl]piperazin-1-yl}pyrimidin-4-yl)phenylamine | * | 1.16 | 486.25 | B |

TABLE II-continued

| Compound | | Name | IC$_{50}$ | Ret. Time | MS (M + 1) | LCMS Method |
|---|---|---|---|---|---|---|
| 590 | | 4-(4-(2,6-dimethylpyridin-4-yl)-6-{4-[3-(trifluoromethyl)pyridin-2-yl]piperazin-1-yl}pyrimidin-2-yl)morpholine | * | 1.21 | 500.28 | B |
| 591 | | 4-(2,6-dimethylpyridin-4-yl)-N,N-diethyl-6-{4-[3-(trifluoromethyl)pyridin-2-yl]piperazin-1-yl}pyrimidin-2-amine | * | 1.27 | 486.30 | B |
| 592 | | 4-(4-(2-isopropylpyridin-4-yl)-6-{4-[3-(trifluoromethyl)pyridin-2-yl]piperazin-1-yl}pyrimidin-2-yl)morpholine | * | 1.24 | 514.29 | B |
| 593 | | 4-(4-(5-chloropyridin-3-yl)-6-{4-[3-(trifluoromethyl)pyridin-2-yl]piperazin-1-yl}pyrimidin-2-yl)morpholine | * | 1.33 | 506.22 | B |

TABLE II-continued
| Compound | | Name | IC$_{50}$ | Ret. Time | MS (M + 1) | LCMS Method |
|---|---|---|---|---|---|---|
| 594 | 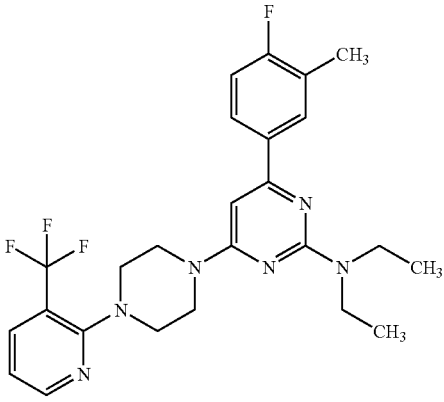 | N,N-diethyl-4-(4-fluoro-3-methylphenyl)-6-{4-[3-(trifluoromethyl)pyridin-2-yl]piperazin-1-yl}pyrimidin-2-amine | * | 1.25 | 489.27 | B |
| 595 | 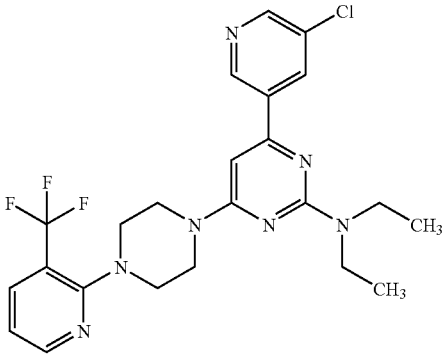 | 4-(5-chloropyridin-3-yl)-N,N-diethyl-6-{4-[3-(trifluoromethyl)pyridin-2-yl]piperazin-1-yl}pyrimidin-2-amine | * | 1.3 | 492.30 | B |
| 596 | 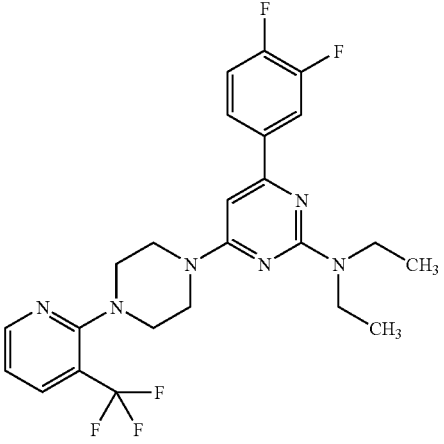 | 4-(3,4-difluorophenyl)-N,N-diethyl-6-{4-[3-(trifluoromethyl)pyridin-2-yl]piperazin-1-yl}pyrimidin-2-amine | * | 1.25 | 494.35 | B |

TABLE II-continued
| Compound | | Name | IC$_{50}$ | Ret. Time | MS (M + 1) | LCMS Method |
|---|---|---|---|---|---|---|
| 597 | 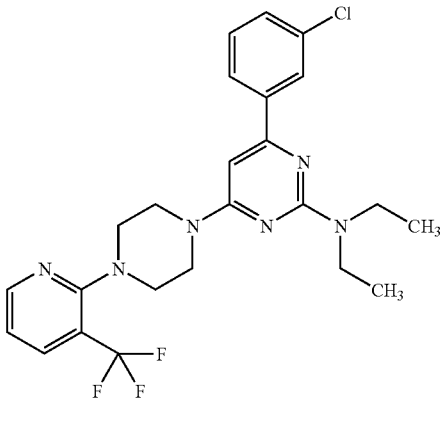 | 4-(3-chlorophenyl)-N,N-diethyl-6-{4-[3-(trifluoromethyl)pyridin-2-yl]piperazin-1-yl}pyrimidin-2-amine | * | 1.26 | 493.32 | B |
| 598 |  | 4-(3-chloro-4-fluorophenyl)-2-(4-isopropylpiperazin-1-yl)-6-{4-[3-(trifluoromethyl)pyridin-2-yl]piperazin-1-yl}pyrimidine | * | 1.26 | 564.27 | B |
| 599 | 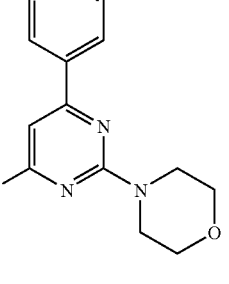 | 4-(4-(1-oxidopyridin-4-yl)-6-{4-[3-(trifluoromethyl)pyridin-2-yl]pyrimidin-2-yl)morpholine | | 1.24 | 488.33 | B |

TABLE II-continued
| Compound | | Name | IC$_{50}$ | Ret. Time | MS (M + 1) | LCMS Method |
|---|---|---|---|---|---|---|
| 600 | 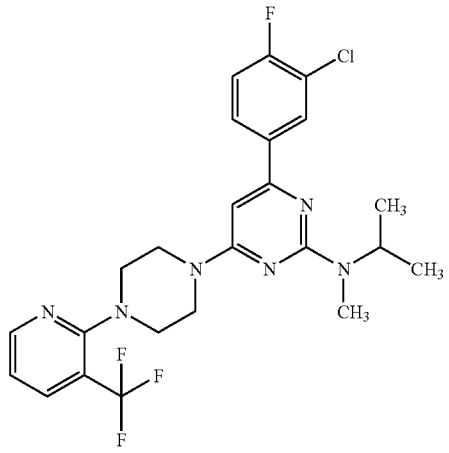 | 4-(3-chloro-4-fluorophenyl)-N-isopropyl-N-methyl-6-{4-[3-(trifluoromethyl)pyridin-2-yl]piperazin-1-yl}pyrimidin-2-amine | * | 1.26 | 509.30 | B |
| 601 | 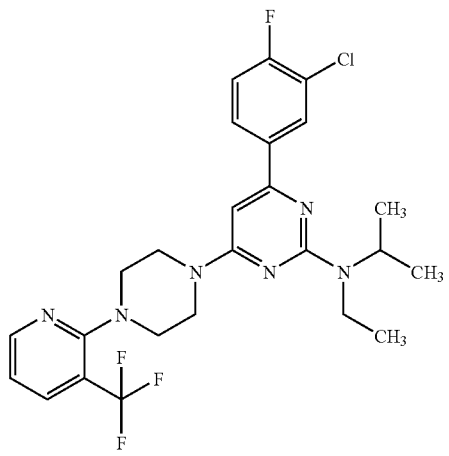 | 4-(3-chloro-4-fluorophenyl)-N-ethyl-N-isopropyl-6-{4-[3-(trifluoromethyl)pyridin-2-yl]piperazin-1-yl}pyrimidin-2-amine | * | 1.3 | 523.35 | B |
| 602 | 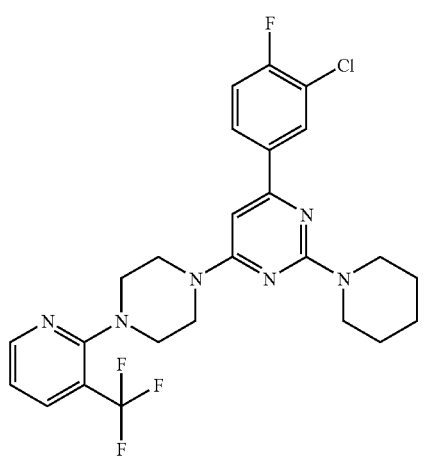 | 4-(3-chloro-4-fluorophenyl)-2-piperidin-1-yl-6-{4-[3-(trifluoromethyl)pyridin-2-yl]piperazin-1-yl}pyrimidine | * | 1.28 | 521.32 | B |

TABLE II-continued
| Compound | | Name | IC$_{50}$ | Ret. Time | MS (M + 1) | LCMS Method |
|---|---|---|---|---|---|---|
| 603 | 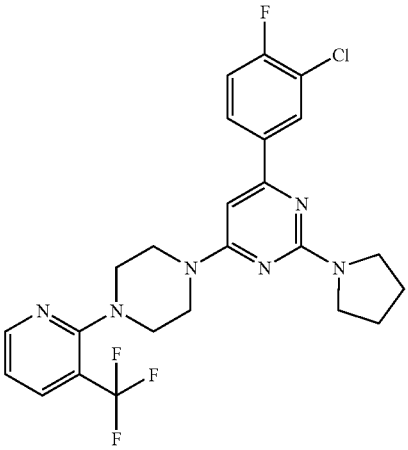 | 4-(3-chloro-4-fluorophenyl)-2-pyrrolidin-1-yl-6-{4-[3-(trifluoromethyl)pyridin-2-yl]piperazin-1-yl}pyrimidine | * | 1.23 | 507.30 | B |
| 604 | 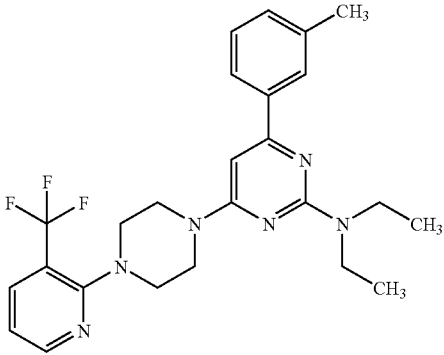 | N,N-diethyl-4-(3-methylphenyl)-6-{4-[3-(trifluoromethyl)pyridin-2-yl]piperazin-1-yl}pyrimidin-2-amine | * | 1.24 | 471.26 | B |
| 605 | 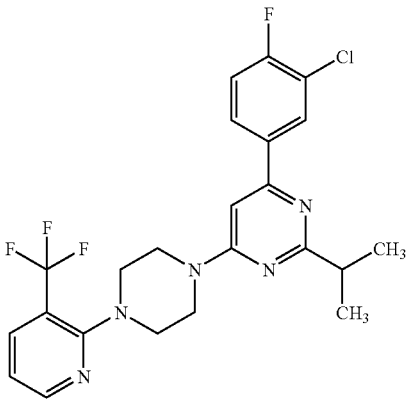 | 4-(3-chloro-4-fluorophenyl)-2-isopropyl-6-{4-[3-(trifluoromethyl)pyridin-2-yl]piperazin-1-yl}pyrimidine | * | 1.24 | 480.28 | B |

TABLE II-continued

| Compound | Name | IC$_{50}$ | Ret. Time | MS (M + 1) | LCMS Method |
|---|---|---|---|---|---|
| 606 | 4-(4-(6-methylpyridin-3-yl)-6-{4-[3-(trifluoromethyl)pyridin-2-yl]piperazin-1-yl}pyrimidin-2-yl)morpholine | * | 1.2 | 486.36 | B |
| 607 | N,N-diethyl-4-(6-methylpyridin-3-yl)-6-{4-[3-(trifluoromethyl)pyridin-2-yl]piperazin-1-yl}pyrimidin-2-amine | * | 1.21 | 472.37 | B |
| 608 | 4-(3-chloro-4-pyrrolidin-1-ylphenyl)-2-pyrrolidin-1-yl-6-{4-[3-(trifluoromethyl)pyridin-2-yl]piperazin-1-yl}pyrimidine | * | 1.29 | 558.38 | B |

TABLE II-continued

| Compound | Name | IC$_{50}$ | Ret. Time | MS (M + 1) | LCMS Method |
|---|---|---|---|---|---|
| 609 | 4-(3-chloro-4-fluorophenyl)-2-(2-methylpyrrolidin-1-yl)-6-{4-[3-(trifluoromethyl)pyridin-2-yl]piperazin-1-yl}pyrimidine | * | 1.26 | 521.20 | B |
| 610 | [(2R)-1-(4-(3-chloro-4-fluorophenyl)-6-{4-[3-(trifluoromethyl)pyridin-2-yl]piperazin-1-yl}pyrimidin-2-yl)pyrrolidin-2-yl]methanol | * | 1.22 | 537.32 | B |
| 611 | 4-(3-chloro-4-fluorophenyl)-2-(2-methylpiperidin-1-yl)-6-{4-[3-(trifluoromethyl)pyridin-2-yl]piperazin-1-yl}pyrimidine | * | 1.3 | 535.34 | B |

TABLE II-continued
| Compound | | Name | IC$_{50}$ | Ret. Time | MS (M + 1) | LCMS Method |
|---|---|---|---|---|---|---|
| 612 | 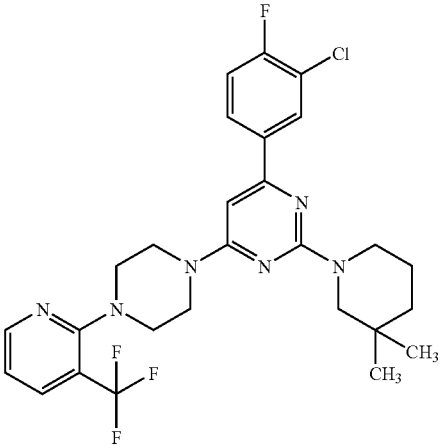 | 4-(3-chloro-4-fluorophenyl)-2-(3,3-dimethylpiperidin-1-yl)-6-{4-[3-(trifluoromethyl)pyridin-2-yl]piperazin-1-yl}pyrimidine | * | 1.32 | 549.36 | B |
| 613 | 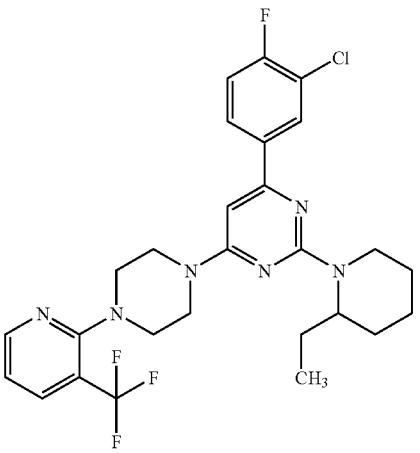 | 4-(3-chloro-4-fluorophenyl)-2-(2-ethylpiperidin-1-yl)-6-{4-[3-(trifluoromethyl)pyridin-2-yl]piperazin-1-yl}pyrimidine | * | 1.32 | 550.39 | B |
| 614 | 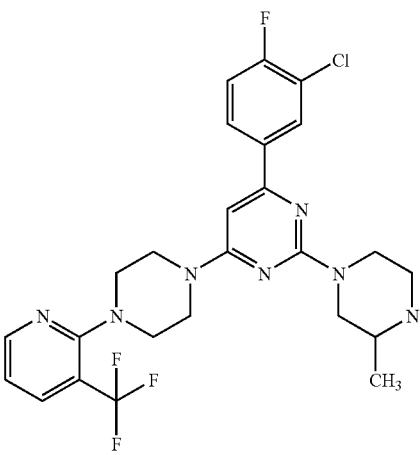 | 4-(3-chloro-4-fluorophenyl)-2-(3-methylpiperazin-1-yl)-6-{4-[3-(trifluoromethyl)pyridin-2-yl]piperazin-1-yl}pyrimidine | * | 1.27 | 536.35 | B |

TABLE II-continued
| Compound | | Name | IC$_{50}$ | Ret. Time | MS (M + 1) | LCMS Method |
|---|---|---|---|---|---|---|
| 615 | 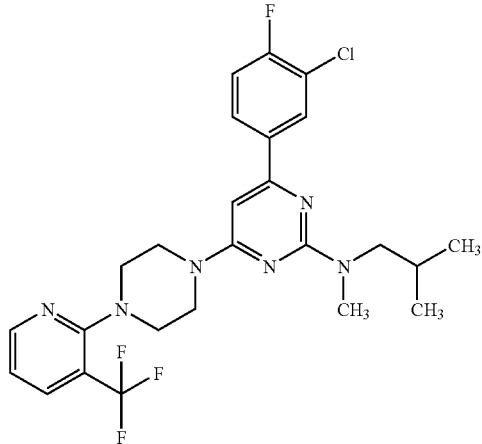 | 4-(3-chloro-4-fluorophenyl)-N-isobuty-methyl-6-{4-[3-(trifluoromethyl)pyridin-2-yl]piperazin-1-yl}pyrimidin-2-amine | * | 1.3 | 525.36 | B |
| 616 | 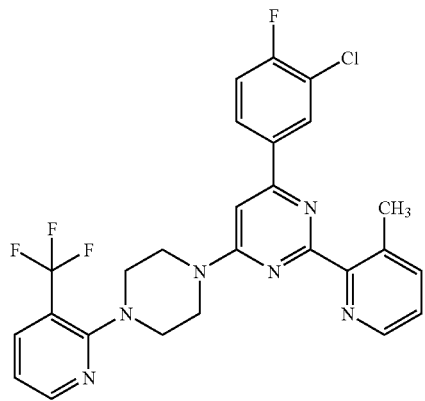 | 4-(3-chloro-4-fluorophenyl)-2-(3-methylpyridin-2-yl)-6-{4-[3-(trifluoromethyl)pyridin-2-yl]piperazin-1-yl}pyrimidine | * | 1.27 | 529.31 | B |
| 617 | 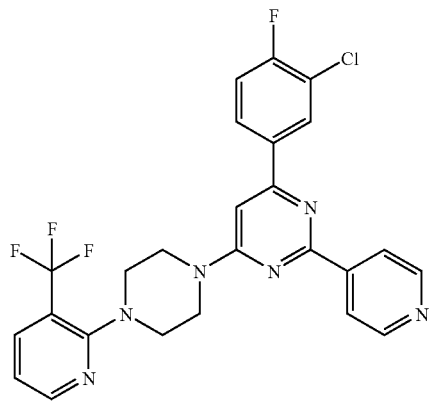 | 4-(3-chloro-4-fluorophenyl)-2-pyridin-4-yl-6-{4-[3-(trifluoromethyl)pyridin-2-yl]piperazin-1-yl}pyrimidine | * | 1.35 | 515.28 | B |

TABLE II-continued

| Compound | | Name | IC$_{50}$ | Ret. Time | MS (M + 1) | LCMS Method |
|---|---|---|---|---|---|---|
| 618 | | 4-(3-chlorophenyl)-2-(2-isopropyl-1H-imidazol-1-yl)-6-{4-[3-(trifluoromethyl)pyridin-2-yl]piperazin-1-yl}pyrimidine | * | 1.26 | 528.33 | B |
| 619 | | N-(4-(3-chloro-4-fluorophenyl)-6-{4-[3-(trifluoromethyl)pyridin-2-yl]piperazin-1-yl}pyrimidin-2-yl)-N-methylglycine | * | 1.24 | 525.30 | B |
| 620 | | N-(4-(3-chloro-4-fluorophenyl)-6-{4-[3-(trifluoromethyl)pyridin-2-yl]piperazin-1-yl}pyrimidin-2-yl)alanine | * | 1.2 | 525.30 | B |
| 621 | | 2-[(4-(3-chloro-4-fluorophenyl)-6-{4-[3-(trifluoromethyl)pyridin-2-yl]piperazin-1-yl}pyrimidin-2-yl)amino]butanoic acid | | 1.22 | 529.32 | B |

TABLE II-continued
| Compound | | Name | IC$_{50}$ | Ret. Time | MS (M + 1) | LCMS Method |
|---|---|---|---|---|---|---|
| 622 | 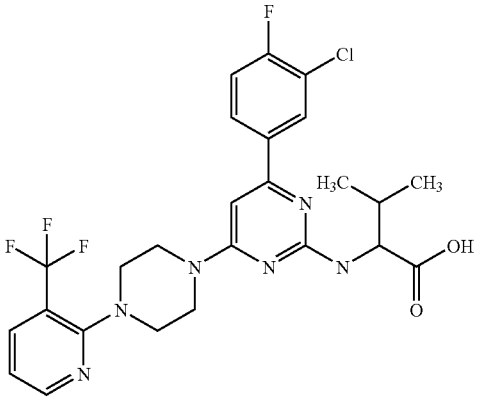 | N-(4-(3-chloro-4-fluorophenyl)-6-{4-[3-(trifluoromethyl)pyridin-2-yl]piperazin-1-yl}pyrimidin-2-yl)valine | | 1.23 | 553.33 | B |
| 623 | 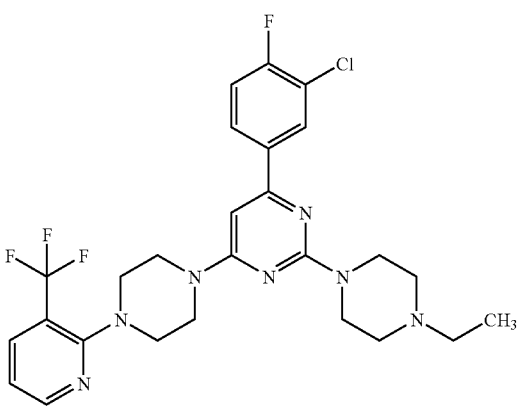 | 4-(3-chloro-4-fluorophenyl)-2-(4-ethylpiperazin-1-yl)-6-{4-[3-(trifluoromethyl)pyridin-2-yl]piperazin-1-yl}pyrimidine | * | 1.25 | 550.37 | B |
| 624 | 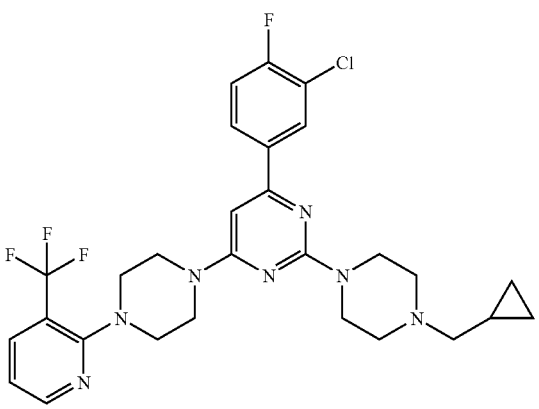 | 4-(3-chloro-4-fluorophenyl)-2-[4-(cyclopropylmethyl)piperazin-1-yl]-6-{4-[3-(trifluoromethyl)pyridin-2-yl]piperazin-1-yl}pyrimidine | * | 1.26 | 576.38 | B |

TABLE II-continued

| Compound | Name | IC$_{50}$ | Ret. Time | MS (M + 1) | LCMS Method |
|---|---|---|---|---|---|
| 625 | 2-(4-acetylpiperazin-1-yl)-4-(3-chloro-4-fluorophenyl)-6-{4-[3-(trifluoromethyl)pyridin-2-yl]piperazin-1-yl}pyrimidine | * | 1.28 | 564.36 | B |
| 626 | 4-(3-chloro-4-fluorophenyl)-2-(4-propionylpiperazin-1-yl)-6-{4-[3-(trifluoromethyl)pyridin-2-yl]piperazin-1-yl}pyrimidine | * | 1.3 | 578.37 | B |
| 627 | 4-(3-chloro-4-fluorophenyl)-2-[(2S,5R)-2,5-dimethylpiperazin-1-yl]-6-{4-[3-(trifluoromethyl)pyridin-2-yl]piperazin-1-yl}pyrimidine | * | 1.29 | 550.36 | B |

TABLE II-continued

| Compound | | Name | IC$_{50}$ | Ret. Time | MS (M + 1) | LCMS Method |
|---|---|---|---|---|---|---|
| 628 | | 4-(3-chloro-4-fluorophenyl)-6-{4-[3-(trifluoromethyl)pyridin-2-yl]piperazin-1-yl}-2-[(2S,5R)-2,4,5-trimethylpiperazin-1-yl]pyrimidine | * | 1.28 | 564.38 | B |
| 629 | | 4-(3-chloro-4-fluorophenyl)-2-(2-methylpiperazin-1-yl)-6-{4-[3-(trifluoromethyl)pyridin-2-yl]piperazin-1-yl}pyrimidine | * | 1.27 | 536.35 | B |
| 630 | | 4-(3-chloro-4-fluorophenyl)-2-(2,4-dimethylpiperazin-1-yl)-6-{4-[3-(trifluoromethyl)pyridin-2-yl]piperazin-1-yl}pyrimidine | * | 1.17 | 550.32 | B |
| 631 | | 4-(4-(5-methylpyridin-3-yl)-6-{4-[3-(trifluoromethyl)pyridin-2-yl]piperazin-1-yl}pyrimidin-2-yl)morpholine | * | 1.21 | 486.35 | B |

TABLE II-continued
| Compound | | Name | IC$_{50}$ | Ret. Time | MS (M + 1) | LCMS Method |
|---|---|---|---|---|---|---|
| 632 | 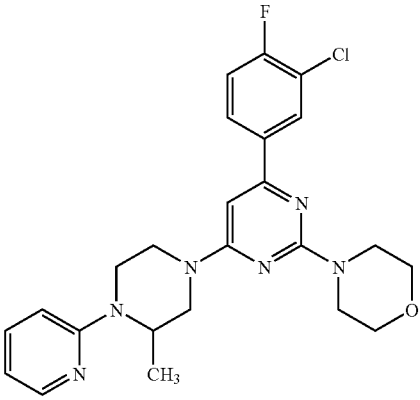 | 4-[4-(3-chloro-4-fluorophenyl)-6-(3-methyl-4-pyridin-2-yl piperazin-1-yl)pyrimidin-2-yl]morpholine | * | 1.14 | 469.33 | B |
| 633 | 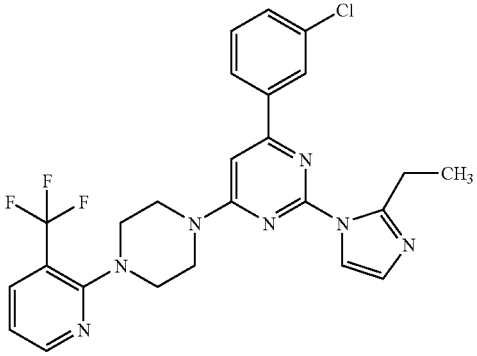 | 4-(3-chlorophenyl)-2-(2-ethyl-1H-imidazol-1-yl)-6-{4-[3-(trifluoromethyl)pyridin-2-yl]peperazin-1-yl}pyrimidine | * | 1.26 | 514.28 | B |
| 634 | 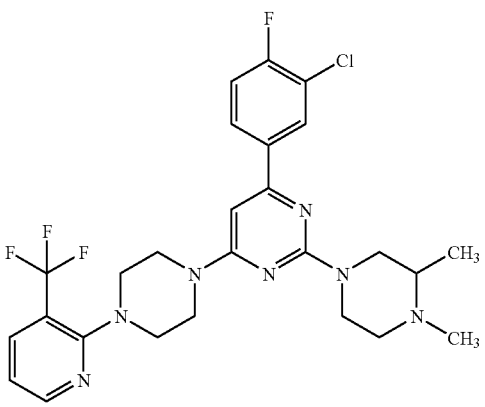 | 4-(3-chloro-4-fluorophenyl)-2-(3,4-dimethylpiperazin-1-yl)-6-{4-[3-(trifluoromethyl)pyridin-2-yl]piperazin-1-yl}pyrimidine | * | 1.26 | 550.32 | B |

TABLE II-continued
| Compound | | Name | IC$_{50}$ | Ret. Time | MS (M + 1) | LCMS Method |
|---|---|---|---|---|---|---|
| 635 | 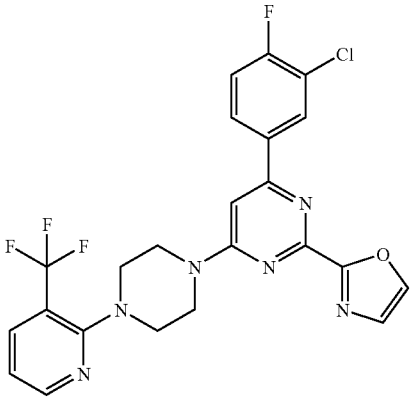 | 4-(3-chloro-4-fluorophenyl)-2-(1,3-oxazol-2-yl)-6-{4-[3-(trifluoromethyl)pyridin-2-yl]piperazin-1-yl}pyrimidine | * | 1.38 | 505.22 | B |
| 636 | 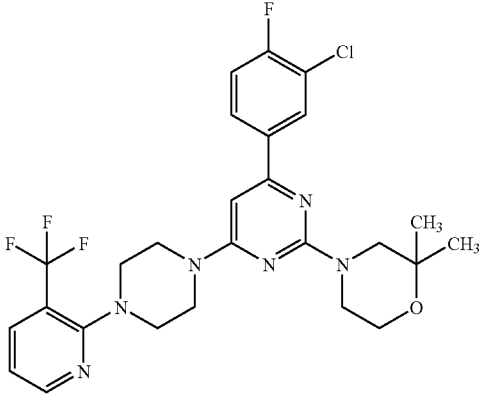 | 4-(4-(3-chloro-4-fluorophenyl)-6-{4-[3-(trifluoromethyl)pyridin-2-yl]piperazin-1-yl}pyrimidin-2-yl)-2,2-dimethylmorpholine | * | 1.34 | 551.29 | B |
| 637 | 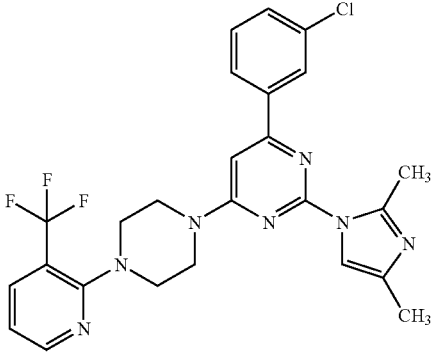 | 4-(3-chlorophenyl)-2-(2,4-dimethyl-1H-imidazol-1-yl)-6-(4-[3-(trifluoromethyl)pyridin-2-yl]piperazin-1-yl}pyrimidine | * | 1.26 | 514.27 | B |

TABLE II-continued

| Compound | Name | IC$_{50}$ | Ret. Time | MS (M + 1) | LCMS Method |
|---|---|---|---|---|---|
| 638 | 2-chloro-4-(4-fluoro-3-methylphenyl)-6-{4-[3-(trifluoromethyl)pyridin-2-yl]piperazin-1-yl}pyrimidine | * | 1.42 | 452.23 | B |
| 639 | 4-(3-chloro-4-fluorophenyl)-N-methyl-6-{4-[3-(trifluoromethyl)pyridin-2-yl]piperazin-1-yl}pyrimidin-2-amine | * | 1.21 | 467.24 | B |
| 640 | 4-(4-fluoro-3-methylphenyl)-N-isopropyl-N-methyl-6-{4-[3-(trifluoromethyl)pyridin-2-yl]piperazin-1-yl}pyrimidin-2-amine | * | 1.24 | 489.34 | B |

TABLE II-continued

| Compound | Name | IC$_{50}$ | Ret. Time | MS (M + 1) | LCMS Method |
|---|---|---|---|---|---|
| 641 | 4-(4-fluoro-3-methylphenyl)-2-(3-methylpiperazin-1-yl)-6-{4-[3-(trifluoromethyl)pyridin-2-yl]piperazin-1-yl}pyrimidine | * | 1.22 | 516.37 | B |
| 642 | 4-(4-fluoro-3-methylphenyl)-2-(2-methylpiperidin-1-yl)-6-{4-[3-(trifluoromethyl)pyridin-2-yl]piperazin-1-yl}pyrimidine | * | 1.26 | 515.35 | B |
| 643 | tert-butyl 4-(4-(4-fluoro-3-methylphenyl)-6-{4-[3-(trifluoromethyl)pyridin-2-yl]piperazin-1-yl}pyrimidin-2-yl)piperazine-1-carboxylate | * | 1.3 | 602.41 | B |

TABLE II-continued

| Compound | Name | IC$_{50}$ | Ret. Time | MS (M + 1) | LCMS Method |
|---|---|---|---|---|---|
| 644 | 2-[(4-(3-chloro-4-fluorophenyl)-6-{4-[3-(trifluoromethyl)pyridin-2-yl]piperazin-1-yl}pyrimidin-2-yl)(isopropyl)amino]ethanol | * | 1.24 | 539.31 | B |
| 645 | 4-(4-fluoro-3-methylphenyl)-2-piperazin-1-yl-6-{4-[3-(trifluoromethyl)pyridin-2-yl]piperazin-1-yl}pyrimidine | * | 1.21 | 502.33 | B |
| 646 | 4-{4-(3-chloro-4-fluorophenyl)-6-[3-methyl-4-(3-methylpyridin-2-yl)piperazin-1-yl]pyrimidin-2-yl}morpholine | * | 1.19 | 483.31 | B |

TABLE II-continued

| Compound | | Name | IC$_{50}$ | Ret. Time | MS (M + 1) | LCMS Method |
|---|---|---|---|---|---|---|
| 647 | | 4-(3-chlorophenyl)-2-(2-ethyl-4-methyl-1H-imidazol-1-yl)-6-(4-[3-(trifluoromethyl)pyridin-2-yl]piperazin-1-yl}pyrimidine | * | 1.26 | 528.31 | B |
| 648 | | 4-(3-chloro-4-fluorophenyl)-2-(2-ethyl-1H-imidazol-1-yl)-6-{4-[3-(trifluoromethyl)pyridin-2-yl]piperazin-1-yl}pyrimidine | * | 1.26 | 532.29 | B |
| 649 | | 2-(benzylthio)-4-(3-chloro-4-fluorophenyl)-6-{4-[3-(trifluoromethyl)pyridin-2-yl]piperazin-1-yl}pyrimidine | * | 1.5 | 560.24 | B |
| 650 | | 2-(benzylsulfonyl)-4-(3-chloro-4-fluorophenyl)-6-{4-[3-(trifluoromethyl)pyridin-2-yl]piperazin-1-yl}pyrimidine | * | 1.35 | 592.25 | B |

TABLE II-continued

| Compound | Name | IC$_{50}$ | Ret. Time | MS (M + 1) | LCMS Method |
|---|---|---|---|---|---|
| 651 | 4-(3-chloro-4-fluorophenyl)-2-(2-isopropyl-1H-imidazo-1-yl)-6-{4-[3-(trifluoromethyl)pyridin-2-yl]piperazin-1-yl}pyrimidine | * | 1.27 | 546.31 | B |
| 652 | 2-[4-(4-(3-chloro-4-fluorophenyl)-6-{4-[3-(trifluoromethyl)pyridin-2-yl]piperazin-1-yl}pyrimidin-2-yl)piperazin-1-yl]-N,N-dimethylacetamide | * | 1.26 | 607.39 | B |
| 653 | 1-(4-(3-chloro-4-fluorophenyl)-6-{4-[3-(trifluoromethyl)pyridin-2-yl]piperazin-1-yl}pyrimidin-2-yl)-N-methylpiperidine-4-carboxamide | * | 1.22 | 578.35 | B |

TABLE II-continued
| Compound | | Name | IC$_{50}$ | Ret. Time | MS (M + 1) | LCMS Method |
|---|---|---|---|---|---|---|
| 654 | 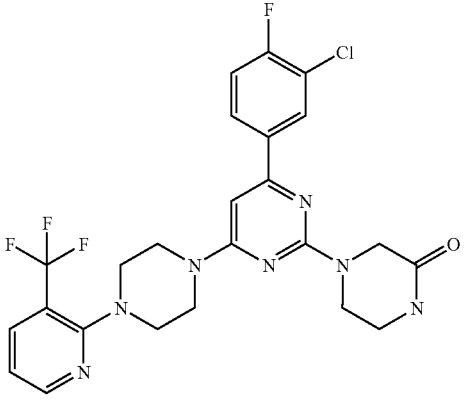 | 4-(4-(3-chloro-4-fluorophenyl)-6-{4-[3-(trifluoromethyl)pyridin-2-yl]piperazin-1-yl}pyrimidin-2-yl)piperazin-2-one | * | 1.32 | 536.21 | B |
| 655 | 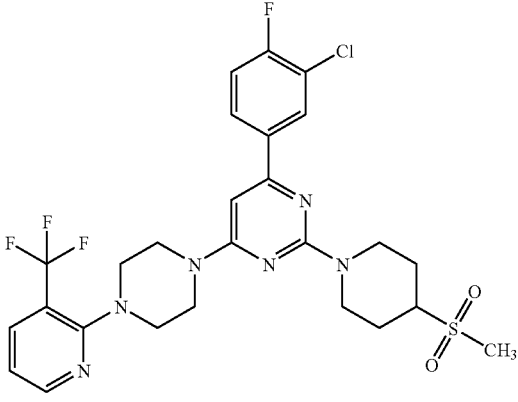 | 4-(3-chloro-4-fluorophenyl)-2-[4-(methylsulfonyl)piperidin-1-yl]-6-{4-[3-(trifluoromethyl)pyridin-2-yl]piperazin-1-yl}pyrimidine | * | 1.26 | 599.22 | B |
| 656 | 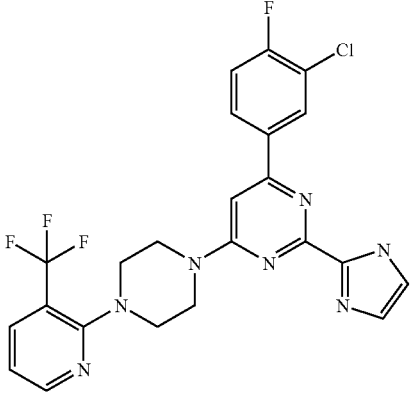 | 4-(3-chloro-4-fluorophenyl)-2-(1H-imidazol-2-yl)-6-{4-[3-(trifluoromethyl)pyridin-2-yl]piperazin-1-yl}pyrimidine | * | 1.26 | 504.27 | B |

TABLE II-continued
| Compound | | Name | IC$_{50}$ | Ret. Time | MS (M + 1) | LCMS Method |
|---|---|---|---|---|---|---|
| 657 | 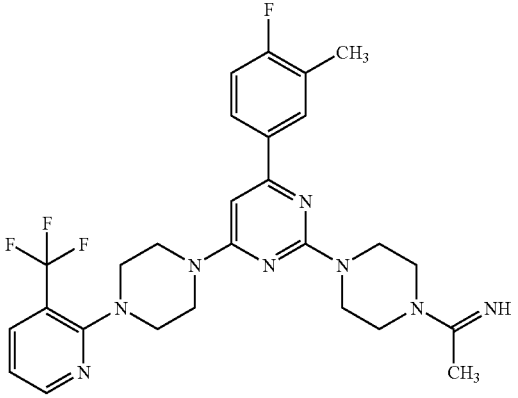 | 1-[4-(4-(4-fluoro-3-methylphenyl)-6-{4-[3-(trifluoromethyl)pyridin-2-yl]piperazin-1-yl}pyrimidin-2-yl)piperazin-1-yl]ethanimine | * | 1.18 | 543.40 | B |
| 658 | 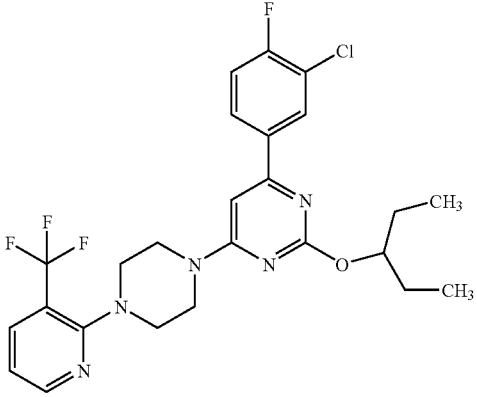 | 4-(3-chloro-4-fluorophenyl)-2-(1-ethylpropoxy)-6-{4-[3-(trifluoromethyl)pyridin-2-yl]piperazin-1-yl}pyrimidine | * | 1.35 | 524.19 | B |
| 659 | 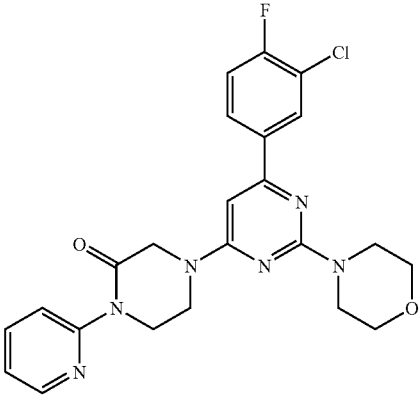 | 4-[6-(3-chloro-4-fluorophenyl)-2-morpholin-4-ylpyrimidin-4-yl]-1-pyridin-2-ylpiperazin-2-one | * | 1.25 | 469.22 | B |

TABLE II-continued
| Compound | | Name | IC$_{50}$ | Ret. Time | MS (M + 1) | LCMS Method |
|---|---|---|---|---|---|---|
| 660 | 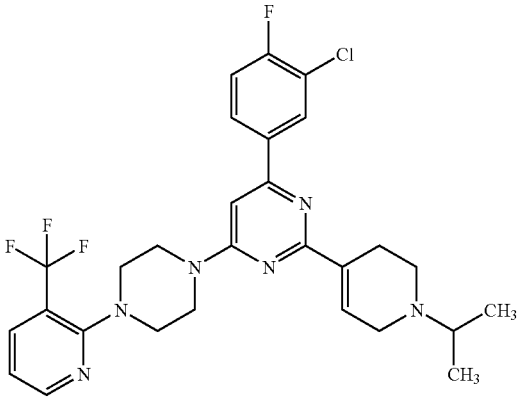 | 4-(3-chloro-4-fluorophenyl)-2-(1-isopropyl-1,2,3,6-tetrahydropyridin-4-yl)-6-{4-[3-(trifluoromethyl)pyridin-2-yl]piperazin-1-yl}pyrimidine | * | 1.26 | 561.26 | B |
| 661 | 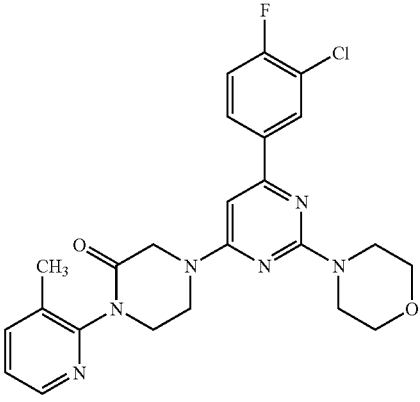 | 4-[6-(3-chloro-4-fluorophenyl)-2-morpholin-4-ylpyrimidin-4-yl]-1-(3-methylpyridin-2-yl)piperazin-2-one | * | 1.22 | 483.21 | B |
| 662 | 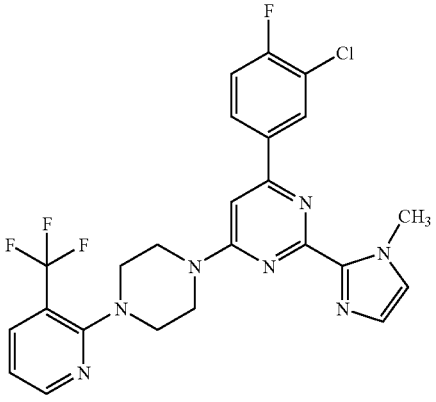 | 4-(3-chloro-4-fluorophenyl)-2-(1-methyl-1H-imidazol-2-yl)-6-{4-[3-(trifluoromethyl)pyridin-2-yl]piperazin-1-yl}pyrimidine | * | 1.25 | 518.22 | B |

TABLE II-continued

| Compound | Name | IC$_{50}$ | Ret. Time | MS (M + 1) | LCMS Method |
|---|---|---|---|---|---|
| 663 | 1-[4-(4-(3-chloro-4-fluorophenyl)-6-{4-[3-(trifluoromethyl)pyridin-2-yl]piperazin-1-yl}pyrimidin-2-yl)piperazin-1-yl]ethanimine | * | 1.25 | 563.29 | B |
| 664 | 4-(3-chloro-4-fluorophenyl)-2-[(2S)-2-(pyrrolidin-1-ylmethyl)pyrrolidin-1-yl]-6-{4-[3-(trifluoromethyl)pyridin-2-yl]piperazin-1-yl}pyrimidine | * | 1.27 | 590.30 | B |
| 665 | 4-(3-chloro-4-fluorophenyl)-2-[4-(2-pyrrolidin-1-ylethyl)piperidin-1-yl]-6-{4-[3-(trifluoromethyl)pyridin-2-yl]piperazin-1-yl}pyrimidine | * | 1.22 | 619.26 | B |

TABLE II-continued

| Compound | Name | IC₅₀ | Ret. Time | MS (M + 1) | LCMS Method |
|---|---|---|---|---|---|
| 666 | 4-(3-chloro-4-fluorophenyl)-2-(4-pyrrolidin-1-ylpiperidin-1-yl)-6-{4-[3-(trifluoromethyl)pyridin-2-yl]piperazin-1-yl}pyrimidine | * | 1.23 | 590.29 | B |
| 667 | 2-(4-ethylpiperazin-1-yl)-4-(4-fluoro-3-methylphenyl)-6-{4-[3-(trifluoromethyl)pyridin-2-yl]piperazin-1-yl}pyrimidine | * | 1.23 | 530.30 | B |
| 668 | 1-(4-(3-chloro-4-fluorophenyl)-6-{4-[3-(trifluoromethyl)pyridin-2-yl]piperazin-1-yl}pyrimidin-2-yl)pyrrolidin-2-one | * | 1.22 | 521.22 | B |

TABLE II-continued

| Compound | Name | IC$_{50}$ | Ret. Time | MS (M + 1) | LCMS Method |
|---|---|---|---|---|---|
| 669 | 4-(3-chloro-4-fluorophenyl)-2-(2,5-dimethylpyrrolidin-1-yl)-6-{4-[3-(trifluoromethyl)pyridin-2-yl]piperazin-1-yl}pyrimidine | * | 1.3 | 535.23 | B |
| 670 | | * | 1.42 | 531.24 | B |
| 671 | 1-(4-(3-chloro-4-fluorophenyl)-6-{4-[3-(trifluoromethyl)pyridin-2-yl]piperazin-1-yl}pyrimidin-2-yl)ethanone | * | 1.36 | 480.24 | B |

TABLE II-continued
| Compound | | Name | IC$_{50}$ | Ret. Time | MS (M + 1) | LCMS Method |
|---|---|---|---|---|---|---|
| 672 | 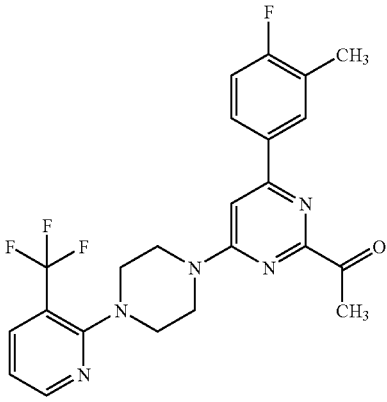 | 1-(4-(4-fluoro-3-methylphenyl)-6-{4-[3-(trifluoromethyl)pyridin-2-yl]piperazin-1-yl}pyrimidin-2-yl)ethanone | * | 1.33 | 460.28 | B |
| 673 | 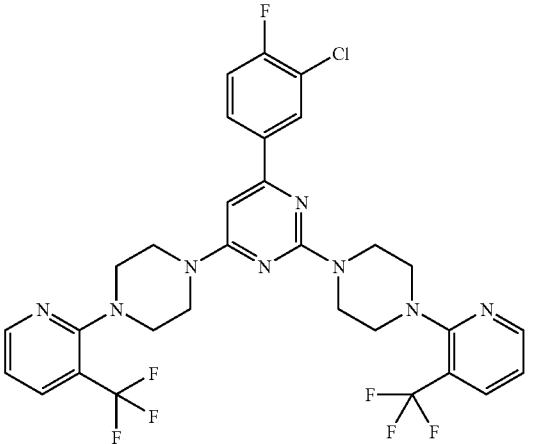 | 4-(3-chloro-4-fluorophenyl)-2,6-bis{4-[3-(trifluoromethyl)pyridin-2-yl]piperazin-1-yl}pyrimidine | * | 1.38 | 667.33 | B |
| 674 | 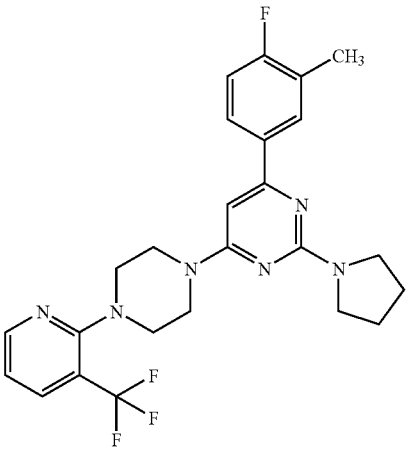 | 4-(4-fluoro-3-methylphenyl)-2-pyrrolidin-1-yl-6-{4-[3-(trifluoromethyl)pyridin-2-yl]piperazin-1-yl}pyrimidine | * | 1.23 | 487.32 | B |

TABLE II-continued
| Compound | | Name | IC$_{50}$ | Ret. Time | MS (M + 1) | LCMS Method |
|---|---|---|---|---|---|---|
| 675 | 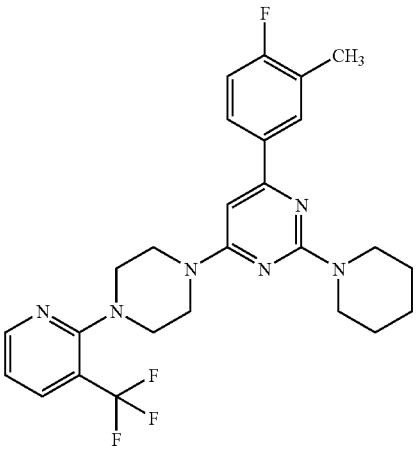 | 4-(4-fluoro-3-methylphenyl)-2-piperidin-1-yl-6-{4-[3-(trifluoromethyl)pyridin-2-yl]piperazin-1-yl}pyrimidine | * | 1.25 | 501.34 | B |
| 676 | 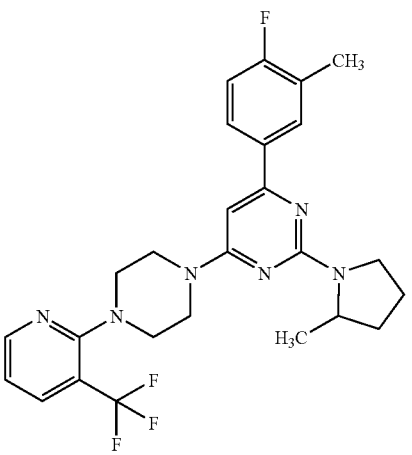 | 4-(4-fluoro-3-methylphenyl)-2-(2-methylpyrrolidin-1-yl)-6-{4-[3-(trifluoromethyl)pyridin-2-yl]piperazin-1-yl}pyrimidine | * | 1.24 | 501.34 | B |
| 677 | 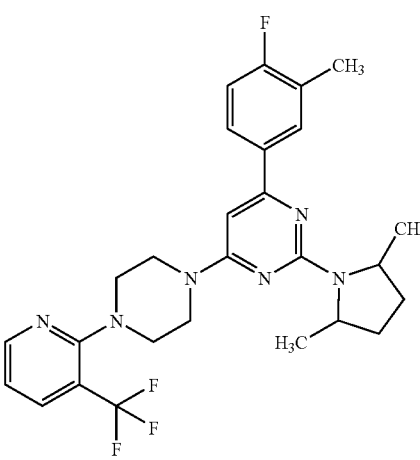 | 2-(2,5-dimethylpyrrolidin-1-yl)-4-(4-fluoro-3-methylphenyl)-6-{4-[3-(trifluoromethyl)pyridin-2-yl]piperazin-1-yl}pyrimidine | * | 1.26 | 515.36 | B |

TABLE II-continued

| Compound | Name | IC$_{50}$ | Ret. Time | MS (M + 1) | LCMS Method |
|---|---|---|---|---|---|
| 678 | | * | 1.19 | 521.35 | B |
| 679 | N-(4-(3-chloro-4-fluorophenyl)-6-{4-[3-(trifluoromethyl)pyridin-2-yl]piperazin-1-yl}pyrimidin-2-yl)-N-methylacetamide | * | 1.38 | 509.27 | B |
| 680 | 1-(4-(3-chloro-4-fluorophenyl)-6-{4-[3-(trifluoromethyl)pyridin-2-yl]piperazin-1-yl}pyrimidin-2-yl)pyrrolidine-2,5-dione | * | 1.28 | 535.27 | B |

TABLE II-continued

| Compound | | Name | IC$_{50}$ | Ret. Time | MS (M + 1) | LCMS Method |
|---|---|---|---|---|---|---|
| 681 | 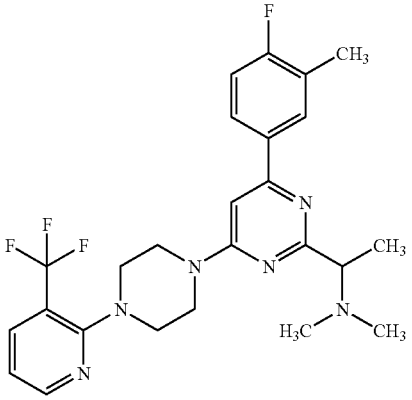 | 1-(4-(4-fluoro-3-methylphenyl)-6-{4-[3-(trifluoromethyl)pyridin-2-yl]piperazin-1-yl}pyrimidin-2-yl)-N,N-dimethylethanamine | * | 1.23 | 489.35 | B |
| 682 | 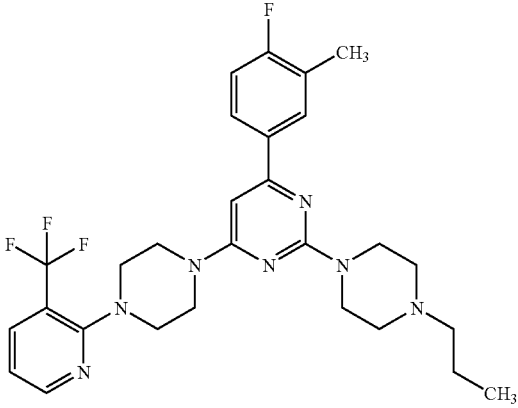 | 4-(4-fluoro-3-methylphenyl)-2-(4-propylpiperazin-1-yl)-6-{4-[3-(trifluoromethyl)pyridin-2-yl]piperazin-1-yl}pyrimidine | * | 1.22 | 544.41 | B |
| 683 | 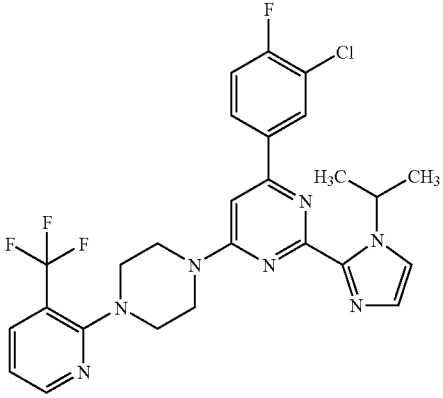 | 4-(3-chloro-4-fluorophenyl)-2-(1-isopropyl-1H-imidazol-2-yl)-6-{4-[3-(trifluoromethyl)pyridin-2-yl]piperazin-1-yl}pyrimidine | * | 1.26 | 546.32 | B |

TABLE II-continued
| Compound | | Name | IC$_{50}$ | Ret. Time | MS (M + 1) | LCMS Method |
|---|---|---|---|---|---|---|
| 684 | 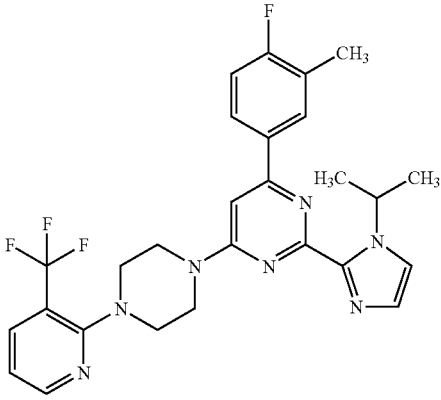 | 4-(4-fluoro-3-methylphenyl)-2-(1-isopropyl-1H-imidazol-2-yl)-6-{4-[3-(trifluoromethyl)pyridin-2-yl]piperazin-1-yl}pyrimidine | * | 1.26 | 526.36 | B |
| 685 | 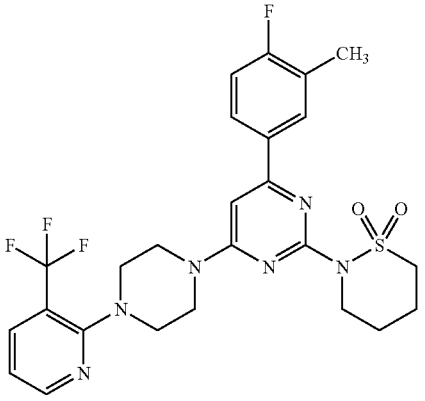 | 2-(4-(4-fluoro-3-methylphenyl)-6-{4-[3-(trifluoromethyl)pyridin-2-yl]piperazin-1-yl}pyrimidin-2-yl)-1,2-thiazinane 1,1-dioxide | * | 1.28 | 551.31 | B |
| 686 | 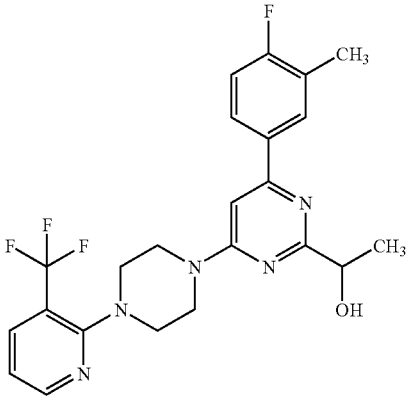 | 1-(4-(4-fluoro-3-methylphenyl)-6-{4-[3-(trifluoromethyl)pyridin-2-yl]piperazin-1-yl}pyrimidin-2-yl)ethanol | * | 1.18 | 462.29 | B |

TABLE II-continued

| Compound | | Name | IC$_{50}$ | Ret. Time | MS (M + 1) | LCMS Method |
|---|---|---|---|---|---|---|
| 687 | 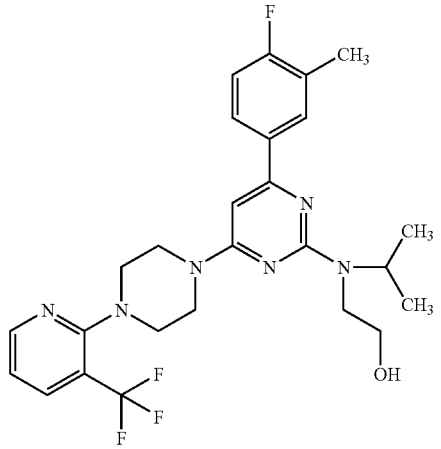 | 2-[(4-(4-fluoro-3-methylphenyl)-6-{4-[3-(trifluoromethyl)pyridin-2-yl]piperazin-1-yl}pyrimidin-2-yl)(isopropyl)amino]ethanol | * | 1.23 | 520.34 | B |
| 688 | 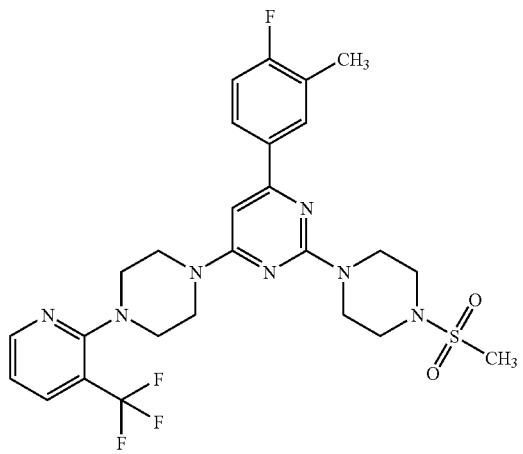 | 4-(4-fluoro-3-methylphenyl)-2-[4-(methylsulfonyl)piperazin-1-yl]-6-{4-[3-(trifluoromethyl)pyridin-2-yl]piperazin-1-yl}pyrimidine | * | 1.22 | 580.31 | B |
| 689 | 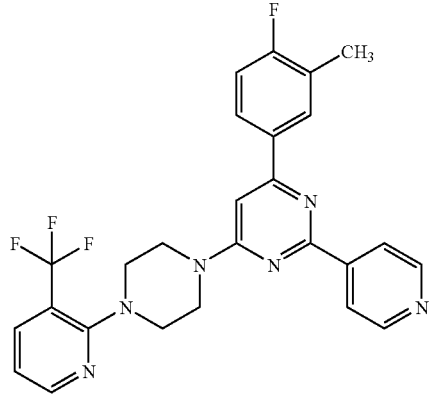 | 4-(4-fluoro-3-methylphenyl)-2-pyridin-4-yl-6-{4-[3-(trifluoromethyl)pyridin-2-yl]piperazin-1-yl}pyrimidine | * | 1.34 | 495.30 | B |

TABLE II-continued

| Compound | | Name | IC$_{50}$ | Ret. Time | MS (M + 1) | LCMS Method |
|---|---|---|---|---|---|---|
| 690 | 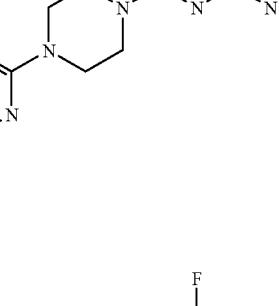 | N-(4-(4-fluoro-3-methylphenyl)-6-{4-[3-(trifluoromethyl)pyridin-2-yl]piperazin-1-yl}pyrimidin-2-yl)propane-2-sulfonamide | * | 1.31 | 539.31 | B |
| 691 | 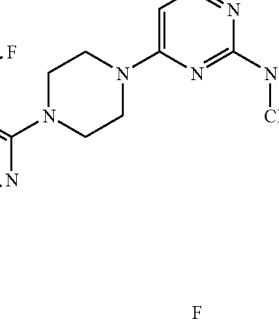 | N-(4-(4-fluoro-3-methylphenyl)-6-{4-[3-(trifluoromethyl)pyridin-2-yl]piperazin-1-yl}pyrimidin-2-yl)-N-methytpropane-2-sulfonamide | * | 1.42 | 553.31 | B |
| 692 | 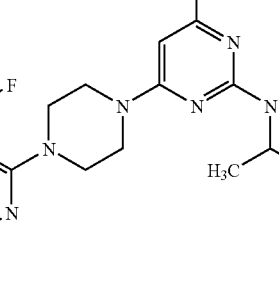 | N-(4-(4-fluoro-3-methylphenyl)-6-{4-[3-(trifluoromethyl)pyridin-2-yl]piperazin-1-yl}pyrimidin-2-yl)-N-isopropylpropane-2-sulfonamide | * | 1.45 | 581.34 | B |

TABLE II-continued

| Compound | | Name | IC$_{50}$ | Ret. Time | MS (M + 1) | LCMS Method |
|---|---|---|---|---|---|---|
| 693 | 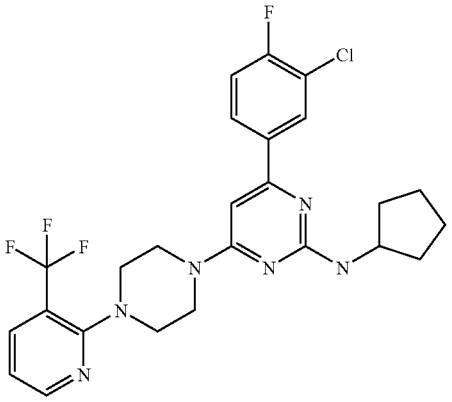 | 4-(3-chloro-4-fluorophenyl)-N-cyclopentyl-6-{4-[3-(trifluoromethyl)pyridin-2-yl]piperazin-1-yl}pyrimidin-2-amine | * | 1.27 | 521.29 | B |
| 694 | 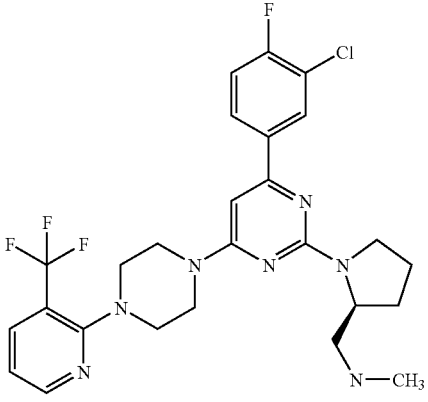 | 1-[(2S)-1-(4-(3-chloro-4-fluorophenyl)-6-{4-[3-(trifluoromethyl)pyridin-2-yl]piperazin-1-yl}pyrimidin-2-yl)pyrrolidin-2-yl]-N-methylmethanamine | * | 1.22 | 550.33 | B |
| 695 | 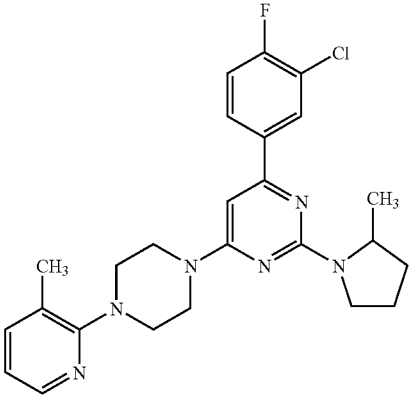 | 4-(3-chloro-4-fluorophenyl)-6-[4-(3-methylpyridin-2-yl)piperazin-1-yl]-2-(2-methylpyrrolidin-1-yl)pyrimidine | * | 1.15 | 467.26 | B |

TABLE II-continued
| Compound | | Name | IC$_{50}$ | Ret. Time | MS (M + 1) | LCMS Method |
|---|---|---|---|---|---|---|
| 696 | 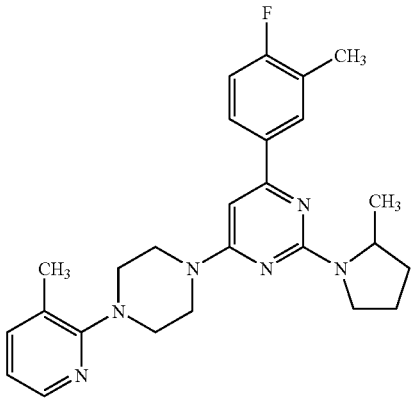 | 4-(4-fluoro-3-methylphenyl)-6-[4-(3-methylpyridin-2-yl)piperazin-1-yl]-2-(2-methylpyrrolidin-1-yl)pyrimidine | * | 1.15 | 447.30 | B |
| 697 | 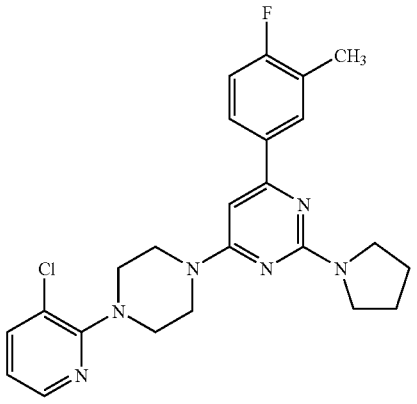 | 4-[4-(3-chloropyridin-2-yl)piperazin-1-yl]-6-(4-fluoro-3-methylphenyl)-2-pyrrolidin-1-ylpyrimidine | * | 1.23 | 453.24 | B |
| 698 | 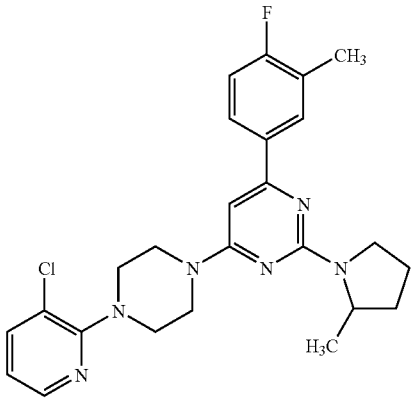 | 4-[4-(3-chloropyridin-2-yl)piperazin-1-yl]-6-(4-fluoro-3-methylphenyl)-2-(2-methylpyrrolidin-1-yl)pyrimidine | * | 1.24 | 467.26 | B |

TABLE II-continued
| Compound | | Name | IC$_{50}$ | Ret. Time | MS (M + 1) | LCMS Method |
|---|---|---|---|---|---|---|
| 699 | 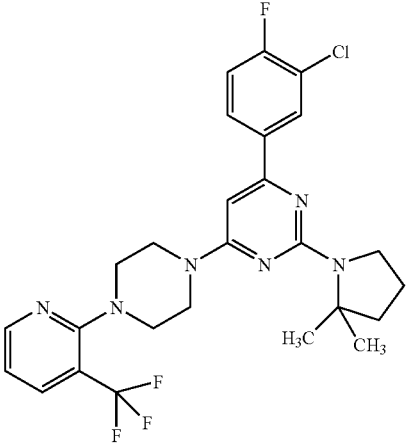 | 4-(3-chloro-4-fluorophenyl)-2-(2,2-dimethylpyrrolidin-1-yl)-6-{4-[3-(trifluoromethyl)pyridin-2-yl]piperazin-1-yl}pyrimidine | * | 1.28 | 535.23 | B |
| 700 | 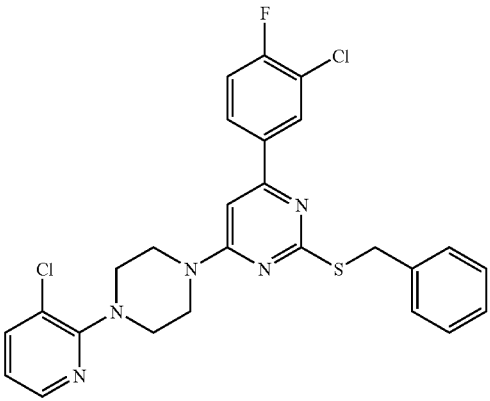 | 2-(benzylthio)-4-(3-chloro-4-fluorophenyl)-6-[4-(3-chloropyridin-2-yl)piperazin-1-yl]pyrimidine | * | 1.52 | 526.18 | B |
| 701 | 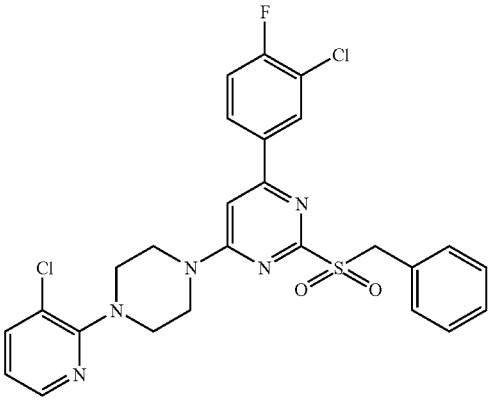 | 2-(benzylsulfonyl)-4-(3-chloro-4-fluorophenyl)-6-[4-(3-chloropyridin-2-yl)piperazin-1-yl]pyrimidine | * | 1.36 | 558.19 | B |

TABLE II-continued
| Compound | | Name | IC$_{50}$ | Ret. Time | MS (M + 1) | LCMS Method |
|---|---|---|---|---|---|---|
| 702 | 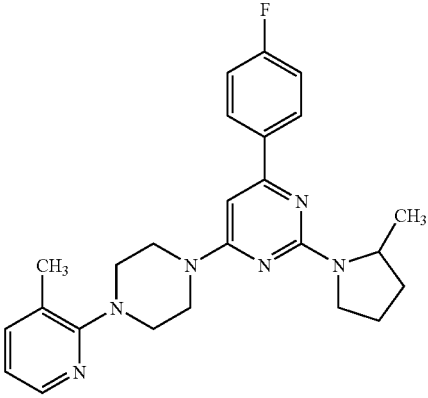 | 4-(4-fluorophenyl)-6-[4-(3-methylpyridin-2-yl)piperazin-1-yl]-2-(2-methylpyrrolidin-1-yl)pyrimidine | * | 1.11 | 433.28 | B |
| 703 | 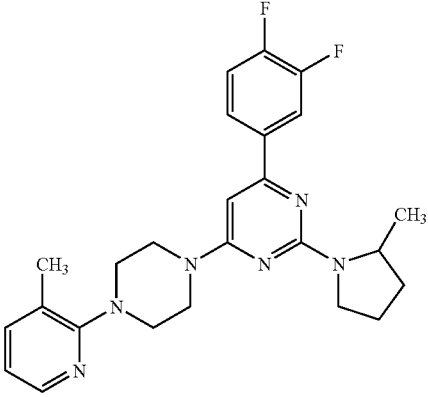 | 4-(3,4-difluorophenyl)-6-[4-(3-methylpyridin-2-yl)piperazin-1-yl]-2-(2-methylpyrrolidin-1-yl)pyrimidine | * | 1.12 | 451.29 | B |
| 704 | 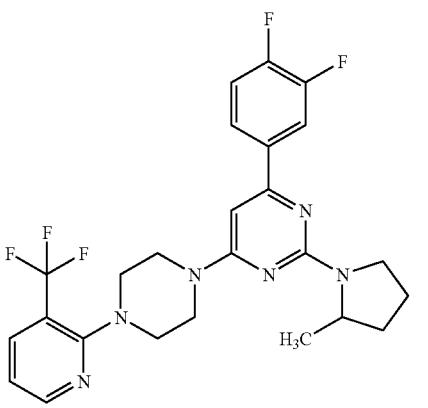 | 4-(3,4-difluorophenyl)-2-(2-methylpyrrolidin-1-yl)-6-{4-[3-(trifluoromethyl)pyridin-2-yl]piperazin-1-yl}pyrimidine | * | 1.25 | 505.23 | B |

TABLE II-continued

| Compound | | Name | IC$_{50}$ | Ret. Time | MS (M + 1) | LCMS Method |
|---|---|---|---|---|---|---|
| 705 | | 4-(4-fluorophenyl)-2-(2-methylpyrrolidin-1-yl)-6-{4-[3-(trifluoromethyl)pyridin-2-yl]piperazin-1-yl}pyrimidine | * | 1.23 | 487.24 | B |
| 706 | | 4-(3-methylphenyl)-2-(2-methylpyrrolidin-1-yl)-6-{4-[3-(trifluoromethyl)pyridin-2-yl]piperazin-1-yl}pyrimidine | * | 1.25 | 483.25 | B |
| 707 | | 4-(3-chloro-4-fluorophenyl)-6-(4-(3-fluoropyridin-2-yl)piperazin-1-yl]-2-(2-methylpyrrolidin-1-yl)pyrimidine | * | 1.24 | 471.23 | B |
| 708 | | 4-(4-fluoro-3-methylphenyl)-6-[4-(3-fluoropyridin-2-yl)piperazin-1-yl]-2-(2-methylpyrrolidin-1-yl)pyrimidine | * | 1.22 | 451.26 | B |

TABLE II-continued

| Compound | Name | IC$_{50}$ | Ret. Time | MS (M + 1) | LCMS Method |
|---|---|---|---|---|---|
| 709 | 2-{4-[6-(3-chloro-4-fluorophenyl)-2-(2-methylpyrrolidin-1-yl)pyrimidin-4-yl]piperazin-1-yl}nicotirionitrile | * | 1.21 | 478.24 | B |
| 710 | 2-azetidin-1-yl-4-(3-chloro-4-fluorophenyl)-6-{4-[3-(trifluoromethyl)pyridin-2-yl]piperazin-1-yl}pyrimidine | * | 1.22 | 493.26 | B |
| 711 | 1-(4-(3-chloro-4-fluorophenyl)-6-{4-[3-(trifluoromethyl)pyridin-2-yl]piperazin-1-yl}pyrimidin-2-yl)-N,N-dimethyl-L-prolinamide | * | 1.2 | 578.33 | B |

TABLE II-continued
| Compound | | Name | IC$_{50}$ | Ret. Time | MS (M + 1) | LCMS Method |
|---|---|---|---|---|---|---|
| 712 | 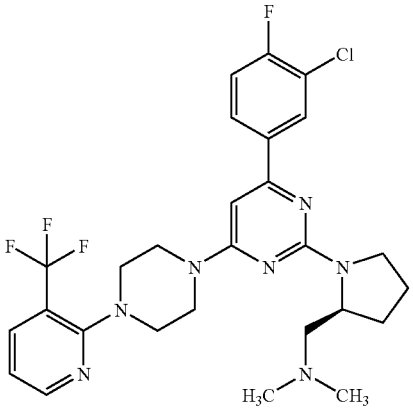 | 1-[(2S)-1-(4-(3-chloro-4-fluorophenyl)-6-{4-[3-(trifluoromethyl)pyridin-2-yl]piperazin-1-yl}pyrimidin-2-yl)pyrrolidin-2-yl]-N,N-dimethylmethanamine | * | 1.24 | 564.34 | B |
| 713 | 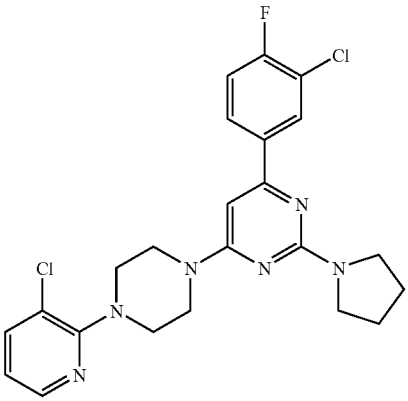 | 4-(3-chloro-4-fluorophenyl)-6-[4-(3-chloropyridin-2-yl)piperazin-1-yl]-2-pyrrolidin-1-ylpyrimidine | * | 1.24 | 473.21 | B |
| 714 | 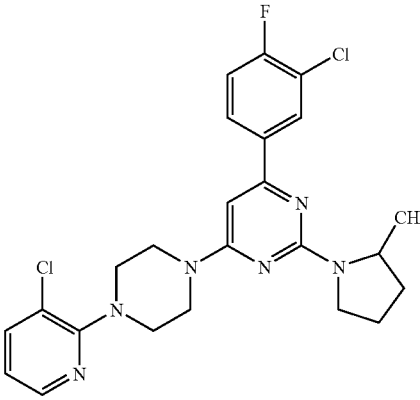 | 4-(3-chloro-4-fluorophenyl)-6-[4-(3-chloropyridin-2-yl)piperazin-1-yl]2-(2-methylpyrrolidin-1-yl)pyrimidine | * | 1.25 | 487.23 | B |

TABLE II-continued
| Compound | | Name | IC$_{50}$ | Ret. Time | MS (M + 1) | LCMS Method |
|---|---|---|---|---|---|---|
| 715 | 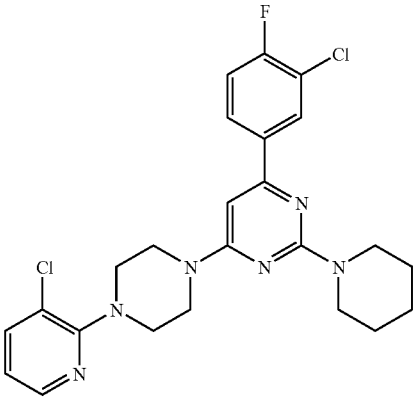 | 4-(3-chloro-4-fluorophenyl)-6-[4-(3-chloropyridin-2-yl)piperazin-1-yl]-2-piperidin-1-ylpyrimidine | * | 1.28 | 487.21 | B |
| 716 | 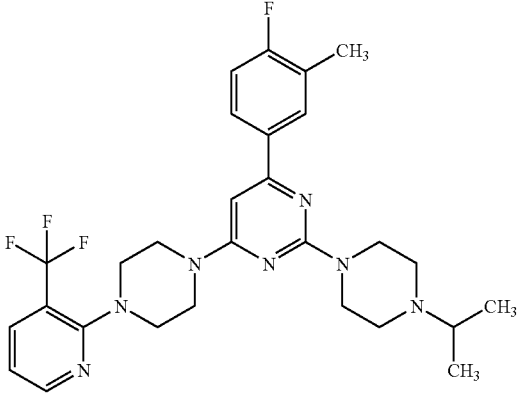 | 4-(4-fluoro-3-methylphenyl)-2-(4-isopropylpiperazin-1-yl)-6-{4-[3-(trifluoromethyl)pyridin-2-yl]piperazin-1-yl}pyrimidine | * | 1.23 | 544.34 | B |
| 717 | 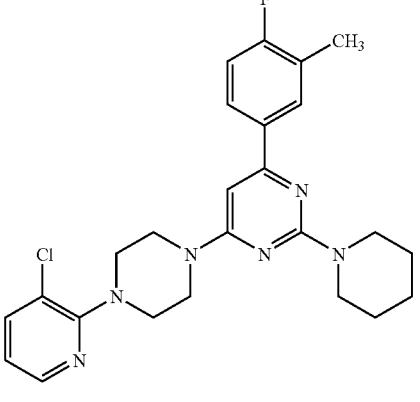 | 4-[4-(3-chloropyridin-2-yl)piperazin-1-yl]-6-(4-fluoro-3-methylphenyl)-2-piperidin-1-ylpyrimidine | * | 1.25 | 467.26 | B |

TABLE II-continued
| Compound | | Name | IC$_{50}$ | Ret. Time | MS (M + 1) | LCMS Method |
|---|---|---|---|---|---|---|
| 718 | 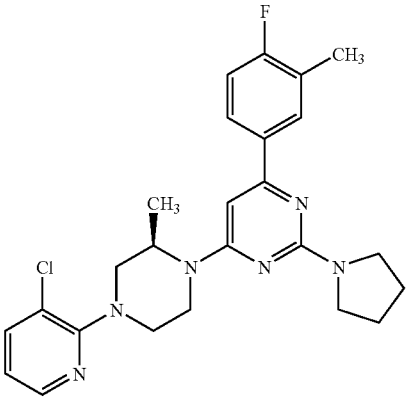 | 4-[(2R)-4-(3-chloropyridin-2-yl)-2-methylpiperazin-1-yl]-6-(4-fluoro-3-methylphenyl)-2-pyrrolidin-1-ylpyrimidine | * | 1.24 | 467.25 | B |
| 719 | 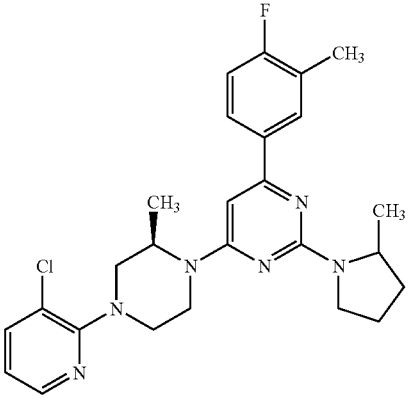 | 4-[(2R)-4-(3-chloropyridin-2-yl)-2-methylpiperazin-1-yl]-6-(4-fluoro-3-methylphenyl)-2-(2-methylpyrrolidin-1-yl)pyrimidine | * | 1.26 | 481.27 | B |
| 720 | 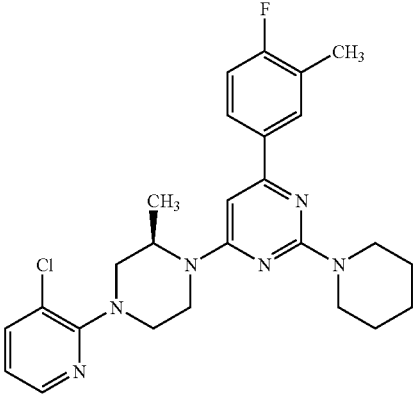 | 4-[(2R)-4-(3-chloropyridin-2-yl)-2-methylpiperazin-1-yl]-6-(4-fluoro-3-methylphenyl)-2-piperidin-1-ylpyrimidine | * | 1.26 | 481.27 | B |

TABLE II-continued
| Compound | | Name | IC$_{50}$ | Ret. Time | MS (M + 1) | LCMS Method |
|---|---|---|---|---|---|---|
| 721 | 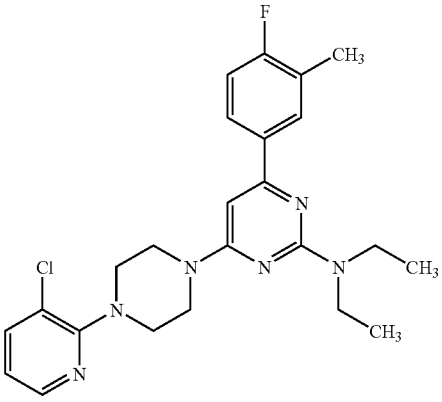 | 4-[4-(3-chloropyridin-2-yl)piperazin-1-yl]-N,N-diethyl-6-(4-fluoro-3-methylphenyl)pyrimidin-2-amine | * | 1.25 | 455.25 | B |
| 722 | 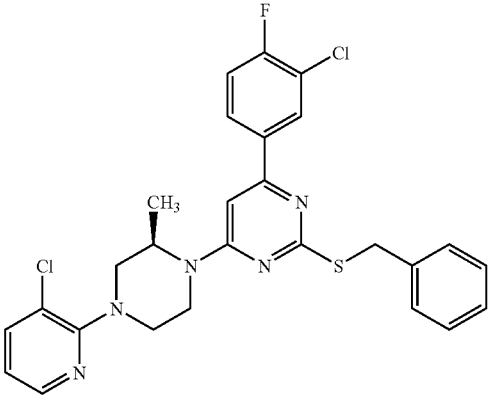 | 2-(benzylthio)-4-(3-chloro-4-fluorophenyl)-6-[(2R)-4-(3-chloropyridin-2-yl)-2-methylpiperazin-1-yl]pyrimidine | * | 1.54 | 540.19 | B |
| 723 | 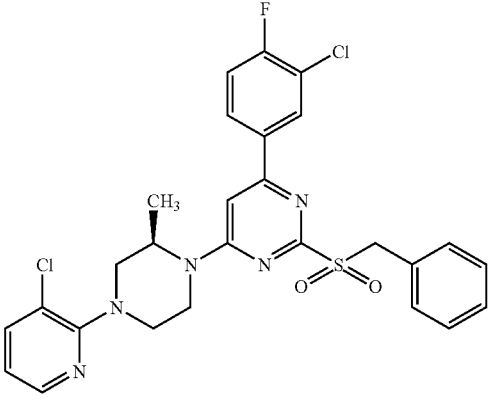 | 2-(benzylsulfonyl)-4-(3-chloro-4-fluorophenyl)-6-[(2R)-4-(3-chloropyridin-2-yl)-2-methylpiperazin-1-yl]pyrimidine | * | 1.37 | 572.19 | B |

TABLE II-continued
| Compound | | Name | IC$_{50}$ | Ret. Time | MS (M + 1) | LCMS Method |
|---|---|---|---|---|---|---|
| 724 | 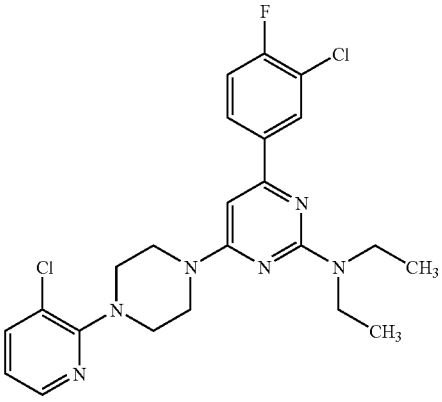 | 4-(3-chloro-4-fluorophenyl)-6-[4-(3-chloropyridin-2-yl)piperazin-1-yl]-N,N-diethylpyrimidin-2-amine | * | 1.28 | 475.22 | B |
| 725 | 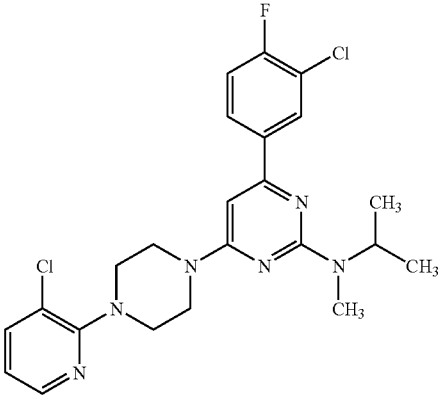 | 4-(3-chloro-4-fluorophenyl)-6-[4-(3-chloropyridin-2-yl)piperazin-1-yl]-N-isopropyl-N-methylpyrimidin-2-amine | * | 1.26 | 475.23 | B |
| 726 | 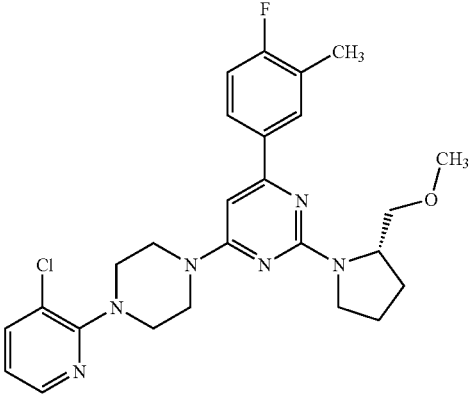 | 4-[4-(3-chloropyridin-2-yl)piperazin-1-yl]-6-(4-fluoro-3-methylphenyl)-2-(methoxymethyl)pyrrolidin-1-yl]pyrimidine | * | 1.23 | 497.24 | B |

TABLE II-continued
| Compound | | Name | IC$_{50}$ | Ret. Time | MS (M + 1) | LCMS Method |
|---|---|---|---|---|---|---|
| 727 | 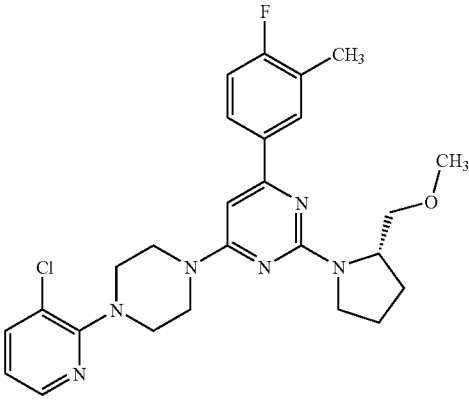 Chiral | | * | 1.23 | 497.25 | B |
| 728 | 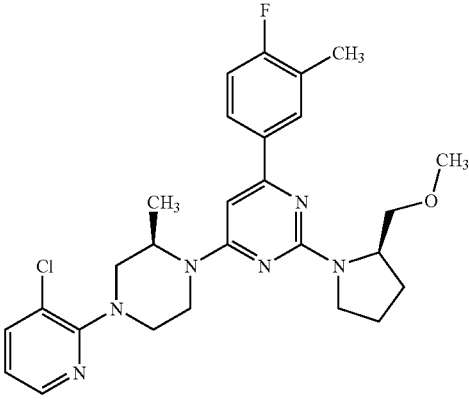 | 4-[(2R)-4-(3-chloropyridin-2-yl)-2-methylpiperazin-1-yl]-6-(4-fluoro-3-methylphenyl)-2-[(2R)-2-(methoxymethyl)pyrrolidin-1-yl]pyrimidine | * | 1.25 | 511.27 | B |
| 729 | 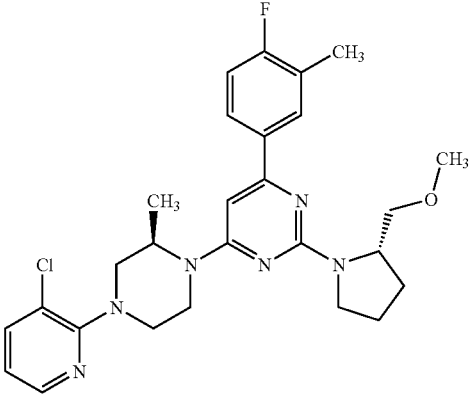 | 4-[(2R)-4-(3-chloropyridin-2-yl)-2-methylpiperazin-1-yl]-6-(4-fluoro-3-methylphenyl)-2-[(2S)-2-(methoxymethyl)pyrrolidin-1-yl]pyrimidine | * | 1.25 | 511.28 | B |

TABLE II-continued
| Compound | | Name | IC$_{50}$ | Ret. Time | MS (M + 1) | LCMS Method |
|---|---|---|---|---|---|---|
| 730 | 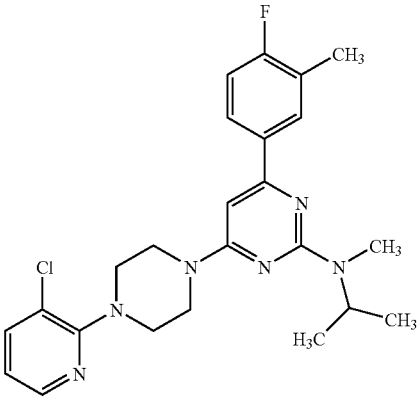 | 4-[4-(3-chloropyridin-2-yl)piperazin-1-yl]-6-(4-fluoro-3-methylphenyl)-N-isopropyl-N-methylpyrimidin-2-amine | * | 1.23 | 455.25 | B |
| 731 | 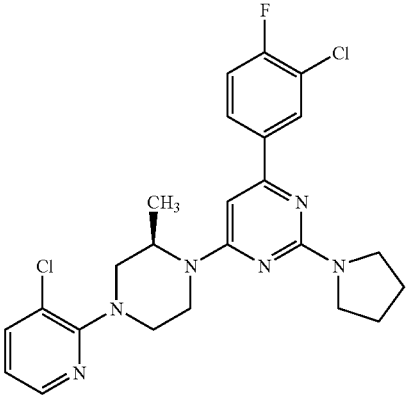 | 4-(3-chloro-4-fluorophenyl)-6-[(2R)-4-(3-chloropyridin-2-yl)-2-methylpiperazin-1-yl]-2-pyrrolidin-1-ylpyrimidine | * | 1.26 | 487.23 | B |
| 732 | 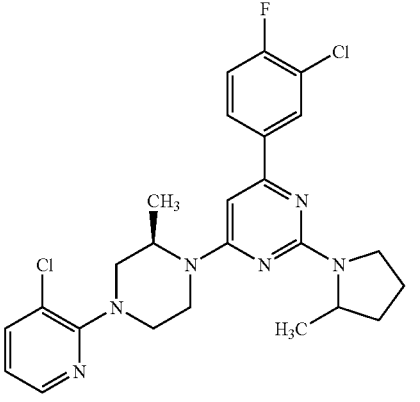 | 4-(3-chloro-4-fluorophenyl)-6-[(2R)-4-(3-chloropyridin-2-yl)-2-methylpiperazin-1-yl]-2-(2-methylpyrrolidin-1-yl)pyrimidine | * | 1.27 | 501.21 | B |

TABLE II-continued

| Compound | | Name | IC$_{50}$ | Ret. Time | MS (M + 1) | LCMS Method |
|---|---|---|---|---|---|---|
| 733 | 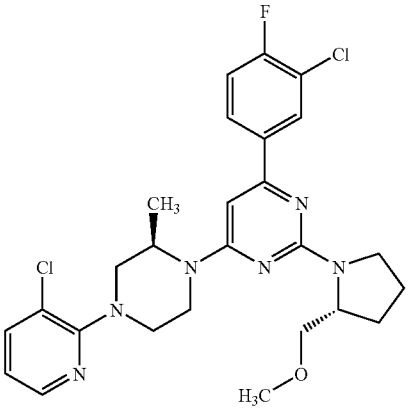 | 4-(3-chloro-4-fluorophenyl)-6-[(2R)-4-(3-chloropyridin-2-yl)-2-methylpiperazin-1-yl]-2-[(2R)-2-(methoxymethyl)pyrrolidin-1-yl]pyrimidine | * | 1.26 | 531.24 | B |
| 734 | 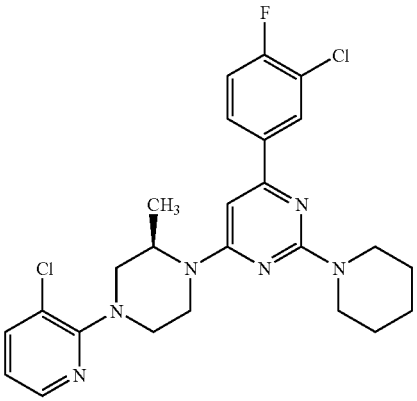 | 4-(3-chloro-4-fluorophenyl)-6-[(2R)-4-(3-chloropyridin-2-yl)-2-methylpiperazin-1-yl]-2-piperidin-1-ylpyrimidine | * | 1.3 | 501.23 | B |
| 735 | 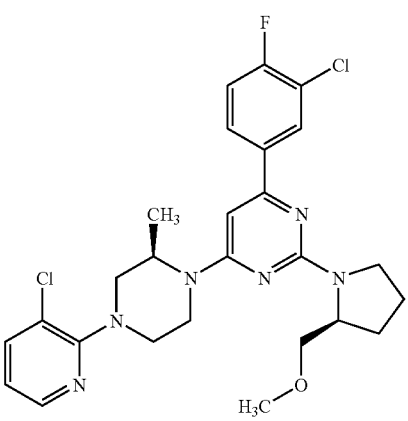 | 4-(3-chloro-4-fluorophenyl)-6-[(2R)-4-(3-chloropyridin-2-yl)-2-methylpiperazin-1-yl]-2-[(2S)-2-(methoxymethyl)pyrrolidin-1-yl]pyrimidine | * | 1.27 | 531.24 | B |

TABLE II-continued

| Compound | | Name | IC$_{50}$ | Ret. Time | MS (M + 1) | LCMS Method |
|---|---|---|---|---|---|---|
| 736 | 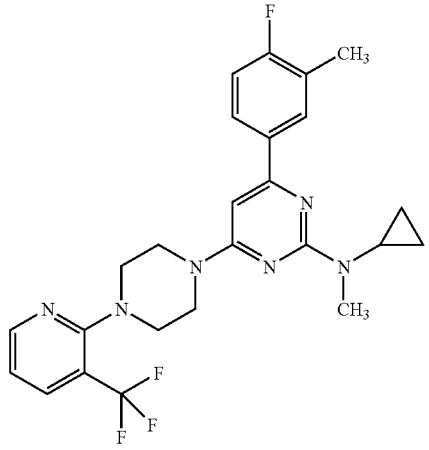 | N-cyclopropyl-4-(4-fluoro-3-methylphenyl)-N-methyl-6-{4-[3-(trifluoromethyl)pyridin-2-yl]piperazin-1-yl}pyrimidin-2-amine | * | 1.27 | 487.29 | B |
| 737 | 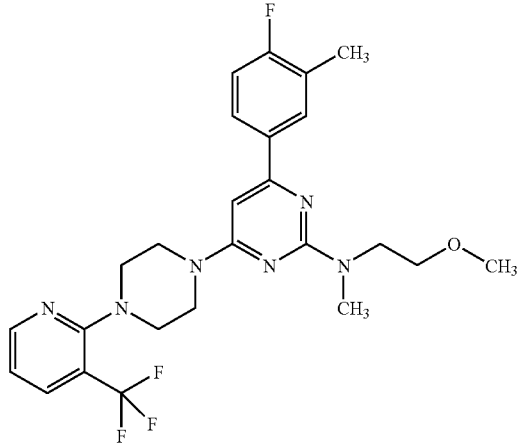 | 4-(4-fluoro-3-methylphenyl)-N-(2-methoxyethyl)-N-methyl-6-{4-[3-(trifluoromethyl)pyridin-2-yl]piperazin-1-yl}pyrimid in-2-amine | * | 1.24 | 505.28 | B |
| 738 | 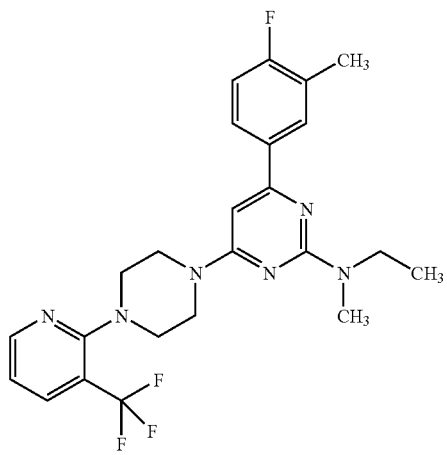 | N-ethyl-4-(4-fluoro-3-methylphenyl)-N-methyl-6-{4-[3-(trifluoromethyl)pyridin-2-yl]piperazin-1-yl)pyrimidin-2-amine | * | 1.24 | 505.28 | B |

TABLE II-continued

| Compound | | Name | IC$_{50}$ | Ret. Time | MS (M + 1) | LCMS Method |
|---|---|---|---|---|---|---|
| 739 | 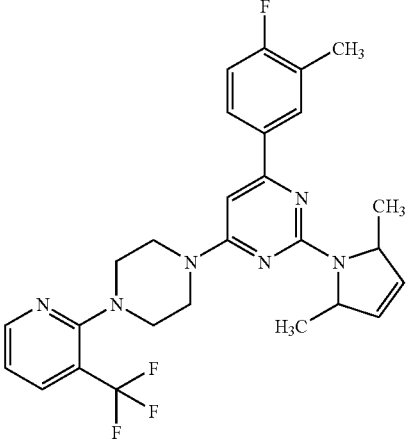 | 2-(2,5-dimethyl-2,5-dihydro-1H-pyrrol-1-yl)-4-(4-fluoro-3-methylphenyl)-6-{4-[3-(trifluoromethyl)pyridin-2-yl]piperazin-1-yl}pyrimidine | * | 1.29 | 513.28 | B |
| 740 | 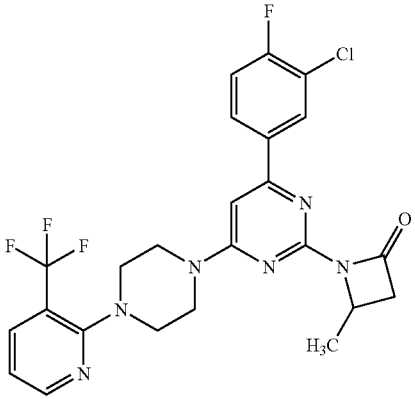 | 1-(4-(3-chloro-4-fluorophenyl)-6-{4-[3-(trifluoromethyl)pyridin-2-yl]piperazin-1-yl}pyrimidin-2-yl)-4-methylazetidin-2-one | * | 1.41 | 521.20 | B |
| 741 | 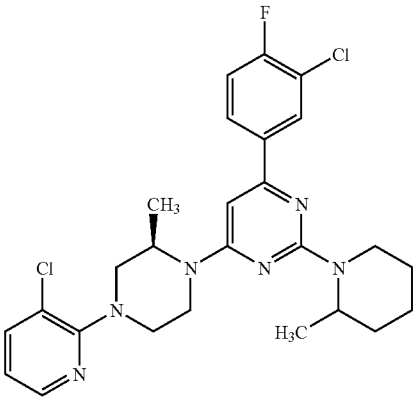 | 4-(3-chloro-4-fluorophenyl)-6-[(2R)-4-(3-chloropyridin-2-yl)-2-methylpiperazin-1-yl]-2-(2-methylpiperidin-1-yl)pyrimidine | * | 1.32 | 515.24 | B |

TABLE II-continued
| Compound | | Name | IC$_{50}$ | Ret. Time | MS (M + 1) | LCMS Method |
|---|---|---|---|---|---|---|
| 742 | 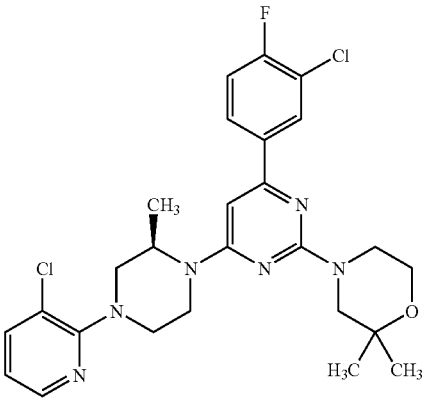 | 4-{4-(3-chloro-4-fluorophenyl)-6-[(2R)-4-(3-chloropyridin-2-yl)-2-methylpiperazin-1-yl]pyrimidin-2-yl}-2,2-dimethylmorpholine | * | 1.36 | 531.25 | B |
| 743 | 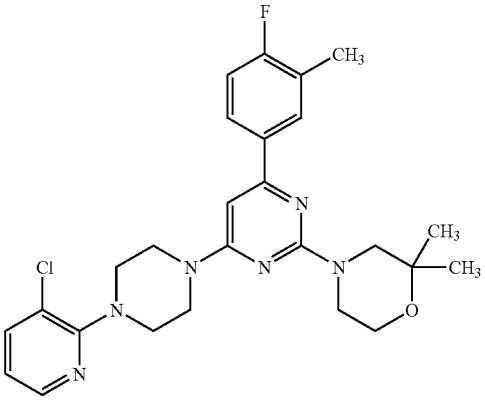 | 4-{4-[4-(3-chloropyridin-2-yl)piperazin-1-yl]-6-(4-fluoro-3-methylphenyl)pyrimidin-2-yl}-2,2-dimethylmorpholine | * | 1.26 | 497.28 | B |
| 744 | 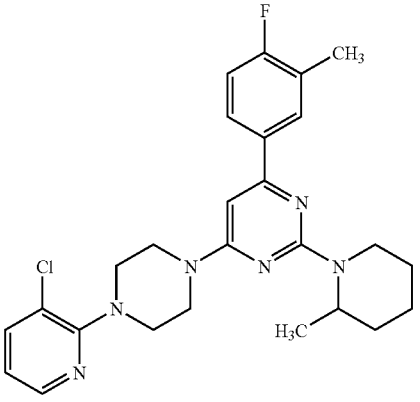 | 4-[4-[4-(3-chloropyridin-2-yl)piperazin-1-yl]-6-(4-fluoro-3-methylphenyl)-2-(2-methylpiperidin-1-yl)pyrimidine | * | 1.28 | 481.26 | B |

TABLE II-continued
| Compound | | Name | IC$_{50}$ | Ret. Time | MS (M + 1) | LCMS Method |
|---|---|---|---|---|---|---|
| 745 | 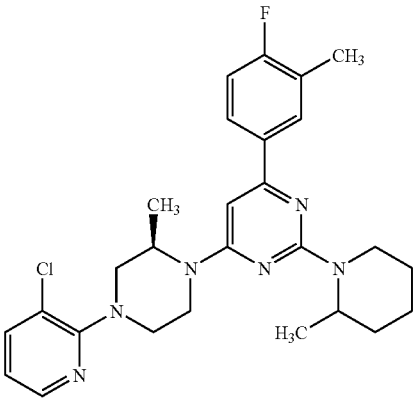 | 4-[(2R)-4-(3-chloropyridin-2-yl)-2-methylpiperazin-1-yl]-6-(4-fluoro-3-methylphenyl)-2-(2-methylpiperidin-1-yl)pyrimidine | * | 1.28 | 495.29 | B |
| 746 | 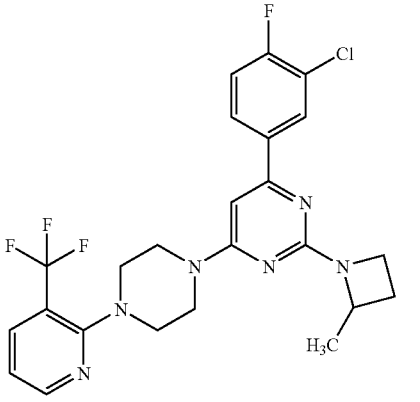 | 4-(3-ohloro-4-fluorophenyl)-2-(2-methylazetidin-1-yl)-6-{4-[3-(trifluoromethyl)pyridin-2-yl]piperazin-1-yl}pyrimidine | * | 1.26 | 507.24 | B |
| 747 | 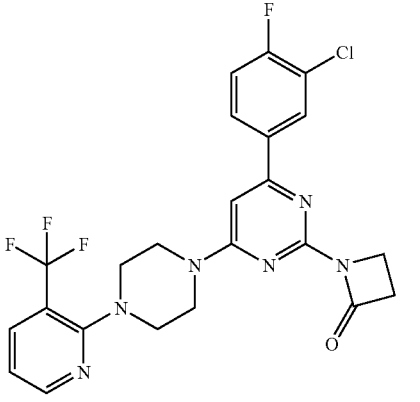 | 1-(4-(3-chloro-4-fluorophenyl)-6-{4-(3-(trifluoromethyl)pyridin-2-yl]piperazin-1-yl}pyrimidin-2-yl)azetidin-2-one | * | 1.38 | 507.21 | B |

TABLE II-continued
| Compound | | Name | IC$_{50}$ | Ret. Time | MS (M + 1) | LCMS Method |
|---|---|---|---|---|---|---|
| 748 | 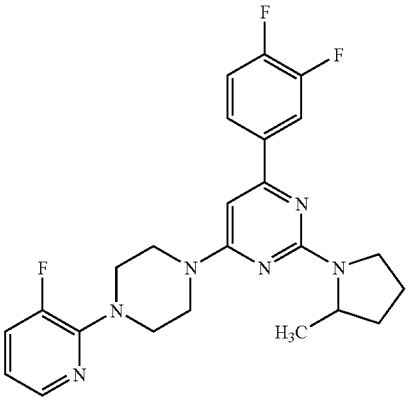 | 4-(3,4-difluorophenyl)-6-[4-(3-fluoropyridin-2-yl)piperazin-1-yl]-2-(2-methylpyrrolidin-1-yl)pyrimidine | * | 1.21 | 455.27 | B |
| 749 | 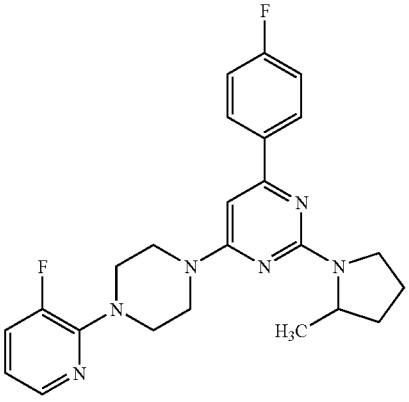 | 4-(4-fluorophenyl)-6-[4-(3-fluoropyridin-2-yl)piperazin-1-yl]-2-(2-methylpyrrolidin-1-yl)pyrimidine | * | 1.21 | 437.28 | B |
| 750 | 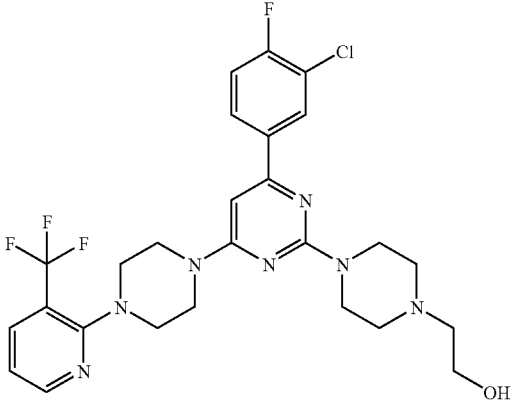 | 2-[4-(4-(3-chloro-4-fluorophenyl)-6-{4-[3-(trifluoromethyl)pyridin-2-yl]piperazin-1-yl}pyrimidin-2-yl)piperazin-1-yl]ethanol | * | 1.27 | 566.29 | B |

TABLE II-continued
| Compound | | Name | IC$_{50}$ | Ret. Time | MS (M + 1) | LCMS Method |
|---|---|---|---|---|---|---|
| 751 | 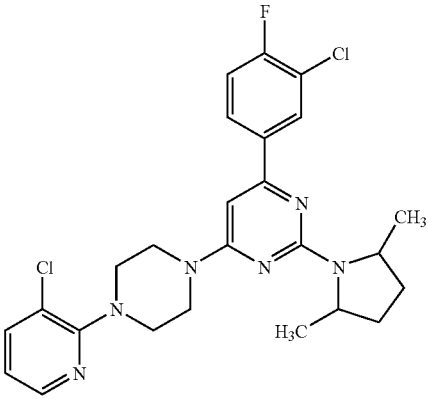 | 4-(3-chloro-4-fluorophenyl)-6-[4-(3-chloropyridin-2-yl)piperazin-1-yl]-2-(2,5-dimethylpyrrolidin-1-yl)pyrimidine | * | 1.3 | 501.26 | B |
| 752 | 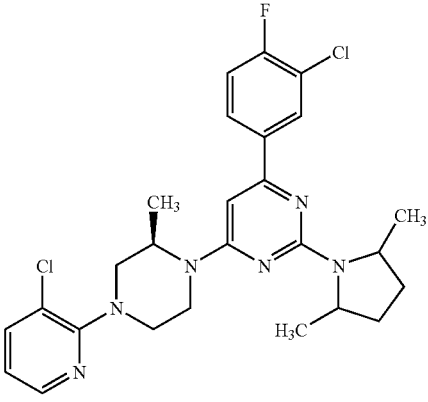 | 4-(3-chloro-4-fluorophenyl)-6-[(2R)-4-(3-chloropyridin-2-yl)-2-methylpiperazin-1-yl]-2-(2,5-dimethylpyrrolidin-1-yl)pyrimidine | * | 1.31 | 515.27 | B |
| 753 | 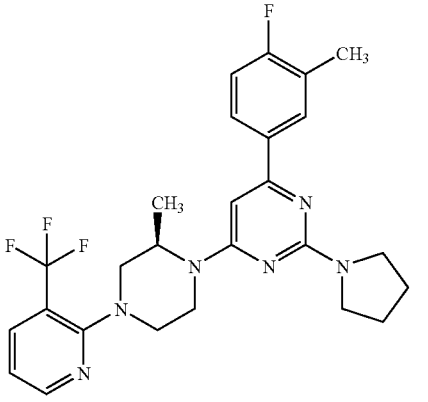 | 4-(4-fluoro-3-methylphenyl)-6-{(2R)-2-methyl-4-[3-(trifluoromethyl)pyridin-2-yl]piperazin-1-yl}-2-pyrrolidin-1-ylpyrimidine | * | 1.26 | 501.30 | B |

TABLE II-continued

| Compound | | Name | IC$_{50}$ | Ret. Time | MS (M + 1) | LCMS Method |
|---|---|---|---|---|---|---|
| 754 | 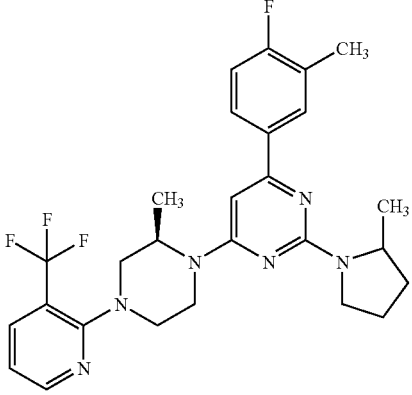 | 4-(4-fluoro-3-methyiphenyl)-2-(2-methylpyrrolidin-1-yl)-6-{(2R)-2-methyt-4-[3-(trifluoromethyl)pyridin-2-yl]piperazin-1-yl}pyrimidine | * | 1.27 | 515.32 | B |
| 755 | 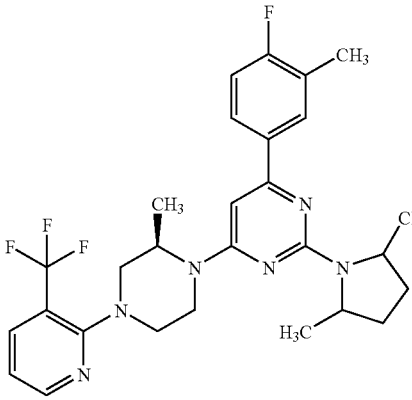 | 2-(2,5-dimethylpyrrolidin-1-yl)-4-(4-fluoro-3-methylphenyl)-6-{(2R)-2-methyl-4-[3-(trifluoromethyl)pyridin-2-yl]piperazin-1-yl}pyrimidine | * | 1.29 | 529.34 | B |
| 756 | 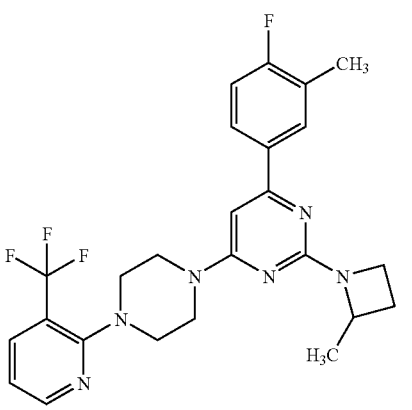 | 4-(4-fluoro-3-methylphenyl)-2-(2-methylazetidin-1-yl)-6-{4-[3-(trifluoromethyl)pyridin-2-yl]piperazin-1-yl}pyrimidine | * | 1.25 | 487.21 | B |

TABLE II-continued

| Compound | | Name | IC$_{50}$ | Ret. Time | MS (M + 1) | LCMS Method |
|---|---|---|---|---|---|---|
| 757 | 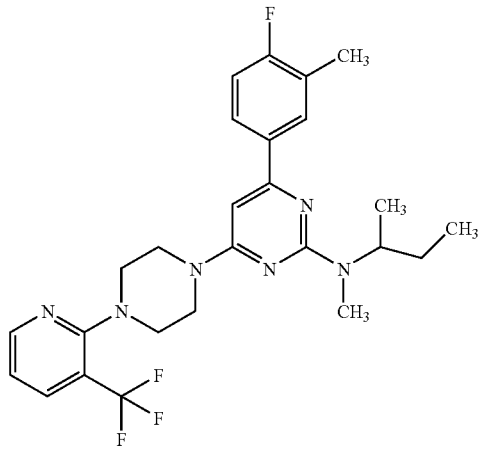 | N-(sec-butyl)-4-(4-fluoro-3-methylphenyl)-N-methyl-6-{4-[3-(trifluoromethyl)pyridin-2-yl]piperazin-1-yl}pyrimidin-2-amine | * | 1.29 | 503.25 | B |
| 758 | 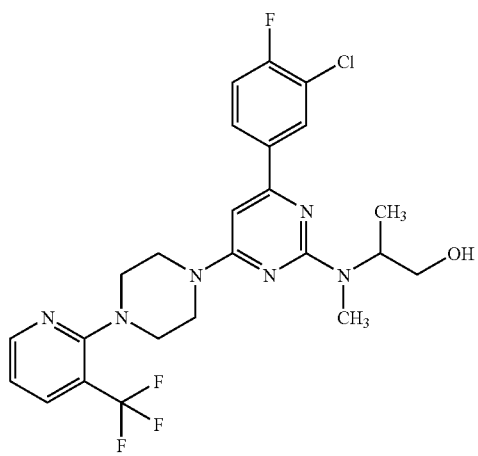 | 2-[(4-(3-chloro-4-fluorophenyl)-6-{4-[3-(trifluoromethyl)pyridin-2-yl]piperazin-1-yl}pyrimidin-2-yl)(methyl)amino]propan-1-ol | * | 1.23 | 525.18 | B |
| 759 | 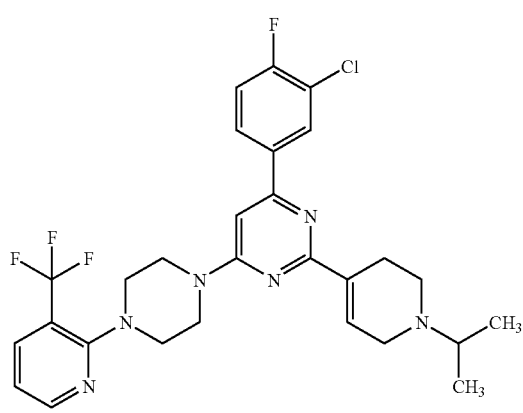 | 4-(4-fluoro-3-methylphenyl)-6-{(2R)-2-methyl-4-[3-(trifluoromethyl)pyridin-2-yl]piperazin-1-yl}-2-piperidin-1-ylpyrimidine | * | 1.28 | 515.24 | B |

TABLE II-continued

| Compound | Name | IC$_{50}$ | Ret. Time | MS (M + 1) | LCMS Method |
|---|---|---|---|---|---|
| 760 | 4-(4-fluoro-3-methylphenyl)-2-[(2S)-2-(methoxymethyl)pyrrolidin-1-yl]-6-{(2R)-2-methyl-4-[3-(trifluoromethyl)pyridin-2-yl]piperazin-1-yl}pyrimidine | * | 1.26 | 545.25 | B |
| 761 | 4-(4-fluoro-3-methylphenyl)-2-[(2R)-2-(methoxymethyl)pyrrolidin-1-yl]-6-{(2R)-2-methyl-4-[3-(trifluoromethyl)pyridin-2-yl]piperazin-1-yl}pyrimidine | * | 1.26 | 545.25 | B |
| 762 | 4-(4-fluoro-3-methylphenyl)-N-isopropyl-N-methyl-6-{(2R)-2-methyl-4-[3-(trifluoromethyl)pyridin-2-yl]piperazin-1-yl}pyrimidin-2-amine | * | 1.26 | 503.24 | B |

TABLE II-continued

| Compound | | Name | IC$_{50}$ | Ret. Time | MS (M + 1) | LCMS Method |
|---|---|---|---|---|---|---|
| 763 | 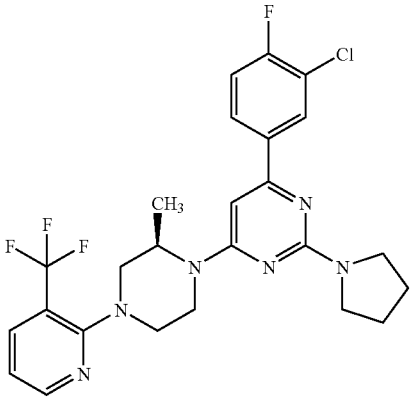 | 4-(3-chloro-4-fluorophenyl)-6-{(2R)-2-methyl-4-[3-(trifluoromethyl)pyridin-2-yl]piperazin-1-yl}-2-pyrrolidin-1-ylpyrimidine | * | 1.27 | 521.18 | B |
| 764 | 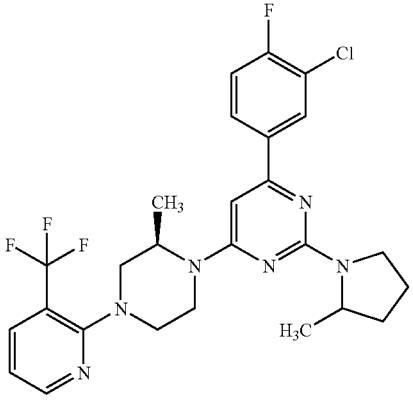 | 4-(3-chloro-4-fluorophenyl)-2-(2-methylpyrrolidin-1-yl)-6-{(2R)-2-methyl-4-[3-(trifluoromethyl)pyridin-2-yl]piperazin-1-yl}pyrimidine | * | 1.28 | 535.20 | B |
| 765 | 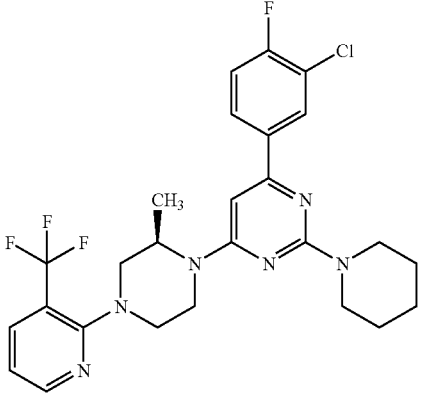 | 4-(3-chloro-4-fluorophenyl)-6-{(2R)-2-methyt-4-[3-(trifluoromethyl)pyridin-2-yl]piperazin-1-yl}-2-piperidin-1-ylpyrimidine | * | 1.31 | 535.20 | B |

TABLE II-continued
| Compound | | Name | IC$_{50}$ | Ret. Time | MS (M + 1) | LCMS Method |
|---|---|---|---|---|---|---|
| 766 | 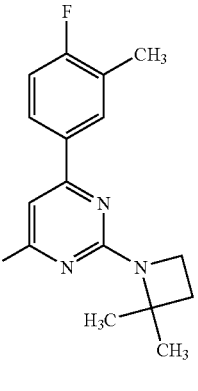 | 2-(2,2-dimethylazetidin-1-yl)-4-(4-fluoro-3-methylphenyl)-6-{4-[3-(trifluoromethyl)pyridin-2-yl]piperazin-1-yl}pyrimidine | * | 1.28 | 501.32 | B |
| 767 | 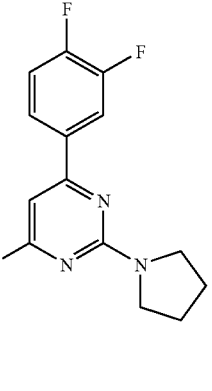 | 4-[(2R)-4-(3-chloropyridin-2-yl)-2-methylpiperazin-1-yl]-6-(3,4-difluorophenyl)-2-pyrrolidin-1-ylpyrimidine | * | 1.24 | 471.19 | B |
| 768 | 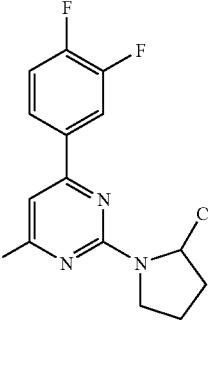 | 4-[(2R)-4-(3-chloropyridin-2-yl)-2-methylpiperazin-1-yl]-6-(3,4-difluorophenyl)-2-(2-methylpyrrolidin-1-yl)pyrimidine | * | 1.26 | 485.21 | B |

TABLE II-continued
| Compound | Name | IC$_{50}$ | Ret. Time | MS (M + 1) | LCMS Method |
|---|---|---|---|---|---|
| 769 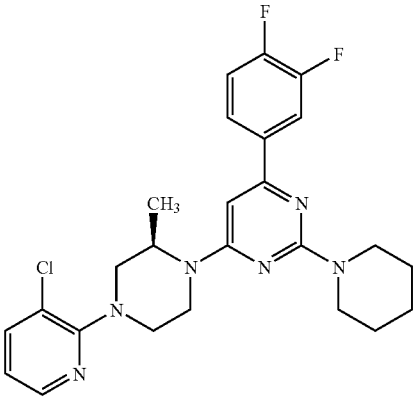 | 4-{(2R)-4-(3-chloropyridin-2-yl)-2-methylpiperazin-1-yl]-6-(3,4-difluorophenyl)-2-piperidin-1-ylpyrimidine | * | 1.28 | 485.21 | B |
| 770 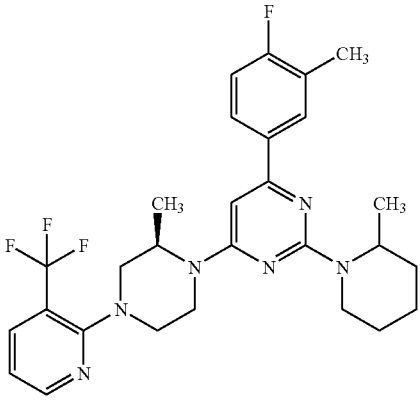 | 4-(4-fluoro-3-methylphenyl)-2-(2-methylpiperidin-1-yl)-6-{(2R)-2-methyl-4-[3-(trifluoromethyl)pyridin-2-yl]piperazin-1-yl}pyrimidine | * | 1.29 | 530.29 | B |
| 771 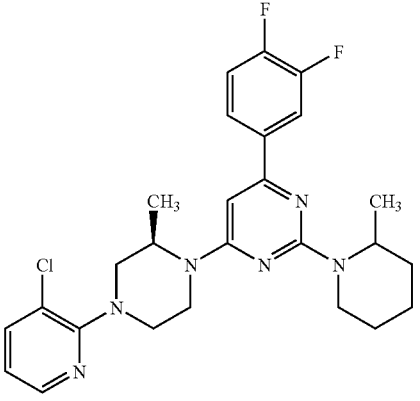 | 4-[(2R)-4-(3-chloropyridin-2-yl)-2-methylpiperazin-1-yl]-6-(3,4-difluorophenyl)-2-(2-methylpiperidin-1-yl)pyrimidine | * | 1.3 | 499.22 | B |

TABLE II-continued

| Compound | Name | IC$_{50}$ | Ret. Time | MS (M + 1) | LCMS Method |
|---|---|---|---|---|---|
| 772 | (3S)-1-(4-(3-chloro-4-fluorophenyl)-6-{4-[3-(trifluoromethyl)pyridin-2-yl]piperazin-1-yl}pyrimidin-2-yl)pyrrolidin-3-ol | * | 1.21 | 523.25 | B |
| 773 | | * | 1.22 | 523.25 | B |
| 774 | 1-(4-(3-chloro-4-fluorophenyl)-6-{4-[3-(trifluoromethyl)pyridin-2-yl]piperazin-1-yl}pyrimidin-2-yl)azetidin-3-ol | * | 1.22 | 509.25 | B |

TABLE II-continued

| Compound | | Name | IC$_{50}$ | Ret. Time | MS (M + 1) | LCMS Method |
|---|---|---|---|---|---|---|
| 775 | 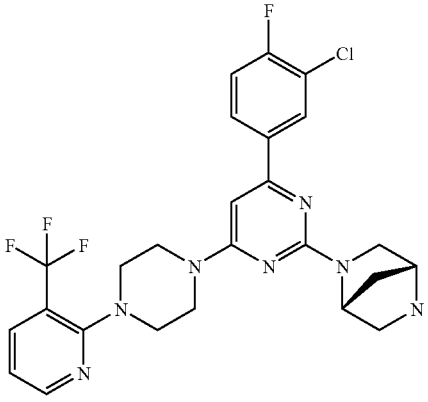 | (1R,4R)-2-(4-(3-chloro-4-fluorophenyl)-6-{4-[3-(trifluoromethyl)pyridin-2-yl]piperazin-1-yl}pyrimidin-2-yl)-2,5-diazabicyclo[2.2.1]heptane | * | 1.23 | 534.27 | B |
| 776 | 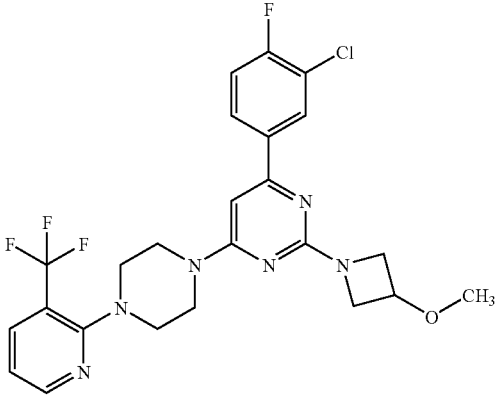 | 4-(3-chloro-4-fluorophenyl)-2-(3-methoxyazetidin-1-yl)-6-{4-[3-(trifluoromethyl)pyridin-2-yl]piperazin-1-yl}pyrimidine | * | 1.25 | 523.25 | B |
| 777 | 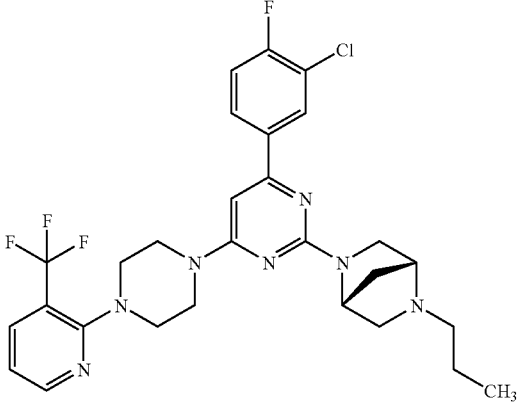 | (1R,4R)-2-(4-(3-chloro-4-fluorophenyl)-6-{4-[3-(trifluoromethyl)pyridin-2-yl]piperazin-1-yl}pyrimidin-2-yl)-5-propyl-2,5-diazabicyclo[2.2.1]heptane | * | 1.25 | 576.32 | B |

TABLE II-continued
| Compound | | Name | IC$_{50}$ | Ret. Time | MS (M + 1) | LCMS Method |
|---|---|---|---|---|---|---|
| 778 | 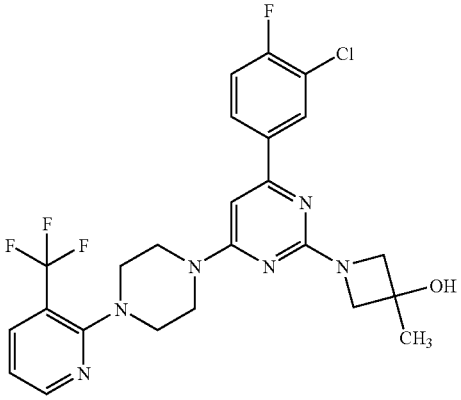 | 1-(4-(3-chloro-4-fluorophenyl)-6-{4-[3-(trifluoromethyl)pyridin-2-yl]piperazin-1-yl}pyrimidin-2-yl)-3-methylazetidin-3-ol | * | 1.23 | 523.25 | B |
| 779 | 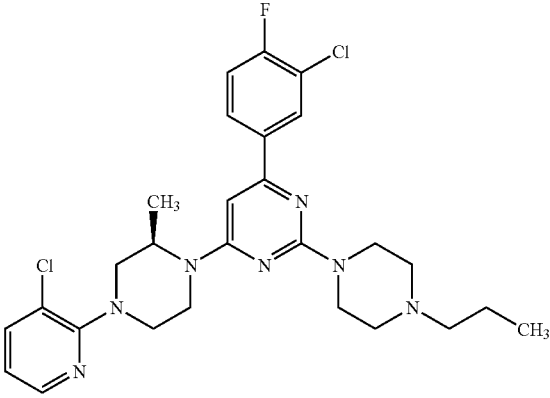 | 4-(3-chloro-4-fluorophenyl)-6-[(2R)-4-(3-chloropyridin-2-yl)-2-methylpiperazin-1-yl]-2-(4-propylpiperazin-1-yl)pyrimidine | * | 1.28 | 544.31 | B |
| 780 | 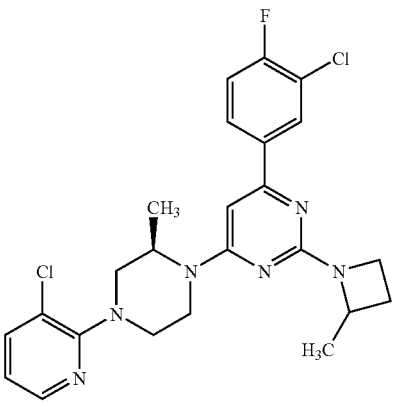 | 4-(3-ohloro-4-fluorophenyi)-6-[(2R)-4-(3-chloropyridin-2-yl)-2-methylpiperazin-1-yl]-2-(2-methylazetidin-1-yl)pyrimidine | * | 1.27 | 487.25 | B |

TABLE II-continued

| Compound | | Name | IC$_{50}$ | Ret. Time | MS (M + 1) | LCMS Method |
|---|---|---|---|---|---|---|
| 781 | 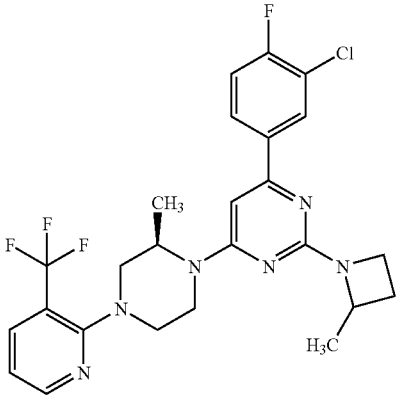 | 4-(3-chloro-4-fluorophenyl)-2-(2-methylazetidin-1-yl)-6-{(2R)-2-methyl-4-[3-(trifluoromethyl)pyridin-2-yl]piperazin-1-yl}pyrimidine | * | 1.27 | 521.27 | B |
| 782 | 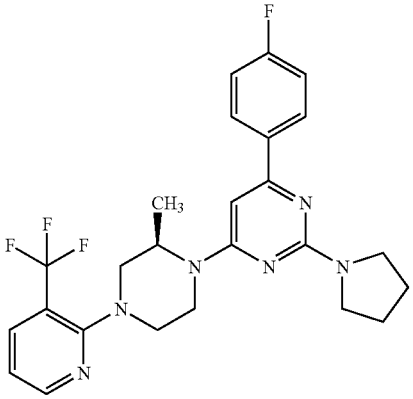 | 4-(4-fluorophenyl)-6-{(2R)-2-methyl-4-[3-(trifluoromethyl)pyridin-2-yl]piperazin-1-yl}-2-pyrrolidin-1-ylpyrimidine | * | 1.25 | 487.30 | B |
| 783 | 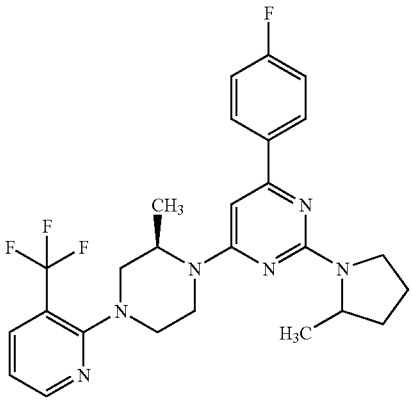 | 4-(4-fluorophenyl)-2-(2-methylpyrrolidin-1-yl)-6-{(2R)-2-methyl-4-[3-(trifluoromethyl)pyridin-2-yl]piperazin-1-yl}pyrimidine | * | 1.26 | 501.32 | B |

TABLE II-continued
| Compound | | Name | IC$_{50}$ | Ret. Time | MS (M + 1) | LCMS Method |
|---|---|---|---|---|---|---|
| 784 | 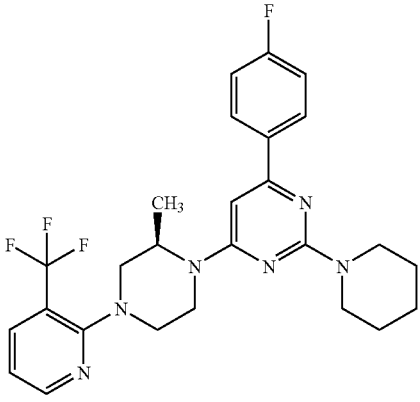 | 4-(4-fluorophenyl)-6-{(2R)-2-methyl-4-[3-(trifluoromethyl)pyridin-2-yl]piperazin-1-yl}-2-piperidin-1-ylpyrimidine | * | 1.26 | 501.31 | B |
| 785 | 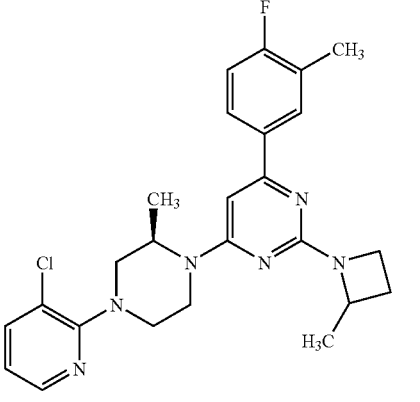 | 4-[(2R)-4-(3-chloropyridin-2-yl)-2-methylpiperazin-1-yl]-6-(4-fluoro-3-methylphenyl)-2-(2-methylazetidin-1-yl)pyrimidine | * | 1.25 | 467.29 | B |
| 786 | 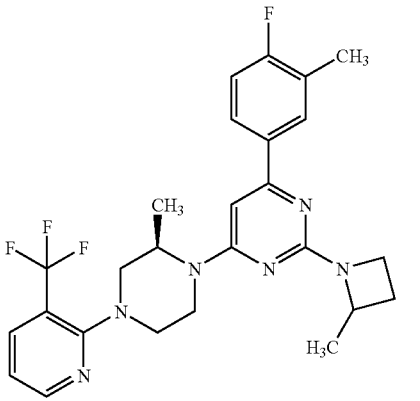 | 4-(4-fluoro-3-methylphenyl)-2-(2-methylazetidin-1-yl)-6-{(2R)-2-methyl-4-[3-(trifluoromethyl)pyridin-2-yl]piperazin-1-yl}pyrimidine | * | 1.27 | 501.32 | B |

TABLE II-continued

| Compound | | Name | IC$_{50}$ | Ret. Time | MS (M + 1) | LCMS Method |
|---|---|---|---|---|---|---|
| 787 | 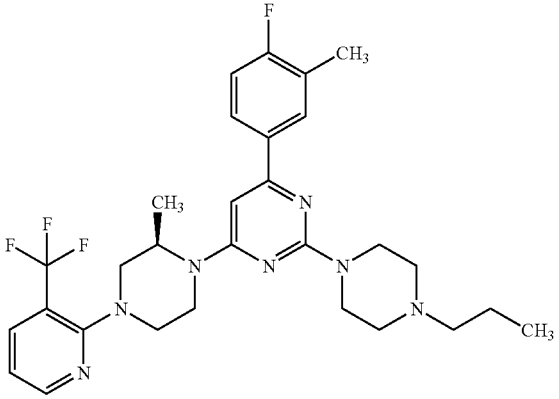 | 4-(4-fluoro-3-methylphenyl)-6-{(2R)-2-methyl-4-[3-(trifluoromethyl)pyridin-2-yl]piperazin-1-yl}-2-(4-propylpiperazin-1-yl)pyrimidine | * | 1.25 | 558.38 | B |
| 788 | 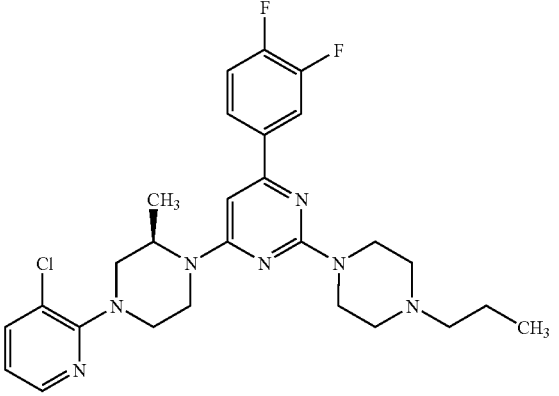 | 4-[(2R)-4-(3-chloropyridin-2-yl)-2-methylpiperazin-1-yl]-6-(3,4-difluorophenyl)-2-(4-propylpiperazin-1-yl)pyrimidine | * | 1.26 | 528.33 | B |
| 789 | 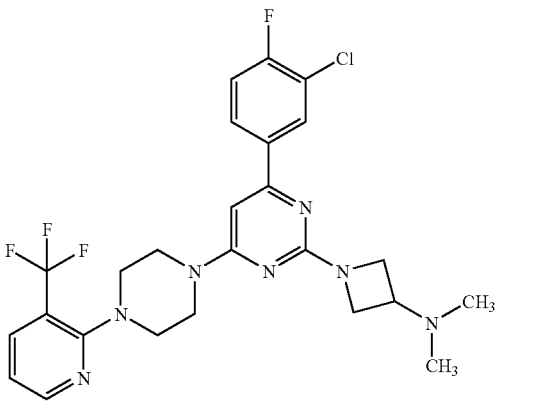 | 1-(4-(3-chloro-4-fluorophenyl)-6-{4-[3-(trifluoromethyl)pyridin-2-yl]piperazin-1-yl}pyrimidin-2-yl)-N,N-dimethylazetidin-3-amine | * | 1.19 | 536.28 | B |

TABLE II-continued

| Compound | | Name | IC$_{50}$ | Ret. Time | MS (M + 1) | LCMS Method |
|---|---|---|---|---|---|---|
| 790 | 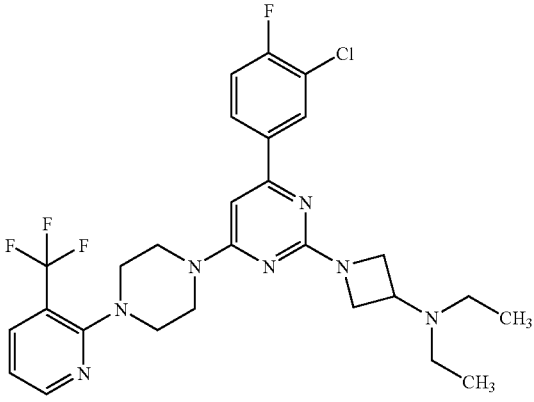 | 1-(4-(3-chloro-4-fluorophenyl)-6-{4-[3-(trifluoromethyl)pyridin-2-yl]piperazin-1-yl}pyrimidin-2-yl)-N,N-diethylazetidin-3-amine | * | 1.21 | 564.32 | B |
| 791 | 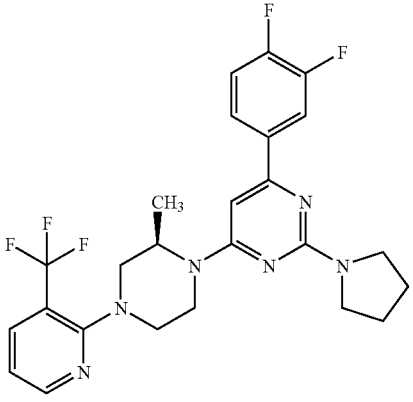 | 4-(3,4-difluorophenyl)-6-{(2R)-2-methyl-4-[3-(trifluoromethyl)pyridin-2-yl]piperazin-1-yl}-2-pyrrolidin-1-ylpyrimidine | * | 1.25 | 505.29 | B |
| 792 | 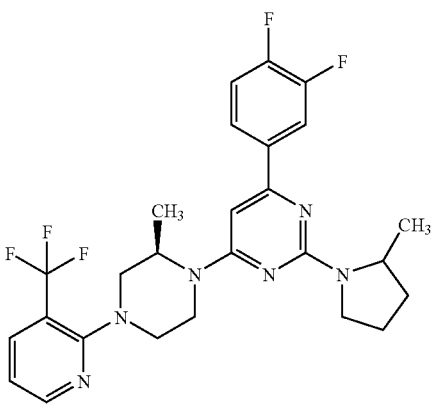 | 4-(3,4-difluorophenyl)-2-(2-methylpyrrolidin-1-yl)-6-{(2R)-2-methyl-4-[3-(trifluoromethyl)pyridin-2-yl]piperazin-1-yl}pyrimidine | * | 1.27 | 519.30 | B |

TABLE II-continued
| Compound | | Name | IC$_{50}$ | Ret. Time | MS (M + 1) | LCMS Method |
|---|---|---|---|---|---|---|
| 793 | 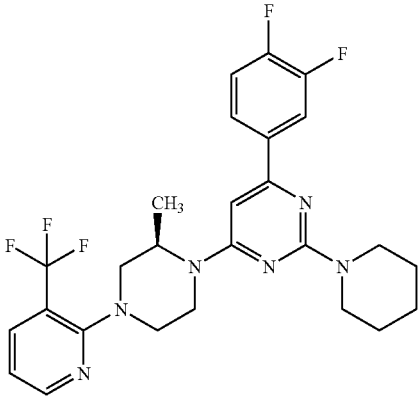 | 4-(3,4-difluorophenyl)-6-{(2R)-2-methyl-4-[3-(trifluoromethyl)pyridin-2-yl]piperazin-1-yl}-2-piperidin-1-ylpyrimidine | * | 1.3 | 519.29 | B |
| 794 | 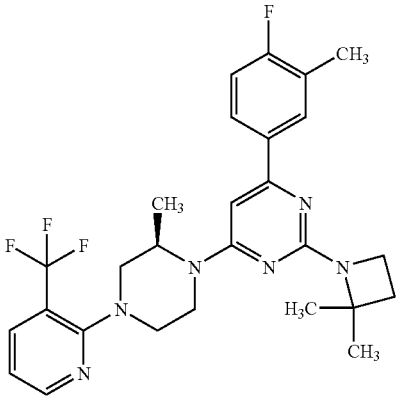 | 2-(2,2-dimethylazetidin-1-yl)-4-(4-fluoro-3-methylphenyl)-6-{(2R)-2-methyl-4-[3-(trifluoromethyl)pyridin-2-yl]piperazin-1-yl}pyrimidine | * | 1.31 | 515.34 | B |
| 795 | 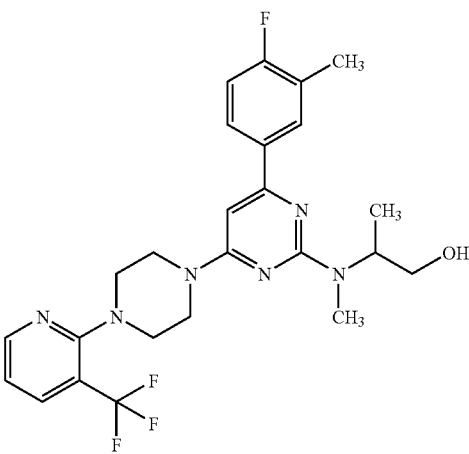 | 2-[(4-(4-fluoro-3-methylphenyl)-6-{4-[3-(trifluoromethyl)pyridin-2-yl]piperazin-1-yl}(methyl)amino]propan-1-ol | * | 1.22 | 505.31 | B |

TABLE II-continued

| Compound | | Name | IC$_{50}$ | Ret. Time | MS (M + 1) | LCMS Method |
|---|---|---|---|---|---|---|
| 796 | 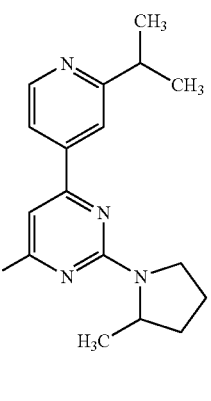 | 4-(2-isopropylpyridin-4-yl)-2-(2-methylpyrrolidin-1-yl)-6-{4-[3-(trifluoromethyl)pyridin-2-yl]piperazin-1-yl}pyrimidine | * | 1.28 | 512.35 | B |
| 797 | 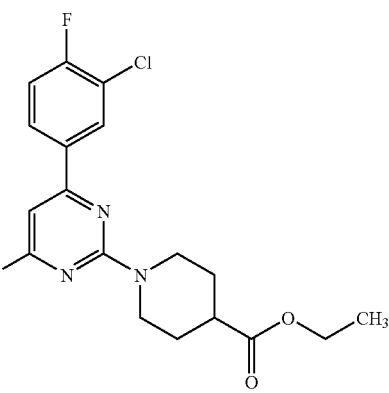 | ethyl 1-(4-(3-chloro-4-fluorophenyl)-6-{4-[3-(trifluoromethyl)pyridin-2-yl]piperazin-1-yl}pyrimidin-2-yl)piperidine-4-carboxylate | * | 1.32 | 593.29 | B |
| 798 | 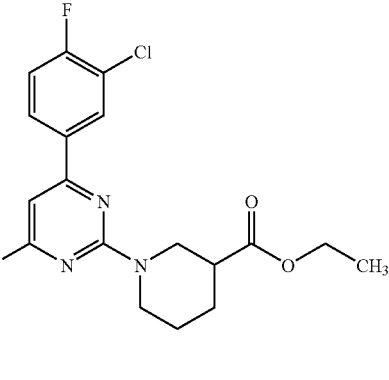 | ethyl 1-(4-(3-chloro-4-fluorophenyl)-6-{4-[3-(trifluoromethyl)pyridin-2-yl]piperazin-1-yl}pyrimidin-2-yl)piperidine-3-carboxylate | * | 1.34 | 593.29 | B |

TABLE II-continued

| Compound | | Name | IC$_{50}$ | Ret. Time | MS (M + 1) | LCMS Method |
|---|---|---|---|---|---|---|
| 799 | 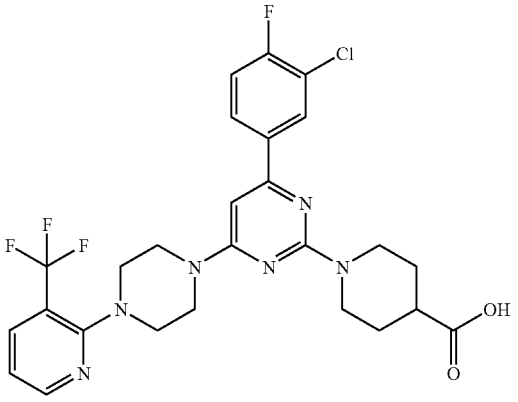 | 1-(4-(3-chloro-4-fluorophenyl)-6-{4-[3-(trifluoromethyl)pyridin-2-yl]piperazin-1-yl}pyrimidin-2-yl)piperidine-4-carboxylic acid | * | 1.26 | 565.26 | B |
| 800 | 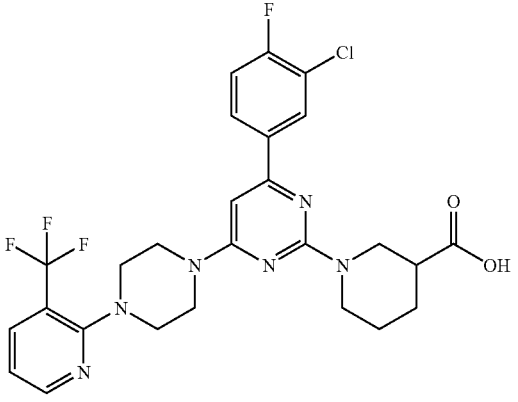 | 1-(4-(3-chloro-4-fluorophenyl)-6-{4-[3-(trifluoromethyl)pyridin-2-yl]piperazin-1-yl}pyrimidin-2-yl)piperidine-3-carboxylic acid | * | 1.27 | 565.27 | B |
| 801 | 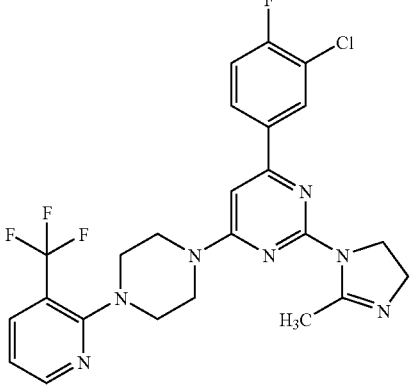 | 4-(3-chloro-4-fluorophenyl)-2-(2-methyl-4,5-dihydro-1H-imidazol-1-yl)-6-{4-[3-(trifluoromethyl)pyridin-2-yl]piperazin-1-yl}pyrimidine | * | 1.26 | 520.25 | B |

TABLE II-continued
| Compound | | Name | IC$_{50}$ | Ret. Time | MS (M + 1) | LCMS Method |
|---|---|---|---|---|---|---|
| 802 | 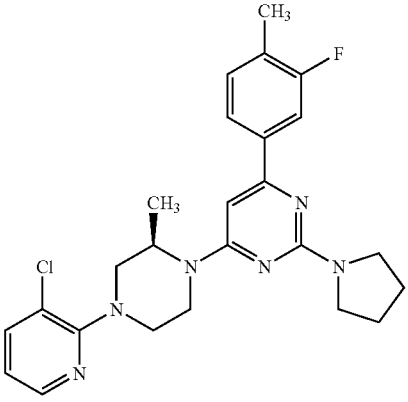 | 4-[(2R)-4-(3-chloropyridin-2-yl)-2-methylpiperazini-1-yl-6-(3-fluoro-4-methylphenyl)-2-pyrrolidin-1-ylpyrimidine | * | | | |
| 803 | 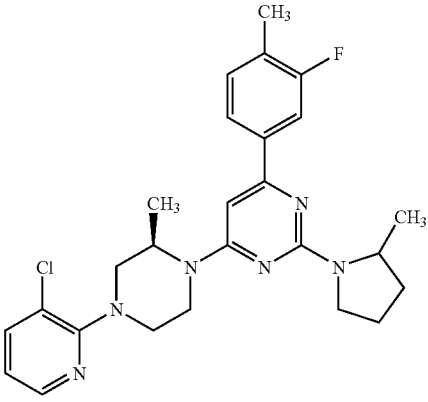 | 4-[(2R)-4-(3-chloropyridin-2-yl)-2-methylpiperazin-1-yl]-6-(3-fluoro-4-methylphenyl)-2-(2-methylpyrrolidin-1-yl)pyrimidine | * | | | |
| 804 | 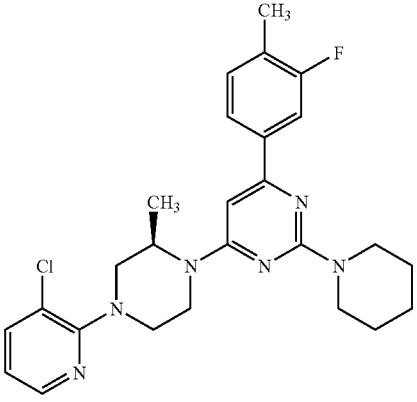 | 4-[(2R)-4-(3-chloropyridin-2-yl)-2-methylpiperazin-1-yl]-6-(3-fluoro-4-methylphenyl)-2-piperidin-1-ylpyrimidine | * | | | |

TABLE II-continued

| Compound | Name | IC$_{50}$ | Ret. Time | MS (M + 1) | LCMS Method |
|---|---|---|---|---|---|
| 805 | 4-[(2R)-4-(3-chloropyridin-2-yl)-2-methylpiperazin-1-yl]-6-(3,4-dimethylphenyl)-2-pyrrolidin-1-ylpyrimidine | * | 1.27 | 463.31 | B |
| 806 | 4-(5-chloropyridin-3-yl)-6-[(2R)-4-(3-chloropyridin-2-yl)-2-methylpiperazin-1-yl]-2-pyrrolidin-1-ylpyrimidine | * | 1.24 | 470.24 | B |
| 807 | 4-(5-chloropyridin-3-yl)-6-[(2R)-4-(3-chloropyridin-yl]-2-(2-methylpyrrolidin-1-yl)pyrimidine | * | 1.27 | 484.25 | B |
| 808 | 4-[(2R)-4-(3-chloropyridin-2-yl)-2-methylpiperazin-1-yl]-6-(3,4-dimethylphenyl)-2-(2-methylpyrrolidin-1-yl)pyrimidine | * | 1.29 | 477.33 | B |

TABLE II-continued

| Compound | | Name | IC$_{50}$ | Ret. Time | MS (M + 1) | LCMS Method |
|---|---|---|---|---|---|---|
| 809 | 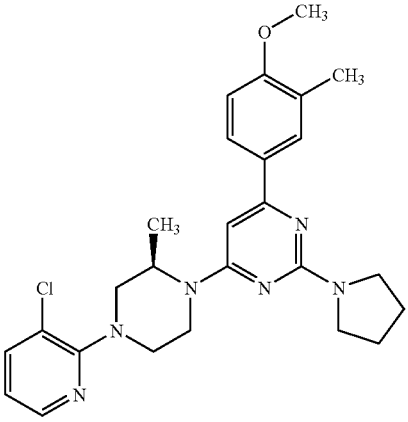 | 4-[(2R)-4-(3-chloropyridin-2-yl)-2-methylpiperazin-1-yl]-6-(4-methoxy-3-methylphenyl)-2-pyrrolidin-1-ylpyrimidine | * | 1.27 | 479.31 | B |
| 810 | 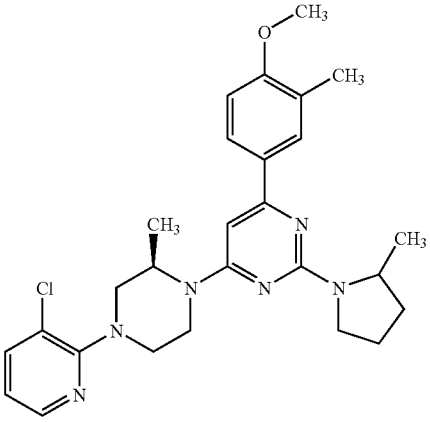 | 4-[(2R)-4-(3-chloropyridin-2-yl)-2-methylpiperazin-1-yl]-6-(4-methoxy-3-methylphenyl)-2-(2-methylpyrrolidin-1-yl)pyrimidine | * | 1.29 | 493.33 | B |
| 811 | 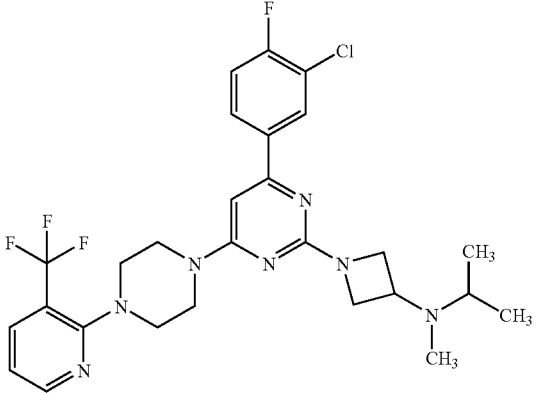 | 1-(4-(3-chloro-4-fluorophenyl)-6-{4-[3-(trifluoromethyl)pyridin-2-yl]piperazin-1-yl}pyrimidin-2-yl)-N-isopropyl-N-methylazetidin-3-amine | * | 1.2 | 564.29 | B |

TABLE II-continued
| Compound | | Name | IC$_{50}$ | Ret. Time | MS (M + 1) | LCMS Method |
|---|---|---|---|---|---|---|
| 812 | 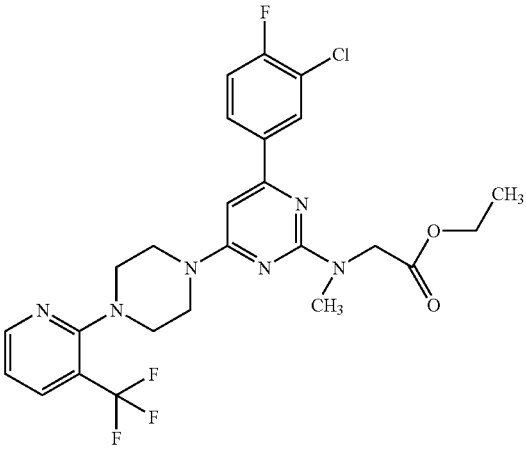 | ethyl N-(4-(3-chloro-4-fluorophenyl)-6-{4-[3-(trifluoromethyl)pyridin-2-yl]piperazin-1-yl}pyrimidin-2-yl)-N-methylglycinate | * | 1.34 | 553.26 | B |
| 813 | 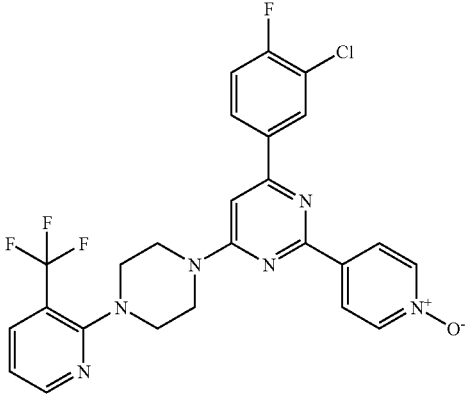 | 4-(3-chloro-4-fluorophenyl)-2-(1-oxidopyridin-4-yl)-6-{4-[3-(trifluoromethyl)pyridin-2-yl]piperazin-1-nl yl}pyrimidine | * | 1.19 | 461.22 | B |
| 814 | 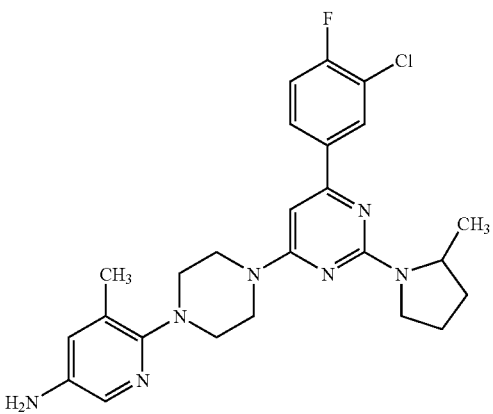 | 6-{4-[6-(3-chloro-4-fluorophenyl)-2-(2-methylpyrrolidin-1-yl)pyrimidin-4-yl]piperazin-1-yl}-5-methylpyridin-3-amine | * | 1.13 | 482.38 | B |

TABLE II-continued

| Compound | Name | IC$_{50}$ | Ret. Time | MS (M + 1) | LCMS Method |
|---|---|---|---|---|---|
| 815 | 6-{4-[6-(3-chloro-4-fluorophenyl)-2-(2-methylpyrrolidin-1-yl)pyrimidin-4-yl]piperazin-1-yl}-5-methylpyridin-3-ol | * | 1.2 | 524.24 | B |
| 816 | N-(6-{4-[6-(3-chloro-4-fluorophenyl)-2-(2-methylpyrrolidin-1-yl)pyrimidin-4-yl]piperazin-1-yl}-5-methylpyridin-3-yl)acetamide | * | 1.2 | 524.24 | B |
| 817 | N-(6-{4-[6-(3-chloro-4-fluorophenyl)-2-(2-methylpyrrolidin-1-yl)pyrimidin-4-yl]piperazin-1-yl}-5-methylpyridin-3-yl)methanesulfonamide | * | 1.19 | 560.21 | B |

TABLE II-continued

| Compound | Name | IC$_{50}$ | Ret. Time | MS (M + 1) | LCMS Method |
|---|---|---|---|---|---|
| 818 | 4-(3-chloro-4-fluorophenyl)-6-[4-(5-methoxy-3-methylpyridin-2-yl)piperazin-1-yl]-2-(2-methylpyrrolidin-1-yl)pyrimidine | * | 1.22 | 497.24 | B |
| 819 | 6-{4-[6-(3-chloro-4-fluorophenyl)-2-(4-propylpiperazin-1-yl)pyrimidin-4-yl]piperazin-1-yl}-5-methylpyridin-3-amine | * | 1.13 | 525.26 | B |
| 820 | 4-[(2R)-4-(3-chloropyrazin-2-yl)-2-methylpiperazin-1-yl]-6-(3,4-difluorophenyl)-2-pyrrolidin-1-ylpyrimidine | * | 1.22 | 472.20 | B |
| 821 | 4-[4-(3-chloropyrazin-2-yl)-2-methylpiperazin-1-yl]-6-(3,4-difluorophenyl)-2-(2-methylpyrrolidin-1-yl)pyrimidine | * | 1.24 | 486.21 | B |

TABLE II-continued
| Compound | | Name | IC$_{50}$ | Ret. Time | MS (M + 1) | LCMS Method |
|---|---|---|---|---|---|---|
| 822 | 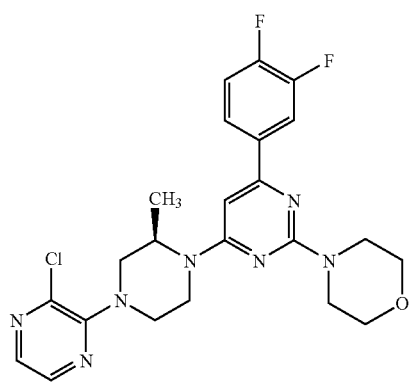 Chiral | 4-[4-[(2R)-4-(3-chloropyrazin-2-yl)-2-methylpiperazin-1-yl]-6-(3,4-difluorophenyl)pyrimidin-2-yl]morpholine | * | 1.28 | 488.19 | B |
| 823 | 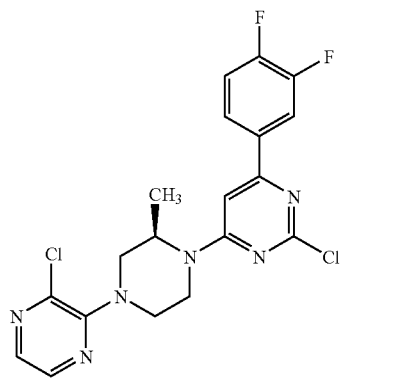 | 2-chloro-4-[4-(3-chloropyrazin-2-yl)-2-methylpiperazin-1-yl]-6-(3,4-difluorophenyl)pyrimidine | * | 1.43 | 437.10 | B |
| 824 | 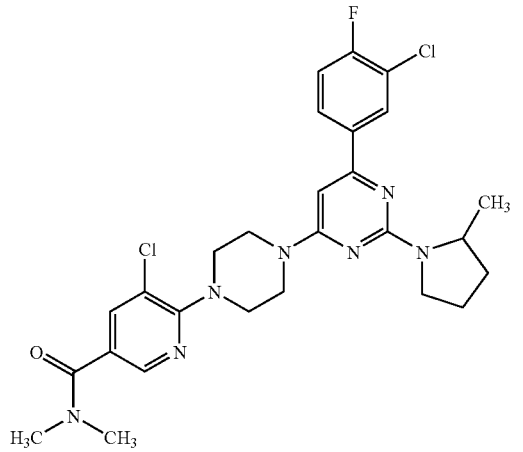 | 5-chloro-6-{4-[6-(3-chloro-4-fluorophenyl)-2-(2-methylpyrrolidin-1-yl)pyrimidin-4-yl]piperazin-1-yl}-N,N-dimethylnicotinamide | * | 1.23 | 558.22 | B |

TABLE II-continued

| Compound | Name | IC$_{50}$ | Ret. Time | MS (M + 1) | LCMS Method |
|---|---|---|---|---|---|
| 825 | 5-chloro-6-{4-[6-(3-chloro-4-fluorophenyl)-2-(2-methylpyrrolidin-1-yl)pyrimidin-4-yl]piperazin-1-yl}-N-methylnicotinamide | * | 1.23 | 544.20 | B |
| 826 (Chiral) | 2-chloro-4-[(2R)-4-(3-chloropyridin-4-yl)-2-methylpiperazin-1-yl]-6-(3,4-difluorophenyl)pyrimidine | * | 1.25 | 436.10 | B |
| 827 | 2-chloro-4-(3-chloro-4-fluorophenyl)-6-[4-(3-chloropyridin-2-yl)-2-methylpiperazin-1-yl]pyrimidine | * | 1.51 | 452.08 | B |

TABLE II-continued

| Compound | | Name | IC$_{50}$ | Ret. Time | MS (M + 1) | LCMS Method |
|---|---|---|---|---|---|---|
| 828 | | 4-[4-(3-chloropyridin-4-yl)-2-methylpiperazin-1-yl]-6-(3,4-difluorophenyl)-2-(2-methylpyrrolidin-1-yl)pyrimidine | * | 1.13 | 485.22 | B |
| 829 | Chiral | 4-[(2R)-4-(3-chloropyridin-4-yl)-2-methylpiperazin-1-yl]-6-(3,4-difluorophenyl)-2-pyrrolidin-1-ylpyrimidine | * | 1.1 | 471.20 | B |
| 830 | | 4-(3-chloro-4-fluorophenyl)-2-pyridin-2-yl-6-{4-[3-(trifluoromethyl)pyridin-2-yl]piperazin-1-yl}pyrimidine | * | 1.27 | 515.15 | B |
| 831 | Chiral | 4-(4-fluoro-3-methylphenyl)-N-methyl-N-[(3S)-1-propylpyrrolidin-3-yl]-6-{4-[3-(trifluoromethyl)pyridin-2-yl]piperazin-1-yl}pyrimidin-2-amine | * | 1.22 | 558.34 | B |

TABLE II-continued

| Compound | | Name | IC$_{50}$ | Ret. Time | MS (M + 1) | LCMS Method |
|---|---|---|---|---|---|---|
| 832 | | 1-(4-(3-chloro-4-fluorophenyl)-6-{4-[3-(trifluoromethyl)pyridin-2-yl]piperazin-1-yl}pyrimidin-2-yl)piperidine-2-carboxylic acid | * | 1.32 | 565.22 | B |
| 833 | Chiral | 4-(4-chloro-3-fluorophenyl)-6-[(2R)-4-(3-chloropyridin-2-yl)-2-methylpiperazin-1-yl]-2-pyrrolidin-1-ylpyrimidine | * | 1.27 | 487.19 | B |
| 834 | | 4-(4-chloro-3-fluorophenyl)-6-[4-(3-chloropyridin-2-yl)-2-methylpiperazin-1-yl]-2-(2-methylpyrrolidin-1-yl)pyrimidine | * | 1.28 | 501.21 | B |
| 835 | Chiral | 4-{4-(4-chloro-3-fluorophenyl)-6-[(2R)-4-(3-chloropyridin-2-yl)-2-methylpiperazin-1-yl]pyrimidin-2-yl}morpholine | * | 1.35 | 503.19 | B |

TABLE II-continued

| Compound | Name | IC$_{50}$ | Ret. Time | MS (M + 1) | LCMS Method |
|---|---|---|---|---|---|
| 836 | 2,4,4-trimethyl-7-(2-(2-methylpyrrolidin-1-yl)-6-{4-[3-(trifluoromethyl)pyridin-2-yl]piperazin-1-yl}pyrimidin-4-yl)-1,2,3,4-tetrahydroisoquinoline | * | 1.17 | 566.37 | B |
| 837 (Chiral) | 4-{4-(5-chloropyridin-3-yl)-6-[(2R)-4-(3-chloropyridin-2-yl)-2-methylpiperazin-1-yl]pyrimidin-2-yl}morpholine | * | 1.37 | 486.19 | B |
| 838 (Chiral) | 4-(5-chloropyridin-3-yl)-6-[(2R)-4-(3-chloropyridin-2-yl)-2-methylpiperazin-1-yl]-2-(4-propylpiperazin-1-yl)pyrimidine | * | 1.23 | 527.26 | B |
| 839 | 4-[4-(3-chloropyridin-2-yl)-2-methylpiperazin-1-yl]-6-(4-fluorophenyl)-2-(methylthio)pyrimidine | * | 1.32 | 430.16 | B |

TABLE II-continued

| Compound | | Name | IC$_{50}$ | Ret. Time | MS (M + 1) | LCMS Method |
|---|---|---|---|---|---|---|
| 840 | | 4-[4-(3-chloropyridin-2-yl)-2-methylpiperazin-1-yl]-6-(4-fluorophenyl)-2-(methylsulfonyl)pyrimidine | * | 1.28 | 462.15 | B |
| 841 | | 4-[4-(3-chloropyridin-2-yl)-2-methylpiperazin-1-yl]-6-(4-fluorophenyl)-2-pyrrolidin-1-ylpyrimidine | * | 1.24 | 453.22 | B |
| 842 | | 4-[4-(3-chloropyridin-2-yl)-2-methylpiperazin-1-yl]-6-(4-fluorophenyl)-2-(2-methylpyrrolidin-1-yl)pyrimidine | * | 1.25 | 467.24 | B |
| 843 | Chiral | 4-[(2R)-4-(3-chloropyridin-2-yl)-2-methylpiperazin-1-yl]-6-(4-fluorophenyl)-2-[(2S)-2-(methoxymethyl)pyrrolidin-1-yl]pyrimidine | * | 1.23 | 497.24 | B |

TABLE II-continued

| Compound | | | Name | IC$_{50}$ | Ret. Time | MS (M + 1) | LCMS Method |
|---|---|---|---|---|---|---|---|
| 844 | 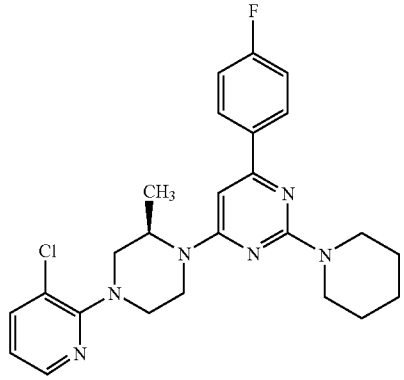 | Chiral | 4-[(2R)-4-(3-chloropyridin-2-yl)-2-methylpiperazin-1-yl]-6-(4-fluorophenyl)-2-piperidin-1-ylpyrimidine | * | 1.25 | 467.23 | B |
| 845 | 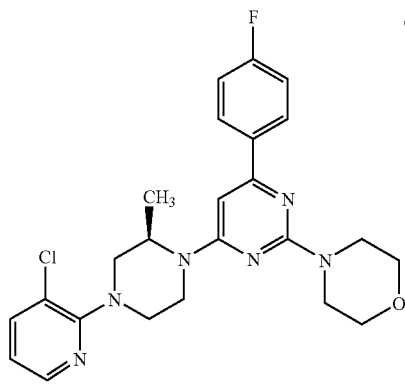 | Chiral | 4-[4-[(2R)-4-(3-chloropyridin-2-yl)-2-methylpiperazin-1-yl]-6-(4-fluorophenyl)pyrimidin-2-yl]morpholine | * | 1.23 | 469.22 | B |
| 846 | 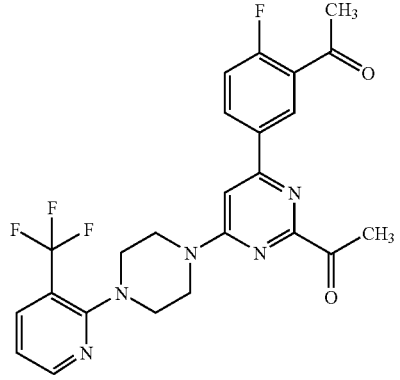 | | 1-(4-(3-acetyl-4-fluorophenyl)-6-{4-[3-(trifluoromethyl)pyridin-2-yl]piperazin-1-yl}pyrimidin-2-yl)ethanone | * | 1.33 | 488.26 | B |
| 847 | 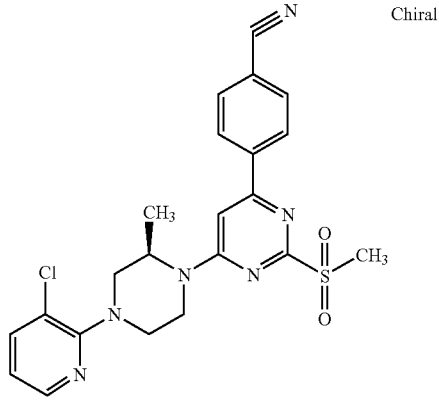 | Chiral | 4-[6-[(2R)-4-(3-chloropyridin-2-yl)-2-methylpiperazin-1-yl]-2-(methylsulfonyl)pyrimidin-4-yl]benzonitrile | * | 1.25 | 469.21 | B |

TABLE II-continued

| Compound | Name | IC$_{50}$ | Ret. Time | MS (M + 1) | LCMS Method |
|---|---|---|---|---|---|
| 848 | 3-(3-(2-morpholin-4-yl-6-{4-[3-(trifluoromethyl)pyridin-2-yl]piperazin-1-yl}pyrimidin-4-yl)phenyl]propanoic acid | * | 1.2 | 543.27 | B |
| 849 | 3-[4-(2-morpholin-4-yl-6-{4-[3-(trifluorormethyl)pyridin-2-yl]piperazin-1-yl}pyrimidin-4-yl)phenyl]propanoic acid | * | 1.2 | 543.27 | B |
| 850 | 3-[3-(2-morpholin-4-yl-6-{4-[3-(trifluoromethyl)pyridin-2-yl]piperazan-1-yl}pyrimidin-4-yl)phenyi]propan-1-ol | * | 1.2 | 529.29 | B |

TABLE II-continued
| Compound | | Name | IC$_{50}$ | Ret. Time | MS (M + 1) | LCMS Method |
|---|---|---|---|---|---|---|
| 851 | 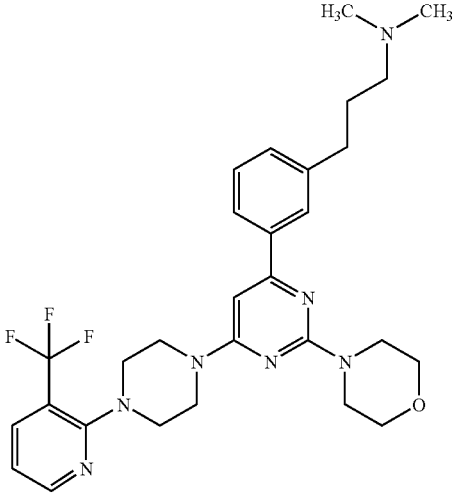 | N,N-dimethyl-3-[3-(2-morpholin-4-yl-6-{4-[3-(trifluoromethyl)pyridin-2-yl]piperazin-1-yl}pyrimidin-4-yl)phenyl]propan-1-amine | * | 1.14 | 556.34 | B |
| 852 | 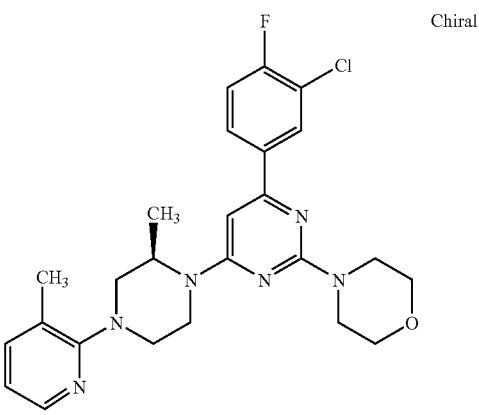 Chiral | 4-{4-(3-chloro-4-fluorophenyl)-6-[(2R)-2-methyl-4-(3-methylpyridin-2-yl)piperazin-1-yl]pyrimidin-2-yl}morpholine | * | 1.22 | 483.26 | B |
| 853 | 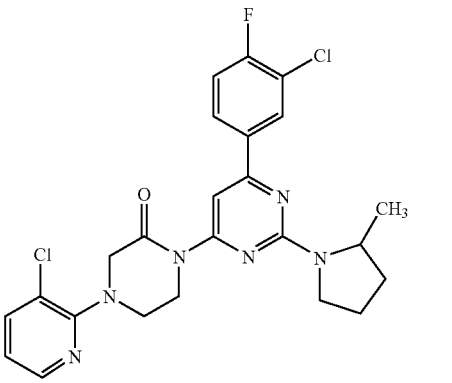 | 1-[6-(3-chloro-4-fluorophenyl)-2-(2-methylpyrrolidin-1-yl)pyrimidin-4-yl]-4-(3-chloropyridin-2-yl)piperazin-2-one | * | 1.63 | 501.19 | B |

TABLE II-continued

| Compound | | | Name | IC$_{50}$ | Ret. Time | MS (M + 1) | LCMS Method |
|---|---|---|---|---|---|---|---|
| 854 | | Chiral | 4-(5-chloropyridin-3-yl)-6-[(2R)-4-(3-chloropyridin-2-yl)-2-methylpiperazin-1-yl]-2-[(2S)-2-(methoxymethyl)pyrrolidin-1-yl]pyrimidine | * | 1.24 | 514.24 | B |
| 855 | | | 4-(5-chloropyridin-3-yl)-6-[4-(3-chloropyridin-2-yl)-2-methylpiperazin-1-yl]-2-(2-methylazetidin-1-yl)pyrimidine | * | 1.25 | 470.22 | B |
| 856 | | Chiral | 1-(4-{6-[(2R)-4-(3-chloropyridin-2-yl)-2-methylpiperazin-1-yl]-2-pyrrolidin-1-ylpyrimidin-4-yl}phenyl)ethanone | * | 1.22 | 477.27 | B |
| 857 | | | 1-{4-[6-[4-(3-chloropyridin-2-yl)-2-methylpiperazin-1-yl]-2-(2-methylpyrrolidin-1-yl)pyrimidin-4-yl]phenyl}ethanone | * | 1.23 | 491.28 | B |

TABLE II-continued
| Compound | | | Name | IC$_{50}$ | Ret. Time | MS (M + 1) | LCMS Method |
|---|---|---|---|---|---|---|---|
| 858 | 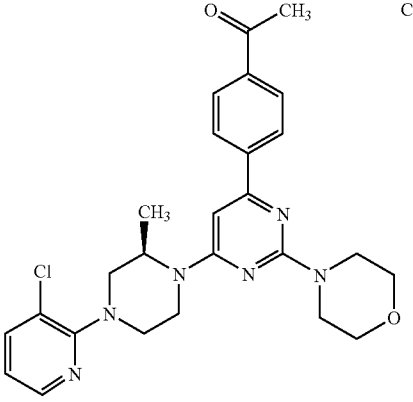 | Chiral | 1-(4-{6-[(2R)-4-(3-chloropyridin-2-yl)-2-methylpiperazin-1-yl]-2-morpholin-4-ylpyrimidin-4-yl}phenyl)ethanone | * | 1.23 | 493.27 | B |
| 859 | 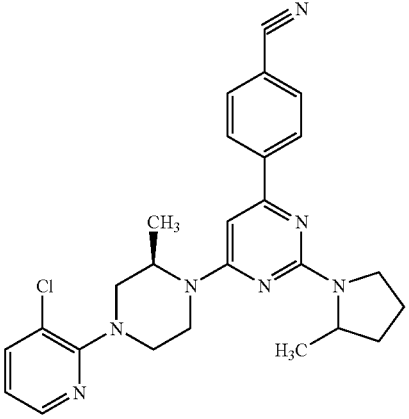 | | 4-[6-[4-(3-chloropyridin-2-yl)-2-methylpiperazin-1-yl]-2-(2-methylpyrrolidin-1-yl)pyrimidin-4-yl]benzonitrile | * | 1.23 | 474.30 | B |
| 860 | 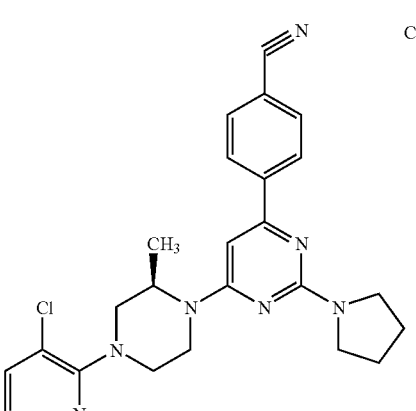 | Chiral | 4-{6-[(2R)-4-(3-chloropyridin-2-yl)-2-methylpiperazin-1-yl]-2-pyrrolidin-1-ylpyrimidin-4-yl}benzonitrite | * | 1.2 | 460.28 | B |

TABLE II-continued
| Compound | | Name | IC$_{50}$ | Ret. Time | MS (M + 1) | LCMS Method |
|---|---|---|---|---|---|---|
| 861 | 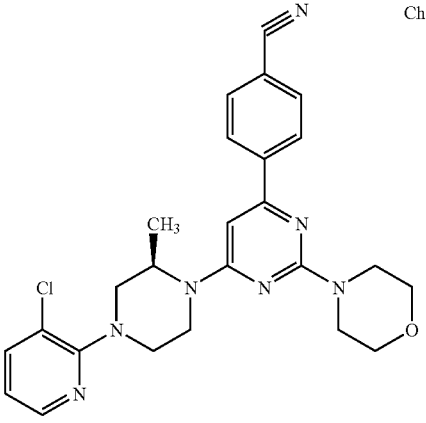 Chiral | 4-{6-[(2R)-4-(3-chloropyridin-2-yl)-2-methylpiperazin-1-yl]-2-morpholin-4-ylpyrimidin-4-yl}benzonitrile | * | 1.27 | 476.28 | B |
| 862 | 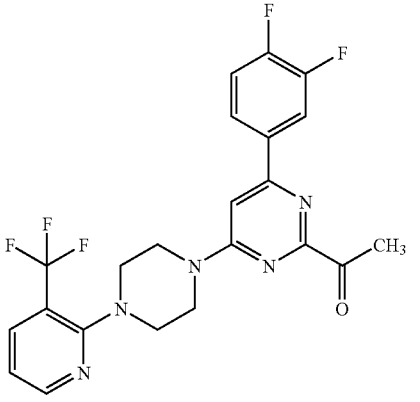 | 1-(4-(3,4-difluorophenyl)-6-{4-[3-(trifluoromethyl)pyridin-2-yl]piperazin-1-yl}pyrimidin-2-yl)ethanone | * | 1.35 | 464.17 | B |
| 863 | 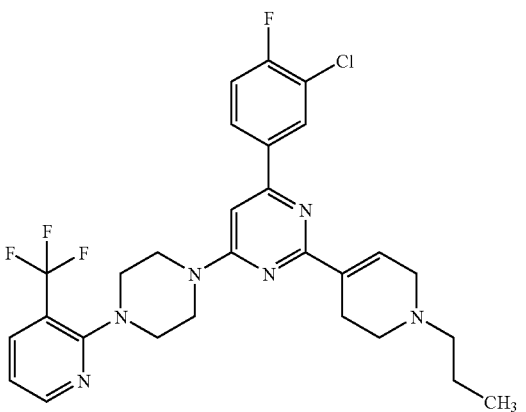 | 4-(3-chloro-4-fluorophenyl)-2-(1-propyl-1,2,3,6-tetrahydropyridin-4-yl)-6-{4-[3-(trifluoromethyl)pyridin-2-yl]piperazin-1-yl}pyrimidine | * | 1.29 | 561.25 | B |

TABLE II-continued
| Compound | | Name | IC$_{50}$ | Ret. Time | MS (M + 1) | LCMS Method |
|---|---|---|---|---|---|---|
| 864 | 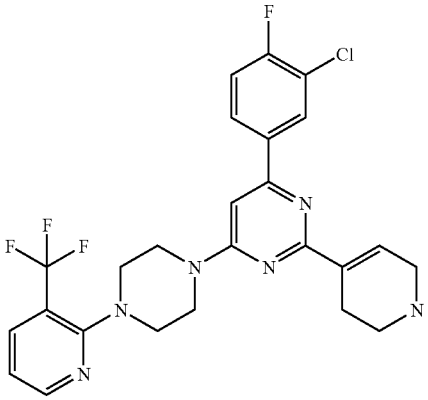 | 4-(3-chloro-4-fluorophenyl)-2-(1,2,3,6-tetrahydropyridin-4-yl)-6-{4-(3-(trifluoromethyl)pyridin-2-yl]piperazin-1-yl}pyrimidine | * | 1.27 | 519.20 | B |
| 865 | 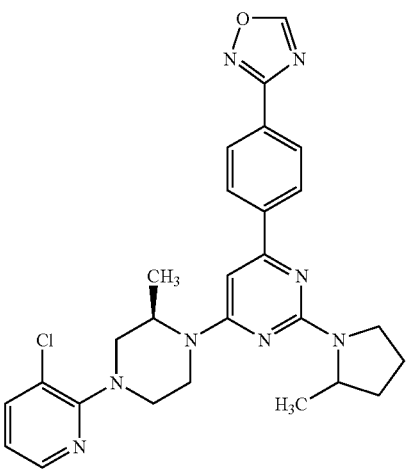 | 4-[4-(3-chloropyridin-2-yl)-2-methylpiperazin-1-yl]-2-(2-methylpyrrolidin-1-yl)-6-[4-(1,2,4-oxadiazol-3-yl)phenyl]pyrimidine | * | 1.27 | 517.24 | B |
| 866 | 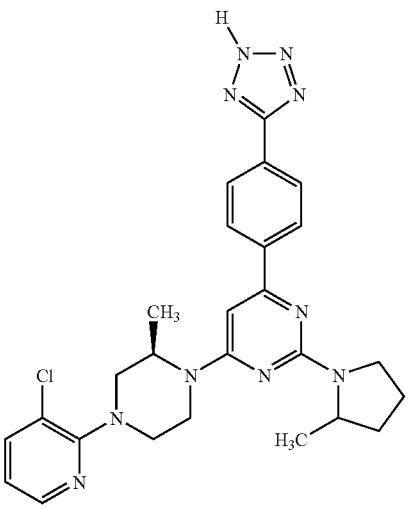 | 4-[4-(3-chloropyridin-2-yl)-2-methylpiperazin-1-yl]-2-(2-methylpyrrolidin-1-yl)-6-[4-(2H-tetrazol-5-yl)phenyl]pyrimidine | | 1.26 | 517.26 | B |

TABLE II-continued

| Compound | Name | IC$_{50}$ | Ret. Time | MS (M + 1) | LCMS Method |
|---|---|---|---|---|---|
| 867 | ethyl 4-[6-[4-(3-chloropyridin-2-yl)-2-methylpiperazin-1-yl]-2-(2-methylpyrrolidin-1-yl)pyrimidin-4-yl]benzoate | * | 1.28 | 521.25 | B |
| 868 | 3-{6-[(2R)-4-(3-chloropyridin-2-yl)-2-methylpiperazin-1-yl]-2-pyrrolidin-1-ylpyrimidin-4-yl}benzonitrile | * | 1.22 | 460.35 | B |
| 869 | 3-[6-[4-(3-chloropyridin-2-yl)-2-methylpiperazin-1-yl]-2-(2-methylpyrrolidin-1-yl)pyrimidin-4-yl]benzonitrile | * | 1.23 | 474.37 | B |
| 870 | 3-{6-[4-(3-chloropyridin-2-yl)-2-methylpiperazin-1-yl]-2-morpholin-4-ylpyrimidin-4-yl}benzonitrile | * | 1.27 | 476.36 | B |

TABLE II-continued
| Compound | | Name | IC$_{50}$ | Ret. Time | MS (M + 1) | LCMS Method |
|---|---|---|---|---|---|---|
| 871 | 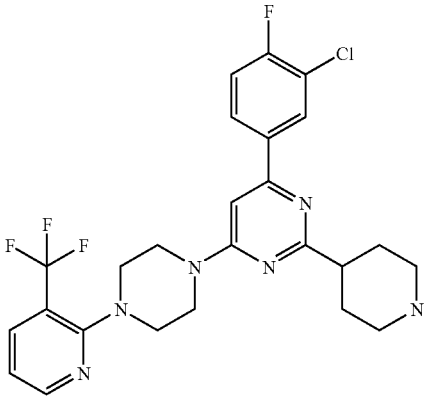 | 4-(3-chloro-4-fluorophenyl)-2-piperidin-4-yl-6-{4-[3-(trifluoromethyl)pyridin-2-yl]piperazin-1-yl}pyrimidine | * | 1.21 | 521.20 | B |
| 872 | 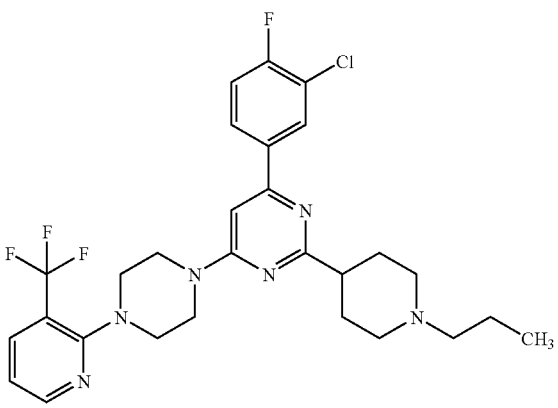 | 4-(3-chloro-4-fluorophenyl)-2-(1-propylpiperidin-4-yl)-6-{4-[3-(trifluoromethyl)pyridin-2-yl]piperazin-1-yl}pyrimidine | * | 1.22 | 563.25 | B |
| 873 | 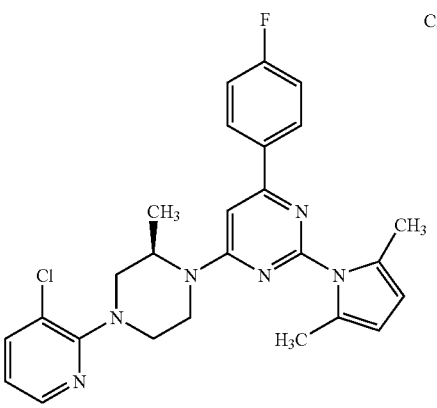 Chiral | 4-((2R)-4-(3-chloropyridin-2-yl)-2-methylpiperazin-1-yl]-2-(2,5-dimethyl-1H-pyrrol-1-yl)-6-(4-fluorophenyl)pyrimidine | * | 1.52 | 477.05 | B |

TABLE II-continued

| Compound | | | Name | IC$_{50}$ | Ret. Time | MS (M + 1) | LCMS Method |
|---|---|---|---|---|---|---|---|
| 874 | (structure) | Chiral | 4-[6-[(2R)-4-(3-chloropyridin-2-yl)-2-methypiperazin-1-yl]-2-(2,5-dimethyl-1H-pyrrol-1-yl)pyrimidin-4-yl]benzonitrile | * | 1.49 | 484.07 | B |
| 875 | (structure) | | 2-(2,5-dimethyl-1H-pyrrol-1-yl)-4-(4-fluorophenyl)-6-{4-[3-(trifluoromethyl)pyridin-2-yl]piperazin-1-yl}pyrimidine | * | 1.5 | 497.04 | B |
| 876 | (structure) | | 4-(2-(2,5-dimethyl-1H-pyrrol-1-yl)-6-{4-[3-(trifluoromethyl)pyridin-2-yl]piperazin-1-yl}pyrimidin-4-yl)benzonitri e | * | 1.48 | 504.06 | B |

TABLE II-continued

| Compound | | Name | IC$_{50}$ | Ret. Time | MS (M + 1) | LCMS Method |
|---|---|---|---|---|---|---|
| 877 | | 2-(2,5-dimethyl-1H-pyrrol-1-yl)-4-(4-fluoro-3-methylphenyl)-6-{4-[3-(trifluoromethyl)pyridin-2-yl]piperazin-1-yl}pyrimidine | * | 1.54 | 511.06 | B |
| 878 | | (2Z)-1-(4-(3,4-difluorophenyl)-6-{4-[3-(trifluoromethyl)pyridin-2-yl]piperazin-1-yl}pyrimidin-2-yl)-3-(dimethylamino)prop-2-en-1-one | * | 1.24 | 519.20 | B |
| 879 | Chiral | 5-{6-[(2R)-4-(3-chloropyridin-2-yl)-2-methylpiperazin-1-yl]-2-pyrrolidin-1-ylpyrimidin-4-yl}nicotinonitrile | * | 1.22 | 461.21 | B |
| 880 | | 5-[6-[4-(3-chloropyridin-2-yl)-2-methylpiperazin-1-yl]-2-(2-methylpyrrolidin-1-yl)pyrimidin-4-yl]nicotinonitrile | * | 1.25 | 475.22 | B |

TABLE II-continued

| Compound | | Name | IC$_{50}$ | Ret. Time | MS (M + 1) | LCMS Method |
|---|---|---|---|---|---|---|
| 881 | | 2-chloro-4-[4-(3-chloropyridin-2-yl)-2-methylpiperazin-1-yl]-6-pyridin-3-ylpyrimidine | | 1.31 | 401.13 | B |
| 882 | | 4-[4-(3-chloropyridin-2-yl)-2-methylpiperazin-1-yl]-2-(2-methylpyrrolidin-1-yl)-6-pyridin-3-ylpyrimidine | * | 1.22 | 450.22 | B |
| 883 | Chiral | 4-[(2R)-4-(3-chloropyridin-2-yl)-2-methylpiperazin-1-yl]-6-pyridin-3-yl-2-pyrrolidin-1-ylpyrimidine | * | 1.2 | 436.21 | B |
| 884 | | 1-(4-(3-chloro-4-fluorophenyl)-6-{4-[3-(trifluoromethyl)pyridin-2-yl]piperazin-1-yl}pyrimidin-2-yl)piperazin-2-one | * | | | |

TABLE II-continued

| Compound | Name | IC$_{50}$ | Ret. Time | MS (M + 1) | LCMS Method |
|---|---|---|---|---|---|
| 885 | 1-(4-(3-chloro-4-fluorophenyl)-6-{4-[3-(trifluoromethyl)pyridin-2-yl]piperazin-1-yl}pyrimidin-2-yl)-4-propylpiperazin-2-one | * | | | |
| 886 | 5-(2-pyrrolidin-1-yl-6-{4-[3-(trifluoromethyl)pyridin-2-yl]piperazin-1-yl}pyrimidin-4-yl)nicotinonitrile | * | 1.22 | 481.22 | B |
| 887 | 5-(2-(2-methylpyrrolidin-1-yl)-6-{4-[3-(trifluoromethyl)pyridin-2-yl]piperazin-1-yl}pyrimidin-4-yl)nicotinonitrile | * | 1.25 | 495.23 | B |
| 888 | 1-{3-[6-[4-(3-chloropyridin-2-yl)-2-methylpiperazin-1-yl]-2-(2-methylpyrrolidin-1-yl)pyrimidin-4-yl]phenyl}ethanone | * | 1.25 | 491.25 | B |

TABLE II-continued

| Compound | | Name | IC$_{50}$ | Ret. Time | MS (M + 1) | LCMS Method |
|---|---|---|---|---|---|---|
| 889 | 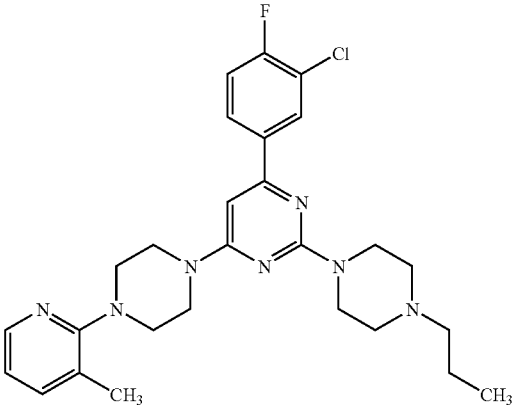 | 4-(3-chloro-4-fluorophenyl)-6-[4-(3-methylpyridin-2-yl)piperazin-1-yl]-2-(4-propylpiperazin-1-yl)pyrimidine | * | 1.15 | 510.28 | B |
| 890 | 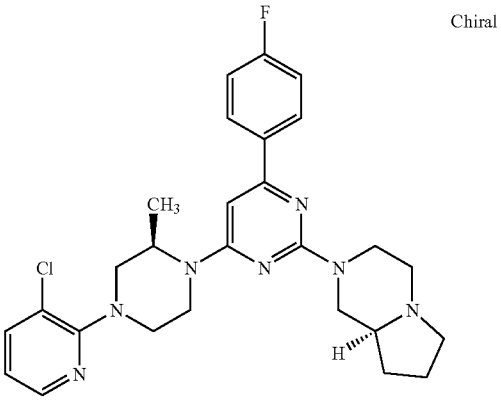 Chiral | (8aS)-2-[4-[(2R)-4-(3-chloropyridin-2-yl)-2-methylpiperazin-1-yl]-6-(4-fluorophenyl)pyrimidin-2-yl]octahydropyrrolo[1,2-a]pyrazine | * | 1.22 | 508.25 | B |
| 891 | 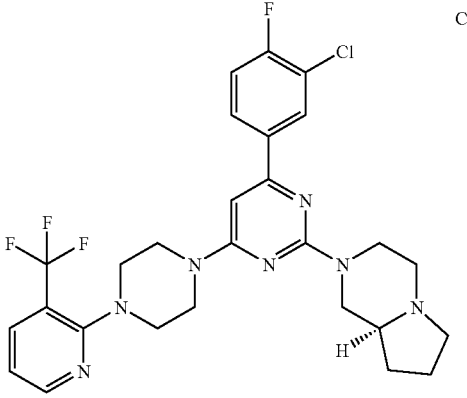 Chiral | (8aS)-2-(4-(3-chloro-4-fluorophenyl)-6-{4-[3-(trifluoromethyl)pyridin-2-yl]piperazin-1-yl}pyrimidin-2-yl)octahydropyrrolo[1,2-a]pyrazine | * | 1.28 | 562.23 | B |

TABLE II-continued

| Compound | Name | IC$_{50}$ | Ret. Time | MS (M + 1) | LCMS Method |
|---|---|---|---|---|---|
| 892 | (8aS)-2-(4-(3-chlorophenyl)-6-{4-[3-(trifluoromethyl)pyridin-2-yl]piperazin-1-yl}pyrimidin-2-yl)octahydropyrrolo[1,2-a]pyrazine | * | 1.27 | 544.24 | B |
| 893 | 1-(4-(3,4-difluorophenyl)-(trifluoromethyl)pyridin-2-yl]piperazin-1-yl}pyrimidin-2-yl)-3-(dimethylamino)propan-1-ol | * | 1.2 | 523.24 | B |
| 894 | 2-chloro-4-(3,4-difluorophenyl)-6-[(2R)-4-(3-fluoropyridin-2-yl)-2-methylpiperazin-1-yl]pyrimidine | * | 1.42 | 420.13 | B |

TABLE II-continued
| Compound | | Name | IC$_{50}$ | Ret. Time | MS (M + 1) | LCMS Method |
|---|---|---|---|---|---|---|
| 895 | 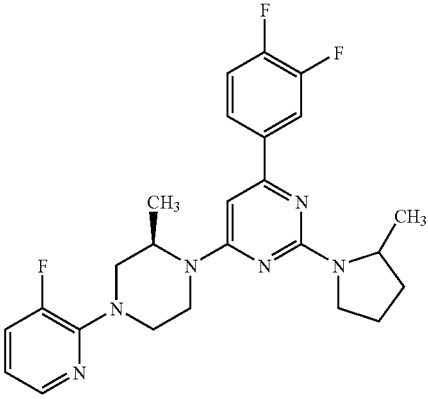 | 4-(3,4-difluorophenyl)-6-[4-(3-fluoropyridin-2-yl)-2-methylpiperazin-1-yl]-2-(2-methylpyrrolidin-1-yl)pyrimidine | * | 1.24 | 469.24 | B |
| 896 | 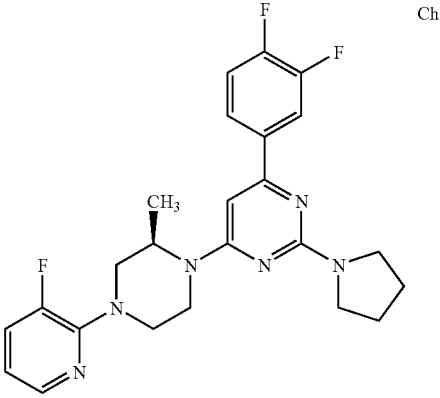 Chiral | 4-(3,4-difluorophenyl)-6-[(2R)-4-(3-fluoropyridin-2-yl)-2-methylpiperazin-1-yl]-2-pyrrolidin-1-ylpyrimidine | * | 1.22 | 455.22 | B |
| 897 | 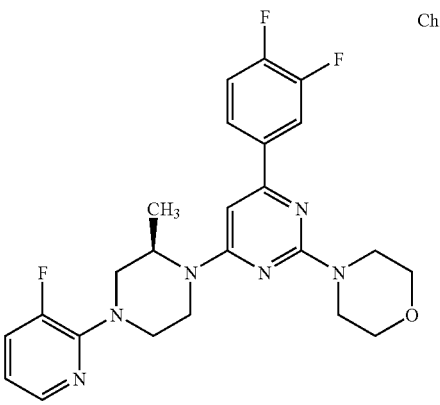 Chiral | 4-{4-(3,4-difluorophenyl)-6-[(2R)-4-(3-fluoropyridin-2-yl)-2-methylpiperazin-1-yl]pyrimidin-2-yl}morpholine | * | 1.28 | 471.23 | B |

TABLE II-continued
| Compound | | Name | IC$_{50}$ | Ret. Time | MS (M + 1) | LCMS Method |
|---|---|---|---|---|---|---|
| 898 | 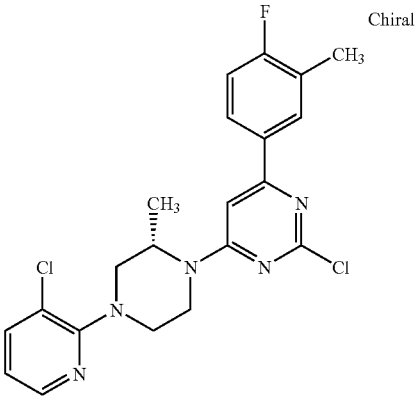 Chiral | 2-chloro-4-[(2S)-4-(3-chloropyridin-2-yl)-2-methylpiperazin-1-yl]-6-(4-fluoro-3-methylphenyl)pyrimidine | * | 1.48 | 432.10 | B |
| 899 | 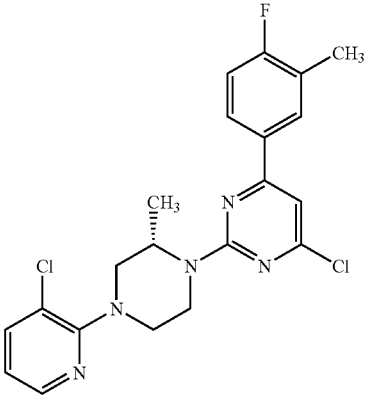 | 4-chloro-2-[4-(3-chloropyridin-2-yl)-2-methylpiperazin-1-yl]-6-(4-fluoro-3-methylphenyl)pyrimidine | * | 1.48 | 432.09 | A |
| 900 | 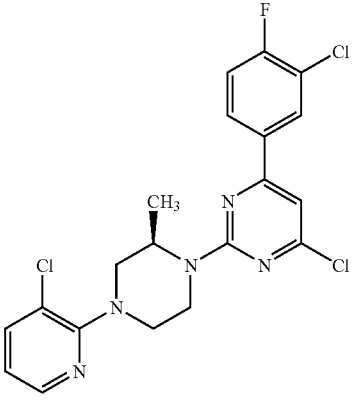 | 4-chloro-6-(3-chloror-4-fluorophenyl)-2-[4-(3-chloropyridin-2-yl)-2-methylpiperazin-1-yl]pyrimidine | | 1.55 | 452.05 | A |

TABLE II-continued
| Compound | | Name | IC$_{50}$ | Ret. Time | MS (M + 1) | LCMS Method |
|---|---|---|---|---|---|---|
| 901 | 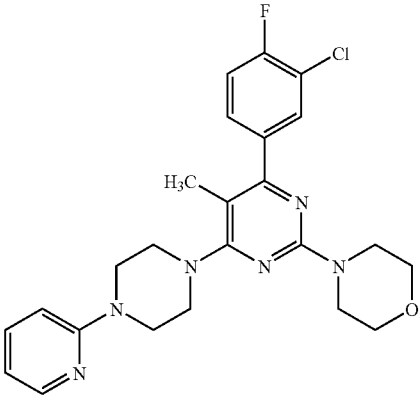 | 4-[4-(3-chloro-4-fluorophenyl)-5-methyl-6-(4-pyridin-2-ylpiperazin-1-yl)pyrimidin-2-yl]morpholine | | 1.1 | 469.21 | B |
| 902 | 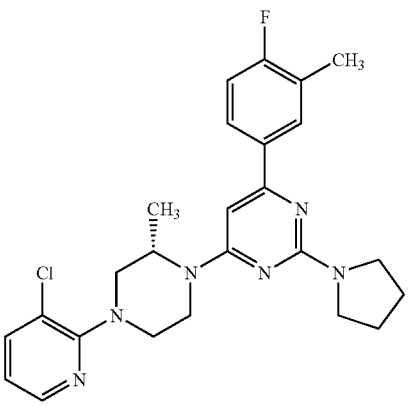 | 4-[(2S)-4-(3-chloropyridin-2-yl)-2-methylpiperazin-1-yl]-6-(4-fluoro-3-methylphenyl)-2-pyrrolidin-1-ylpyrimidine | * | 1.26 | 467.23 | B |
| 903 | 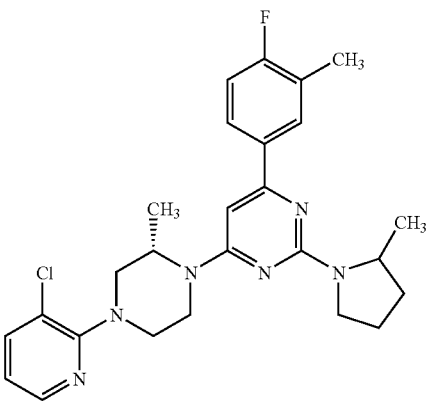 | 4-[4-(3-chloropyridin-2-yl)-2-methylpiperazin-1-yl]-6-(4-fluoro-3-methylphenyl)-2-(2-methylpyrrolidin-1-yl)pyrimidine | * | 1.27 | 481.25 | B |

TABLE II-continued
| Compound | | Name | IC$_{50}$ | Ret. Time | MS (M + 1) | LCMS Method |
|---|---|---|---|---|---|---|
| 904 | 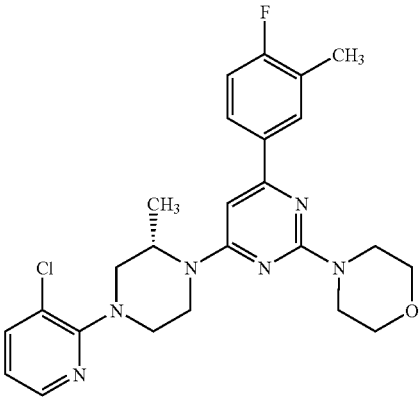 | 4-[4-[(2S)-4-(3-chloropyridin-2-yl)-2-methylpiperazin-1-yl]-6-(4-fluoro-3-methylphenyl)pyrimidin-2-yl]morpholine | * | 1.25 | 483.22 | B |
| 905 | 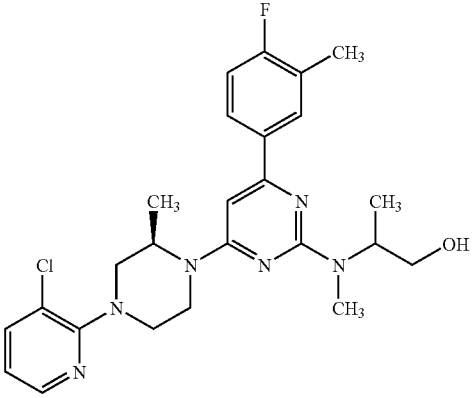 | 2-[[4-[4-(3-chloropyridin-2-yl)-2-methylpiperazin-1-yl]-6-(4-fluoro-3-methylphenyl)pyrimidin-2-yl](methyl)amino]propan-1-ol | * | 1.23 | 485.24 | B |
| 906 | 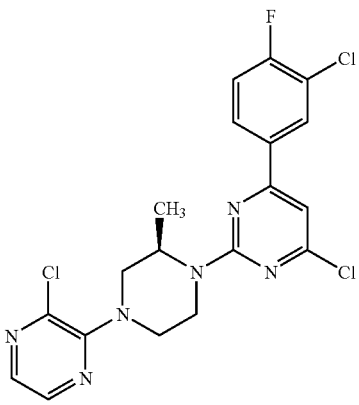 | 4-chloro-6-(3-ohloro-4-fluorophenyl)-2-[4-(3-chloropyrazin-2-yl)-2-methylpiperazin-1-yl]pyrimidine | * | 1.5 | 455.07 | A |

TABLE II-continued
| Compound | | Name | IC$_{50}$ | Ret. Time | MS (M + 1) | LCMS Method |
|---|---|---|---|---|---|---|
| 907 | 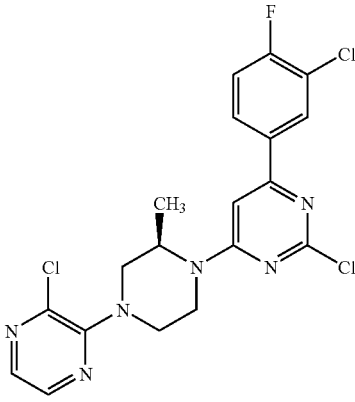 | 2-chloro-4-(3-chloro-4-fluorophenyl)-6-[4-(3-chloropyrazin-2-yl)-2-methylpiperazin-1-yl]pyrimidine | * | 1.47 | 45309 | B |
| 908 | 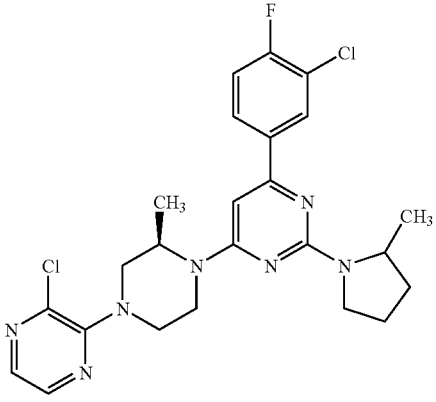 | 4-(3-chloro-4-fluorophenyl)-6-[4-(3-methylpiperazin-1-yl]-2-chloropyrazin-2-yl)-2-(2-methylpyrrolidin-1-yl)pyrimidine | * | 1.26 | 502.19 | B |
| 909 | 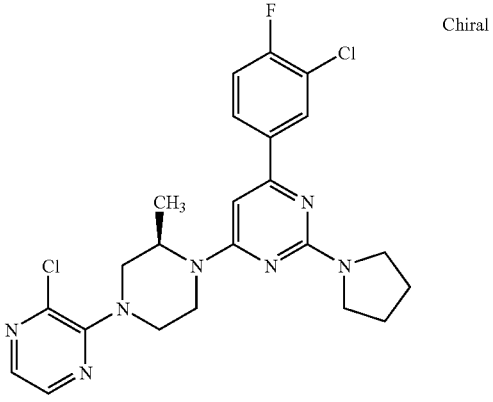 Chiral | 4-(3-chloro-4-fluorophenyl)-6-[(2R)-4-(3-chloropyrazin-2-yl)-2-methylpiperazin-1-yl]-2-pyrrolidin-1-ylpyrimidine | * | 1.24 | 488.18 | B |

TABLE II-continued

| Compound | | Name | IC$_{50}$ | Ret. Time | MS (M + 1) | LCMS Method |
|---|---|---|---|---|---|---|
| 910 | Chiral | 4-{4-(3-chloro-4-fluorophenyl)-6-[(2R)-4-(3-chloropyrazin-2-yl)-2-methylpiperazin-1-yl]pyrimidin-2-yl}morpholine | * | 1.32 | 504.17 | B |
| 911 | | 4-(3-chloro-4-fluorophenyl)-2-[4-(3-chloropyrazin-2-yl)-2-methyipiperazin-1-yl]-6-yl)pyrimidine | * | 1.31 | 502.19 | B |
| 912 | Chiral | 2-chloro-4-[(2R)-4-(3-chloropyrazin-2-yl)-2-methylpiperazin-1-yl]-6-(4-fluoro-3-methylphenyl)pyrimidine | * | 1.45 | 433.13 | B |

TABLE II-continued
| Compound | | Name | IC$_{50}$ | Ret. Time | MS (M + 1) | LCMS Method |
|---|---|---|---|---|---|---|
| 913 | 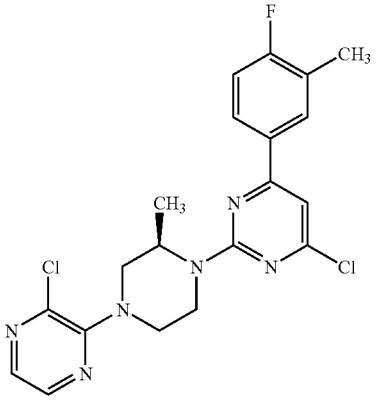 Chiral | 4-chloro-2-[(2R)-4-(3-chloropyrazin-2-yl)-2-methylpiperazin-1-yl]-6-(4-fluoro-3-methylphenyl)pyrimidine | | 1.5 | 433.11 | A |
| 914 | 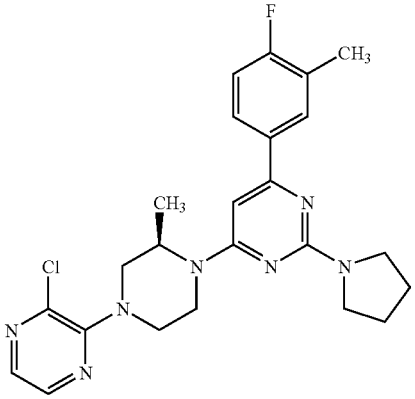 Chiral | 4-[(2R)-4-(3-chloropyrazin-2-yl)-2-methylpiperazin-1-yl]-6-(4-fluoro-3-methylphenyl)-2-pyrrolidin-1-ylpyrimidine | * | 1.23 | 468.21 | B |
| 915 | 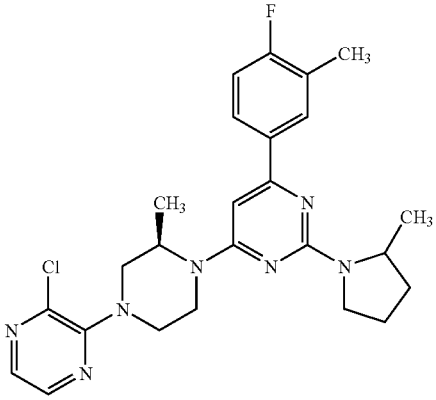 | 4-[4-(3-chloropyrazin-2-yl)-2-methylpiperazin-1-yl]-6-(4-fluoro-3-methylphenyl)-2-(2-methylpyrrolidin-1-yl)pyrimidine | * | 1.25 | 482.22 | B |

TABLE II-continued
| Compound | | Name | IC$_{50}$ | Ret. Time | MS (M + 1) | LCMS Method |
|---|---|---|---|---|---|---|
| 916 | 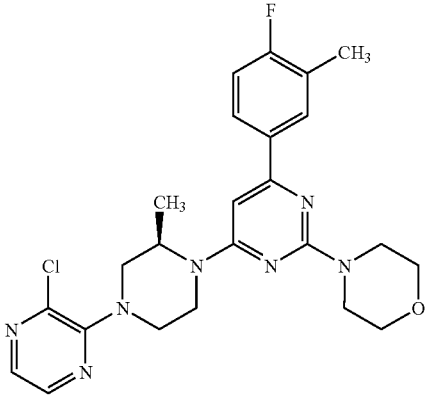 Chiral | 4-[4-[(2R)-4-(3-chloropyrazin-2-yl)-2-methylpiperazin-1-yl]-6-(4-fluoro-3-methylphenyl)pyrimidin-2-yl]morpholine | * | 1.23 | 484.21 | B |
| 917 | 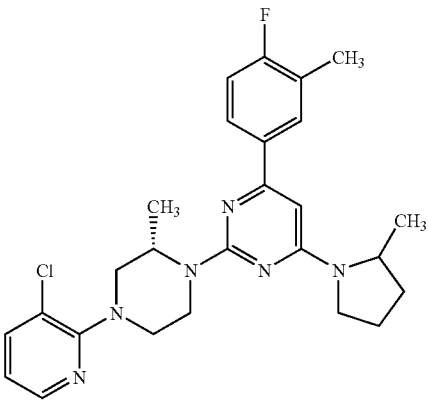 | 2-[4-(3-chloropyridin-2-yl)-2-methylpiperazin-1-yl]-4-(4-fluoro-3-methylphenyl)-6-(2-methylpyrrolidin-1-yl)pyrimidine | * | 1.27 | 481.22 | B |
| 918 | 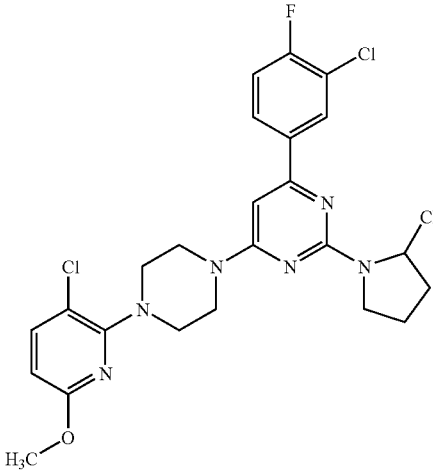 | 4-(3-chloro-4-fluorophenyl)-6-[4-(3-chloro-6-methoxypyridin-2-yl)piperazin-1-yl]-2-(2-methylpyrrolidin-1-yl)pyrimidine | * | 1.3 | 517.18 | B |

TABLE II-continued

| Compound | | Name | IC$_{50}$ | Ret. Time | MS (M + 1) | LCMS Method |
|---|---|---|---|---|---|---|
| 919 | Chiral | 4-chloro-2-[(2R)-4-(3-chloropyrazin-2-yl)-2-methylpiperazin-1-yl]-6-(4-fluorophenyl)pyrimidine | * | 1.56 | 419.14 | B |
| 920 | Chiral | 2-chloro-4-[(2R)-4-(3-chloropyrazin-2-yl)-2-methylpiperazin-1-yl]-6-(4-fluorophenyl)pyrimidine | * | 1.4 | 419.12 | B |
| 921 | Chiral | 4-[(2S)-4-(3-chloropyridin-2-yl)-2-methylpiperazin-1-yl]-6-(3,4-difluorophenyl)-2-pyrrolidin-1-ylpyrimidine | * | 1.24 | 471.21 | B |

TABLE II-continued

| Compound | | Name | IC$_{50}$ | Ret. Time | MS (M + 1) | LCMS Method |
|---|---|---|---|---|---|---|
| 922 | Chiral | 4-[(2S)-4-(3-chloropyridin-2-yl)-2-methylpiperazin-1-yl]-6-(3,4-difluorophenyl)-2-(2-methylpyrrolidin-1-yl)pyrimidine | * | 1.26 | 485.23 | B |
| 923 | Chiral | 4-[4-[(2S)-4-(3-chloropyridin-2-yl)-2-methylpiperazin-1-yl]-6-(3,4-difluorophenyl)pyrimidin-2-yl]morpholine | * | 1.31 | 487.22 | B |
| 924 | Chiral | 4-[(2R)-4-(3-chloropyridin-2-yl)-2-methylpiperazin-1-yl]-6-(4-fluoro-3-methylphenyl)-2-[(2R)-2-methylpyrrolidin-1-yl]pyrimidine | * | 1.26 | 481.17 | B |

TABLE II-continued
| Compound | | Name | IC$_{50}$ | Ret. Time | MS (M + 1) | LCMS Method |
|---|---|---|---|---|---|---|
| 925 | 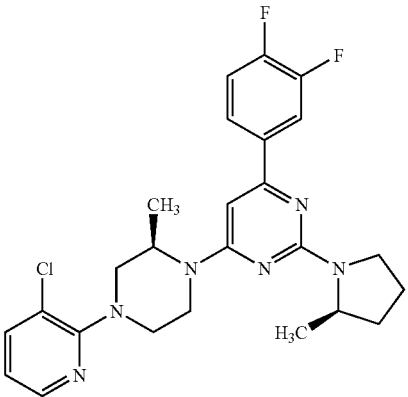 Chiral | 4-[(2R)-4-(3-chloropyridin-2-yl)-2-methylpiperazin-1-yl]-6-(3,4-difluorophenyl)-2-[(2R)-2-methylpyrrolidin-1-yl]pyrimidine | * | 1.27 | 485.26 | B |
| 926 | 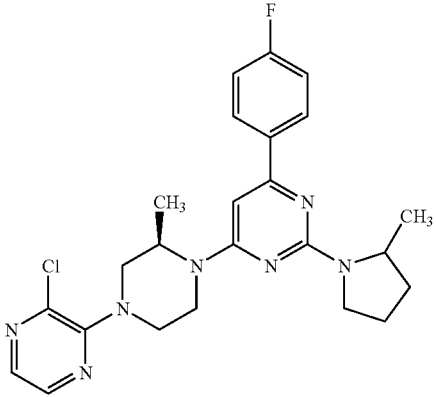 | 4-[4-(3-chloropyrazin-2-yl)-2-methylpiperazin-1-yl]-6-(4-fluorophenyl)-2-(2-methylpyrrolidin-1-yl)pyrimidine | * | 1.22 | 468.26 | B |
| 927 | 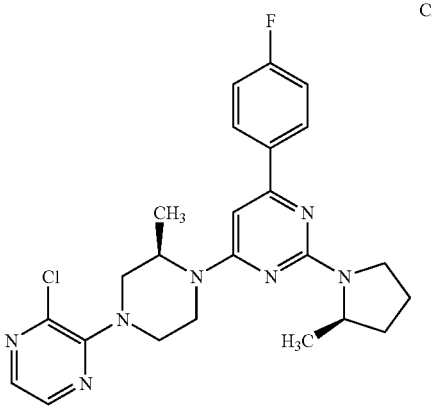 Chiral | 4-[(2R)-4-(3-chloropyrazin-2-yl)-2-methylpiperazin-1-yl]-6-(4-fluorophenyl)-2-[(2R)-2-methylpyrrolidin-1-yl]pyrimidine | * | 1.22 | 468.26 | B |

TABLE II-continued

| Compound | | | Name | IC$_{50}$ | Ret. Time | MS (M + 1) | LCMS Method |
|---|---|---|---|---|---|---|---|
| 928 | | Chiral | 4-[(2R)-4-(3-chloropyrazin-2-yl)-2-methylpiperazin-1-yl]-6-(4-fluorophenyl)-2-pyrrolidin-1-ylpyrimidine | * | 1.21 | 454.25 | B |
| 929 | | Chiral | 4-[4-[(2R)-4-(3-chloropyrazin-2-yl)-2-methylpiperazin-1-yl]-6-(4-fluorophenyl)pyrimidin-2-yl]morpholine | * | 1.2 | 470.24 | B |
| 930 | | Chiral | 4-[(2S)-4-(3-chloropyridin-2-yl)-2-methylpiperazin-1-yl]-6-(3,4-difluorophenyl)-2-[(2R)-2-methylpyrrolidin-1-yl]pyrimidine | * | 1.25 | 485.17 | B |

TABLE II-continued
| Compound | | Name | IC$_{50}$ | Ret. Time | MS (M + 1) | LCMS Method |
|---|---|---|---|---|---|---|
| 931 | 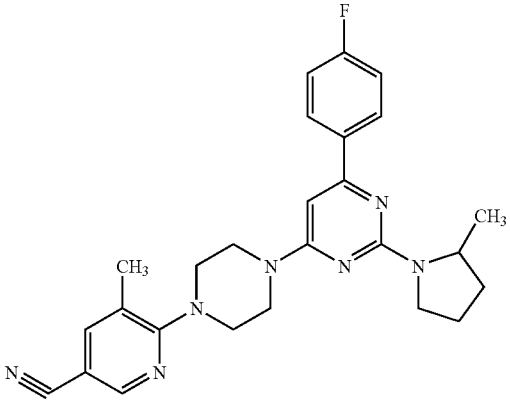 | 6-{4-[6-(4-fluorophenyl)-2-(2-methylpyrrolidin-1-yl)pyrimidin-4-yl]piperazin-1-yl}-5-methylnicotinonitrile | * | 1.2 | 458.29 | B |
| 932 | 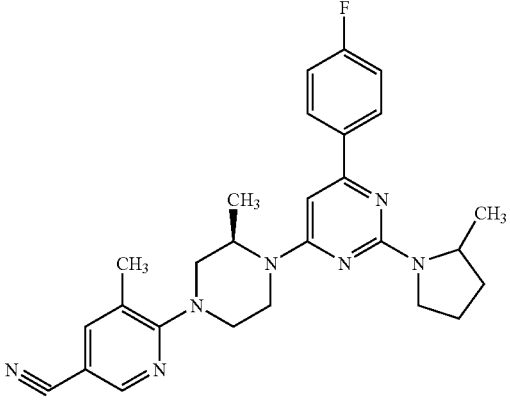 | 6-{4-[6-(4-fluorophenyl)-2-(2-methylpyrrolidin-1-yl)pyrimidin-4-yl]-3-methylpiperazin-1-yl}-5-methylnicotinonitrile | * | 1.21 | 472.31 | B |
| 933 | 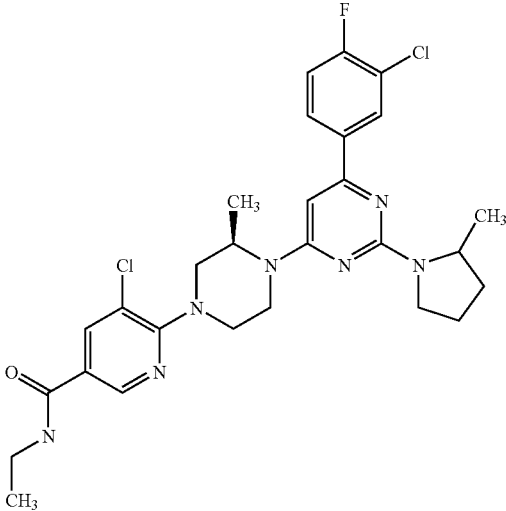 | 5-chloro-6-{4-[6-(3-chloro-4-fluorophenyl)-2-(2-methylpyrrolidin-1-yl)pyrimidin-4-yl]-3-methylpiperazin-1-yl}-N-ethylnicotinamide | * | 1.26 | 572.28 | B |

TABLE II-continued

| Compound | | Name | IC$_{50}$ | Ret. Time | MS (M + 1) | LCMS Method |
|---|---|---|---|---|---|---|
| 934 | Chiral 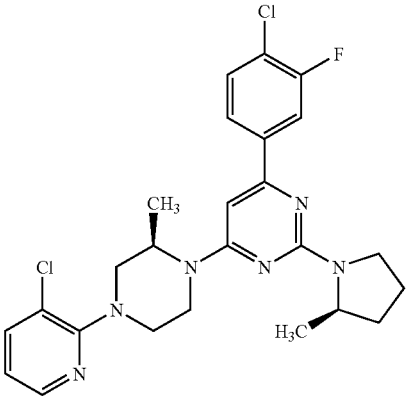 | 4-(4-chloro-3-fluorophenyl)-6-[(2R)-4-(3-chloropyridin-2-yl)-2-methylpiperazin-1-yl]-2-[(2R)-2-methylpyrrolidin-1-yl]pyrimidine | * | 1.28 | 501.23 | B |
| 935 | Chiral 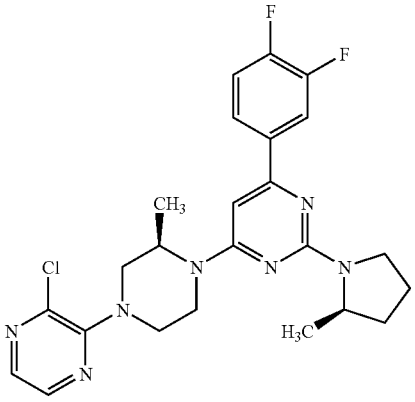 | 4-[(2R)-4-(3-chloropyrazin-2-yl)-2-methylpiperazin-1-yl]-6-(3,4-difluorophenyl)-2-[(2R)-2-methylpyrrolidin-1-yl]pyrimidine | * | 1.23 | 486.25 | B |
| 936 | Chiral 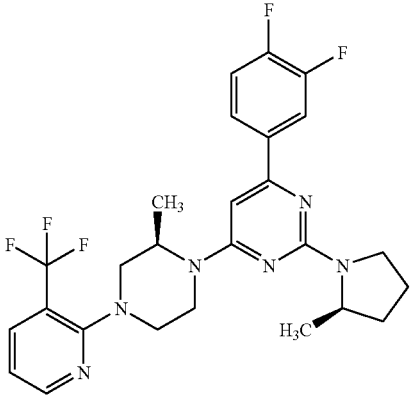 | 4-(3,4-difluorophenyl)-2-[(2R)-2-methylpyrrolidin-1-yl]-6-{(2R)-2-methyl-4-[3-(trifluoromethyl)pyridin-2-yl]piperazin-1-yl}pyrimidine | * | 1.28 | 519.28 | B |

TABLE II-continued

| Compound | | Name | IC$_{50}$ | Ret. Time | MS (M + 1) | LCMS Method |
|---|---|---|---|---|---|---|
| 937 | Chiral | 4-[(2S)-4-(3-chloropyrazin-2-yl)-2-methylpiperazin-1-yl]-6-(3,4-difluorophenyl)-2-pyrrolidin-1-ylpyrimidine | * | 1.21 | 472.24 | B |
| 938 | Chiral | 4-[(2S)-4-(3-chloropyrazin-2-yl)-2-methylpiperazin-1-yl]-6-(3,4-difluorophenyl)-2-(2-methylpyrrolidin-1-yl)pyrimidine | * | 1.24 | 486.25 | B |
| 939 | | 4-[4-[4-(3-chloropyrazin-2-yl)-2-methylpiperazin-1-yl]-6-(3,4-difluorophenyl)pyrimidin-2-yl]morpholine | * | 1.29 | 488.24 | B |

TABLE II-continued

| Compound | | | Name | IC$_{50}$ | Ret. Time | MS (M + 1) | LCMS Method |
|---|---|---|---|---|---|---|---|
| 940 | 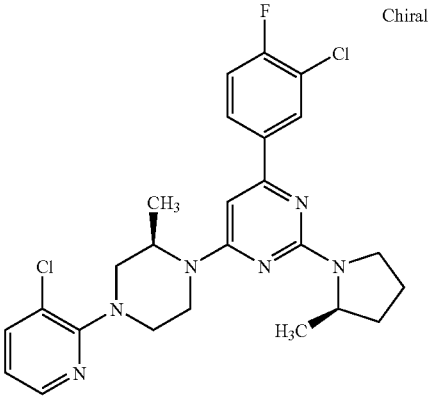 | Chiral | 4-(3-chloro-4-fluorophenyl)-6-[(2R)-4-(3-chloropyridin-2-yl)-2-methylpiperazin-1-yl]-2-[(2R)-2-methylpyrrolidin-1-yl]pyrimidine | * | 1.28 | 501.23 | B |
| 941 | 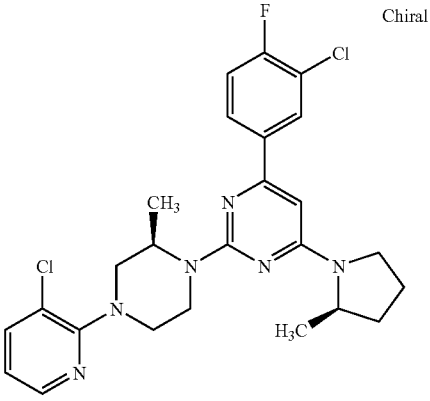 | Chiral | 4-(3-chloro-4-fluorophenyl)-2-[(2R)-4-(3-chloropyridin-2-yl)-2-methylpiperazin-1-yl]-6-[(2R)-2-methylpyrrolidin-1-yl]pyrimidine | * | 1.31 | 501.23 | B |
| 942 | 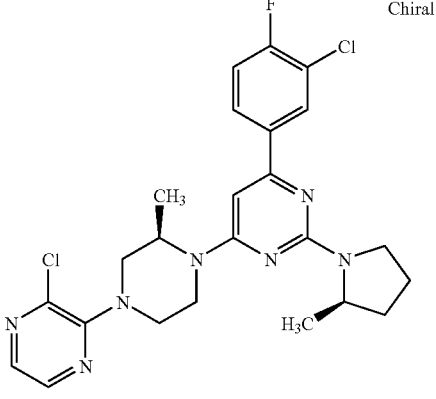 | Chiral | 4-(3-chloro-4-fluorophenyl)-6-[(2R)-4-(3-chloropyrazin-2-yl)-2-methylpiperazin-1-yl]-2-[(2R)-2-methylpyrrolidin-1-yl]pyrimidine | * | 1.25 | 502.23 | B |

TABLE II-continued

| Compound | | | Name | IC$_{50}$ | Ret. Time | MS (M + 1) | LCMS Method |
|---|---|---|---|---|---|---|---|
| 943 | 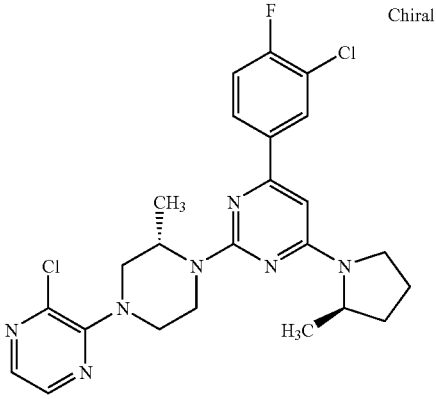 | Chiral | 4-(3-chloro-4-fluorophenyl)-2-[(2R)-4-(3-chloropyrazin-2-yl)-2-methylpiperazin-1-yl]-6-[(2R)-2-methylpyrrolidin-1-yl]pyrimidine | * | 1.31 | 502.23 | B |
| 944 | 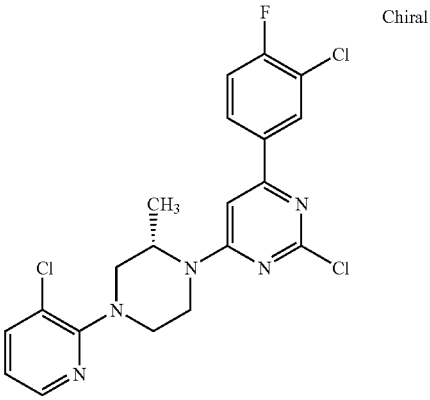 | Chiral | 2-chloro-4-(3-chloro-4-fluorophenyl)-6-[(2S)-4-(3-chloropyridin-2-yl)-2-methylpiperazin-1-yl]pyrimidine | * | 1.51 | 452.13 | B |
| 945 | 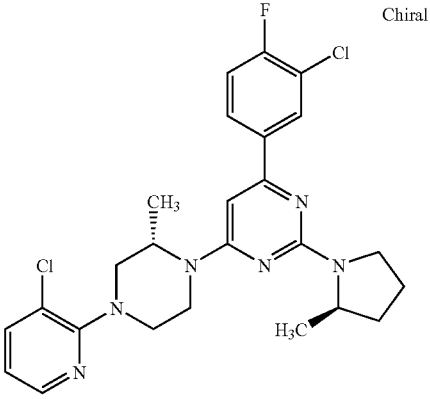 | Chiral | 4-(3-chloro-4-fluorophenyl)-6-[(2S)-4-(3-chloropyridin-2-yl)-2-methylpiperazin-1-yl]-2-[(2R)-2-methylpyrrolidin-1-yl]pyrimidine | * | 1.3 | 501.24 | B |

TABLE II-continued
| Compound | | Name | IC$_{50}$ | Ret. Time | MS (M + 1) | LCMS Method |
|---|---|---|---|---|---|---|
| 946 | 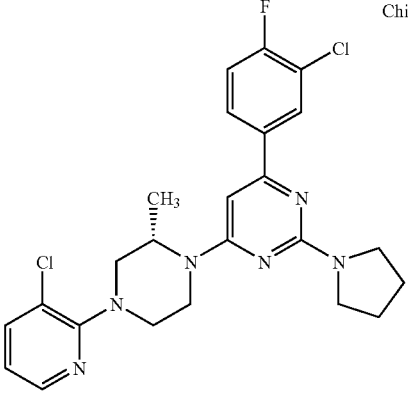 Chiral | 4-(3-chloro-4-fluorophenyl)-6-[(2S)-4-(3-chloropyridin-2-yl)-2-methylpiperazin-1-yl]-2-pyrrolidin-1-ylpyrimidine | * | 1.28 | 487.22 | B |
| 947 | 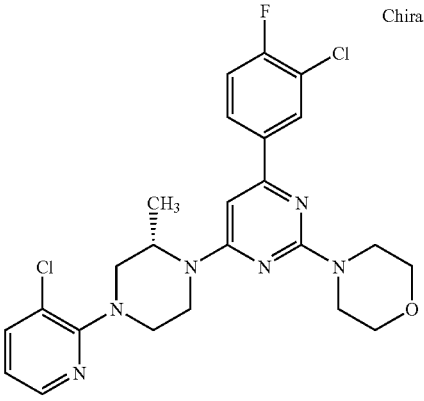 Chiral | 4-{4-(3-chloro-4-fluorophenyl)-6-[(2S)-4-(3-chloropyridin-2-yl)-2-methylpiperazin-1-yl]pyrimidin-2-yl}morpholine | * | 1.34 | 503.19 | B |
| 948 | 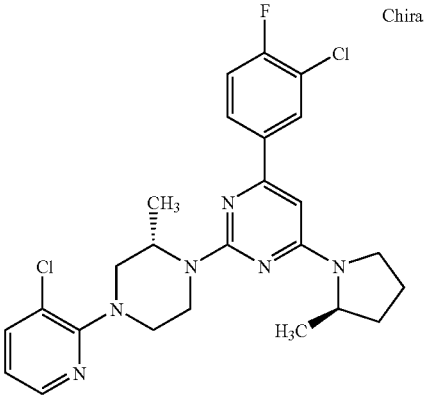 Chiral | 4-(3-chloro-4-fluorophenyl)-2-[(2S)-4-(3-chloropyridin-2-yl)-2-methylpiperazin-1-yl]-6-[(2R)-2-methylpyrrolidin-1-yl]pyrimidine | * | 1.32 | 501.21 | B |

TABLE II-continued

| Compound | | | Name | IC$_{50}$ | Ret. Time | MS (M + 1) | LCMS Method |
|---|---|---|---|---|---|---|---|
| 949 | 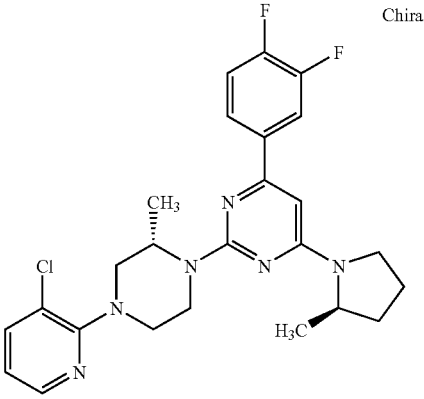 | Chiral | 2-[(2S)-4-(3-chloropyridin-2-yl)-2-methylpiperazin-1-yl]-4-(3,4-difluorophenyl)-6-[(2R)-2-methylpyrrolidin-1-yl]pyrimidine | * | 1.29 | 485.24 | B |
| 950 | 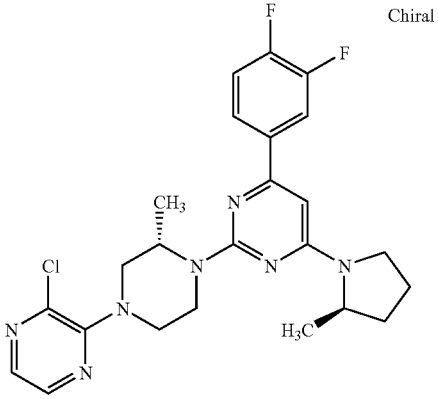 | Chiral | 2-[(2S)-4-(3-chloropyrazin-2-yl)-2-methylpiperazin-1-yl]-4-(3,4-difluorophenyl)-6-[(2R)-2-methylpyrrolidin-1-yl]pyrimidine | * | 1.28 | 486.23 | B |
| 951 | 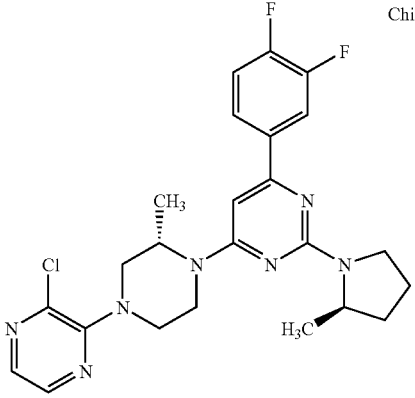 | Chiral | 4-[(2S)-4-(3-chloropyrazin-2-yl)-2-methylpiperazin-1-yl]-6-(3,4-difluorophenyl)-2-[(2R)-2-methylpyrrolidin-1-yl]pyrimidine | * | 1.24 | 486.24 | B |

TABLE II-continued
| Compound | | Name | IC$_{50}$ | Ret. Time | MS (M + 1) | LCMS Method |
|---|---|---|---|---|---|---|
| 953 | 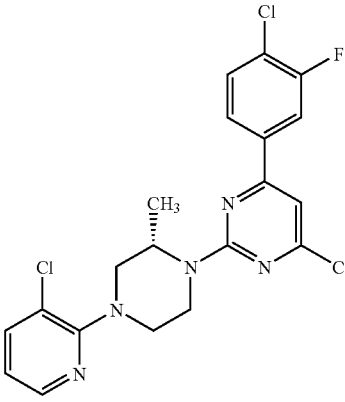 Chiral | 4-chloro-6-(4-chloro-3-fluorophenyl)-2-[(2S)-4-(3-chloropyridin-2-yl)-2-methylpiperazin-1-yl]pyrimidine | | 1.57 | 454.07 | A |
| 953 | 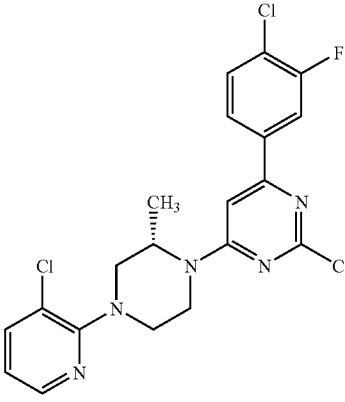 Chiral | 2-chloro-4-(4-chloro-3-fluorophenyl)-6-[(2S)-4-(3-chloropyridin-2-yl)-2-methylpiperazin-1-yl]pyrimidine | * | 1.52 | 452.10 | B |
| 954 | 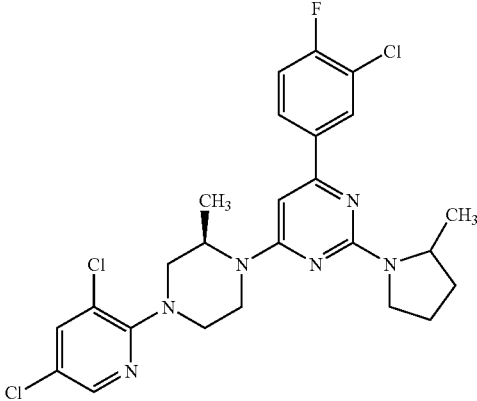 | 4-(3-chloro-4-fluorophenyl)-6-[4-(3,5-dichloropyridin-2-yl)-2-methylpiperazin-1-yl]-2-(2-methylpyrrolidin-1-yl)pyrimidine | * | | | |

TABLE II-continued

| Compound | Name | IC$_{50}$ | Ret. Time | MS (M + 1) | LCMS Method |
|---|---|---|---|---|---|
| 955 | 4-[4-(3-chloro-6-methoxypyridin-2-yl)-2-methylpiperazin-1-yl]-6-(4-fluorophenyl)-2-(2-methylpyrrolidin-1-yl)pyrimidine | * | 1.31 | 497.24 | B |
| 956 | 2-chloro-4-(4-chloro-3-fluorophenyl)-6-[(2S)-4-(3-chloropyrazin-2-yl)-2-methylpiperazin-1-yl]pyrimidine | * | 1.48 | 453.11 | B |
| 957 | 4-(4-chloro-3-fluorophenyl)-6-[(2S)-4-(3-chloropyridin-2-yl)-2-methylpiperazin-1-yl]-2-pyrrolidin-1-ylpyrimidine | * | 1.26 | 487.20 | B |

TABLE II-continued

| Compound | | Name | IC$_{50}$ | Ret. Time | MS (M + 1) | LCMS Method |
|---|---|---|---|---|---|---|
| 958 | 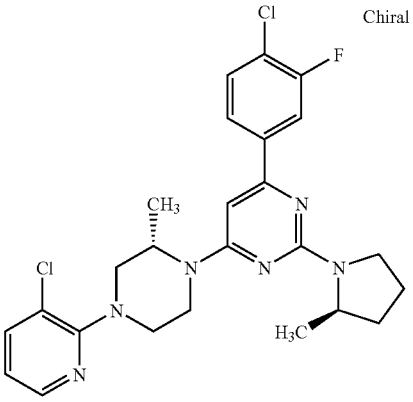 Chiral | 4-(4-chloro-3-fluorophenyl)-6-[(2S)-4-(3-chloropyridin-2-yl)-2-methylpiperazin-1-yl]-2-[(2R)-2-methylpyrrolidin-1-yl]pyrimidine | * | 1.28 | 501.22 | B |
| 959 | 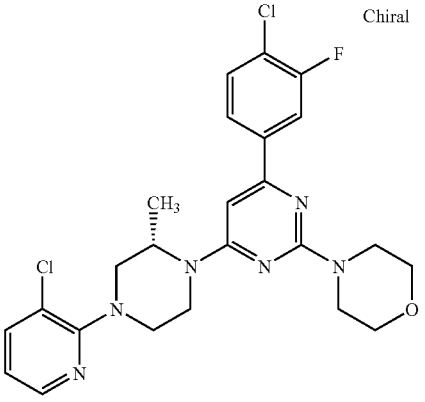 Chiral | 4-{4-(4-chloro-3-fluorophenyl)-6-[(2S)-4-(3-chloropyridin-2-yl)-2-methylpiperazin-1-yl]pyrimidin-2-yl}morpholine | * | 1.36 | 503.20 | B |
| 960 | 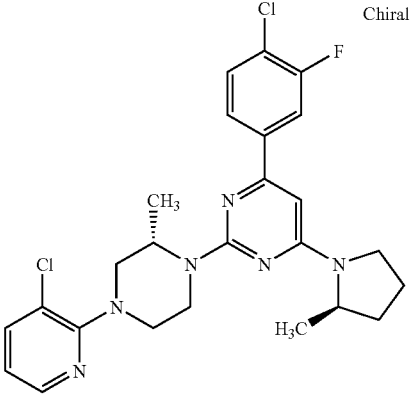 Chiral | 4-(4-chloro-3-fluorophenyl)-2-[(2S)-4-(3-chloropyridin-2-yl)-2-methylpiperazin-1-yl]-6-[(2R)-2-methylpyrrolidin-1-yl]pyrimidine | * | 1.33 | 501.22 | B |

TABLE II-continued
| Compound | | Name | IC$_{50}$ | Ret. Time | MS (M + 1) | LCMS Method |
|---|---|---|---|---|---|---|
| 961 | 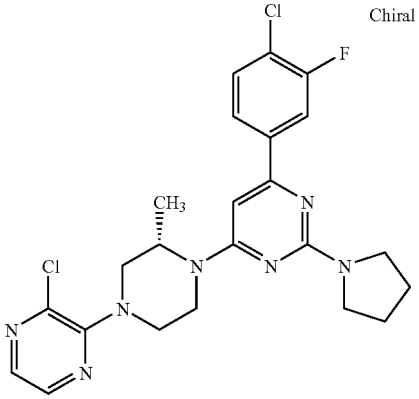 Chiral | 4-(4-chloro-3-fluorophenyl)-6-[(2S)-4-(3-chloropyrazin-2-yl)-2-methylpiperazin-1-yl]-2-pyrrolidin-1-ylpyrimidine | * | 1.24 | 488.13 | B |
| 962 | 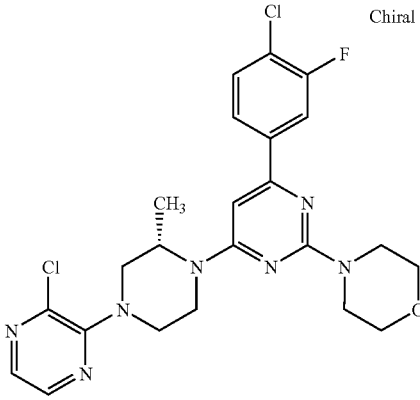 Chiral | 4-{4-(4-chloro-3-fluorophenyl)-6-[(2S)-4-(3-chloropyrazin-2-yl)-2-methylpiperazin-1-yl]pyrimidin-2-yl}morpholine | * | 1.35 | 504.12 | B |
| 963 | 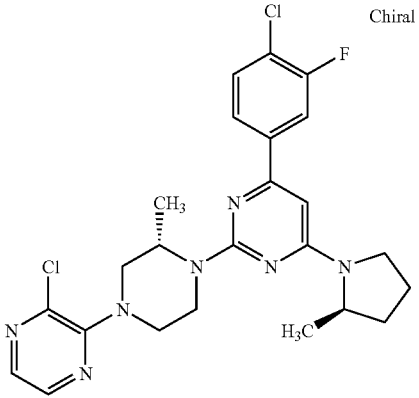 Chiral | 4-(4-chloro-3-fluorophenyl)-2-[(2S)-4-(3-chloropyrazin-2-yl)-2-methylpiperazin-1-yl]-6-[(2R)-2-methylpyrrolidin-1-yl]pyrimidine | * | 1.33 | 502.22 | B |

TABLE II-continued
| Compound | | | Name | IC$_{50}$ | Ret. Time | MS (M + 1) | LCMS Method |
|---|---|---|---|---|---|---|---|
| 964 | 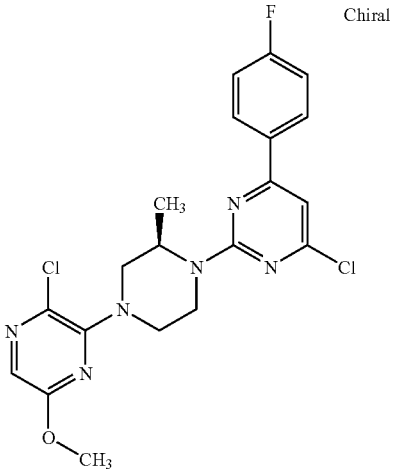 | Chiral | 5-chloro-4-{(3R)-4-[4-chloro-6-(4-fluorophenyl)pyrimidin-2-yl]-3-methylpiperazin-1-yl}-2-methoxypyrimidine | * | 1.5 | 449.15 | B |
| 965 | 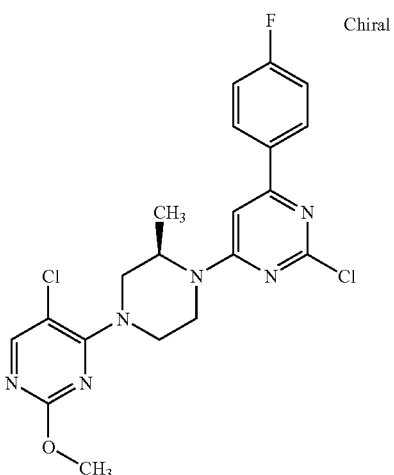 | Chiral | 5-chloro-4-{(3R)-4-[2-chloro-6-(4-fluorophenyl)pyrimidin-4-yl]-3-methylpiperazin-1-yl}-2-methoxypyrimidine | * | 1.38 | 449.15 | B |
| 966 | 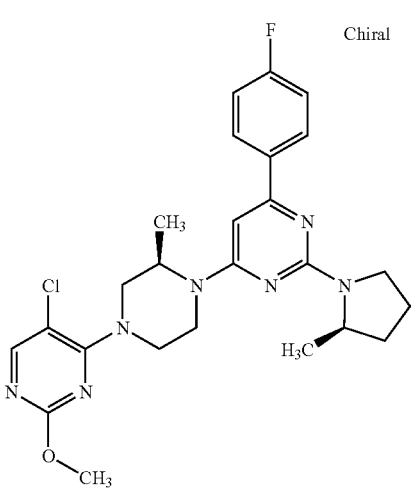 | Chiral | 5-chloro-4-((3R)-4-{6-(4-fluorophenyl)-2-[(2R)-2-methylpyrrolidin-1-yl]pyrimidin-4-yl}-3-methylpiperazin-1-yl)-2-methoxypyrimidine | * | 1.21 | 498.27 | B |

TABLE II-continued

| Compound | Name | IC$_{50}$ | Ret. Time | MS (M + 1) | LCMS Method |
|---|---|---|---|---|---|
| 967 (Chiral) | 5-chloro-4-{(3R)-4-[6-(4-fluorophenyl)-2-pyrrolidin-1-ylpyrimidin-4-yl]-3-methylpiperazin-1-yl}-2-methoxypyrimidine | * | 1.2 | 484.25 | B |
| 968 (Chiral) | 5-chloro-4-((3R)-4-{4-(4-fluorophenyl)-6-[(2R)-2-methylpyrrolidin-1-yl]pyrimidin-2-yl}-3-methylpiperazin-1-yl)-2-methoxypyrimidine | * | 1.24 | 498.27 | B |
| 969 | rel-4-(4-chloro-3-fluorophenyl)-6-[(2R)-4-(3-chloropyrazin-2-yl)-2-methylpiperazin-1-yl]-2-[(2S)-2-methylpyrrolidin-1-yl]pyrimidine | * | 1.26 | 502.21 | B |

TABLE II-continued
| Compound | | Name | IC$_{50}$ | Ret. Time | MS (M + 1) | LCMS Method |
|---|---|---|---|---|---|---|
| 970 | 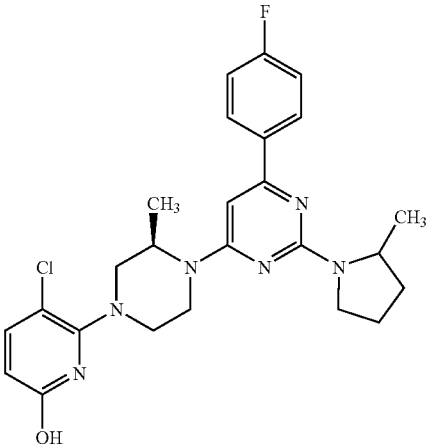 | 5-chloro-6-{4-[6-(4-fluorophenyl)-2-(2-methylpyrrolidin-1-yl)pyrimidin-4-yl]-3-methylpiperazin-1-yl}pyridin-2-ol | * | 1.26 | 483.25 | B |
| 971 | 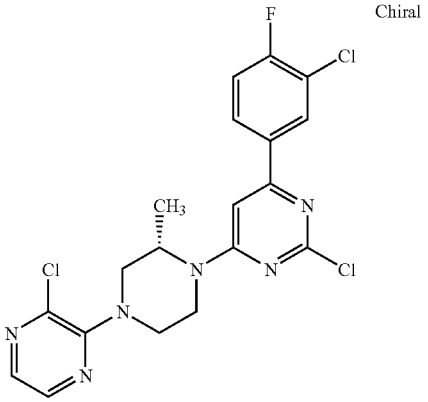 Chiral | 2-chloro-4-(3-chloro-4-fluorophenyl)-6-[(2S)-4-(3-chloropyrazin-2-yl)-2-methylpiperazin-1-yl]pyrimidine | * | 1.47 | 453.09 | B |
| 972 | 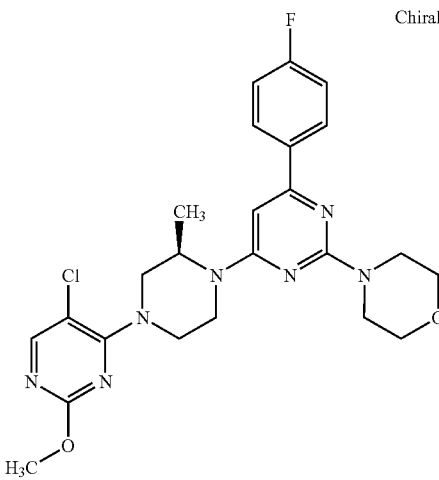 Chiral | 4-[4-[(2R)-4-(5-chloro-2-methoxypyrimidin-4-yl)-2-methylpiperazin-1-yl]-6-(4-fluorophenyl)pyrimidin-2-yl]morpholine | * | 1.21 | 500.23 | B |

TABLE II-continued
| Compound | | Name | IC$_{50}$ | Ret. Time | MS (M + 1) | LCMS Method |
|---|---|---|---|---|---|---|
| 973 | 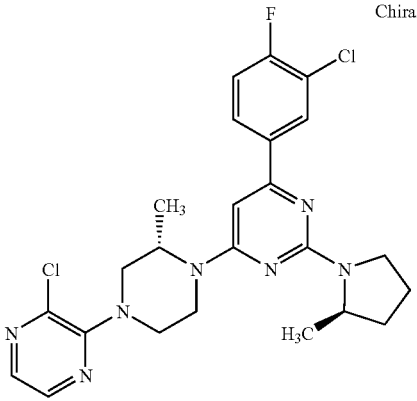 Chiral | 4-(3-chloro-4-fluorophenyl)-6-[(2S)-4-(3-chloropyrazin-2-yl)-2-methylpiperazin-1-yl]-2-[(2R)-2-methylpyrrolidin-1-yl]pyrimidine | * | 1.27 | 502.20 | B |
| 974 | 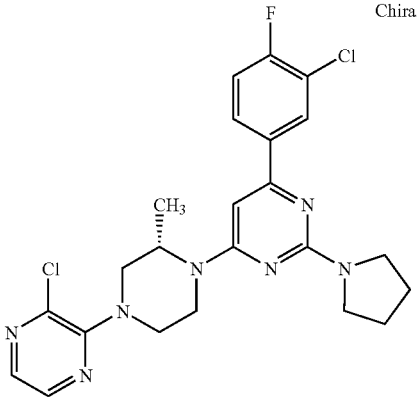 Chiral | 4-(3-chloro-4-fluorophenyl)-6-[(2S)-4-(3-chloropyrazin-2-yl)-2-methylpiperazin-1-yl]-2-pyrrolidin-1-ylpyrimidine | * | 1.26 | 488.19 | B |
| 975 | 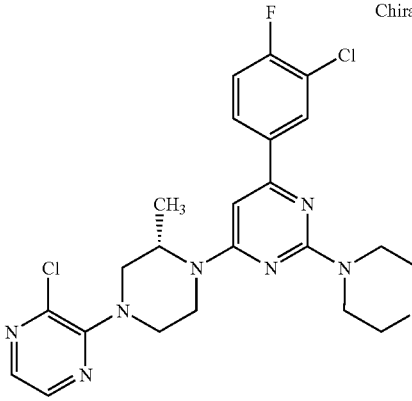 Chiral | 4-{4-(3-chloro-4-fluorophenyl)-6-[(2S)-4-(3-chloropyrazin-2-yl)-2-methylpiperazin-1-yl]pyrimidin-2-yl}morpholine | * | 1.32 | 504.18 | B |

TABLE II-continued
| Compound | | Name | IC$_{50}$ | Ret. Time | MS (M + 1) | LCMS Method |
|---|---|---|---|---|---|---|
| 976 | 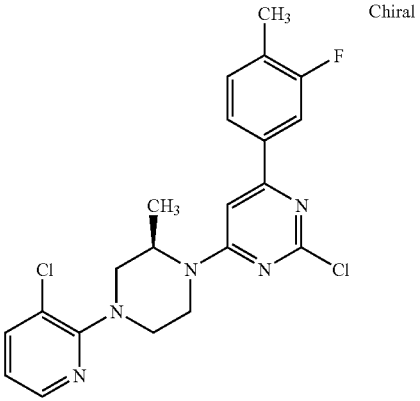 Chiral | 2-chloro-4-[(2R)-4-(3-chloropyridin-2-yl)-2-methylpiperazin-1-yl]-6-(3-fluoro-4-methylphenyl)pyrimidine | | 1.48 | 432.16 | B |
| 977 | 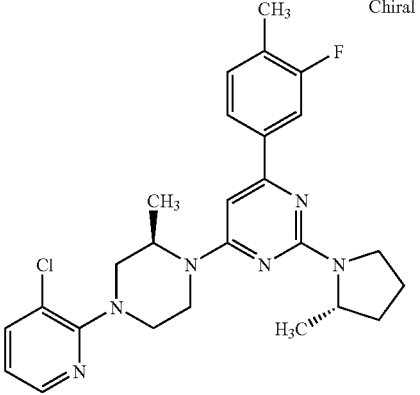 Chiral | 4-(4-chloro-3-fluorophenyl)-6-[(2R)-4-(3-chloropyridin-2-yl)-2-methylpiperazin-1-yl]-2-[(2S)-2-methylpyrrolidin-1-yl]pyrimidine | * | 1.29 | 501.21 | B |
| 978 | 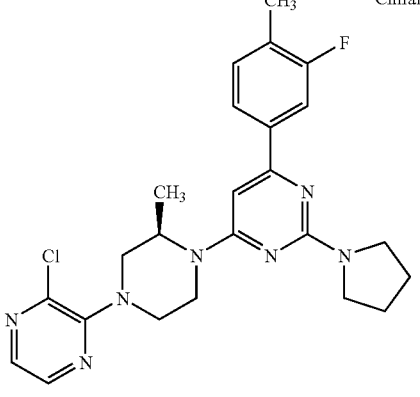 Chiral | 4-[(2R)-4-(3-chloropyrazin-2-yl)-2-methylpiperazin-1-yl]-6-(3-fluoro-4-methylphenyl)-2-pyrrolidin-1-ylpyrimidine | * | 1.25 | 468.24 | B |

TABLE II-continued

| Compound | | Name | IC$_{50}$ | Ret. Time | MS (M + 1) | LCMS Method |
|---|---|---|---|---|---|---|
| 979 | Chiral | 4-[(2R)-4-(3-chloropyridin-2-yl)-2-methylpiperazin-1-yl]-6-(3-fluoro-4-methylphenyl)-2-[(2R)-2-methylpyrrolidin-1-yl]pyrimidine | * | 1.28 | 481.25 | B |
| 980 | Chiral | 4-[4-[(2R)-4-(3-chloropyridin-2-yl)-2-methylpiperazin-1-yl]-6-(3-fluoro-4-methylphenyl)pyrimidin-2-yl]morpholine | * | 1.29 | 483.25 | B |
| 981 | Chiral | 4-[(2R)-4-(3-chloropyrazin-2-yl)-2-methylpiperazin-1-yl]-6-(3-fluoro-4-methylphenyl)-2-[(2R)-2-methylpyrrolidin-1-yl]pyrimidine | * | 1.26 | 482.25 | B |

TABLE II-continued
| Compound | | Name | IC$_{50}$ | Ret. Time | MS (M + 1) | LCMS Method |
|---|---|---|---|---|---|---|
| 982 | 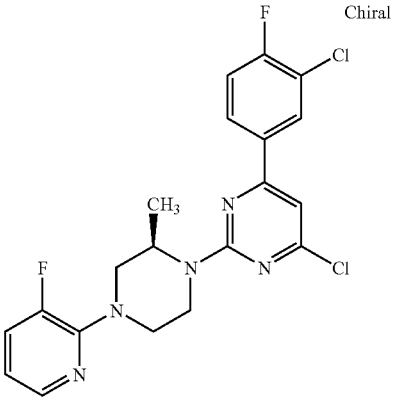 Chiral | 4-chloro-6-(3-chloro-4-fluorophenyl)-2-[(2R)-4-(3-fluoropyridin-2-yl)-2-methylpiperazin-1-yl]pyrimidine | | 1.46 | 436.12 | A |
| 983 | 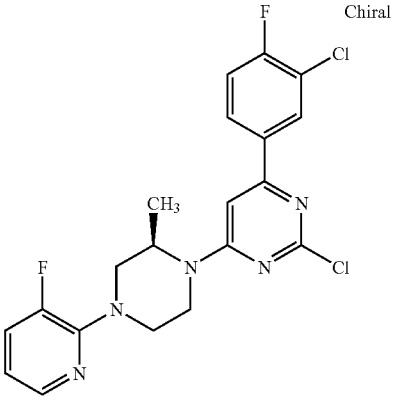 Chiral | 2-chloro-4-(3-chloro-4-fluorophenyl)-6-[(2R)-4-(3-fluoropyridin-2-yl)-2-methylpiperazin-1-yl]pyrimidine | * | 1.47 | 436.14 | B |
| 984 | 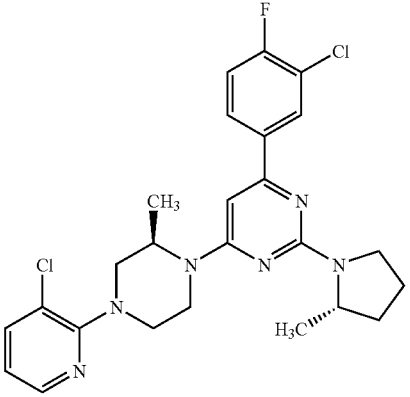 Chiral | 4-(3-chloro-4-fluorophenyl)-6-[(2R)-4-(3-chloropyridin-2-yl)-2-methylpiperazin-1-yl]-2-[(2S)-2-methylpyrroiidin-1-yl]pyrimidine | * | 1.3 | 501.22 | B |

TABLE II-continued

| Compound | | Name | IC$_{50}$ | Ret. Time | MS (M + 1) | LCMS Method |
|---|---|---|---|---|---|---|
| 985 | Chiral | 4-(3-chloro-4-fluorophenyl)-6-[(2S)-4-(3-chloropyridin-2-yl)-2-methylpiperazin-1-yl]-2-[(2S)-2-methylpyrrolidin-1-yl]pyrimidine | * | 1.29 | 501.22 | B |
| 986 | Chiral | 4-(3-chloro-4-fluorophenyl)-6-[(2R)-4-(3-chloropyrazin-2-yl)-2-methylpiperazin-1-yl]-2-[(2S)-2-methylpyrrolidin-1-yl]pyrimidine | * | 1.26 | 502.21 | B |
| 987 | Chiral | 4-(3-chloro-4-fluorophenyl)-6-[(2S)-4-(3-chloropyrazin-2-yl)-2-methylpiperazin-1-yl]-2-[(2S)-2-methylpyrrolidin-1-yl]pyrimidine | * | 1.27 | 502.21 | B |

TABLE II-continued

| Compound | | Name | IC$_{50}$ | Ret. Time | MS (M + 1) | LCMS Method |
|---|---|---|---|---|---|---|
| 988 | Chiral | 4-(3-chloro-4-fluorophenyl)-6-[(2R)-4-(2-fluorophenyl)-2-methylpiperazin-1-yl]-2-[(2R)-2-methylpyrrolidin-1-yl]pyrimidine | | 1.26 | 485.17 | B |
| 989 | Chiral | 4-(3-chloro-4-fluorophenyl)-6-[(2R)-4-(2-fluorophenyl)-2-methylpiperazin-1-yl]-2-[(2S)-2-methylpyrrolidin-1-yl]pyrimidine | * | 1.25 | 485.17 | B |
| 990 | Chiral | 4-(3-chloro-4-fluorophenyl)-6-[(2R)-4-(2-fluorophenyl)-2-methylpiperazin-1-yl]-2-pyrrolidin-1-ylpyrimidine | * | 1.23 | 471.16 | B |

TABLE II-continued

| Compound | | Name | IC$_{50}$ | Ret. Time | MS (M + 1) | LCMS Method |
|---|---|---|---|---|---|---|
| 991 | Chiral | 4-{4-(3-chloro-4-fluorophenyl)-6-[(2R)-4-(2-fluorophenyl)-2-methylpiperazin-1-yl]pyrimidin-2-yl}morpholine | * | 1.31 | 487.16 | B |
| 992 | Chiral | 4-[(2R)-4-(3-chloropyrazin-2-yl)-2-methylpiperazin-1-yl]-6-(3-fluoro-4-methylphenyl)-2-[(2S)-2-methylpyrrolidin-1-yl]pyrimidine | * | 1.26 | 482.23 | B |
| 993 | Chiral | 4-[4-[(2R)-4-(3-chloropyrazin-2-yl)-2-methylpiperazin-1-yl]-6-(3-fluoro-4-methylphenyl)pyrimidin-2-yl]morpholine | * | 1.27 | 484.22 | B |

TABLE II-continued

| Compound | | Name | IC$_{50}$ | Ret. Time | MS (M + 1) | LCMS Method |
|---|---|---|---|---|---|---|
| 994 | 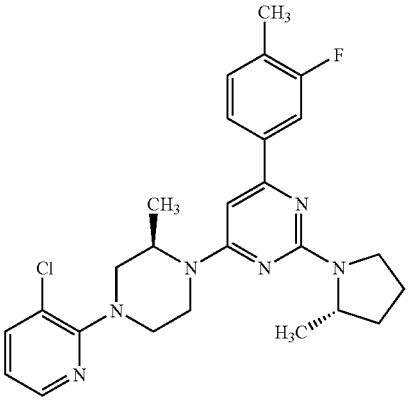 Chiral | 4-[(2R)-4-(3-chloropyridin-2-yl)-2-methylpiperazin-1-yl]-6-(3-fluoro-4-methylphenyl)-2-[(2S)-2-methylpyrrolidin-1-yl]pyrimidine | * | 1.28 | 481.24 | B |
| 995 | 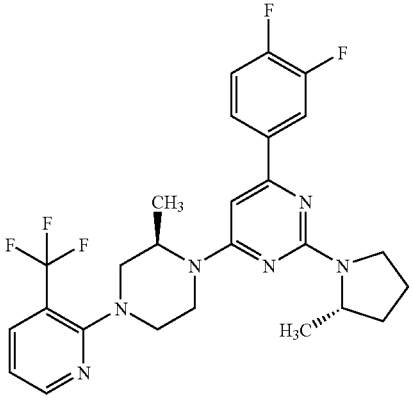 Chiral | 4-(3,4-difluorophenyl)-2-[(2S)-2-methylpyrrolidin-1-yl]-6-{(2R)-2-methyl-4-[3-(trifluoromethyl)pyridin-2-yl]piperazin-1-yl}pyrimidine | * | 1.28 | 519.24 | B |
| 996 | 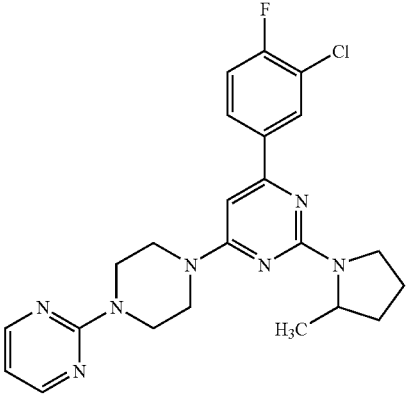 | 4-(3-chloro-4-fluorophenyl)-2-(2-methylpyrrolidin-1-yl)-6-(4-pyrimidin-2-ylpiperazin-1-yl)pyrimidine | * | 1.23 | 454.18 | B |

TABLE II-continued
| Compound | | | Name | IC$_{50}$ | Ret. Time | MS (M + 1) | LCMS Method |
|---|---|---|---|---|---|---|---|
| 997 | 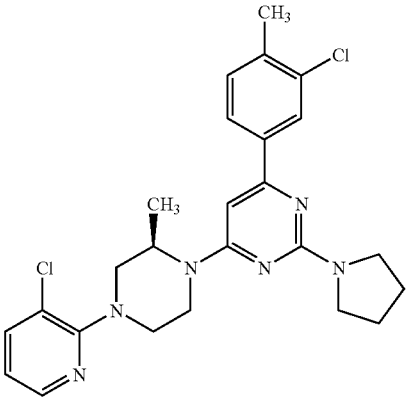 | Chiral | 4-(3-chloro-4-methylphenyl)-6-[(2R)-4-(3-chloropyridin-2-yl)-2-methylpiperazin-1-yl]-2-pyrrolidin-1-ylpyrimidine | * | 1.29 | 483.20 | B |
| 998 | 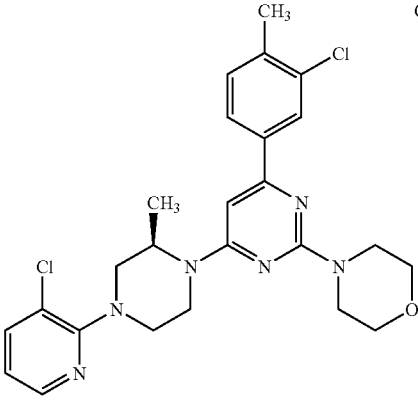 | Chiral | 4-{4-(3-chloro-4-methylphenyl)-6-[(2R)-4-(3-chloropyridin-2-yl)-2-methylpiperazin-1-yl]pyrimidin-2-yl}morpholine | * | 1.32 | 499.20 | B |
| 999 | 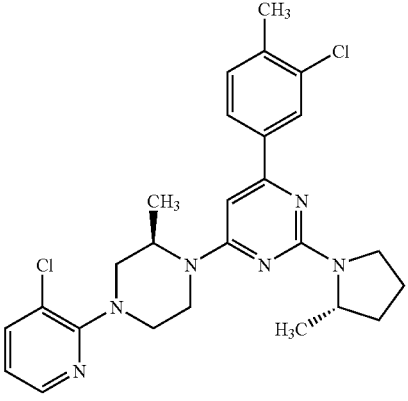 | Chiral | 4-(3-ohloro-4-methylphenyl)-6-[(2R)-4-(3-chloropyridin-2-yl)-2-methylpiperazin-1-yl]-2-[(2S)-2-methylpyrrolidin-1-yl]pyrimidine | * | 1.3 | 497.21 | B |

TABLE II-continued

| Compound | Name | IC$_{50}$ | Ret. Time | MS (M + 1) | LCMS Method |
|---|---|---|---|---|---|
| 1000 | (3S)-4-{4-(3-chloro-4-fluorophenyl)-6-[(2R)-4-(3-chloropyridin-2-yl)-2-methylpiperazin-1-yl]pyrimidin-2-yl}-3-methylmorpholine | * | 1.37 | 517.22 | B |
| 1001 | 3-{4-[6-(3-chloro-4-fluorophenyl)-2-(2-methylpyrrolidin-1-yl)pyrimidin-4-yl]piperazin-1-yl}-4-methylpyridazine | * | 1.16 | 468.25 | B |
| 1002 | 4-[4-(5-bromopyrimidin-2-yl)piperazin-1-yl]-6-(3-chloro-4-fluorophenyl)-2-(2-methylpyrrolidin-1-yl)pyrimidine | * | 1.3 | 534.15 | B |

TABLE II-continued

| Compound | Name | IC$_{50}$ | Ret. Time | MS (M + 1) | LCMS Method |
|---|---|---|---|---|---|
| 1003 | (3S)-4-{4-(3-chloro-4-fluorophenyl)-6-[(2R)-4-(3-chloropyrazin-2-yl)-2-methylpiperazin-1-yl]pyrimidin-2-yl}-3-methylmorpholine | * | 1.36 | 518.22 | B |
| 1004 | (3S)-4-{4-(3-chloro-4-fluorophenyl)-6-[(2R)-4-(3-fluoropyridin-2-yl)-2-methylpiperaztn-1-yl]pyrimidin-2-yl}-3-methylmorpholine | * | 1.34 | 501.25 | B |
| 1005 | (3S)-4-{4-(3-chloro-4-fluorophenyl)-6-[(2S)-4-(3-chloropyridin-2-yl)-2-methylpiperazin-1-yl]pyrimidin-2-yl}-3-methylmorpholine | * | 1.37 | 517.22 | B |

TABLE II-continued

| Compound | | Name | IC$_{50}$ | Ret. Time | MS (M + 1) | LCMS Method |
|---|---|---|---|---|---|---|
| 1006 | Chiral | (3S)-4-{4-(3,4-difluorophenyl)-6-[(2R)-4-(3-fluoropyridin-2-yl)-2-methylpiperazin-1-yl]pyrimidin-2-yl}-3-methylmorpholine | * | 1.32 | 485.26 | B |
| 1007 | | (3R)-4-{4-(4-fluorophenyl)-6-[(2R)-4-(3-chloropyridin-2-yl)-2-methylpiperazin-1-yl]pyrimidin-2-yl}-3-methylmorpholine | | | | |
| 1008 | | (3R)-4-{4-(phenyl)-6-[(2R)-4-(3-methylpyridin-2-yl)-2-methylpiperazin-1-yl]pyrimidin-2-yl}-3-methylmorpholine | | | | |
| 1009 | | 2-{4-[6-(3-chloro-4-fluorophenyl)-2-(2-methylpyrrolidin-1-yl)pyrimidin-4-yl]piperazin-1-yl}pyrimidine-5-carbonitrile | * | 1.22 | 479.22 | B |

TABLE II-continued
| Compound | | Name | IC$_{50}$ | Ret. Time | MS (M + 1) | LCMS Method |
|---|---|---|---|---|---|---|
| 1010 | 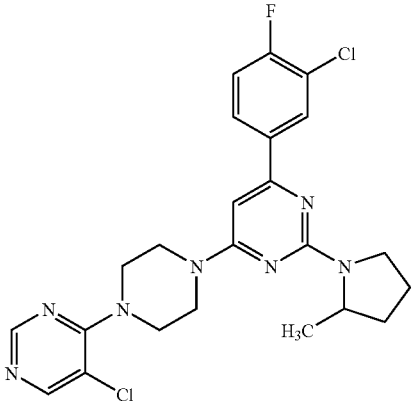 | 4-(3-chloro-4-fluorophenyl)-6-[4-(5-chloropyrimidin-4-yl)piperazin-1-yl]-2-(2-methylpyrrolidin-1-yl)pyrimidine | * | 1.26 | 488.21 | B |
| 1011 | 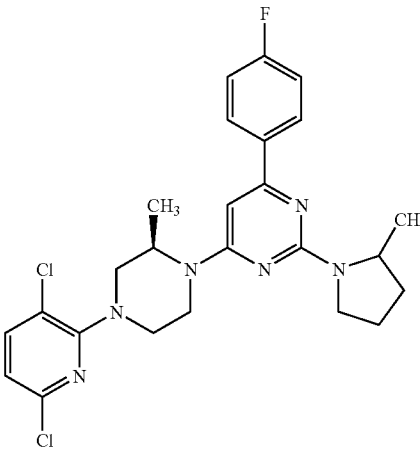 | 4-[4-(3,6-dichloropyridin-2-yl)-2-methylpiperazin-1-yl]-6-(4-fluorophenyl)-2-(2-methylpyrrolidin-1-yl)pyrimidine | * | 1.32 | 501.23 | B |
| 1012 | 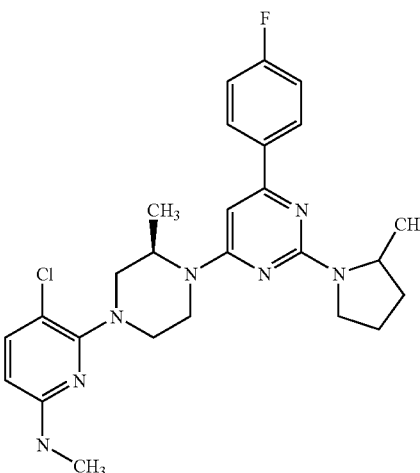 | 5-chloro-6-{4-[6-(4-fluorophenyl)-2-(2-methylpyrrolidin-1-yl)pyrimidin-4-yl]-3-methylpiperazin-1-yl}-N-methylpyridin-2-amine | * | 1.3 | 496.3 | B |

TABLE II-continued

| Compound | Name | IC$_{50}$ | Ret. Time | MS (M + 1) | LCMS Method |
|---|---|---|---|---|---|
| 1013 | 4-[(2R)-4-(5-chloropyrimidin-4-yl)-2-methylpiperazin-1-yl]-6-(4-fluorophenyl)-2-(2-methylpyrrolidin-1-yl)pyrimidine | * | 1.23 | 468.25 | B |
| 1014 | 6-{4-[6-(4-fluorophenyl)-2-(2-methylpyrrolidin-1-yl)pyrimidin-4-yl]-3-methylpiperazin-1-yl}pyridine-2,5-dicarbonitrile | * | 1.24 | 483.29 | B |
| 1015 | 5-chloro-6-{4-[6-(4-fluorophenyl)-2-(2-methylpyrrolidin-1-yl)pyrimidin-4-yl]-3-methylpiperazin-1-yl}-N,N-dimethylpyridin-2-amine | | 1.36 | 510.3 | B |

TABLE II-continued

| Compound | | Name | IC$_{50}$ | Ret. Time | MS (M + 1) | LCMS Method |
|---|---|---|---|---|---|---|
| 1016 | Chiral structure with 4-fluoro-3-chlorophenyl, pyrimidine, piperazine-(3-methylpyridin-2-yl), N-methyl-(2S)-propan-1-ol | (2S)-2-[{4-(3-chloro-4-fluorophenyl)-6-[4-(3-methylpyridin-2-yl)piperazin-1-yl]pyrimidin-2-yl}(methyl)amino]propan-1-ol | * | 1.15 | 471.26 | B |
| 1017 | Chiral structure (enantiomer of 1016) | (2S)-2-[{4-(3-chloro-4-fluorophenyl)-6-[4-(3-methylpyridin-2-yl)piperazin-1-yl]pyrimidin-2-yl}(methyl)amino]propan-1-ol | * | 1.14 | 471.25 | B |
| 1018 | Chiral structure with 4-fluorophenyl pyrimidine, methylmorpholine, methylpiperazine, chloro-methoxypyridine | (3R)-4-(4-[(2R)-4-(3-chloro-6-methoxypyridin-2-yl)-2-methylpiperazin-1-yl]-6-(4-fluorophenyl)pyrimidin-2-yl]-3-methylmorpholine | | | | |

Example 4

VR1-Transfected Cells and Membrane Preparations

This Example illustrates the preparation of VR1-transfected cells and VR1-containing membrane preparations for use in capsaicin binding assays (Example 5).

A cDNA encoding full length human capsaicin receptor (SEQ ID NO: 1, 2 or 3 of U.S. Pat. No. 6,482,611) was subcloned in the plasmid pBK-CMV (Stratagene, La Jolla, Calif.) for recombinant expression in mammalian cells.

Human embryonic kidney (HEK293) cells were transfected with the pBK-CMV expression construct encoding the full length human capsaicin receptor using standard methods. The transfected cells were selected for two weeks in media containing G418 (400 μg/ml) to obtain a pool of stably transfected cells. Independent clones were isolated from this pool by limiting dilution to obtain clonal stable cell lines for use in subsequent experiments.

For radioligand binding experiments, cells were seeded in T175 cell culture flasks in media without antibiotics and grown to approximately 90% confluency. The flasks were then washed with PBS and harvested in PBS containing 5 mM EDTA. The cells were pelleted by gentle centrifugation and stored at −80° C. until assayed.

Previously frozen cells were disrupted with the aid of a tissue homogenizer in ice-cold HEPES homogenization buffer (5 mM KCl 5, 5.8 mM NaCl, 0.75 mM $CaCl_2$, 2 mM $MgCl_2$, 320 mM sucrose, and 10 mM HEPES pH 7.4). Tissue homogenates were first centrifuged for 10 minutes at 1000×g (4° C.) to remove the nuclear fraction and debris, and then the supernatant from the first centrifugation is further centrifuged for 30 minutes at 35,000×g (4° C.) to obtain a partially purified membrane fraction. Membranes were resuspended in the HEPES homogenization buffer prior to the assay. An aliquot of this membrane homogenate was used to determine protein concentration via the Bradford method (BIO-RAD Protein Assay Kit, #500-0001, BIO-RAD, Hercules, Calif.).

Example 5

Capsaicin Receptor Binding Assay

This Example illustrates a representative assay of capsaicin receptor binding that may be used to determine the binding affinity of compounds for the capsaicin (VR I) receptor.

Binding studies with [$^3$H] Resiniferatoxin (RTX) are carried out essentially as described by Szallasi and Blumberg (1992) *J. Pharmacol. Exp. Ter.* 262:883-888. In this protocol, non-specific RTX binding is reduced by adding bovine alpha, acid glycoprotein (100 μg per tube) after the binding reaction has been termninated.

[$^3$H] RTX (37 Ci/mmol) is synthesized by and obtained from the Chemical Synthesis and Analysis Laboratory, National Cancer Institute-Frederick Cancer Research and Development Center, Frederick, Md. [$^3$H] RTX may also be obtained from commercial vendors (e.g., Amersham Pharmacia Biotech, Inc.; Piscataway, N.J.).

The membrane homogenate of Example 4 is centrifuged as before and resuspended to a protein concentration of 333 μg/ml in homogenization buffer. Binding assay mixtures are set up on ice and contain [$^3$H]RTX (specific activity 2200 mCi/ml), 2 PI non-radioactive test compound, 0.25 mg/ml bovine serum albumin (Cohn fraction V), and $5×10^4$–$1×10^5$ VR1-transfected cells. The final volume is adjusted to 500 μl (for competition binding assays) or 1,000 μl (for saturation binding assays) with the ice-cold HEPES homogenization buffer solution (pH 7.4) described above. Non-specific binding is defined as that occurring in the presence of 1 μM non-radioactive RTX (Alexis Corp.; San Diego, Calif.). For saturation binding, [$^3$H]RTX is added in the concentration range of 7-1,000 pM, using 1 to 2 dilutions. Typically 11 concentration points are collected per saturation binding curve.

Competition binding assays are performed in the presence of 60 pM [$^3$H]RTX and various concentrations of test compound. The binding reactions are initiated by transferring the assay mixtures into a 37° C. water bath and are terminated following a 60 minute incubation period by cooling the tubes on ice. Membrane-bound RTX is separated from free, as well as any $alpha_1$ acid glycoprotein-bound RTX, by filtration onto WALLAC glass fiber filters (PERKIN-ELMER, Gaithersburg, Md.) which were pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

Equilibrium binding parameters are determined by fitting the allosteric Hill equation to the measured values with the aid of the computer program FIT P (Biosoft, Ferguson, Mo.) as described by Szallasi, et al. (1993) *J. Pharmacol. Exp. Ther.* 266:678-683. Compounds provided herein generally exhibit $K_i$ values for capsaicin receptor of less than 1 μM, 100 nM, 50 nM, 25 nM, 10 nM, or 1 nM in this assay.

Example 6

Calcium Mobilization Assay

This Example illustrates representative calcium mobilization assays for use in evaluating test compounds for agonist and antagonist activity.

Cells transfected with expression plasmids (as described in Example 4) and thereby expressing human capsaicin receptor are seeded and grown to 70-90% confluency in FALCON black-walled, clear-bottomed 96-well plates (#3904, BECTON-DICKINSON, Franklin Lakes, N.J.). The culture medium is emptied from the 96 well plates and FLUO-3 AM calcium sensitive dye (Molecular Probes, Eugene, Oreg.) is added to each well (dye solution: 1 mg FLUO-3 AM, 440 μL DMSO and 440 pi 20% pluronic acid in DMSO, diluted 1:250 in Krebs-Ringer HEPES (KRH) buffer (25 mM HEPES, 5 mM KCl, 0.96 mM $NaH_2PO_4$, 1 mM $MgSO_4$, 2 mM $CaCl_2$, 5 mM glucose, 1 mM probenecid, pH 7.4), 50 μl diluted solution per well). Plates are covered with aluminum foil and incubated at 37° C. for 1-2 hours in an environment containing 5% $CO_2$. After the incubation, the dye is emptied from the plates, and the cells are washed once with KRH buffer, and resuspended in KRH buffer.

Determination Capsaicin $EC_{50}$

To measure the ability of a test compound to agonize or antagonize a calcium mobilization response in cells expressing capsaicin receptors to capsaicin or other vanilloid agonist, the $EC_{50}$ of the agonist capsaicin is first determined. An additional 20 μl of KRH buffer and 1 μl DMSO is added to each well of cells, prepared as described above. 100 μl capsaicin in KRH buffer is automatically transferred by the FLIPR instrument to each well. Capsaicin-induced calcium mobilization is monitored using either FLUOROSKAN ASCENT (Labsystems; Franklin, Mass.) or FLIPR (fluorometric imaging plate reader system; Molecular Devices, Sunnyvale, Calif.) instruments. Data obtained between 30 and 60 seconds after agonist application are used to generate an 8-point concentration response curve, with final capsaicin concentrations of 1 nM to 3 μM. KALEIDAGRAPH software (Synergy Software, Reading, Pa.) is used to fit the data to the equation:

$$y=a*(1/(1+(b/x)^c))$$

to determine the 50% excitatory concentration ($EC_{50}$) for the response. In this equation, y is the maximum fluorescence signal, x is the concentration of the agonist or antagonist (in this case, capsaicin), a is the $E_{max}$, b corresponds to the $EC_{50}$ value and c is the Hill coefficient.

Determination of Agonist Activity

Test compounds are dissolved in DMSO, diluted in KRH buffer, and immediately added to cells prepared as described above. 100 nM capsaicin (an approximate ECgo concentration) is also added to cells in the same 96-well plate as a positive control. The final concentration of test compounds in the assay wells is between 0.1 nM and 5 µM.

The ability of a test compound to act as an agonist of the capsaicin receptor is determined by measuring the fluorescence response of cells expressing capsaicin receptors elicited by the compound as function of compound concentration. This data is fit as described above to obtain the $EC_{50}$, which is generally less than 1 micromolar, preferably less than 100 nM, and more preferably less than 10 nM. The extent of efficacy of each test compound is also determined by calculating the response elicited by a concentration of test compound (typically 1 µM) relative to the response elicited by 100 nM capsaicin. This value, called Percent of Signal (POS), is calculated by the following equation:

POS=100*test compound response/100 nM capsaicin response

This analysis provides quantitative assessment of both the potency and efficacy of test compounds as human capsaicin receptor agonists. Agonists of the human capsaicin receptor generally elicit detectable responses at concentrations less than 100 µM, or preferably at concentrations less than 1 µM, or most preferably at concentrations less than 10 nM. Extent of efficacy at human capsaicin receptor is preferably greater than 30 POS, more preferably greater than 80 POS at a concentration of 1 µM. Certain agonists are essentially free of antagonist activity as demonstrated by the absence of detectable antagonist activity in the assay described below at compound concentrations below 4 nM, more preferably at concentrations below 10 µM and most preferably at concentrations less than or equal to 100 µM.

Determination of Antagonist Activity

Test compounds are dissolved in DMSO, diluted in 20 µl KRH buffer so that the final concentration of test compounds in the assay well is between 1 µM and 5 µM, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 pi capsaicin in KRH buffer at twice the $EC_{50}$ concentration determined as described above is automatically added by the FLIPR instrument to each well of the 96 well plate for a final sample volume of 200 µl and a final capsaicin concentration equal to the $EC_{50}$. The final concentration of test compounds in the assay wells is between 1 µM and 5 µM. Antagonists of the capsaicin receptor decrease this response by at least about 20%, preferably by at least about 50%, and most preferably by at least 80%, as compared to matched control (i.e., cells treated with capsaicin at twice the $EC_{50}$ concentration in the absence of test compound), at a concentration of 10 micromolar or less, preferably 1 micromolar or less. The concentration of antagonist required to provide a 50% decrease, relative to the response observed in the presence of capsaicin and without antagonist, is the $IC_{50}$ for the antagonist, and is preferably below 1 micromolar, 100 nanomolar, 10 nanomolar or 1 nanomolar.

Certain preferred VR1 modulators are antagonists that are essentially free of agonist activity as demonstrated by the absence of detectable agonist activity in the assay described above at compound concentrations below 4 nM, more preferably at concentrations below 10 µM and most preferably at concentrations less than or equal to 100 µM.

Example 7

Microsomal in vitro Half-Life

This Example illustrates the evaluation of compound half-life values ($t_{1/2}$ values) using a representative liver microsomal half-life assay.

Pooled human liver microsomes are obtained from Xeno Tech LLC (Kansas City, Kans.). Such liver microsomes may also be obtained from In Vitro Technologies (Baltimore, Md.) or Tissue Transformation Technologies (Edison, N.J.). Six test reactions are prepared, each containing 25 µl microsomes, 5 µl of a 100 µM solution of test compound, and 399 µl 0.1 M phosphate buffer (19 mL 0.1 M $NaH_2PO_4$, 81 mL 0.1 M $Na_2HPO_4$, adjusted to pH 7.4 with $H_3PO_4$). A seventh reaction is prepared as a positive control containing 25 µl microsomes, 399 µl 0.1 M phosphate buffer, and 5 µl of a 100 µM solution of a compound with known metabolic properties (e.g., DIAZEPAM or CLOZAPINE). Reactions are preincubated at 39° C. for 10 minutes.

CoFactor Mixture is prepared by diluting 16.2 mg NADP and 45.4 mg Glucose-6-phosphate in 4 mL 100 mM $MgCl_2$. Glucose-6-phosphate dehydrogenase solution is prepared by diluting 214.3 µl glucose-6-phosphate dehydrogenase suspension (Roche Molecular Biochemicals; Indianapolis, Ind.) into 1285.7 µl distilled water. 71 µl Starting Reaction Mixture (3 mL CoFactor Mixture; 1.2 mL Glucose-6-phosphate dehydrogenase solution) is added to 5 of the 6 test reactions and to the positive control. 71 µl 100 mM $MgCl_2$ is added to the sixth test reaction, which is used as a negative control. At each time point (0, 1, 3, 5, and 10 minutes), 75 µl of each reaction mix is pipetted into a well of a 96-well deep-well plate containing 75 µl ice-cold acetonitrile. Samples are vortexed and centrifuged 10 minutes at 3500 rpm (Sorval T 6000D centrifuge, H1000B rotor). 75 µl of supernatant from each reaction is transferred to a well of a 96-well plate containing 150 µl of a 0.5 µM solution of a compound with a known LCMS profile (internal standard) per well. LCMS analysis of each sample is carried out and the amount of unmetabolized test compound is measured as AUC, compound concentration vs. time is plotted, and the $t_{1/2}$ value of the test compound is extrapolated.

Preferred compounds provided herein exhibit in vitro $t_{1/2}$ values of greater than 10 minutes and less than 4 hours, preferably between 30 minutes and 1 hour, in human liver microsomes.

Example 8

MDCK Toxicity Assay

This Example illustrates the evaluation of compound toxicity using a Madin Darby canine kidney (MDCK) cell cytotoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog # 30-2003). 100 μL of diluted cells is added to each well, except for five standard curve control wells that contain 100 μL of warm medium without cells. The plate is then incubated at 37° C. under 95% $O_2$, 5% $CO_2$ for 2 hours with constant shaking. After incubation, 50 μL of mammalian cell lysis solution (from the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The ATP-LITE-M Luminescent ATP detection kit is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 μL of serially diluted PACKARD standard is added to each of the standard curve control wells to yield a final concentration in each subsequent well of 200 nM, 100 nM, 50 nM, 25 nM and 12.5 nM. PACKARD substrate solution (50 μL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

Example 9

Dorsal Root Ganglion Cell Assay

This Example illustrates a representative dorsal root ganglian cell assay for evaluating VR1 antagonist or agonist activity of a compound.

DRG are dissected from neonatal rats, dissociated and cultured using standard methods (Aguayo and White (1992) *Brain Research* 570:61-67). After 48 hour incubation, cells are washed once and incubated for 30-60 minutes with the calcium sensitive dye Fluo 4 AM (2.5-10 ug/ml; TefLabs, Austin, Tex.). Cells are then washed once. Addition of capsaicin to the cells results in a VR1-dependent increase in intracellular calcium levels which is monitored by a change in Fluo-4 fluorescence with a fluorometer. Data are collected for 60-180 seconds to determine the maximum fluorescent signal.

For antagonist assays, various concentrations of compound are added to the cells. Fluorescent signal is then plotted as a function of compound concentration to identify the concentration required to achieve a 50% inhibition of the capsaicin-activated response, or $IC_{50}$. Antagonists of the capsaicin receptor preferably have an $IC_{50}$ below 1 micromolar, 100 nanomolar, 10 nanomolar or 1 nanomolar.

For agonist assays, various concentrations of compound are added to the cells without the addition of capsaicin. Compounds that are capsaicin receptor agonists result in a VR1-dependent increase in intracellular calcium levels which is monitored by a change in Fluo-4 fluorescence with a fluorometer. The $EC_{50}$, or concentration required to achieve 50% of the maximum signal for a capsaicin-activated response, is preferably below 1 micromolar, below 100 nanomolar or below 10 nanomolar.

Example 10

Animal Models for Determining Pain Relief

This Example illustrates representative methods for assessing the degree of pain relief provided by a compound.

A. Pain Relief Testing

The following methods may be used to assess pain relief.

Mechanical Allodynia

Mechanical allodynia (an abnormal response to an innocuous stimulus) is assessed essentially as described by Chaplan et al. (1994) *J. Neurosci. Methods* 53:55-63 and Tal and Eliav (1998) Pain 64(3):511-518. A series of von Frey filaments of varying rigidity (typically 8-14 filaments in a series) are applied to the plantar surface of the hind paw with just enough force to bend the filament. The filaments are held in this position for no more than three seconds or until a positive allodynic response is displayed by the rat. A positive allodynic response consists of lifting the affected paw followed immediately by licking or shaking of the paw. The order and frequency with which the individual filaments are applied are determined by using Dixon up-down method. Testing is initiated with the middle hair of the series with subsequent filaments being applied in consecutive fashion, ascending or descending, depending on whether a negative or positive response, respectively, is obtained with the initial filament.

Compounds are effective in reversing or preventing mechanical allodynia-like symptoms if rats treated with such compounds require stimulation with a Von Frey filament of higher rigidity strength to provoke a positive allodynic response as compared to control untreated or vehicle treated rats. Alternatively, or in addition, testing of an animal in chronic pain may be done before and after compound administration. In such an assay, an effective compound results in an increase in the rigidity of the filament needed to induce a response after treatment, as compared to the filament that induces a response before treatment or in an animal that is also in chronic pain but is left untreated or is treated with vehicle. Test compounds are administered before or after onset of pain. When a test compound is administered after pain onset, testing is performed 10 minutes to three hours after administration.

Mechanical Hyperalgesia

Mechanical hyperalgesia (an exaggerated response to painful stimulus) is tested essentially as described by Koch et al. (1996) *Analgesia* 2(3):157-164. Rats are placed in individual compartments of a cage with a warmed, perforated metal floor. Hind paw withdrawal duration (i.e., the amount of time for which the animal holds its paw up before placing it back on the floor) is measured after a mild pinprick to the plantar surface of either hind paw.

Compounds produce a reduction in mechanical hyperalgesia if there is a statistically significant decrease in the duration of hindpaw withdrawal. Test compound may be administered before or after onset of pain. For compounds administered after pain onset, testing is performed 10 minutes to three hours after administration.

Thermal Hyperalgesia

Thermal hyperalgesia (an exaggerated response to noxious thermal stimulus) is measured essentially as described by Hargreaves et al. (1988) *Pain.* 32(1):77-88. Briefly, a constant radiant heat source is applied the animals' plantar surface of either hind paw. The time to withdrawal (i.e., the amount of time that heat is applied before the animal moves its paw), otherwise described as thermal threshold or latency, determines the animal's hind paw sensitivity to heat.

Compounds produce a reduction in thermal hyperalgesia if there is a statistically significant increase in the time to hindpaw withdrawal (i.e., the thermal threshold to response or latency is increased). Test compound may be administered before or after onset of pain. For compounds administered after pain onset, testing is performed 10 minutes to three hours after administration.

B. Pain Models

Pain may be induced using any of the following methods, to allow testing of analgesic efficacy of a compound. In general, compounds provided herein result in a statistically significant reduction in pain as determined by at least one of the previously described testing methods, using male SD rats and at least one of the following models.

Acute Inflammatory Pain Model

Acute inflammatory pain is induced using the carrageenan model essentially as described by Field et al. (1997) *Br. J. Pharmacol.* 121(8):1513-1522. 100-200 μl of 1-2% carrageenan solution is injected into the rats' hind paw. Three to four hours following injection, the animals' sensitivity to thermal and mechanical stimuli is tested using the methods described above. A test compound (0.01 to 50 mg/kg) is administered to the animal, prior to testing, or prior to injection of carrageenan. The compound can be administered orally or through any parenteral route, or topically on the paw. Compounds that relieve pain in this model result in a statistically significant reduction in mechanical allodynia and/or thermal hyperalgesia.

Chronic Inflammatory Pain Model

Chronic inflammatory pain is induced using one of the following protocols:

1. Essentially as described by Bertorelli et al. (1999) *Br. J. Pharmacol.* 128(6):1252-1258, and Stein et al. (1998) *Pharmacol. Biochem. Behav.* 31(2):455-51, 200 μl Complete Freund's Adjuvant (0.1 mg heat killed and dried *M. Tuberculosis*) is injected to the rats' hind paw: 100 μl into the dorsal surface and 100 μl into the plantar surface.
2. Essentially as described by Abbadie et al. (1994) *J Neurosci.* 14(10):5865-5871 rats are injected with 150 μl of CFA (1.5 mg) in the tibio-tarsal joint.

Prior to injection with CFA in either protocol, an individual baseline sensitivity to mechanical and thermal stimulation of the animals' hind paws is obtained for each experimental animal.

Following injection of CFA, rats are tested for thermal hyperalgesia, mechanical allodynia and mechanical hyperalgesia as described above. To verify the development of symptoms, rats are tested on days 5, 6, and 7 following CFA injection. On day 7, animals are treated with a test compound, morphine or vehicle. An oral dose of morphine of 1-5 mg/kg is suitable as positive control. Typically, a dose of 0.01-50 mg/kg of test compound is used. Compounds can be administered as a single bolus prior to testing or once or twice or three times daily, for several days prior to testing. Drugs are administered orally or through any parenteral route, or applied topically to the animal.

Results are expressed as Percent Maximum Potential Efficacy (MPE). 0% MPE is defined as analgesic effect of vehicle, 100% MPE is defined as an animal's return to pre-CFA baseline sensitivity. Compounds that relieve pain in this model result in a MPE of at least 30%.

Chronic Neuropathic Pain Model

Chronic neuropathic pain is induced using the chronic constriction injury (CCI) to the rat's sciatic nerve essentially as described by Bennett and Xie (1988) *Pain* 33:87-107. Rats are anesthetized (e.g. with an intraperitoneal dose of 50-65 mg/kg pentobarbital with additional doses administered as needed). The lateral aspect of each hind limb is shaved and disinfected. Using aseptic technique, an incision is made on the lateral aspect of the hind limb at the mid thigh level. The biceps femoris is bluntly dissected and the sciatic nerve is exposed. On one hind limb of each animal, four loosely tied ligatures are made around the sciatic nerve approximately 1-2 mm apart. On the other side the sciatic nerve is not ligated and is not manipulated. The muscle is closed with continuous pattern and the skin is closed with wound clips or sutures. Rats are assessed for mechanical allodynia, mechanical hyperalgesia and thermal hyperalgesia as described above.

Compounds that relieve pain in this model result in a statistically significant reduction in mechanical allodynia, mechanical hyperalgesia and/or thermal hyperalgesia when administered (0.01-50 mg/kg, orally, parenterally or topically) immediately prior to testing as a single bolus, or for several days: once or twice or three times daily prior to testing.

What is claimed is:
1. A compound of the formula:

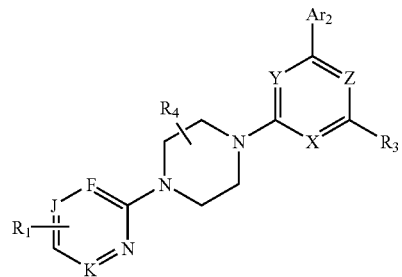

or a pharmaceutically acceptable salt thereof, wherein:
$Ar_2$ is phenyl or a 6-membered aromatic heterocycle, each of which is substituted with from 1 to 3 substituents independently chosen from $R_2$, and $Ar_2$ is substituted at a carbon atom meta and/or para to the point of attachment;

X, Y and Z are each N;

K, J and F are independently N, CH or carbon substituted with $R_1$;

$R_1$ represents from 1 to 3 substituents independently chosen from halogen, hydroxy, amino, cyano, $C_1$-$C_6$alkyl, $C_2$-$C_6$alkenyl, $C_2$-$C_6$alkynyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- and di-($C_1$-$C_6$alkyl)amino, $C_1$-$C_6$alkylsulfonyl, mono- and di-($C_1$-$C_6$alkyl)sulfonamido and mono- and di-($C_1$-$C_6$alkyl)aminocarbonyl;

Each $R_2$ is independently chosen from:
 (a) hydroxy, amino, cyano, halogen, —COOH, —$SO_2NH_2$, nitro and aminocarbonyl; and
 (b) $C_1$-$C_6$alkyl, $C_2$-$C_6$alkenyl, $C_2$-$C_6$alkynyl, ($C_3$-$C_8$cycloalkyl)$C_0$-$C_4$alkyl, $C_1$-$C_6$haloalkyl, $C_1$-$C_6$alkoxy, $C_1$-$C_6$alkylthio, $C_2$-$C_6$alkyl ether, $C_2$-$C_6$alkanoyl, $C_1$-$C_6$alkoxycarbonyl, $C_2$-$C_6$alkanoyloxy, $C_3$-$C_6$alkanone, mono- and di-($C_1$-$C_6$alkyl)amino$C_0$-$C_6$alkyl, mono- and di-($C_3$-$C_8$cycloalkyl)amino$C_0$-$C_4$alkyl, (4- to 7-membered heterocycle)$C_0$-$C_4$alkyl, $C_1$-$C_6$alkylsulfonyl, mono- and di-($C_1$-$C_6$alkyl)sulfonamido, and mono- and di-($C_1$-$C_6$alkyl)aminocarbonyl, each of which is substituted with from 0 to 4 substituents independently chosen from halogen, hydroxy, cyano, amino, —COOH and oxo;

$R_3$ is selected from:
 (i) hydrogen and halogen;
 (ii) phenyl$C_0$-$C_2$alkyl or ($C_4$-$C_7$cycloalkyl)$C_0$-$C_2$alkyl; and
 (iii) groups of the formula:

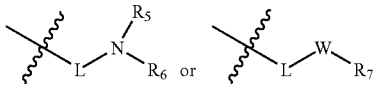

wherein:
 L is $C_0$-$C_6$alkyl or $C_1$-$C_6$alkyl that is taken together with $R_5$, $R_6$ or $R_7$ to form a 4- to 7-membered carbocycle or heterocycle;
 W is O, CO, S, SO or $SO_2$;
 $R_5$ and $R_6$ are:
  (a) independently chosen from hydrogen, $C_1$-$C_{12}$alkyl, $C_2$-$C_{12}$alkenyl, ($C_3$-$C_8$cycloalkyl)$C_0$-$C_4$alkyl, $C_2$-$C_6$alkanoyl, $C_1$-$C_6$alkylsulfonyl, phenyl$C_0$-$C_6$alkyl, (4- to 7-membered heterocycle)$C_0$-$C_6$alkyl and groups that are joined to L to form a 4- to 7-membered heterocycle, such that if L is a single covalent bond then at least one of $R_5$ and $R_6$ is not hydrogen; or
  (b) joined to form a 4- to 12-membered heterocycle; and
 $R_7$ is hydrogen, $C_1$-$C_{12}$alkyl, $C_2$-$C_{12}$alkenyl, $C_2$-$C_{12}$alkynyl, ($C_3$-$C_8$cycloalkyl)$C_0$-$C_4$alkyl, $C_2$-$C_6$alkanoyl, phenyl$C_0$-$C_6$alkyl, (4- to 7-membered heterocycle)$C_0$-$C_6$alkyl or a group that is joined to L to form a 4- to 7-membered carbocycle or heterocycle, such that if L is a single covalent bond, then $R_7$ is not hydrogen;
wherein each of (ii) and (iii) is substituted with from 0 to 4 substituents independently chosen from:
 (1) halogen, hydroxy, amino, cyano, —COOH, —$SO_2NH_2$, oxo, nitro and aminocarbonyl; and
 (2) $C_1$-$C_6$alkyl, $C_3$-$C_8$cycloalkyl, $C_1$-$C_6$alkoxy, $C_1$-$C_6$haloalkyl, $C_1$-$C_6$alkanoyl, mono- and di-($C_1$-$C_6$alkyl)amino$C_0$-$C_4$alkyl, $C_1$-$C_6$alkylsulfonyl, mono- and di-($C_1$-$C_6$alkyl) sulfonamido, $C_2$-$C_6$alkanoylamino, mono- and di-($C_1$-$C_6$alkyl)aminocarbonyl$C_0$-$C_4$alkyl, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, oxo, imino, $C_0$-$C_4$alkyl, $C_1$-$C_4$alkoxy and $C_1$-$C_4$haloalkyl; and $R_4$ represents from 0 to 2 substituents independently chosen from $C_1$-$C_3$alkyl, $C_1$-$C_3$haloalkyl and oxo.

2. A compound or salt according to claim 1, wherein K is N.
3. A compound or salt according to claim 1, wherein J is N.
4. A compound or salt according to claim 1, wherein F is N.
5. A compound or salt according to claim 1, wherein $R_1$ represents from 1 to 3 substituents independently chosen from halogen, hydroxy, amino, cyano, $C_1$-$C_4$alkyl, $C_1$-$C_4$alkoxy, $C_2$-$C_4$alkyl ether, $C_2$-$C_4$alkanoyl, $C_1$-$C_6$haloalkyl, $C_1$-$C_4$haloalkoxy, mono- and di-($C_1$-$C_4$alkyl)amino, $C_1$-$C_4$alkylsulfonyl, mono- and di-($C_1$-$C_4$alkyl)sulfonamido and mono- and di-($C_1$-$C_4$alkyl)aminocarbonyl.
6. A compound or salt according to claim 5, wherein $R_1$ represents 1 or 2 substituents.
7. A compound or salt according to claim 6, wherein at least one substituent represented by $R_1$ is $C_1$-$C_3$alkyl, $C_1$-$C_3$alkoxy, $C_1$-$C_3$alkylsulfonyl, mono- or di-($C_1$-$C_4$alkyl)aminocarbonyl, mono- or di-($C_1$-$C_6$alkyl)sulfonamido or mono- and di-($C_1$-$C_3$alkyl)amino.
8. A compound or salt according to claim 7, wherein F is substituted carbon.
9. A compound or salt according to claim 8, wherein J and K are CH.
10. A compound or salt according to claim 9, wherein $R_1$ represents one chosen from halogen, cyano, methyl, trifluoromethyl and methylsulfonyl.
11. A compound or salt according to claim 1, wherein $R_3$ is a group of the formula:

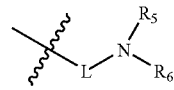

wherein:
 L is $C_0$-$C_6$alkyl or $C_1$-$C_6$alkyl that is taken together with $R_5$ or $R_6$ to form a 4- to 7-membered heterocycle; and
 $R_5$ and $R_6$ are:
  (a) independently chosen from hydrogen, $C_1$-$C_6$alkyl, $C_2$-$C_6$alkenyl, ($C_5$-$C_7$cycloalkyl)$C_0$-$C_4$alkyl, $C_2$-$C_4$alkanoyl and groups that are joined to L to form a 4- to 7-membered heterocycle; or
  (b) joined to form a 4- to 12-membered heterocycloalkyl;
  each of which alkyl, alkenyl, (cycloalkyl)alkyl, alkanoyl and heterocycloalkyl is substituted with from 0 to 4 substituents independently chosen from (i) halogen, hydroxy, amino, aminocarbonyl, oxo, —COOH and —$SO_2NH_2$; and (ii) $C_1$-$C_4$alkyl, $C_5$-$C_7$cycloalkyl, $C_1$-$C_4$alkoxy, $C_2$-$C_4$alkanoyl, $C_1$-$C_4$haloalkyl, mono- and di-($C_1$-$C_4$alkyl)amino$C_0$-$C_2$alkyl, mono- and di-($C_1$-$C_4$alkyl)aminocarbonyl$C_0$-$C_2$alkyl, phenyl$C_0$-$C_4$alkyl and (4- to 7-membered heterocycle)$C_0$-$C_2$alkyl, each of which is substituted with from 0 to 4 secondary substituents independently chosen from halogen, hydroxy, cyano, $C_0$-$C_4$alkyl, $C_1$-$C_4$alkoxy and $C_0$-$C_4$haloalkyl.

12. A compound or salt according to claim 11, wherein $R_3$ is di($C_1$-$C_4$alkyl)amino substituted with from 0 to 4 substituents independently chosen from halogen, hydroxy, amino, oxo, aminocarbonyl, —COOH, —$SO_2NH_2$, $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino.

13. A compound or salt according to claim 11, wherein $R_3$ is azetidinyl, pyrrolidinyl, morpholinyl, thiomorpholinyl, piperidinyl, piperazinyl, tetrahydropyridyl or azepanyl, each of which is substituted with from 0 to 4 substituents independently chosen from:
(a) halogen, hydroxy, amino, oxo, aminocarbonyl, $SO_2NH_2$ and —COOH; and
(b) $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino, each of which is substituted with from 0 to 4 secondary substituents independently chosen from hydroxy and halogen.

14. A compound or salt according to claim 1, wherein $R_3$ is phenyl or 4- to 7-membered heterocycle, each of which is substituted with from 0 to 4 substituents independently chosen from (a) halogen, hydroxy, amino, oxo, aminocarbonyl, —$SO_2NH_2$ and —COOH; and (b) $C_1$-$C_4$alkyl, $(C_5C_7$cycloalkyl)$C_0$-$C_2$alkyl, $C_1$-$C_4$alkoxy, $C_2$-$C_4$alkyl ether, $C_2$-$C_4$alkanoyl, $C_1$-$C_4$haloalkyl, mono- and di-($C_1$-$C_4$alkyl)amino, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, $C_1$-$C_4$alkyl and $C_1$-$C_4$haloalkyl.

15. A compound or salt according to claim 14, wherein $R_3$ is phenyl, pyridyl, pyrimidyl, pyrazinyl, pyridazinyl, imidazolyl, thienyl, oxazolyl or tetrahydrofuranyl, each of which is substituted with from 0 to 4 substituents independently chosen from halogen, hydroxy, amino, —$SO_2NH_2$, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino.

16. A compound or salt according to claim 1, wherein $R_3$ is a group of the formula:

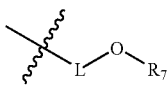

wherein:
L is $C_0$-$C_3$alkyl; and
$R_7$ is $C_1$-$C_6$alkyl, $C_2$-$C_6$alkenyl, $(C_5$-$C_7$cycloalkyl)$C_0$-$C_4$alkyl, $C_2$-$C_4$alkanoyl, phenyl$C_0$-$C_6$alkyl or (6-membered heteroaryl)$C_0$-$C_4$alkyl, each of which is substituted with from 0 to 4 substituents independently chosen from halogen, hydroxy, amino, aminocarbonyl, —$SO_2NH_2$, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino.

17. A compound or salt according claim 1, wherein $R_3$ is a halogen.

18. A compound or salt according to claim 1, wherein each $R_2$ is independently chosen from amino, cyano, halogen, —$SO_2NH_2$, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, mono- and di-($C_3$-$C_8$cycloalkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)sulfonamido.

19. A compound or salt according to claim 18, wherein $Ar_2$ is phenyl or pyridyl, substituted with from 1 to 3 substituents independently chosen from amino, cyano, halogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, and mono- and di-($C_1$-$C_4$alkyl)amino$C_0$-$C_4$alkyl.

20. A compound or salt according to claim 1, having the formula:

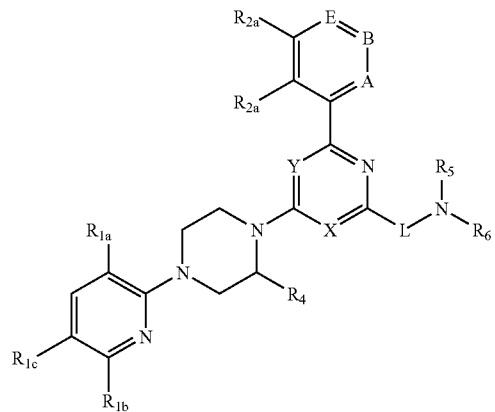

wherein:
A, B and E are independently nitrogen or $CR_{2a}$;
Each $R_{2a}$ is independently chosen from hydrogen, amino, cyano, halogen, —$SO_2NH_2$, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, mono- and di-($C_3$-$C_8$cycloalkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)sulfonamido, such that at least one $R_{2a}$ is not hydrogen;
$R_{1a}$ is halogen, amino, cyano, $C_1$-$C_6$alkyl, $C_1$-$C_6$haloalkyl, $C_1$-$C_6$alkoxy, $C_1$-$C_6$alkylsulfonyl or mono- or di-($C_1$-$C_6$alkyl)sulfonamido;
$R_{1b}$ and $R_{1c}$ are independently chosen from hydrogen, halogen, amino, cyano, $C_1$-$C_6$alkyl, $C_1$-$C_6$haloalkyl, $C_1$-$C_6$alkoxy, $C_1$-$C_6$alkylsulfonyl and mono- and di-($C_1$-$C_6$alkyl)sulfonamido;
$R_4$ is hydrogen, methyl, ethyl or oxo; and
with the proviso that at least one $R_{2a}$ meta and/or para to the point of attachment is not hydrogen.

21. A compound or salt according to claim 20, wherein:
$R_{1a}$ is halogen, cyano, methyl or trifluoromethyl;
$R_{1b}$ and $R_{1c}$ are independently hydrogen, halogen, amino, $C_1$-$C_3$alkyl, $C_1$-$C_3$alkoxy, mono- or di-($C_1$-$C_4$alkyl)amino, mono- or di-($C_1$-$C_4$alkyl)aminocarbonyl, $C_1$-$C_3$alkylsulfonyl, or mono- or di-($C_1$-$C_4$alkyl)sulfonamido;
each $R_{2a}$ is independently chosen from hydrogen, halogen, cyano, amino, $C_1$-$C_4$alkyl, $C_1$-$C_4$alkoxy, and $C_1$-$C_4$haloalkyl; and
$R_5$ and $R_6$ are independently chosen from:
(i) hydrogen; and
(ii) $C_1$-$C_6$alkyl, $C_2$-$C_6$alkenyl, $(C_3$-$C_8$cycloalkyl)$C_0$-$C_2$alkyl, $C_2$-$C_6$alkanoyl, phenyl$C_0$-$C_2$alkyl, (4- to 7-membered heterocycloalkyl)$C_0$-$C_2$alkyl and groups that are joined to L to form a 4- to 7-membered heterocycle; each of which is substituted with from 0 to 2 substituents independently chosen from halogen, hydroxy, oxo, COOH, aminocarbonyl, —$SO_2NH_2$, $C_1$-$C_4$alkyl, $C_1$-$C_4$haloalkyl, $C_1$-$C_4$alkoxy, $C_1$-$C_4$alkoxycarbonyl, $C_1$-$C_4$alkylsulfonyl and mono- and di-($C_1$-$C_6$alkyl)amino;

or $R_5$ and $R_6$, together with the N to which they are bound, form a 4- to 7-membered heterocycloalkyl that is substituted with from 0 to 2 substituents independently chosen from halogen, hydroxy, amino, oxo, aminocarbonyl, —$SO_2NH_2$, COOH, $C_1$-$C_4$alkyl, $C_1$-$C_4$alkoxy, $C_1$-$C_4$hydroxyalkyl, $C_2$-$C_4$alkyl ether, $C_1$-$C_4$alkoxycarbonyl, $C_2$-$C_4$alkanoyl, $C_2$-$C_4$alkanoylamino, ($C_3$-$C_7$cycloalkyl)$C_0$-$C_2$alkyl, (4- to 7 membered heterocycloalkyl)$C_0$-$C_2$alkyl, mono- and di-($C_1$-$C_6$alkyl)aminocarbonyl, $C_1$-$C_4$alkylsulfonyl, and mono- and di-($C_1$-$C_6$alkyl)amino$C_0$-$C_2$alkyl.

22. A compound or salt according to claim 21, wherein the compound has the formula:

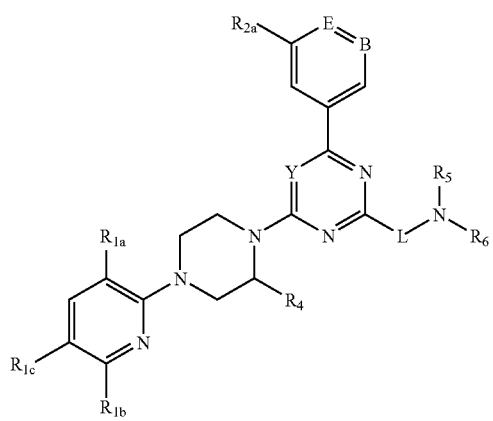

wherein L is a single covalent bond or methylene, and wherein at least one of B and E is $CR_{2a}$.

23. A compound or salt according to claim 1, having the formula:

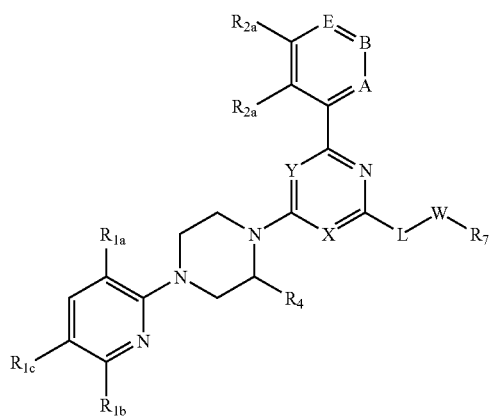

wherein:
A, B and E are independently nitrogen or $CR_{2a}$;
Each $R_{2a}$ is independently hydrogen, amino, cyano, halogen, —$SO_2NH_2$, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- or di-($C_1$-$C_4$alkyl)amino$C_0$-$C_4$alkyl, mono- and di-($C_3$-$C_8$cycloalkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl or mono- or di-($C_1$-$C_4$alkyl)sulfonamido, such that at least one $R_{2a}$ is not hydrogen;

$R_{1a}$ is halogen, amino, cyano, $C_1$-$C_6$alkyl, $C_1$-$C_6$alkoxy, $C_1$-$C_6$haloalkyl, $C_1$-$C_6$alkylsulfonyl or mono- or di-($C_1$-$C_6$alkyl)sulfonamido;

$R_{1b}$ and $R_{1c}$ are independently chosen from hydrogen, halogen, amino, cyano, $C_1$-$C_6$alkyl, $C_1$-$C_6$alkoxy, $C_1$-$C_6$haloalkyl, $C_1$-$C_6$alkylsulfonyl, mono- and di-($C_1$-$C_6$alkyl)aminocarbonyl, mono- and di-($C_1$-$C_6$alkyl)amino and mono- and di-($C_1$-$C_6$alkyl)sulfonamido;

$R_4$ is hydrogen, methyl, ethyl or oxo; and with the proviso that at least one $R_{2a}$ meta and/or para to the point of attachment is not hydrogen.

24. A compound or salt according to claim 23, wherein:
$R_{1a}$ is halogen, cyano, methyl or trifluoromethyl;
$R_{1b}$ and $R_{1c}$ are independently hydrogen, halogen, amino, $C_1$-$C_3$alkyl, $C_1$-$C_3$alkoxy, mono- or di-($C_1$-$C_4$alkyl) amino, mono- or di-($C_1$-$C_4$alkyl)aminocarbonyl, $C_1$-$C_3$alkylsulfonyl, or mono- or di-($C_1$-$C_4$alkyl)sulfonamido;
each $R_{2a}$ is independently chosen from hydrogen, halogen, cyano, amino, $C_1$-$C_4$alkyl, $C_1$-$C_4$alkoxy, and $C_1$-$C_4$haloalkyl; and
$R_7$ is $C_1$-$C_6$alkyl, $C_2$-$C_6$alkenyl, $C_2$-$C_6$alkyl ether, ($C_3$-$C_8$cycloalkyl)$C_0$-$C_2$alkyl, $C_2$-$C_6$alkanoyl, phenyl$C_0$-$C_2$alkyl or (4- to 7-membered heterocycloalkyl)$C_0$-$C_2$alkyl, each of which is substituted with from 0 to 2 substituents independently chosen from halogen, hydroxy, oxo, $C_1$-$C_4$alkyl, $C_1$-$C_4$haloalkyl and $C_2$-$C_4$alkanoyl.

25. A compound or salt according to claim 23, wherein the compound has the formula:

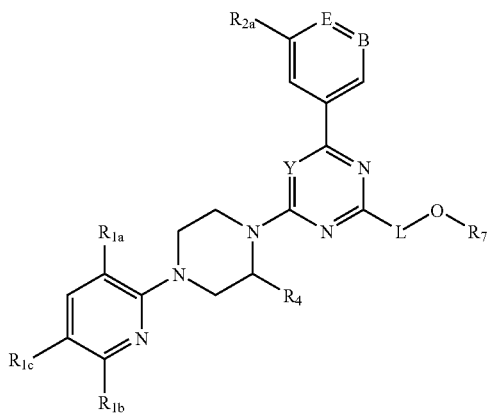

wherein L is a single covalent bond or methylene, and wherein at least one of B and E is $CR_{2a}$.

26. A compound or salt according to claim 1, wherein the compound exhibits no detectable agonist activity an in vitro assay of capsaicin receptor agonism at a concentration of compound equal to the $IC_{50}$.

27. A compound or salt according to claim 26, wherein the compound exhibits no detectable agonist activity an in vitro assay of capsaicin receptor agonism at a concentration of compound that is 100-fold higher than the $IC_{50}$.

28. A compound of the formula:

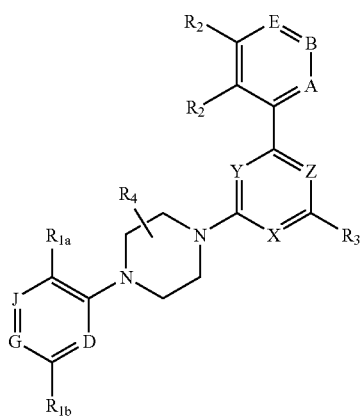

or a pharmaceutically acceptable salt thereof, wherein:

A, B and E are independently CH, $CR_{2a}$ or N, such that at least one of B and E is $CR_{2a}$;

J, G and D are independently N or $CR_{1b}$;

X, Y and Z are each N;

$R_{1a}$ is halogen, hydroxy, amino, cyano, $C_1$-$C_6$alkyl, $C_2$-$C_6$alkenyl, $C_2$-$C_6$alkynyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)sulfonamido or mono- or di-($C_1$-$C_6$alkyl)aminocarbonyl;

Each $R_{1b}$ is independently hydrogen, halogen, hydroxy, amino, cyano, $C_1$-$C_6$alkyl, $C_2$-$C_6$alkenyl, $C_2$-$C_6$alkynyl, $C_1$-$C_6$alkoxy, $C_2$-$C_6$alkyl ether, $C_2$-$C_6$alkanoyl, $C_3$-$C_6$alkanone, $C_1$-$C_6$haloalkyl, $C_1$-$C_6$haloalkoxy, mono- or di-($C_1$-$C_6$alkyl)amino, $C_1$-$C_6$alkylsulfonyl, mono- or di-($C_1$-$C_6$alkyl)sulfonamido or mono- or di-($C_1$-$C_6$alkyl)aminocarbonyl;

Each $R_2$ is independently H or $R_{2a}$;

Each $R_{2a}$ is:
(a) independently chosen from (i) hydroxy, amino, cyano, halogen, —COOH, —$SO_2NH_2$ and nitro; and (ii) $C_1$-$C_6$alkyl, $C_2$-$C_6$alkenyl, $C_2$-$C_6$alkynyl, ($C_3$-$C_8$cycloalkyl)$C_0$-$C_4$alkyl, $C_1$-$C_6$haloalkyl, $C_1$-$C_6$alkoxy, $C_1$-$C_6$alkylthio, $C_2$-$C_6$alkyl ether, $C_2$-$C_6$alkanoyl, $C_1$-$C_6$alkoxycarbonyl, $C_2$-$C_6$alkanoyloxy, $C_3$-$C_6$alkanone, mono- and di-($C_1$-$C_6$alkyl)amino$C_0$-$C_6$alkyl, mono- and di-($C_3$-$C_8$cycloalkyl)amino$C_0$-$C_4$alkyl, (4- to 7-membered heterocycle)$C_0$-$C_4$alkyl, $C_1$-$C_6$alkylsulfonyl, mono- and di-($C_1$-$C_6$alkyl)sulfonamido, and mono- and di-($C_1$-$C_6$alkyl)aminocarbonyl, each of which is substituted with from 0 to 4 substituents independently chosen from halogen, hydroxy, cyano, amino, —COOH and oxo; or
(b) taken together with an adjacent $R_{2a}$ to form a fused 5- to 13-membered carbocyclic or heterocyclic group that is substituted with from 0 to 4 substituents independently chosen from halogen, oxo and $C_1$-$C_6$alkyl;

$R_3$ is selected from:
(i) hydrogen and halogen;
(ii) $C_1$-$C_6$alkyl, ($C_3$-$C_8$cycloalkyl)$C_0$-$C_2$alkyl, $C_1$-$C_6$haloalkyl and phenyl$C_0$-$C_2$alkyl; and
(iii) groups of the formula:

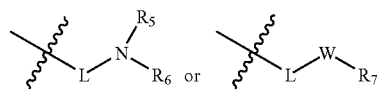

wherein:

L is $C_0$-$C_6$alkyl or $C_1$-$C_6$alkyl that is taken together with $R_5$, $R_6$ or $R_7$ to form a 4- to 7-membered carbocycle or heterocycle;

W is O, CO, S, SO or $SO_2$;

$R_5$ and $R_6$ are:
(a) independently chosen from hydrogen, $C_1$-$C_{12}$alkyl, $C_2$-$C_{12}$alkenyl, $C_2$-$C_{12}$alkynyl, ($C_3$-$C_8$cycloalkyl)$C_0$-$C_4$alkyl, $C_2$-$C_6$alkanoyl, $C_1$-$C_6$alkylsulfonyl, phenyl$C_0$-$C_6$alkyl, (4- to 7-membered heterocycle)$C_0$-$C_6$alkyl and groups that are joined to L to form a 4- to 7-membered heterocycle; or
(b) joined to form a 4- to 12-membered heterocycle; and $R_7$ is hydrogen, $C_1$-$C_{12}$alkyl, $C_2$-$C_{12}$alkenyl, ($C_3$-$C_8$cycloalkyl)$C_0$-$C_4$alkyl, $C_2$-$C_6$alkanoyl, phenyl$C_0$-$C_6$alkyl, (4- to 7-membered heterocycle)$C_0$-$C_6$alkyl or a group that is joined to L to form a 4- to 7-membered carbocycle or heterocycle, such that if L is a single covalent bond, then $R_7$ is not hydrogen;

wherein each of (ii) and (iii) is substituted with from 0 to 4 substituents independently chosen from:
(1) halogen, hydroxy, amino, cyano, —COOH, —$SO_2NH_2$, oxo, nitro and aminocarbonyl; and
(2) $C_1$-$C_6$alkyl, $C_3$-$C_8$cycloalkyl, $C_1$-$C_6$alkoxy, $C_1$-$C_6$haloalkyl, $C_1$-$C_6$alkanoyl, mono- and di-($C_1$-$C_6$alkyl)amino$C_0$-$C_4$alkyl, $C_1$-$C_6$alkylsulfonyl, mono- and di-($C_1$-$C_6$alkyl)sulfonamido, $C_2$-$C_6$alkanoylamino, mono- and di-($C_1$-$C_6$alkyl)aminocarbonyl$C_0$-$C_4$alkyl, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, oxo, imino, $C_0$-$C_4$alkyl, $C_1$-$C_4$alkoxy and $C_0$-$C_4$haloalkyl; and $R_4$ represents from 0 to 2 substituents independently chosen from $C_1$-$C_3$alkyl, $C_1$-$C_3$haloalkyl and oxo.

29. A compound or salt according to claim 28, wherein the compound has the formula:

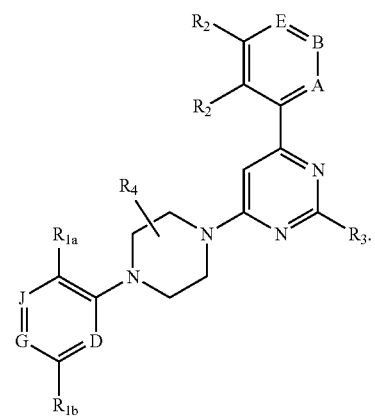

30. A compound or salt according to claim 28, wherein G is N.

31. A compound or salt according to claim 28, wherein J is N.

32. A compound or salt according to claim 28, wherein D is N.

33. A compound or salt according to claim 28, wherein G is $CR_{1b}$, and wherein $R_{1b}$ at the G position is not hydrogen.

34. A compound or salt according to claim 33, wherein $R_{1b}$ at the G position is halogen, hydroxy, amino, cyano, $C_1$-$C_6$alkyl, $C_1$-$C_6$haloalkyl, $C_1$-$C_6$alkoxy, $C_2$-$C_6$alkyl ether, $C_2$-$C_6$alkanoyl, $C_3$-$C_6$alkanone, mono- or di-($C_1$-$C_6$alkyl)amino, $C_1$-$C_6$alkylsulfonyl, mono- or di-($C_1$-$C_6$alkyl)sulfonamido, or mono- or di-($C_1$-$C_6$alkyl)aminocarbonyl.

35. A compound or salt according to claim 28, wherein $R_{1a}$ is halogen, amino, cyano, $C_1$-$C_6$alkyl, $C_1$-$C_6$alkoxy, $C_1$-$C_6$haloalkyl, $C_1$-$C_6$alkylsulfonyl or mono- or di-($C_1$-$C_6$alkyl)sulfonamido.

36. A compound or salt according to claim 35, wherein $R_{1a}$ is halogen, cyano, methyl, trifluoromethyl or methylsulfonyl.

37. A compound or salt according to claim 28, wherein $R_3$ is a group of the formula:

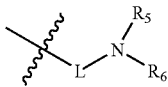

wherein:
L is $C_0$-$C_6$alkyl or $C_1$-$C_6$alkyl that is taken together with $R_5$ or $R_6$ to form a 4- to 7-membered heterocycle; and
$R_5$ and $R_6$ are:
(a) independently chosen from hydrogen, $C_1$-$C_6$alkyl, $C_2$-$C_6$alkenyl, ($C_5$-$C_7$cycloalkyl)$C_0$-$C_4$alkyl, $C_2$-$C_4$alkanoyl and groups that are joined to L to form a 4- to 7-membered heterocycle; or
(b) joined to form a 4- to 12-membered heterocycloalkyl;
each of which alkyl, alkenyl, (cycloalkyl)alkyl, alkanoyl and heterocycloalkyl is substituted with from 0 to 4 substituents independently chosen from (i) halogen, hydroxy, amino, aminocarbonyl, oxo, —COOH and —$SO_2NH_2$; and (ii) $C_1$-$C_4$alkyl, $C_5$-$C_7$cycloalkyl, $C_1$-$C_4$alkoxy, $C_2$-$C_4$alkanoyl, $C_1$-$C_4$haloalkyl, mono- and di-($C_1$-$C_4$alkyl)amino$C_0$-$C_2$alkyl, mono- and di-($C_1$-$C_4$alkyl)aminocarbonyl$C_0$-$C_2$alkyl, phenyl$C_0$-$C_4$alkyl and (4- to 7-membered heterocycle)$C_0$-$C_2$alkyl, each of which is substituted with from 0 to 4 secondary substituents independently chosen from halogen, hydroxy, cyano, $C_0$-$C_4$alkyl, $C_1$-$C_4$alkoxy and $C_0$-$C_4$haloalkyl.

38. A compound or salt according to claim 37, wherein $R_3$ is mono- or di-($C_1$-$C_4$alkyl)amino substituted with from 0 to 4 substituents independently chosen from halogen, hydroxy, amino, oxo, aminocarbonyl, —COOH, —$SO_2NH_2$, $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino.

39. A compound or salt according to claim 28, wherein $R_3$ is phenyl or 4- to 7-membered heterocycle, each of which is substituted with from 0 to 4 substituents independently chosen from (a) halogen, hydroxy, amino, oxo, aminocarbonyl, —$SO_2NH_2$ and —COOH; and (b) $C_1$-$C_4$alkyl, $C_1$-$C_4$haloalkyl, $C_2$-$C_4$alkenyl, ($C_5$-$C_7$cycloalkyl)$C_0$-$C_2$alkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino, mono- and di-($C_1$-$C_4$alkyl)amino, mono- and di-($C_1$-$C_4$alkyl)aminocarbonyl, mono- or di-($C_1$-$C_6$alkyl)sulfonamido, phenyl$C_0$-$C_4$alkyl and (4- to 7-membered heterocycle)$C_0$-$C_4$alkyl, each of which is substituted with from 0 to 4 secondary substituents independently chosen from halogen, hydroxy, cyano, —COOH, $C_1$-$C_4$alkyl and $C_1$-$C_4$haloalkyl.

40. A compound or salt according to claim 39, wherein $R_3$ is pyrrolidinyl, morpholinyl, thiomorpholinyl, piperidinyl, piperazinyl, tetrahydropyridyl or azepanyl, each of which is substituted with from 0 to 4 substituents independently chosen from:
(a) halogen, hydroxy, amino, oxo, aminocarbonyl, —$SO_2NH_2$ and —COOH; and
(b) $C_1$-$C_4$alkyl, $C_2$-$C_4$alkenyl, $C_5$-$C_7$cycloalkyl, $C_1$-$C_4$haloalkyl, $C_1$-$C_4$alkoxy, $C_2$-$C_4$alkyl ether, $C_2$-$C_4$alkanoyl, $C_1$-$C_4$alkylsulfonyl, $C_2$-$C_4$alkanoylamino and mono- and di-($C_1$-$C_4$alkyl)amino, each of which is substituted with from 0 to 4 secondary substituents independently chosen from hydroxy and halogen.

41. A compound or salt according to claim 39, wherein $R_3$ is phenyl, pyridyl, pyrimidyl, pyrazinyl, pyridazinyl, imidazolyl, thienyl, oxazolyl or tetrahydrofuranyl, each of which is substituted with from 0 to 4 substituents independently chosen from halogen, hydroxy, amino, aminocarbonyl, —$SO_2NH_2$, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino.

42. A compound or salt according to claim 28, wherein $R_3$ is a group of the formula:

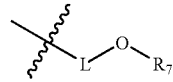

wherein:
L is $C_0$-$C_3$alkyl; and
$R_7$ is $C_1$-$C_6$alkyl, $C_2$-$C_6$alkenyl, ($C_5$-$C_7$cycloalkyl)$C_0$-$C_4$alkyl, $C_2$-$C_4$alkanoyl, phenyl$C_0$-$C_6$alkyl or (6-membered heteroaryl)$C_0$-$C_4$alkyl, each of which is substituted with from 0 to 4 substituents independently chosen from halogen, hydroxy, amino, aminocarbonyl, —$SO_2NH_2$, —COOH, $C_1$-$C_4$alkyl, $C_5$-$C_7$cycloalkyl, $C_2$-$C_4$alkyl ether, $C_1$-$C_4$alkoxy, $C_2$-$C_4$alkanoyl, $C_1$-$C_4$haloalkyl and mono- and di-($C_1$-$C_4$alkyl)amino.

43. A compound or salt according to claim 28, wherein $R_3$ is $C_1$-$C_4$alkyl, $C_3$-$C_7$cycloalkyl or $C_1$-$C_4$haloalkyl, each of which is substituted with from 0 to 4 substituents independently chosen from halogen, hydroxy, cyano, oxo, aminocarbonyl, —$SO_2NH_2$, —COOH, $C_3$-$C_7$cycloalkyl, phenyl and 4-to 7-membered heterocycle.

44. A compound or salt according to claim 28, wherein $R_3$ is a halogen.

45. A compound or salt according to claim 28, wherein each $R_{2a}$ is independently chosen from amino, cyano, halogen, —$SO_2NH_2$, —COOH, $C_1$-$C_4$alkyl, $C_1$-$C_4$haloalkyl, $C_1$-$C_4$hydroxyalkyl, $C_1$-$C_4$alkoxy, $C_1$-$C_4$alkylthio, $C_1$-$C_4$haloalkoxy, mono- and di-($C_1$-$C_4$alkyl)amino$C_0$-$C_4$alkyl, mono- and di-($C_3$-$C_8$cycloalkyl)amino$C_0$-$C_4$alkyl, $C_2$-$C_4$alkanoyl, $C_1$-$C_4$alkoxycarbonyl, $C_1$-$C_4$alkylsulfonyl, $C_1$-$C_4$haloalkylsulfonyl and mono- and di-($C_1$-$C_4$alkyl)sulfonamido.

46. A compound or salt according to claim 45, wherein A is CH or $CR_{2a}$, and wherein each $R_{2a}$ is independently chosen from cyano, halogen, $C_1$-$C_4$alkyl, $C_1$-$C_4$haloalkyl, $C_1$-$C_4$alkoxy and mono- and di-($C_1$-$C_4$alkyl)amino$C_0$-$C_2$alkyl.

47. A compound or salt according to claim 28, wherein at least one of A, B and E is N.

48. A compound or salt according to claim 28, wherein the compound exhibits no detectable agonist activity an in vitro assay of capsaicin receptor agonism at a concentration of compound equal to the $IC_{50}$.

49. A compound or salt according to claim 28, wherein the compound exhibits no detectable agonist activity an in vitro assay of capsaicin receptor agonism at a concentration of compound that is 100-fold higher than the $IC_{50}$.

50. A compound or salt according to claim 1, wherein the compound has an $IC_{50}$ value of 1 micromolar or less in a capsaicin receptor calcium mobilization assay.

51. A compound or salt according to claim 1, wherein the compound has an $IC_{50}$ value of 100 nanomolar or less in a capsaicin receptor calcium mobilization assay.

52. A compound or salt according to claim 1, wherein the compound has an $IC_{50}$ value of 10 nanomolar or less in a capsaicin receptor calcium mobilization assay.

53. A compound or salt according to claim 1, wherein the compound has an $IC_{50}$ value of 1 nanomolar or less in a capsaicin receptor calcium mobilization assay.

54. A pharmaceutical composition, comprising at least one compound or salt according to claim 1 in combination with a physiologically acceptable carrier or excipient.

55. A pharmaceutical composition according to claim 54 wherein the composition is formulated as an injectible fluid, an aerosol, a cream, a gel, a pill, a capsule, a syrup or a transdermal patch.

56. A packaged pharmaceutical preparation, comprising:
   (a) a pharmaceutical composition according to claim 54 in a container; and
   (b) instructions for using the composition to treat pain.

57. A pharmaceutical composition, comprising one or more compounds or salts according to claim 28 in combination with a physiologically acceptable carrier or excipient.

58. A packaged pharmaceutical preparation, comprising:
   (a) a pharmaceutical composition according to claim 57 in a container; and
   (b) instructions for using the composition to treat pain.

59. A compound or pharmaceutically acceptable salt thereof, wherein the compound is selected from the group consisting of:
   Cyclopentyl-[4-[2-methyl-4-(3-trifluoromethyl-pyridin-2-yl)-piperazin-1-yl]-6-(3-trifluoromethyl-phenyl)-[1,3,5]triazin-2-ylmethyl]-amine,
   [4-(2,5-Dimethoxy-phenyl)-6-(4-pyridin-2-yl-piperazin-1-yl)-[1,3,5]triazin-2-yl]-diethyl-amine,
   {4-(3,4-Difluoro-phenyl)-6-[4-(3-trifluoromethyl-pyridin-2-yl)-piperazin-1-yl]-[1,3,5]triazin-2-yl}-diethyl-amine,
   {4-(3-Chloro-4-fluoro-phenyl)-6-[4-(3-trifluoromethyl-pyridin-2-yl)-piperazin-1-yl]-[1,3,5]triazin-2-yl}-diethyl-amine,
   {4-(3-Chloro-phenyl)-6-[4-(3-trifluoromethyl-pyridin-2-yl)-piperazin-1-yl]-[1,3,5]triazin-2-yl}-diethyl-amine,
   1-(4-{4-(3,4-Difluoro-phenyl)-6-[4-(3-trifluoromethyl-pyridin-2-yl)-piperazin-1-yl]-[1,3,5]triazin-2-yl}-piperazin-1-yl)-ethanone,
   1-(4-{4-(3-Chloro-4-fluoro-phenyl)-6-[4-(3-trifluoromethyl-pyridin-2-yl)-piperazin-1-yl]-[1,3,5]triazin-2-yl}-piperazin-1-yl)-ethanone,
   1-(4-{4-(3-Chloro-phenyl)-6-[4-(3-trifluoromethyl-pyridin-2-yl)-piperazin-1-yl]-[1,3,5]triazin-2-yl}-piperazin-1-yl)-ethanone,
   1-(4-{4-m-Tolyl-6-[4-(3-trifluoromethyl-pyridin-2-yl)-piperazin-1-yl]-[1,3,5]triazin-2-yl}-piperazin-1-yl)-ethanone,
   2-(2,2-Dimethyl-morpholin-4-ylmethyl)-4-[2-methyl-4-(3-trifluoromethyl-pyridin-2-yl)-piperazin-1-yl]-6-(3-trifluoromethyl-phenyl)-[1,3,5]triazine (R),
   2-(2,6-Dimethyl-morpholin-4-ylmethyl)-4-(3-trifluoromethyl-phenyl)-6-[4-(3-trifluoromethyl-pyridin-2-yl)-piperazin-1-yl]-[1,3,5]triazine (cis),
   2-(2,6-Dimethyl-morpholin-4-ylmethyl)-4-[2-methyl-4-(3-trifluoromethyl-pyridin-2-yl)-piperazin-1-yl]-6-(3-trifluoromethyl-phenyl)-[1,3,5]triazine (R; cis),
   2-(2-Methoxymethyl-pyrrolidin-1-yl)-4-(3-trifluoromethyl-phenyl)-6-[4-(3-trifluoromethyl-pyridin-2-yl)-piperazin-1-yl]-[1,3,5]triazine,
   2-(2-Methoxymethyl-pyrrolidin-1-yl)-4-m-tolyl-6-[4-(3-trifluoromethyl-pyridin-2-yl)-piperazin-1-yl]-[1,3,5]triazine,
   2-(3,4-Difluoro-phenyl)-4-(4-methyl-piperazin-1-yl)-6-[4-(3-trifluoromethyl-pyridin-2-yl)-piperazin-1-yl]-[1,3,5]triazine,
   2-(3,4-Difluoro-phenyl)-4-morpholin-4-yl-6-[4-(3-trifluoromethyl-pyridin-2-yl)-piperazin-1-yl]-[1,3,5]triazine,
   2-(3,4-Difluoro-phenyl)-4-pyrrolidin-1-yl-6-[4-(3-trifluoromethyl-pyridin-2-yl)-piperazin-1-yl]-[1,3,5]triazine,
   2-(3-Chloro-4-fluoro-phenyl)-4-(2-methoxymethyl-pyrrolidin-1-yl)-6-[4-(3-trifluoromethyl-pyridin-2-yl)-piperazin-1-yl]-[1,3,5]triazine,
   2-(3-Chloro-4-fluoro-phenyl)-4-(4-methyl-piperazin-1-yl)-6-[4-(3-trifluoromethyl-pyridin-2-yl)-piperazin-1-yl]-[1,3,5]triazine,
   2-(3-Chloro-4-fluoro-phenyl)-4-morpholin-4-yl-6-[4-(3-trifluoromethyl-pyridin-2-yl)-piperazin-1-yl]-[1,3,5]triazine,
   2-(3-Chloro-4-fluoro-phenyl)-4-pyrrolidin-1-yl-6-[4-(3-trifluoromethyl-pyridin-2-yl)-piperazin-1-yl]-[1,3,5]triazine,
   2-(3-Chloro-4-fluoro-phenyl)-4-morpholin-4-yl-6-[4-(3-trifluoromethyl-pyridin-2-yl)-piperazin-1-yl]-[1,3,5]triazine,
   2-(3-Chloro-4-fluoro-phenyl)-4-pyrrolidin-1-yl-6-[4-(3-trifluoromethyl-pyridin-2-yl)-piperazin-1-yl]-[1,3,5]triazine,
   2-(3-Chloro-phenyl)-4-(2-methoxymethyl-pyrrolidin-1-yl)-6-[4-(3-trifluoromethyl-pyridin-2-yl)-piperazin-1-yl]-[1,3,5]triazine,
   2-(3-Chloro-phenyl)-4-morpholin-4-yl-6-[4-(3-trifluoromethyl-pyridin-2-yl)-piperazin-1-yl]-[1,3,5]triazine,
   2-(3-Chloro-phenyl)-4-pyrrolidin-1-yl-6-[4-(3-trifluoromethyl-pyridin-2-yl)-piperazin-1-yl]-[1,3,5]triazine,
   2-[2-Methyl-4-(3-trifluoromethyl-pyridin-2-yl)-piperazin-1-yl]-4-morpholin-4-ylmethyl-6-(3-trifluoromethyl-phenyl)-[1,3,5]triazine (R),
   2-Methoxy-4-[2-methyl-4-(3-trifluoromethyl-pyridin-2-yl)-piperazin-1-yl]-6-(4-trifluoromethyl-phenyl)-[1,3,5]triazine (S),
   2-Methoxymethyl-4-(3-trifluoromethyl-phenyl)-6-[4-(3-trifluoromethyl-pyridin-2-yl)-piperazin-1-yl]-[1,3,5]triazine,
   2-Methoxymethyl-4-[2-methyl-4-(3-trifluoromethyl-pyridin-2-yl)-piperazin-1-yl]-6-(4-trifluoromethyl-phenyl)-[1,3,5]triazine (R), 2-Methyl-4-[2-methyl-4-(3-trifluoromethyl-pyridin-2-yl)-piperazin-1-yl]-6-(4-trifluoromethyl-phenyl)-[1,3,5]triazine (R),
2-Morpholin-4-yl-4-(3-trifluoromethyl-phenyl)-6-[4-(3-trifluoromethyl-pyridin-2-yl)-piperazin-1-yl]-[1,3,5]triazine,
2-Morpholin-4-yl-4-m-tolyl-6-[4-(3-trifluoromethyl-pyridin-2-yl)-piperazin-1-yl]-[1,3,5]triazine,
2-Pyrrolidin-1-yl-4-(3-trifluoromethyl-phenyl)-6-[4-(3-trifluoromethyl-pyridin-2-yl)-piperazin-1-yl]-[1,3,5]triazine,
2-Pyrrolidin-1-yl-4-m-tolyl-6-[4-(3-trifluoromethyl-pyridin-2-yl)-piperazin-1-yl]-[1,3,5]triazine,
3-{4-(2-Methoxymethyl-pyrrolidin-1-yl)-6-[4-(3-trifluoromethyl-pyridin-2-yl)-piperazin-1-yl]-[1,3,5]triazin-2-yl}-benzonitrile,
3-{4-(4-Acetyl-piperazin-1-yl)-6-[4-(3-trifluoromethyl-pyridin-2-yl)-piperazin-1-yl]-[1,3,5]triazin-2-yl}-benzonitrile,
3-{4-Diethylamino-6-[4-(3-trifluoromethyl-pyridin-2-yl)-piperazin-1-yl]-[1,3,5]triazin-2-yl}-benzonitrile,
3-{4-Morpholin-4-yl-6-[4-(3-trifluoromethyl-pyridin-2-yl)-piperazin-1-yl]-[1,3,5]triazin-2-yl}-benzonitrile,
3-{4-Pyrrolidin-1-yl-6-[4-(3-trifluoromethyl-pyridin-2-yl)-piperazin-1-yl]-[1,3,5]triazin-2-yl}-benzonitrile,
4-{4-[4-(3-Chloro-pyridin-2-yl)-piperazin-1-yl]-6-diethylamino-[1,3,5]triazin-2-yl}-benzonitrile,
Diethyl-[4-[2-methyl-4-(3-trifluoromethyl-pyridin-2-yl)-piperazin-1-yl]-6-(4-trifluoromethyl-phenyl)-[1,3,5]triazin-2-yl]-amine,
Diethyl-{4-(3-trifluoromethyl-phenyl)-6-[4-(3-trifluoromethyl-pyridin-2-yl)-piperazin-1-yl]-[1,3,5]triazin-2-ylmethyl}-amine,
Diethyl-{4-(3-trifluoromethyl-phenyl)-6-[4-(3-trifluoromethyl-pyridin-2-yl)-piperazin-1-yl]-[1,3,5]triazin-2-yl}-amine,
Diethyl-{4-m-tolyl-6-[4-(3-trifluoromethyl-pyridin-2-yl)-piperazin-1-yl]-[1,3,5]triazin-2-yl}-amine,
2-(3-chlorophenyl)-4-pyrrolidin-1-yl-6-{4-[3-(trifluoromethyl)pyridin-2-yl]piperazin-1-yl}-1,3,5-triazine,
2-(3-chlorophenyl)-4-piperidin-1-yl-6-{4-[3-(trifluoromethyl)pyridin-2-yl]piperazin-1-yl}-1,3,5-triazine,
2-(3-chlorophenyl)-4-morpholin-4-yl-6-{4-[3-(trifluoromethyl)pyridin-2-yl]piperazin-1-yl}-1,3,5-triazine,
2-(4-chlorophenyl)-4-pyrrolidin-1-yl-6-{4-[3-(trifluoromethyl)pyridin-2-yl]piperazin-1-yl}-1,3,5-triazine,
2-(4-chlorophenyl)-4-piperidin-1-yl-6-{4-[3-(trifluoromethyl)pyridin-2-yl]piperazin-1-yl}-1,3,5-triazine,
2-(4-chlorophenyl)-4-morpholin-4-yl-6-{4-[3-(trifluoromethyl)pyridin-2-yl]piperazin-1-yl}-1,3,5-triazine,
2-(4-fluorophenyl)-4-pyrrolidin-1-yl-6-{4-[3-(trifluoromethyl)pyridin-2-yl]piperazin-1-yl}-1,3,5-triazine,
2-(4-fluorophenyl)-4-piperidin-1-yl-6-{4-[3-(trifluoromethyl)pyridin-2-yl]piperazin-1-yl}-1,3,5-triazine,
2-(4-fluorophenyl)-4-morpholin-4-yl-6-{4-[3-(trifluoromethyl)pyridin-2-yl]piperazin-1-yl}-1,3,5-triazine,
2-(4-fluorophenyl)-4-thiomorpholin-4-yl-6-{4-[3-(trifluoromethyl)pyridin-2-yl]piperazin-1-yl}-1,3,5-triazine,
2-(3-fluorophenyl)-4-pyrrolidin-1-yl-6-{4-[3-(trifluoromethyl)pyridin-2-yl]piperazin-1-yl}-1,3,5-triazine,
2-(3-fluorophenyl)-4-piperidin-1-yl-6-{4-[3-(trifluoromethyl)pyridin-2-yl]piperazin-1-yl}-1,3,5-triazine,
2-(3-fluorophenyl)-4-morpholin-4-yl-6-{4-[3-(trifluoromethyl)pyridin-2-yl]piperazin-1-yl}-1,3,5-triazine,
2-(2-fluorophenyl)-4-morpholin-4-yl-6-{4-[3-(trifluoromethyl)pyridin-2-yl]piperazin-1-yl}-1,3,5-triazine,
2-(3-fluoro-4-methylphenyl)-4-pyrrolidin-1-yl-6-{4-[3-(trifluoromethyl)pyridin-2-yl]piperazin-1-yl}-1,3,5-triazine,
2-(3-fluoro-4-methylphenyl)-4-morpholin-4-yl-6-{4-[3-(trifluoromethyl)pyridin-2-yl]piperazin-1-yl}-1,3,5-triazine,
2-(4-fluoro-3-methylphenyl)-4-pyrrolidin-1-yl-6-{4-[3-(trifluoromethyl)pyridin-2-yl]piperazin-1-yl}-1,3,5-triazine,
2-(4-fluoro-3-methylphenyl)-4-piperidin-1-yl-6-{4-[3-(trifluoromethyl)pyridin-2-yl]piperazin-1-yl}-1,3,5-triazine,
2-(4-fluoro-3-methylphenyl)-4-morpholin-4-yl-6-{4-[3-(trifluoromethyl)pyridin-2-yl]piperazin-1-yl}-1,3,5-triazine,
2-(4-fluoro-3-methylphenyl)-4-thiomorpholin-4-yl-6-{4-[3-(trifluoromethyl)pyridin-2-yl]piperazin-1-yl}-1,3,5-triazine,
2-(3-methylphenyl)-4-pyrrolidin-1-yl-6-{4-[3-(trifluoromethyl)pyridin-2-yl]piperazin-1-yl}-1,3,5-triazine,
2-(3-methylphenyl)-4-piperidin-1-yl-6-{4-[3-(trifluoromethyl)pyridin-2-yl]piperazin-1-yl}-1,3,5-triazine,
2-(3-methylphenyl)-4-morpholin-4-yl-6-{4-[3-(trifluoromethyl)pyridin-2-yl]piperazin-1-yl}-1,3,5-triazine,
2-(3-methylphenyl)-4-thiomorpholin-4-yl-6-{4-[3-(trifluoromethyl)pyridin-2-yl]piperazin-1-yl}-1,3,5-triazine,
2-(4-methylphenyl)-4-pyrrolidin-1-yl-6-{4-[3-(trifluoromethyl)pyridin-2-yl]piperazin-1-yl}-1,3,5-triazine,
2-(4-methylphenyl)-4-piperidin-1-yl-6-{4-[3-(trifluoromethyl)pyridin-2-yl]piperazin-1-yl}-1,3,5-triazine,
2-(4-methylphenyl)-4-morpholin-4-yl-6-{4-[3-(trifluoromethyl)pyridin-2-yl]piperazin-1-yl}-1,3,5-triazine,
2-(3,4-dimethylphenyl)-4-pyrrolidin-1-yl-6-{4-[3-(trifluoromethyl)pyridin-2-yl]piperazin-1-yl}-1,3,5-triazine,
2-(3,4-dimethylphenyl)-4-morpholin-4-yl-6-{4-[3-(trifluoromethyl)pyridin-2-yl]piperazin-1-yl}-1,3,5-triazine,
2-(3-methoxyphenyl)-4-pyrrolidin-1-yl-6-{4-[3-(trifluoromethyl)pyridin-2-yl]piperazin-1-yl}-1,3,5-triazine,
2-(3-methoxyphenyl)-4-piperidin-1-yl-6-{4-[3-(trifluoromethyl)pyridin-2-yl]piperazin-1-yl}-1,3,5-triazine,
2-(3-methoxyphenyl)-4-morpholin-4-yl-6-{4-[3-(trifluoromethyl)pyridin-2-yl]piperazin-1-yl}-1,3,5-triazine,
2-morpholin-4-yl-4-[4-(trifluoromethoxy)phenyl]-6-{4-[3-(trifluoromethyl)pyridin-2-yl]piperazin-1-yl}-1,3,5-triazine,
2-[3-(methylthio)phenyl]-4-morpholin-4-yl-6-{4-[3-(trifluoromethyl)pyridin-2-yl]piperazin-1-yl}-1,3,5-triazine,
2-(4-methoxyphenyl)-4-pyrrolidin-1-yl-6-{4-[3-(trifluoromethyl)pyridin-2-yl]piperazin-1-yl}-1,3,5-triazine,
2-(3-chloro-4-fluorophenyl)-4-piperidin-1-yl-6-{4-[3-(trifluoromethyl)pyridin-2-yl]piperazin-1-yl}-1,3,5-triazine,
2-(3-chloro-4-fluorophenyl)-4-morpholin-4-yl-6-{4-[3-(trifluoromethyl)pyridin-2-yl]piperazin-1-yl}-1,3,5-triazine,
2-(3-chloro-4-fluorophenyl)-4-thiomorpholin-4-yl-6-{4-[3-(trifluoromethyl)pyridin-2-yl]piperazin-1-yl}-1,3,5-triazine,
2-(2,4-difluorophenyl)-4-pyrrolidin-1-yl-6-{4-[3-(trifluoromethyl)pyridin-2-yl]piperazin-1-yl}-1,3,5-triazine,
2-(3,4-difluorophenyl)-4-morpholin-4-yl-6-{4-[3-(trifluoromethyl)pyridin-2-yl]piperazin-1-yl}-1,3,5-triazine, 2-(4-chloro-3-fluorophenyl)-4-morpholin-4-yl-6-{4-[3-(trifluoromethyl)pyridin-2-yl]piperazin-1-yl}-1,3,5-triazine,
2-(3,4-dichlorophenyl)-4-morpholin-4-yl-6-{4-[3-(trifluoromethyl)pyridin-2-yl]piperazin-1-yl}-1,3,5-triazine,
2-(2,4-dichlorophenyl)-4-pyrrolidin-1-yl-6-{4-[3-(trifluoromethyl)pyridin-2-yl]piperazin-1-yl}-1,3,5-triazine,
2-(2,4-dichlorophenyl)-4-morpholin-4-yl-6-{4-[3-(trifluoromethyl)pyridin-2-yl]piperazin-1-yl}-1,3,5-triazine,
2-(3-chlorophenyl)-4-morpholin-4-yl-6-(4-pyridin-2-ylpiperazin-1-yl)-1,3,5-triazine,
2-(4-fluorophenyl)-4-morpholin-4-yl-6-(4-pyridin-2-ylpiperazin-1-yl)-1,3,5-triazine,
2-(3-fluorophenyl)-4-morpholin-4-yl-6-(4-pyridin-2-ylpiperazin-1-yl)-1,3,5-triazine,
2-morpholin-4-yl-4-(2-naphthyl)-6-(4-pyridin-2-ylpiperazin-1-yl)-1,3,5-triazine,
2-(2-fluoro-5-methylphenyl)-4-morpholin-4-yl-6-(4-pyridin-2-ylpiperazin-1-yl)-1,3,5-triazine,
2-(3-chlorophenyl)-4-morpholin-4-yl-6-{4-[3-(trifluoromethyl)pyridin-2-yl]piperazin-1-yl}-1,3,5-triazine,
2-(3-chlorophenyl)-4-[4-(3-chloropyridin-2-yl)piperazin-1-yl]-6-morpholin-4-yl-1,3,5-triazine,
2-(4-chlorophenyl)-4-morpholin-4-yl-6-{4-[3-(trifluoromethyl)pyridin-2-yl]piperazin-1-yl}-1,3,5-triazine,
2-(4-fluorophenyl)-4-morpholin-4-yl-6-{4-[3-(trifluoromethyl)pyridin-2-yl]piperazin-1-yl}-1,3,5-triazine,
2-(3-fluorophenyl)-4-morpholin-4-yl-6-{4-[3-(trifluoromethyl)pyridin-2-yl]piperazin-1-yl}-1,3,5-triazine,
2-(3-fluoro-4-methylphenyl)-4-morpholin-4-yl-6-{4-[3-(trifluoromethyl)pyridin-2-yl]piperazin-1-yl}-1,3,5-triazine,
2-(4-fluoro-3-methylphenyl)-4-morpholin-4-yl-6-{4-[3-(trifluoromethyl)pyridin-2-yl]piperazin-1-yl}-1,3,5-triazine,
2-(3-methylphenyl)-4-morpholin-4-yl-6-(4-pyridin-2-ylpiperazin-1-yl)-1,3,5-triazine,
2-(3-isopropylphenyl)-4-morpholin-4-yl-6-(4-pyridin-2-ylpiperazin-1-yl)-1,3,5-triazine,
2-(3,5-dimethylphenyl)-4-morpholin-4-yl-6-(4-pyridin-2-ylpiperazin-1-yl)-1,3,5-triazine,
2-(3-ethylphenyl)-4-morpholin-4-yl-6-(4-pyridin-2-ylpiperazin-1-yl)-1,3,5-triazine,
2-(3-methylphenyl)-4-morpholin-4-yl-6-{4-[3-(trifluoromethyl)pyridin-2-yl]piperazin-1-yl}-1,3,5-triazine,
2-[4-(3-chloropyridin-2-yl)piperazin-1-yl]-4-(3-methylphenyl)-6-morpholin-4-yl-1,3,5-triazine,
2-(4-methylphenyl)-4-morpholin-4-yl-6-{4-[3-(trifluoromethyl)pyridin-2-yl]piperazin-1-yl}-1,3,5-triazine,
2-(3-isopropylphenyl)-4-morpholin-4-yl-6-{4-[3-(trifluoromethyl)pyridin-2-yl]piperazin-1-yl}-1,3,5-triazine,
2-(3,4-dimethylphenyl)-4-morpholin-4-yl-6-{4-[3-(trifluoromethyl)pyridin-2-yl]piperazin-1-yl}-1,3,5-triazine,
2-(4-ethylphenyl)-4-morpholin-4-yl-6-{4-[3-(trifluoromethyl)pyridin-2-yl]piperazin-1-yl}-1,3,5-triazine,
2-morpholin-4-yl-4-(4-propylphenyl)-6-{4-[3-(trifluoromethyl)pyridin-2-yl]piperazin-1-yl}-1,3,5-triazine,
4-(3-chlorophenyl)-N-ethyl-N-methyl-6-{4-[3-(trifluoromethyl)pyridin-2-yl]piperazin-1-yl}-1,3,5-triazin-2-amine,
4-(4-chlorophenyl)-N-methyl-N-propyl-6-{4-[3-(trifluoromethyl)pyridin-2-yl]piperazin-1-yl}-1,3,5-triazin-2-amine,
4-(4-chlorophenyl)-N-ethyl-N-methyl-6-{4-[3-(trifluoromethyl)pyridin-2-yl]piperazin-1-yl}-1,3,5-triazin-2-amine,
4-(4-fluorophenyl)-N-methyl-N-propyl-6-{4-[3-(trifluoromethyl)pyridin-2-yl]piperazin-1-yl}-1,3,5-triazin-2-amine,
4-(4-fluoro-3-methylphenyl)-N-methyl-N-propyl-6-{4-[3-(trifluoromethyl)pyridin-2-yl]piperazin-1-yl}-1,3,5-triazin-2-amine,
N-ethyl-4-(4-fluoro-3-methylphenyl)-N-methyl-6-{4-[3-(trifluoromethyl)pyridin-2-yl]piperazin-1-yl}-1,3,5-triazin-2-amine,
4-(3-chloro-4-fluorophenyl)-N-methyl-N-propyl-6-{4-[3-(trifluoromethyl)pyridin-2-yl]piperazin-1-yl}-1,3,5-triazin-2-amine,
N-butyl-4-(3-chloro-4-fluorophenyl)-N-methyl-6-{4-[3-(trifluoromethyl)pyridin-2-yl]piperazin-1-yl}-1,3,5-triazin-2-amine,
4-(3-chloro-4-fluorophenyl)-N-ethyl-N-methyl-6-{4-[3-(trifluoromethyl)pyridin-2-yl]piperazin-1-yl}-1,3,5-triazin-2-amine,
4-(3,4-difluorophenyl)-N-ethyl-N-methyl-6-{4-[3-(trifluoromethyl)pyridin-2-yl]piperazin-1-yl}-1,3,5-triazin-2-amine,
4-(3,4-dichlorophenyl)-N-ethyl-N-methyl-6-{4-[3-(trifluoromethyl)pyridin-2-yl]piperazin-1-yl}-1,3,5-triazin-2-amine,
2-(3-chlorophenyl)-4-(3,6-dihydropyridin-1(2H)-yl)-6-{4-[3-(trifluoromethyl)pyridin-2-yl]piperazin-1-yl}-1,3,5-triazine,
2-(3-chlorophenyl)-4-(2,6-dimethylmorpholin-4-yl)-6-{4-[3-(trifluoromethyl)pyridin-2-yl]piperazin-1-yl}-1,3,5-triazine,
2-(4-chlorophenyl)-4-(3,6-dihydropyridin-1(2H)-yl)-6-{4-[3-(trifluoromethyl)pyridin-2-yl]piperazin-1-yl}-1,3,5-triazine,
2-(3,6-dihydropyridin-1(2H)-yl)-4-(4-fluoro-3-methylphenyl)-6-{4-[3-(trifluoromethyl)pyridin-2-yl]piperazin-1-yl}-1,3,5-triazine,
2-(3,6-dihydropyridin-1(2H)-yl)-4-(3-methylphenyl)-6-{4-[3-(trifluoromethyl)pyridin-2-yl]piperazin-1-yl}-1,3,5-triazine,
1-(4-(3-methylphenyl)-6-{4-[3-(trifluoromethyl)pyridin-2-yl]piperazin-1-yl}-1,3,5-triazin-2-yl)azepane,
2-(2,6-dimethylmorpholin-4-yl)-4-(3-methylphenyl)-6-{4-[3-(trifluoromethyl)pyridin-2-yl]piperazin-1-yl}-1,3,5-triazine,
2-(3,6-dihydropyridin-1(2H)-yl)-4-(4-methylphenyl)-6-{4-[3-(trifluoromethyl)pyridin-2-yl]piperazin-1-yl}-1,3,5-triazine,
1-(4-(3-chloro-4-fluorophenyl)-6-{4-[3-(trifluoromethyl)pyridin-2-yl]piperazin-1-yl}-1,3,5-triazin-2-yl)azepane,
2-(3-chloro-4-fluorophenyl)-4-(2,6-dimethylmorpholin-4-yl)-6-{4-[3-(trifluoromethyl)pyridin-2-yl]piperazin-1-yl}-1,3,5-triazine,
2-(2,4-difluorophenyl)-4-(3,6-dihydropyridin-1(2H)-yl)-6-{4-[3-(trifluoromethyl)pyridin-2-yl]piperazin-1-yl}-1,3,5-triazine,
2-(2,5-dimethylphenyl)-4-morpholin-4-yl-6-(4-pyridin-2-ylpiperazin-1-yl)-1,3,5-triazine,
2-morpholin-4-yl-4-(1-naphthyl)-6-(4-pyridin-2-ylpiperazin-1-yl)-1,3,5-triazine,
2-(2,3-dimethylphenyl)-4-morpholin-4-yl-6-(4-pyridin-2-ylpiperazin-1-yl)-1,3,5-triazine,
2-(5-fluoro-2-methylphenyl)-4-morpholin-4-yl-6-(4-pyridin-2-ylpiperazin-1-yl)-1,3,5-triazine, 2-(4-fluoro-2-methylphenyl)-4-morpholin-4-yl-6-(4-pyridin-2-ylpiperazin-1-yl)-1,3,5-triazine,
2-morpholin-4-yl-4-(4-pyridin-2-ylpiperazin-1-yl)-6-(2,4,5-trimethylphenyl)-1,3,5-triazine,
2-(4-methyl-1-naphthyl)-4-morpholin-4-yl-6-(4-pyridin-2-ylpiperazin-1-yl)-1,3,5-triazine,
2-(3-ethoxyphenyl)-4-morpholin-4-yl-6-(4-pyridin-2-ylpiperazin-1-yl)-1,3,5-triazine,
2-morpholin-4-yl-4-(4-pyridin-2-ylpiperazin-1-yl)-6-[3-(trifluoromethoxy)phenyl]-1,3,5-triazine,
2-[3-(methylthio)phenyl]-4-morpholin-4-yl-6-(4-pyridin-2-ylpiperazin-1-yl)-1,3,5-triazine,
2-(3-isopropoxyphenyl)-4-morpholin-4-yl-6-(4-pyridin-2-ylpiperazin-1-yl)-1,3,5-triazine,
2-[3-(methylthio)phenyl]-4-morpholin-4-yl-6-{4-[3-(trifluoromethyl)pyridin-2-yl]piperazin-1-yl}-1,3,5-triazine,
4-(3-chlorophenyl)-N,N-diethyl-6-{4-[3-(trifluoromethyl)pyridin-2-yl]piperazin-1-yl}-1,3,5-triazin-2-amine,
4-(3-chlorophenyl)-N,N-dipropyl-6-{4-[3-(trifluoromethyl)pyridin-2-yl]piperazin-1-yl}-1,3,5-triazin-2-amine,
4-(4-chlorophenyl)-N,N-diethyl-6-{4-[3-(trifluoromethyl)pyridin-2-yl]piperazin-1-yl}-1,3,5-triazin-2-amine,
N,N-diethyl-4-(4-fluorophenyl)-6-{4-[3-(trifluoromethyl)pyridin-2-yl]piperazin-1-yl}-1,3,5-triazin-2-amine,
N,N-diethyl-4-(3-fluorophenyl)-6-{4-[3-(trifluoromethyl)pyridin-2-yl]piperazin-1-yl}- 1,3,5-triazin-2-amine,
N,N-diethyl-4-(2-fluoro-4-methylphenyl)-6-{4-[3-(trifluoromethyl)pyridin-2-yl]piperazin-1-yl}-1,3,5-triazin-2-amine,
N,N-diethyl-4-(3-fluoro-4-methylphenyl)-6-{4-[3-(trifluoromethyl)pyridin-2-yl]piperazin-1-yl}-1,3,5-triazin-2-amine,
N,N-diethyl-4-(4-fluoro-3-methylphenyl)-6-{4-[3-(trifluoromethyl)pyridin-2-yl]piperazin-1-yl}-1,3,5-triazin-2-amine,
4-(4-fluoro-3-methylphenyl)-N,N-dipropyl-6-{4-[3-(trifluoromethyl)pyridin-2-yl]piperazin-1-yl}-1,3,5-triazin-2-amine,
N-butyl-N-ethyl-4-(4-fluoro-3-methylphenyl)-6-{4-[3-(trifluoromethyl)pyridin-2-yl]piperazin-1-yl}-1,3,5-triazin-2-amine,
N,N-diethyl-4-(3-methylphenyl)-6-{4-[3-(trifluoromethyl)pyridin-2-yl]piperazin-1-yl}- 1,3,5-triazin-2-amine,
N,N-diethyl-4-(4-methylphenyl)-6-{4-[3-(trifluoromethyl)pyridin-2-yl]piperazin-1-yl}- 1,3,5-triazin-2-amine,
N,N-diethyl-4-(3-isopropylphenyl)-6-{4-[3-(trifluoromethyl)pyridin-2-yl]piperazin-1-yl}-1,3,5-triazin-2-amine,
4-(3-isopropylphenyl)-N,N-dipropyl-6-{4-[3-(trifluoromethyl)pyridin-2-yl]piperazin-1-yl}-1,3,5-triazin-2-amine,
4-(3,4-dimethylphenyl)-N,N-diethyl-6-{4-[3-(trifluoromethyl)pyridin-2-yl]piperazin-1-yl}-1,3,5-triazin-2-amine,
N,N-diethyl-4-(4-ethylphenyl)-6-{4-[3-(trifluoromethyl)pyridin-2-yl]piperazin-1-yl}-1,3,5-riazin-2-amine,
N,N-diethyl-4-(3-ethylphenyl)-6-{4-[3-(trifluoromethyl)pyridin-2-yl]piperazin-1-yl}-1,3,5-triazin-2-amine,
N,N-diethyl-4-(3-methoxyphenyl)-6-{4-[3-(trifluoromethyl)pyridin-2-yl]piperazin-1-yl}-1,3,5-triazin-2-amine,
N,N-diethyl-4-[3-(methylthio)phenyl]-6-{4-[3-(trifluoromethyl)pyridin-2-yl]piperazin-1-yl}-1,3,5-triazin-2-amine,
4-(1,3-benzodioxol-5-yl)-N,N-diethyl-6-{4-[3-(trifluoromethyl)pyridin-2-yl]piperazin-1-yl}-1,3,5-triazin-2-amine,
4-(3-chloro-4-fluorophenyl)-N,N-diethyl-6-{4-[3-(trifluoromethyl)pyridin-2-yl]piperazin-1-yl}-1,3,5-triazin-2-amine,
4-(3-chloro-4-fluorophenyl)-N,N-dipropyl-6-{4-[3-(trifluoromethyl)pyridin-2-yl]piperazin-1-yl}-1,3,5-triazin-2-amine,
N-butyl-4-(3-chloro-4-fluorophenyl)-N-ethyl-6-{4-[3-(trifluoromethyl)pyridin-2-yl]piperazin-1-yl}-1,3,5-triazin-2-amine,
4-(3-chloro-4-fluorophenyl)-N-(cyclopropylmethyl)-N-propyl-6-{4-[3-(trifluoromethyl)pyridin-2-yl]piperazin-1-yl}-1,3,5-triazin-2-amine,
4-(2,4-difluorophenyl)-N,N-diethyl-6-{4-[3-(trifluoromethyl)pyridin-2-yl]piperazin-1-yl}-1,3,5-triazin-2-amine,
4-(3,4-difluorophenyl)-N,N-diethyl-6-{4-[3-(trifluoromethyl)pyridin-2-yl]piperazin-1-yl}-1,3,5-triazin-2-amine,
4-(4-chloro-3-fluorophenyl)-N,N-diethyl-6-{4-[3-(trifluoromethyl)pyridin-2-yl]piperazin-1-yl}-1,3,5-triazin-2-amine,
4-(3,4-dichlorophenyl)-N,N-diethyl-6-{4-[3-(trifluoromethyl)pyridin-2-yl]piperazin-1-yl}-1 ,3,5-triazin-2-amine,
4-(2,3-difluorophenyl)-N,N-diethyl-6-{4-[3-(trifluoromethyl)pyridin-2-yl]piperazin-1-yl}-1,3,5-triazin-2-amine,
4-(2,3-dichlorophenyl)-N,N-diethyl-6-{4-[3-(trifluoromethyl)pyridin-2-yl]piperazin-1-yl}-1,3,5-triazin-2-amine,
2-morpholin-4-yl-4-(4-pyridin-2-ylpiperazin-1-yl)-6-(3,4,5-trimethoxyphenyl)-1,3,5-triazine,
2-(4-methoxyphenyl)-4-morpholin-4-yl-6-(4-pyridin-2-ylpiperazin-1-yl)-1,3,5-triazine,
2-(4-ethoxyphenyl)-4-morpholin-4-yl-6-(4-pyridin-2-ylpiperazin-1-yl)-1,3,5-triazine,
N,N-dimethyl-3-[4-morpholin-4-yl-6-(4-pyridin-2-ylpiperazin-1-yl)-1,3,5-triazin-2-yl]aniline
2-(1,3-benzodioxol-5-yl)-4-morpholin-4-yl-6-{4-[3-(trifluoromethyl)pyridin-2-yl]piperazin-1-yl}-1,3,5-triazine,
4-(3-chlorophenyl)-N-isopropyl-N-methyl-6-{4-[3-(trifluoromethyl)pyridin-2-yl]piperazin-1-yl}-1,3,5-triazin-2-amine,
2-(3-chlorophenyl)-4-(2-methylpiperidin-1-yl)-6-{4-[3-(trifluoromethyl)pyridin-2-yl]piperazin-1-yl}-1,3,5-triazine,
2-(3-chlorophenyl)-4-(2-ethylpiperidin-1-yl)-6-{4-[3-(trifluoromethyl)pyridin-2-yl]piperazin-1-yl}-1,3,5-triazine,
2-(3-chlorophenyl)-4-(2-methylpyrrolidin-1-yl)-6-{4-[3-(trifluoromethyl)pyridin-2-yl]piperazin-1-yl}-1,3,5-triazine,
4-(4-chlorophenyl)-N-isopropyl-N-methyl-6-{4-[3-(trifluoromethyl)pyridin-2-yl]piperazin-1-yl}-1,3,5-triazin-2-amine, 2-(4-chlorophenyl)-4-(2-methylpiperidin-1-yl)-6-{4-[3-(trifluoromethyl)pyridin-2-yl]piperazin-1-yl}-1,3,5-triazine, 2-(4-chlorophenyl)-4-(2-methylpyrrolidin-1-yl)-6-{4-[3-(trifluoromethyl)pyridin-2-yl]piperazin-1-yl}-1,3,5-triazine, 4-(4-fluorophenyl)-N-isopropyl-N-methyl-6-{4-[3-(trifluoromethyl)pyridin-2-yl]piperazin-1-yl}-1,3,5-triazin-2-amine, 2-(4-fluorophenyl)-4-(2-methylpiperidin-1-yl)-6-{4-[3-(trifluoromethyl)pyridin-2-yl]piperazin-1-yl}-1,3,5-triazine, 2-(2-ethylpiperidin-1-yl)-4-(4-fluorophenyl)-6-{4-[3-(trifluoromethyl)pyridin-2-yl]piperazin-1-yl}-1,3,5-triazine, 2-(4-fluorophenyl)-4-(2-methylpyrrolidin-1-yl)-6-{4-[3-(trifluoromethyl)pyridin-2-yl]piperazin-1-yl}-1,3,5-triazine, 2-(3-fluorophenyl)-4-(2-methylpiperidin-1-yl)-6-{4-[3-(trifluoromethyl)pyridin-2-yl]piperazin-1-yl}-1,3,5-triazine, 2-(3-fluorophenyl)-4-(2-methylpyrrolidin-1-yl)-6-{4-[3-(trifluoromethyl)pyridin-2-yl]piperazin-1-yl}-1,3,5-triazine, 2-(2-fluoro-4-methylphenyl)-4-(2-methylpyrrolidin-1-yl)-6-{4-[3-(trifluoromethyl)pyridin-2-yl]piperazin-1-yl}-1,3,5-triazine, 4-(3-fluoro-4-methylphenyl)-N-isopropyl-N-methyl-6-{4-[3-(trifluoromethyl)pyridin-2-yl]piperazin-1-yl}-1,3,5-triazin-2-amine, 2-(3-fluoro-4-methylphenyl)-4-(2-methylpiperidin-1-yl)-6-{4-[3-(trifluoromethyl)pyridin-2-yl]piperazin-1-yl}-1,3,5-triazine, 2-(3-fluoro-4-methylphenyl)-4-(2-methylpyrrolidin-1-yl)-6-{4-[3-(trifluoromethyl)pyridin-2-yl]piperazin-1-yl}-1,3,5-triazine, 4-(4-fluoro-3-methylphenyl)-N-isopropyl-N-methyl-6-{4-[3-(trifluoromethyl)pyridin-2-yl]piperazin-1-yl}-1,3,5-triazin-2-amine, 2-(4-fluoro-3-methylphenyl)-4-(2-methylpiperidin-1-yl)-6-{4-[3-(trifluoromethyl)pyridin-2-yl]piperazin-1-yl}-1,3,5-triazine, 2-(2-ethylpiperidin-1-yl)-4-(4-fluoro-3-methylphenyl)-6-{4-[3-(trifluoromethyl)pyridin-2-yl]piperazin-1-yl}-1,3,5-triazine, 2-(4-fluoro-3-methylphenyl)-4-(2-methylpyrrolidin-1-yl)-6-{4-[3-(trifluoromethyl)pyridin-2-yl]piperazin-1-yl}-1,3,5-triazine, N-isopropyl-N-methyl-4-(3-methylphenyl)-6-{4-[3-(trifluoromethyl)pyridin-2-yl]piperazin-1-yl}-1,3,5-triazin-2-amine, 2-(3-methylphenyl)-4-(2-methylpiperidin-1-yl)-6-{4-[3-(trifluoromethyl)pyridin-2-yl]piperazin-1-yl}-1,3,5-triazine, 2-(3-methylphenyl)-4-(2-methylpyrrolidin-1-yl)-6-{4-[3-(trifluoromethyl)pyridin-2-yl]piperazin-1-yl}-1,3,5-triazine, N-isopropyl-N-methyl-4-(4-methylphenyl)-6-{4-[3-(trifluoromethyl)pyridin-2-yl]piperazin-1-yl}-1,3,5-triazin-2-amine, 2-(4-methylphenyl)-4-(2-methylpiperidin-1-yl)-6-{4-[3-(trifluoromethyl)pyridin-2-yl]piperazin-1-yl}-1,3,5-triazine, 2-(4-methylphenyl)-4-(2-methylpyrrolidin-1-yl)-6-{4-[3-(trifluoromethyl)pyridin-2-yl]piperazin-1-yl}-1,3,5-triazine, 2-(3-isopropylphenyl)-4-(2-methylpyrrolidin-1-yl)-6-{4-[3-(trifluoromethyl)pyridin-2-yl]piperazin-1-yl}-1,3,5-triazine, 2-(4-isopropylphenyl)-4-(2-methylpyrrolidin-1-yl)-6-{4-[3-(trifluoromethyl)pyridin-2-yl]piperazin-1-yl}-1,3,5-triazine, 4-(3,4-dimethylphenyl)-N-isopropyl-N-methyl-6-{4-[3-(trifluoromethyl)pyridin-2-yl]piperazin-1-yl}-1,3,5-triazin-2-amine, 2-(3,4-dimethylphenyl)-4-(2-methylpiperidin-1-yl)-6-{4-[3-(trifluoromethyl)pyridin-2-yl]piperazin-1-yl}-1,3,5-triazine, 2-(3,4-dimethylphenyl)-4-(2-methylpyrrolidin-1-yl)-6-{4-[3-(trifluoromethyl)pyridin-2-yl]piperazin-1-yl}-1,3,5-triazine, 2-(4-ethylphenyl)-4-(2-methylpyrrolidin-1-yl)-6-{4-[3-(trifluoromethyl)pyridin-2-yl]piperazin-1-yl}-1,3,5-triazine, 2-(2-methylpyrrolidin-1-yl)-4-(4-propylphenyl)-6-{4-[3-(trifluoromethyl)pyridin-2-yl]piperazin-1-yl}-1,3,5-triazine, 2-(3-ethylphenyl)-4-(2-methylpyrrolidin-1-yl)-6-{4-[3-(trifluoromethyl)pyridin-2-yl]piperazin-1-yl}-1,3,5-triazine, 2-(4-fluoro-2-methylphenyl)-4-(2-methylpyrrolidin-1-yl)-6-{4-[3-(trifluoromethyl)pyridin-2-yl]piperazin-1-yl}-1,3,5-triazine, 2-(3-methoxyphenyl)-4-(2-methylpyrrolidin-1-yl)-6-{4-[3-(trifluoromethyl)pyridin-2-yl]piperazin-1-yl}-1,3,5-triazine, 2-(2-methylpyrrolidin-1-yl)-4-[3-(trifluoromethoxy)phenyl]-6-{4-[3-(trifluoromethyl)pyridin-2-yl]piperazin-1-yl}-1,3,5-triazine, 2-(2-methylpiperidin-1-yl)-4-[3-(methylthio)phenyl]-6-{4-[3-(trifluoromethyl)pyridin-2-yl]piperazin-1-yl}-1,3,5-triazine, 2-(2-methylpyrrolidin-1-yl)-4-[3-(methylthio)phenyl]-6-{4-[3-(trifluoromethyl)pyridin-2-yl]piperazin-1-yl}-1,3,5-triazine, 2-(3-fluoro-4-methoxyphenyl)-4-(2-methylpyrrolidin-1-yl)-6-{4-[3-(trifluoromethyl)pyridin-2-yl]piperazin-1-yl}-1,3,5-triazine, 2-(4-methoxyphenyl)-4-(2-methylpyrrolidin-1-yl)-6-{4-[3-(trifluoromethyl)pyridin-2-yl]piperazin-1-yl}-1,3,5-triazine, 4-(1,3-benzodioxol-5-yl)-N-isopropyl-N-methyl-6-{4-[3-(trifluoromethyl)pyridin-2-yl]piperazin-1-yl}-1,3,5-triazin-2-amine, 2-(1,3-benzodioxol-5-yl)-4-(2-methylpiperidin-1-yl)-6-{4-[3-(trifluoromethyl)pyridin-2-yl]piperazin-1-yl}-1,3,5-triazine, 2-(1,3-benzodioxol-5-yl)-4-(2-methylpyrrolidin-1-yl)-6-{4-[3-(trifluoromethyl)pyridin-2-yl]piperazin-1-yl}-1,3,5-triazine, 4-[4-(dimethylamino)phenyl]-N-isopropyl-N-methyl-6-{4-[3-(trifluoromethyl)pyridin-2-yl]piperazin-1-yl}-1,3,5-triazin-2-amine, N,N-dimethyl-4-(4-(2-methylpyrrolidin-1-yl)-6-{4-[3-(trifluoromethyl)pyridin-2-yl]piperazin--yl}-1,3,5-triazin-2-yl)aniline, 2-(2,3-dihydro-1,4-benzodioxin-6-yl)-4-(2-methylpyrrolidin-1-yl)-6-{4-[3-(trifluoromethyl)pyridin-2-yl]piperazin-1-yl}-1,3,5-triazine, N,N-dimethyl-3-(4-(2-methylpyrrolidin-1-yl)-6-{4-[3-(trifluoromethyl)pyridin-2-yl]piperazin-1-yl}-1,3,5-triazin-2-yl)aniline, 4-(3-chloro-4-fluorophenyl)-N-isopropyl-N-methyl-6-{4-[3-(trifluoromethyl)pyridin-2-yl]piperazin-1-yl}-1,3,5-triazin-2-amine,
2-(3-chloro-4-fluorophenyl)-4-(2-methylpiperidin-1-yl)-6-{4-[3-(trifluoromethyl)pyridin-2-yl]piperazin-1-yl}-1,3,5-triazine,
2-(3-chloro-4-fluorophenyl)-4-(2-ethylpiperidin-1-yl)-6-{4-[3-(trifluoromethyl)pyridin-2-yl]piperazin-1-yl}-1,3,5-triazine,
2-(3-chloro-4-fluorophenyl)-4-(2-methylpyrrolidin-1-yl)-6-{4-[3-(trifluoromethyl)pyridin-2-yl]piperazin-1-yl}-1,3,5-triazine,
4-(2,4-difluorophenyl)-N-isopropyl-N-methyl-6-{4-[3-(trifluoromethyl)pyridin-2-yl]piperazin-1-yl}-1,3,5-triazin-2-amine,
2-(2,4-difluorophenyl)-4-(2-methylpiperidin-1-yl)-6-{4-[3-(trifluoromethyl)pyridin-2-yl]piperazin-1-yl}-1,3,5-triazine,
2-(2,4-difluorophenyl)-4-(2-methylpyrrolidin-1-yl)-6-{4-[3-(trifluoromethyl)pyridin-2-yl]piperazin-1-yl}-1,3,5-triazine,
4-(3,4-difluorophenyl)-N-isopropyl-N-methyl-6-{4-[3-(trifluoromethyl)pyridin-2- yl]piperazin-1-yl}-1,3,5-triazin-2-amine,
2-(3,4-difluorophenyl)-4-(2-methylpiperidin-1-yl)-6-{4-[3-(trifluoromethyl)pyridin-2-yl]piperazin-1-yl}-1,3,5-triazine,
2-(3,4-difluorophenyl)-4-(2-methylpyrrolidin-1-yl)-6-{4-[3-(trifluoromethyl)pyridin-2-yl]piperazin-1-yl}-1,3,5-triazine,
4-(4-chloro-2-fluorophenyl)-N-isopropyl-N-methyl-6-{4-[3-(trifluoromethyl)pyridin-2-yl]piperazin-1-yl}-1,3,5-triazin-2-amine,
2-(4-chloro-2-fluorophenyl)-4-(2-methylpyrrolidin-1-yl)-6-{4-[3-(trifluoromethyl)pyridin-2-yl]piperazin-1-yl}-1,3,5-triazine,
4-(4-chloro-3-fluorophenyl)-N-isopropyl-N-methyl-6-{4-[3-(trifluoromethyl)pyridin-2-yl]piperazin-1-yl}-1,3,5-triazin-2-amine,
2-(4-chloro-3-fluorophenyl)-4-(2-methylpiperidin-1-yl)-6-{4-[3-(trifluoromethyl)pyridin-2-yl]piperazin-1-yl}-1,3,5-triazine,
2-(4-chloro-3-fluorophenyl)-4-(2-methylpyrrolidin-1-yl)-6-{4-[3-(trifluoromethyl)pyridin-2-yl]piperazin-1-yl}-1,3,5-triazine,
4-(3,4-dichlorophenyl)-N-isopropyl-N-methyl-6-{4-[3-(trifluoromethyl)pyridin-2-yl]piperazin-1-yl}-1,3,5-triazin-2-amine,
2-(3,4-dichlorophenyl)-4-(2-methylpiperidin-1-yl)-6-{4-[3-(trifluoromethyl)pyridin-2-yl]piperazin-1-yl}-1,3,5-triazine,
2-(3,4-dichlorophenyl)-4-(2-methylpyrrolidin-1-yl)-6-{4-[3-(trifluoromethyl)pyridin-2-yl]piperazin-1-yl}-1,3,5-triazine,
2-(3,5-difluorophenyl)-4-(2-methylpyrrolidin-1-yl)-6-{4-[3-(trifluoromethyl)pyridin-2-yl]piperazin-1-yl}-1,3,5-triazine,
2-(2,3-difluorophenyl)-4-(2-methylpyrrolidin-1-yl)-6-{4-[3-(trifluoromethyl)pyridin-2-yl]piperazin-1-yl}-1,3,5-triazine,
4-(2,3-dichlorophenyl)-N-isopropyl-N-methyl-6-{4-[3-(trifluoromethyl)pyridin-2-yl]piperazin-1-yl}-1,3,5-triazin-2-amine,
2-(2,3-dichlorophenyl)-4-(2-methylpyrrolidin-1-yl)-6-{4-[3-(trifluoromethyl)pyridin-2-yl]piperazin-1-yl}-1,3,5-triazine,
2-(2,4-dichlorophenyl)-4-(2-methylpyrrolidin-1-yl)-6-{4-[3-(trifluoromethyl)pyridin-2-yl]piperazin-1-yl}-1,3,5-triazine,
2-(2,5-dichlorophenyl)-4-(2-methylpyrrolidin-1-yl)-6-{4-[3-(trifluoromethyl)pyridin-2-yl]piperazin-1-yl}-1,3,5-triazine,
4-(3-chlorophenyl)-N-ethyl-N-isopropyl-6-{4-[3-(trifluoromethyl)pyridin-2-yl]piperazin-1-yl}-1,3,5-triazin-2-amine,
4-(3-chlorophenyl)-N-cyclohexyl-N-methyl-6-{4-[3-(trifluoromethyl)pyridin-2-yl]piperazin-1-yl}-1,3,5-triazin-2-amine,
4-(3-chlorophenyl)-N-cyclohexyl-N-ethyl-6-{4-[3-(trifluoromethyl)pyridin-2-yl]piperazin-1-yl}-1,3,5-triazin-2-amine,
1-(4-(3-chlorophenyl)-6-{4-[3-(trifluoromethyl)pyridin-2-yl]piperazin-1-yl}-1,3,5-triazin-2-yl)decahydroquinoline,
4-(4-chlorophenyl)-N-cyclohexyl-N-methyl-6-{4-[3-(trifluoromethyl)pyridin-2-yl]piperazin-1-yl}-1,3,5-triazin-2-amine,
4-(4-chlorophenyl)-N-cyclohexyl-N-ethyl-6-{4-[3-(trifluoromethyl)pyridin-2-yl]piperazin-1-yl}-1,3,5-triazin-2-amine,
N-cyclohexyl-4-(4-fluorophenyl)-N-methyl-6-{4-[3-(trifluoromethyl)pyridin-2-yl]piperazin-1-yl}-1,3,5-triazin-2-amine,
N-cyclohexyl-N-ethyl-4-(4-fluorophenyl)-6-{4-[3-(trifluoromethyl)pyridin-2-yl]piperazin-1-yl}-1,3,5-triazin-2-amine,
N-cyclohexyl-4-(3-fluorophenyl)-N-methyl-6-{4-[3-(trifluoromethyl)pyridin-2-yl]piperazin-1-yl}-1,3,5-triazin-2-amine,
N-ethyl-4-(4-fluoro-3-methylphenyl)-N-isopropyl-6-{4-[3-(trifluoromethyl)pyridin-2-yl]piperazin-1-yl}-1,3,5-triazin-2-amine,
N-cyclohexyl-4-(4-fluoro-3-methylphenyl)-N-methyl-6-{4-[3-(trifluoromethyl)pyridin-2-yl]piperazin-1-yl}-1,3,5-triazin-2-amine
N-cyclohexyl-N-ethyl-4-(4-fluoro-3-methylphenyl)-6-{4-[3-(trifluoromethyl)pyridin-2-yl]piperazin-1-yl}-1,3,5-triazin-2-amine,
1-(4-(4-fluoro-3-methylphenyl)-6-{4-[3-(trifluoromethyl)pyridin-2-yl]piperazin-1-yl}-1,3,5-triazin-2-yl)decahydroquinoline,
N-ethyl-N-isopropyl-4-(3-methylphenyl)-6-{4-[3-(trifluoromethyl)pyridin-2-yl]piperazin-1-yl}-1,3,5-triazin-2-amine,
N-cyclohexyl-N-methyl-4-(3-methylphenyl)-6-{4-[3-(trifluoromethyl)pyridin-2-yl]piperazin-1-yl}-1,3,5-triazin-2-amine,
N-cyclohexyl-N-methyl-4-(4-methylphenyl)-6-{4-[3-(trifluoromethyl)pyridin-2-yl]piperazin-1-yl}-1,3,5-triazin-2-amine,
N-cyclohexyl-4-(3,4-di methylphenyl)-N-methyl-6-{4-[3-(trifluoromethyl)pyridin-2-yl]piperazin-1-yl}-1,3,5-triazin-2-amine,
4-(1,3-benzodioxol-5-yl)-N-cyclohexyl-N-methyl-6-{4-[3-(trifluoromethyl)pyridin-2-yl]piperazin-1-yl}-1,3,5-triazin-2-amine,
4-(3-chloro-4-fluorophenyl)-N-ethyl-N-isopropyl-6-{4-[3-(trifluoromethyl)pyridin-2-yl]piperazin-1-yl}-1,3,5-triazin-2-amine,
4-(3-chloro-4-fluorophenyl)-N-cyclohexyl-N-methyl-6-{4-[3-(trifluoromethyl)pyridin-2-yl]piperazin-1-yl}-1,3,5-triazin-2-amine, 4-(3-chloro-4-fluorophenyl)-N-cyclohexyl-N-ethyl-6-{4-[3-(trifluoromethyl)pyridin-2-yl]piperazin-1-yl}-1,3,5-triazin-2-amine,
1-(4-(3-chloro-4-fluorophenyl)-6-{4-[3-(trifluoromethyl)pyridin-2-yl]piperazin-1-yl}-1,3,5-triazin-2-yl)decahydroquinoline,
N-cyclohexyl-4-(2,4-difluorophenyl)-N-methyl-6-{4-[3-(trifluoromethyl)pyridin-2-yl]piperazin-1-yl}-1,3,5-triazin-2-amine,
4-(3,4-difluorophenyl)-N-ethyl-N-isopropyl-6-{4-[3-(trifluoromethyl)pyridin-2-yl]piperazin-1-yl}-1,3,5-triazin-2-amine,
N-cyclohexyl-4-(3,4-difluorophenyl)-N-ethyl-6-{4-[3-(trifluoromethyl)pyridin-2-yl]piperazin-1-yl}-1,3,5-triazin-2-amine,
4-(4-chloro-2-fluorophenyl)-N-cyclohexyl-N-methyl-6-{4-[3-(trifluoromethyl)pyridin-2-yl]piperazin-1-yl}-1,3,5-triazin-2-amine,
4-(4-chloro-3-fluorophenyl)-N-cyclohexyl-N-methyl-6-{4-[3-(trifluoromethyl)pyridin-2-yl]piperazin-1-yl}-1,3,5-triazin-2-amine,
4-(3,4-dichlorophenyl)-N-ethyl-N-isopropyl-6-{4-[3-(trifluoromethyl)pyridin-2-yl]piperazin-1-yl}-1,3,5-triazin-2-amine,
2-(2,5-difluorophenyl)-4-morpholin-4-yl-6-(4-pyridin-2-ylpiperazin-1-yl)-1,3,5-triazine,
2-(2,4-difluorophenyl)-4-morpholin-4-yl-6-(4-pyridin-2-ylpiperazin-1-yl)-1,3,5-triazine,
2-(3,4-difluorophenyl)-4-morpholin-4-yl-6-(4-pyridin-2-ylpiperazin-1-yl)-1,3,5-triazine,
2-(3,5-difluorophenyl)-4-morpholin-4-yl-6-(4-pyridin-2-ylpiperazin-1-yl)-1,3,5-triazine,
2-(3-chloro-4-fluorophenyl)-4-morpholin-4-yl-6-{4-[3-(trifluoromethyl)pyridin-2-yl]piperazin-1-yl}-1,3,5-triazine,
2-(3-chloro-4-fluorophenyl)-4-[4-(3-chloropyridin-2-yl)piperazin-1-yl]-6-morpholin-4-yl-1,3,5-triazine,
2-(3,4-difluorophenyl)-4-morpholin-4-yl-6-{4-[3-(trifluoromethyl)pyridin-2-yl]piperazin-1-yl}-1,3,5-triazine,
2-(3,4-dichlorophenyl)-4-morpholin-4-yl-6-{4-[3-(trifluoromethyl)pyridin-2-yl]piperazin-1-yl}-1,3,5-triazine,
2-(5-isopropyl-2-methoxyphenyl)-4-morpholin-4-yl-6-(4-pyridin-2-ylpiperazin-1-yl)-1,3,5-triazine,
2-(5-chloro-2-methoxyphenyl)-4-morpholin-4-yl-6-(4-pyridin-2-ylpiperazin-1-yl)-1,3,5-triazine,
2-dibenzo[b,d]furan-4-yl-4-morpholin-4-yl-6-(4-pyridin-2-ylpiperazin-1-yl)-1,3,5-triazine,
2-[3,5-bis(trifluoromethyl)phenyl]-4-morpholin-4-yl-6-(4-pyridin-2-ylpiperazin-1-yl)-1,3,5-triazine,
ethyl 3-[4-morpholin-4-yl-6-(4-pyridin-2-ylpiperazin-1-yl)-1,3,5-triazin-2-yl]benzoate,
3-(4-morpholin-4-yl-6-{4-[3-(trifluoromethyl)pyridin-2-yl]piperazin-1-yl}-1,3,5-triazin-2-yl)benzonitrile,
4-(4-morpholin-4-yl-6-{4-[3-(trifluoromethyl)pyridin-2-yl]piperazin-1-yl}-1,3,5-triazin-2-yl)benzonitrile,
2-morpholin-4-yl-4-[4-(trifluoromethyl)phenyl]-6-{4-[3-(trifluoromethyl)pyridin-2-yl]piperazin-1-yl}-1,3,5-triazine,
2-morpholin-4-yl-4-[3-(trifluoromethyl)phenyl]-6-{4-[3-(trifluoromethyl)pyridin-2-yl]piperazin-1-yl}-1,3,5-triazine,
2-[4-chloro-3-(trifluoromethyl)phenyl]-4-morpholin-4-yl-6-{4-[3-(trifluoromethyl)pyridin-2-yl]piperazin-1-yl}-1,3,5-triazine,
2-(4-allylpiperazin-1-yl)-4-(3-chlorophenyl)-6-{4-[3-(trifluoromethyl)pyridin-2-yl]piperazin-1-yl}-1,3,5-triazine,
2-(3-chlorophenyl)-4-(4-methylpiperazin-1-yl)-6-{4-[3-(trifluoromethyl)pyridin-2-yl]piperazin-1-yl}-1,3,5-triazine,
2-(3-chlorophenyl)-4-(4-ethylpiperazin-1-yl)-6-{4-[3-(trifluoromethyl)pyridin-2-yl]piperazin-1-yl}-1,3,5-triazine,
2-(4-butylpiperazin-1-yl)-4-(3-chlorophenyl)-6-{4-[3-(trifluoromethyl)pyridin-2-yl]piperazin-1-yl}-1,3,5-triazine,
2-(4-allylpiperazin-1-yl)-4-(4-chlorophenyl)-6-{4-[3-(trifluoromethyl)pyridin-2-yl]piperazin-1-yl}-1,3,5-triazine,
2-(4-allylpiperazin-1-yl)-4-(4-fluorophenyl)-6-{4-[3-(trifluoromethyl)pyridin-2-yl]piperazin-1-yl}-1,3,5-triazine,
2-(4-butylpiperazin-1-yl)-4-(4-fluorophenyl)-6-{4-[3-(trifluoromethyl)pyridin-2-yl]piperazin-1-yl}-1,3,5-triazine,
2-(4-allylpiperazin-1-yl)-4-(3-fluorophenyl)-6-{4-[3-(trifluoromethyl)pyridin-2-yl]piperazin-1-yl}-1,3,5-triazine,
2-(4-allylpiperazin-1-yl)-4-(3-fluoro-4-methylphenyl)-6-{4-[3-(trifluoromethyl)pyridin-2-yl]piperazin-1-yl}-1,3,5-triazine,
2-(4-allylpiperazin-1-yl)-4-(4-fluoro-3-methylphenyl)-6-{4-[3-(trifluoromethyl)pyridin-2-yl]piperazin-1-yl}-1,3,5-triazine,
2-(4-ethylpiperazin-1-yl)-4-(4-fluoro-3-methylphenyl)-6-{4-[3-(trifluoromethyl)pyridin-2-yl]piperazin-1-yl}-1,3,5-triazine,
2-(4-butylpiperazin-1-yl)-4-(4-fluoro-3-methylphenyl)-6-{4-[3-(trifluoromethyl)pyridin-2-yl]piperazin-1-yl}-1,3,5-triazine,
2-(4-allylpiperazin-1-yl)-4-(3-methylphenyl)-6-{4-[3-(trifluoromethyl)pyridin-2-yl]piperazin-1-yl}-1,3,5-triazine,
2-(4-allylpiperazin-1-yl)-4-(4-methylphenyl)-6-{4-[3-(trifluoromethyl)pyridin-2-yl]piperazin-1-yl}-1,3,5-triazine,
2-(4-allylpiperazin-1-yl)-4-(3,4-dimethylphenyl)-6-{4-[3-(trifluoromethyl)pyridin-2-yl]piperazin-1-yl}-1,3,5-triazine,
2-(4-allylpiperazin-1-yl)-4-[3-(methylthio)phenyl]-6-{4-[3-(trifluoromethyl)pyridin-2-yl]piperazin-1-yl}-1,3,5-triazine,
N,N-diethyl-4-(3-fluorophenyl)-6-[4-(4-methoxyphenyl)piperazin-1-yl]-1,3,5-triazin-2-amine,
N,N-diethyl-4-[4-(4-fluorophenyl)piperazin-1-yl]-6-(4-methylphenyl)-1,3,5-triazin-2-amine,
N,N-diethyl-4-(3-isopropylphenyl)-6-(4-phenylpiperazin-1-yl)-1,3,5-triazin-2-amine,
N,N-diethyl-4-[4-(2-fluorophenyl)piperazin-1-yl]-6-(3-isopropylphenyl)-1,3,5-triazin-2-amine,
4-(3,4-dimethylphenyl)-N,N-diethyl-6-(4-phenylpiperazin-1-yl)-1,3,5-triazin-2-amine,
4-(3,4-dimethylphenyl)-N,N-diethyl-6-[4-(4-fluorophenyl)piperazin-1-yl]-1,3,5-triazin-2-amine,
4-(3,4-dimethylphenyl)-N,N-diethyl-6-[4-(3-fluorophenyl)piperazin-1-yl]-1,3,5-triazin-2-amine,
4-(4-butylphenyl)-N,N-diethyl-6-(4-phenylpiperazin-1-yl)-1,3,5-triazin-2-amine,
4-(4-butylphenyl)-N,N-diethyl-6-[4-(2-fluorophenyl)piperazin-1-yl]-1,3,5-triazin-2-amine, 4-(4-butylphenyl)-N,N-diethyl-6-[4-(3-fluorophenyl)piperazin-1-yl]-1,3,5-triazin-2-amine, 4-(3,5-dimethylphenyl)-N,N-diethyl-6-(4-phenylpiperazin-1-yl)-1,3,5-triazin-2-amine, 4-[4-(4-chlorophenyl)piperazin-1-yl]-N,N-diethyl-6-(3-methylphenyl)-1,3,5-triazin-2-amine, 4-[4-(3,4-dichlorophenyl)piperazin-1-yl]-N,N-diethyl-6-(3-methylphenyl)-1,3,5-triazin-2-amine, 4-[4-(3,5-dichlorophenyl)piperazin-1-yl]-N,N-diethyl-6-(3-methylphenyl)-1,3,5-triazin-2-amine, 4-[4-(3-chlorophenyl)piperazin-1-yl]-6-(3,5-dimethylphenyl)-N,N-diethyl-1,3,5-triazin-2-amine, 2-(3,4-dimethoxyphenyl)-4-[4-(2-fluorophenyl)piperazin-1-yl]-6-morpholin-4-yl-1,3,5-triazine, 2-(3-chloro-4-fluorophenyl)-4-[4-(5-chloro-2-methoxyphenyl)piperazin-1-yl]-6-morpholin-4-yl-1,3,5-triazine, 2-[4-(2,4-dimethylphenyl)piperazin-1-yl]-4-(2-ethoxyphenyl)-6-morpholin-4-yl-1,3,5-triazine, and 2-mesityl-4-[4-(3-methylphenyl)piperazin-1-yl]-6-morpholin-4-yl-1,3,5-triazine.

* * * * *

UNITED STATES PATENT AND TRADEMARK OFFICE
CERTIFICATE OF CORRECTION

| | | |
|---|---|---|
| PATENT NO. | : 7,566,712 B2 | Page 1 of 1 |
| APPLICATION NO. | : 10/893799 | |
| DATED | : July 28, 2009 | |
| INVENTOR(S) | : Bakthavatchalam et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 743 days.

Delete the phrase "by 743 days" and insert -- by 1,230 days --

Signed and Sealed this

Fourth Day of May, 2010

David J. Kappos
*Director of the United States Patent and Trademark Office*